(12) United States Patent
Lee et al.

(10) Patent No.: US 10,124,069 B2
(45) Date of Patent: Nov. 13, 2018

(54) PEPTIDOMIMETIC COMPOUNDS AND ANTIBODY-DRUG CONJUGATES THEREOF

(71) Applicant: Genentech, Inc., South San Francisco, CA (US)

(72) Inventors: Ho Huat Lee, Auckland (NZ); Moana Tercel, Auckland (NZ); John A. Flygare, Burlingame, CA (US); Janet Gunzner-Toste, Berkeley, CA (US); Thomas H. Pillow, San Francisco, CA (US); Brian Safina, Redwood City, CA (US); Leanna Staben, San Francisco, CA (US); Vishal Verma, San Carlos, CA (US); BinQing Wei, Belmont, CA (US); Guiling Zhao, Palo Alto, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/182,429

(22) Filed: Jun. 14, 2016

(65) Prior Publication Data

US 2016/0279261 A1    Sep. 29, 2016

Related U.S. Application Data

(63) Continuation of application No. PCT/US2014/070660, filed on Dec. 16, 2014.

(60) Provisional application No. 61/916,661, filed on Dec. 16, 2013, provisional application No. 61/916,691, filed on Dec. 16, 2013.

(51) Int. Cl.
| | |
|---|---|
| *A61K 47/00* | (2006.01) |
| *A61K 47/48* | (2006.01) |
| *C07K 16/28* | (2006.01) |
| *C07K 16/30* | (2006.01) |
| *A61K 47/68* | (2017.01) |
| *A61K 39/00* | (2006.01) |

(52) U.S. Cl.
CPC .... *A61K 47/48715* (2013.01); *A61K 47/6803* (2017.08); *A61K 47/6851* (2017.08); *A61K 47/6889* (2017.08); *C07K 16/28* (2013.01); *C07K 16/2851* (2013.01); *C07K 16/2863* (2013.01); *C07K 16/30* (2013.01); *A61K 2039/505* (2013.01); *C07K 2317/24* (2013.01); *C07K 2317/56* (2013.01); *C07K 2317/76* (2013.01)

(58) Field of Classification Search
None
See application file for complete search history.

(56) References Cited

U.S. PATENT DOCUMENTS

| | | |
|---|---|---|
| 6,214,345 B1 | 4/2001 | Firestone et al. |
| 7,521,541 B2 | 4/2009 | Eigenbrot et al. |
| 7,855,275 B2 | 12/2010 | Eigenbrot et al. |
| 8,309,300 B2 | 11/2012 | Junutula et al. |
| 9,000,130 B2 | 4/2015 | Bhakta et al. |
| 9,290,578 B2 | 3/2016 | Asundi et al. |
| 2007/0092940 A1 | 4/2007 | Eigenbrot et al. |
| 2009/0175865 A1 | 7/2009 | Eigenbrot et al. |
| 2010/0003766 A1 | 1/2010 | Eigenbrot et al. |
| 2010/0111856 A1 | 5/2010 | Gill et al. |
| 2011/0137017 A1 | 6/2011 | Eigenbrot et al. |
| 2011/0142859 A1 | 6/2011 | Ebens, Jr. et al. |
| 2011/0301334 A1 | 12/2011 | Bhakta et al. |
| 2014/0288280 A1 | 9/2014 | Bhakta et al. |
| 2014/0356375 A1 | 12/2014 | Brown et al. |
| 2015/0017094 A1 | 1/2015 | Gill et al. |
| 2015/0017188 A1 | 1/2015 | Eigenbrot, Jr. et al. |
| 2015/0032218 A1 | 1/2015 | Landon |
| 2015/0165063 A1 | 6/2015 | Flygare et al. |
| 2015/0366985 A1 | 12/2015 | Brown et al. |
| 2016/0074529 A1 | 3/2016 | Brown et al. |
| 2016/0130358 A1 | 5/2016 | Bhakta et al. |
| 2016/0199508 A1 | 7/2016 | Sakanaka et al. |
| 2016/0279260 A1 | 9/2016 | Flygare et al. |
| 2016/0310611 A1 | 10/2016 | Flygare et al. |
| 2016/0354485 A1 | 12/2016 | Flygare et al. |
| 2017/0002086 A1 | 1/2017 | Polakis et al. |

FOREIGN PATENT DOCUMENTS

| | | |
|---|---|---|
| DE | 102009051799 A1 | 5/2011 |
| WO | 98/19705 A1 | 5/1998 |
| WO | 2006/130669 A2 | 12/2006 |
| WO | 2009/141240 A1 | 11/2009 |
| WO | 2009/148554 A1 | 12/2009 |
| WO | 2011/156328 A1 | 12/2011 |
| WO | 2013/041606 A1 | 3/2013 |
| WO | 2013/065009 A1 | 5/2013 |
| WO | 2013/177055 A2 | 11/2013 |
| WO | 2014/039092 A1 | 3/2014 |
| WO | 2014/193722 A1 | 12/2014 |

(Continued)

OTHER PUBLICATIONS

Doronina et al., "Novel peptide linkers for highly potent antibody-auristatin conjugate" Bioconjug Chem. 19(10):1960-3 ( 2008).
Ducry et al., "Antibody—Drug Conjugates: Linking Cytotoxic Payloads to Monoclonal Antibodies" Bioconjugate Chem. 21:5-13 ( 2010).
Nolting, Methods in Molecular Biology "Chapter 5 Linker Technologies for AntibodyDrug Conjugates" ED Laurent Ducry, Humana Press edition, vol. 1045:71-100 ( Jan. 1, 2013).

(Continued)

*Primary Examiner* — Thomas S Heard
(74) *Attorney, Agent, or Firm* — Viksnins Harris Padys Malen LLP

(57) ABSTRACT

This invention relates to peptidomimetic linkers and antibody drug conjugates thereof, to pharmaceutical compositions containing them, and to their use in therapy for the prevention or treatment of cancer.

26 Claims, 2 Drawing Sheets

Specification includes a Sequence Listing.

(56) References Cited

FOREIGN PATENT DOCUMENTS

| WO | 2014/194247 A1 | 12/2014 |
|----|----------------|---------|
| WO | 2015/023355 A1 | 2/2015 |
| WO | 2015/061209 A1 | 4/2015 |
| WO | 2015/095124 A1 | 6/2015 |
| WO | 2015/095212 A1 | 6/2015 |
| WO | 2015/095223 A2 | 6/2015 |
| WO | 2016/040856 A2 | 3/2016 |
| WO | 2016/090038 A1 | 6/2016 |
| WO | 2016/090040 A1 | 6/2016 |
| WO | 2016/090050 A1 | 6/2016 |
| WO | 2016/205176 A1 | 12/2016 |

OTHER PUBLICATIONS

PCT ISR and Written Opinion for PCT/US2014/070660.
Pozzo et al., "Conjugates of a Novel 7-Substituted Campthothecin with RGD-Peptides as $\alpha v \beta 3$ Integrin Ligands: An Approach to Tumor-Targeted Therapy" Bioconjugate Chem. 21(11):195667 (Nov. 17, 2010).
Tercel et al., "Unsymmetrical DNA cross-linking agents: Combination of the CBI and PBD Pharmacophores" J. Med. Chem. 46(11):2132-2151 (Jan. 2003).

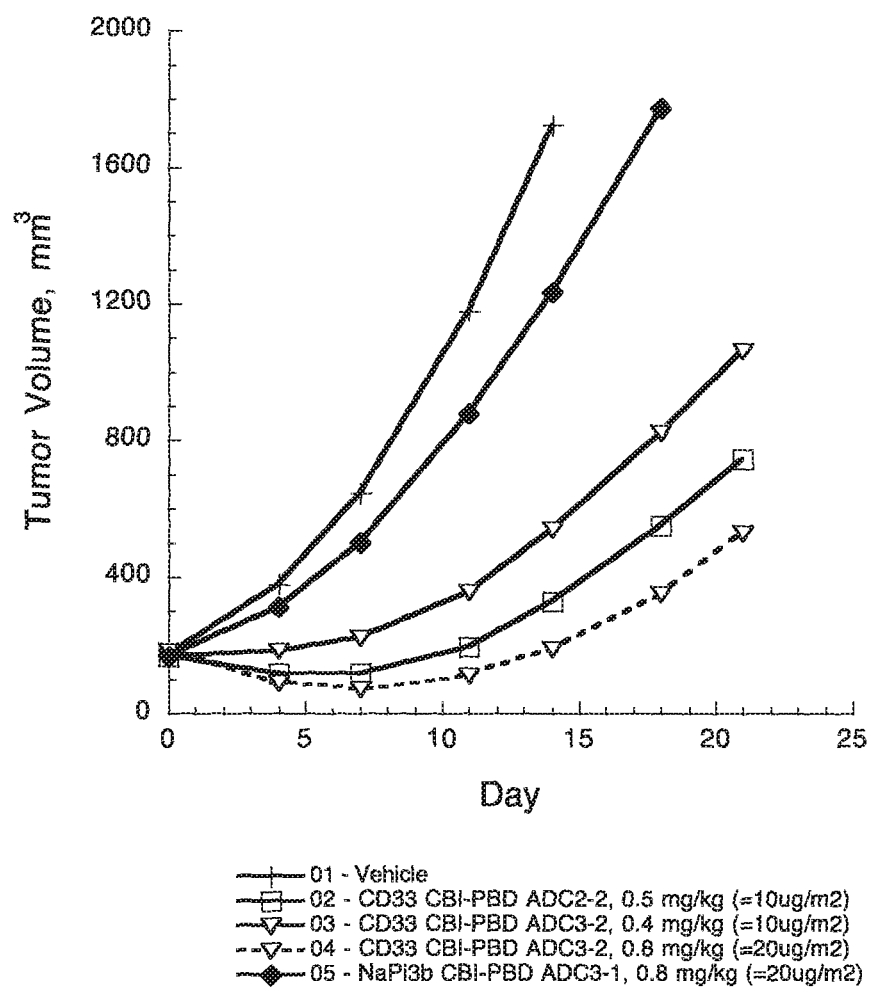
Figure 1 (HL-60)

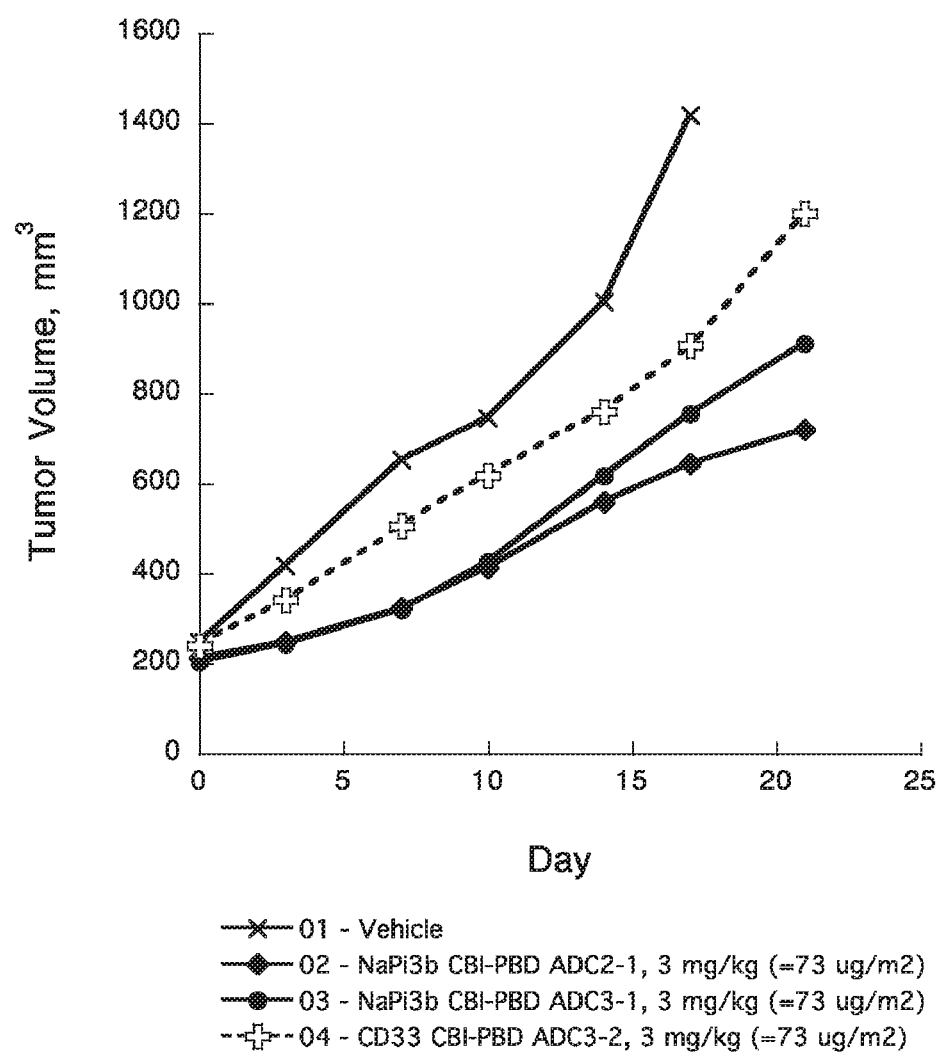
Figure 2 (OVCAR3X2.1)

PEPTIDOMIMETIC COMPOUNDS AND ANTIBODY-DRUG CONJUGATES THEREOF

CROSS REFERENCE TO RELATED APPLICATIONS

This application is a continuation of and claims priority to PCT patent application no. PCT/US2014/070660, filed 16 Dec. 2014, and also claims priority to U.S. provisional application No. 61/916,661 filed on 16 Dec. 2013, and U.S. provisional application No. 61/916,691 filed on 16 Dec. 2013, all of which applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jun. 13, 2016, is named P05760_US_2_Sequence_Listing.txt and is 35,111 bytes in size.

FIELD OF INVENTION

This invention relates to novel peptidomimetic compounds which are useful as linkers of antibody-drug conjugates (ADC). This invention also relates to ADCs containing peptidomimetic linkers. This invention also relates to methods of treating diseases in humans.

BACKGROUND OF THE INVENTION

The use of monoclonal antibodies (mABs) to deliver anticancer drugs directly to tumor cells has attracted a great deal of focus in recent years. Two new antibody-drug conjugates have been approved by the FDA for the treatment of cancer. Adcetris® (brentuximab vedotin) is a CD30-directed antibody-drug conjugate (ADC) indicated for the treatment of relapsed or refractory Hodgkin lymphoma and systemic anaplastic large cell lymphoma (ALCL). Kadcyla® (ado-trastuzumab emtansine), is a new therapy approved for patients with HER2-positive, late-stage (metastatic) breast cancer. To obtain a therapeutic both potent anti-tumor activity and acceptable therapeutic index in an ADC, several aspects of design may be optimized. Particularly, it is well known that the chemical structure of the linker can have significant impact on both the efficacy and the safety of ADC (Ducry & Stump, Bioconjugate Chem, 2010, 21, 5-13). Choosing the right linker influences proper drug delivery to the intended cellular compartment of cancer cells. Linkers can be generally divided into two categories: cleavable (such as peptide, hydrzone, or disulfide) or non-cleavable (such as thioether). Peptide linkers, such as Valine-Citrulline (Val-Cit), that can be hydrolyzed by lysosomal enzymes (such as Cathepsin B) have been used to connect the drug with the antibody (U.S. Pat. No. 6,214,345). They have been particularly useful, due in part to their relative stability in systemic circulation and the ability to efficiently release the drug in tumor. ADCs containing the Val-Cit linker have been shown to be relatively stable in vivo (t1/2 for drug release ~7 days (Doronina et al (2008), Bioconjugate Chem., 19, 1960-1963). However, the chemical space represented by natural peptides is limited; therefore, it is desirable to have a variety of non-peptide linkers which act like peptides and can be effectively cleaved by lysosomal proteases. The greater diversity of non-peptide structures may yield novel, beneficial properties that are not afforded by the peptide linkers. Provided herein are different types of non-peptide linkers for ADC that can be cleaved by lysosomal enzymes.

SUMMARY OF THE INVENTION

This invention relates to antibody-drug conjugates represented by Formula (I)

Ab is an antibody;
L is a peptidomimetic linker represented by the following formula

wherein
Str is a stretcher unit covalently attached to Ab;
Sp is a bond or spacer unit covalently attached to a drug moiety;
PM is a non-peptide chemical moiety selected from the group consisting of:

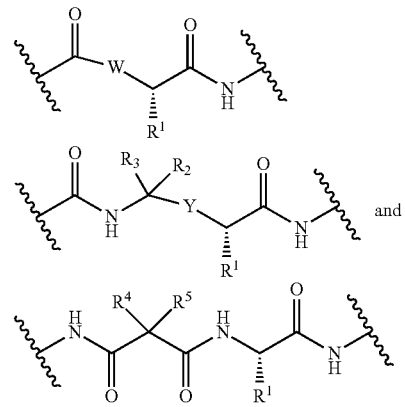

W is —NH-heterocycloalkyl- or heterocycloalkyl;
Y is heteroaryl, aryl, —C(O)C$_1$-C$_6$alkylene, C$_1$-C$_6$alkylene-NH$_2$, C$_1$-C$_6$alkylene-NH—CH$_3$, C$_1$-C$_6$alkylene-N—(CH$_3$)$_2$, C$_1$-C$_6$alkenyl or C$_1$-C$_6$alkylenyl;
each R$^1$ is independently C$_1$-C$_{10}$alkyl, C$_1$-C$_{10}$alkenyl, (C$_1$-C$_{10}$alkyl)NHC(NH)NH$_2$ or (C$_1$-C$_{10}$alkyl)NHC(O)NH$_2$;
R$^3$ and R$^2$ are each independently H, C$_1$-C$_{10}$alkyl, C$_1$-C$_{10}$alkenyl, arylalkyl or heteroarylalkyl, or R$^3$ and R$^2$ together may form a C$_3$-C$_7$cycloalkyl;
R$^4$ and R$^5$ are each independently C$_1$-C$_{10}$alkyl, C$_1$-C$_{10}$alkenyl, arylalkyl, heteroarylalkyl, (C$_1$-C$_{10}$alkyl)OCH$_2$—, or R$^4$ and R$^5$ may form a C$_3$-C$_7$cycloalkyl ring;
p is an integer from 1 to 8;
D is a drug moiety.

This invention also relates to pharmaceutical compositions of antibody-drug conjugates of Formula (I).

This invention also relates to a method of treating cancer, use of antibody-drug conjugates of Formula (I) in therapy, and use of compounds of Formula (I) in manufacturing a medicament for treating cancer.

This invention also relates to method of preparing antibody-drug conjugates of Formula (I).

BRIEF DESCRIPTION OF THE FIGURES

FIG. 1 shows efficacy comparison of CD33 ADCs (CD33 CBI-PBD ADC3-2 and ADC2-2) in SCID mice with HL-60 human acute myeloid leukemia tumors.

FIG. 2 shows efficacy comparison of NaPi2b ADCs (NaPi2b CBI-PBD ADC2-1 and ADC3-1) in SCID-beige mice with OVCAR3X2.1 human ovarian tumors.

DETAILED DESCRIPTION OF THE INVENTION

Provided herein are different types of non-peptide linkers for ADC that are cleavable by lysosomal enzymes. For example, the amide bond in the middle of a dipeptide (e.g. Val-Cit) was replaced with an amide mimic; and/or entire amino acid (e.g., valine amino acid in Val-Cit dipeptide) was replaced with a non-amino acid moiety (e.g., cycloalkyl dicarbonyl structures (for example, ring size=4 or 5)).

This invention relates to antibody-drug conjugates of Formula (I).

This invention also relates to antibody-drug conjugates of Formula (I), wherein Y is heteroaryl; $R^4$ and $R^5$ together form a cyclobutyl ring.

This invention also relates to antibody-drug conjugates of Formula (I), wherein Y is a moiety selected from the group consisting of

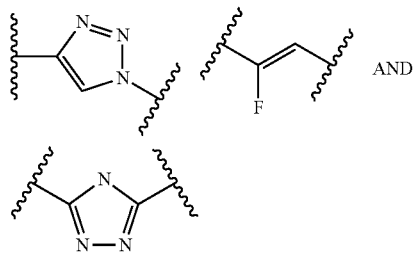

AND

This invention also relates to antibody-drug conjugates of Formula (I), wherein Str is a chemical moiety represented by the following formula:

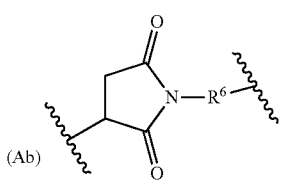

wherein $R^6$ is selected from the group consisting of $C_1$-$C_{10}$alkylene, $C_1$-$C_{10}$alkenyl, $C_3$-$C_8$cycloalkyl, ($C_1$-$C_8$alkylene)O—, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$cycloalkyl, $C_4$-$C_7$heterocycloalkyl, aryl, arylalkyl, heteroarylalkyl and heteroaryl each $R^a$ is independently H or $C_1$-$C_6$alkyl; Sp is —Ar—$R^b$—, wherein Ar is aryl or heteroaryl, $R^b$ is ($C_1$-$C_{10}$alkylene)O—.

This invention also relates to antibody-drug conjugates of Formula (I), wherein Str has the formula:

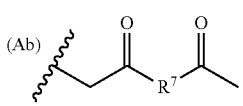

wherein $R^7$ is selected from $C_1$-$C_{10}$alkylene, $C_1$-$C_{10}$alkenyl, ($C_1$-$C_{10}$alkylene)O—, N($R^c$)—($C_2$-$C_6$ alkylene)-N($R_c$) and N($R^c$)—($C_2$-$C_6$alkylene); where each $R^c$ is independently H or $C_1$-$C_6$ alkyl; Sp is —Ar—$R^b$—, wherein Ar is aryl or heteroaryl, $R^b$ is ($C_1$-$C_{10}$alkylene)O— or Sp—$C_1$-$C_6$alkylene-C(O)NH—.

This invention also relates to antibody-drug conjugates of Formula (I), wherein Ab is an antibody; L is non-peptide chemical moiety represented by the following formula

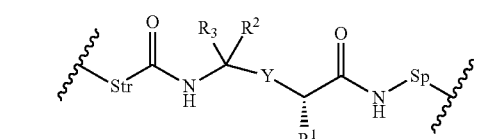

$R^1$ is $C_1$-$C_6$alkyl, $C_1$-$C_6$alkenyl, ($C_1$-$C_6$alkyl)NHC(NH)NH$_2$ or ($C_1$-$C_6$alkyl)NHC(O)NH$_2$;

$R^3$ and $R^2$ are each independently H or $C_1$-$C_{10}$alkyl.

This invention also relates to antibody-drug conjugates of Formula (I), wherein Ab is an antibody; L is non-peptide chemical moiety represented by the following formula

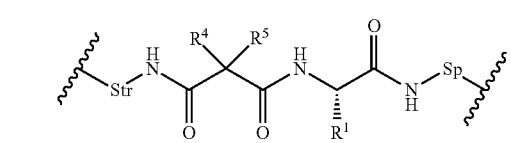

$R^1$ is $C_1$-$C_6$alkyl, ($C_1$-$C_6$alkyl)NHC(NH)NH$_2$ or ($C_1$-$C_6$alkyl)NHC(O)NH$_2$;

$R^4$ and $R^5$ together form a $C_3$-$C_7$cycloalkyl ring.

This invention also relates to antibody-drug conjugates of Formula (I), wherein Ab is an antibody; L is non-peptide chemical moiety represented by the following formula

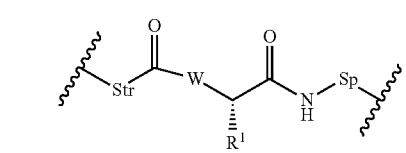

$R^1$ is $C_1$-$C_6$alkyl, ($C_1$-$C_6$alkyl)NHC(NH)NH$_2$ or ($C_1$-$C_6$alkyl)NHC(O)NH$_2$.

This invention also relates to antibody-drug conjugates of Formula (I), which is represented by the following formula

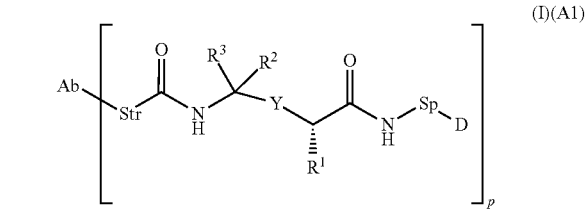

(I)(A1)

wherein

Str is a chemical moiety represented by the following formula:

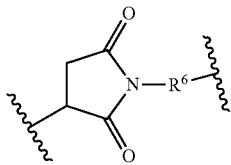

(Ab)

wherein $R^6$ is selected from the group consisting of $C_1$-$C_{10}$alkylene, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$cycloalkyl, $C_4$-$C_7$heterocycloalkyl, aryl, arylalkyl, heteroarylalkyl and heteroaryl, each $R^a$ is independently H or $C_1$-$C_6$alkyl;

p is 1, 2, 3 or 4.

This invention also relates to antibody-drug conjugates of Formula (I) represented by the following formula:

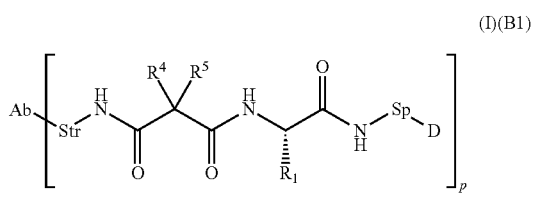

(I)(B1)

wherein

Str is a chemical moiety represented by the following formula:

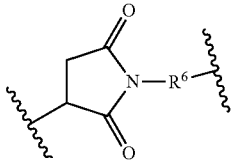

(Ab)

wherein $R^6$ is selected from the group consisting of $C_1$-$C_{10}$alkylene, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$cycloalkyl, $C_4$-$C_7$heterocycloalkyl, aryl, arylalkyl, heteroarylalkyl and heteroaryl, each $R^a$ is independently H or $C_1$-$C_6$alkyl;

p is 1, 2, 3 or 4.

This invention also relates to antibody-drug conjugates of Formula (I) represented by the following formula:

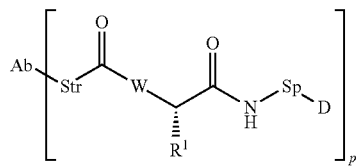

(I)(C1)

wherein

Str is a chemical moiety represented by the following formula:

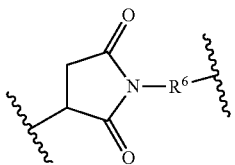

(Ab)

wherein $R^6$ is selected from the group consisting of $C_1$-$C_{10}$alkylene, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$cycloalkyl, $C_4$-$C_7$heterocycloalkyl, aryl, arylalkyl, heteroarylalkyl and heteroaryl, each $R^a$ is independently H or $C_1$-$C_6$alkyl;

p is 1, 2, 3 or 4.

This invention also relates to any one of the above antibody-conjugates, wherein Y is heteroaryl, aryl or alkenyl; $R^6$ is $C_1$-$C_{10}$alkylene.

This invention also relates to any one of the above antibody-conjugates (I) and (I)(A1), wherein Y is

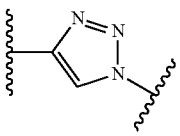 [SMILES: *c1cn(*)nn1]

This invention also relates to any one of the above antibody-conjugates (I) and (I)(A1), wherein Y is

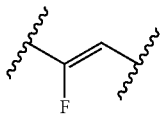 [SMILES: */C=C(/*)F]

This invention also relates to any one of the above antibody-conjugates (I) and (I)(A1), wherein Y is

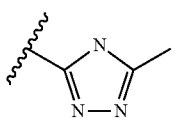 [SMILES: *c1nnc(C)[nH]1]

This invention also relates to any one of the above antibody-conjugates (I)(A1), (I)(B1), and (I)(C1), wherein Str is a chemical moiety represented by the following formula:

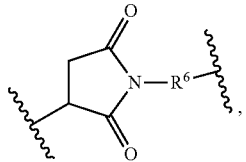

$R^6$ is $C_1$-$C_6$alkylene which may be substituted with 1-3 groups selected from aryl and heteroaryl;
Sp is —$C_1$-$C_6$alkylene-C(O)NH— or —Ar—$R^b$—, where Ar is aryl, $R^b$ is ($C_1$-$C_3$alkylene)O—.

This invention also relates to any one of the above antibody-conjugates (I)(A1), (I)(B1), and (I)(C1), wherein Str is a chemical moiety represented by the following formula:

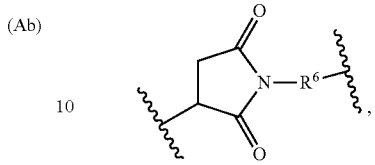

$R^6$ is $C_1$-$C_6$alkylene which may be substituted with 1-3 groups selected from aryl and heteroaryl;
Sp is —$C_1$-$C_6$alkylene-C(O)NH—.

This invention also relates to any one of the above antibody-conjugates (I) and (I)(A1), represented by the following formula:

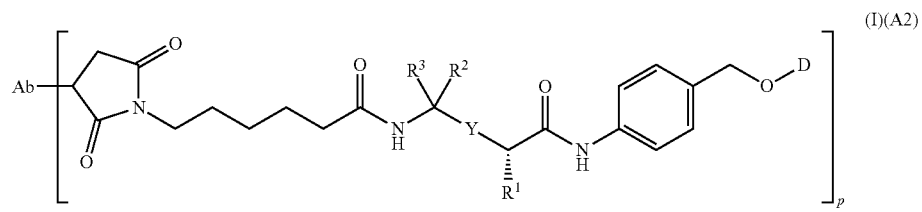

wherein
$R^1$ is $C_1$-$C_6$alkyl-NH$_2$, ($C_1$-$C_6$alkyl)NHC(NH)NH$_2$ or ($C_1$-$C_6$alkyl)NHC(O)NH$_2$
p is 1, 2, 3 or 4.

This invention also relates to any one of the above antibody-conjugates (I) and (I)(B1), represented by the following formula:

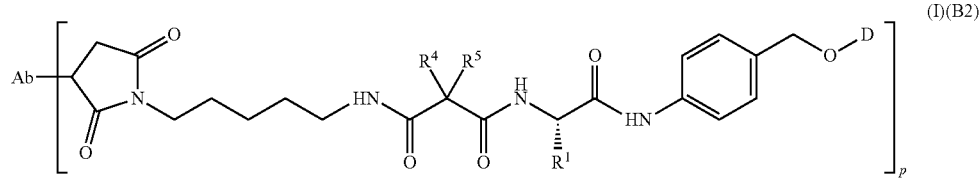

wherein
p is 1, 2, 3 or 4;
$R^1$ is $C_1$-$C_6$alkyl-NH$_2$, ($C_1$-$C_6$alkyl)NHC(NH)NH$_2$ or ($C_1$-$C_6$alkyl)NHC(O)NH$_2$;
$R^4$ and $R^5$ are each independently $C_1$-$C_6$alkyl, wherein said alkyl are unsubstituted, or $R^4$ and $R^5$ may form a $C_3$-$C_7$cycloalkyl ring.

This invention also relates to any one of the above antibody-conjugates (I) and (I)(C1), represented by the following formula:

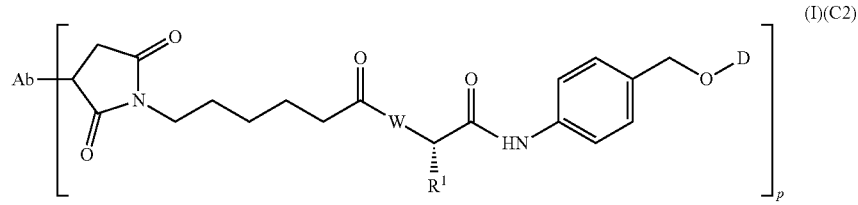

wherein p is 1, 2, 3 or 4;

$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$.

This invention also relates to antibody-conjugates of (I), which is represented by the following formula:

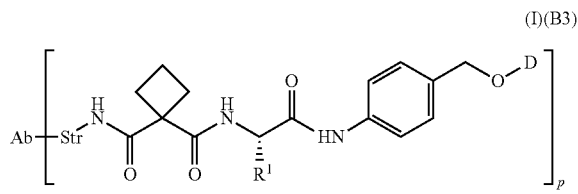

(I)(B3)

wherein p is 1, 2, 3 or 4;

$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$;

This invention also relates to antibody-drug conjugates of (I)(B3), wherein

Str is a chemical moiety represented by the following formula:

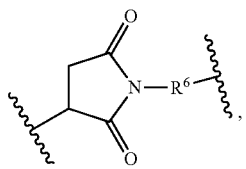

(Ab)

$R^6$ is $C_1$-$C_6$alkylene which may be substituted with 1-3 groups selected from aryl and heteroaryl;

This invention also relates to antibody-drug conjugates of (I)(B3) wherein $R^1$ is $(CH_2)_3$NHC(O)$NH_2$.

This invention also relates to antibody-drug conjugates of (I)(B3) wherein $R^1$ is $(CH_2)_4NH_2$.

This invention also relates to antibody-drug conjugates of (I), (I)(B1), (I)(B2) and (I)(B3), wherein $R^1$ is ($C_1$-$C_6$alkyl)NHC(NH)$NH_2$.

This invention also relates to any one of the above antibody-drug conjugates, wherein D is the dimer drug moiety having the formula:

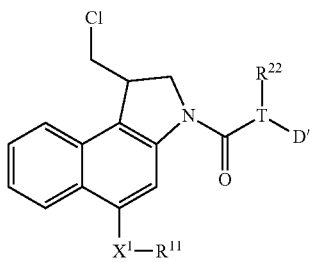

wherein $R^{11}$ is selected from H, $P(O)_3H_2$, $C(O)NR^{aa}R^{bb}$, or a bond to L;

$R^{22}$ is selected from H, $P(O)_3H_2$, $C(O)NR^{aa}R^{bb}$, or a bond to L;

$R^{aa}$ and $R^{bb}$ are independently selected from H and $C_1$-$C_6$alkyl optionally substituted with one or more F, or $R^{aa}$ and $R^{bb}$ form a five or six membered heterocycloalkyl group;

T is a tether group selected from $C_3$-$C_{12}$alkylene, $Y^1$, ($C_1$-$C_6$alkylene)-$Y^1$—($C_1$-$C_6$ alkylene), ($C_1$-$C_6$alkylene)-$Y^1$—($C_1$-$C_6$alkylene)-$Y^1$—($C_1$-$C_6$alkylene), ($C_2$-$C_6$alkenylene)-$Y^1$—($C_2$-$C_6$alkenylene), and ($C_2$-$C_6$alkynylene)-$Y^1$—($C_2$-$C_6$alkynylene);

where $Y^1$ is independently selected from O, S, $NR^{11}$, aryl, and heteroaryl;

where alkylene, alkenylene, aryl, and heteroaryl are independently and optionally substituted with F, OH, O($C_1$-$C_6$alkyl), $NH_2$, $NHCH_3$, $N(CH_3)_2$, NHC(O)($C_1$-$C_6$alkylene)$_m$, $OP(O)_3H_2$, and $C_1$-$C_6$alkyl, where alkyl is optionally substituted with one or more F, m is 0 or 1;

or alkylene, alkenylene, aryl, and heteroaryl are independently and optionally substituted with a bond to L, wherein the bond to L may connect through one of the optional substituents;

D' is a drug moiety selected from:

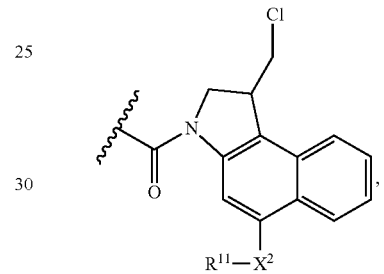

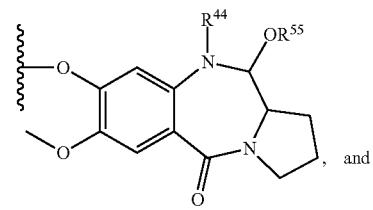
, and

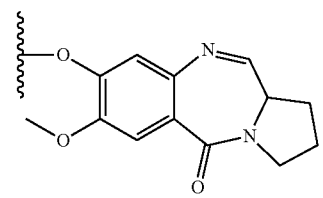

where the wavy line indicates the site of attachment to T;

$X^1$ and $X^2$ are independently selected from O and $NR^{33}$, where $R^{33}$ is selected from H, C(O), and $C_1$-$C_6$alkyl optionally substituted with one or more F, or $X^1$ and $X^2$ are each independently absent;

$R^{44}$ is H, $CO_2R$, C(O), or a bond to L, where R is $C_1$-$C_6$alkyl or benzyl; and $R^{55}$ is H or $C_1$-$C_6$alkyl.

This invention also relates to antibody-drug conjugates of formula (I), which is represented by the following formula:

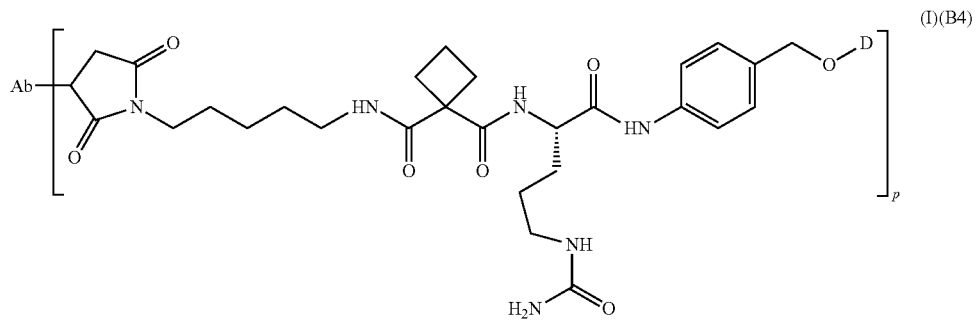

(I)(B4)

wherein,
Ab is an antibody that binds to a target selected from Her2, CLL1, CD33, CD22 and NaPi2b;
P is 1-4;
D is

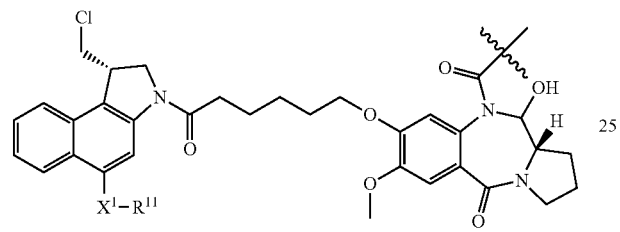

$X^1$ is absent or O;
$R^{11}$ is C(O)N-piperazine(CH$_3$) or P(O)$_3$H$_2$.

This invention also relates to antibody-drug conjugates of formula (I), which is represented by the following formula:

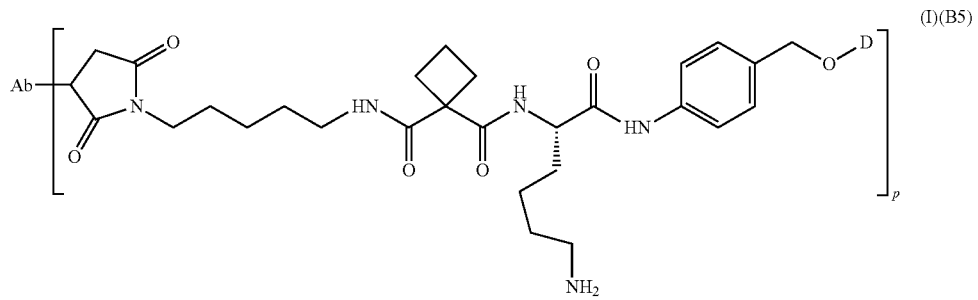

(I)(B5)

wherein,
Ab is an antibody that binds to a target selected from Her2, CLL1, CD33, CD22 and NaPi2b;
P is 1-4;
D is

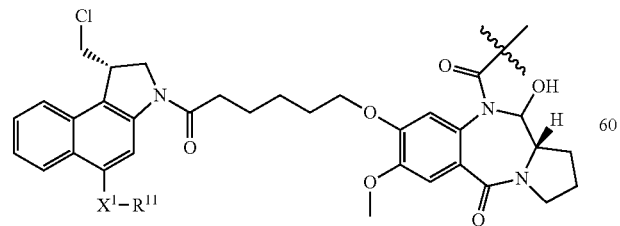

$X^1$ is absent or O;
$R^{11}$ is C(O)N-piperazine(CH$_3$) or P(O)$_3$H$_2$.

This invention also relates to antibody-drug conjugates of formula (I), which is represented by the following formula:

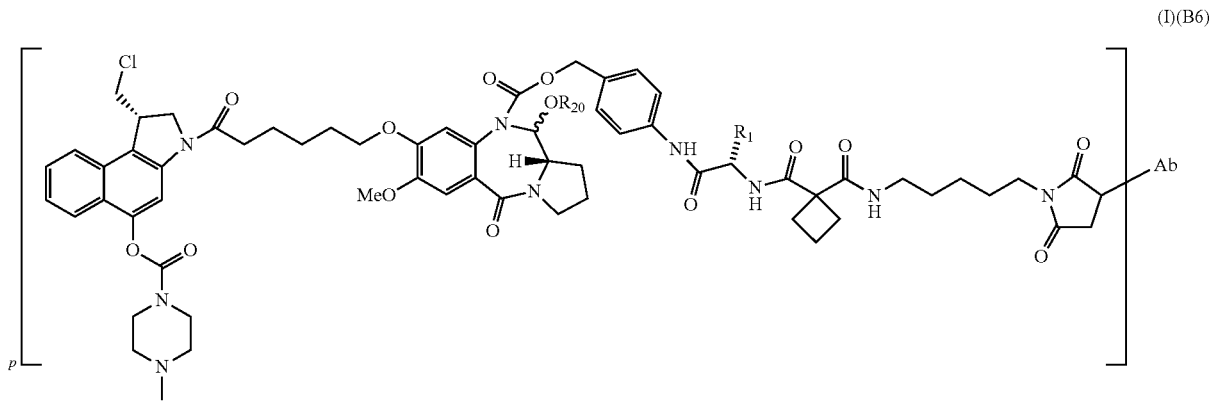

(I)(B6)

wherein,
Ab is an antibody that binds to a target selected from Her2, CLL1, CD33, CD22 and NaPi2b;
P is 1-4; and
$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$;
$R^{20}$ is H or Me;

This invention also relates to antibody-drug conjugates of formula (I)(B6), wherein
$R^{20}$ is H, $R^1$ is $(CH_2)_4NH_2$.

This invention also relates to antibody-drug conjugates of formula (I)(B6), wherein
$R^{20}$ is Me, $R^1$ is $(CH_2)_4NH_2$.

This invention also relates to antibody-drug conjugates of formula (I), which is represented by the following formula:

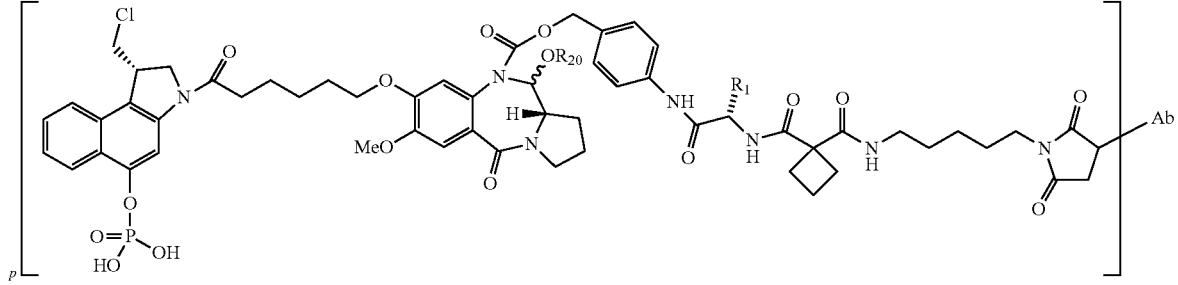

(I)(B7)

wherein,
Ab is an antibody that binds to a target selected from Her2, CLL1, CD33, CD22 and NaPi2b;
P is 1-4;
$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$;
$R^{20}$ is H or Me;

This invention also relates to antibody-drug conjugates of formula (I)(B7), wherein
$R^{20}$ is H, $R^1$ is $(CH_2)_4NH_2$.

This invention also relates to antibody-drug conjugates of formula (I)(B7), wherein
$R^{20}$ is Me, $R^1$ is $(CH_2)_4NH_2$.

This invention also relates to antibody-drug conjugates of formula (I), which is represented by the following formula:

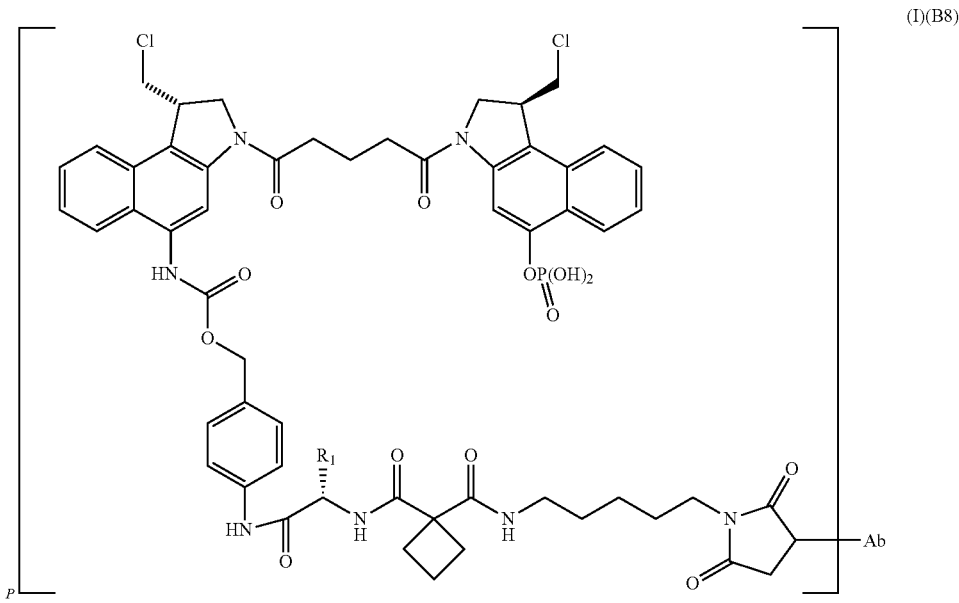

wherein,
Ab is an antibody that binds to a target selected from Her2, CLL1, CD33, CD22 and NaPi2b;
P is 1-4; and
$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$;

This invention also relates to antibody-drug conjugates of formula (I)(B8), wherein
$R^1$ is $(CH_2)_4NH_2$.

This invention also relates to antibody-drug conjugates of formula (I), which is represented by the following formula:

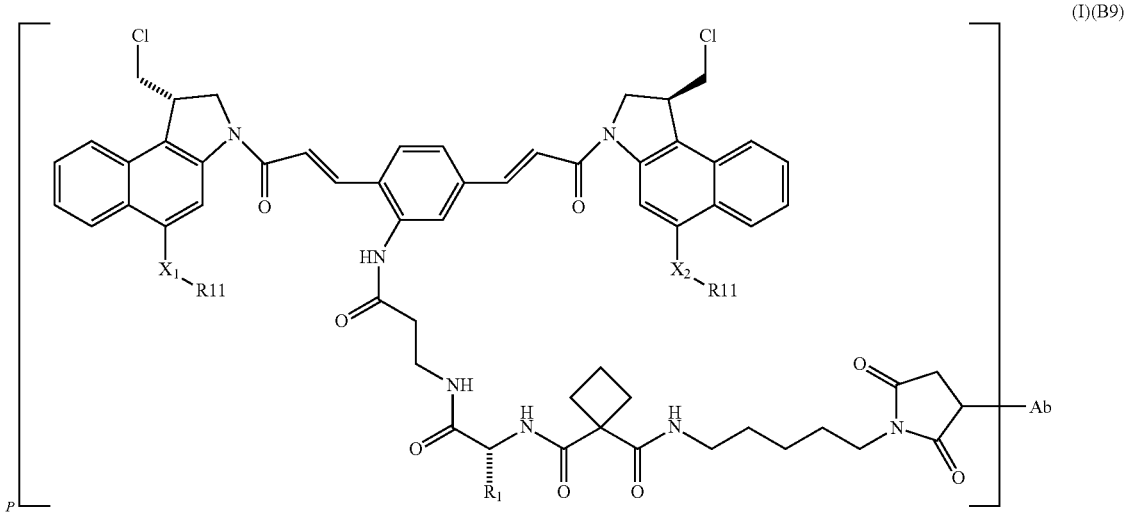

wherein,
Ab is an antibody that binds to a target selected from Her2, CLL1, CD33, CD22 and NaPi2b;
P is 1-4;
$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$;
$X^1$ and $X^2$ are each independently absent or O;

Each $R^{11}$ is independently C(O)N-piperazine($CH_3$) or $P(O)_3H_2$.

This invention also relates to antibody-drug conjugates of formula (I)(B9), wherein
$X^1$ is absent, $R^{11}$ is $P(O)_3H_2$, $R^1$ is $(CH_2)_4NH_2$.

This invention also relates to any of the above antibody-drug conjugates of formula (I)(B6), (I)(B7), (I)(B8) and (I)(B9), wherein the Ab is an antibody that binds to Her2.

This invention also relates to any of the above antibody-drug conjugates of formula (I)(B6), (I)(B7), (I)(B8) and (I)(B9), wherein the Ab is an antibody that binds to CLL1.

This invention also relates to any of the above antibody-drug conjugates of formula (I)(B6), (I)(B7), (I)(B8) and (I)(B9), wherein the Ab is an antibody that binds to CD33.

This invention also relates to any of the above antibody-drug conjugates of formula (I)(B6), (I)(B7), (I)(B8) and (I)(B9), wherein the Ab is an antibody that binds to CD22.

This invention also relates to any of the above antibody-drug conjugates of formula (I)(B6), (I)(B7), (I)(B8) and (I)(B9), wherein the Ab is an antibody that binds to NaPi2b.

This invention also relates to any of the above antibody-drug conjugates, wherein
where $Y^1$ is phenyl which is optionally substituted with F, OH, O($C_1$-$C_6$alkyl), $NH_2$, $NHCH_3$, $N(CH_3)_2$, NHC(O)($C_1$-$C_6$alkylene)$_m$, $OP(O)_3H_2$, and $C_1$-$C_6$alkyl, where alkyl is optionally substituted with one or more F, m is 0 or 1;

This invention also relates to non-peptide compounds of Formula (I)(B)(LD1):

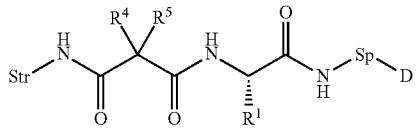

(I)(B)(LD1)

wherein
Str is a stretcher unit which can be covalently attached to an antibody;
Sp is a bond or a spacer unit covalently attached to a drug moiety;
$R^1$ is $C_1$-$C_{10}$alkyl, ($C_1$-$C_{10}$alkyl)NHC(NH)$NH_2$ or ($C_1$-$C_{10}$alkyl)NHC(O)$NH_2$;
$R^4$ and $R^5$ are each independently $C_1$-$C_{10}$alkyl, arylalkyl, heteroarylalkyl, ($C_1$-$C_{10}$alkyl)$OCH_2$—, or
$R^4$ and $R^5$ may form a $C_3$-$C_7$cycloalkyl ring;
D is a drug moiety.

This invention also relates to non-peptide compounds represented by the following formula

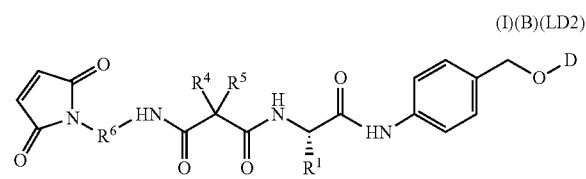

(I)(B)(LD2)

wherein $R_6$ is $C_1$-$C_{10}$alkylene; $R^4$ and $R^5$ together form a $C_3$-$C_7$cycloalkyl ring.

This invention also relates to non-peptide compounds represented by the following formula

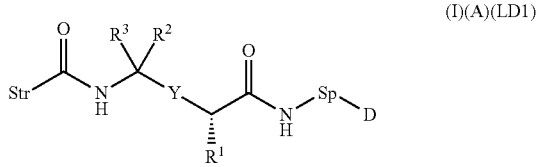

(I)(B)(LD3)

This invention also relates to non-peptide compounds of Formula:

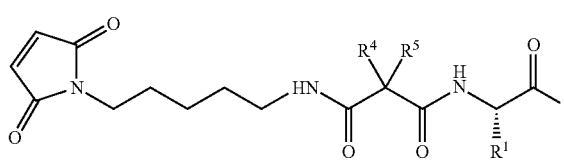

(I)(A)(LD1)

wherein
Str is a stretcher unit which can be covalently attached to an antibody;
Sp is an optional spacer unit covalently attached to a drug moiety;
Y is heteroaryl, aryl, —C(O)$C_1$-$C_6$alkylene, $C_1$-$C_6$alkylene-$NH_2$, $C_1$-$C_6$alkylene-NH—$CH_3$, $C_1$-$C_6$alkylene-N—$(CH_3)_2$, $C_1$-$C_6$alkenyl or $C_1$-$C_6$alkylenyl;
$R^1$ is $C_1$-$C_{10}$alkyl, ($C_1$-$C_{10}$alkyl)NHC(NH)$NH_2$ or ($C_1$-$C_{10}$alkyl)NHC(O)$NH_2$;
$R^3$ and $R^2$ are each independently H, $C_1$-$C_{10}$alkyl, arylalkyl or heteroarylalkyl, or $R^3$ and $R^2$ together may form a $C_3$-$C_7$cycloalkyl;
D is a drug moiety.

This invention also relates to non-peptide compounds represented by the following formula:

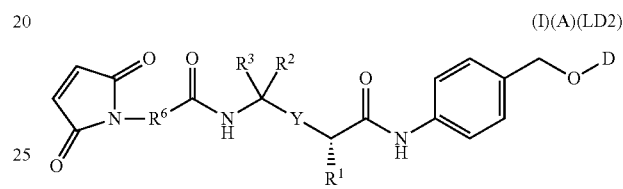

(I)(A)(LD2)

wherein
$R_6$ is $C_1$-$C_{10}$alkylene.

This invention also relates to non-peptide compounds represented by the following formula:

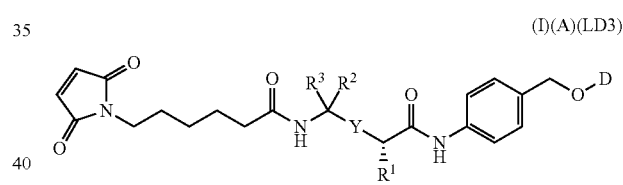

(I)(A)(LD3)

This invention also relates to any of the above non-peptide compounds, wherein Str has the following formula:

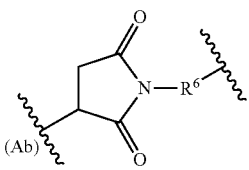

(I)(B)(LD3)

wherein $R^6$ is selected from the group consisting of $C_1$-$C_{10}$alkylene, $C_3$-$C_8$cycloalkyl, O—($C_1$-$C_8$alkylene), and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$cycloalkyl, $C_4$-$C_7$heterocycloalkyl aryl, arylalkyl, heteroarylalkyl and heteroaryl; each $R^a$ is independently H or $C_1$-$C_6$alkyl; Sp is —Ar—$R^b$—, wherein Ar is aryl or heteroaryl, $R^b$ is ($C_1$-$C_{10}$alkylene)O—.

This invention also relates to non-peptide compounds, wherein $R^6$ is $C_1$-$C_{10}$alkylene, Sp is —Ar—$R^b$—, wherein Ar is aryl $R^b$ is ($C_1$-$C_6$alkylene)O—.

This invention also relates to non-peptide compounds, where $R_6$ is —$(CH_2)_q$ is 1-10;

This invention also relates to non-peptide compounds, wherein Str has the formula:

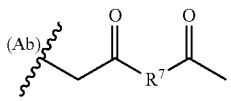

wherein $R^7$ is selected from $C_1$-$C_{10}$alkylene, $C_1$-$C_{10}$alkylene-O, N($R^c$)—($C_2$-$C_6$ alkylene)-N($R^c$) and N($R^c$)—($C_2$-$C_6$alkylene); where each $R^c$ is independently H or $C_1$-$C_6$ alkyl; Sp is —Ar—$R^b$—, wherein Ar is aryl or heteroaryl, $R^b$ is ($C_1$-$C_{10}$ alkylene)O—.

This invention also relates to non-peptide compounds, wherein $R^6$ is $C_1$-$C_{10}$ alkylene, Sp is —Ar—$R^b$—, wherein Ar is aryl $R^b$ is ($C_1$-$C_6$ alkylene)O—.

This invention also relates to any one of the above non-peptide compounds of Formula (IV), (IV)(A), (IV)(B), (V), (V)(A) and (V)(B), wherein D is the dimer drug moiety having the formula:

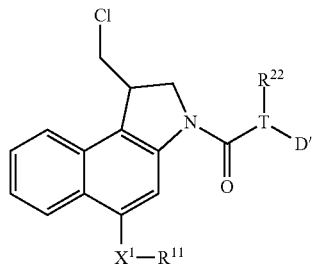

$R^{11}$ is selected from H, $P(O)_3H_2$, $C(O)NR^{aa}R^{bb}$, or a bond to L;
$R^{22}$ is selected from H, $P(O)_3H_2$, $C(O)NR^{aa}R^{bb}$, or a bond to L;
$R^{aa}$ and $R^{bb}$ are independently selected from H and $C_1$-$C_6$alkyl optionally substituted with one or more F, or $R^{aa}$ and $R^{bb}$ form a five or six membered heterocycloalkyl group;
T is a tether group selected from $C_3$-$C_{12}$alkylene, $Y^1$, ($C_1$-$C_6$alkylene)-$Y^1$—($C_1$-$C_6$ alkylene), ($C_1$-$C_6$alkylene)-$Y^1$—($C_1$-$C_6$alkylene)-$Y^1$—($C_1$-$C_6$alkylene), ($C_2$-$C_6$alkenylene)-$Y^1$—($C_2$-$C_6$alkenylene), and ($C_2$-$C_6$alkynylene)-$Y^1$—($C_2$-$C_6$alkynylene);
where $Y^1$ is independently selected from O, S, $NR^{11}$, aryl, and heteroaryl;
where alkylene, alkenylene, aryl, and heteroaryl are independently and optionally substituted with F, OH, O($C_1$-$C_6$alkyl), $NH_2$, $NHCH_3$, $N(CH_3)_2$, $NHC(O)(C_1$-$C_6$alkylene$)_m$, $OP(O)_3H_2$, and $C_1$-$C_6$alkyl, where alkyl is optionally substituted with one or more F, m is 0 or 1;

or alkylene, alkenylene, aryl, and heteroaryl are independently and optionally substituted with a bond to L, wherein the bond to L may connect through one of the optional substituents;

D' is a drug moiety selected from:

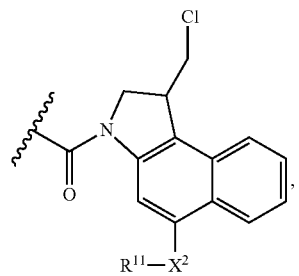

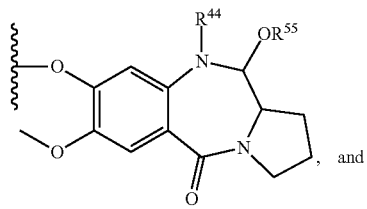

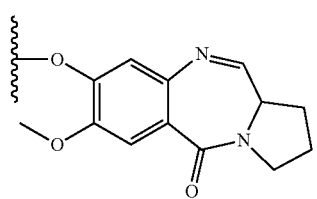

where the wavy line indicates the site of attachment to T;
$X^1$ and $X^2$ are independently selected from O and $NR^{33}$, where $R^{33}$ is selected from H, C(O), and $C_1$-$C_6$alkyl optionally substituted with one or more F, or $X^1$ and $X^2$ are each independently absent;
$R^{44}$ is H, $CO_2R$, C(O), or a bond to L, where R is $C_1$-$C_6$alkyl or benzyl; and
$R^{55}$ is H or $C_1$-$C_6$alkyl.

This invention also relates to any of the above linker drug compounds, wherein where $Y^1$ is phenyl which is optionally substituted with F, OH, O($C_1$-$C_6$alkyl), $NH_2$, $NHCH_3$, $N(CH_3)_2$, $NHC(O)(C_1$-$C_6$alkylene$)_m$, $OP(O)_3H_2$, and $C_1$-$C_6$alkyl, where alkyl is optionally substituted with one or more F, m is 0 or 1;

This invention also relates to compounds of the following formula:

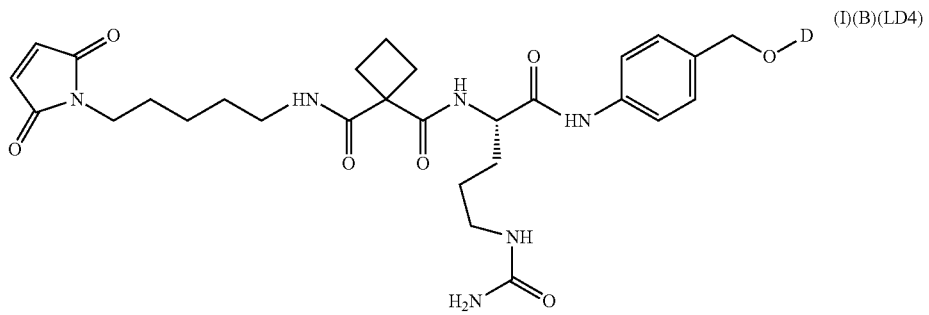
wherein,
D is a drug moiety of the following formula
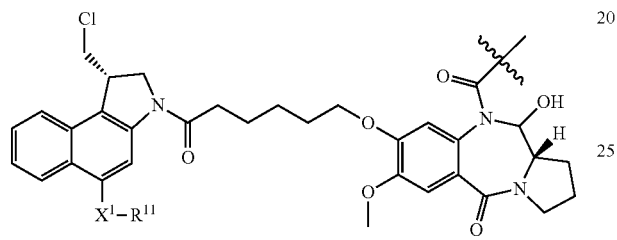
This invention also relates to compounds of the following formula:
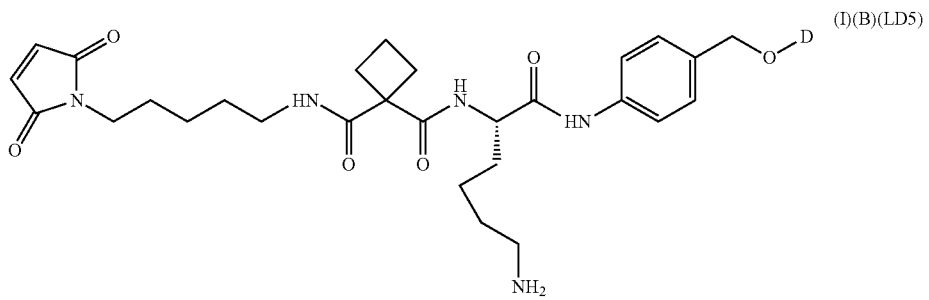
wherein,
D is a drug moiety of the following formula
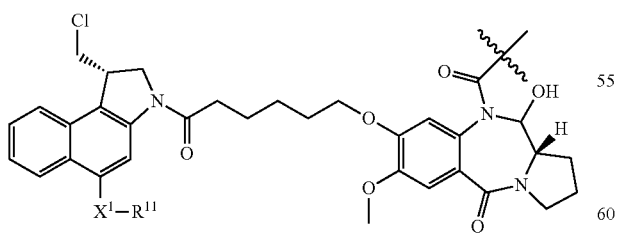
$X^1$ is absent or O;
$R^{11}$ is C(O)N-piperazine(CH$_3$) or P(O)$_3$H$_2$.
This invention also relates to compounds of the following formula:

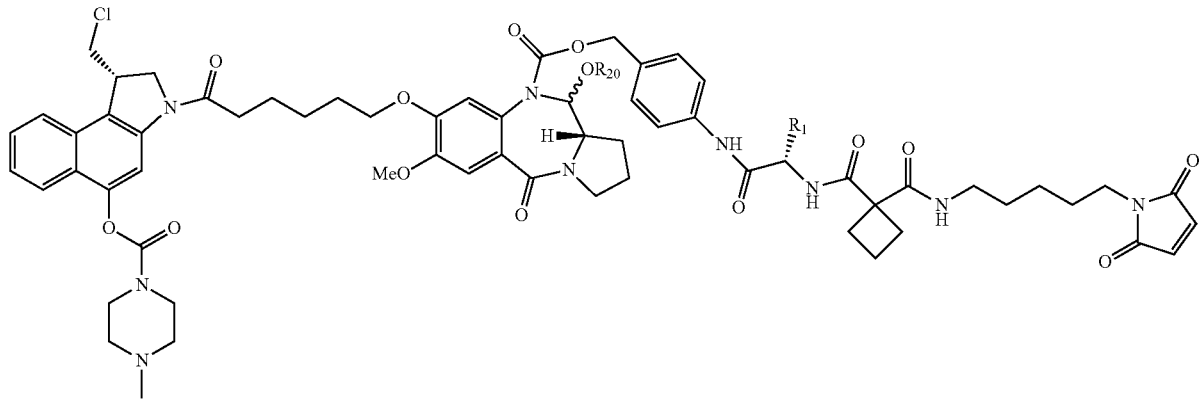

(I)(B)(LD6)

wherein,
$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$;
$R^{20}$ is H or Me;

This invention also relates to compounds of formula (I)(B((LD6), wherein
$R^{20}$ is H, $R^1$ is $(CH_2)_4NH_2$.

This invention also relates to compounds of formula (I)(B((LD6), wherein
$R^{20}$ is Me, $R^1$ is $(CH_2)_4NH_2$.

This invention also relates to compounds of the following formula:

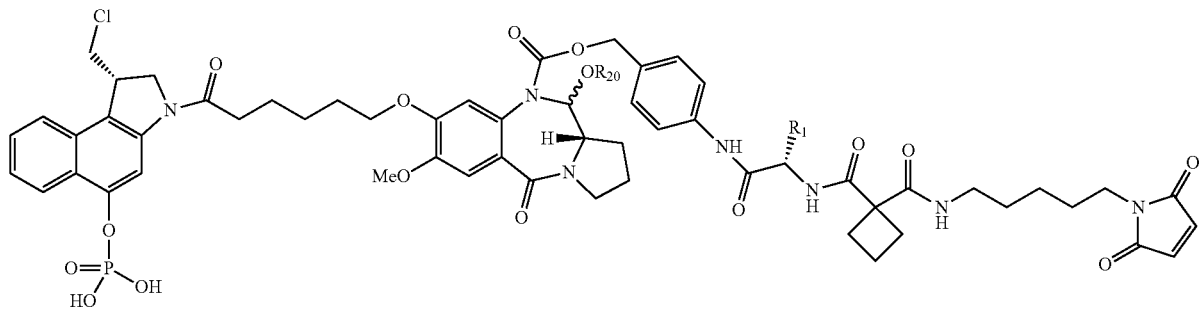

(I)(B)(LD7)

wherein,
$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$;
$R^{20}$ is H or Me;

This invention also relates to compounds of formula (I)(B((LD7), wherein
$R^{20}$ is H, $R^1$ is $(CH_2)_4NH_2$.

This invention also relates to compounds of formula (I)(B((LD7), wherein
$R^{20}$ is Me, $R^1$ is $(CH_2)_4NH_2$.

This invention also relates to compounds of the following formula:

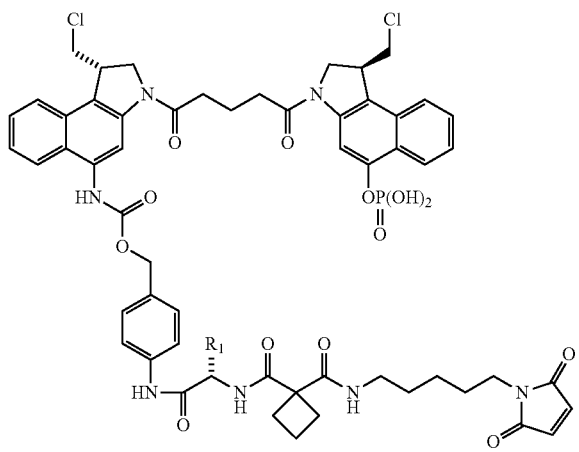

(I)(B)(LD8)

wherein,
$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$;

This invention also relates to compounds of formula (I)(B)(LD8), wherein
$R^1$ is $(CH_2)_4NH_2$.

This invention also relates to compounds of the following formula:

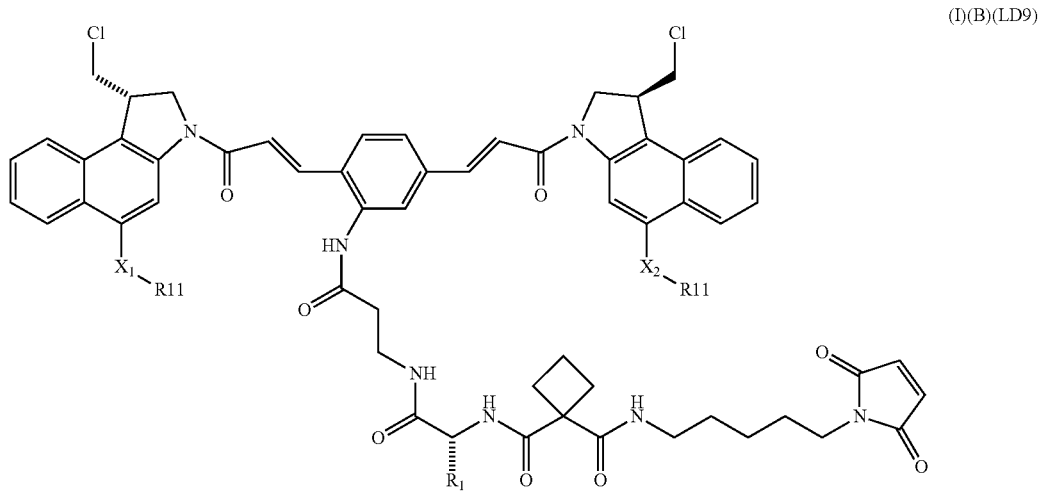

(I)(B)(LD9)

wherein,
$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$;
$X^1$ and $X^2$ are each independently absent or O;
each $R^{11}$ is independently C(O)N-piperazine($CH_3$) or $P(O)_3H_2$.

This invention also relates to any one of the above conjugates, wherein D is an antibiotic moiety selected from the group consisting of clindamycin, novobiocin, retapamulin, daptomycin, GSK-2140944, CG-400549, sitafloxacin, teicoplanin, triclosan, napthyridone, radezolid, doxorubicin, ampicillin, vancomycin, imipenem, doripenem, gemcitabine, dalbavancin, and azithromycin. The mechanisms of bactericidal and bacteriostatic action of such antibiotics include, but are not limited to: (i) inhibition of cell wall, peptidoglycan elongation (vancomycin, teicoplanin, dalbavancin); (ii) inhibition of cell wall, penicillin-binding protein crosslinks (imipenem, doripenem, ampicillin); (iii) cell membrane depolarization (daptomycin); (iv) disruption of DNA replication (gemcitabine); (v) DNA binding (doxorubicin); (vi) enoyl ACP-reductase FABI (CG-400549, triclosan, napthyridone); (vii) inhibition of ribosomal protein synthesis, ribosome 30S (clindamycin, retapamulin, radezolid); and (viii) topoisomerase (topoIIA) inhibitors (novobiocin, sitafloxacin, GSK-2140944). Structurally, most antibiotics can be grouped into: (i) aminoglycosides; (ii) beta-lactams; (iii) macrolides/cyclic peptides; (iv) tetracyclines; (v) fluoroquinolines/fluoroquinolones; (vi) and oxazolidinones. See: Shaw, K. and Barbachyn, M. (2011) Ann. N.Y. Acad. Sci. 1241:48-70; Sutcliffe, J. (2011) Ann. N.Y. Acad. Sci. 1241:122-152.

This invention also relates to any one of the above antibody-drug conjugates or antibody-antibiotic conjugates described herein, wherein p is 1.

This invention also relates to any one of the above antibody-drug conjugates or antibody-antibiotic conjugates described herein, wherein p is 2.

This invention also relates to any one of the above antibody-drug conjugates or antibody-antibiotic conjugates described herein, wherein p is 3.

This invention also relates to any one of the above antibody-drug conjugates or antibody-antibiotic conjugates described herein, wherein p is 4.

The invention provides novel antibacterial therapy that aims to prevent antibiotic escape by targeting populations of bacteria that evade conventional antibiotic therapy. The novel antibacterial therapy is achieved with an Antibody Antibiotic Conjugate (AAC) in which an antibody specific for cell wall components found on *S. aureus* (including MRSA) is chemically linked to a potent antibiotic. The antibiotic is joined to the antibody via a protease cleavable, peptide linker that is designed to be cleaved by cathepsin B, a lysosomal protease found in most mammalian cell types (Dubowchik et al (2002) Bioconj. Chem. 13:855-869). The AAC acts as a pro-drug in that the antibiotic is inactive (due to the large size of the antibody) until the linker is cleaved. Since a significant proportion of *S. aureus* found in a natural infection is taken up by host cells, primarily neutrophils and macrophages, at some point during the course of infection in the host, and that the time spent inside host cells provides a significant opportunity for the bacterium to evade antibiotic activity. The AACs of the invention are designed to bind to *S. aureus* and release the antibiotic inside the phagolysosome after bacteria are taken up by host cells. By this mechanism, AAC are able to concentrate the active antibiotic specifically in a location where *S. aureus* is poorly treated by conventional antibiotics. While the invention is not limited or defined by an particular mechanism of action, the AAC improve antibiotic activity via three potential mechanisms: (1) The AAC delivers antibiotic inside mammalian cells that take up the bacteria, thereby increasing the potency of antibiotics that diffuse poorly into the phagolysosomes where bacteria are sequestered. (2) AAC opsonize bacteria—thereby increasing uptake of free bacteria by phagocytic cells—and release the antibiotic locally to kill the bacteria while they are sequestered in the phagolysosome. (3) AAC improve the half-life of antibiotics in vivo (improved pharmacokinetics) by linking the antibiotic to an antibody. Improved pharmacokinetics of AAC enable delivery of sufficient antibiotic in regions where *S. aureus* is concentrated while limiting the overall dose of antibiotic that needs to be administered systemically. This property should permit long-term therapy with AAC to target persistent infection with minimal antibiotic side effects.

This invention also relates to antibody-drug conjugates which are antibody-antibiotic conjugates, wherein the antibody binds to bacteria and D is an antibiotic moiety.

This invention also relates to any one of the above antibody-antibiotic conjugates, wherein the D is a drug selected from the group comprising clindamycin, novobiocin, retapamulin, daptomycin, GSK-2140944, CG-400549, sitafloxacin, teicoplanin, triclosan, napthyridone, radezolid, doxorubicin, ampicillin, vancomycin, imipenem, doripenem, gemcitabine, dalbavancin, and azithromycin.

Another aspect of the invention is a pharmaceutical composition comprising an antibody-antibiotic conjugate compound of the invention.

Another aspect of the invention is a method of treating a bacterial infection by administering to a patient a therapeutically-effective amount of an antibody-antibiotic conjugate compound of the invention. In one embodiment, the patient is a human. In one embodiment the bacterial infection is a *Staphylococcus aureus* infection. In some embodiments, the patient has been diagnosed with a *Staph aureus* infection. In some embodiments, treating the bacterial infection comprises reducing bacterial load.

In another embodiment, the method of treatment further comprises administering a second therapeutic agent. In a further embodiment, the second therapeutic agent is an antibiotic.

In one embodiment, the second antibiotic administered in combination with the antibody-antibiotic conjugate compound of the invention is selected from the structural classes: (i) aminoglycosides; (ii) beta-lactams; (iii) macrolides/cyclic peptides; (iv) tetracyclines; (v) fluoroquinolines/fluoroquinolones; (vi) and oxazolidinones.

In one embodiment, the second antibiotic administered in combination with the antibody-antibiotic conjugate compound of the invention is selected from rifamycin, clindamycin, novobiocin, retapamulin, daptomycin, GSK-2140944, CG-400549, sitafloxacin, teicoplanin, triclosan, napthyridone, radezolid, doxorubicin, ampicillin, vancomycin, imipenem, doripenem, gemcitabine, dalbavancin, and azithromycin.

Another aspect of the invention is a process for making an antibody or an antibody-antibiotic conjugate compound of the invention.

Another aspect of the invention is a kit for treating a bacterial infection comprising a pharmaceutical composition of the invention and instructions for use.

This invention also relates to any one of the above antibody-drug conjugates, wherein the antibody binds to one or more of polypeptides selected from the group consisting of:

CLL1
BMPR1B;
E16;
STEAP1;
0772P;
MPF;
NaPi2b;
Sema 5b;
PSCA hlg;
ETBR;
MSG783;
STEAP2;
TrpM4;
CRIPTO;
CD21;
CD79b;
FcRH2;
HER2;
NCA;
MDP;
IL20Rα;
Brevican;
EphB2R;
ASLG659;
PSCA;
GEDA;
BAFF-R;
CD22;
CD79a;
CXCR5;
HLA-DOB;
P2X5;
CD72;
LY64;
FcRH1;
IRTA2;
TENB2;
PMEL17;
TMEFF1;
GDNF-Ra1;
Ly6E;
TMEM46;
Ly6G6D;
LGR5;
RET;
LY6K;
GPR19;
GPR54;
ASPHD1;
Tyrosinase;
TMEM118;
GPR172A;
MUC16 and
CD33.

This invention also relates to methods of treating a disease in a human in need thereof, comprising administering to said human an effective amount of an Antibody-drug conjugate of claim 1.

This invention also relates to pharmaceutical compositions comprising a compound of claim 1 and a pharmaceutically acceptable carrier thereof.

This invention also relates to any one of the above antibody-drug conjugates, wherein the antibody binds to one or more of polypeptides selected from the group consisting of:
CLL1;
STEAP1;
NaPi2b;
STEAP2;
TrpM4;
CRIPTO;
CD21;
CD79b;
FcRH2;
HER2;
CD22;
CD79a;
CD72;
LY64;
Ly6E;
MUC16; and
CD33.

This invention also relates to any one of the above antibody-drug conjugates, wherein the antibody binds to CD33.

This invention also relates to any one of the above antibody-drug conjugates, wherein the antibody binds to CD22.

This invention also relates to any one of the above antibody-drug conjugates, wherein the antibody binds to NaPi2b.

This invention also relates to any one of the above antibody-drug conjugates, wherein the antibody binds to CLL1.

This invention also relates to any one of the above antibody-drug conjugates, wherein the antibody binds to Her2.

This invention also relates to any one of the above antibody-drug conjugates, wherein the antibody binds to CD33 and the anti-CD33 antibody comprise an HVR-L1 comprising the amino acid sequence of SEQ ID NO: 11, an HVR-L2 comprising the amino acid sequence of SEQ ID NO: 12, an HVR-L3 comprising the amino acid sequence of SEQ ID NO: 13, an HVR-H1 comprising the amino acid sequence of SEQ ID NO: 14, an HVR-H2 comprising the amino acid sequence of SEQ ID NO: 15, and an HVR-H3 comprising the amino acid sequence of SEQ ID NO: 16.

This invention also relates to any one of the above antibody-drug conjugates, wherein the antibody binds to CD33 and the anti-CD33 antibody comprises a VL domain comprising the amino acid sequence of SEQ ID NO: 17 and a VH domain comprising the amino acid sequence of SEQ ID NO:18.

In some embodiments, the antibody of the antibody-drug conjugate binds CD33. In some embodiments, the antibody of the antibody-drug conjugate comprises (a) HVR-H1 comprising the amino acid sequence of SEQ ID NO:22; (b) HVR-H2 comprising the amino acid sequence of SEQ ID NO:23; (c) HVR-H3 comprising the amino acid sequence of SEQ ID NO:24; (d) HVR-L1 comprising the amino acid sequence of SEQ ID NO:19; (e) HVR-L2 comprising the amino acid sequence of SEQ ID NO:20; and (f) HVR-L3 comprising an amino acid sequence selected from SEQ ID NO:21.

In some embodiments, the antibody comprises a VH as in any of the embodiments provided above, and a VL as in any of the embodiments provided above. In one embodiment, the antibody comprises the VL and VH sequences in SEQ ID NO:25 and SEQ ID NO:26, respectively, including post-translational modifications of those sequences.

This invention also relates to any one of the above antibody-drug conjugates, wherein the antibody binds to NaPi2b.

This invention also relates to any one of the above antibody-drug conjugates, wherein the antibody binds to NaPi2b and the NaPi2b antibody comprise an HVR-L1 comprising the amino acid sequence of SEQ ID NO: 1, an HVR-L2 comprising the amino acid sequence of SEQ ID NO:2, an HVR-L3 comprising the amino acid sequence of SEQ ID NO:3, an HVR-H1 comprising the amino acid sequence of SEQ ID NO:4, an HVR-H2 comprising the amino acid sequence of SEQ ID NO:5, and an HVR-H3 comprising the amino acid sequence of SEQ ID NO: 6.

This invention also relates to any one of the above antibody-drug conjugates, wherein the antibody binds to NaPi2b and the NaPi2b antibody comprise s a VL domain comprising the amino acid sequence of SEQ ID NO:7 and a VH domain comprising the amino acid sequence of SEQ ID NO:8.

This invention also relates to any one of the above antibody-drug conjugates, wherein the antibody binds to NaPi2b and the NaPi2b antibody comprises an amino acid sequence of SEQ ID NO:9 and an amino acid sequence of SEQ ID NO: 10.

This invention also relates to any one of the above antibody-drug conjugates, wherein the antibody binds to CD22.

This invention also relates to any one of the above antibody-drug conjugates, wherein the antibody binds to CD22 and the CD22 antibody comprise an HVR-L1 comprising the amino acid sequence of SEQ ID NO:41, an HVR-L2 comprising the amino acid sequence of SEQ ID NO:42, an HVR-L3 comprising the amino acid sequence of SEQ ID NO:43, an HVR-H1 comprising the amino acid sequence of SEQ ID NO:44, an HVR-H2 comprising the amino acid sequence of SEQ ID NO:45, and an HVR-H3 comprising the amino acid sequence of SEQ ID NO: 46.

This invention also relates to any one of the above antibody-drug conjugates, wherein the antibody binds to CD22 and the CD22 antibody comprise s a VL domain comprising the amino acid sequence of SEQ ID NO:47 and a VH domain comprising the amino acid sequence of SEQ ID NO:48.

This invention also relates to any one of the above antibody-drug conjugates, wherein the antibody binds to CD22 and the CD22 antibody comprises an amino acid sequence of SEQ ID NO:49 and an amino acid sequence of SEQ ID NO: 50.

Definitions

Unless stated otherwise, the following terms and phrases as used herein are intended to have the following meanings: when trade names are used herein, applicants intend to independently include the trade name product formulation, the generic drug, and the active pharmaceutical ingredient(s) of the trade name product.

The term "peptidomimetic" or PM as used herein means a non-peptide chemical moiety. Peptides are short chains of amino acid monomers linked by peptide (amide) bonds, the covalent chemical bonds formed when the carboxyl group of one amino acid reacts with the amino group of another.

The shortest peptides are dipeptides, consisting of 2 amino acids joined by a single peptide bond, followed by tripeptides, tetrapeptides, etc. A peptidomimetic chemical moiety includes non-amino acid chemical moieties. A peptidomimetic chemical moiety may also include one or more amino acid that are separated by one or more non-amino acid chemical units. A peptidomimetic chemical moiety does not contain in any portion of its chemical structure two or more adjacent amino acids that are linked by peptide bonds.

The term "amino acid" as used herein means glycine, alanine, valine, leucine, isoleucine, phenylalanine, proline, serine, threonine, tyrosine, cysteine, methionine, lysine, arginine, histidine, tryptophan, aspartic acid, glutamic acid, asparagine, glutamine or citrulline.

The term "antibiotic" (abx or Abx) includes any molecule that specifically inhibits the growth of or kill micro-organisms, such as bacteria, but is non-lethal to the host at the concentration and dosing interval administered. In a specific aspect, an antibiotic is non-toxic to the host at the administered concentration and dosing intervals. Antibiotics effective against bacteria can be broadly classified as either bactericidal (i.e., directly kills) or bacteriostatic (i.e., prevents division). Anti-bactericidal antibiotics can be further subclassified as narrow-spectrum or broad-spectrum. A broad-spectrum antibiotic is one effective against a broad range of bacteria including both Gram-positive and Gram-negative bacteria, in contrast to a narrow-spectrum antibiotic, which is effective against a smaller range or specific families of bacteria. Examples of antibiotics include: (i) aminoglycosides, e.g., amikacin, gentamicin, kanamycin, neomycin, netilmicin, streptomycin, tobramycin, paromycin, (ii) ansamycins, e.g., geldanamycin, herbimycin, (iii) carbacephems, e.g., loracarbef, (iv) carbapenems, e.g., ertapenum, doripenem, imipenem/cilastatin, meropenem, (v) cephalosporins (first generation), e.g., cefadroxil, cefazolin, cefalotin, cefalexin, (vi) cephalosporins (second generation), e.g., ceflaclor, cefamandole, cefoxitin, cefprozil, cefuroxime, (vi) cephalosporins (third generation), e.g., cefixime, cefdinir, cefditoren, cefoperazone, cefotaxime, cefpodoxime, ceftazidime, ceftibuten, ceftizoxime, ceftriaxone, (vii) cephalosporins (fourth generation), e.g., cefepime, (viii) cephalosporins (fifth generation), e.g., ceftobiprole, (ix) glycopeptides, e.g., teicoplanin, vancomycin, (x) macrolides, e.g., axithromycin, clarithromycin, dirithromycine, erythromycin, roxithromycin, troleandomycin, telithromycin, spectinomycin, (xi) monobactams, e.g., axtreonam, (xii) penicilins, e.g., amoxicillin, ampicillin, axlocillin, carbenicillin, cloxacillin, dicloxacillin, flucloxacillin, mezlocillin, meticilin, nafcilin, oxacillin, penicillin, peperacillin, ticarcillin, (xiii) antibiotic polypeptides, e.g., bacitracin, colistin, polymyxin B, (xiv) quinolones, e.g., ciprofloxacin, enoxacin, gatifloxacin, levofloxacin, lemefloxacin, moxifloxacin, norfloxacin, orfloxacin, trovafloxacin, (xv) sulfonamides, e.g., mafenide, prontosil, sulfacetamide, sulfamethizole, sulfanilamide, sulfasalazine, sulfisoxazole, trimethoprim, trimethoprim-sulfamethoxazole (TMP-SMX), (xvi) tetracyclines, e.g., demeclocycline, doxycycline, minocycline, oxytetracycline, tetracycline and (xvii) others such as arspenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin or tinidazole.

The term "methicillin-resistant *Staphylococcus aureus*" (MRSA), alternatively known as multidrug resistant *Staphylococcus aureus* or oxacillin-resistant *Staphylococcus aureus* (ORSA), refers to any strain of *Staphylococcus aureus* that is resistant to beta-lactam antibiotics, which in include the penicillins (e.g., methicillin, dicloxacillin, nafcillin, oxacillin, etc.) and the cephalosporins. "Methicillin-sensitive *Staphylococcus aureus*" (MSSA) refers to any strain of *Staphylococcus aureus* that is sensitive to beta-lactam antibiotics.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

The term "antibody fragment(s)" as used herein comprises a portion of a full length antibody, generally the antigen binding or variable region thereof. Examples of antibody fragments include Fab, Fab', F(ab')$_2$, and Fv fragments; diabodies; linear antibodies; minibodies (Olafsen et al (2004) Protein Eng. Design & Sel. 17(4):315-323), fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature, 256:495, or may be made by recombinant DNA methods (see for example: U.S. Pat. No. 4,816,567; U.S. Pat. No. 5,807,715). The monoclonal antibodies may also be isolated from phage antibody libraries using the techniques described in Clackson et al (1991) Nature, 352: 624-628; Marks et al (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape, etc.) and human constant region sequences.

The term "intact antibody" as used herein is one comprising a VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

The term "Fc region" as used hererin means a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

The term "framework" or "FR" as used herein refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4. Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$, and g, respectively. The subunit structures and three-dimensional configurations of different classes of immunoglobulins are well known. Ig forms include hinge-modifications or hingeless forms (Roux et al (1998) J. Immunol. 161:4083-4090; Lund et al (2000) Eur. J. Biochem. 267:7246-7256; US 2005/0048572; US 2004/0229310).

The term "human antibody" as used herein refers to an antibody which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "human consensus framework" as used herein refers to a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

The term "humanized antibody" as used herein refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci. 13:1619-1633 (2008).) Unless otherwise indicated, HVR residues and other residues in the variable domain (e.g., FR residues) are numbered herein according to Kabat et al., supra.

The term "variable region" or "variable domain" as used herein refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector" as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "free cysteine amino acid" as used herein refers to a cysteine amino acid residue which has been engineered into a parent antibody, has a thiol functional group (—SH), and is not paired as an intramolecular or intermolecular disulfide bridge.

Ther term "Linker", "Linker Unit", or "link" as used herein means a chemical moiety comprising a chain of atoms that covalently attaches a drug moiety to an antibody. In various embodiments, a linker is a divalent radical, specified as L.

The term "drug moiety" as used herein means a substance that that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{86}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; and the various antitumor or anticancer agents disclosed below.

As used herein, unless defined otherwise in a claim, the term "acyl" refers to the group —C(O)R', where R' is alkyl, $C_3$-$C_6$cycloalkyl, or heterocyclyl, as each is defined herein.

As used herein, unless defined otherwise in a claim, the term "alkoxy" refers to the group —OR', where R' is $C_1$-$C_4$alkyl or $C_3$-$C_6$cycloalkyl as defined above. Examples of "alkoxy" include methoxy, ethoxy, isopropoxy, propoxy, butoxy, t-butoxy, isobutoxy, cyclopropoxy, and cyclobutoxy, and halogenated forms thereof, e.g. fluoromethoxy and difluoromethoxy.

As used herein, unless defined otherwise in a claim, the term "alkyl" refers to a straight or branched, monovalent or divalent hydrocarbon chain radical having from one to twelve ($C_1$-$C_{12}$) carbon atoms, which may be unsubstituted or substituted with multiple degrees of substitution, for example one, two, three, four, five or six included within the present invention. Examples of substituents are selected from the group consisting of halo, trifluoromethyl, difluoromethyl, amino, alkylamino, cyano, sulfonyl, sulfonamide, sulfoxide, hydroxy, alkoxy, ester, carboxylic acid and alkylthio. Examples of "alkyl" as used herein include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH (CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH (CH$_3$)CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), 3,3-dimethyl-2-butyl (—CH(CH$_3$)C (CH$_3$)$_3$, as well as the divalent ("alkylene") and substituted versions thereof. Examples of substituted alkyl include but are not limited to, hydroxymethyl, difluoromethyl and trifluoromethyl.

As used herein unless otherwise defined in a claim, the term "alkenyl" means a linear or branched, monovalent or divalent hydrocarbon chain radical of any length from two to eight carbon atoms ($C_2$-$C_{10}$) with at least one site of unsaturation, i.e., a carbon-carbon, sp$^2$ double bond, wherein the alkenyl radical may be optionally substituted independently with one or more substituents described above in the definition of "alkyl", and includes radicals having "cis" and "trans" orientations, or alternatively, "E" and "Z" orientations. Examples of alkenyl include, but are not limited to, ethenyl or vinyl (—CH═CH$_2$), prop-1-enyl (—CH═CHCH$_3$), prop-2-enyl (—CH$_2$CH═CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, hexa-1,3-dienyl as well as the divalent ("alkenylene") and substituted versions thereof.

As used herein unless otherwise defined in a claim, the term "alkynyl" refers to a linear or branched, monovalent or divalent hydrocarbon radical of any length from two to eight carbon atoms ($C_2$-$C_{10}$) with at least one site of unsaturation, i.e., a carbon-carbon, sp triple bond, wherein the alkynyl radical may be optionally substituted independently with one or more substituents described above in the definition of alkyl, examples of alkynyl includes, but not limited to, ethynyl (—C≡CH), prop-1-ynyl (—C≡CCH$_3$), prop-2-ynyl (propargyl, —CH$_2$C≡CH), but-1-ynyl, but-2-ynyl and but-3-ynyl, as well as the divalent ("alkynylene") and substituted versions thereof.

As used herein, unless defined otherwise in a claim, the term "alkylamino" refers to the group —NR'R", wherein R' is H, $C_1$-$C_6$alkyl or $C_3$-$C_6$cycloalkyl, and R" is $C_1$-$C_6$alkyl or $C_3$-$C_6$cycloalkyl, examples of alkylamino include, but are not limited to, methylamino, dimethylamino, ethylamino, diethylamino, propylamino and cyclopropylamino.

As used herein, unless defined otherwise in a claim, the term "amide" refers to the group —C(O)NR'R", wherein R' and R" are each independently H, $C_1$-$C_6$alkyl, or $C_3$-$C_6$cycloalkyl; examples of amide include, but are not limited to, —C(O)NH$_2$, —C(O)NHCH$_3$, and —C(O)N(CH$_3$)$_2$.

As used herein, unless defined otherwise in a claim, the term "aryl" refers to an aromatic, hydrocarbon, ring system. The ring system may be monocyclic or fused polycyclic (e.g., bicyclic, tricyclic, etc.), substituted or unsubstituted. In various embodiments, the monocyclic aryl ring is $C_5$-$C_{10}$, or $C_5$-$C_7$, or $C_5$-$C_6$, where these carbon numbers refer to the number of carbon atoms that form the ring system. A $C_6$ ring system, i.e. a phenyl ring, is an aryl group. In various embodiments, the polycyclic ring is a bicyclic aryl group, where examples of bicyclic aryl groups include are $C_8$-$C_{12}$, or $C_9$-$C_{10}$. A naphthyl ring, which has 10 carbon atoms, is a polycyclic aryl group. Examples of substituents for aryl are described below in the definition of "optionally substituted".

As used herein, unless defined otherwise in a claim, the term "cyano" refers to the group —CN.

As used herein, unless defined otherwise in a claim, "cycloalkyl" refers to a non-aromatic, substituted or unsubstituted, saturated or partially unsaturated hydrocarbon ring group. Examples of substituents are described in the definition of "optionally substituted". In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane.

As used herein, unless defined otherwise in a claim, the term "ester" refers to the group —C(O)OR', where R' is $C_1$-$C_6$alkyl, or $C_3$-$C_6$cycloalkyl.

As used herein, unless defined otherwise in a claim, the term "heterocycle" "heterocycloalkyl" or "heterocyclyl" refers to unsubstituted and substituted mono- or polycyclic non-aromatic ring system containing 2 to 12 ring carbon atoms and 1 to 3 ring hetero atoms. Polycyclic ring systems can be fused bi- or tri-cyclic, spiro or bridged. Examples of heteroatoms include N, O, and S, including N-oxides, sulfur oxides, and dioxides. In one embodiment, the ring is three to eight-membered and is either fully saturated or has one or more degrees of unsaturation. Multiple degrees of substitution are included within the present definition. Examples of substituents are defined hereunder. Examples of "heterocyclic" groups include, but are not limited to tetrahydrofuranyl, pyranyl, 1,4-dioxanyl, 1,3-dioxanyl, oxolanyl, oxetanyl, 2-oxa-6-azaspiro[3.3]heptan-6-yl, piperidinyl, pyrrolidinyl, morpholinyl, azetidinyl, piperazinyl, pyrrolidinonyl, piperazinonyl, pyrazolidinyl, imidazolinyl, imidazolidinyl, and their various tautomers.

As used herein, unless defined otherwise in a claim, the term "heteroaryl", unless defined otherwise in a claim, refers to an aromatic ring system containing 1 to 9 carbon(s) and at least one heteroatom. Examples of heteroatoms include N, O, and S. Heteroaryl may be monocyclic or polycyclic, substituted or unsubstituted. A monocyclic heteroaryl group may have 2 to 6 ring carbon atoms and 1 to 3 ring hetero atoms in the ring, while a polycyclic heteroaryl may contain 3 to 9 ring carbon atoms and 1 to 5 ring hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include but are not limited to: benzofuranyl, benzothiophenyl, furanyl, imidazolyl, indolyl, azaindolyl, azabenzimidazolyl, benzoxazolyl, benzthiazolyl, benzothiadiazolyl, benzotriazolyl, benzoimidazolyl, tetrazinyl, tetrazolyl, isothiazolyl, oxazolyl, isoxazolyl, pyrazinyl, pyrazolyl, pyridazinyl, pyridinyl, pyrimidinyl, pyrrolyl, quinolinyl, quinazolinyl, quinoxalinyl, triazinyl, triazolyl, thiazolyl and thiophenyl. Examples of substituents for heteroaryl are described below in the definition of "optionally substituted".

As used herein, unless defined otherwise in a claim, the term "heteroarylalkyl" means the group (heteroaryl)$C_1$-$C_3$alkyl.

As used herein, unless defined otherwise in a claim, the term "arylalkyl" means the group (aryl)$C_1$-$C_3$alkyl.

As used herein, unless defined otherwise in a claim, the term "urea" refers to the group —NR'C(O)NR", wherein R' and R" are each independently H, $C_1$-$C_6$alkyl, or $C_3$-$C_6$cycloalkyl.

As used herein, unless defined otherwise in a claim, the term "optionally" means that the subsequently described event(s) may or may not occur, and includes both event(s) that occur and event(s) that do not occur.

As used herein, unless defined otherwise, the phrase "optionally substituted", "substituted" or variations thereof denote an optional substitution, including multiple degrees of substitution, with one or more substituent group, for example, one, two or three. The phrase should not be interpreted as duplicative of the substitutions herein described and depicted. Exemplary optional substituent groups include acyl, $C_1$-$C_6$alkyl, sulfonyl, amino, sulfonamide, sulfoxide, alkoxy, cyano, halo, urea, ester, carboxylic acid, amide, hydroxy, oxo, and nitro.

As used herein, unless defined otherwise in a claim, the term "treatment" refers to alleviating the specified condition, eliminating or reducing one or more symptoms of the condition, slowing or eliminating the progression of the condition As used herein, unless defined otherwise in a claim, the term "effective amount" means that amount of a drug or pharmaceutical agent that will elicit the biological or medical response of a tissue, system, animal, or human that is being sought, for instance, by a researcher or clinician.

As used herein, unless defined otherwise in a claim, the term "therapeutically effective amount" means any amount which, as compared to a corresponding subject who has not received such amount, results in treatment of a disease, disorder, or side effect, or a decrease in the rate of advancement of a disease or disorder. The term also includes within its scope amounts effective to enhance normal physiological function. For use in therapy, therapeutically effective amounts of a compound of Formula I, as well as salts thereof, may be administered as the raw chemical. Additionally, the active ingredient may be presented as a pharmaceutical composition.

This invention also relates to any one of the examples in the Experimental section.

The phrase "pharmaceutically acceptable salt," as used herein, refers to pharmaceutically acceptable organic or inorganic salts of an antibody-drug conjugate (ADC) or a linker-drug moiety. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

Compounds of the present invention may exist in solid or liquid form. In the solid state, it may exist in crystalline or noncrystalline form, or as a mixture thereof. The skilled artisan will appreciate that pharmaceutically acceptable solvates may be formed for crystalline or noncrystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties.

Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

Compounds of the present invention or a salt thereof may exist in stereoisomeric forms (e.g., it contains one or more asymmetric carbon atoms). The individual stereoisomers (enantiomers and diastereomers) and mixtures of these are included within the scope of the present invention. Likewise, it is understood that a compound or salt of Formula (I) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. It is to be understood that the present invention includes all combinations and subsets of the particular groups defined hereinabove.

The subject invention also includes isotopically-labelled forms of the compounds of the present invention, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as 2H, 3H, 11C, 13C, 14C, 15N, 17O, 18O, 31P, 32P, 35S, 18F, 36Cl, 123I and 125I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as 3H, 14C are incorporated, are useful in drug and/or substrate tissue distribution assays. Tritiated, i.e., 3H, and carbon-14, i.e., 14C, isotopes are commonly used for their ease of preparation and detectability. 11C and 18F isotopes are useful in PET (positron emission tomography), and 125I isotopes are useful in SPECT (single photon emission computerized tomography), all useful in brain imaging. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Pharmaceutical Composition of ADCs

Pharmaceutical formulations of therapeutic antibody-drug conjugates (ADC) of the invention are typically prepared for parenteral administration, i.e. bolus, intravenous, intratumor injection with a pharmaceutically acceptable parenteral vehicle and in a unit dosage injectable form. An antibody-drug conjugate (ADC) having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation or an aqueous solution.

Cysteine Engineered Antibodies

The compounds of the invention include antibody-drug conjugates comprising cysteine engineered antibodies where one or more amino acids of a wild-type or parent antibody are replaced with a cysteine amino acid. Any form of antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. Mutants with replaced ("engineered") cysteine (Cys) residues are evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies of the invention are in the ranges of 0.6 to 1.0; 0.7 to 1.0; or 0.8 to 1.0.

To prepare a cysteine engineered antibody by mutagenesis, DNA encoding an amino acid sequence variant of the starting polypeptide is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide. Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies. General guidance can be found in Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. No. 7,521,541; U.S. Pat. No. 7,723,485; WO2009/052249, Shen et al (2012) Nature Biotech., 30(2):184-191; Junutula et al (2008) Jour of Immun. Methods 332:41-52). The engineered cysteine thiols may react with linker reagents or the linker-drug intermediates of the present invention which have thiol-reactive, electrophilic groups such as maleimide or alpha-halo amides to form ADC with cysteine engineered antibodies (ThioMabs) and the drug (D) moiety. The location of the drug moiety can thus be designed, controlled, and known. The drug loading can be controlled since the engineered cysteine thiol groups typically react with thiol-reactive linker reagents or linker-drug intermediates in high yield. Engineering an antibody to introduce a cysteine amino acid by substitution at a single site on the heavy or light chain gives two new cysteines on the symmetrical antibody. A drug loading near 2 can be achieved and near homogeneity of the conjugation product ADC.

Cysteine engineered antibodies of the invention preferably retain the antigen binding capability of their wild type, parent antibody counterparts. Thus, cysteine engineered antibodies are capable of binding, preferably specifically, to antigens. Such antigens include, for example, tumor-associated antigens (TAA), cell surface receptor proteins and other cell surface molecules, transmembrane proteins, signaling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which a cysteine engineered antibody is capable of binding may be a member of a subset of one of the above-mentioned categories, wherein the other subset(s) of said category comprise other molecules/antigens that have a distinct characteristic (with respect to the antigen of interest).

Cysteine engineered antibodies are prepared for conjugation with linker-drug intermediates by reduction and reoxidation of intrachain disulfide groups.

Tumor-Associated Antigens:

Antibodies, including but not limited to cysteine engineered antibodies, which may be useful in the antibody-drug conjugates of the invention in the treatment of cancer include, but are not limited to, antibodies against cell surface receptors and tumor-associated antigens (TAA). Certain tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to more specifically target cancer cells for destruction via antibody-based therapies. Examples of tumor-associated antigens TAA include, but are not limited to, those listed below. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to TAA listed below are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, and/or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

(1) BMPR1B (bone morphogenetic protein receptor-type IB, Genbank accession no. NM_001203)

ten Dijke, P., et al Science 264 (5155):101-104 (1994), Oncogene 14 (11):1377-1382 (1997)); WO2004063362

(Claim 2); WO2003042661 (Claim 12); US2003134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358 (Claim 1; Page 183); WO200254940 (Page 100-101); WO200259377 (Page 349-350); WO200230268 (Claim 27; Page 376); WO200148204 (Example; FIG. 4)
NP_001194 bone morphogenetic protein receptor, type IB/pid=NP_001194.1—Cross-references: MIM:603248; NP_001194.1; AY065994
(2) E16 (LAT1, SLC7A5, Genbank accession no. NM_003486)
Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004048938 (Example 2); WO2004032842 (Example IV); WO2003042661 (Claim 12); WO2003016475 (Claim 1); WO200278524 (Example 2); WO200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5; Page 133-136); US2003224454 (FIG. 3); WO2003025138 (Claim 12; Page 150);
NP_003477 solute carrier family 7 (cationic amino acid transporter, y+ system), member 5/pid=NP_003477.3—*Homo sapiens*
Cross-references: MIM:600182; NP_003477.3; NM_015923; NM_003486_1
(3) STEAP1 (six transmembrane epithelial antigen of prostate, Genbank accession no. NM_012449)
Cancer Res. 61 (15), 5857-5860 (2001), Hubert, R. S., et al (1999) Proc. Natl. Acad. Sci. U.S.A. 96 (25):14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A);
NP_036581 six transmembrane epithelial antigen of the prostate
Cross-references: MIM:604415; NP_036581.1; NM_012449_1
(4) 0772P (CA125, MUC16, Genbank accession no. AF361486)
J. Biol. Chem. 276 (29):27371-27375 (2001)); WO2004045553 (Claim 14); WO200292836 (Claim 6; FIG. 12); WO200283866 (Claim 15; Page 116-121); US2003124140 (Example 16); Cross-references: GI:34501467; AAK74120.3; AF361486_1
(5) MPF (MPF, MSLN, SMR, megakaryocyte potentiating factor, mesothelin, Genbank accession no. NM_005823)
Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (Claim 14); (WO2002102235 (Claim 13; Page 287-288); WO2002101075 (Claim 4; Page 308-309); WO200271928 (Page 320-321); WO9410312 (Page 52-57); Cross-references: MIM:601051; NP_005814.2; NM_005823_1
(6) Napi3b/NaPi2b (NAPI-3B, NPTIIb, SLC34A2, solute carrier family 34 (sodium phosphate), member 2, type II sodium-dependent phosphate transporter 3b, Genbank accession no. NM_006424)
J. Biol. Chem. 277 (22):19665-19672 (2002), Genomics 62 (2):281-284 (1999), Feild, J. A., et al (1999) Biochem. Biophys. Res. Commun. 258 (3):578-582); WO2004022778 (Claim 2); EP1394274 (Example 11); WO2002102235 (Claim 13; Page 326); EP875569 (Claim 1; Page 17-19); WO200157188 (Claim 20; Page 329); WO2004032842 (Example IV); WO200175177 (Claim 24; Page 139-140);
Cross-references: MIM:604217; NP_006415.1; NM_006424_1
(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878) Nagase T., et al (2000) DNA Res. 7 (2):143-150); WO2004000997 (Claim 1); WO2003003984 (Claim 1); WO200206339 (Claim 1; Page 50); WO200188133 (Claim 1; Page 41-43, 48-58); WO2003054152 (Claim 20); WO2003101400 (Claim 11); Accession: Q9P283; EMBL; AB040878; BAA95969.1. Genew; HGNC:10737;
(8) PSCA hlg (2700050C12Rik, C530008O16Rik, RIKEN cDNA 2700050C12, RIKEN cDNA 2700050C12 gene, Genbank accession no. AY358628); Ross et al (2002) Cancer Res. 62:2546-2553; US2003129192 (Claim 2); US2004044180 (Claim 12); US2004044179 (Claim 11); US2003096961 (Claim 11); US2003232056 (Example 5); WO2003105758 (Claim 12); US2003206918 (Example 5); EP1347046 (Claim 1); WO2003025148 (Claim 20);
Cross-references: GI:37182378; AAQ88991.1; AY358628_1
(9) ETBR (Endothelin type B receptor, Genbank accession no. AY275463);
Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al J. Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (Claim 1); WO2004048938 (Example 2); WO2004040000 (Claim 151); WO2003087768 (Claim 1); WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172 (Claim 1; Page 297-299); US2003109676; U.S. Pat. No. 6,518,404 (FIG. 3); U.S. Pat. No. 5,773,223 (Claim 1a; Col 31-34); WO2004001004;
(10) MSG783 (RNF124, hypothetical protein FLJ20315, Genbank accession no. NM_017763); WO2003104275 (Claim 1); WO2004046342 (Example 2); WO2003042661 (Claim 12); WO2003083074 (Claim 14; Page 61); WO2003018621 (Claim 1); WO2003024392 (Claim 2; FIG. 93); WO200166689 (Example 6);

Cross-references: LocusID:54894; NP_060233.2; NM_017763_1

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138) Lab. Invest. 82 (11):1573-1582 (2002)); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WO200226822 (Claim 23; FIG. 2); WO200216429 (Claim 12; FIG. 10);

Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636)

Xu, X. Z., et al Proc. Natl. Acad. Sci. U.S.A. 98 (19):10692-10697 (2001), Cell 109 (3):397-407 (2002), J. Biol. Chem. 278 (33):30813-30820 (2003)); US2003143557 (Claim 4); WO200040614 (Claim 14; Page 100-103); WO200210382 (Claim 1; FIG. 9A); WO2003042661 (Claim 12); WO200230268 (Claim 27; Page 391); US2003219806 (Claim 4); WO200162794 (Claim 14; FIG. 1A-D);

Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212)

Ciccodicola, A., et al EMBO J. 8 (7):1987-1991 (1989), Am. J. Hum. Genet. 49 (3):555-565 (1991)); US2003224411 (Claim 1); WO2003083041 (Example 1); WO2003034984 (Claim 12); WO200288170 (Claim 2; Page 52-53); WO2003024392 (Claim 2; FIG. 58); WO200216413 (Claim 1; Page 94-95, 105); WO200222808 (Claim 2; FIG. 1); U.S. Pat. No. 5,854,399 (Example 2; Col 17-18); U.S. Pat. No. 5,792,616 (FIG. 2);

Cross-references: MIM:187395; NP_003203.1; NM_003212_1

(14) CD21 (CR2 (Complement receptor 2) or C3DR (C3d/Epstein Barr virus receptor) or Hs.73792 Genbank accession no. M26004)

Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (Claim 9); WO2004045520 (Example 4); WO9102536 (FIGS. 9.1-9.9); WO2004020595 (Claim 1); Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674)

Proc. Natl. Acad. Sci. U.S.A. (2003) 100 (7):4126-4131, Blood (2002) 100 (9):3068-3076, Muller et al (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146);

Cross-references: MIM:147245; NP_000617.1; NM_000626_1

(16) FcRH2 (IFGP4, IRTA4, SPAP1A (SH2 domain containing phosphatase anchor protein 1a), SPAP1B, SPAP1C, Genbank accession no. NM_030764, AY358130)

Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (Claim 2); WO2003077836; WO200138490 (Claim 5; FIG. 18D-1-18D-2); WO2003097803 (Claim 12); WO2003089624 (Claim 25);

Cross-references: MIM:606509; NP_110391.2; NM_030764_1

(17) HER2 (ErbB2, Genbank accession no. M11730)

Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 11); WO2004009622; WO2003081210; WO2003089904 (Claim 9); WO2003016475 (Claim 1); US2003118592; WO2003008537 (Claim 1); WO2003055439 (Claim 29; FIG. 1A-B); WO2003025228 (Claim 37; FIG. 5C); WO200222636 (Example 13; Page 95-107); WO200212341 (Claim 68; FIG. 7); WO200213847 (Page 71-74); WO200214503 (Page 114-117); WO200153463 (Claim 2; Page 41-46); WO200141787 (Page 15); WO200044899 (Claim 52; FIG. 7); WO200020579 (Claim 3; FIG. 2); U.S. Pat. No. 5,869,445 (Claim 3; Col 31-38); WO9630514 (Claim 2; Page 56-61); EP1439393 (Claim 7); WO2004043361 (Claim 7); WO2004022709; WO200100244 (Example 3; FIG. 4);

Accession: P04626; EMBL; M11767; AAA35808.1. EMBL; M11761; AAA35808.1.

(18) NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (Claim 7); WO2004044178 (Example 4); WO2004031238; WO2003042661 (Claim 12); WO200278524 (Example 2); WO200286443 (Claim 27; Page 427); WO200260317 (Claim 2);

Accession: P40199; Q14920; EMBL; M29541; AAA59915.1. EMBL; M18728;

(19) MDP (DPEP1, Genbank accession no. BC017023)

Proc. Natl. Acad. Sci. U.S.A. 99 (26):16899-16903 (2002)); WO2003016475 (Claim 1); WO200264798 (Claim 33; Page 85-87); JP05003790 (FIG. 6-8); WO9946284 (FIG. 9);

Cross-references: MIM:179780; AAH17023.1; BC017023_1

(20) IL20Rα (IL20Ra, ZCYTOR7, Genbank accession no. AF184971); Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (Claim 2; Page 63); WO200222153 (Page 45-47); US2002042366 (Page 20-21);

WO200146261 (Page 57-59); WO200146232 (Page 63-65); WO9837193 (Claim 1; Page 55-59);

Accession: Q9UHF4; Q6UWA9; Q96SH8; EMBL; AF184971; AAF01320.1.

(21) Brevican (BCAN, BEHAB, Genbank accession no. AF229053)

Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (Claim 11); US2003186373 (Claim 11); US2003119131 (Claim 1; FIG. 52); US2003119122 (Claim 1; FIG. 52); US2003119126 (Claim 1); US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1);

(22) EphB2R (DRT, ERK, Hek5, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42);

Cross-references: MIM:600997; NP_004433.2; NM_004442_1

(23) ASLG659 (B7h, Genbank accession no. AX092328) US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7b); WO200202624 (Claim 13; FIG. 1A-1B); US2002034749 (Claim 54; Page 45-46); WO200206317 (Example 2; Page 320-321, Claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (Claim 12); WO2003004989 (Claim 1); WO200271928 (Page 233-234, 452-453); WO 0116318;

(24) PSCA (Prostate stem cell antigen precursor, Genbank accession no. AJ297436)

Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709; EP1394274 (Example 11); US2004018553 (Claim 17); WO2003008537 (Claim 1); WO200281646 (Claim 1; Page 164); WO2003003906 (Claim 10; Page 288); WO200140309 (Example 1; FIG. 17); US2001055751 (Example 1; FIG. 1b); WO200032752 (Claim 18; FIG. 1); WO9851805 (Claim 17; Page 97); WO9851824 (Claim 10; Page 94); WO9840403 (Claim 2; FIG. 1B);

Accession: O43653; EMBL; AF043498; AAC39607.1.

(25) GEDA (Genbank accession No. AY260763);

AAP14954 lipoma HMGIC fusion-partner-like protein/ pid=AAP14954.1—*Homo sapiens* Species: *Homo sapiens* (human)

WO2003054152 (Claim 20); WO2003000842 (Claim 1); WO2003023013 (Example 3, Claim 20); US2003194704 (Claim 45);

Cross-references: GI:30102449; AAP14954.1; AY260763_1

(26) BAFF-R (B cell-activating factor receptor, BLyS receptor 3, BR3, Genbank accession No. AF116456); BAFF receptor/pid=NP_443177.1—*Homo sapiens*

Thompson, J. S., et al Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616); WO200294852 (Col 136-137); WO200238766 (Claim 3; Page 133); WO200224909 (Example 3; FIG. 3);

Cross-references: MIM:606269; NP_443177.1; NM_052945_1; AF132600

(27) CD22 (B-cell receptor CD22-B isoform, BL-CAM, Lyb-8, Lyb8, SIGLEC-2, FLJ22814, Genbank accession No. AK026467);

Wilson et al (1991) J. Exp. Med. 173:137-146; WO2003072036 (Claim 1; FIG. 1);

Cross-references: MIM:107266; NP_001762.1; NM_001771_1

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q113.2, Genbank accession No. NP_001774.10)

WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11):3457-3464;

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1)

WO2004040000; WO2004015426; US2003105292 (Example 2); U.S. Pat. No. 6,555,339 (Example 2); WO200261087 (FIG. 1); WO200157188 (Claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al (1992) Eur. J. Immunol. 22:2795-2799; Barella et al (1995) Biochem. J. 309:773-779;

(30) HLA-DOB (Beta subunit of MHC class II molecule (Ia antigen) that binds peptides and presents them to CD4+T lymphocytes); 273 aa, pI: 6.56 MW: 30820 TM: 1 [P] Gene Chromosome: 6p21.3, Genbank accession No. NP_002111.1)

Tonnelle et al (1985) EMBO J. 4(11):2839-2847; Jonsson et al (1989) Immunogenetics 29(6):411-413; Beck et al (1992) J. Mol. Biol. 228:433-441; Strausberg et al (2002) Proc. Natl. Acad. Sci USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) Immunogenetics 30(1):66-68; Larhammar et al (1985) J. Biol. Chem. 260(26):14111-14119;

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1

[P] Gene Chromosome: 17p13.3, Genbank accession No. NP_002552.2) Le et al (1997) FEBS Lett. 418(1-2):195-199; WO2004047749; WO2003072035 (claim 10); Touchman et al (2000) Genome Res. 10:165-173; WO200222660 (claim 20); WO2003093444 (claim 1); WO2003087768 (claim 1); WO2003029277 (page 82);

(32) CD72 (B-cell differentiation antigen CD72, Lyb-2) PROTEIN SEQUENCE Full maeaity . . . tafrfpd (1 . . . 359; 359 aa), pI: 8.66, MW: 40225 TM: 1 [P] Gene Chromosome: 9p13.3, Genbank accession No. NP_001773.1)
WO2004042346 (claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci USA 99:16899-16903;

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1) US2002193567; WO9707198 (claim 11, pages 39-42); Miura et al (1996) Genomics 38(3):299-304; Miura et al (1998) Blood 92:2815-2822; WO2003083047; WO9744452 (claim 8, pages 57-61); WO200012130 (pages 24-26);

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1)
WO2003077836; WO200138490 (claim 6, FIG. 18E-1-18-E-2); Davis et al (2001) Proc. Natl. Acad. Sci USA 98(17): 9772-9777; WO2003089624 (claim 8); EP1347046 (claim 1); WO2003089624 (claim 7);

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P] Gene Chromosome: 1q21, Genbank accession No. Human: AF343662, AF343663, AF343664, AF343665, AF369794, AF397453, AK090423, AK090475, AL834187, AY358085; Mouse: AK089756, AY158090, AY506558; NP_112571.1 WO2003024392 (claim 2, FIG. 97); Nakayama et al (2000) Biochem. Biophys. Res. Commun. 277(1):124-127; WO2003077836; WO200138490 (claim 3, FIG. 18B-1-18B-2);

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436
WO2004074320 (SEQ ID NO 810); JP2004113151 (SEQ ID NOS 2, 4, 8); WO2003042661 (SEQ ID NO 580); WO2003009814 (SEQ ID NO 411); EP1295944 (pages 69-70); WO200230268 (page 329); WO200190304 (SEQ ID NO 2706); US2004249130; US2004022727; WO2004063355; US2004197325; US2003232350; US2004005563; US2003124579; Horie et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. October 15; 94(2):178-84;

(37) PMEL17 (silver homolog; SILV; D12S53E; PMEL17; (SI); (SIL); ME20; gp100) BC001414; BT007202; M32295; M77348; NM_006928; McGlinchey, R. P. et al (2009) Proc. Natl. Acad. Sci. U.S.A. 106 (33), 13731-13736; Kummer, M. P. et al (2009) J. Biol. Chem. 284 (4), 2296-2306;

(38) TMEFF1 (transmembrane protein with EGF-like and two follistatin-like domains 1: Tomoregulin-1; H7365; C9orf2; C9ORF2; U19878; X83961) NM_080655; NM_003692; Harms, P. W. (2003) Genes Dev. 17 (21), 2624-2629; Gery, S. et al (2003) Oncogene 22 (18):2723-2727;

(39) GDNF-Ra1 (GDNF family receptor alpha 1; GFRA1; GDNFR; GDNFRA; RETL1; TRNR1; RET1L; GDNFR-alpha1; GFR-ALPHA-1; U95847; BC014962; NM_145793) NM_005264; Kim, M. H. et al (2009) Mol. Cell. Biol. 29 (8), 2264-2277; Treanor, J. J. et al (1996) Nature 382 (6586):80-83;

(40) Ly6E (lymphocyte antigen 6 complex, locus E; Ly67, RIG-E, SCA-2,TSA-1) NP_002337.1; NM_002346.2; de Nooij-van Dalen, A. G. et al (2003) Int. J. Cancer 103 (6), 768-774; Zammit, D. J. et al (2002) Mol. Cell. Biol. 22 (3):946-952;

(41) TMEM46 (shisa homolog 2 (Xenopus laevis); SHISA2) NP_001007539.1; NM_001007538.1; Furushima, K. et al (2007) Dev. Biol. 306 (2), 480-492; Clark, H. F. et al (2003) Genome Res. 13 (10):2265-2270;

(42) Ly6G6D (lymphocyte antigen 6 complex, locus G6D; Ly6-D, MEGT1) NP_067079.2; NM_021246.2; Mallya, M. et al (2002) Genomics 80 (1):113-123; Ribas, G. et al (1999) J. Immunol. 163 (1):278-287;

(43) LGR5 (leucine-rich repeat-containing G protein-coupled receptor 5; GPR49, GPR67) NP_003658.1; NM_003667.2; Salanti, G. et al (2009) Am. J. Epidemiol. 170 (5):537-545; Yamamoto, Y. et al (2003) Hepatology 37 (3):528-533;

(44) RET (ret proto-oncogene; MEN2A; HSCR1; MEN2B; MTC1; (PTC); CDHF12; Hs.168114; RET51; RET-ELE1) NP_066124.1; NM_020975.4; Tsukamoto, H. et al (2009) Cancer Sci. 100 (10):1895-1901; Narita, N. et al (2009) Oncogene 28 (34):3058-3068;

(45) LY6K (lymphocyte antigen 6 complex, locus K: LY6K; HSJ001348; FLJ35226) NP_059997.3; NM_017527.3; Ishikawa, N. et al (2007) Cancer Res. 67 (24):11601-11611; de Nooij-van Dalen, A. G. et al (2003) Int. J. Cancer 103 (6):768-774;

(46) GPR19 (G protein-coupled receptor 19; Mm.4787) NP_006134.1; NM_006143.2; Montpetit, A. and Sinnett, D. (1999) Hum. Genet. 105 (1-2):162-164; O'Dowd, B. F. et al (1996) FEBS Lett. 394 (3):325-329;

(47) GPR54 (KISS1 receptor; KISS1R; GPR54; HOT7T175; AXOR12) NP_115940.2; NM_032551.4; Navenot, J. M. et al (2009) Mol. Pharmacol. 75 (6):1300-1306; Hata, K. et al (2009) Anticancer Res. 29 (2):617-623;

(48) ASPHD1 (aspartate beta-hydroxylase domain containing 1; LOC253982) NP_859069.2; NM_181718.3; Gerhard, D. S. et al (2004) Genome Res. 14 (10B):2121-2127;

(49) Tyrosinase (TYR; OCAIA; OCA1A; tyrosinase; SHEP3) NP_000363.1; NM_000372.4; Bishop, D. T. et al (2009) Nat. Genet. 41 (8):920-925; Nan, H. et al (2009) Int. J. Cancer 125 (4):909-917;

(50) TMEM118 (ring finger protein, transmrembrane 2; RNFT2; FLJ14627) NP_001103373.1; NM_001109903.1; Clark, H. F. et al (2003) Genome Res. 13 (10):2265-2270; Scherer, S. E. et al (2006) Nature 440 (7082):346-351

(51) GPR172A (G protein-coupled receptor 172A; GPCR41; FLJ11856; D15Ertd747e) NP_078807.1; NM_024531.3; Ericsson, T. A. et al (2003) Proc. Natl. Acad.

Sci. U.S.A. 100 (11):6759-6764; Takeda, S. et al (2002) FEBS Lett. 520 (1-3):97-101.

In one embodiment, the antibody binds to one or more of the following polypeptides: BMPR1B; E16; STEAP1; 0772P; MPF; NaPi2b; Sema 5b; PSCA hlg; ETBR; MSG783; STEAP2; TrpM4; CRIPTO; CD21; CD79b; FcRH2; HER2; NCA; MDP; IL20Rα; Brevican; EphB2R; ASLG659; PSCA; GEDA; BAFF-R; CD22; CD79a; CXCR5; HLA-DOB; P2X5; CD72; LY64; FcRH1; IRTA2; TENB2; PMEL17; TMEFF1; GDNF-Ra1; Ly6E; TMEM46; Ly6G6D; LGR5; RET; LY6K; GPR19; GPR54; ASPHD1; Tyrosinase; TMEM118; GPR172A; and CD33.

In one embodiment, the antibody binds to BMPR1B;
In one embodiment, the antibody binds to E16;
In one embodiment, the antibody binds to STEAP1;
In one embodiment, the antibody binds to 0772P;
In one embodiment, the antibody binds to MPF;
In one embodiment, the antibody binds to NaPi2b;
In one embodiment, the antibody binds to Sema 5b;
In one embodiment, the antibody binds to PSCA hlg;
In one embodiment, the antibody binds to ETBR;
In one embodiment, the antibody binds to MSG783;
In one embodiment, the antibody binds to STEAP2;
In one embodiment, the antibody binds to TrpM4;
In one embodiment, the antibody binds to CRIPTO;
In one embodiment, the antibody binds to CD21;
In one embodiment, the antibody binds to CD79b;
In one embodiment, the antibody binds to FcRH2;
In one embodiment, the antibody binds to HER2;
In one embodiment, the antibody binds to NCA;
In one embodiment, the antibody binds to MDP;
In one embodiment, the antibody binds to IL20Rα;
In one embodiment, the antibody binds to Brevican;
In one embodiment, the antibody binds to EphB2R;
In one embodiment, the antibody binds to ASLG659;
In one embodiment, the antibody binds to PSCA;
In one embodiment, the antibody binds to GEDA;
In one embodiment, the antibody binds to BAFF-R;
In one embodiment, the antibody binds to CD22;
In one embodiment, the antibody binds to CD79a;
In one embodiment, the antibody binds to CXCR5;
In one embodiment, the antibody binds to HLA-DOB;
In one embodiment, the antibody binds to P2X5;
In one embodiment, the antibody binds to CD72;
In one embodiment, the antibody binds to LY64;
In one embodiment, the antibody binds to FcRH1;
In one embodiment, the antibody binds to IRTA2;
In one embodiment, the antibody binds to TENB2;
In one embodiment, the antibody binds to PMEL17;
In one embodiment, the antibody binds to TMEFF1;
In one embodiment, the antibody binds to GDNF-Ra1;
In one embodiment, the antibody binds to Ly6E;
In one embodiment, the antibody binds to TMEM46;
In one embodiment, the antibody binds to Ly6G6D;
In one embodiment, the antibody binds to LGR5;
In one embodiment, the antibody binds to RET;
In one embodiment, the antibody binds to LY6K;
In one embodiment, the antibody binds to GPR19;
In one embodiment, the antibody binds to GPR54;
In one embodiment, the antibody binds to ASPHD1;
In one embodiment, the antibody binds to Tyrosinase;
In one embodiment, the antibody binds to TMEM118;
In one embodiment, the antibody binds to GPR172A;
In one embodiment, the antibody binds to CD33.

The parent antibody may also be a fusion protein comprising an albumin-binding peptide (ABP) sequence (Dennis et al. (2002) "Albumin Binding As A General Strategy For Improving The Pharmacokinetics Of Proteins" J Biol Chem. 277:35035-35043; WO 01/45746). Antibodies of the invention include fusion proteins with ABP sequences taught by: (i) Dennis et al (2002) J Biol Chem. 277:35035-35043 at Tables III and IV, page 35038; (ii) US 20040001827 at [0076]; and (iii) WO 01/45746 at pages 12-13, and all of which are incorporated herein by reference. Antibodies may be produced using recombinant methods and compositions, e.g., as described in U.S. Pat. No. 4,816,567 and known in the art. In some embodiments, the antibody is produced in a eukaryotic host cell (e.g., mammalian host cell). In some embodiments, the antibody is produced in a prokaryotic host cell (e.g., E. coli).

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability.

Drug Loading of ADC

The drug loading is the average number of drug moieties per antibody. Drug loading may range from 1 to 8 drugs (D) per antibody (Ab), i.e. where 1, 2, 3, 4, 5, 6, 7, and 8 drug moieties are covalently attached to the antibody. Compositions of ADC include collections of antibodies conjugated with a range of drugs, from 1 to 8. The average number of drugs per antibody in preparations of ADC from conjugation reactions may be characterized by conventional means such as mass spectroscopy, ELISA assay, electrophoresis, and HPLC. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody-drug conjugates.

Typically, fewer than the theoretical maximum of drug moieties is conjugated to an antibody during a conjugation reaction. An antibody may contain, for example, many lysine residues that do not react with the linker-drug intermediate (X-L-D) or linker reagent. Only the most reactive lysine groups may react with an amine-reactive linker reagent. Also, only the most reactive cysteine thiol groups may react with a thiol-reactive linker reagent or linker-drug intermediate. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio, "DAR") of an ADC may be controlled in several different manners, including: (i) limiting the molar excess of linker-drug intermediate or linker reagent relative to antibody, (ii) limiting the conjugation reaction time or temperature, and (iii) partial or limiting reductive conditions for cysteine thiol modification.

Where more than one nucleophilic or electrophilic group of the antibody reacts with a linker-drug intermediate, or linker reagent followed by dimer drug moiety reagent, then the resulting product is a mixture of Antibody-drug conjugate s with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody. Thus the antibody-drug conjugate compositions of the invention include mixtures of antibody-drug conjugate compounds where the antibody has one or more drug moieties and where the drug moieties may be attached to the antibody at various amino acid residues.

Exemplary Drug Moieties

Maytansine and Maytansinoids

In some embodiments, an immunoconjugate comprises an antibody conjugated to one or more maytansinoid molecules. Maytansinoids are derivatives of maytansine, and are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Certain maytansinoids suitable for use as maytansinoid drug moieties are known in the art and can be isolated from natural sources according to known methods or produced using genetic engineering techniques (see, e.g., Yu et al (2002) PNAS 99:7968-7973). Maytansinoids may also be prepared synthetically according to known methods.

Exemplary maytansinoid drug moieties include, but are not limited to, those having a modified aromatic ring, such as: C-19-dechloro (U.S. Pat. No. 4,256,746) (prepared, for example, by lithium aluminum hydride reduction of ansamytocin P2); C-20-hydroxy (or C-20-demethyl)+/−C-19-dechloro (U.S. Pat. Nos. 4,361,650 and 4,307,016) (prepared, for example, by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared, for example, by acylation using acyl chlorides), and those having modifications at other positions of the aromatic ring.

Exemplary maytansinoid drug moieties also include those having modifications such as: C-9-SH (U.S. Pat. No. 4,424,219) (prepared, for example, by the reaction of maytansinol with $H_2S$ or $P_2S5$); C-14-alkoxymethyl(demethoxy/$CH_2$OR)(U.S. Pat. No. 4,331,598); C-14-hydroxymethyl or acyloxymethyl ($CH_2OH$ or $CH_2OAc$) (U.S. Pat. No. 4,450,254) (prepared, for example, from *Nocardia*); C-15-hydroxy/acyloxy (U.S. Pat. No. 4,364,866) (prepared, for example, by the conversion of maytansinol by *Streptomyces*); C-15-methoxy (U.S. Pat. Nos. 4,313,946 and 4,315,929) (for example, isolated from *Trewia nudlflora*); C-18-N-demethyl (U.S. Pat. Nos. 4,362,663 and 4,322,348) (prepared, for example, by the demethylation of maytansinol by *Streptomyces*); and 4,5-deoxy (U.S. Pat. No. 4,371,533) (prepared, for example, by the titanium trichloride/LAH reduction of maytansinol).

Many positions on maytansinoid compounds are useful as the linkage position. For example, an ester linkage may be formed by reaction with a hydroxyl group using conventional coupling techniques. In some embodiments, the reaction may occur at the C-3 position having a hydroxyl group, the C-14 position modified with hydroxymethyl, the C-15 position modified with a hydroxyl group, and the C-20 position having a hydroxyl group. In some embodiments, the linkage is formed at the C-3 position of maytansinol or a maytansinol analogue.

Maytansinoid drug moieties include those having the structure:

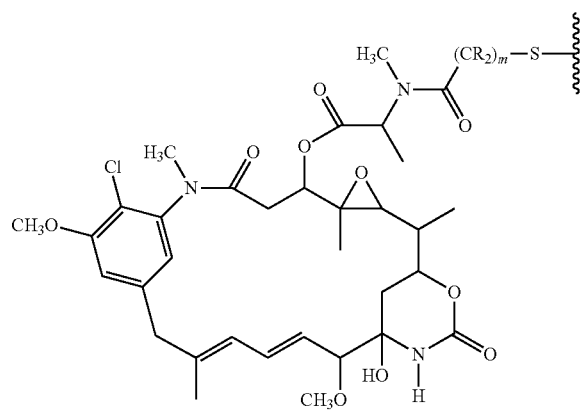

where the wavy line indicates the covalent attachment of the sulfur atom of the maytansinoid drug moiety to a linker of an ADC. Each R may independently be H or a $C_1$-$C_6$ alkyl. The alkylene chain attaching the amide group to the sulfur atom may be methanyl, ethanyl, or propyl, i.e., m is 1, 2, or 3 (U.S. Pat. No. 633,410; U.S. Pat. No. 5,208,020; Chari et al (1992) *Cancer Res.* 52:127-131; Liu et al (1996) *Proc. Natl. Acad. Sci USA* 93:8618-8623).

All stereoisomers of the maytansinoid drug moiety are contemplated for the ADC of the invention, i.e. any combination of R and S configurations at the chiral carbons (U.S.

Pat. No. 7,276,497; U.S. Pat. No. 6,913,748; U.S. Pat. No. 6,441,163; U.S. Pat. No. 633,410 (RE39151); U.S. Pat. No. 5,208,020; Widdison et al (2006) J. Med. Chem. 49:4392-4408, which are incorporated by reference in their entirety). In some embodiments, the maytansinoid drug moiety has the following stereochemistry:

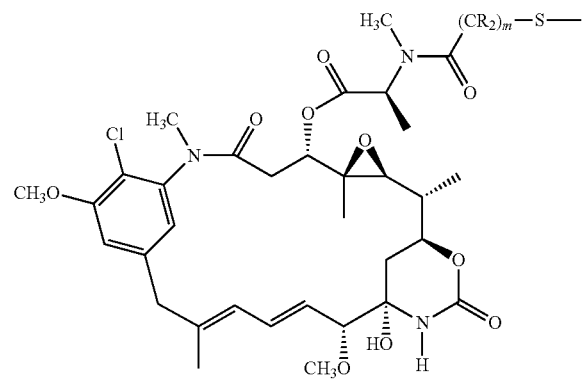

Exemplary embodiments of maytansinoid drug moieties include, but are not limited to, DM1; DM3; and DM4, having the structures:

DM1

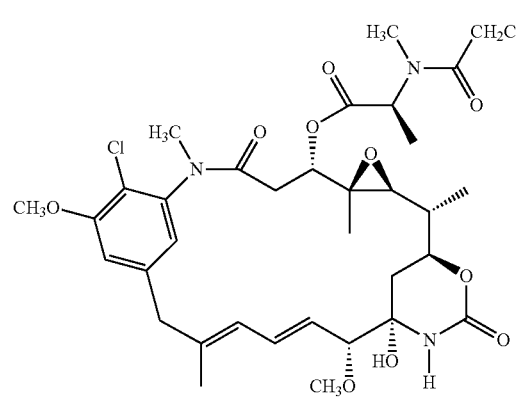

DM3

DM4

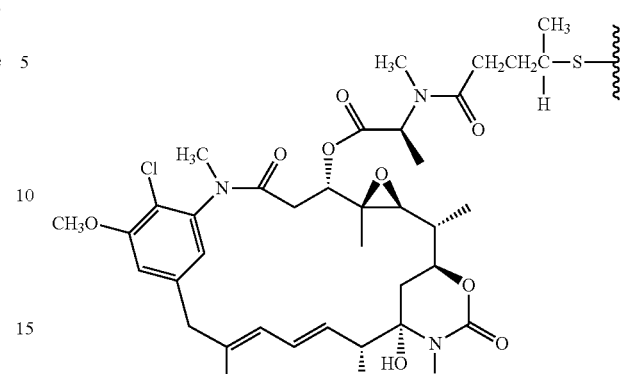

wherein the wavy line indicates the covalent attachment of the sulfur atom of the drug to a linker (L) of an antibody-drug conjugate.

Other exemplary maytansinoid antibody-drug conjugates have the following structures and abbreviations (wherein Ab is antibody and p is 1 to about 20. In some embodiments, p is 1 to 10, p is 1 to 7, p is 1 to 5, or p is 1 to 4):

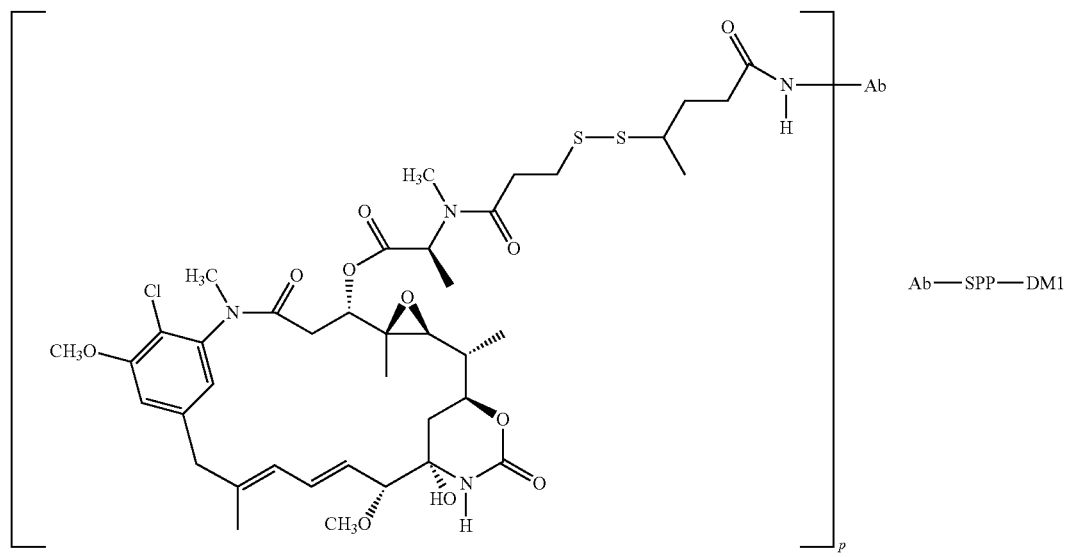

Ab—SPP—DM1

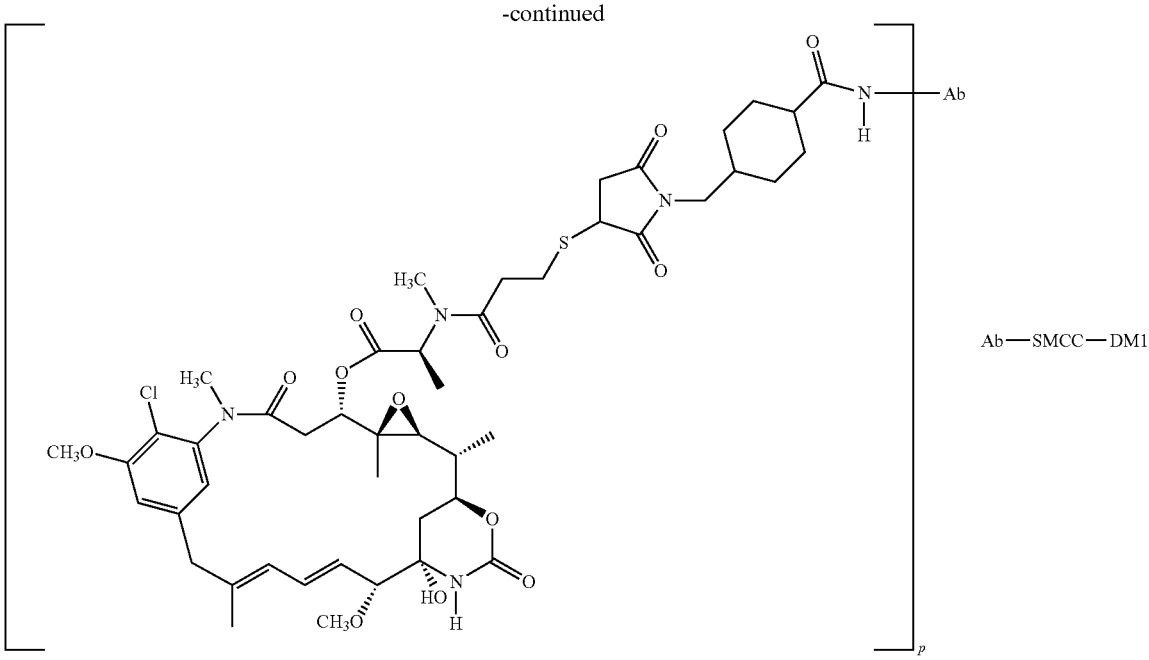

Exemplary antibody-drug conjugates where DM1 is linked through a BMPEO linker to a thiol group of the antibody have the structure and abbreviation:

by reference. See also Liu et al. *Proc. Natl. Acad. Sci. USA* 93:8618-8623 (1996); and Chari et al. *Cancer Research* 52:127-131 (1992).

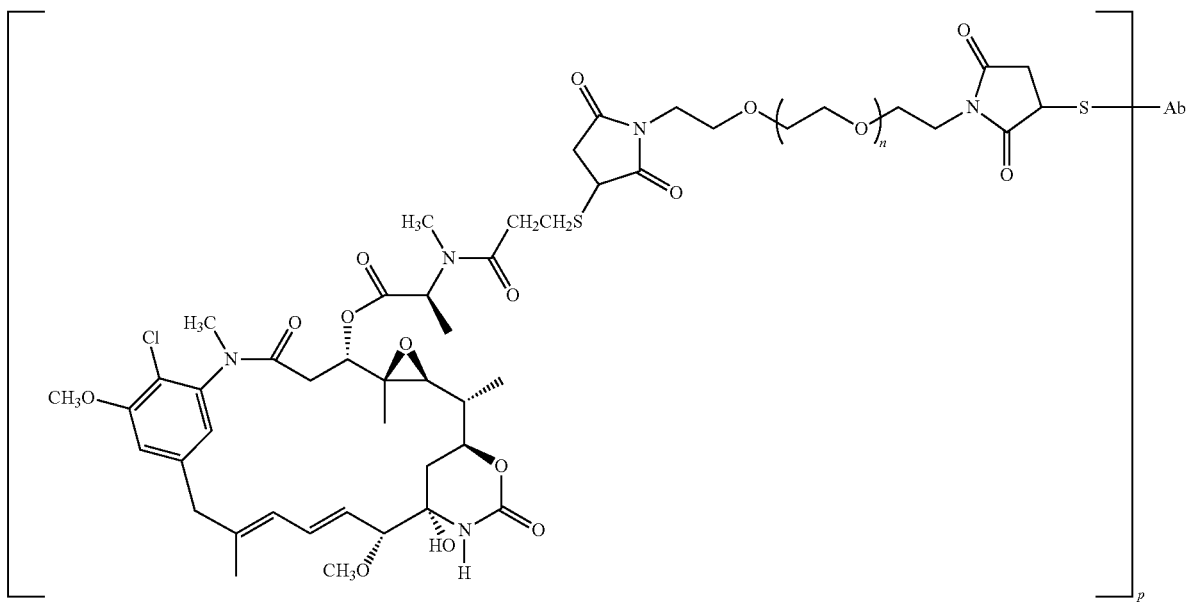

where Ab is antibody; n is 0, 1, or 2; and p is 1 to about 20. In some embodiments, p is 1 to 10, p is 1 to 7, p is 1 to 5, or p is 1 to 4.

Immunoconjugates containing maytansinoids, methods of making the same, and their therapeutic use are disclosed, for example, in U.S. Pat. Nos. 5,208,020 and 5,416,064; US 2005/0276812 A1; and European Patent EP 0 425 235 B1, the disclosures of which are hereby expressly incorporated In some embodiments, antibody-maytansinoid conjugates may be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). In some embodiments, ADC with an average of 3-4 maytansinoid molecules conjugated per antibody molecule has shown efficacy in enhancing cytotoxicity of target cells without negatively affecting the function or solubility of the antibody. In some instances, even one molecule of toxin/antibody is expected to enhance cytotoxicity over the use of naked antibody.

Exemplary linking groups for making antibody-maytansinoid conjugates include, for example, those described herein and those disclosed in U.S. Pat. No. 5,208,020; EP Patent 0 425 235 B1; Chari et al. *Cancer Research* 52:127-131 (1992); US 2005/0276812 A1; and US 2005/016993 A1, the disclosures of which are hereby expressly incorporated by reference.

Calicheamicin

In some embodiments, the immunoconjugate comprises an antibody conjugated to one or more calicheamicin molecules. The calicheamicin family of antibiotics, and analogues thereof, are capable of producing double-stranded DNA breaks at sub-picomolar concentrations (Hinman et al., (1993) *Cancer Research* 53:3336-3342; Lode et al., (1998) *Cancer Research* 58:2925-2928). Calicheamicin has intracellular sites of action but, in certain instances, does not readily cross the plasma membrane. Therefore, cellular uptake of these agents through antibody-mediated internalization may, in some embodiments, greatly enhances their cytotoxic effects. Nonlimiting exemplary methods of preparing antibody-drug conjugates with a calicheamicin drug moiety are described, for example, in U.S. Pat. No. 5,712, 374; U.S. Pat. No. 5,714,586; U.S. Pat. No. 5,739,116; and U.S. Pat. No. 5,767,285.

CBI Dimers

In some embodiments, the drug moiety is a CBI dimer having the following the formula:

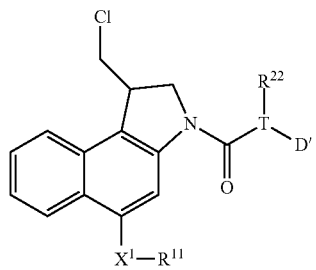

wherein
$R^{11}$ is selected from H, $P(O)_3H_2$, $C(O)NR^{aa}R^{bb}$, or a bond to L;
$R^{22}$ is selected from H, $P(O)_3H_2$, $C(O)NR^{aa}R^{bb}$, or a bond to L;
$R^{aa}$ and $R^{bb}$ are independently selected from H and $C_1$-$C_6$alkyl optionally substituted with one or more F, or $R^{aa}$ and $R^{bb}$ form a five or six membered heterocycloalkyl group;
T is a tether group selected from $C_3$-$C_{12}$alkylene, $Y^1$, $(C_1$-$C_6$alkylene)-$Y^1$—$(C_1$-$C_6$ alkylene), $(C_1$-$C_6$alkylene)-$Y^1$—$(C_1$-$C_6$alkylene)-$Y^1$—$(C_1$-$C_6$alkylene), $(C_2$-$C_6$alkenylene)-$Y^1$—$(C_2$-$C_6$alkenylene), and $(C_2$-$C_6$alkynylene)-$Y^1$—$(C_2$-$C_6$alkynylene);
where $Y^1$ is independently selected from O, S, $NR^{11}$, aryl, and heteroaryl;
where alkylene, alkenylene, aryl, and heteroaryl are independently and optionally substituted with F, OH, $O(C_1$-$C_6$alkyl), $NH_2$, $NHCH_3$, $N(CH_3)_2$, $OP(O)_3H_2$, and $C_1$-$C_6$alkyl, where alkyl is optionally substituted with one or more F;
or alkylene, alkenylene, aryl, and heteroaryl are independently and optionally substituted with a bond to L;

D' is a drug moiety selected from:

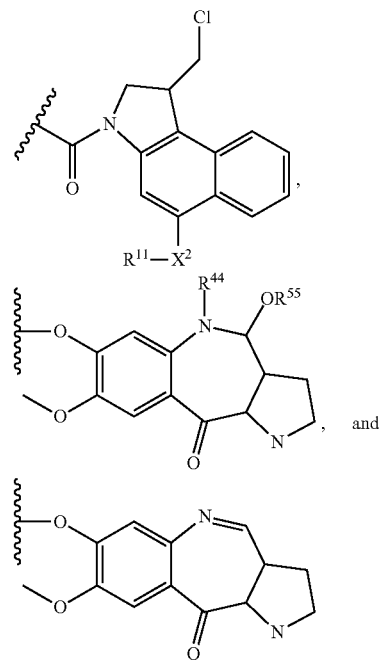

where the wavy line indicates the site of attachment to T;
$X^1$ and $X^2$ are independently selected from O and $NR^{33}$, where $R^{33}$ is selected from H and $C_1$-$C_6$alkyl optionally substituted with one or more F, or $X^1$ and $X^2$ are each independently absent;
$R^{44}$ is H, $CO_2R$, $C(O)$ or a bond to L, where R is $C_1$-$C_6$alkyl or benzyl; and
$R^{55}$ is H or $C_1$-$C_6$alkyl.

Other Drug Moieties

Drug moieties also include geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791); and enzymatically active toxins and fragments thereof, including, but not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, e.g., WO 93/21232. Drug moieties also include compounds with nucleolytic activity (e.g., a ribonuclease or a DNA endonuclease).

Antibiotics

Antibiotics that can be conjugated to an antibody includes clindamycin, novobiocin, retapamulin, daptomycin, GSK-2140944, CG-400549, sitafloxacin, teicoplanin, triclosan, napthyridone, radezolid, doxorubicin, ampicillin, vancomycin, imipenem, doripenem, gemcitabine, dalbavancin, and azithromycin. The mechanisms of bactericidal and bacteriostatic action of such antibiotics include, but are not limited to: (i) inhibition of cell wall, peptidoglycan elongation (vancomycin, teicoplanin, dalbavancin); (ii) inhibition of cell wall, penicillin-binding protein crosslinks (imipenem, doripenem, ampicillin); (iii) cell membrane depolarization (daptomycin); (iv) disruption of DNA replication (gemcitabine); (v) DNA binding (doxorubicin); (vi) enoyl ACP-reductase FABI (CG-400549, triclosan, napthyridone); (vii) inhibition of ribosomal protein synthesis, ribosome 30S (clindamycin, retapamulin, radezolid); and (viii) topoisomerase (topoIIA) inhibitors (novobiocin, sitafloxacin, GSK-2140944). Structurally, most antibiotics can be grouped into: (i) aminoglycosides; (ii) beta-lactams; (iii) macrolides/cyclic peptides; (iv) tetracyclines; (v) fluoroquinolines/fluoroquinolones; (vi) and oxazolidinones. See: Shaw, K. and Barbachyn, M. (2011) Ann. N.Y. Acad. Sci. 1241:48-70; Sutcliffe, J. (2011) Ann. N.Y. Acad. Sci. 1241: 122-152.

In certain embodiments, an immunoconjugate may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. In some embodiments, when an immunoconjugate is used for detection, it may comprise a radioactive atom for scintigraphic studies, for example $Tc^{99}$ or $I^{123}$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983). The radio- or other labels may be incorporated in the immunoconjugate in known ways. For example, a peptide may be biosynthesized or chemically synthesized using suitable amino acid precursors comprising, for example, one or more fluorine-19 atoms in place of one or more hydrogens. In some embodiments, labels such as $Tc^{99}$, $I^{123}$, $Re^{186}$, $Re^{188}$ and $In^{111}$ can be attached via a cysteine residue in the antibody. In some embodiments, yttrium-90 can be attached via a lysine residue of the antibody. In some embodiments, the IODOGEN method (Fraker et al (1978) *Biochem. Biophys. Res. Commun.* 80: 49-57 can be used to incorporate iodine-123. "Monoclonal Antibodies in Immunoscintigraphy" (Chatal, CRC Press 1989) describes certain other methods.

In certain embodiments, an immunoconjugate may comprise an antibody conjugated to a prodrug-activating enzyme. In some such embodiments, a prodrug-activating enzyme converts a prodrug (e.g., a peptidyl chemotherapeutic agent, see WO 81/01145) to an active drug, such as an anti-cancer drug. Such immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), which are useful for converting peptide-containing prodrugs into free drugs; D-alanylcarboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature* 312:604-608 (1984).

Indications and Methods of Treatment

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant solid tumors and hematological disorders such as leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

In certain embodiments, an ADC of the invention comprising an anti-NaPi2b antibody, such as those described above, is used in a method of treating solid tumor, e.g., ovarian, In another embodiment, an ADC of the invention comprising an anti-CD33 antibody, such as those described herein, is used in a method of treating hematological malignancies such as non-Hodgkin's lymphoma (NHL), diffuse large hematopoietic lymphoma, follicular lymphoma, mantle cell lymphoma, chronic lymphocytic leukemia, multiple myeloma, acute myeloid leukemia (AML), and myeloid cell leukemia (MCL), and including B-cell related cancers and proliferative disorders. See: U.S. Pat. No. 8,226, 945; Li et al (2013) Mol. Cancer. Ther. 12(7):1255-1265; Polson et al (2010) Leukemia 24:1566-1573; Polson et al (2011) Expert Opin. Investig. Drugs 20(1):75-85, the contents of which are incorporated by reference.

In another embodiment, an ADC of the invention comprising an anti-MUC16 antibody, such as those described herein, is used in a method of treating ovarian, breast and pancreatic cancers. The cancer may be associated with the expression or activity of a MUC16/CA125/0772P polypeptide. See: WO 2007/001851; U.S. Pat. No. 7,989,595; U.S. Pat. No. 8,449,883; U.S. Pat. No. 7,723,485; Chen et al (2007) Cancer Res. 67(10): 4924-4932; Junutula, et al., (2008) Nature Biotech., 26(8):925-932, the contents of which are incorporated by reference.

In certain embodiments, an ADC of the invention comprising an anti-HER2 antibody, such as those described above, is used in a method of treating cancer, e.g., breast or gastric cancer, more specifically HER2+ breast or gastric cancer, wherein the method comprises administering such ADC to a patient in need of such treatment. In one such embodiment, the ADC comprises the anti-HER2 antibody trastuzumab or pertuzumab.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the Antibody-drug conjugate s may be used in treatment include rheumatologic disorders (such as, for example, rheumatoid arthritis, Sjögren's syndrome, scleroderma, lupus such as systemic lupus erythematosus (SLE) and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight.

EXPERIMENTALS

Method of preparing Peptidomimetic Linker Drug moieties; PCT/US2014/042560 is incorporated by reference herein.

Example 1. 7-(4-((4-(((2R,5S,Z)-5-(benzyloxycarbonylamino)-4-fluoro-6-methyl-2-(3-ureidopropyl)hept-3-enamido)benzyloxy)carbonyl)piperazin-1-yl)-1-ethyl-6-fluoro-4-oxo-1,4-dihydroquinoline-3-carboxylic acid

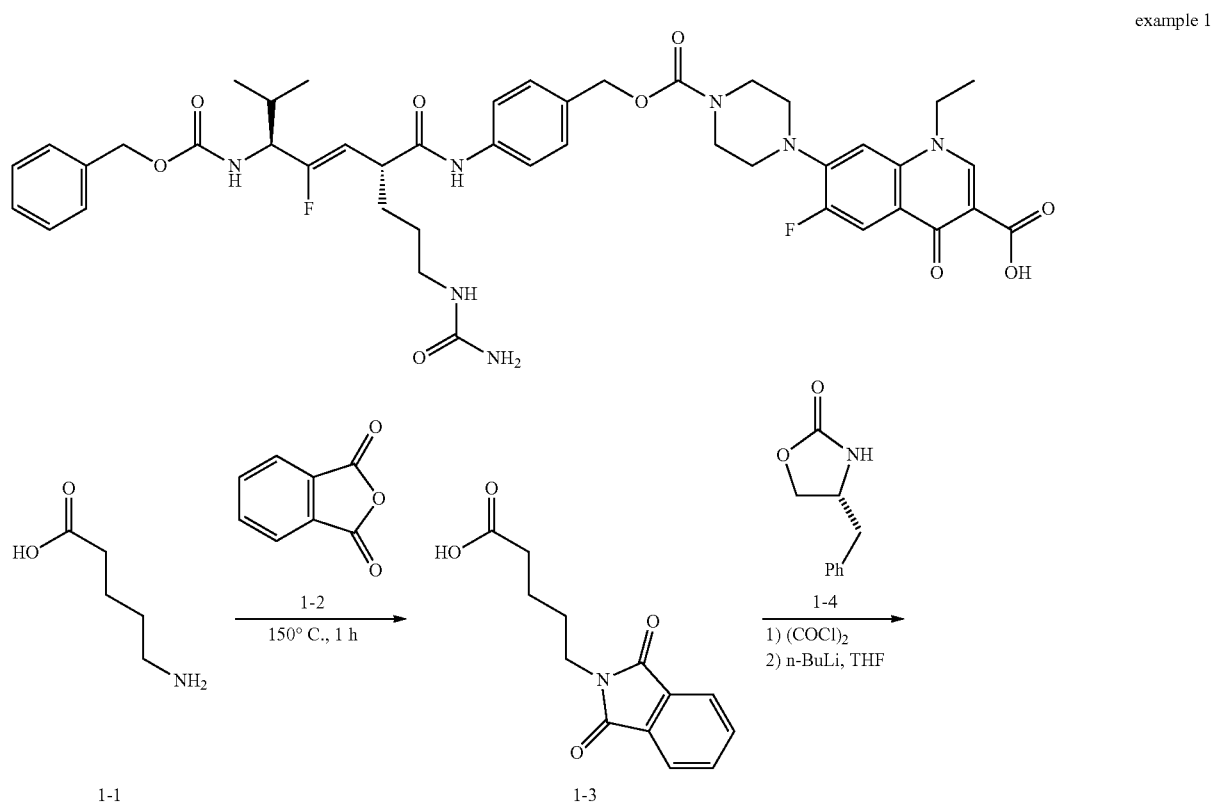

example 1

-continued
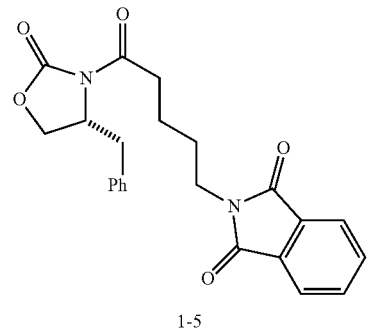
1-5
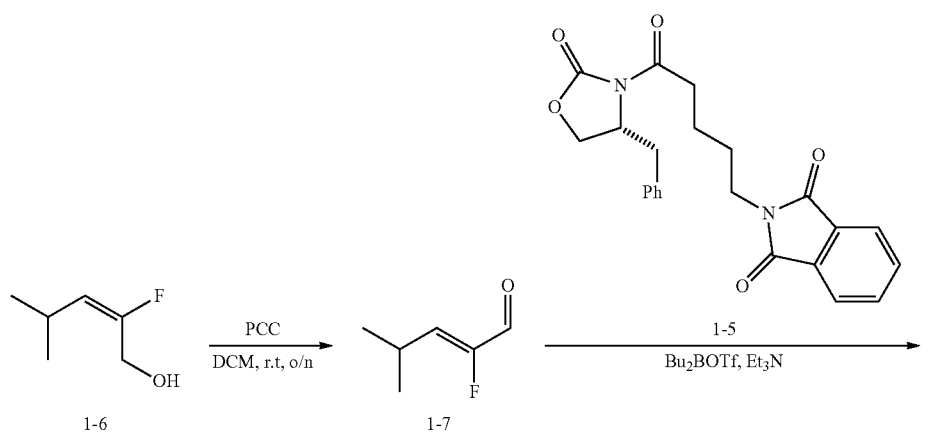
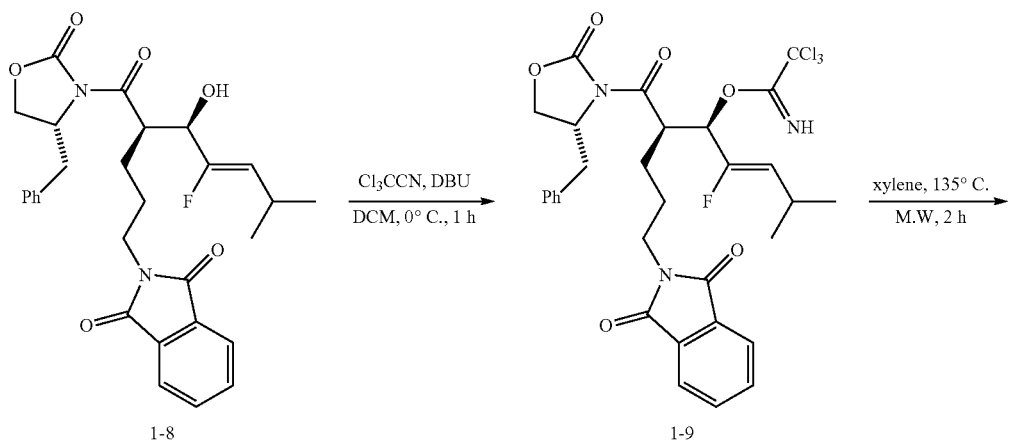
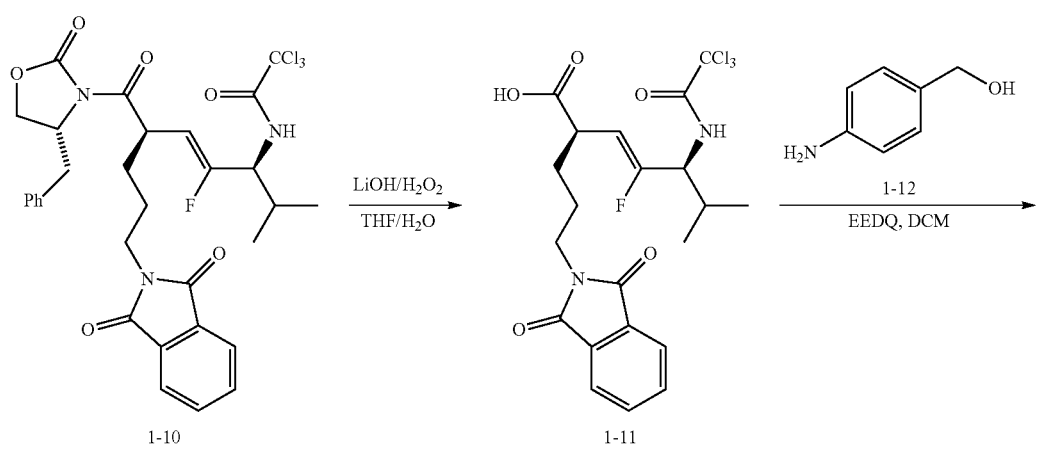

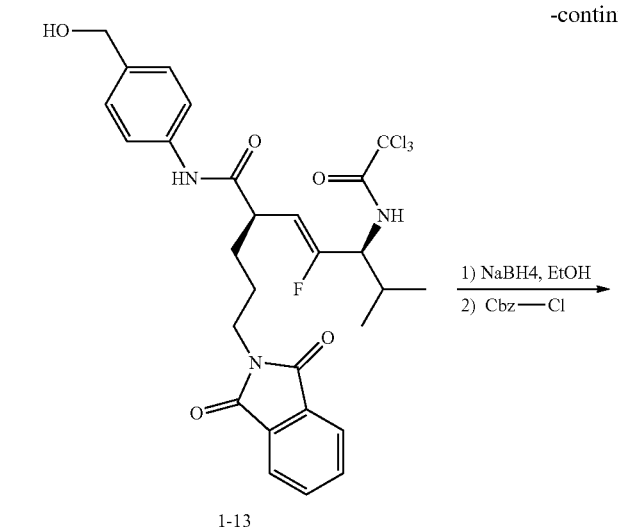

1-13

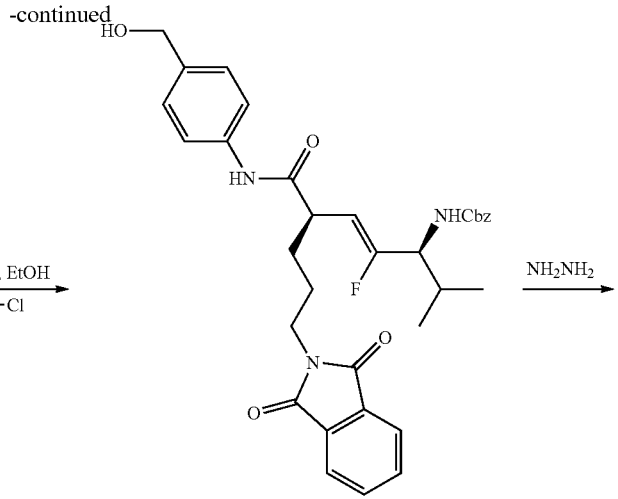

1-14

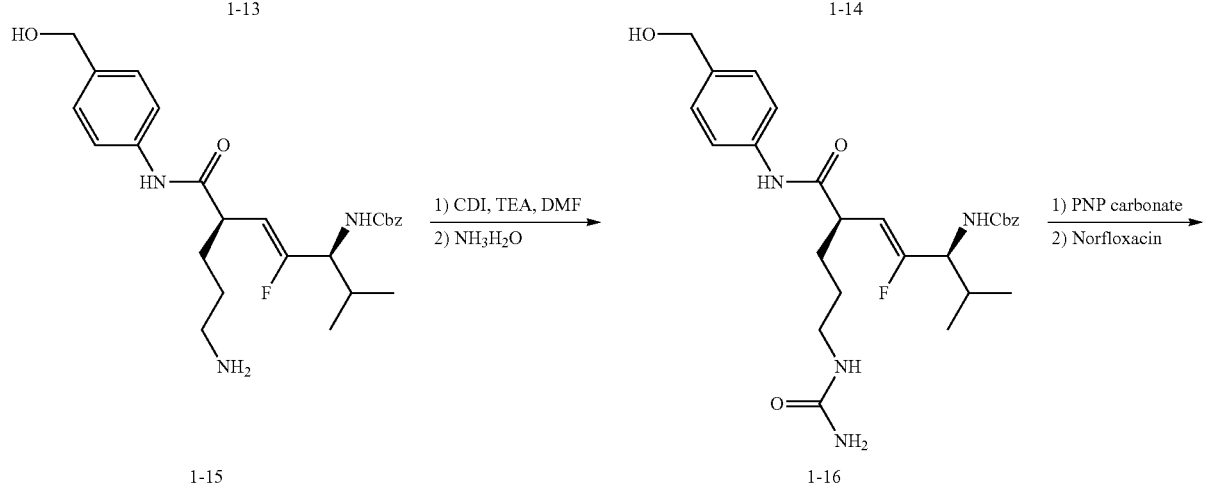

example 1

Step 1

A mixture of 1-1 (10.0 g, 85.36 mmol), 1-2 (13.3 g, 89.79 mmol) was stirred at 150° C. for 1 h. The mixture was cooled to 25° C., the solid was dissolved in hot water. The mixture was cooled in an ice bath and the precipitate was collected by filtration and washed with water. The filter cake was dried to give 1-3 as white solid (19.0 g, 90.0%).

$^1$H NMR (400 MHz, DMSO-$d_6$) δ 11.96 (br, 1H), 7.78-7.77 (m, 4H), 3.52 (t, J=6.8 Hz, 2H), 2.18 (t, J=7.2 Hz, 2H), 1.59-1.51 (m, 2H), 1.47-1.41 (m, 2H).

Step 2

To a mixture of 1-3 (9.0 g, 36.40 mmol) in anhydrous DCM (100 mL) were added (COCl)$_2$ (15.0 mL, 157.76 mmol), DMF (1 mL) dropwise at r.t. After the reaction mixture was stirred at r.t for 0.5 h, it was concentrated under reduced pressure. The residue co-evaporated with anhydrous THF (60 mL) to give the acyl chlorine as yellow solid.

To a mixture of 1-4 (6.6 g, 37.25 mmol) in anhydrous THF (60 mL) was added n-BuLi (15.0 mL, 2.5 M, 37.5 mmol) dropwise at −78° C. under N$_2$. The acyl chloride in THF (40 mL) was added slowly into the mixture at −78° C.

The reaction mixture was stirred at −78° C. for 15 min, and quenched with aq. NH$_4$Cl solution (30 mL). The mixture was partitioned between EtOAc and water. The combined organic layers was dried over Na$_2$SO$_4$, filtered, and concentrated. The residue was purified by column chromatography on silica gel (PE/EtOAc 3:1) to give crude compound 1-5 as white solid (13.0 g, 87.9%).

$^1$H NMR (400 MHz, DMSO-d$_6$) δ 7.89-7.83 (m, 4H), 7.32-7.28 (m, 2H), 7.25-7.22 (m, 1H), 7.19-7.17 (m, 2H), 4.66-4.60 (m, 1H), 4.30 (t, J=8.4 Hz, 1H), 4.17 (dd, J=9.2, 2.8 Hz, 1H), 3.61 (t, J=6.4 Hz, 2H), 3.00-2.78 (m, 4H), 1.70-1.60 (m, 4H).

Step 3

To a solution of 1-6 (3.0 g, 25.39 mmol) in DCM (100 mL) was added PCC (10.9 g, 50.78 mmol). After the mixture was stirred at 25° C. for 16 h under N$_2$, it was filtered through a silica plug. The filtrate was concentrated under reduced pressure at a bath temperature of 25° C. to give compound 1-7 as an oil (1.8 g, 61.0%).

$^1$H NMR (400 MHz, CDCl$_3$) δ 9.18 (d, J=18.4 Hz, 1H), 5.79 (dd, J=32.8, 9.2 Hz, 1H), 3.02-2.93 (m, 1H), 1.13 (d, J=6.8 Hz, 6H).

Step 4

A solution of 1-5 (6.0 g, 14.7 mmol) in DCM (20 mL) was cooled to 0° C. with an ice bath. Bu$_2$BOTf in DCM (1M, 15 mL, 15 mmol) was added dropwise, followed by Et$_3$N (3.03 g, 30 mmol) at a rate to keep the internal temperature below 3° C. The ice bath was replaced by a dry ice-acetone bath. When the internal temperature dropped below −65° C., compound 1-7 (1.5 g, 12.9 mmol) in DCM (10 mL) was added dropwise. The solution was stirred for 20 min in the dry ice-acetone bath, then for 1 h at ice bath temperature. The reaction mixture was quenched with aqueous phosphate buffer (pH=7.0, 20 mL) and MeOH (10 mL). To this cloudy solution was added a mixture of MeOH/30% H$_2$O$_2$ (2:1, 20 mL) at a rate to keep the internal temperature below 10° C. After the solution was stirred for an additional 1 h, the volatile was removed on a rotary evaporator at a bath temperature of 25-30° C. The slurry was extracted with EtOAc (50 mL×3). The combined organic layer was washed with saturated Na$_2$SO$_3$ solution (15 mL), 5% NaHCO$_3$ solution (30 mL) and brine (25 mL), dried over Na$_2$SO$_4$, filtered and concentrated. The residue was purified by column chromatography on silica gel (PE/EtOAc 3:1) to give crude 1-8 as oil (4.0 g, 59.7%).

LCMS (ESI): m/z 505.0 [M−17].

Step 5

To a solution of 1-8 (4.0 g, 7.65 mmol) and Cl$_3$CCN (1.67 g, 11.48 mmol) in DCM (20 mL) was added DBU (234 mg, 1.53 mmol) at 0° C. under N$_2$. The mixture was stirred at 0° C. for 1 h. After removal of the solvent, the residue was purified by column chromatography on silica gel (5%-20% petroleum in EtOAc) to give 1-9 (3.0 g, 58.8%).

LCMS (ESI): m/z 505.1 [M−160].

$^1$H NMR (400 MHz, CDCl$_3$) δ 8.47 (s, 1H), 7.83-7.80 (m, 2H), 7.72-7.69 (m, 2H), 7.36-7.28 (m, 2H), 7.28-7.22 (m, 3H), 5.69-5.63 (q, 1H), 4.89 (dd, J=37.6, 9.6 Hz, 1H), 4.63-4.58 (m, 1H), 4.20-4.11 (m, 2H), 3.74-3.69 (m, 2H), 3.35 (dd, J=13.2, 3.2 Hz, 1H), 2.78-2.69 (m, 2H), 1.99-1.85 (m, 2H), 1.80-1.76 (m, 2H), 0.96-0.92 (q, 6H).

Step 6

A solution of 1-9 (3.0 g, 4.50 mmol) in xylene (5 mL) was heated in microwave for 2 h at 135° C. The mixture was cooled to 25° C. and purified by column chromatography on silica gel (5%-10%-50% PE in EtOAc) to give 1-10 (1.4 g, 46.7%).

LCMS (ESI): m/z 685.0 [M+H$_2$O].

$^1$H NMR (400 MHz, CDCl$_3$) δ 7.83-7.81 (m, 2H), 7.71-7.69 (m, 2H), 7.36-7.32 (m, 2H), 7.29-7.25 (m, 1H), 7.21-7.19 (m, 2H), 6.90 (d, J=8.8 Hz, 1H), 5.11 (dd, J=36.4, 9.6 Hz, 1H), 4.81-4.76 (m, 1H), 4.68-4.64 (m, 1H), 4.30-4.16 (m, 3H), 3.75-3.68 (m, 2H), 3.27 (dd, J=13.2, 3.2 Hz, 1H), 2.80-2.74 (q, 1H), 2.08-2.05 (m, 1H), 1.93-1.90 (m, 1H), 1.76-1.70 (m, 2H), 1.65-1.62 (m, 1H), 1.00 (dd, J=6.8, 3.2 Hz, 6H).

Step 7

To a solution of compound 1-10 (1.4 g, 2.1 mmol) in THF/H$_2$O (v/v 4:1, 10 mL) was added H$_2$O$_2$ (1.43 g, 30% in water, 12.6 mmol), followed by LiOH.H$_2$O (264.6 mg, 6.3 mmol). After the solution was stirred for 1.5 h at 25° C., saturated Na$_2$SO$_3$ solution (8 mL) was added. Solvent was removed and the residue was extracted with DCM (20 mL×2). The aqueous solution was acidified to pH=1 with 1M HCl, extracted with EtOAc/MeOH (10/1, 25 mL×3). The combined organic layer was dried over Na$_2$SO$_4$, filtered, and concentrated to give compound 1-11 (1.0 g, 93.4%).

LCMS (ESI): m/z 527.0 [M+Na$^+$].

Step 8

To a solution of compound 1-11 (1.0 g, 1.97 mmol) and (4-aminophenyl) methanol (364 mg, 2.96 mmol) in DCM/MeOH (v/v 2:1, 7.5 mL) was added EEDQ (732 mg, 2.96 mmol) at 0° C. under N$_2$. The mixture was stirred at 25° C. for 16 h. The solvent was removed, the residue was purified by column chromatography on silica gel (30% petroleum in EtOAc) to give crude compound 1-13 (1.0 g, 82.8%).

LCMS (ESI): m/z 614.0 [M+H$^+$].

Step 9

To a solution of compound 1-13 (1.0 g, 1.63 mmol) in EtOH (15 mL) was added NaBH$_4$ (364.8 mg, 9.60 mmol) at 0° C. The mixture was stirred at 25° C. for 2 h and water (10 mL) was added to quench the reaction. Then Cbz-Cl (410.4 mg, 2.40 mmol) was added dropwise at 0° C. The mixture was stirred at 0° C. for 1 h. The mixture was diluted with water, and extracted with DCM (25 mL×3). The organic layer was dried over Na$_2$SO$_4$, concentrated under reduced pressure. The residue was purified by column chromatography on silica gel (DCM/MeOH=20:1-5:1) to give crude compound 1-14 (300 mg, 31.2%).

LCMS (ESI): m/z 602.0 [M+H].

Step 10

To a solution of compound 1-14 (300 mg, 0.498 mmol) in EtOH (10 mL) was added NH$_2$NH$_2$.xH$_2$O (48 mg, 50%, 0.748 mmol) dropwise. The mixture was heated at reflux for 1 h. The reaction mixture was concentrated, and the residue (1-15) was used directly to the next reaction without further purification.

Step 11

To a stirred solution of compound 1-15 (281.0 mg, 0.496 mmol) in DMF (5 mL) was added TEA (100 mg, 0.992 mmol) and CDI (162.7 mg, 0.992 mmol). After the mixture was stirred at 29° C. for 1 h, NH$_3$H$_2$O (5 mL) was added, and the mixture was stirred at 29° C. for 16 h. The reaction mixture was filtered and the filtrate was purified by prep-HPLC to give compound 1-16 (50 mg, 19.6%) as white solid.

LCMS (ESI): m/z 515.1 [M+1].

$^1$H NMR (400 MHz, DMSO-d$_6$) δ 9.94 (s, 1H), 7.66 (d, J=9.2 Hz, 1H), 7.53 (d, J=8.4 Hz, 2H), 7.35-7.29 (m, 5H), 7.22 (d, J=8.4 Hz, 2H), 5.94 (t, J=6.0 Hz, 1H), 5.36 (s, 2H), 5.10 (t, J=6.0 Hz, 1H), 5.05-4.94 (m, 3H), 4.42 (d, J=4.2 Hz, 2H), 3.92-3.83 (m, 1H), 3.46-3.44 (m, 1H), 3.01-2.90 (m, 2H), 1.92-1.85 (m, 1H), 1.65-1.63 (m, 1H), 1.44-1.28 (m, 3H), 0.88 (t, J=6.4 Hz, 6H).

Step 12

To the mixture of compound 1-16 (50 mg, 0.097 mmol) in anhydrous DMF (3 mL) was added DIPEA (63 mg, 0.485 mmol). PNP carbonate (87 mg, 0.291 mmol) was added at 25° C. The reaction mixture was stirred at 25° C. for 8 h, and norfloxacin (93 mg, 0.291 mmol) was added. After the mixture was stirred at 25° C. for another 3 h, it was filtered, and the filtrate was purified by prep-HPLC to give example 1 (35 mg, 42.0%).

LCMS (ESI): RT=0.885 min, M/2+H$^+$=430.7. method=5-95/2 min.

$^1$H NMR (400 MHz, DMSO-d$_6$) δ 15.32 (s, 1H), 10.04 (s, 1H), 8.95 (s, 1H), 7.94 (d, J=12.8 Hz, 1H), 7.66 (d, J=8.8 Hz, 1H), 7.60 (d, J=8.8 Hz, 2H), 7.34-7.28 (m, 7H), 7.21 (d, J=7.2 Hz, 1H), 5.94 (t, J=5.2 Hz, 1H), 5.36 (s, 2H), 5.06-4.94 (m, 5H), 4.59-4.57 (q, 2H), 3.92-3.84 (m, 1H), 3.61 (s, 4H), 3.49-3.43 (q, 1H), 3.33-3.31 (m, 4H), 3.01-2.90 (m, 2H), 1.90-1.83 (m, 1H), 1.68-1.65 (m, 1H), 1.41 (d, J=6.8 Hz, 5H), 1.33-1.23 (m, 1H), 0.86 (t, J=6.8 Hz, 6H).

Example 2. 7-(4-((4-(((2R,5S,Z)-5-(benzyloxycarbonylamino)-4-fluoro-2,6-dimethylhept-3-enamido)benzyloxy)carbonyl)piperazin-1-yl)-1-ethyl-6-fluoro-4-oxo-1,4-dihydroquinoline-3-carboxylic acid

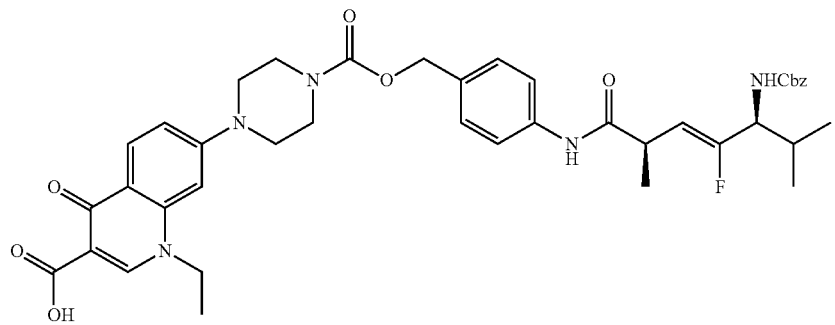

example 2

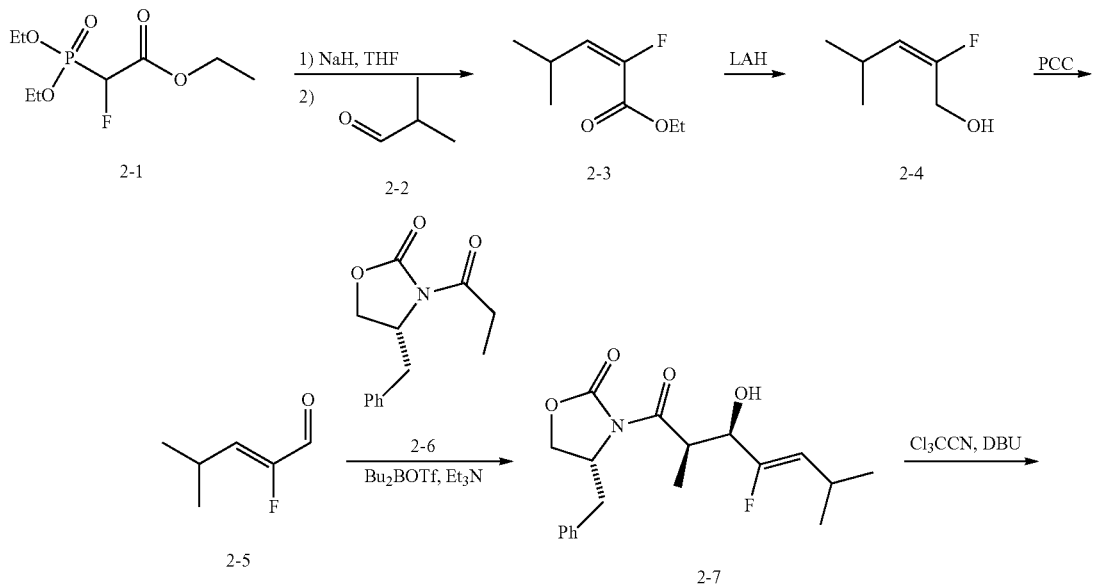

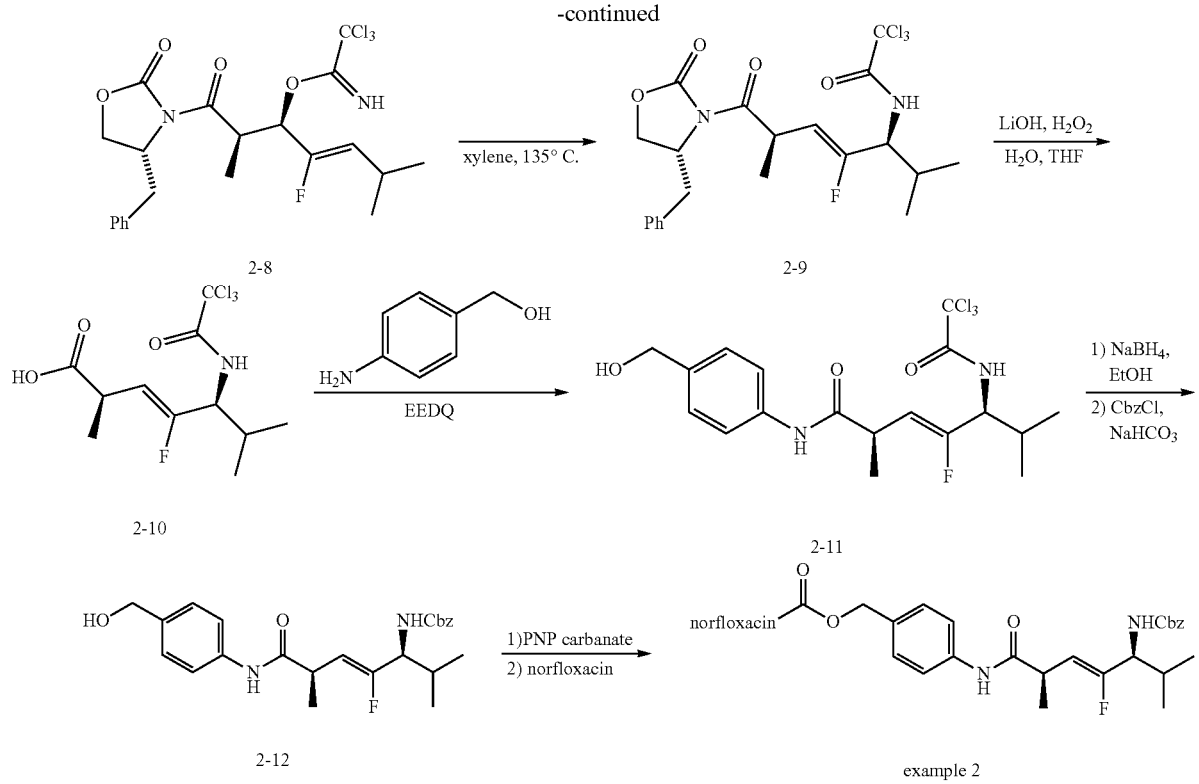

Step 1

To a mixture of NaH (1.82 g, 45.5 mmol) in THF (200 mL) was added 2-1 (10.0 g, 41.3 mmol) in THF (20 mL) dropwise at 0° C. The mixture was stirred at 0° C. for 1 h and then cooled to −78° C. Compound 2-2 (2.98 g, 41.3 mmol) in THF (5 mL) was added dropwise and the mixture was warmed to 25° C. slowly, and stirred at 25° C. for 16 h. Saturated NH$_4$Cl solution was slowly added at 0° C. followed by water (50 mL) and the mixture was extracted with EtOAc (80 mL×2).

The organic layer was dried over Na$_2$SO$_4$, filtered, concentrated and purified by column chromatography on silica gel (PE/EtOAc=50:1) to give 2-3 (2.2 g, 33%).

$^1$H NMR (400 MHz, CDCl$_3$) δ 5.73 (dd, J=10.4, 22.0 Hz, 1H), 4.30 (q, J=7.2 Hz, 2H), 3.37-3.31 (m, 1H), 1.35 (t, J=7.2 Hz, 3H), 1.08-1.04 (m, 6H).

Step 2

To a solution of 2-3 (12.0 g, 74.91 mmol) in THF (80 mL) was added LiAlH$_4$ (5.69 g, 149.82 mmol) at 0° C. After the mixture was stirred for 2 h at 0° C., it was quenched with saturated NH$_4$Cl solution (1 mL). The organic solvent was removed under reduced pressure and the mixture was diluted with water (50 mL) and extracted with EtOAc (100 mL×2). The organic layer was dried over Na$_2$SO$_4$, filtered, concentrated to give crude product 2-4 (8.0 g).

$^1$H NMR (400 MHz, CDCl$_3$) δ 5.06 (dd, J=10.4, 21.2 Hz, 1H), 4.24 (d, J=21.2 Hz, 2H), 2.42-2.37 (m, 1H), 1.03-0.99 (m, 6H).

Step 3

To a solution of 2-4 (8.0 g, 33.86 mmol) in DCM (100 mL) was added PCC (29.2 g, 67.72 mmol) at 25° C. After the mixture was heated at reflux for 3 h under N$_2$, it was cooled to 25° C. and filtered through a plug of silica gel. The filtrate concentrated to give crude 2-5 (5.1 g).

$^1$H NMR (400 MHz, CDCl$_3$) δ 9.19 (d, J=18.0 Hz, 1H), 5.79 (dd, J=9.6, 32.8 Hz, 1H), 3.01-2.95 (m, 1H), 1.15-1.13 (m, 6H).

Step 4

Bu$_2$BOTf in DCM (1M, 66 mL, 66 mmol) was added dropwise to solution of 2-6 (15.37 g, 65.88 mmol) in DCM (200 mL), followed by Et$_3$N (8.89 g, 87.84 mmol) at a rate as to keep the internal temperature below 3° C. It was cooled to −65° C., and 2-5 (5.1 g, 43.92 mmol) in DCM (10 mL) was added dropwise. The solution was stirred for 20 min in the dry ice-acetone bath, then for 1 h at ice bath. The reaction mixture was quenched with a pH 7 aqueous phosphate buffer (50 mL) and MeOH (150 mL). To this cloudy solution was added a mixture of MeOH/30% H$_2$O$_2$ (2:1, 90 mL) at such a rate as keep the internal temperature below 10° C. After the solution was stirred for an additional 1 h, the volatile was removed on a rotary evaporator at a bath temperature of 25-30° C. The resulting slurry was extracted with EtOAc (150 mL×3). The combined organic layer was washed with saturated Na$_2$SO$_3$ solution (150 mL), 5% NaHCO$_3$ solution (150 mL) and brine (150 mL), dried over Na$_2$SO$_4$, filtered and concentrated. The residue was purified by column chromatography on silica gel (PE/EtOAc 3:1) to give 2-7 (8.8 g, 57%).

$^1$H NMR (400 MHz, CDCl$_3$) δ 7.36-7.27 (m, 3H), 7.21-7.19 (m, 2H), 4.85 (dd, J=9.2, 38.4 Hz, 1H), 4.73-4.67 (m, 1H), 4.53-4.50 (m, 1H), 4.27-4.19 (m, 2H), 3.99-3.95 (m, 1H), 3.24 (dd, J=3.2, 13.6 Hz, 1H), 3.17-3.16 (m, 1H), 2.83-2.74 (m, 2H), 1.29 (d, J=6.8 Hz, 3H), 1.02-0.99 (m, 6H).

Step 5

To a solution of 2-7 (2.0 g, 5.72 mmol) and Cl$_3$CCN (1.24 g, 8.58 mmol) in DCM (15 mL) was added DBU (174 mg, 1.14 mmol) at 0° C. under N$_2$. After the mixture was stirred at 0° C. for 1 h, solvent was removed and the residue was purified by column chromatography on silica gel (5%-20% petroleum in EtOAc) to give 2-8 (1.55 g, 55%).

$^1$H NMR (400 MHz, CDCl$_3$) δ 8.47 (s, 1H), 7.35-7.27 (m, 3H), 7.25-7.19 (m, 2H), 5.81-5.75 (m, 1H), 4.98-4.85 (m, 1H), 4.64-4.59 (m, 1H), 4.40-4.36 (m, 1H), 4.22-4.17 (m, 2H), 3.27-3.24 (m, 1H), 2.83-2.71 (m, 2H), 1.40-1.38 (m, 3H), 0.99-0.95 (m, 6H).

Step 6

A solution of 2-8 (1.55 g, 3.14 mmol) in xylene (10 mL) was heated at 135° C. for 30 h. It was cooled to r.t. and the solvent was removed under reduced pressure. The residue was purified by column chromatography on silica gel (5%-10%-50% of petroleum in EtOAc) to give 2-9 (450 mg, 29%).

$^1$H NMR (400 MHz, CDCl$_3$) δ 7.35-7.28 (m, 3H), 7.21-7.20 (m, 2H), 6.75 (d, J=8.4 Hz, 1H), 5.20 (dd, J=9.2, 37.6 Hz, 1H), 4.76-4.65 (m, 2H), 4.28-4.17 (m, 3H), 3.27-3.23 (m, 1H), 2.79 (dd, J=9.6, 13.2 Hz, 1H), 2.07-2.00 (m, 1H), 1.33 (d, J=7.2 Hz, 3H), 1.00-0.94 (m, 6H).

Step 7

To a solution of 2-9 (950 mg, 1.92 mmol) in THF and H$_2$O (v/v 4:1, 10 mL) was added H$_2$O$_2$ (1.38 mg, 11.52 mmol), followed by LiOH.H$_2$O (242 mg, 5.76 mmol) in water (2 mL). After the solution was stirred at 10° C. for 1 h, saturated Na$_2$SO$_3$ solution (8 mL) was added. Solvent was removed, and the residue was washed with DCM (20 mL×2). The aqueous solution was acidified to pH 1 with 1M HCl, and extracted with EtOAc (25 mL×3). The organic layer was dried over Na$_2$SO$_4$, filtered, concentrated to give 2-10 (420 mg, 65%).

LCMS (ESI): m/z 334.0 [M+H$^+$].

Step 8

To a solution of 2-10 (420 mg, 1.26 mmol) and (4-aminophenyl)methanol (233 mg, 1.89 mmol) in DCM (10 mL) was added EEDQ (623 mg, 2.52 mmol) at 0° C. under N$_2$. After the mixture was stirred at 10° C. for 3 h, solvent was removed, and the residue was purified by column chromatography on silica gel (30% of petroleum in ethyl acetate) to give 2-11 (300 mg, 54%).

LCMS (ESI): m/z 439.0 [M+H$^+$].

Step 9

To a solution of 2-11 (300 mg, 0.682 mmol) in EtOH (6 mL) was added NaBH$_4$ (300 mg, 7.94 mmol) at 0° C. The mixture was stirred at 10° C. for 3 h. Water (0.5 mL) was added, and EtOH was removed under reduced pressure. The crude was dissolved in a mixture of THF (4 mL) and saturated NaHCO$_3$ solution (4 mL), and CbzCl (140 mg, 8.18 mmol) was added at 10° C. After the mixture was stirred at 10° C. for 2 h, solvent was removed and the residue was extracted with DCM (8 mL×2). The organic layer was dried over Na$_2$SO$_4$, concentrated, and purified by column chromatography on silica gel (PE/EtOAc=2:1) to give 2-12 (125 mg, 43%).

$^1$H NMR (400 MHz, MeOD) δ 7.53-7.46 (m, 2H), 7.36-7.25 (m, 7H), 5.11-5.00 (m, 3H), 4.56 (s, 2H), 3.94-3.87 (m, 1H), 3.63-3.59 (m, 1H), 1.98-1.92 (m, 1H), 1.27 (d, J=6.8 Hz, 3H), 0.96-0.93 (m, 6H).

LCMS (ESI): m/z 429.2 [M+H$^+$].

Step 10

To a solution of 2-12 (20 mg, 0.0467 mmol) in DCM (2 mL) was added PNP carbonate (43 mg, 0.140 mmol) and DIEA (24 mg, 0.187 mmol) at 10° C. After the mixture was heated at reflux for 16 h, solvent was removed, and the residue was dissolved in DMF (2 mL). To this solution were added DIEA (24 mg, 0.187 mmol) and norfloxacin (22 mg, 0.070 mmol) at 10° C., and the resulting solution was stirred at 10° C. for 1 h. After the solvent was removed, the residue was purified by prep-HPLC to give example 2 (14.1 mg, 39%).

$^1$H NMR (400 MHz, DMSO-d$_6$) δ 15.35 (br, 1H), 10.02 (s, 1H), 8.95 (s, 1H), 7.95-7.91 (m, 1H), 7.69-7.58 (m, 3H), 7.34-7.19 (m, 8H), 5.12-5.00 (m, 5H), 4.59-4.57 (m, 2H), 3.87-3.81 (m, 1H), 3.60-3.51 (m, 5H), 3.30 (s, 4H), 1.89-1.83 (m, 1H), 1.40 (t, J=7.2 Hz, 3H), 1.20-1.81 (m, 3H), 0.87 (m, 6H).

LCMS (ESI): m/z 774.8 [M+H$^+$]

Example 3. 1-ethyl-6-fluoro-4-oxo-7-(4-((4-((S)-2-(1-((S)-1-(thiophen-3-yl)ethylcarbamoyl) cyclobutanecarboxamido)-5-ureidopentanamido)benzyloxy) carbonyl)piperazin-1-yl)-1,4-dihydroquinoline-3-carboxylic acid

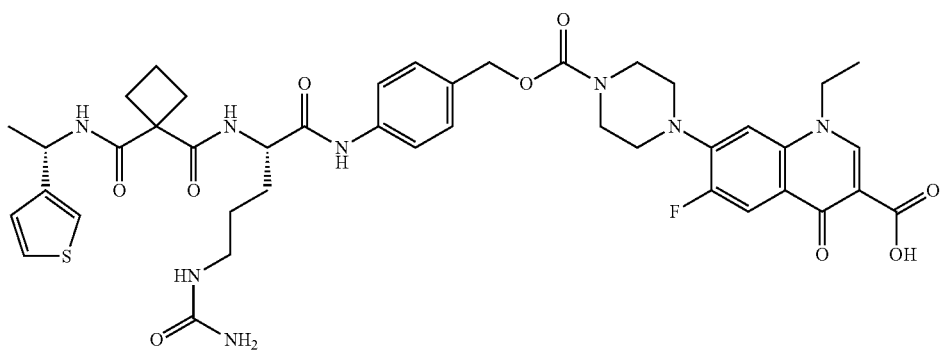

example 3

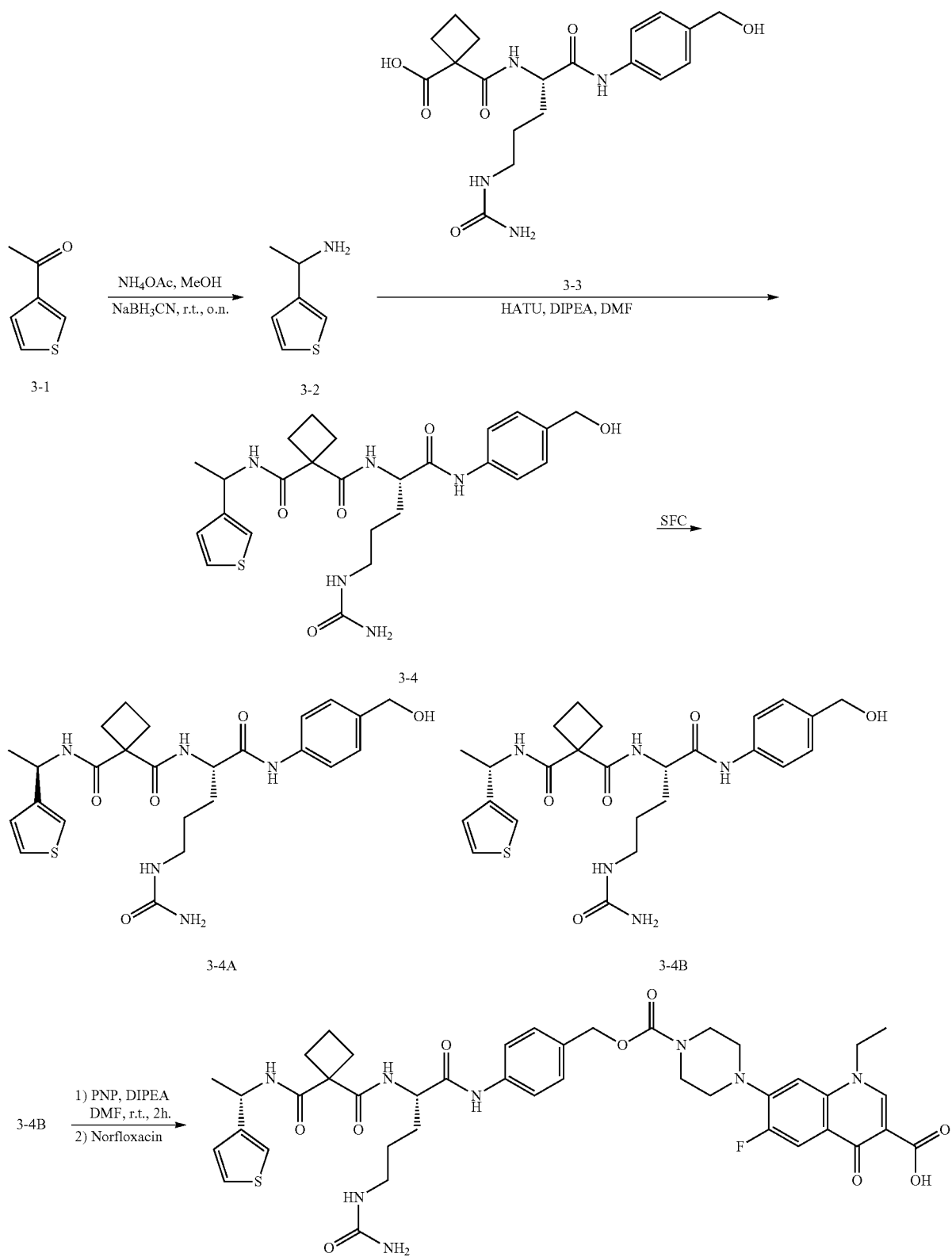
example 3

Step 1

To a solution of compound 3-1 (2 g, 15.9 mmol) in MeOH (20 mL) was added NH$_4$OAc (12.2 g, 0.159 mol) and NaBH$_3$CN (3.5 g, 55.5 mmol) at 20° C. After the mixture was stirred at 20° C. for 16 h, it was concentrated. The residual was partitioned between EtOAc (50 mL) and NaOH solution (5 M, 5 mL) (adjust pH>13). The organic layer was washed with brine (20 mL×2), concentrated and purified by column (20%-30% MeOH in DCM) to give the crude compound 3-2 (800 mg, 40% yield).

$^1$H NMR (400 MHz, DMSO-d$_6$) δ 7.63-7.61 (d, J=8.0 Hz, 1H), 7.58-5.57 (m, 1H), 7.25-7.23 (d, J=8.0 Hz, 2H), 4.53-4.48 (m, 1H), 1.51-1.49 (d, J=8.0 Hz, 3H).

Step 2

To a solution of compound 3-3 (500 mg, 1.23 mmol) in DMF (3 mL) was added compound 3-2 (600 mg, 4.7 mmol), DIPEA (0.5 mL, 3 mmol) and HATU (740 mg, 2 mmol) at 20° C. After the mixture was stirred at 20° C. for 2 h, it was purified by prep-HPLC to give 3-4 (360 mg, 57% yield). Compound 3-4 (300 mg) was separated by SFC separation to give 2 isomers 3-4A and 3-4B.

$^1$H NMR (400 MHz, DMSO-d$_6$) δ 10.03 (s, 1H), 8.12-8.10 (m, 1H), 7.9-7.75 (m, 1H), 7.55-7.52 (m, 2H), 7.45-7.35 (m, 2H), 7.3-7.2 (m, 3H), 7.04 (m, 1H), 6.0 (m, 1H), 5.5-5.2 (m, 2H), 5.1-5.0 (m, 1H), 4.45-4.35 (m, 3H), 3.1-2.9 (m, 4H), 2.43-2.39 (m, 4H), 1.8-1.7 (m, 3H), 1.7-1.5 (m, 1H), 1.5-1.33 (m, 5H).

Step 3

To a solution of compound 3-4B (110 mg, 0.21 mmol) in dry DMF (3 mL) was added PNP (130 mg, 0.43 mmol) and DIPEA (0.5 ml, 3 mmol) at 20° C. After the mixture was stirred at 20° C. for 1.5 h under N$_2$, norfloxacin (100 mg, 0.31 mmol) was added. The mixture was stirred at 20° C. for another 1 h and purified by prep-HPLC (FA), to give example 3 (102.1 mg, 57%).

$^1$H NMR (400 MHz, DMSO-d$_6$) δ 10.15 (s, 1H), 8.93 (s, 1H), 8.10-8.08 (d, 1H), 8.04 (s, 1H), 7.93-7.90 (m, 2H), 7.60-7.58 (d, J=8.0 Hz, 2H), 7.41-7.39 (d, 2H), 7.32-7.30 (d, J=8.0 Hz, 2H), 7.25 (d, 1H), 7.20 (d, 1H), 7.04-7.02 (d, 1H), 6.0 (m, 1H), 5.40 (s, 2H), 5.1-5.0 (m, 3H), 4.6-4.5 (m, 2H), 4.5-4.35 (m, 1H), 3.59 (s, 1H), 3.2 (s, 4H), 3.1-2.9 (m, 2H), 2.42-2.40 (m, 4H), 1.8-1.7 (m, 3H), 1.7-1.6 (m, 1H), 1.5-1.3 (m, 8H).

Example 4. (S)-1-ethyl-7-(4-((4-(2-(1-(ethylcarbamoyl)cyclobutanecarboxamido)-5-guanidinopentanamido)benzyloxy)carbonyl)piperazin-1-yl)-6-fluoro-4-oxo-1,4-dihydroquinoline-3-carboxylic acid

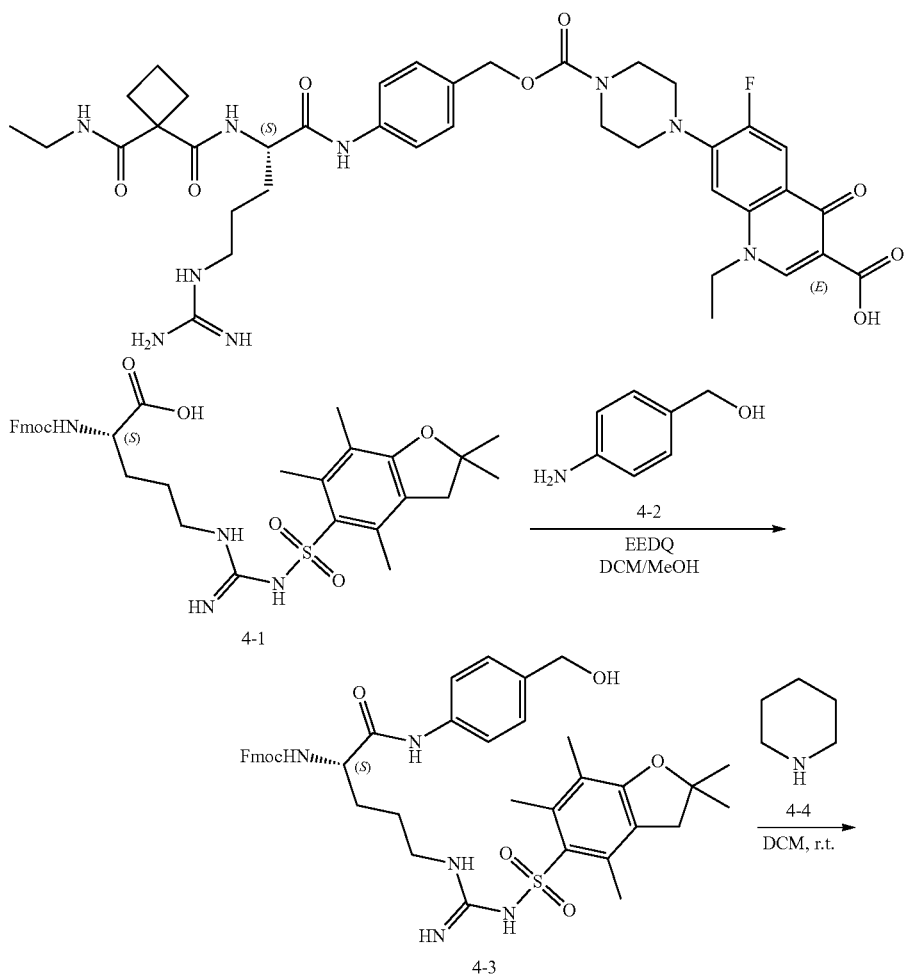

example 4

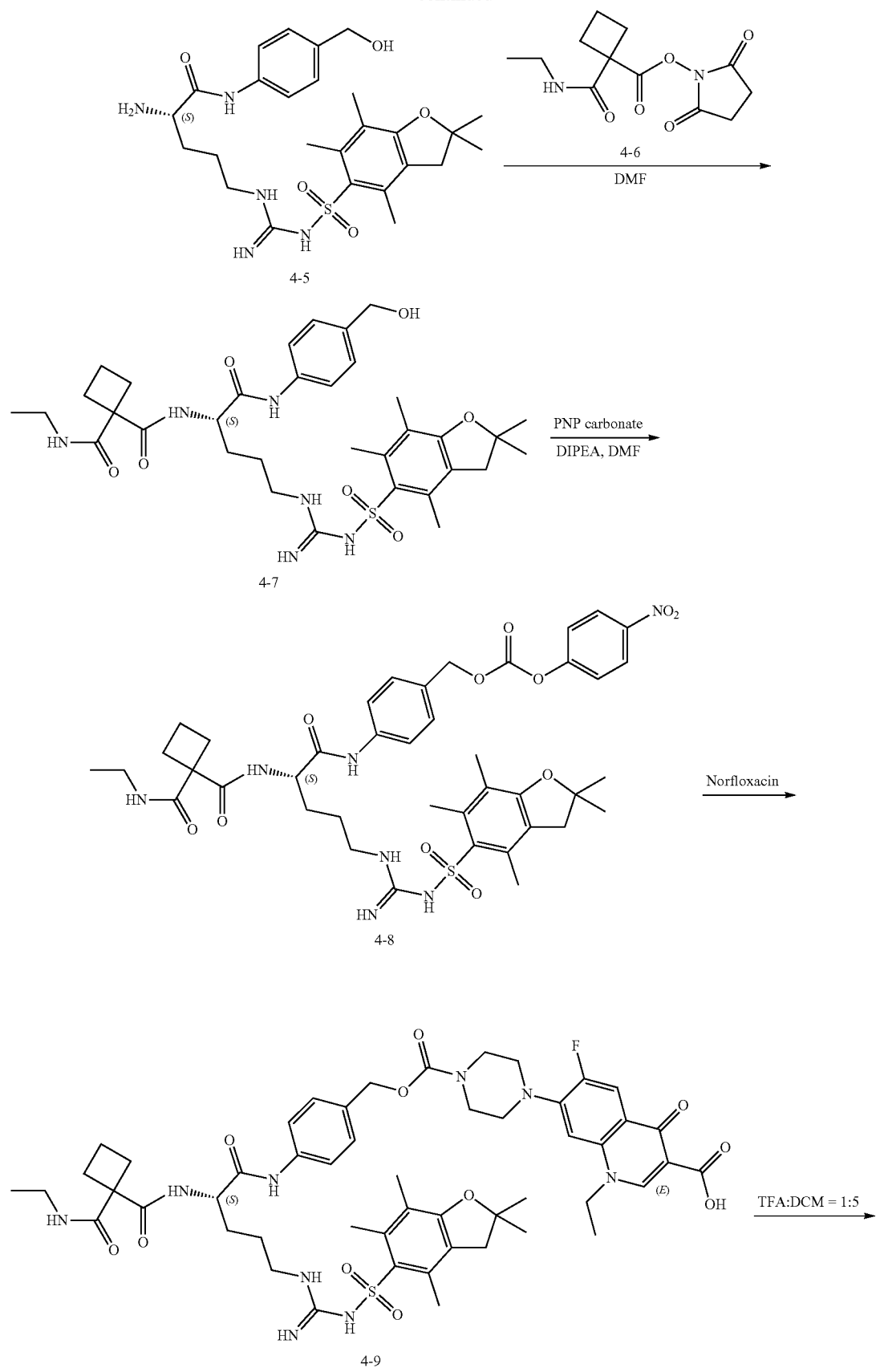

-continued

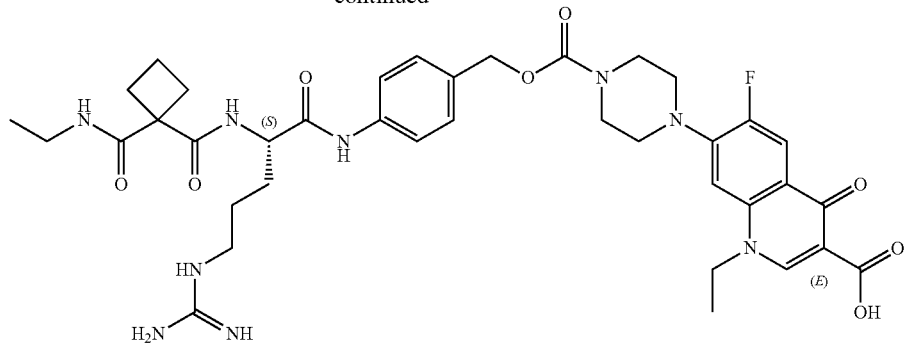

example 4

Step 1

To a solution of compound 4-1 (1.3 g, 2 mmol) in DCM/MeOH (20 mL/20 mL) were added 4-amino-phenyl)-methanol (370 mg, 3 mmol) and EEDQ (989 mg, 4 mmol). The mixture was stirred at r.t. for 16 h. The residue was purified by column (PE/EtOAc=1/3) to give 4-3 (1.94 g, Yield: 90%)

To a solution of 4-3 (1.44 g, 2 mmol) in DCM (50 mL) were added 4-4 (1.2 ml, 9.56 mmol) via syringe at r.t. The mixture was stirred at r.t. for 16 h. The residue was concentrated and washed by methyl tert-butyl ether, then filtered and the filtrate cake was combined to give 4-5 (700 mg, Yield: 70%).

Step 2

To a solution of 4-5 (700 mg, 1.32 mmol) in DME (10 ml) was added a solution of 4-6 (424 mg, 1.58 mmol) and NaHCO$_3$ (222 mg, 2.64 mmol) in water (10 ml). The mixture was stirred at r.t. for 16 h. The mixture was washed with EtOAc and adjusted to pH=3 with 10% HCl. The resulting suspension was extracted with EtOAc. The combined organic layers was concentrated and purified by column (PE/EtOAc=1/3) to give 4-7 (400 mg, Yield: 37%)

Step 3

To a solution of 4-7 (250 mg, 0.365 mmol), PNP carbonate (223 mg, 0.731 mmol) in DMF (4 mL) was added DIPEA (142 mg, 1.095 mmol) at 0° C. The mixture was stirred at r.t. for 16 h. The mixture (4-8) was used for next step without further purification.

Step 4

To the mixture from last step was added norfloxacin (234 mg, 0.73 mmol) at r.t. After the mixture was stirred at r.t. for 1 h, it was purified by prep-HPLC and SFC to give 4-9 (Yield: 30%).

Step 5

To compound 4-9 (100 mg, 0.1 mmol) was added a solution of TFA in DCM (1:5) at 0° C. The mixture was stirred at r.t. for 3 h. The mixture was basified to pH=9 by NH$_3$.H$_2$O. The residue was purified by prep-HPLC then SFC to give example 4 (16.0 mg, Yield: 15%).

$^1$H NMR (400 MHz, Methanol-d$_4$) δ 8.83 (s, 1H), 8.55 (s, 1H), 7.97 (d, J=13.2 Hz, 1H), 7.62 (d, J=7.6 Hz, 2H), 7.35 (d, J=7.6 Hz, 2H), 7.17 (s, 1H), 5.13 (s, 2H), 4.55-4.52 (m, 3H), 3.72 (s, 4H), 3.34 (s, 4H), 3.31-3.24 (m, 4H), 2.58-2.54 (m, 4H), 2.00-1.69 (m, 6H), 1.52 (s, 3H), 1.15-0.11 (m, 3H).

Example 5. 1-ethyl-6-fluoro-4-oxo-7-(4-((4-((S)-2-(1-((S)-1-phenylethylcarbamoyl) cyclobutanecarboxamido)-5 ureidopentanamido)benzyloxy)carbonyl) piperazin-1-yl)-1,4-dihydroquinoline-3-carboxylic acid

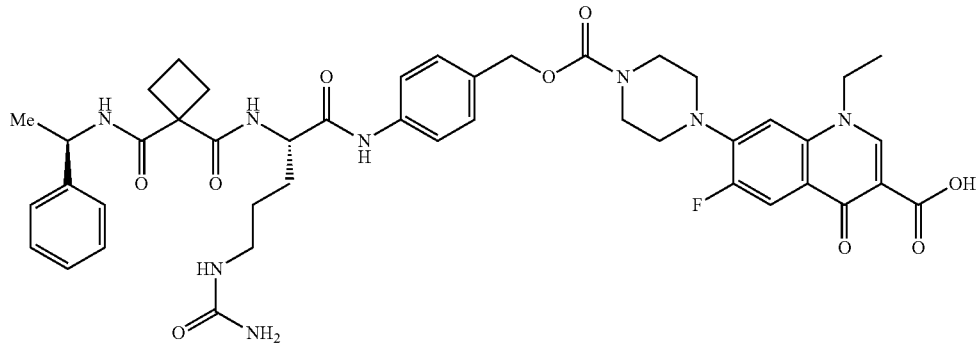

example 5

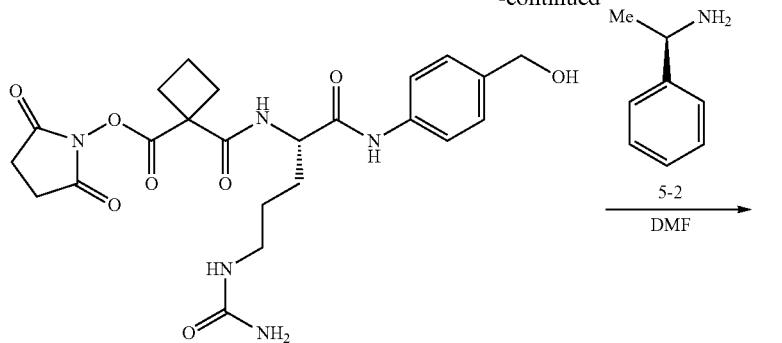
5-1
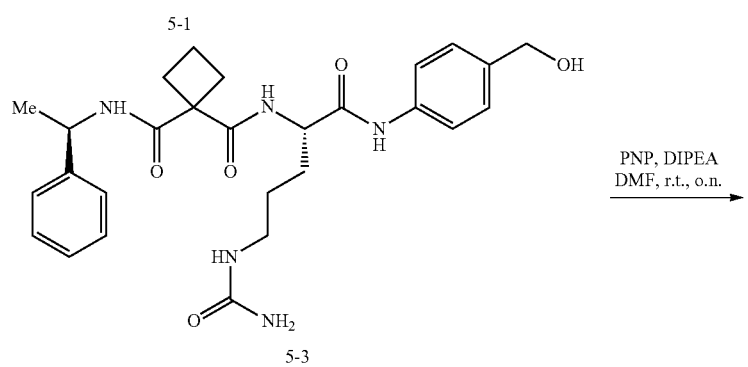
5-3
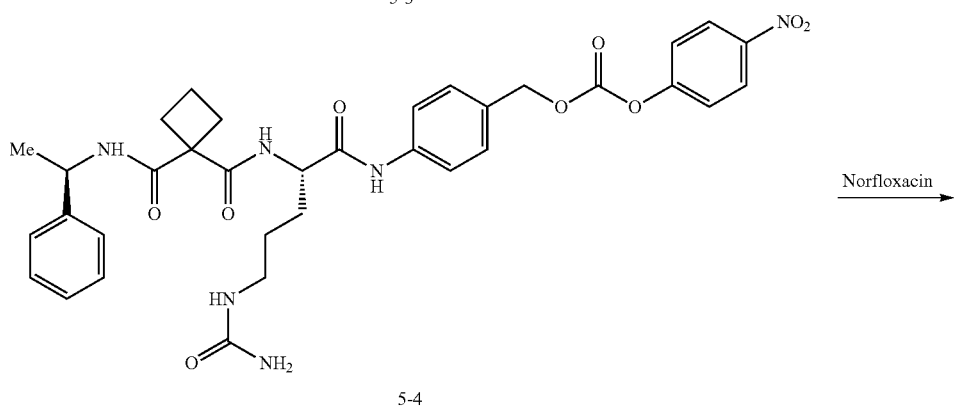
5-4
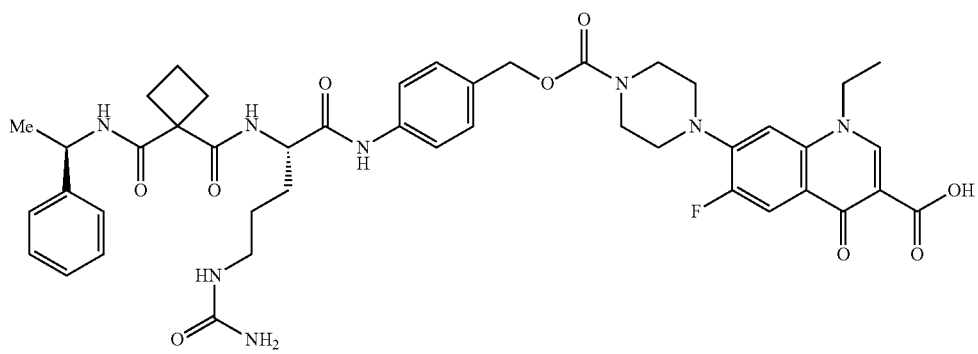
example 5
Step 1
A mixture of compound 5-1 (50 mg, 0.1 mmol) and 5-2 (15 mg, 0.12 mmol) in DMF (10 mL) was stirred at r.t. for 3 h. The mixture was concentrated and purified by prep-TLC (MeOH/DCM=1/10) to give the 5-3 (50 mg, 99%).
Step 2
To a solution of compound 5-3 (40 mg, 0.078 mmol), PNP carbonate (48 mg, 0.157 mmol) in DMF (4 mL) was added DIPEA (30 mg, 0.236 mmol) at 0° C. The mixture was stirred at r.t. for 16 h. The mixture (5-4) was used for next step without further purification.

Step 3

To the mixture from last step was added norfloxacin (51 mg, 0.157 mmol) at r.t. and stirred for 1 h. The residue was purified by prep-HPLC to give example 5. (7 mg, Yield: 8%)

$^1$H NMR (400 MHz, MeOH-d$_4$) δ 8.86 (s, 1H), 8.46 (s, 1H), 8.00 (d, J=12.8 Hz, 1H), 7.61 (d, J=8 Hz, 2H), 7.35-7.33 (m, 2H), 7.30 (d, J=7.2 Hz, 2H), 7.24 (d, J=7.2 Hz, 2H), 7.20 (d, J=14 Hz, 2H), 7.16 (s, 2H), 5.12 (s, 2H), 5.04 (d, J=7.2 Hz, 1H), 4.50-4.47 (m, 4H), 3.71 (s, 4H), 3.34 (s, 4H), 3.22-3.03 (m, 2H), 2.60-2.51 (m, 4H), 1.94-1.86 (m, 3H), 1.74-1.71 (m, 1H), 1.60-1.45 (m, 7H).

Example 6. 1-ethyl-6-fluoro-4-oxo-7-(4-((4-((S)-2-(1-((S)-1-(thiophen-2-yl)ethylcarbamoyl) cyclobutanecarboxamido)-5-ureidopentanamido)benzyloxy)carbonyl)piperazin-1-yl)-1,4-dihydroquinoline-3-carboxylic acid

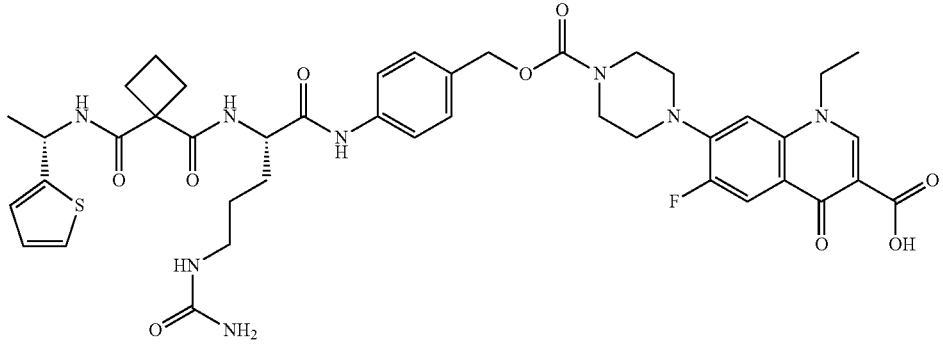

example 6

Example 6 was made using the procedure as Example 3. It shared the intermediate with Example 10.

$^1$H NMR (400 MHz, DMSO-d$_6$) δ 15.3 (s, 1H), 10.13 (s, 1H), 8.93 (s, 1H), 8.25 (d, 1H), 7.94-7.91 (d, J=12.0 Hz, 1H), 7.8 (d, 1H), 7.60-7.58 (d, J=8.0 Hz, 2H), 7.33-7.30 (d, J=8.0 Hz, 3H), 7.20 (d, 1H), 6.92-6.91 (m, 2H), 5.95 (m, 1H), 5.40 (s, 1H), 5.25-5.15 (m, 1H), 5.04 (s, 2H), 4.65-4.4 (m, 2H), 4.5-4.4 (m, 1H), 3.7-3.5 (s, 4H), 3.3 (s, 4H), 3.1-2.85 (m, 2H), 2.44-2.42 (m, 4H), 1.8-1.7 (m, 3H), 1.7-1.55 (m, 1H), 1.46-1.45 (d, J=4.0 Hz, 1H), 1.45-1.3 (m, 5H).

Example 7. 7-(4-((4-((S)-2-(1-((R)-3-(allyloxy)-3-oxo-1-(thiophen-3-yl)propylcarbamoyl)cyclobutanecarboxamido)-5-ureidopentanamido)benzyloxy)carbonyl)piperazin-1-yl)-1-ethyl-6-fluoro-4-oxo-1,4-dihydroquinoline-3-carboxylic acid

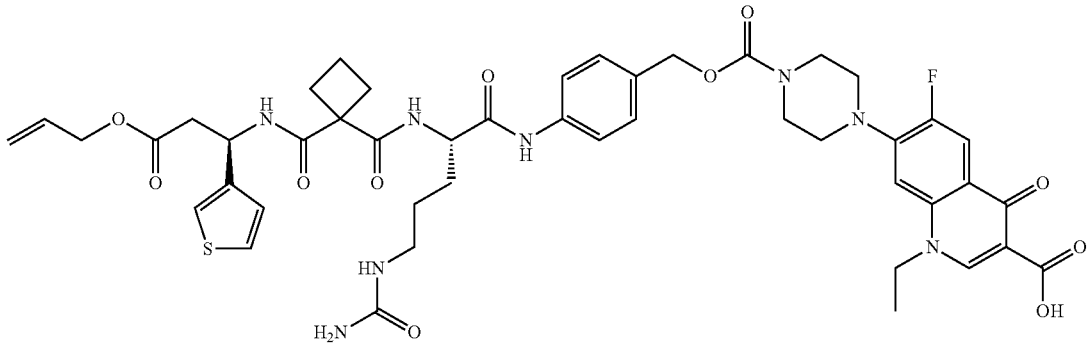

example 7

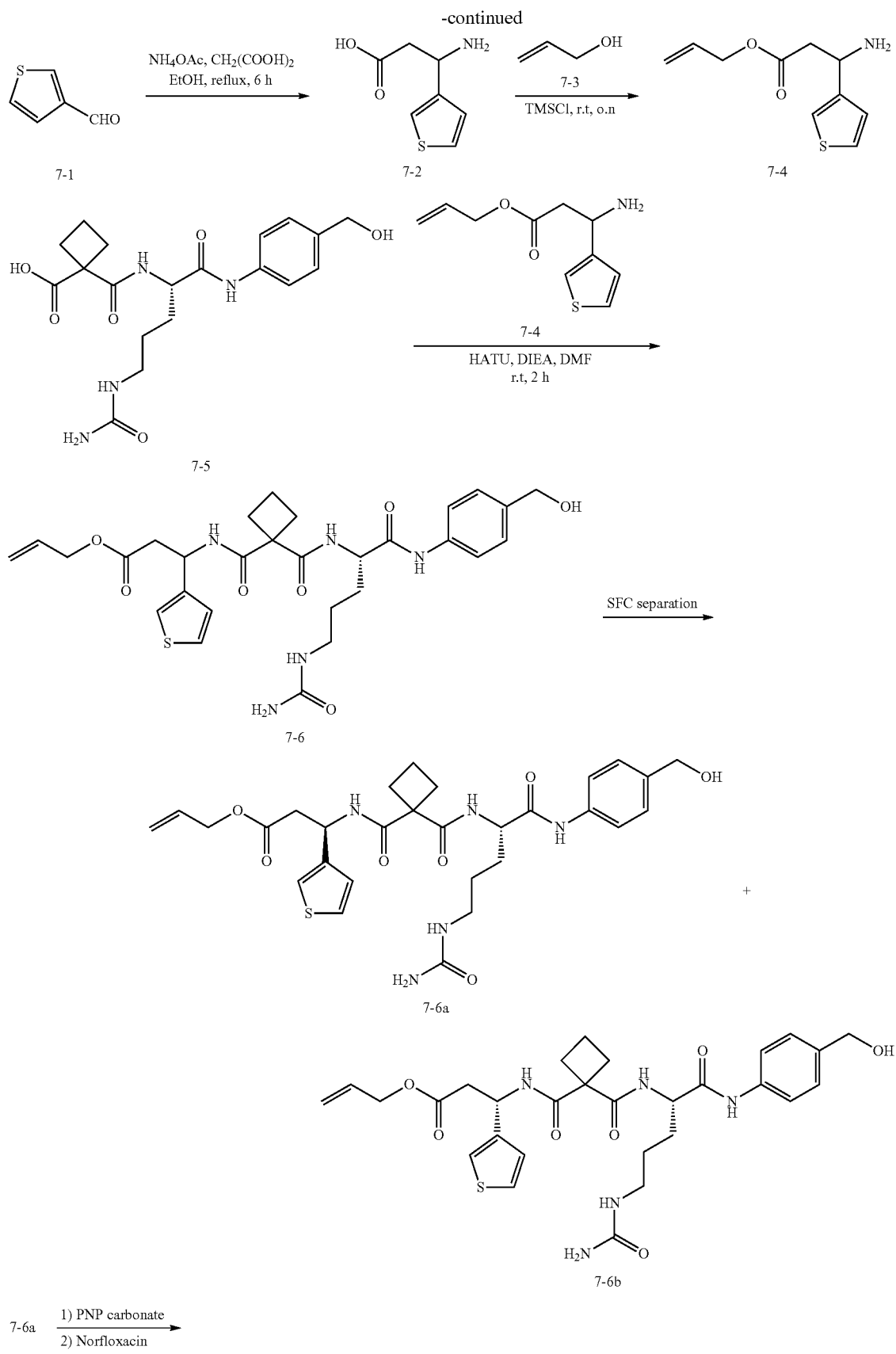

-continued

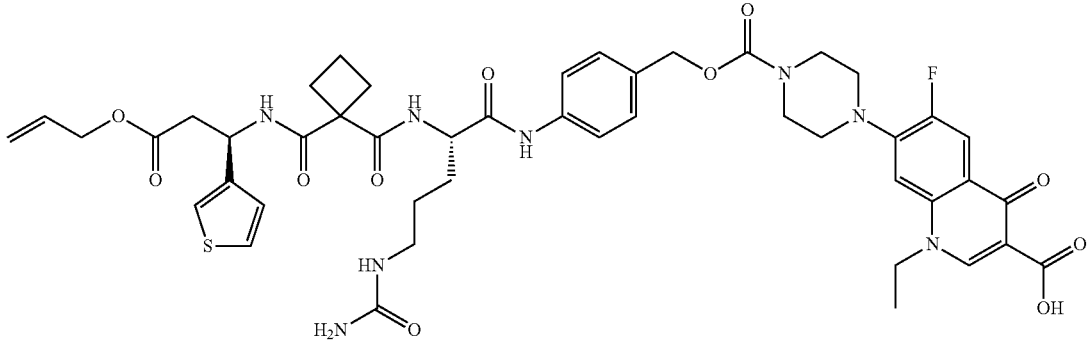

example 7

Step 1

To a solution of compound 7-1 (10.0 g, 89.17 mmol) and CH$_2$(COOH)$_2$ (9.3 g, 89.17 mmol) in EtOH (100 mL) was added NH$_4$OAc (13.7 g, 178.33 mmol). The mixture was stirred at 80° C. for 6 h. It was cooled to r.t, filtered, and washed with EtOH (100 mL). The filter cake was collected, and concentrated under reduced pressure to afford compound 7-2 (8.0 g, 52.6%) as white solid.

$^1$H NMR D$_2$O 400 MHz, δ 7.44 (s, 2H), 7.13 (d, J=3.2 Hz, 1H), 4.69 (t, J=7.2 Hz, 1H), 2.84-2.73 (m, 2H).

Step 2

To a mixture of compound 7-2 (6.0 g, 35.04 mmol) in compound 7-3 (60.0 g) was added TMSCl (13.4 mL, ρ=0.85, 105.13 mmol) dropwise. The reaction mixture was stirred at r.t. under N$_2$ overnight. The mixture was concentrated under reduced pressure, and the residue was diluted with H$_2$O (50 mL), adjusted to pH 1 by HCl solution, and washed with EtOAc (50 mL×3). The water phase was adjusted to pH 12 by NH$_3$H$_2$O, and extracted with EtOAc (50 mL×3). The combined EtOAc layer was dried over Na$_2$SO$_4$, filtered, and concentrated under reduced pressure to afford compound 7-4 as an oil (4.0 g, 54.1%).

$^1$H NMR DMSO-d$_6$ 400 MHz, δ 7.45-7.43 (q, 1H), 7.31 (s, 1H), 7.15 (d, J=4.8 Hz, 1H), 5.91-5.85 (m, 1H), 5.27 (dd, J=17.2, 1.6 Hz, 1H), 5.20-5.17 (m, 1H), 4.53 (d, J=5.2 Hz, 2H), 4.31-4.27 (m, 1H), 2.73-2.61 (m, 2H).

Step 3

To a mixture of compound 7-5 (1.0 g, 2.46 mmol) in DMF (20 mL) was added DIPEA (636 mg, 4.92 mmol), followed by HATU (1.4 g, 3.69 mmol). The mixture was stirred at r.t. for 15 min, and compound 7-4 (624 mg, 2.95 mmol) was added. The reaction mixture was stirred at r.t. for 2 h and purified by prep-HPLC to afford compound 7-6 as white solid (800 mg, 54.1%). Compound 7-6 was scaled up to 1.5 g, and was separated by SFC to afford 7-6a (580 mg) and 7-6b (560 mg).

7-6a

LCMS: (5-95, AB, 1.5 min, ESI), 0.773 min, MS=600.1 [M+1]

$^1$H NMR DMSO-d$_6$ 400 MHz, δ 10.05 (s, 1H), 8.25 (d, J=8.4 Hz, 1H), 7.74 (d, J=7.9 Hz, 1H), 7.56 (d, J=8.4 Hz, 2H), 7.45-7.43 (q, 1H), 7.31 (d, J=2.6 Hz, 1H), 7.24 (d, J=8.4 Hz, 2H), 7.08 (d, J=4.0 Hz, 1H), 5.97 (t, J=5.6 Hz, 1H), 5.90-5.80 (m, 1H), 5.43-5.37 (m, 3H), 5.27 (dd, J=17.4, 1.5 Hz, 1H), 5.17 (dd, J=10.4 Hz, 1.3 Hz, 1H), 5.17 (t, J=5.7 Hz, 1H), 4.51 (d, J=5.3 Hz, 2H), 4.44-4.39 (m, 3H), 3.06-2.98 (m, 1H), 2.97-2.88 (m, 3H), 2.48-2.39 (m, 4H), 1.78-1.70 (m, 3H), 1.64-1.55 (m, 1H), 1.42-1.28 (m, 2H).

7-6b

LCMS: (5-95, AB, 1.5 min, ESI), 0.762 min, MS=600.1 [M+1]

$^1$H NMR DMSO-d$_6$ 400 MHz, δ 10.04 (s, 1H), 8.26 (d, J=8.4 Hz, 1H), 7.79 (d, J=7.7 Hz, 1H), 7.57 (d, J=8.4 Hz, 2H), 7.39-7.37 (q, 1H), 7.31 (s, 1H), 7.24 (d, J=8.4 Hz, 2H), 7.07 (d, J=4.9 Hz, 1H), 5.97 (t, J=5.5 Hz, 1H), 5.91-5.81 (m, 1H), 5.43-5.36 (m, 3H), 5.26 (dd, J=17.3, 1.4 Hz, 1H), 5.18 (d, J=10.4 Hz, 1H), 5.11 (t, J=5.7 Hz, 1H), 4.53-4.52 (m, 2H), 4.44-4.40 (m, 3H), 3.05-2.98 (m, 1H), 2.97-2.85 (m, 3H), 2.46-2.33 (m, 4H), 1.77-1.72 (m, 3H), 1.64-1.56 (m, 1H), 1.42-1.30 (m, 2H).

Step 4

To a solution of 7-6a (50 mg, 0.083 mmol) in anhydrous DMF (5 mL) was added DIPEA (107 mg, 0.83 mmol), followed by PNP carbonate (60 mg, 0.20 mmol). The reaction mixture was stirred at r.t. overnight. Then norfloxacin (64 mg, 0.20 mmol) was added. The reaction mixture was stirred at r.t. for another 2 h. The mixture was filtered, and the filtrate was purified by prep-HPLC to afford example 7 as a white solid (41.7 g, 53.5%).

LCMS: (5-95, AB, 1.5 min, ESI), 0.858 min, MS=473.3 [½M+1]

$^1$H NMR DMSO-d$_6$ 400 MHz, δ 15.32 (br, 1H), 10.15 (s, 1H), 8.95 (s, 1H), 8.23 (d, J=8.0 Hz, 1H), 7.91 (d, J=13.0 Hz, 1H), 7.77 (d, J=7.5 Hz, 1H), 7.62 (d, J=8.0 Hz, 2H), 7.44-7.42 (q, 1H), 7.35-7.31 (m, 3H), 7.19 (br, 1H), 7.08 (d, J=4.5 Hz, 1H), 5.98 (br, 1H), 5.89-5.80 (m, 1H), 5.44-5.37 (m, 3H), 5.23 (d, J=17.6 Hz, 1H), 5.16 (d, J=10.5 Hz, 1H), 5.07 (s, 2H), 4.57 (br, 2H), 4.51 (d, J=5.5 Hz, 2H), 4.45-4.40 (m, 1H), 3.61 (br, 4H), 3.31 (br, 4H), 3.06-3.01 (m, 1H), 2.95-2.90 (m, 3H), 2.47-2.40 (m, 4H), 1.76-1.72 (m, 3H), 1.62-1.59 (m, 1H), 1.40-1.35 (m, 5H).

Example 8. 1-ethyl-6-fluoro-4-oxo-7-(4-((4-((S)-2-(1-((R)-1-(thiophen-3-yl)ethylcarbamoyl)cyclobutanecarboxamido)-5-ureidopentanamido)benzyloxy)carbonyl)piperazin-1-yl)-1,4-dihydroquinoline-3-carboxylic acid

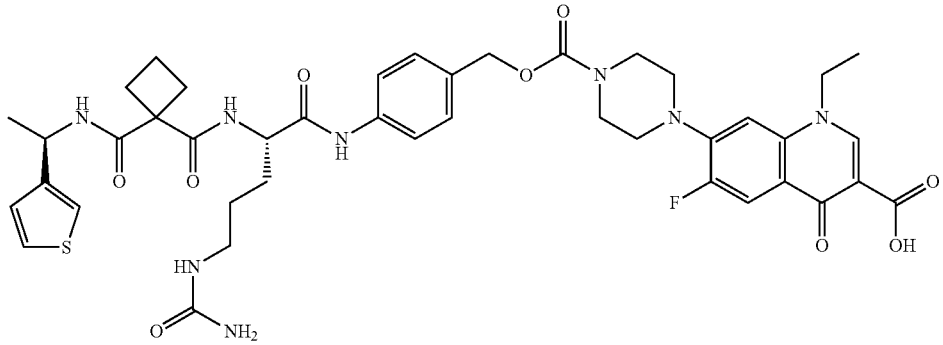

example 8

Example 8 was made using the procedure as Example 3, with the intermediate from the synthesis of Example 3.

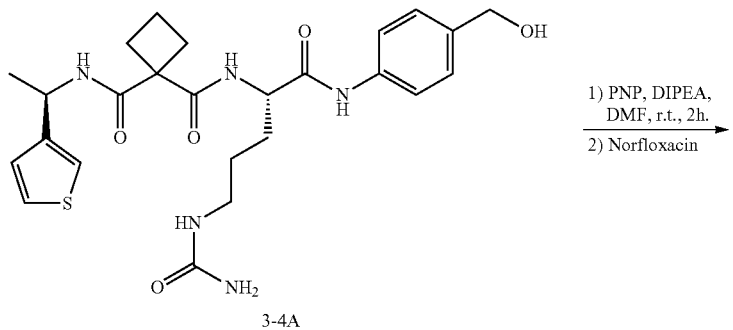

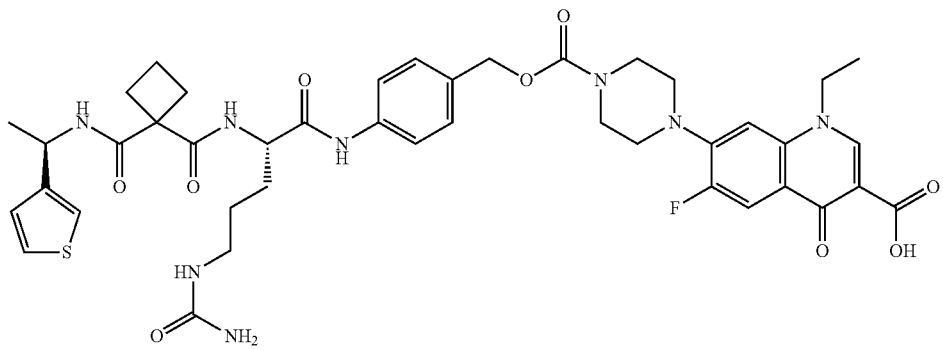

example 8

$^1$H NMR (400 MHz, DMSO-d$_6$) δ 10.14 (s, 1H), 8.92 (s, 1H), 8.05-8.03 (d, 1H), 7.93-7.90 (d, J=12.0 Hz, 1H), 7.85-7.83 (d, 1H), 7.61-7.59 (d, J=8.0 Hz, 1H), 7.36-7.35 (m, 1H), 7.33-7.31 (d, J=8.0 Hz, 2H), 7.24 (s, 1H), 7.20 (m, 1H), 5.5 (m, 1H), 7.04-7.03 (m, 1H), 6.0 (m, 1H), 5.40 (s, 2H), 5.1-5.0 (m, 3H), 4.6-4.5 (m, 2H), 4.5-4.35 (m, 1H), 3.59 (s, 1H), 3.2 (s, 4H), 3.05-2.9 (m, 2H), 2.44-2.41 (m, 4H), 1.8-1.7 (m, 3H), 1.7-1.6 (m, 1H), 1.5-1.35 (m, 8H).

Example 9. 1-ethyl-6-fluoro-7-(4-((4-((2S)-2-(1-(4-methylpentan-2-ylcarbamoyl)cyclobutanecarboxamido)-5-ureidopentanamido)benzyloxy)carbonyl)piperazin-1-yl)-4-oxo-1,4-dihydroquinoline-3-carboxylic acid

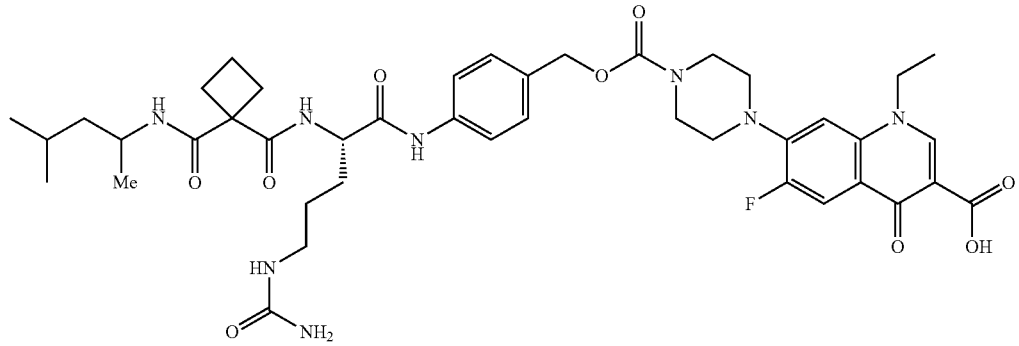

example 9

Example 9 was made using the procedure as Example 5
LCMS: (5-95 AB, 1.5 min), T=0.858 min, M=8.352 (M+1);
$^1$H NMR (400 MHz, DMSO-d6) δ 10.22 (s, 1H), 8.85 (s, 1H), 7.89-7.71 (m, 2H), 7.65-7.64 (d, J=8.8 Hz, 2H), 7.53-7.50 (m, 1H), 7.34-7.31 (d, J=8.8 Hz, 2H), 7.18-7.13 (m, 1H), 6.06 (s, 1H), 5.45 (d, J=3.2 Hz, 2H), 5.05 (s, 2H), 4.60-4.42 (m, 2H), 3.91-3.88 (t, J=6.4 Hz, 1H), 3.59 (s, 4H), 3.26 (s, 4H), 3.03-2.99 (m, 1H), 2.97-2.91 (m, 1H), 2.41-2.39 (m, 5H), 1.74-1.71 (m, 3H), 1.7-1.5 (m, 2H), 1.5-1.3 (m, 6H), 1.2-1.1 (m, 1H), 1.03-1.00 (m, 3H), 0.81 (m, 6H).

Example 10. 1-ethyl-6-fluoro-4-oxo-7-(4-((4-((S)-2-(1-((R)-1-(thiophen-2-yl)ethylcarbamoyl)cyclobutanecarboxamido)-5-ureidopentanamido)benzyloxy)carbonyl)piperazin-1-yl)-1,4-dihydroquinoline-3-carboxylic acid

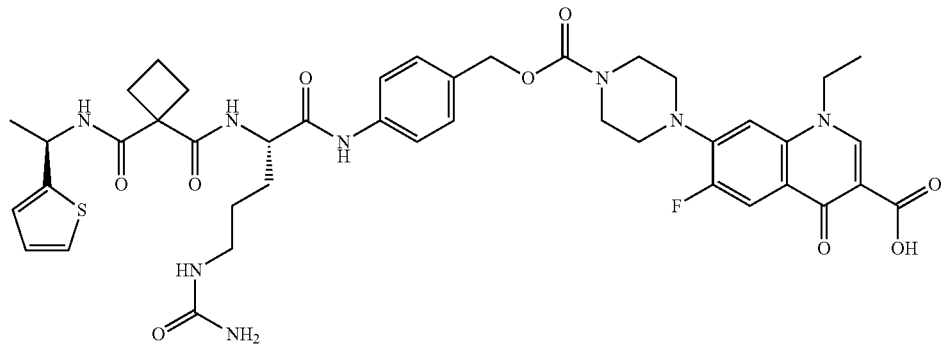

example 10

Example 10 was made using the procedure as Example 3. It shared the intermediate with Example 6.
$^1$H NMR (400 MHz, DMSO-d$_6$) δ 15.3 (s, 1H), 10.13 (s, 1H), 8.94 (s, 1H), 8.25 (d, 1H), 7.94-7.91 (d, J=12.0 Hz, 1H), 7.8 (d, 1H), 7.62-7.60 (d, J=8.0 Hz, 2H), 7.34-7.31 (d, J=8.0 Hz, 2H), 7.28-7.27 (d, J=4.0 Hz, 1H), 7.20 (d, 1H), 6.93 (s, 1H), 6.90-6.88 (m, 1H), 5.95 (m, 1H), 5.40 (s, 1H), 5.25-5.15 (m, 1H), 5.05 (s, 2H), 4.65-4.4 (m, 2H), 4.5-4.4 (m, 1H), 3.7-3.5 (s, 4H), 3.3 (s, 4H), 3.1-2.85 (m, 2H), 2.44-2.42 (m, 4H), 1.85-1.7 (m, 3H), 1.7-1.55 (m, 1H), 1.47-1.46 (d, J=4.0 Hz, 1H), 1.46-1.3 (m, 5H).

Example 11. 1-ethyl-6-fluoro-4-oxo-7-(4-((4-((2S)-2-(1-(pentan-2-ylcarbamoyl)cyclobutanecarboxamido)-5-ureidopentanamido)benzyloxy)carbonyl)piperazin-1-yl)-1,4-dihydroquinoline-3-carboxylic acid

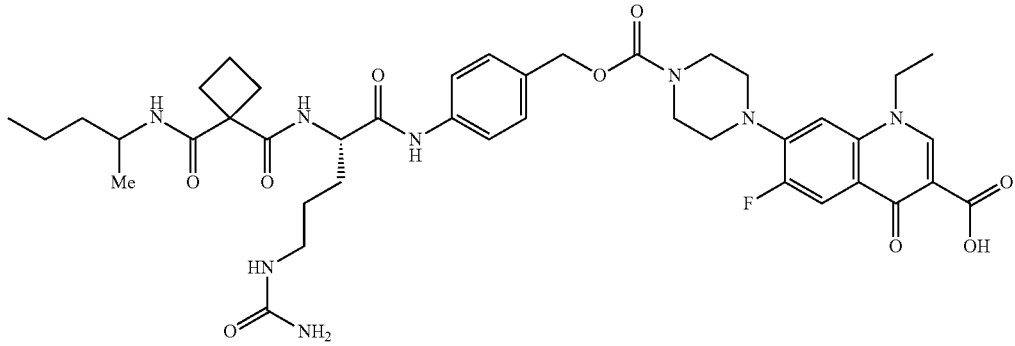

example 11

Example 11 was made using the procedure as Example 5. LCMS: (5-95 AB, 1.5 min), T=0.848 min, M=821.2 (M+1);
$^1$H NMR (400 MHz, DMSO-d6) δ 10.15-10.13 (m, 1H), 8.96 (s, 1H), 7.97-7.93 (d, J=13.2 Hz, 1H), 7.81-7.74 (m, 1H), 7.63 (d, J=8.8 Hz, 2H), 7.50-7.46 (m, 1H), 7.34 (d, J=8.4 Hz, 2H), 7.21 (d, J=7.2 Hz, 1H), 5.98-5.95 (t, J=5.6 Hz, 1H), 5.42 (s, 2H), 5.06 (s, 2H), 4.60-4.57 (q, J=6.8 Hz, 2H), 4.44-4.42 (m, 1H), 3.81 (m, 1H), 3.60 (s, 4H), 3.49-3.36 (s, 4H), 3.33-3.29 (m, 2H), 3.1-2.9 (m, 2H), 2.42-2.39 (m, 4H), 1.73 (m, 4H), 1.63-1.58 (m, 1H), 1.41 (m, 5H), 1.35-1.30 (m, 2H), 1.04-1.02 (m, 3H), 0.84-0.78 (m, 3H).

Example 12. (S)-1-ethyl-6-fluoro-7-(4-((4-(2-(1-(isopropylcarbamoyl)cyclobutanecarboxamido)-5-ureidopentanamido)benzyloxy)carbonyl)piperazin-1-yl)-4-oxo-1,4-dihydroquinoline-3-carboxylic acid

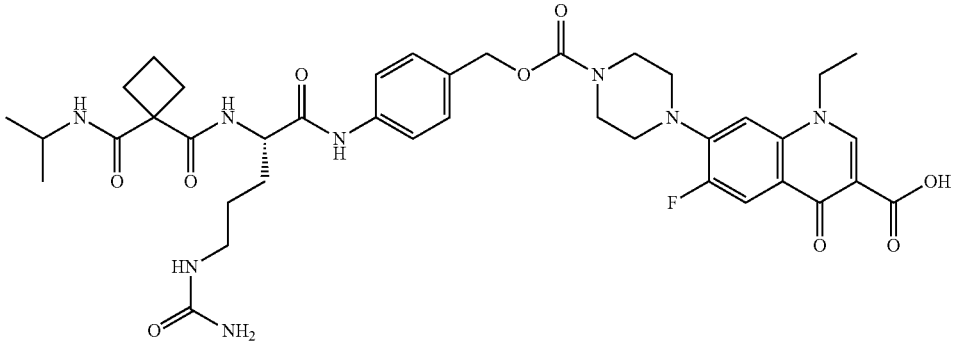

example 12

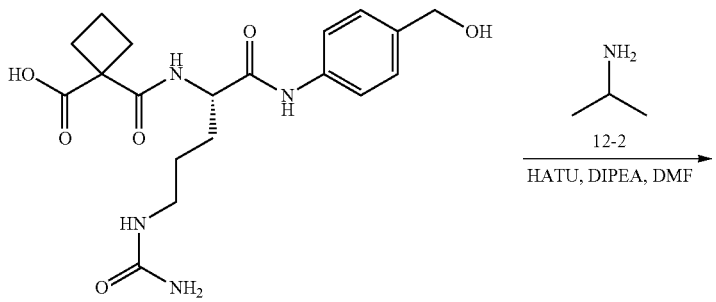

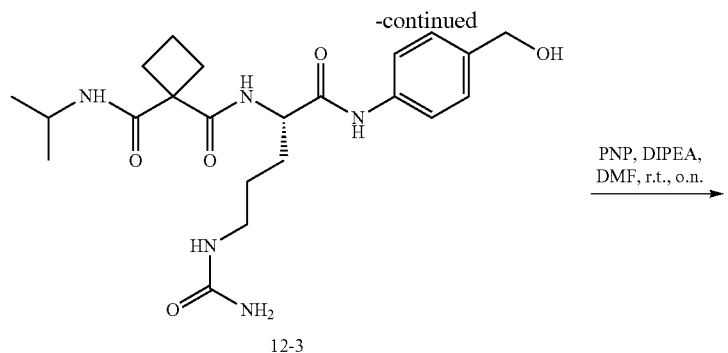

12-3

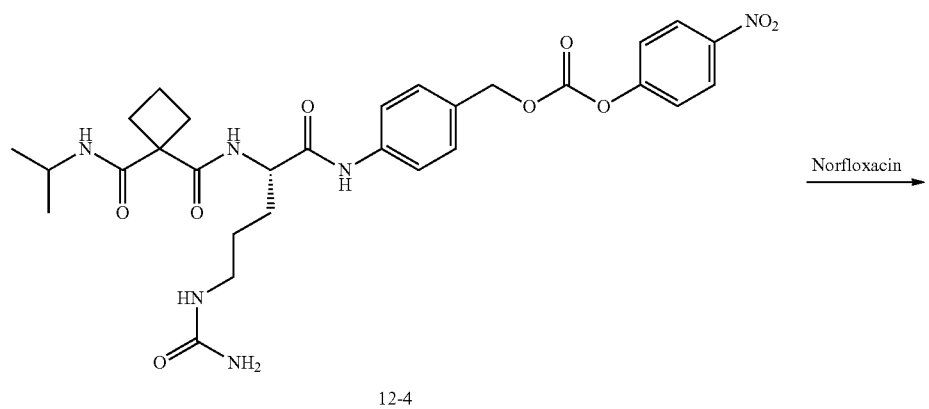

12-4

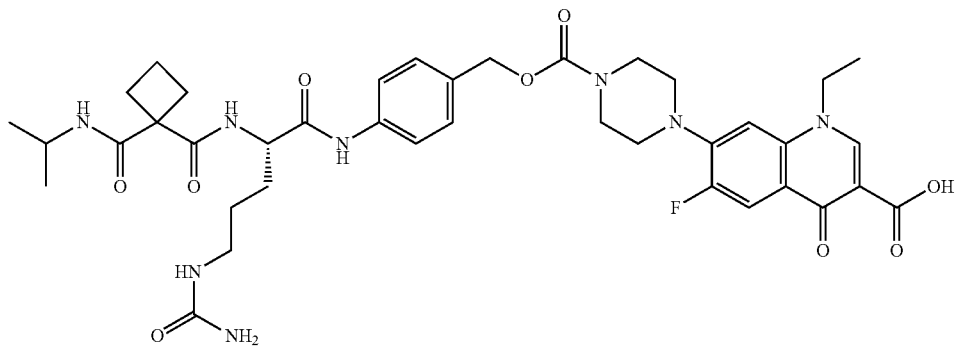

example 12

Step 1

A mixture pf compound 12-1 (120 mg, 0.3 mmol), HATU (171 mg, 0.45 mmol), DIPEA (195 mg, 1.5 mmol) in DMF (10 mL) was stirred at r.t. for 30 min. Then compound 12-2 (9 mg, 0.3 mmol) was added. The reaction mixture was stirred at r.t. for 3 h. The mixture was concentrated and purified by Prep-TLC (MeOH/DCM=1/10) to give 12-3 (180 mg, 136%).

Step 2

To a solution of compound 12-3 (180 mg, 0.4 mmol), PNP carbonate (245 mg, 0.81 mmol) in DMF (4 mL) was added DIPEA (156 mg, 1.21 mmol) at 0° C. The mixture was stirred at r.t. for 16 h. The mixture (12-4) was used for next step without further purification.

Step 3

To the mixture of last step was added norfloxacin (259 mg, 0.81 mmol) at r.t. The mixture was stirred at r.t. for 1 h. The residue was purified by prep-HPLC to give example 12 (18.5 mg, Yield: 6% over two steps).

$^1$H NMR (400 MHz, MeOH-$d_4$) δ 8.88 (s, 1H), 8.02-7.99 (d, J=13.2 Hz, 1H), 7.65-7.62 (d, J=8.8 Hz, 3H), 7.37-7.35 (d, J=8.4 Hz, 2H), 7.19 (d, J=6.4 Hz, 1H), 5.13 (s, 2H), 4.54-4.50 (m, 4H), 4.06-4.01 (m, 1H), 3.73 (s, 4H), 3.35 (s, 4H), 3.26-3.19 (m, 2H), 2.57-2.52 (m, 4H), 1.94-1.90 (m, 2H), 1.81-1.74 (m, 2H), 1.59-1.53 (m, 3H), 1.21-1.13 (m, 6H).

Example 13. (S)-1-ethyl-7-(4-((4-(2-(1-(ethylcarbamoyl)cyclobutanecarboxamido)-5-ureidopentanamido)benzyloxy)carbonyl)piperazin-1-yl)-6-fluoro-4-oxo-1,4-dihydroquinoline-3-carboxylic acid
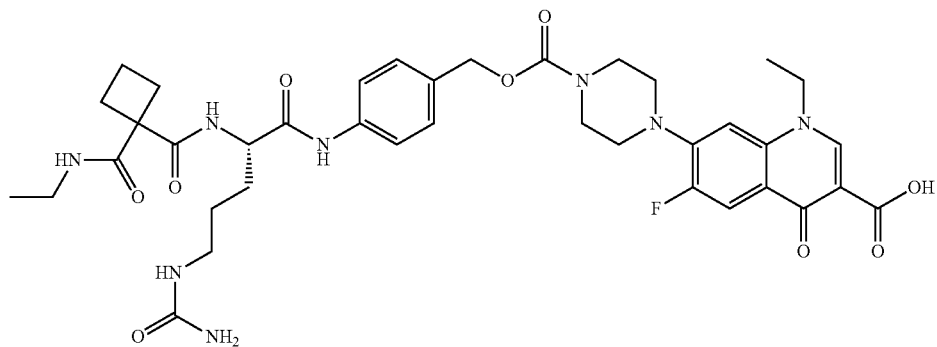
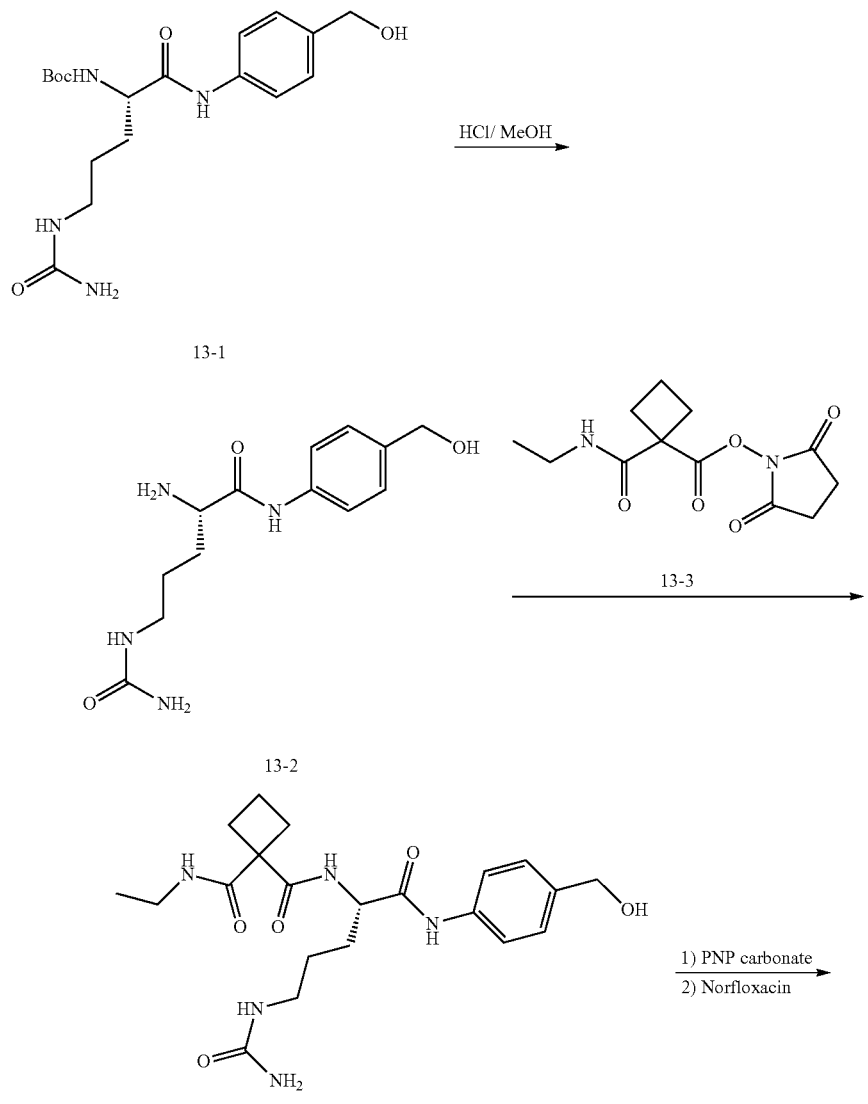

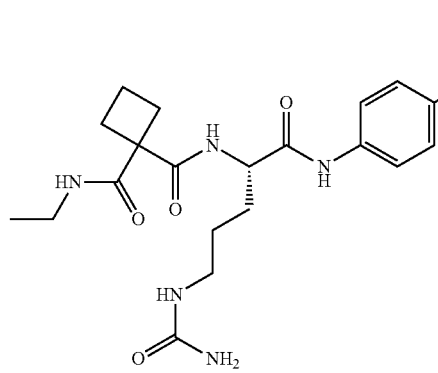
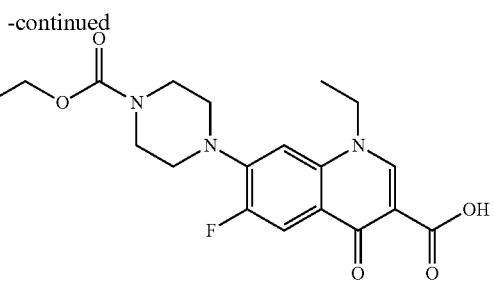

example 13

Step 1

A mixture of compound 13-1 (1 g, 2.63 mmol) and HCl in dioxane (4 M, 10 mL) was stirred at r.t. for 2 h. The solution was concentrated to give the 13-2.

Step 2

To a solution of compound 13-2 (651 mg, 2.326 mmol) in DME-H$_2$O (10 mL/2 mL) were added a mixture of compound 13-3 (623 mg, 2.326 mmol) and sat. NaHCO$_3$ (10 mL). The mixture was stirred at r.t. for 16 h. The solution was concentrated and the residue was purified by prep-HPLC to give 13-4.

$^1$H NMR (400 MHz, Methanol-d$_4$) δ 7.62 (d, J=8.4 Hz, 2H), 7.33 (d, J=8.8 Hz, 2H), 4.57-4.52 (m, 3H), 3.29-3.10 (m, 4H), 2.60-2.53 (m, 4H), 2.05-1.50 (m, 6H), 1.16 (t, J=7.6 Hz, 3H).
LCMS (ESI): m/z 434.1 [M+H$^+$].

Step 3

To a solution of 13-4 (60 mg, 0.139 mmol) in DCM (10 mL) were added DIPEA (90 mg, 0.695 mmol) and PNP carbonate (84 mg, 0.277 mmol). The mixture was stirred at 25° C. for 2 days. The mixture was concentrated and dissolved in DMF (5 mL) and norfloxacin (88 mg, 0.278 mmol) was added. The mixture was stirred at 25° C. for 1.5 h. After removal of the solvent, the residue was purified by prep-HPLC to give example 13.

$^1$H NMR (400 MHz, Methanol-d$_4$) δ 8.86 (s, 1H), 8.00 (d, J=13.2 Hz, 1H), 7.63 (d, J=8.4 Hz, 2H), 7.35 (d, J=8.8 Hz, 2H), 7.18 (d, J=6.8 Hz, 1H), 5.11 (s, 2H), 4.57-4.48 (m, 3H), 3.71 (s, 4 H), 3.33-3.32 (m, 4H), 3.26-3.08 (m, 4H), 2.60-2.47 (m, 4H), 1.93-1.50 (m, 10H), 1.14 (t, J=7.2 Hz, 3H).
LCMS (ESI): m/z 779.4. [M+H].

Example 14. 1-ethyl-6-fluoro-7-(4-((4-((S)-2-(1-((R)-3-methylbutan-2-ylcarbamoyl)cyclobutanecarboxamido)-5-ureidopentanamido)benzyloxy)carbonyl)piperazin-1-yl)-4-oxo-1,4-dihydroquinoline-3-carboxylic acid

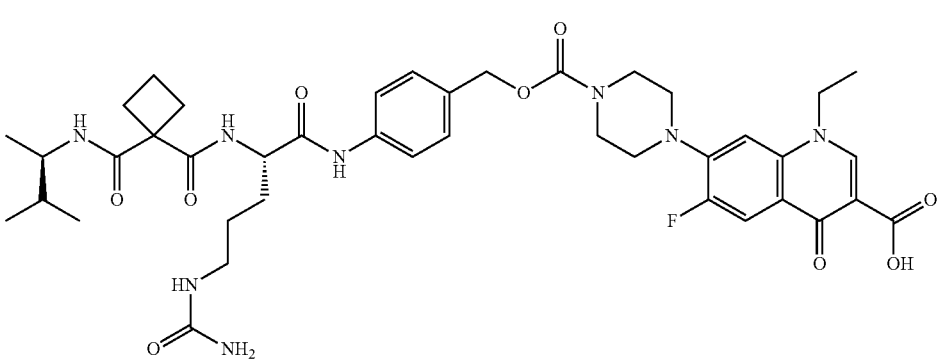

example 14

Example 14 was made using the procedure as Example 5.
$^1$H NMR (400 MHz, DMSO-d$_6$) δ 10.16 (s, 1H), 8.96 (s, 1H), 7.97-7.93 (d, J=13.2 Hz, 1H), 7.85-7.83 (d, J=7.6 Hz, 1H), 7.63-7.61 (d, J=8.8 Hz, 2H), 7.43-7.41 (d, J=8.8 Hz, 1H), 7.35-7.33 (d, J=8.8 Hz, 2H), 7.22-7.21 (d, J=6.8 Hz, 1H), 6.00-5.97 (m, 1H), 5.43 (s, 2H), 5.07 (s, 2H), 4.61-4.56 (m, 2H), 4.46-4.41 (m, 1H), 3.62 (m, 6H), 3.41 (s, 2H), 3.30 (s, 4H), 3.12-2.89 (m, 2H), 2.45-2.39 (m, 4H), 1.76-1.62 (m, 4H), 1.44-1.39 (m, 3H), 1.00 (d, J=6.8 Hz, 3H), 0.82 (d, J=5.6 Hz, 6H).

Example 15. 7-(4-((4-((S)-2-(3,3-dimethyl-1-((R)-1-phenylethylcarbamoyl)cyclobutanecarboxamido)-5-ureidopentanamido)benzyloxy)carbonyl)piperazin-1-yl)-1-ethyl-6-fluoro-4-oxo-1,4-dihydroquinoline-3-carboxylic acid
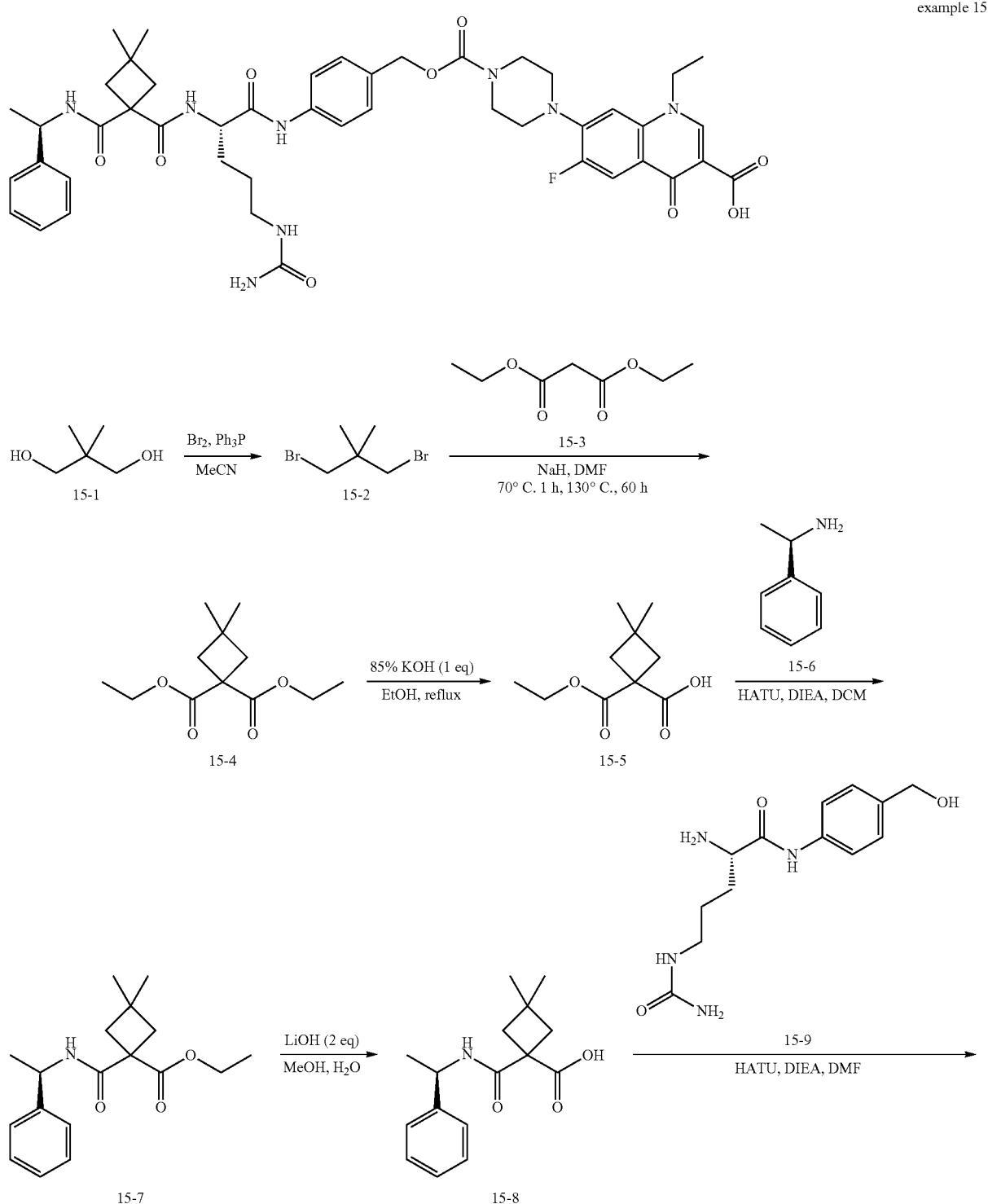

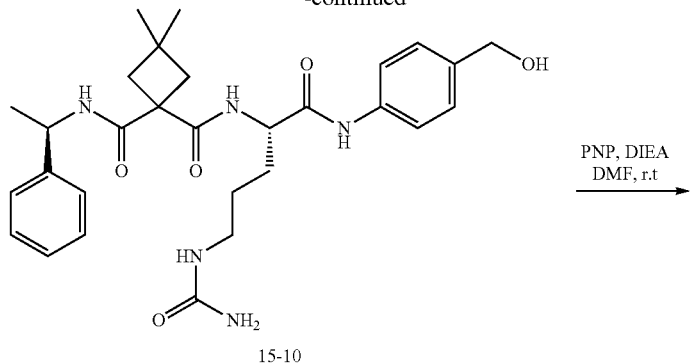

15-10

PNP, DIEA
DMF, r.t

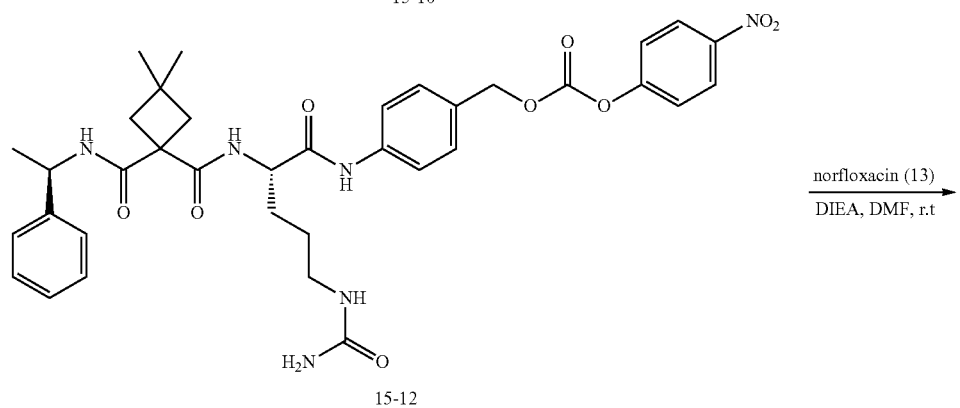

15-12 norfloxacin (13)
DIEA, DMF, r.t

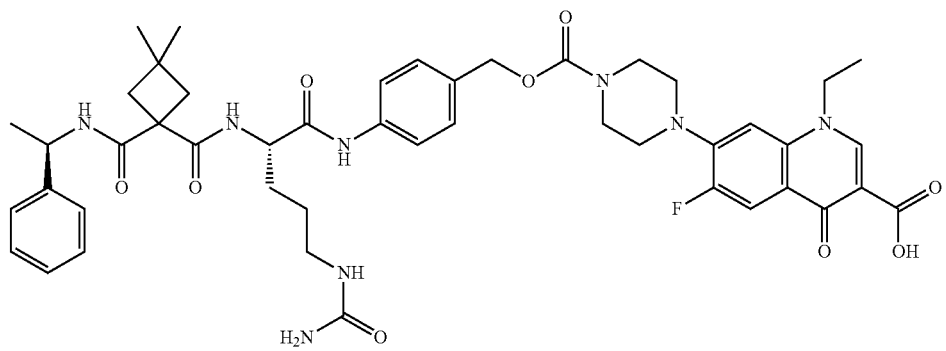

example 15

Step 1

To a stirred solution of Ph₃P (91.8 g, 350 mmol) in MeCN (250 mL) was added dropwise a solution of bromine (56 g, 350 mmol) in MeCN (40 mL) at 0° C. Then compound 15-1 (18.2 g, 175 mmol) was added to the mixture. The reaction was heated at reflux for 16 h. The solvent was removed and the residue wad distilled to give 15-2 as a light yellow oil (14 g, 35%).

$^1$H NMR CDCl₃ 400 MHz, δ 3.40 (s, 4H), 1.17 (s, 6H).

Step 2

To a suspension of NaH (3.4 g, 60%, 84.9 mmol) in DMF (40 mL), compound 15-3 (11.14 g, 69.6 mmol) was added dropwise at 0° C. The mixture was heated at 70° C. for 1 h under N₂. Then compound 15-2 (8.0 g, 34.8 mmol) was added and stirred for 60 h under N₂. The mixture was poured into an aqueous solution of NH₄Cl (20 g in 300 mL) and extracted with PE (50 mL×5). The organic phase was concentrated and purified by chromatography (PE) to afford compound 15-4 (3.0 g, Yield: 37.9%).

$^1$H NMR CDCl₃ 400 MHz δ 4.21-4.16 (m, 4H), 2.36 (s, 4H), 1.26-1.22 (m, 6H), 1.11 (s, 6H).

Step 3

To a stirred solution of compound 15-4 (3.0 g, 13.9 mmol) in EtOH (10 mL) was added aqueous KOH (85%, 779 mg, 13.9 mmol) at r.t. The reaction mixture was stirred at 76° C. for 3 h. The mixture was concentrated and partitioned between EtOAc (75 mL) and H₂O (125 mL). The aqueous phase was acidified with 1N HCl till pH=3 and extracted with EtOAc (75 mL×2). The organic layer was concentrated to give compound 15-5 (1.9 g, 68.3%) as oil.

$^1$H NMR CDCl₃ 400 MHz, δ 11.62 (s, 1H), 4.26-4.21 (m, 2H), 2.42 (s, 4H), 1.29-1.26 (m, 3H), 1.15-1.13 (d, J=7.2 Hz, 6H).

Step 4

To a stirred solution of compound 15-5 (500 mg, 0.5 mmol) in DCM (8 mL) was added HATU (285.0 mg, 0.75 mmol) and DIPEA (193.5 mg, 1.5 mmol) at r.t. After the reaction mixture was stirred at r.t. for 30 min, 15-6 (90.9 mg, 0.75 mmol) was added and stirred at r.t. for 16 h. The mixture was concentrated and purified by chromatography (DCM:MeOH=90:10) give compound 15-7 as white solid (70 mg, 46.2%)

LCMS: (5-95, AB, 1.5 min, ESI), 0.807 min, MS=303.9 [M+1]

$^1$H NMR CDCl$_3$ 400 MHz, δ 7.34-7.22 (m, 5H), 6.19 (d, J=7.2 Hz, 1H), 5.14-5.06 (m, 1H), 4.22-4.16 (m, 2H), 2.46-2.31 (m, 4H), 1.46 (d, J=6.8 Hz, 3H), 1.25-1.21 (m, 3H), 1.09 (s, 6H).

Step 5

To a stirred solution of compound 15-7 (70 mg, 0.23 mmol) in MeOH/THF/H$_2$O (1 mL/2 mL/2 mL) was added LiOH.H$_2$O (19.4 mg, 0.462 mmol) at r.t. The reaction mixture was stirred at r.t. for 1 h. Organic solvent was removed and partitioned between EtOAc (30 mL) and H$_2$O (25 mL). The aqueous phase was acidified with 1N HCl to pH=3 and extracted with EtOAc (30 mL). The organic phase was concentrated to afford compound 15-8 as white solid (50 mg, 78.7%).

$^1$H NMR CDCl$_3$ 400 MHz, δ 7.34-7.23 (m, 5H), 6.30 (d, J=7.2 Hz, 1H), 5.14-5.07 (m, 1H), 2.50-2.31 (m, 4H), 1.48 (d, J=6.8 Hz, 3H), 1.11 (d, J=16 Hz, 6H).

Step 6

To a stirred solution of compound 15-8 (50 mg, 0.18 mmol) in DCM (10 ml) was added HATU (102.6 mg, 0.27 mmol) and DIPEA (46.44 mg, 0.36 mmol) at r.t. and stirred for 30 min. Compound 15-9 (53 mg, 0.19 mmol) was added into the reaction mixture and stirred at r.t. for 16 h. The mixture was concentrated and purified by chromatography (DCM:MeOH=85:15) to afford compound 15-10 (60 mg, 61.8%) as white solid.

LCMS: (5-95, AB, 1.5 min, ESI), 0.803 min, MS=538.2 [M+1]

$^1$H NMR Methanol-d$_4$ 400 MHz, δ 8.19 (d, J=8 Hz, 1H), 7.58 (d, J=8.4 Hz, 2H), 7.31-7.17 (m, 7H), 5.07-5.00 (m, 1H), 4.56 (s, 2H), 4.51-4.47 (m, 1H), 3.21-3.17 (m, 1H), 2.45-2.35 (m, 4H), 1.89-1.85 (m, 1H), 1.75-1.72 (m, 1H), 1.55-1.47 (m, 5H), 1.08 (d, J=2 Hz, 6H).

Step 7

To a stirred solution of compound 15-10 (60 mg, 0.11 mmol) in dry DMF (3 mL) was added PNP carbonate (15-11) (66.9 mg, 0.22 mmol) and DIPEA (70.9 mg, 0.55 mmol) at r.t. and stirred at r.t. for 3 h. The mixture (15-12) was used for next step without further purification.

Step 8

To the reaction mixture of last step was added norfloxacin (70.2 mg, 0.22 mmol) at r.t. The mixture was stirred at r.t. for 16 h and purified by prep-HPLC to give example 15 (14.4 mg, Yield: 14.8%).

LCMS: (5-95, AB, 1.5 min, ESI), 0.887 min, MS=883.4.4 [M+1], 442.4 [½M+1]

$^1$H NMR DMSO-d$_6$ 400 MHz, δ 10.24 (s, 1H), 8.94 (s, 1H), 8.39 (s, 1H), 8.13 (d, J=2 Hz, 1H), 7.965-7.963 (m, 2H), 7.63 (d, J=8.4 Hz, 2H), 7.47 (d, J=8.8 Hz, 2H), 7.30-7.26 (m, 4H), 7.19-7.18 (m, 2H), 6.05 (s, 1H), 5.46 (s, 2H), 5.07 (s, 2H), 4.97-4.91 (m, 1H), 4.57 (s, 2H), 4.45 (s, 1H), 3.62 (s, 4H), 3.35 (s, 4H), 3.05-3.02 (m, 1H), 2.96-2.92 (m, 1H), 2.32-2.26 (m, 4H), 1.73-1.71 (m, 1H), 1.63-1.61 (m, 1H), 1.42-1.37 (m, 8H), 0.99 (s, 6H).

Example 16. (S)-1-ethyl-7-(4-((4-(2-(1-(ethylcarbamoyl)cyclopentanecarboxamido)-5-ureidopentanamido)benzyloxy)carbonyl)piperazin-1-yl)-6-fluoro-4-oxo-1,4-dihydroquinoline-3-carboxylic acid

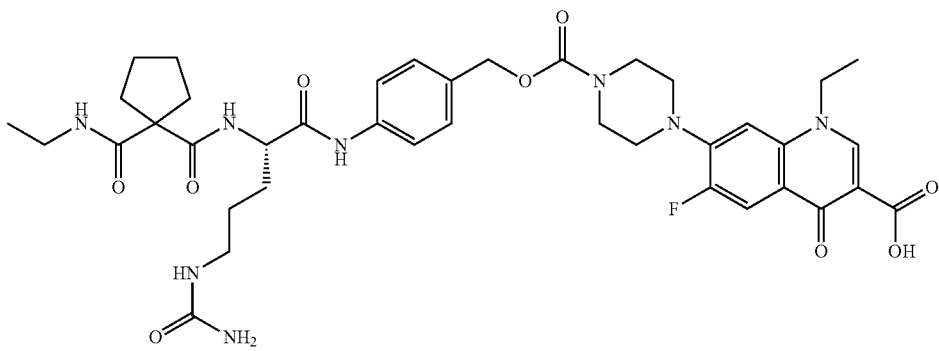

example 16

-continued
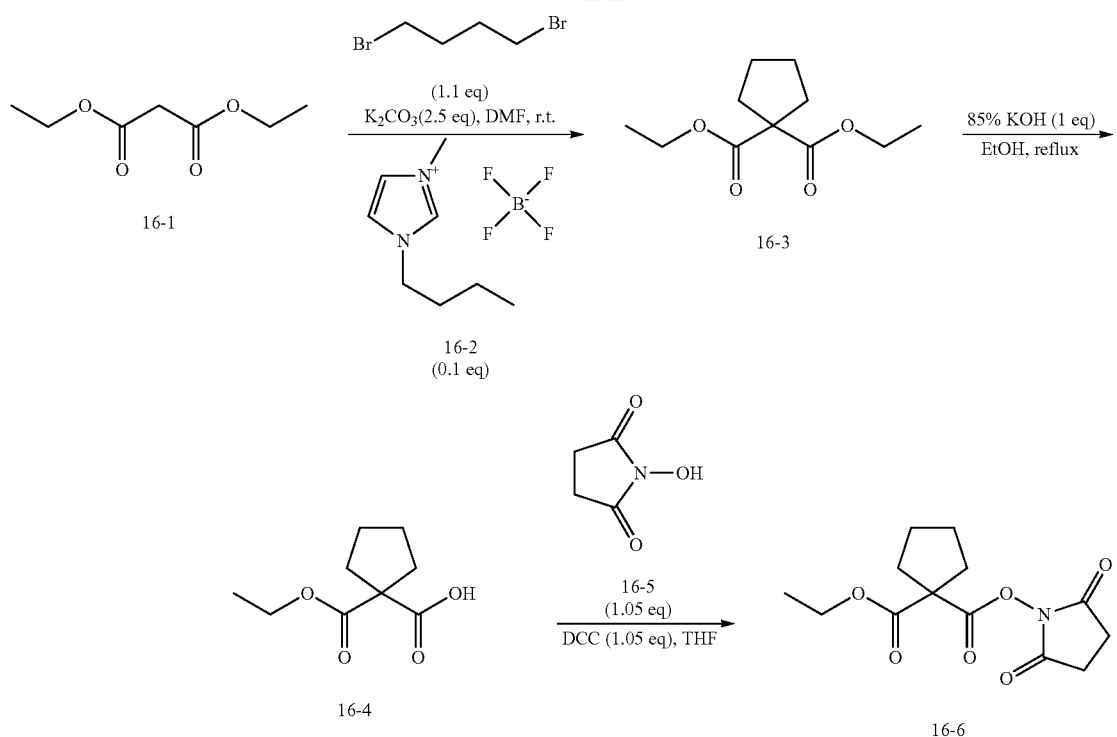
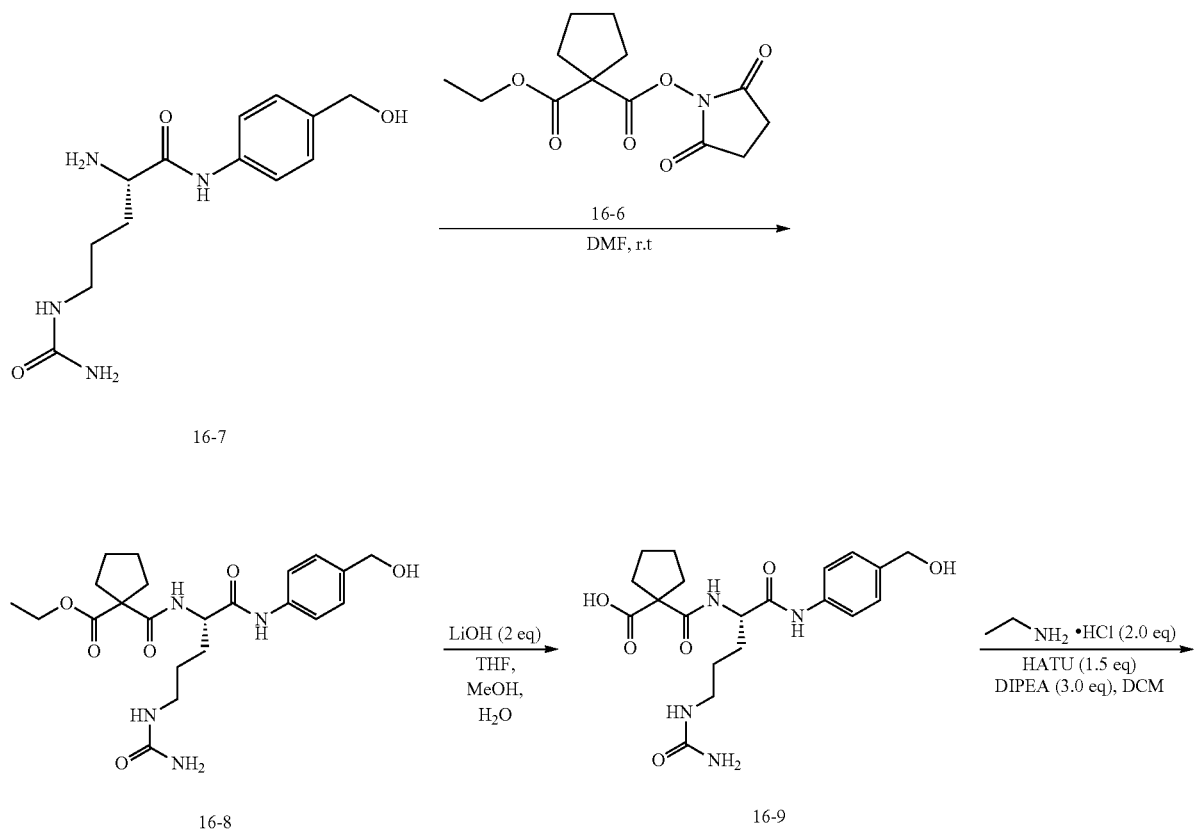

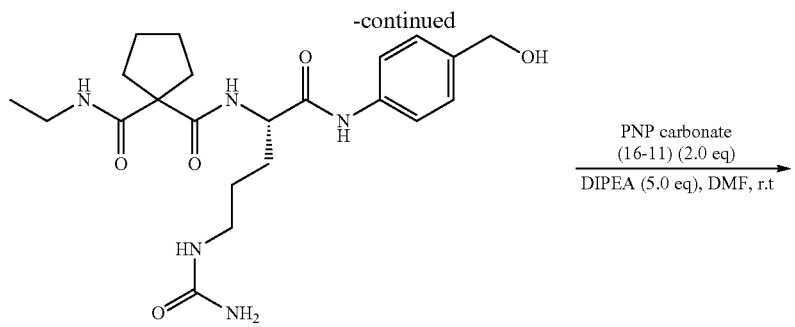

16-10

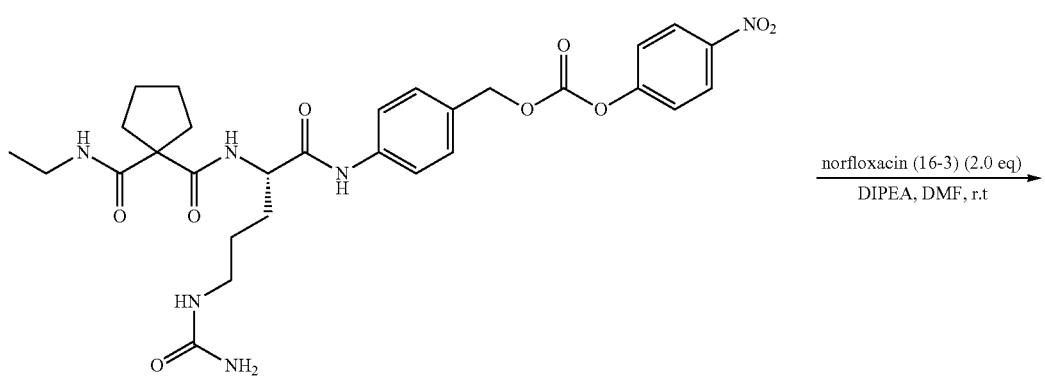

16-12

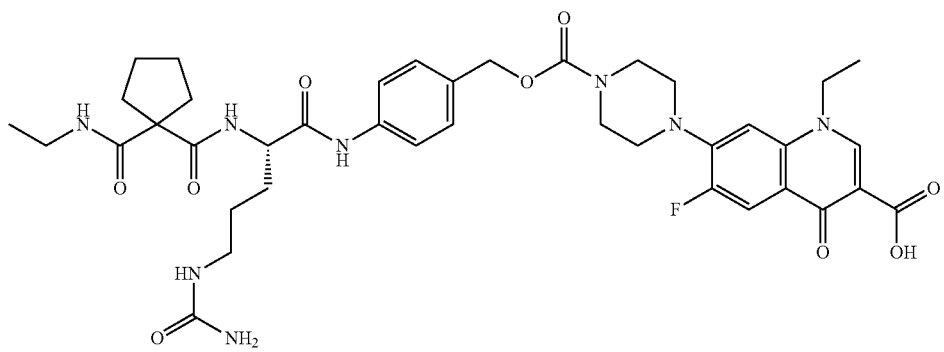

example 16

Step 1

To a solution of compound 16-1 (10 g, 62.4 mmol) in DMF (50 mL) was added 1,4-dibromobutane (14.8 g, 68.6 mmol), K₂CO₃ (21.5 g, 155.8 mmol) and compound 16-2 (1.4 g, 6.2 mmol) at r.t. and stirred at r.t. for 16 h. The solvent was removed under reduced pressure, and the residue was partitioned between EtOAc (200 mL) and H₂O (80 mL), the combined organic phase was dried and concentrated to give compound 16-3 as oil (10.0 g, Yield: 75%).

¹H NMR (400 MHz, CDCl₃) δ 4.15-4.10 (m, 4H), 2.14-2.10 (m, 4H), 1.64-1.61 (m, 4H), 1.20-1.17 (m, 6H).

Step 2

To a solution of compound 16-3 (6.0 g, 28.0 mmol) in EtOH (20 mL) was added 85% aqueous KOH solution (1.85 g, 28.0 mmol) at r.t. and stirred at 76° C. for 3 h. Solvent was removed and the residue was partitioned between EtOAc (20 mL) and H₂O (30 mL). The aqueous phase was acidified with 1N HCl to pH=3 and extracted with EtOAc (20 mL×2). The organic layer was dried and concentrated to give compound 16-4 as oil (2.5 g, yield: 48.0%).

¹H NMR (400 MHz, CDCl₃) δ 10.61-10.60 (m, 1H), 4.21-4.15 (m, 2H), 2.21-2.18 (m, 4H), 1.72-1.65 (m, 4H), 1.26-1.22 (m, 3H).

Step 3

To a solution of compound 16-4 (2.5 g, 13.4 mmol) and compound 16-5 (1.62 g, 14.1 mmol) in dry THF (20 mL) was added DCC (3.04 g, 14.74 mmol) at 0° C. The mixture was stirred at r.t. for 16 h under N₂. The mixture was filtered and the filtrate was concentrated to give crude compound 16-6 which was used for next step without further purification.

¹H NMR (400 MHz, MeOH-d₄) δ 4.23-4.18 (m, 2H), 2.79 (s, 4H), 2.36-2.23 (m, 4H), 1.76-1.72 (m, 4H), 1.30-1.28 (t, J=7.2 Hz, 3H).

Step 4

To a solution of compound 16-6 (1.0 g, 3.53 mmol) in DMF (15 mL) was added compound 16-7 (658.7 mg, 2.35 mmol) at r.t. The reaction mixture was stirred at r.t. for 16 h. The mixture was concentrated and purified by silica gel column chromatography (DCM:MeOH=10:1) to give compound 16-8 as white solid (150 mg, Yield: 14.2%).

LCMS (ESI): m/z 449.0 [M+1].

Step 5

To a solution of compound 16-8 (150 mg, 0.33 mmol) in THF/MeOH/H₂O (3 mL/3 mL/1.5 mL) was added LiOH.H₂O (28.14 mg, 0.67 mmol) at r.t. The reaction mixture was stirred at r.t. for 16 h. The mixture was concentrated and partitioned between EtOAc (15 mL) and H₂O (20 mL). The aqueous phase was acidified with 1N HCl to pH=3, extracted with EtOAc (15 mL×3) and concentrated to give crude compound 16-9 as white solid which was used to the next step without further purification.

LCMS (ESI): m/z 420.9 [M+1].

Step 6

To a solution of compound 16-9 (250 mg, 0.595 mmol) in DMF (15 mL) was added HATU (339.2 mg, 0.89 mmol) and DIPEA (268.6 mg, 2.08 mmol) at r.t. and stirred for 30 min. Ethylamine hydrochloride (96.98 mg, 1.19 mmol) was added into the reaction mixture and stirred at r.t. for 16 h. The mixture was filtered and purified by prep-HPLC and SFC to give compound 16-10 as white solid (30 mg, Yield: 11.3%).

LCMS (ESI): m/z 447.9 [M+1].

¹H NMR (400 MHz, DMSO-d₆) δ 9.99 (s, 1H), 7.75-7.73 (m, 2H), 7.57-7.55 (m, 2H), 7.23-7.21 (m, 2H), 5.97-5.94 (m, 1H), 5.39 (s, 2H), 5.11-5.08 (m, 1H), 4.41-4.36 (m, 2H), 4.35-4.32 (s, 1H), 3.13-3.06 (m, 2H), 2.97-2.90 (m, 2H), 2.16-2.14 (m, 2H), 2.11-2.05 (m, 1H), 1.95-1.93 (m, 1H), 1.92-1.91 (m, 1H), 1.51-1.49 (m, 4H), 1.39-1.37 (m, 1H), 1.20-1.19 (m, 2H), 1.02-0.98 (t, J=7.2 Hz, 3H).

Step 7

To a solution of compound 16-10 (30 mg, 0.067 mmol) in dry DMF (3 mL) was added compound 16-11 (40.7 mg, 0.134 mmol) and DIPEA (43.22 mg, 0.335 mmol) at 0° C. After the mixture was stirred at r.t. for 5 h, it was used for next step directly without further purification.

Step 8

To the mixture from last step (16-12) was added compound 16-13 (42.8 mg, 0.134 mmol) at r.t. The mixture was stirred at r.t. for 1 h and then purified by prep-HPLC to give the desired product example 16. (35.0 mg Yield: 66.0%)

¹H NMR (400 MHz, DMSO-d₆) δ 15.32 (s, 1H), 10.09 (s, 1H), 8.95 (s, 1H), 7.93 (d, J=13.2 Hz, 1H), 7.80-7.71 (m, 2H), 7.62 (d, J=8.4 Hz, 2H), 7.32 (d, J=8.4 Hz, 2H), 7.18 (d, J=8.0 Hz, 1H), 5.98-5.91 (m, 1H), 5.39 (s, 2H), 5.04 (s, 2H), 4.60-4.52 (m, 2H), 4.38-4.32 (m, 1H), 3.59 (s, 4H), 3.30 (s, 4H), 3.12-3.08 (m, 2H), 2.96-2.85 (m, 2H), 2.14-2.11 (m, 2H), 2.10-2.00 (m, 1H), 1.94-1.89 (m, 1H), 1.63-1.40 (m, 5H), 1.38-1.30 (m, 5H), 1.02-0.98 (t, J=7.2 Hz, 3H).

Example 17. 7-(4-((4-((S)-2-(1-((S)-3-(allyloxy)-3-oxo-1-(thiophen-3-yl)propylcarbamoyl)cyclobutan-ecarboxamido)-5-ureidopentanamido)benzyloxy)carbonyl)piperazin-1-yl)-1-ethyl-6-fluoro-4-oxo-1,4-dihydroquinoline-3-carboxylic acid

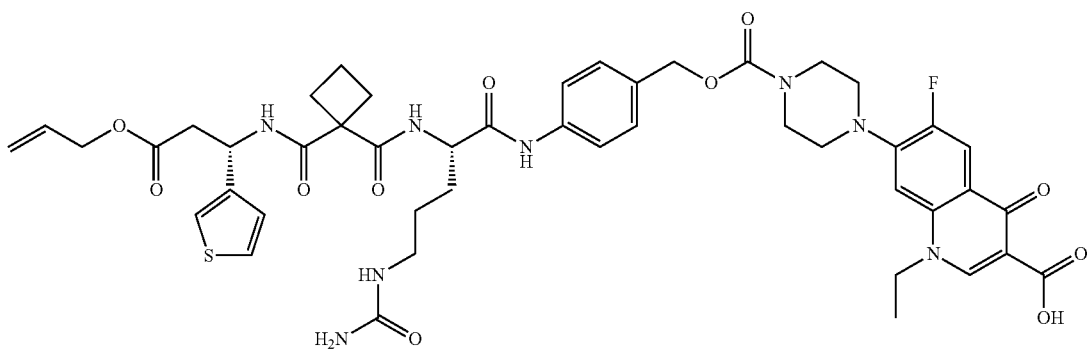

example 17

Example 17 was made using the procedure as Example 7, with the intermediates from the synthesis of Example 7.
Example 18. (S)-1-ethyl-7-(4-((4-(2-(1-(ethylcarbamoyl)cyclohexanecarboxamido)-5-ureidopentanamido)benzyloxy)carbonyl)piperazin-1-yl)-6-fluoro-4-oxo-1,4-dihydroquinoline-3-carboxylic acid
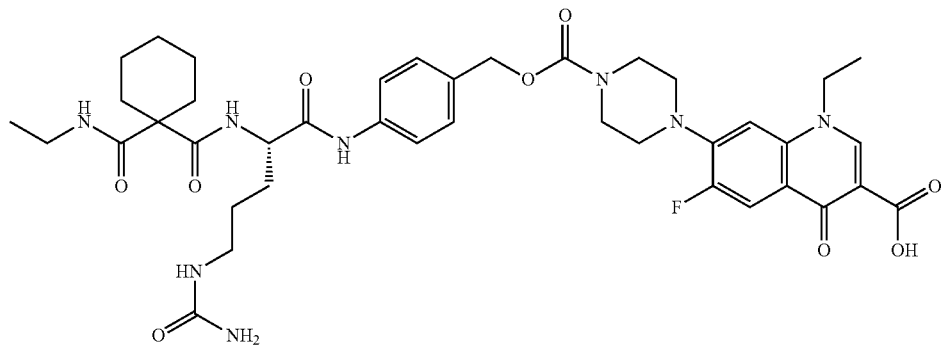
example 18
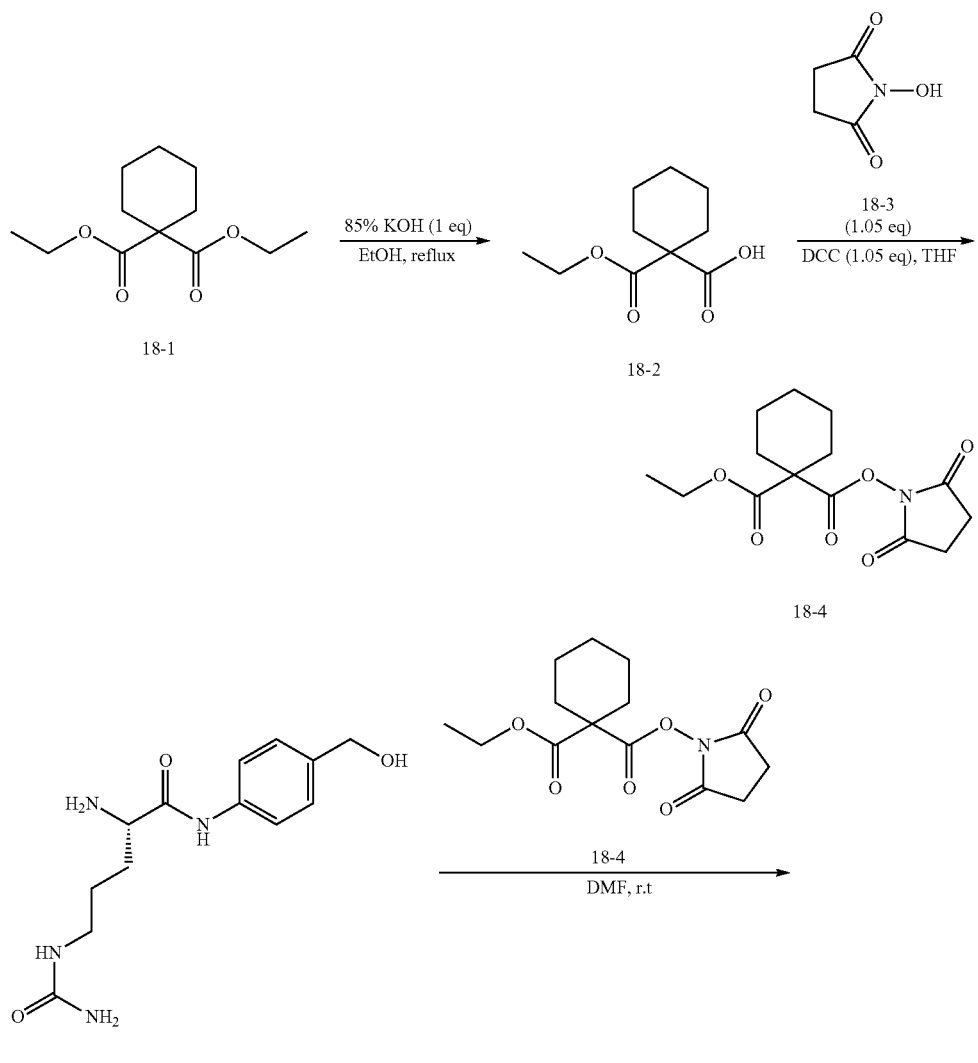

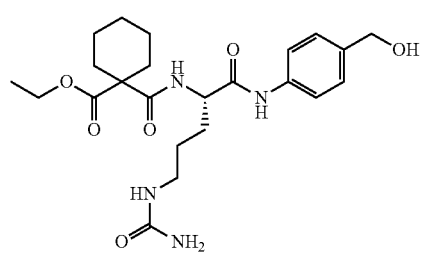

18-6

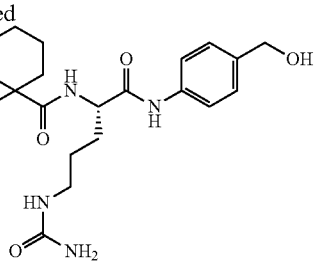

18-7

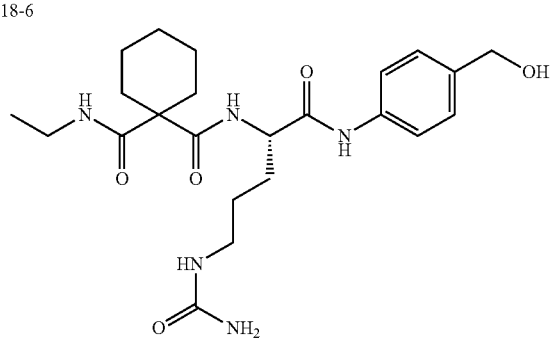

18-8

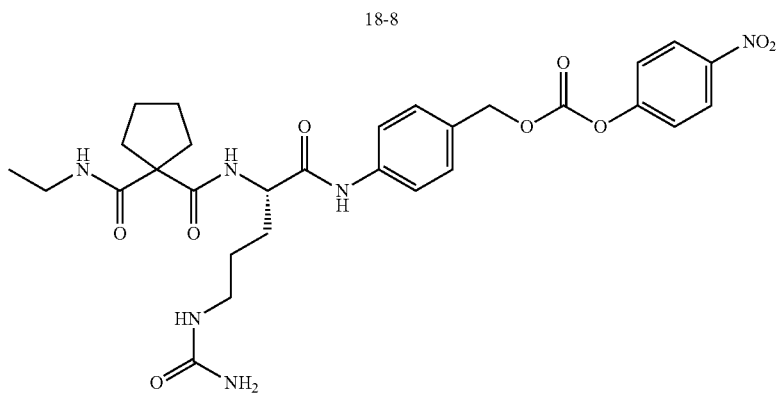

18-10

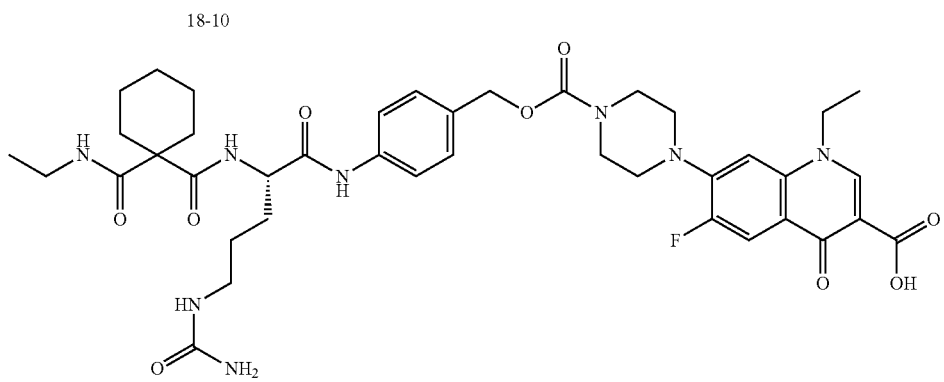

example 18

Step 1

To a solution of compound 18-1 (4.0 g, 17.5 mmol) in EtOH (20 mL) was added 85% aqueous KOH solution (1.15 g, 17.5 mmol) at r.t. After the reaction mixture was stirred at 76° C. for 3 h, it was concentrated and partitioned between EtOAc (15 mL) and H$_2$O (25 mL). The aqueous phase was acidified with 1N HCl to pH=3 and extracted with EtOAc (15 mL×2). The organic layer was concentrated to give compound 18-2 as an oil (2.5 g, yield: 71.4%).

$^1$H NMR (400 MHz, CDCl$_3$) δ 4.20-4.15 (m, 2H), 2.03-1.90 (m, 4H), 1.56-1.47 (m, 6H), 1.45-1.43 (t, 4.0 Hz, 3H).

Step 2

To a solution of compound 18-2 (2.5 g, 12.5 mmol) and 18-3 (1.51 g, 13.13 mmol) in dry THF (20 mL) was added DCC (2.83 g, 13.35 mmol) at 0° C. The mixture was stirred at r.t. for 16 h under $N_2$. The mixture was filtered and the filtrate was concentrated to give the crude compound 18-4 which was used for next step without further purification (2.0 g, Yield: 53.8%).

Step 3

To a stirred solution of compound 18-4 (2.0 g, 6.7 mmol) in DMF (15 mL) was added compound 18-5 (1.26 g, 4.5 mmol) at r.t. The reaction mixture was stirred at r.t. for 16 h. The mixture was concentrated and purified by column chromatography (DCM:MeOH=10:1) to give compound 18-6 as white solid (700 mg, Yield: 22.4%).

LCMS (ESI): m/z 463.0 [M+1].

Step 4

To a solution of compound 18-6 (700 mg, 1.50 mmol) in THF/MeOH/$H_2O$ (4 mL/4 mL/2 mL) was added LiOH.$H_2O$ (126.0 mg, 3.0 mmol) at r.t. After the reaction mixture was stirred at r.t. for 16 h, it was concentrated and partitioned between EtOAc (25 mL) and $H_2O$ (30 mL), the aqueous phase was acidified with 1N HCl to pH=3, extracted with EtOAc (25 mL×2) and concentrated to give crude compound 18-7 as white solid which was used in the next step without further purification.

LCMS (ESI): m/z 435.0 [M+1].

Step 5

To a solution of compound 18-7 (300 mg, 0.69 mmol) in DMF (15 mL) was added HATU (395.2 mg, 1.04 mmol) and DIPEA (267.03 mg, 2.07 mmol) at r.t. and stirred at r.t. for 30 min. Ethylamine (112.47 mg, 1.38 mmol) was added into the reaction mixture and stirred at r.t. for 16 h. The mixture was filtered and purified by prep-HPLC and SFC to give compound 18-8 (60 mg, Yield: 18.8%) as white solid.

LCMS (ESI): m/z 462.0 [M+1].

$^1$H NMR (400 MHz, MeOH-$d_4$) δ 7.62 (d, J=8.4 Hz, 2H), 7.28 (d, J=8.8 Hz, 2H), 4.58 (s, 1H), 4.54-4.50 (m, 3H), 3.62-3.57 (m, 1H), 3.26-3.18 (s, 2H), 3.10-3.07 (m, 2H), 2.16-2.02 (m, 2H), 1.85-1.81 (m, 3H), 1.73-1.71 (m, 1H), 1.59-1.50 (m, 5H), 1.18-1.14 (m, 1H), 1.12-1.09 (m, 3H).

Step 6

To a stirred solution of compound 18-8 (100 mg, 0.216 mmol) in dry DMF (3 ml) was added compound 18-9 (131.3 mg, 0.432 mmol) and DIPEA (139.3 mg, 1.08 mmol) at 0° C. The mixture (18-10) was stirred at r.t. for 3 h and used for next step without further purification.

Step 7

To the mixture (18-10) from last step was added norfloxacin (18-11) (137.9 mg, 0.432 mmol) at r.t. and stirred at r.t. for 1 h. The mixture was purified by prep-HPLC to give example 18 (98.0 mg Yield: 56.2%).

$^1$H NMR (400 MHz, DMSO-$d_6$) δ 15.30 (s, 1H), 10.09 (s, 1H), 8.93 (s, 1H), 7.92 (d, J=13.2 Hz, 1H), 7.78-7.72 (m, 1H), 7.67 (d, J=7.6 Hz, 1H), 7.63 (d, J=8.8 Hz, 2H), 7.32 (d, J=8.8 Hz, 2H), 7.18 (d, J=8.0 Hz, 1H), 5.98-5.92 (m, 1H), 5.38 (s, 2H), 5.04 (s, 2H), 4.57-4.55 (m, 2H), 4.39-4.31 (m, 1H), 3.59 (s, 4H), 3.31 (s, 4H), 3.31-3.08 (m, 2H), 3.00-2.86 (m, 2H), 2.12-2.03 (m, 1H), 2.01-1.91 (m, 1H), 1.90-1.83 (m, 3H), 1.58-1.67 (m, 1H), 1.40-1.25 (m, 11H), 1.01-0.97 (t, J=7.2 Hz, 3H).

Example 19. 7-(4-((4-((S)-2-(2,2-dimethyl-3-oxo-3-((R)-1-phenylethylamino)propanamido)-5-ureidopentanamido)benzyloxy)carbonyl)piperazin-1-yl)-1-ethyl-6-fluoro-4-oxo-1,4-dihydroquinoline-3-carboxylic acid

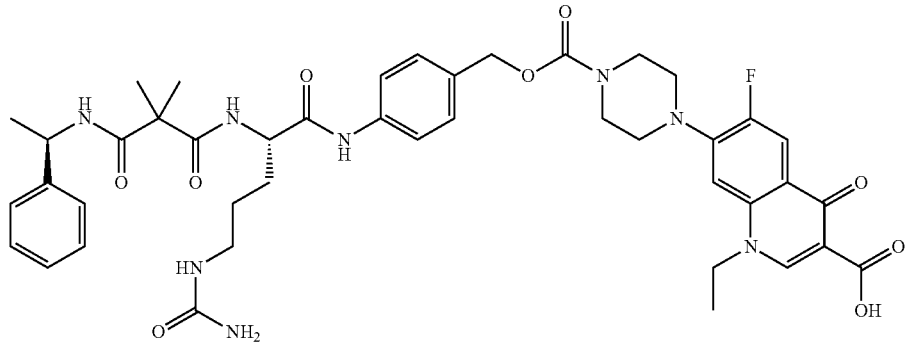

example 19

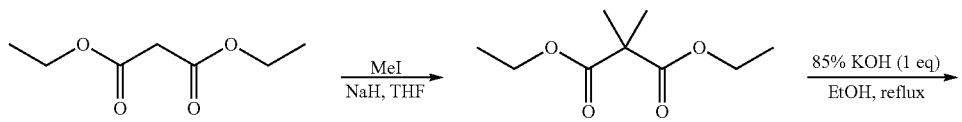

19-1          19-2

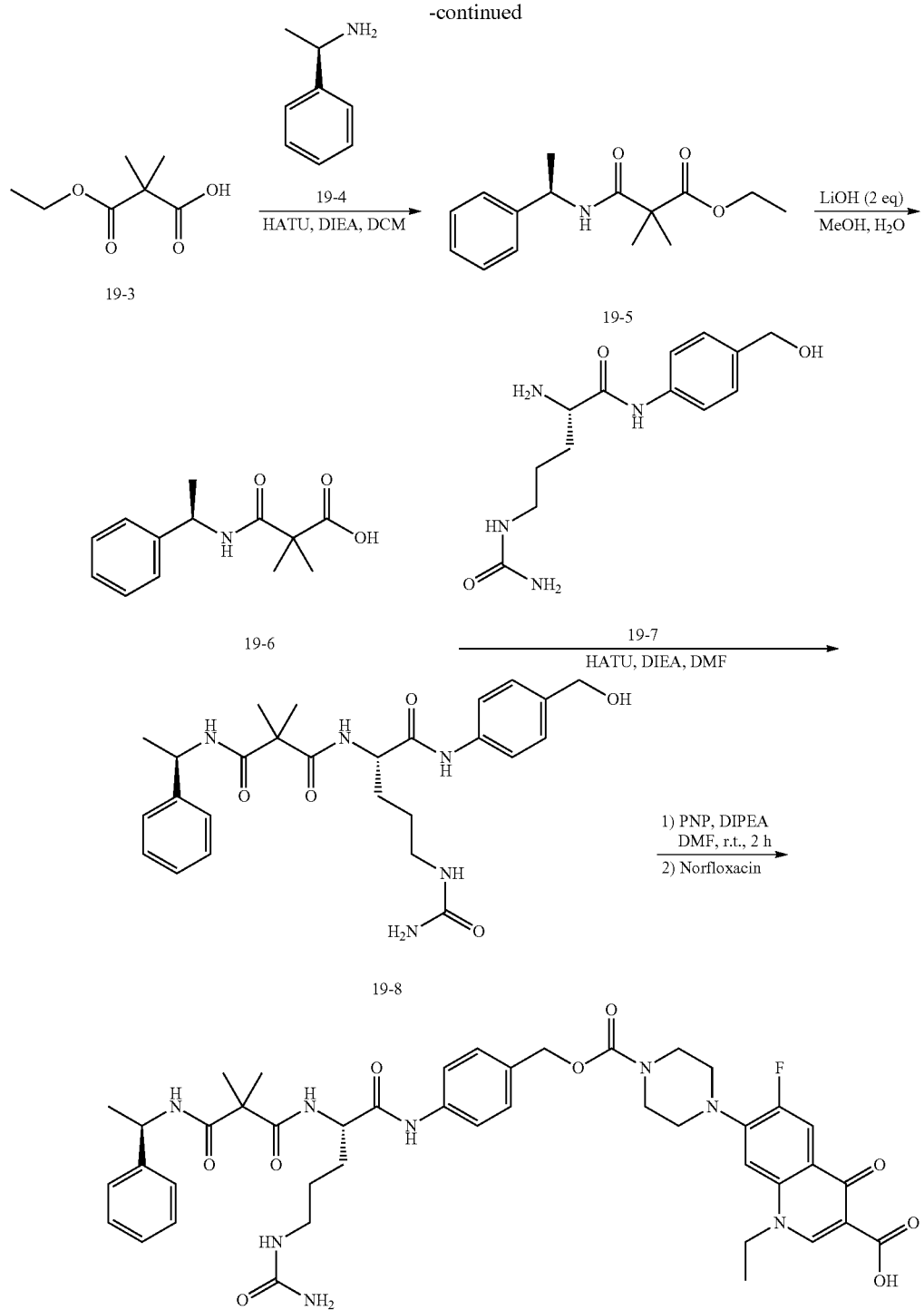

example 19

Step 1

To a solution of compound 19-1 (5.0 g, 31.22 mmol) in anhydrous THF (70 mL) was added NaH (3.75 g, 93.65 mmol, c=60%) slowly at 0° C. After the mixture was stirred at 0° C. for 10 m. MeI (6.15 mL, 124.88 mmol) was added dropwise at 0° C., and the reaction mixture was stirred at 0° C. for 2 h. The mixture was diluted with EtOAc (50 mL), filtered, the filtrate was concentrated under reduced pressure. The residue was diluted with EtOAc (50 mL), filtered, and the filtrate was concentrated to afford compound 19-2 (3.5 g, 59.6%) as an oil.

$^1$H NMR (400 MHz, DMSO-$d_6$) δ 4.13-4.08 (q, 4H), 1.33 (s, 6H), 1.16 (t, J=6.8 Hz, 6H).

Step 2

To a solution of compound 19-2 (3.0 g, 15.94 mmol) in EtOH (20 mL) was added aq. KOH solution (85%, 894 mg, 15.94 mmol). The reaction mixture was heated at reflux for 1 h. After organic solvent was removed under reduced pressure, it was diluted with H$_2$O (20 mL), and washed with PE (10 mL×2). The aqueous phase was adjusted to pH 2 with conc. HCl solution and extracted with EtOAc (20 mL×3). The combined EtOAc layer was dried over Na$_2$SO$_4$, filtered, and concentrated under reduced pressure to afford compound 19-3 (1.5 g, 58.8%).

$^1$H NMR (400 MHz, DMSO-d$_6$) δ 3.98-3.93 (q, 4H), 1.17 (s, 6H), 1.12 (t, J=7.2 Hz, 3H).

Step 3

To a mixture of compound 19-3 (1.0 g, 6.24 mmol) in anhydrous DCM (20 mL) was added DIPEA (1.61 g, 12.48 mmol), followed by HATU (2.85 g, 7.49 mmol). After the mixture was stirred at r.t. for 15 min, and compound 19-4 (908 mg, 7.49 mmol) was added. The reaction mixture was stirred at r.t. for 3 h, and washed with citric acid solution (10 mL×3), brine (10 mL×1), dried over Na$_2$SO$_4$, filtered, and concentrated under reduced pressure. The residue was purified by column chromatography (PE/EtOAc=5:1) to afford compound 19-5 as a white solid (1.30 g, 79.3%).

$^1$H NMR (400 MHz, DMSO-d$_6$) δ 8.00 (d, J=8.0 Hz, 1H), 7.31-7.28 (m, 4H), 7.22-7.18 (m, 1H), 4.97-4.90 (m, 1H), 4.12-4.01 (m, 2H), 1.36 (d, J=6.8 Hz, 3H), 1.33 (d, J=2.4 Hz, 6H), 1.14 (d, J=6.8 Hz, 3H).

Step 4

To a solution of compound 19-5 (1.5 g, 5.70 mmol) in a mixture of MeOH/H$_2$O (15 mL/5 mL) was added LiOH—H$_2$O (478 mg, 11.40 mmol). The reaction mixture was heated at reflux for 2 h. Organic solvent was removed under reduced pressure, and the water slurry was washed with DCM (5 mL×3). It was adjusted to pH 1 with con. HCl solution and extracted with EtOAc (10 mL×3). The combined EtOAc layer was dried over Na$_2$SO$_4$, filtered, and concentrated under reduced pressure to afford compound 19-6 as white solid (800 mg, 59.7%).

$^1$H NMR (400 MHz, DMSO-d$_6$) δ 12.45 (br, 1H), 7.95 (d, J=8.0 Hz, 1H), 7.32-7.27 (m, 4H), 7.23-7.17 (m, 1H), 4.97-4.90 (m, 1H), 1.36 (d, J=6.8 Hz, 3H), 1.31 (d, J=3.6 Hz, 6H).

Step 5

To a solution of compound 19-6 (167 mg, 0.71 mmol) in DMF (5 mL) was added DIPEA (183 mg, 1.42 mmol), followed by HATU (323 mg, 0.85 mmol). The mixture was stirred at r.t. for 10 min, and compound 19-7 (200 mg, 0.71 mmol) was added. After the reaction mixture was stirred at r.t. for 2 h, it was purified by prep-HPLC to afford compound 19-8 as white solid (80 mg, 22.7%).

$^1$H NMR (400 MHz, DMSO-d$_6$) δ 10.05 (s, 1H), 8.11 (d, J=8.0 Hz, 1H), 7.88 (d, J=7.6 Hz, 1H), 7.57-7.54 (m, 2H), 7.32-7.25 (m, 4H), 7.22-7.15 (m, 3H), 5.95 (t, J=5.6 Hz, 1H), 5.39 (s, 2H), 5.08 (br, 1H), 4.98-4.94 (m, 1H), 4.41 (s, 2H), 4.36-4.31 (m, 1H), 3.00-2.89 (m, 2H), 1.78-1.75 (m, 1H), 1.63-1.59 (m, 1H), 1.40-1.33 (m, 8H), 1.30 (s, 3H).

Step 6

To a solution of compound 19-8 (80 mg, 0.16 mmol) in anhydrous DMF (4 mL) was added DIPEA (103 mg, 0.80 mmol), followed by PNP carbonate (97 mg, 0.32 mmol). After it was stirred at r.t. under N$_2$ for 2 h, norfloxacin (102 mg, 0.32 mmol) was added. The mixture was stirred at r.t. for another 1 h, filtered, and the filtrate was purified by prep-HPLC to afford example 19 as white solid (81 mg, 60.0%).

LCMS (ESI): RT=0.854 min, M/2+H$^+$=422.2. method=5-95/1.5 min.

$^1$H NMR (400 MHz, DMSO-d$_6$) δ 15.30 (br, 1H), 10.16 (s, 1H), 8.95 (s, 1H), 8.11 (d, J=8.0 Hz, 1H), 7.95-7.91 (m, 2H), 7.64 (d, J=8.8 Hz, 2H), 7.35-7.27 (m, 6H), 7.21-7.17 (m, 2H), 5.97 (t, J=5.6 Hz, 1H), 5.42 (s, 2H), 5.07 (s, 2H), 5.00-4.97 (m, 1H), 4.58-4.55 (m, 2H), 4.39-4.33 (m, 1H), 3.61 (s, 4H), 3.31 (s, 4H), 3.02-2.92 (m, 2H), 1.80-1.78 (m, 1H), 1.64-1.62 (m, 1H), 1.42-1.33 (m, 14H).

Example 20. (S)-7-(4-((4-(6-amino-2-(1-(ethylcarbamoyl)cyclobutanecarboxamido)hexanamido)benzyloxy)carbonyl)piperazin-1-yl)-1-ethyl-6-fluoro-4-oxo-1,4-dihydroquinoline-3-carboxylic acid

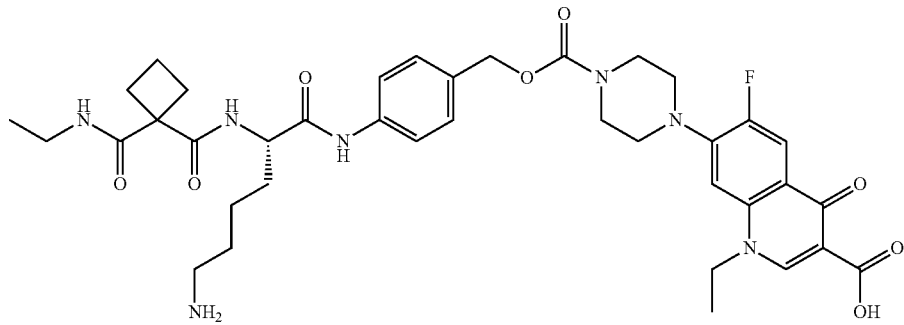

example 20

-continued
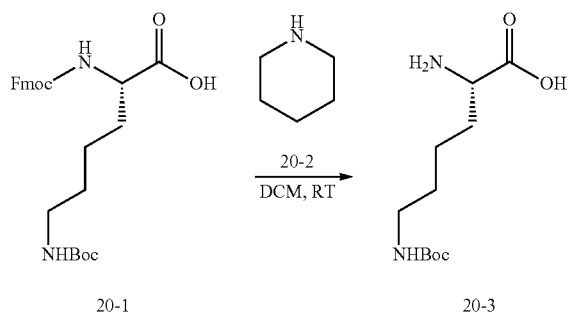
20-1
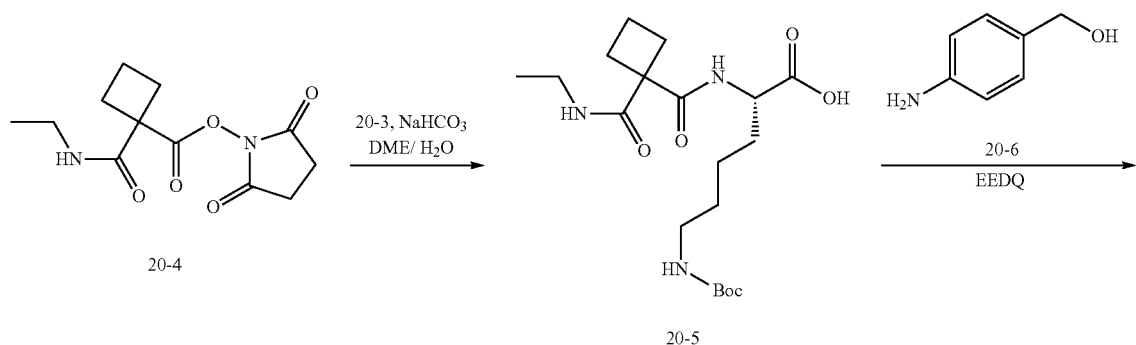
20-5
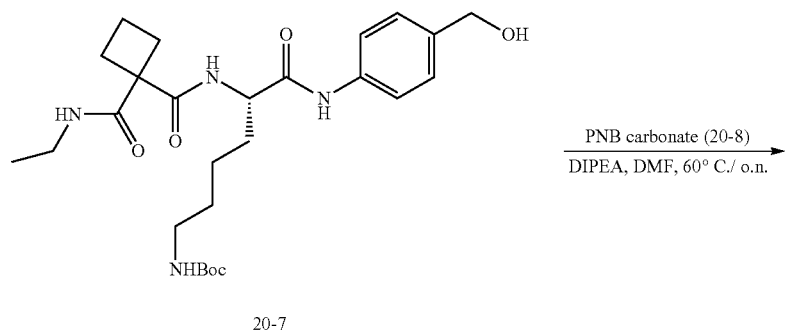
20-7
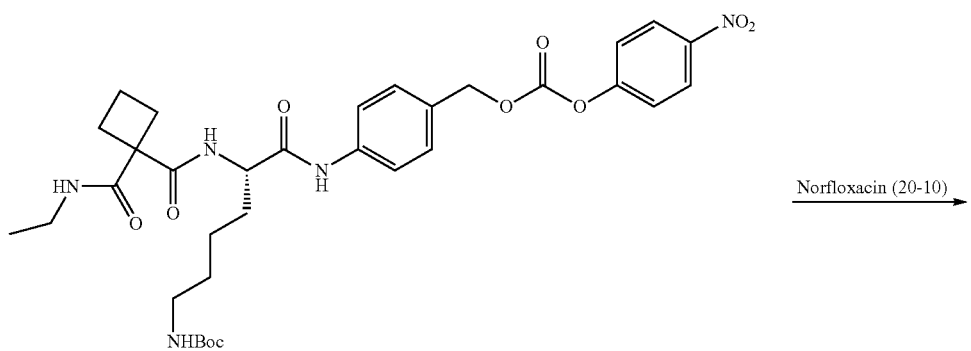
20-9

-continued

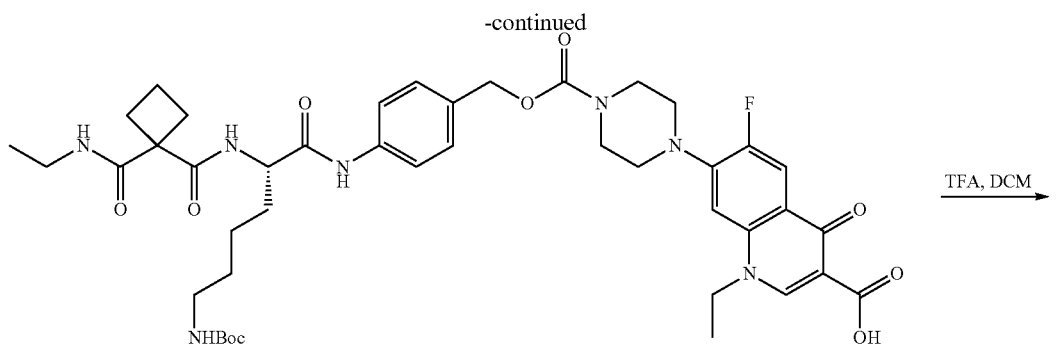

20-11

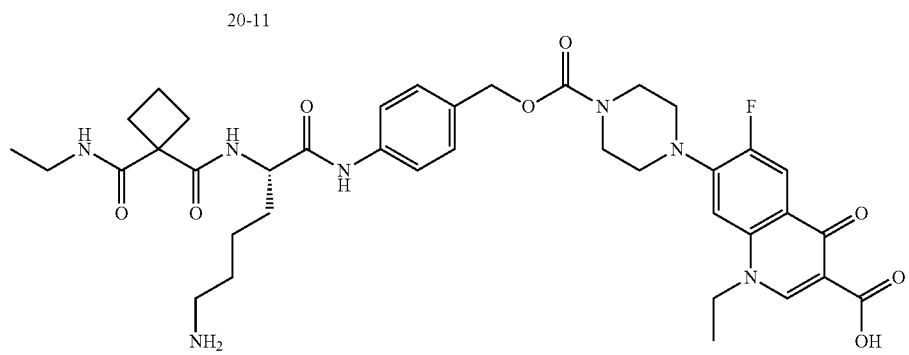

example 20

Step 1

To a stirred solution of compound 20-1 (5 g, 10.7 mmol) in DCM was added compound 20-2 (5.5 ml, 53 mmol) at r.t. The mixture was stirred at r.t. for 16 h. The reaction mixture was extracted with H₂O and the combined aqueous layers were concentrated to give 20-3. (Yield: 95%)

Step 2

To a solution of compound 20-4 (1.5 g, 5.6 mmol) in DME (50 ml) was added a solution of compound 20-3 (2.75 g, 11.2 mmol) and NaHCO₃ (940 mg, 11.2 mmol) in water (50 mL). The mixture was stirred at r.t. for 16 h. The mixture was washed with EtOAc and acidified to pH 3 with 10% HCl. The resulting suspension was extracted with EtOAc. The combined organic layer was concentrated to give compound 20-5. (Yield: 80%)

LCMS (ESI): m/z 400.0 [M+H⁺].

Step 3

To a solution of compound 20-5 (1 g, 2.5 mmol) in a mixture of DCM and MeOH (20 mL, 10 mL) were added 4-amino-phenyl)methanol (20-6) (462 mg, 3.75 mmol) and EEDQ (1.236 g, 5 mmol). The mixture was stirred at r.t. for 16 h. The residue was purified by column (PE/EtOAc=1/3) to give 20-7 (Yield: 60%).

LCMS (ESI): m/z 505.1 [M+H⁺].

Step 4

To a solution of compound 20-7 (180 mg, 0.36 mmol) in DMF (6 mL) was added compound 20-8 (219 mg, 0.72 mmol) and DIPEA (140 mg, 1.08 mmol) at 0° C. The mixture was stirred at r.t. for 16 h. The mixture (20-9) was used in next step without further purification.

(Yield: 100%)

LCMS (ESI): m/z 670.6 [M+H⁺].

Step 5

To the mixture of crude 20-9 was added norfloxacin (230 mg, 0.72 mmol) at r.t. and stirred at r.t. for 1 h. The residue was purified by prep-HPLC to give compound 20-11. (Yield: 60%)

LCMS (ESI): m/z 850.5 [M+H⁺].

Step 6

To compound 20-11 was added a solution of TFA and DCM (1:1) at 0° C. The mixture was stirred at r.t. for 1 h. The mixture was basified to pH=9 with NH₃.H₂O. The residue was purified by prep-HPLC and SFC to give example 20 (Yield: 30%).

¹H NMR (400 MHz, DMSO-d₆)

δ 10.26 (s, 1H), 9.43 (HCOOH), 8.97 (d, J=7.6 Hz, 1H), 7.99-7.89 (m, 6H), 7.67-7.65 (m, 2H), 7.39-7.33 (m, 2H), 7.23-7.21 (m, 1H), 5.06 (s, 2H), 4.72-4.60 (m, 2H), 4.40 (s, 1H), 3.80-3.55 (m, 6H), 3.31 (s, 4H), 3.15-3.12 (m, 2H), 2.76-2.73 (m, 2H), 2.48-2.41 (m, 2H), 1.81-1.69 (m, 4H), 1.59-1.55 (m, 2H), 1.43-1.34 (m, 5H), 1.07-0.98 (m, 3H).

Example 21. (S)-7-(4-((4-(5-amino-2-(1-(ethylcarbamoyl)cyclobutanecarboxamido) pentanamido) benzyloxy)carbonyl)piperazin-1-yl)-1-ethyl-6-fluoro-4-oxo-1,4-dihydroquinoline-3-carboxylic acid
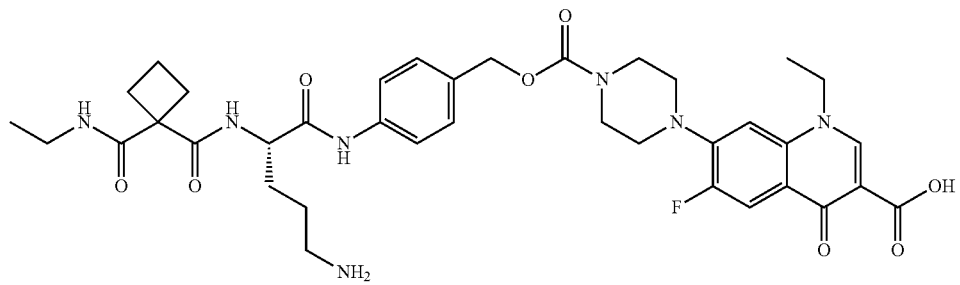
example 21
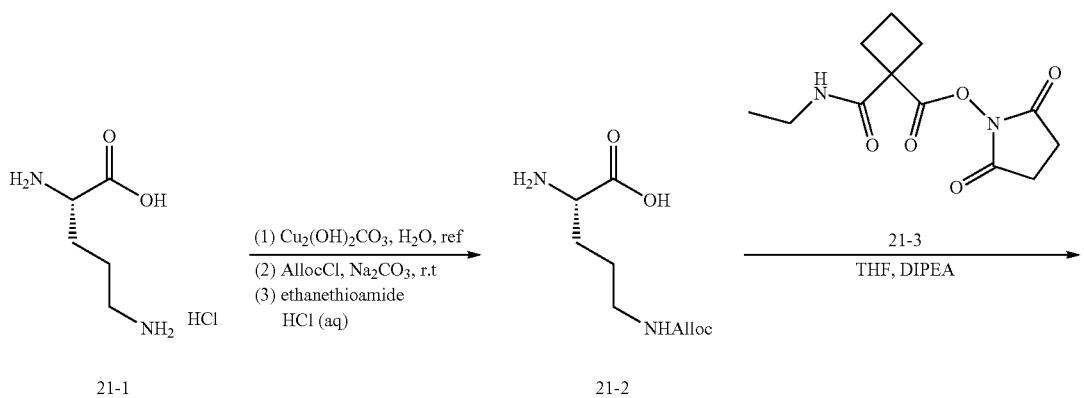
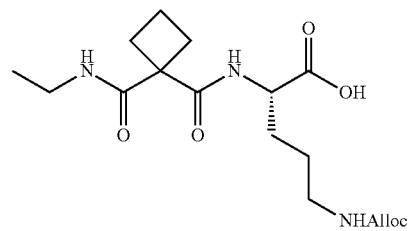
21-4
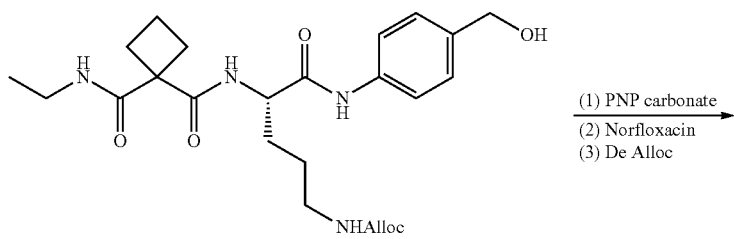
21-5

-continued

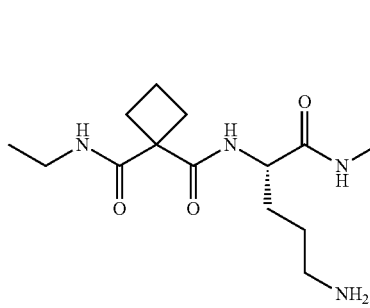
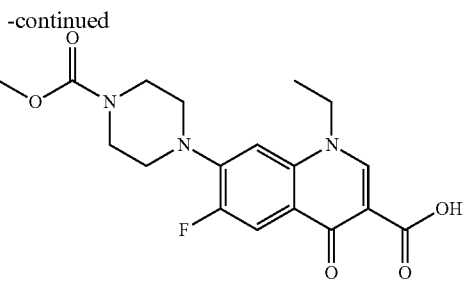

example 21

Step 1

To a solution of 21-1 (10.0 g, 0.06 mol) in H₂O (300 mL) was added Cu₂(OH)₂CO₃ (24.0 g, 0.12 mol). After the mixture was stirred at 100° C. for 1 h, it was filtrated quickly. Na₂CO₃ (20.0 g, 0.18 mol) was added to the filtrate. After it was stirred at r.t. for 20 min, AllocCl (12.0 g, 0.10 mol) was added to dropwise at r.t. and stirred at r.t. for 3 h. The mixture was filtered and washed with H₂O, then ethanethioamide (7.5 g, 0.10 mol) was added. After it was stirred at 50° C. for 3 h, HCl (aq) was added to adjust pH=3-4. The mixture was heated at reflux for 1 h. After the hot mixture was filtered, the filtrate was concentrated until white solid precipitated out. It was cooled to r.t. and filtered to give 21-2 as white solid (4.5 g, 35%) Step 2. To a solution of 21-2 (1.0 g, 4.6 mmol) in THF (30 mL) was added DIPEA (1.9 g, 15.0 mmol) and compound 21-3 (1.2 g, 4.6 mmol). After it was stirred at 100° C. for 4 h, the mixture was cooled to r.t. Water (100 mL) was added, followed by HCl (aq) to adjust pH=2-3. The mixture was extracted with EtOAc (50 mL×2). The organic layer was washed with brine (50 mL), dried over Na₂SO₄ and concentrated to give the crude 21-4 as brown solid (1.3 g, crude).

Step 3

To a solution of 21-4 (1.2 g, 3.2 mmol) in DCM (50 mL) was added EEDQ (1.1 g, 4.5 mmol) and (4-aminophenyl) methanol (750 mg, 6.0 mmol). After the mixture was stirred at r.t. for 4 h, water (50 mL) was added. The mixture was extracted with DCM (60 mL×2), dried over Na₂SO₄, concentrated, and purified by column (PE:EtOAc=1:20) to give 21-5 as yellow oil (500 mg, 30%).

Step 4

To a solution of 21-5 (500 mg, 1.05 mmol) in DCM (30 mL) was added DIPEA (650 mg, 5.0 mmol) and PNP carbonate (320 mg, 1.5 mmol). The mixture was heated at reflux for 16 h. Solvent was removed, and the residue was dissolved in DMF (20 mL). DIPEA (400 mg, 3.0 mol) and norfloxacin (380 mg, 1.2 mmol) were added. The mixture was stirred at 100° C. for 5 h, then cooled to r.t. Saturated NaCl (100 mL) was added to and filtered to give the crude product as yellow solid (300 mg, MS=820.2, M+1).

To a solution of the above crude product (300 mg) in THF (30 mL) was added Pd(PPh₃)₄ (80 mg, 0.07 mmol) and 1,3-dimethylpyrimidine-2,4,6(1H,3H,5H)-trione (1.0 g, 6.4 mmol). The mixture was stirred at 50° C. for 16 h under N₂ and cooled to r.t. The mixture was filtered, concentrated and purified by prep-HPLC to give example 21 (24 mg, 8%).

¹H NMR (400 MHz, DMSO-d₆) δ 10.37 (s, 1H), 8.94 (s, 1H), 7.94-7.89 (m, 6H), 7.65-7.63 (d, J=8.4 Hz, 2H), 7.37-7.31 (m, 2H), 7.19 (d, J=7.6 Hz, 1H), 5.04 (s, 2H), 4.63-4.54 (m, 2H), 4.47-4.41 (m, 1H), 3.68-3.53 (m, 6H), 3.29 (s, 4H), 3.14-3.08 (m, 2H), 2.80-2.77 (m, 2H), 2.48-2.42 (m, 2H), 1.88-1.63 (m, 6H), 1.48 (t, J=6.8 Hz, 3H), 1.05-0.95 (t, J=7.2 Hz, 3H).

Example 22. 7-(4-((4-(2-(3-((S)-1-(benzyloxycarbonylamino)-2-methylpropyl)isoxazol-5-yl)propanamido)benzyloxy)carbonyl)piperazin-1-yl)-1-ethyl-6-fluoro-4-oxo-1,4-dihydroquinoline-3-carboxylic acid

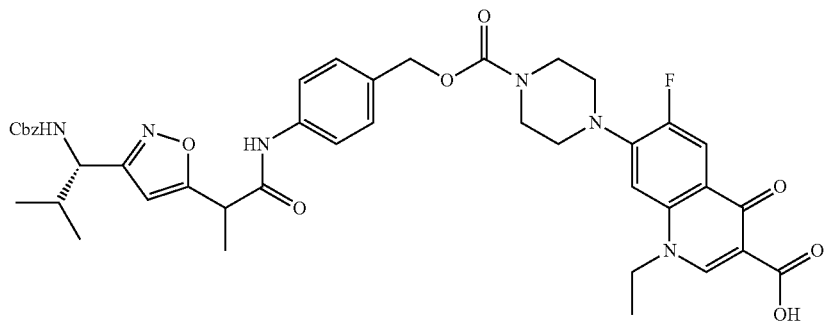

example 22

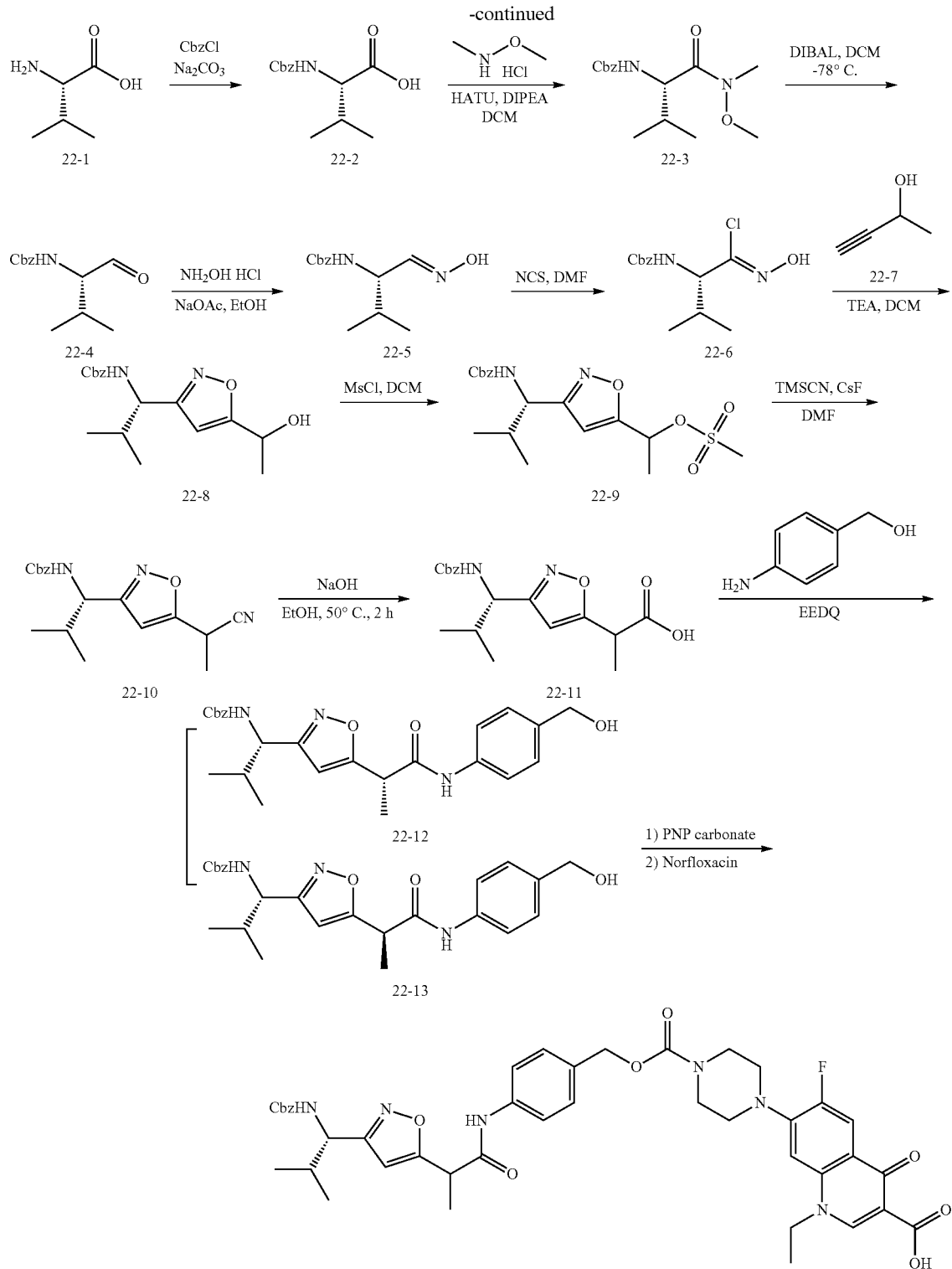

example 22

Step 1

To a suspension of compound 22-1 (50.0 g, 0.43 mol) and Na₂CO₃ (90.0 g, 0.85 mol) in THF and H₂O (300 mL/300 mL) at 0° C. was added CbzCl (84.0 g, 0.49 mol) slowly. The reaction mixture was allowed to warm to r.t. and stirred at r.t. for 16 h. The organic solvent was removed and the aqueous solution was extracted with EtOAc (200 mL). The aqueous solution was acidified to pH=2 with 1M HCl, and then extracted with EtOAc (200 mL×2). The combined organic layer was washed with brine (150 mL), dried over anhydrous Na$_2$SO$_4$, filtered and concentrated to afford the crude 22-2 as a white solid, which was used in next step without further purification.

Step 2

To the solution of compound 22-2 (20 g, 79.6 mmol) in dry DCM (200 mL) was added HATU (35 g, 92.1 mmol) and DIPEA (28 g, 217 mmol). After it was stirred at r.t. for 15 min, N-methoxymethanamine hydrochloride (11 g, 112.8 mmol) was added. After the solution was stirred for 3 h, it was washed with 1M HCl, saturated NaHCO$_3$, and brine. The organic layer was dried over Na$_2$SO$_4$, filtered, concentrated and purified by the column chromatography on silica gel to give compound 22-3 (12 g, 51.2%).

Step 3

DIBAL-H (30 mL, 1M in toluene) was added dropwise to a solution of compound 22-3 (4 g, 13.6 mmol) in dry DCM (150 mL) at −78° C. under N$_2$. After the solution was stirred at −78° C. for 6 h, it was quenched with MeOH (100 mL) and water (10 mL). The suspension was filtered off and the filtrate was dried over Na$_2$SO$_4$. Solvent was removed and the residue was purified on silica gel column to afford compound 22-4 as colorless oil (1.1 g, 34.4%).

$^1$H NMR (400 MHz, CDCl$_3$) δ 9.65 (s, 1H), 7.37-7.32 (m, 5H), 5.35-5.33 (m, 1H), 5.12 (s, 2H), 4.38-4.32 (m, 1H), 2.36-2.28 (m, 1H), 1.05-1.03 (d, J=7.2 Hz, 3H), 0.95 (d, J=6.8 Hz, 3H).

Step 4

To the solution of compound 22-4 (110 mg, 0.47 mmol) in EtOH (10 mL) was added sodium acetate (57.5 mg, 0.7 mmol) and hydroxylamine hydrochloride (49 mg, 0.7 mmol). After the reaction was stirred at 80° C. for 16 h, the solvent was removed and the residue was dissolved in water and extracted with EtOAc (30 mL×2). The combined organic layers were washed with brine (30 mL), dried over anhydrous sodium sulfate, filtered and concentrated to give compound 22-5 as a white solid which was used in next step without further purification.

$^1$H NMR (400 MHz, DMSO-d$_6$) δ 10.97 (s, 0.6H), 10.73 (s, 0.3H), 7.49-7.45 (m, 1H), 7.39-7.29 (m, 5H), 7.18 (d, J=7.2 Hz, 0.3H), 6.54 (d, J=6.8 Hz, 0.6H), 5.02 (s, 2H), 4.63-4.58 (m, 0.6H), 3.88-3.82 (m, 0.3H), 1.89-1.78 (m, 1H), 0.84 (q, J=6.8 Hz, 6H).

LCMS (ESI): m/z 251.0 [M+H$^+$].

Step 5

To a solution of compound 22-5 (800 mg, 3.2 mmol) in DMF (5 mL) was added NCS (470 mg, 3.5 mmol). After the mixture was stirred for 1 h at 40° C., it was diluted with EtOAc (50 mL) and water (20 mL). The organic layer separated and washed with brine (30 mL×5), dried over Na$_2$SO$_4$, filtered and concentrated to afford compound 22-6, which was used directly in the next step.

Step 6

To a stirred solution of compound 22-7 (168 mg, 2.4 mmol) in DCM (10 mL) was added TEA (240 mg, 2.4 mmol) at 0° C. After it was stirred for 30 min, a solution of compound 22-6 (1.2 mmol) in DCM (10 mL) was added slowly. The reaction mixture was warmed to r.t. and stirred at r.t. for 16 h. Water was added to the reaction mixture and the layers were separated and the aqueous layer was extracted with DCM (20 mL×3). The combined organic layers were washed with brine (20 mL), dried over anhydrous sodium sulfate, filtered and concentrated. The residue was purified on silica gel column to give compound 22-8 as a pale yellow solid (150 mg, 39.3%).

$^1$H NMR (400 MHz, CDCl$_3$) δ 7.34-7.31 (m, 5H), 6.09 (s, 1H), 5.41 (d, J=8.0 Hz, 1H), 5.14-5.06 (m, 2H), 4.96 (d, J=6.4 Hz, 1H), 4.78-4.74 (q, J=9.2 Hz, 1H), 2.17-2.08 (m, 1H), 1.55 (d, J=6.8 Hz, 3H), 1.03 (d, J=6.8 Hz, 3H), 0.96-0.91 (t, J=9.6 Hz, 6H).

Step 7

To the solution of compound 22-8 (1 g, 3.14 mmol) in dry DCM (50 mL) was added MsCl (5 g, 43.9 mmol) at 0° C. The reaction mixture was allowed to warm to r.t. and stirred at r.t. for 3 h. Water was added to the reaction mixture and the layers were separated and the aqueous layer was extracted with DCM (50 mL×3). The combined organic layers were washed with brine (50 mL), dried over anhydrous sodium sulfate, filtered and concentrated. The crude product was purified on silica gel column to afford compound 22-9 as colorless oil (1.2 g, 96.4%).

$^1$H NMR (400 MHz, CDCl$_3$) δ 7.36-7.33 (m, 5H), 6.26 (s, 1H), 5.82-5.77 (q, J=13.6 Hz, 1H), 5.32-5.31 (d, J=8.8 Hz, 1H), 5.14-5.08 (m, 2H), 4.80-4.77 (m, 1H), 3.00 (s, 3H), 2.20-2.12 (m, 1H), 1.79-1.77 (d, J=6.8 Hz, 3H), 0.97-0.93 (q, J=10 Hz, 6H).

Step 8

A flask containing CsF (690 mg, 4.54 mmol) was purged with N$_2$, TMSCN (750 mg, 7.57 mmol) and dry DMF (2.5 mL) was added. The mixture was stirred at r.t. for 15 min and a pale yellow suspension formed. The solution of compound 22-9 (600 mg, 1.51 mmol) in dry DMF (2 mL) was added. After the mixture was stirred at 50° C. for 16 h under N$_2$, water (50 mL) and EtOAc (50 mL) was added and the layers were separated. The aqueous layer was extracted with EtAc (50 mL×2). The combined organic layers were washed with aq. NaHCO$_3$, brine and dried over Na$_2$SO$_4$. Solvent was removed, and the residue was purified by prep-HPLC to give compound 22-10 (60 mg, 12.1%).

$^1$H NMR (400 MHz, CDCl$_3$) δ 7.37-7.33 (m, 5H), 6.22 (s, 1H), 5.28-5.26 (m, 1H), 5.15-5.08 (m, 2H), 4.80-4.76 (m, 1H), 4.12-4.06 (m, J=14.8 Hz, 1H), 2.19-2.14 (m, 1H), 1.74-1.70 (d, J=7.2 Hz, 3H), 0.98-0.93 (m, 6H).

LCMS (ESI): m/z 327.9 [M+H$^+$].

Step 9

To a stirred solution of compound 22-10 (500 mg, 1.5 mmol) in EtOH (10 mL) was added NaOH aqueous solution (4 M, 5 mL). After the reaction mixture was stirred at 50° C. for 2 h, organic solvent was removed and the aqueous layer was diluted with H$_2$O (20 mL) and EtOAc (30 mL). The layers were separated and the aqueous layer was acidified to pH=2 with 1 M HCl. It was extracted with EtOAc (30 mL×2). The combined organic layers were washed with brine, dried and concentrated to afford the crude compound 22-11 which was used in next step without further purification.

Step 10

EEDQ (300 mg, 1.22 mmol) was added to the solution of compound 22-11 (220 mg, 0.61 mmol) and (4-aminophenyl)

methanol (155 mg, 1.22 mmol) in dry DCM (10 mL) at 0° C. under $N_2$. The reaction mixture was warmed to r.t. and stirred at r.t. for 1 h under $N_2$. The solvent was removed and the residue was purified by prep-HPLC and SFC separation to afford 22-12 and 22-13.

$^1$H NMR (400 MHz, MeOD-d$_4$) δ 7.49-7.47 (d, J=8.4 Hz, 2H), 7.27-7.23 (m, 7H), 6.23 (s, 1H), 5.05-4.97 (m, 2H), 4.48 (s, 3H), 4.00-3.94 (q, J=14.0 Hz, 1H), 2.04-1.95 (m, 1H), 1.52 1.51 (d, J=7.2 Hz, 3H), 0.91-0.90 (d, J=6.8 Hz, 3H), 0.82-0.80 (d, J=6.8 Hz, 3H).

LCMS (ESI): m/z 473.9 [M+Na$^+$], 497.0 [M+2Na$^+$].

$^1$H NMR (400 MHz, MeOD) δ 7.54-7.52 (d, J=8.4 Hz, 2H), 7.31-7.29 (m, 7H), 6.29 (s, 1H), 5.05 (s, 2H), 4.55 (s, 3H), 4.05-4.00 (m, 1H), 2.10-2.00 (m, 1H), 1.58-1.56 (d, J=7.2 Hz, 3H), 0.97-0.96 (d, J=6.8 Hz, 3H), 0.87-0.85 (d, J=6.8 Hz, 3H).

LCMS (ESI): m/z 473.8 [M+Na$^+$], 496.9 [M+2Na$^+$].

Step 11

To the solution of 22-12 or 22-13 (30 mg, 0.066 mmol) in dry DCM (5 mL) was added PNP carbonate (40.4 mg, 0.13 mmol) and DIPEA (0.5 mL). The mixture was heated at reflux for 20 h. After the solvent was removed, the residue was dissolved in DMF (3 mL). DIPEA (0.5 mL) and norfloxacin (63.5 mg, 0.2 mmol) were added. After the mixture was stirred at r.t. for 2 h, solvent was removed, and the residue was purified by prep-HPLC to give example 22.

$^1$H NMR (400 MHz, DMSO-d$_6$) δ 15.32 (s, 1H), 10.37 (s, 1H), 8.97 (s, 1H), 7.97-7.94 (d, J=13.2 Hz, 1H), 7.83-7.81 (d, J=10.8 Hz, 1H), 7.62-7.60 (d, J=8.4 Hz, 2H), 7.37-7.21 (m, 8H), 6.34 (s, 1H), 5.07-5.01 (m, 4H), 4.60-4.56 (m, 2H), 4.47-4.43 (m, 1H), 4.08-4.03 (m, 1H), 3.61 (s, 4H), 3.33 (s, 4H), 1.97-1.92 (m, 1H), 1.49-1.47 (d, J=7.2 Hz, 3H), 1.43-1.39 (t, J=7.2 Hz, 3H), 0.91-0.90 (d, J=4.8 Hz, 3H), 0.77-0.76 (d, J=6.8 Hz, 3H).

LCMS (ESI): m/z 797.0 [M+H$^+$].

Example 23. 7-(4-((4-(((S)-2-((R)-3-(benzyloxycarbonylamino)-3-methyl-2-oxopyrrolidin-1-yl)propanamido)benzyloxy)carbonyl)piperazin-1-yl)-1-ethyl-6-fluoro-4-oxo-1,4-dihydroquinoline-3-carboxylic acid

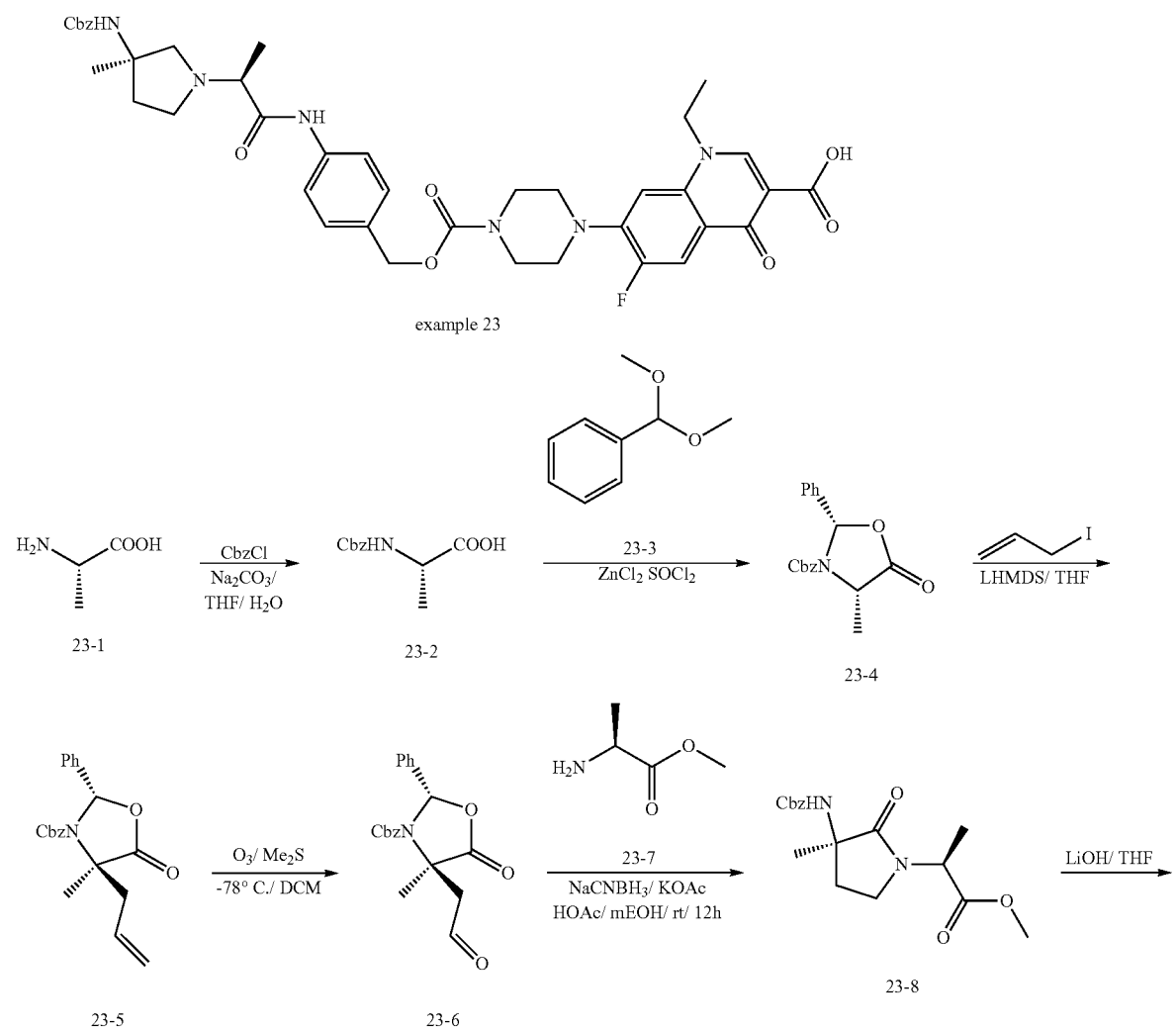

example 23

-continued

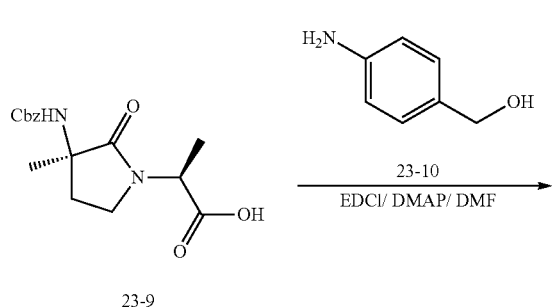
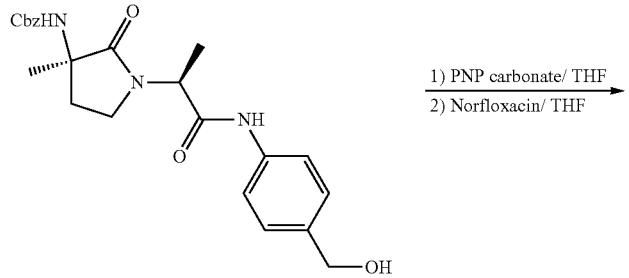
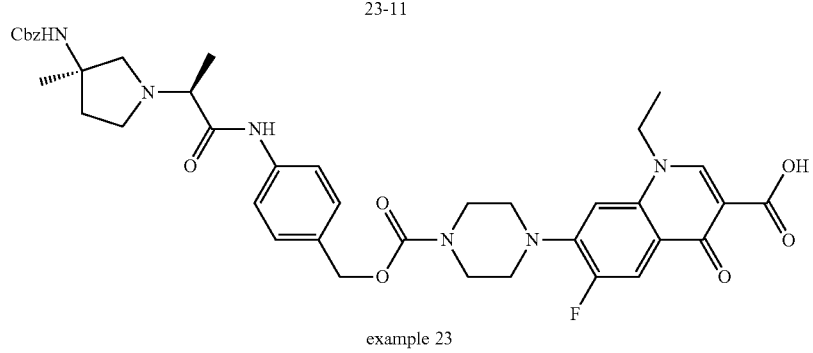

example 23

Step 1

To the solution of L-alanine 23-1 (18 g, 0.2 mol) in water (100 mL) was added sodium carbonate (32 g, 0.30 mol). The solution became clear and was cooled to 0° C. CbzCl (40 g, 235 mmol) in THF (200 mL) was added in 1 h, maintaining the temperature below 5° C. After it was stirred at r.t. for another 3 h, the solution was washed with EtOAc. Aq. solution was then acidified and extracted with EtOAc (300 mL×3). The organic layer was dried over $Na_2SO_4$ and concentrated to give compound 23-2.

Step 2

Thionyl chloride (3.27 mL, 44.8 mmol) was added to the stirring mixture of CBz-L-alanine 23-2 (10.0 g, 44.8 mmol) and benzaldehyde dimelthyl acetal (6.73 mml, 44.8 mmol) in dry THF at 0° C. After it was stirred for 30 min, anhydrous $ZnCl_2$ (6.11 g, 44.8 mmol) was added. The mixture was stirred at 0° C. for 3 h and another 0.2 equiv. of $ZnCl_2/SOCl_2$ was then added. The mixture was then quenched with water (below 10° C.) and extracted with MTBE (150 mL×3). The organic layer was dried over $Na_2SO_4$ and purified by column on silica gel to give compound 23-4.
$^1$H NMR (400 MHz, $CDCl_3$) δ 7.41-7.39 (m, 10H), 6.65 (s, 1H), 5.18-5.16 (m, 2H), 4.47-4.52 (m, 1H), 1.63-1.57 (m, 3H).

Step 3

To a solution of compound 23-4 (15.0 g, 48.2 mmol) in dry THF (80 mL) at −78° C. was added LiHMDS (1M, 63 mL) dropwise in 1 h and the solution was stirred at −78° C. for 20 min. Allyl iodide (6.3 mL, 68.9 mmol) was then added slowly and the reaction was stirred at −78° C. for 3 h. The mixture was warmed to r.t. and stirred for another 12 h. The mixture was diluted with ether and quenched with aq. $NH_4Cl$ (100 mL). The mixture was extracted with ether (150 mL×3). The organic layer was dried over $Na_2SO_4$ and purified by column on silica gel to give compound 23-5 (15 g, 88%).
$^1$H NMR (400 MHz, $CDCl_3$) δ 7.34-7.14 (m, 9H), 6.82-6.81 (m, 1H), 6.28-6.21 (m, 2H), 5.62-5.56 (m, 1H), 5.23-5.08 (m, 2H), 5.01-4.84 (m, 2H), 3.36-3.19 (m, 1H), 2.50-2.45 (m, 1H), 1.65 (s, 2H), 1.62-1.60 (m, 1H).

Step 4

Ozone was bubbled to a solution of compound 23-5 (7.8 g, 22.2 mmol) in DCM at −78° C., until the solution turned to blue. $N_2$ was bubbled to the solution util it turned to colorless and $Me_2S$ (33 mL) was then added and stirred at −78° C. for 1 h. After it was warmed to r.t., solvent was evaporated to give compound 23-6.
$^1$H NMR (400 MHz, $CDCl_3$) δ 9.66 (s, 1H), 7.42-7.16 (m, 9H), 6.80-6.78 (m, 2H), 6.57 (s, 1H), 4.99-4.96 (m, 1H), 4.86-4.83 (m, 1H), 4.13-4.02 (m, 1H), 3.10-3.05 (m, 1H), 1.76 (s, 3H).

Step 5

To a solution of compound 23-6 (1.0 g, 2.83 mmol) in MeOH (20 mL) was added compound 23-7 (438 mg, 4.24 mmol), $NaCNBH_3$ (263 mg, 4.24 mmol) and NaOAc (100 mg). Acetic acid was added to adjust pH to 6.0. The reaction was stirred at r.t. under $N_2$ for 24 h. After solvent was removed, the residue was extracted with DCM (50 mL×2), washed with 10% HCl and water (30 mL). The organic layer was dried over $Na_2SO_4$, concentrated and purified with column to give compound 23-8.

$^1$H NMR (400 MHz, CDCl$_3$) δ 7.37-7.29 (m, 5H), 5.35 (s, 1H), 5.11-5.03 (m, 2H), 4.89-4.88 (m, 1H), 3.71 (s, 3H), 3.41-3.35 (m, 2H), 2.45-2.43 (m, 2H), 2.32-2.31 (m, 1H), 1.47-1.39 (m, 6H).

Step 6

To the solution of compound 23-8 (334 mg, 1 mmol) in THF (1 mL) was added aq. LiOH (4 equiv.). The mixture was stirred at r.t. for 3 h. After solvent was removed, the residue was dissolved in water and acidified to pH 3.0 with aq. HCl. It was extracted with ether (20 mL×3). The organic layer was combined, dried and concentrated to afford compound 23-9, which was used directly in the next step.

Step 7

To the solution of compound 23-9 (320 mg, 1.0 mmol) in DCM (20 mL) was added EEDQ (247 mg, 1.0 mmol) and compound 23-10 (123 mg, 1.0 mmol). After the reaction was stirred at r.t. for 1 h, solvent was removed and the residue was purified with prep-HPLC to give 23-11.
$^1$H NMR (400 MHz, MeOD) δ 7.55-7.52 (m, 2H), 7.34-7.27 (m, 7H), 5.05 (s, 2H), 4.65-4.58 (m, 1H), 4.54 (s, 2H), 3.61-3.59 (m, 2H), 2.60-2.45 (m, 1H), 2.10-2.00 (m, 1H), 1.56-1.54 (m, 3H), 1.33 (s, 3H).
LCMS (ESI): m/z 448.1 [M+Na$^+$].

Step 8

To the solution of 23-11 (42 mg, 0.1 mmol) in DCM (20 mL) was added PNP carbonate (2 equiv.) and DIPEA (0.2 mL). The solution was heated at reflux for 16 h. Solvents were evaporated and the residue was dissolved in dry DMF (5 mL). DIPEA (0.2 mL) and norfloxacin (4 eq.) was added. The mixture was stirred at r.t. for 30 min, after the solvent was removed, the residue was purified by the prep-HPLC to give example 23.
$^1$H NMR (400 MHz, MeOD) δ 8.77 (s, 1H), 7.91-7.88 (m, 1H), 7.50-7.48 (m, 2H), 7.25-7.23 (m, 7H), 7.10-7.00 (m, 1H), 5.02 (s, 2H), 4.96 (s, 2H), 4.61-4.42 (m, 6H), 4.15-4.08 (m, 1H), 3.62 (s, 4H), 3.52-3.50 (m, 2H), 2.50-2.40 (m, 1H), 2.00-1.92 (m, 1H), 1.47-1.41 (m, 6H), 1.27 (s, 3H).
LCMS (ESI): m/z 771.1 [M+H$^+$].

Example 24. 7-(4-((4-((S)-2-((2S,3S)-3-(benzyloxy-carbonylamino)-1,1,1-trifluoro-4-methylpentan-2-ylamino)propanamido)benzyloxy)carbonyl)piper-azin-1-yl)-1-ethyl-6-fluoro-4-oxo-1,4-dihydroquinoline-3-carboxylic acid

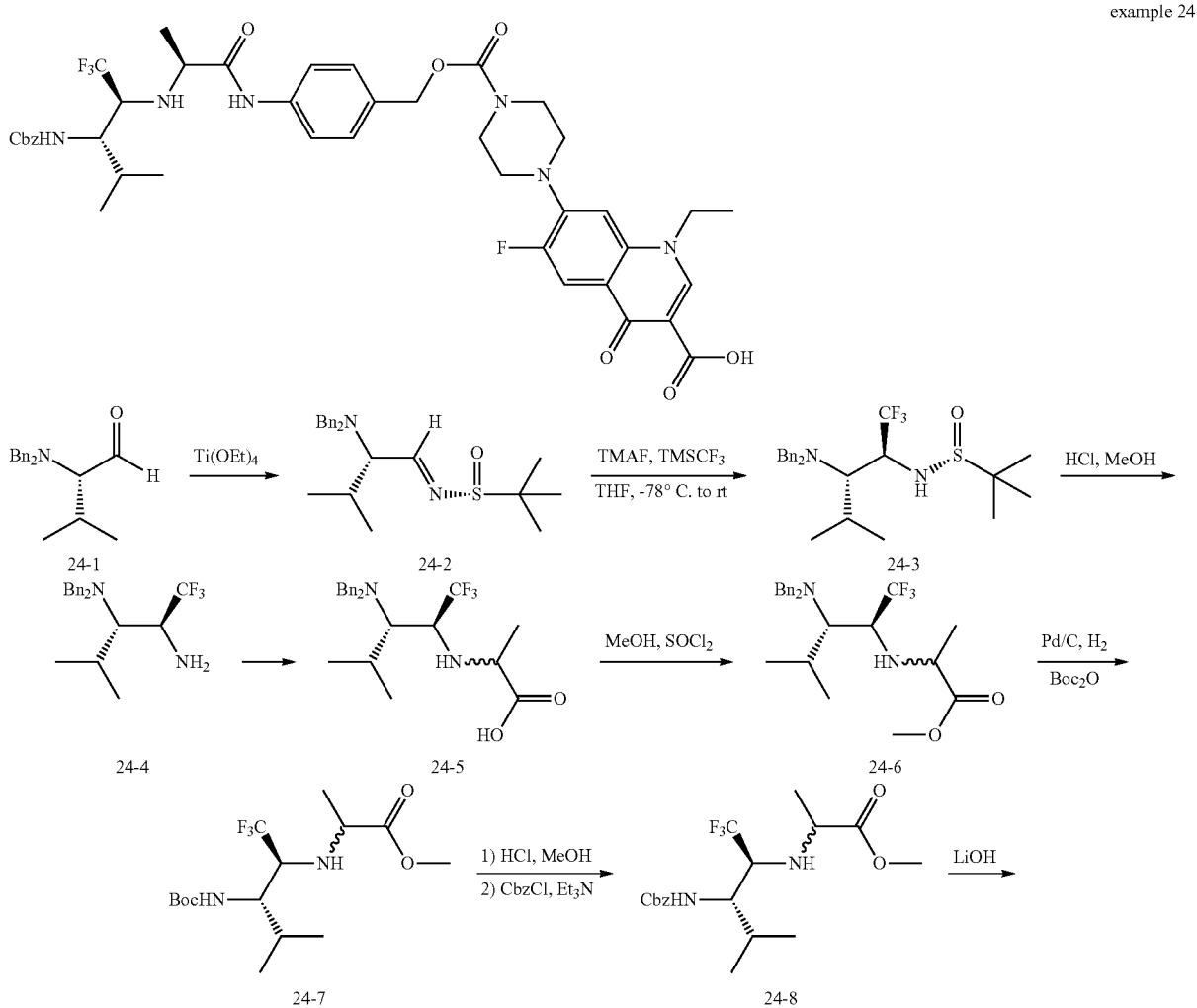

example 24

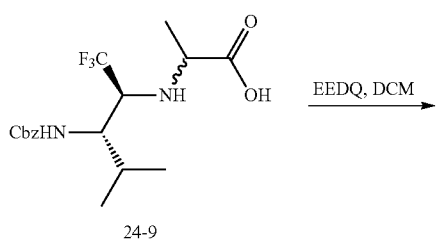

24-9

-continued

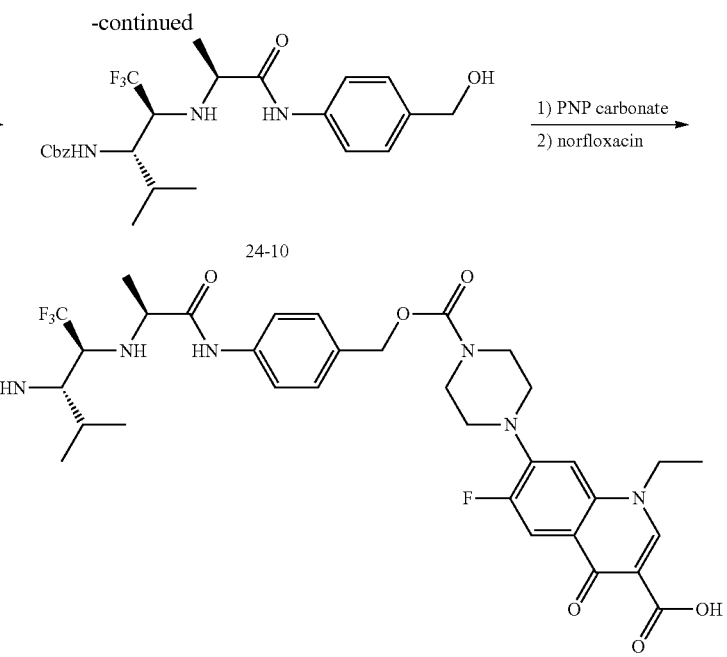

example 24

Step 1

To a solution of compound 24-1 (9.93 g, 35.28 mmol) and 2-methylpropane-2-sulfinamide (4.28 g, 35.28 mmol) in THF (100 mL) was added Ti(OEt)$_4$ (32.19 g, 141.12 mmol) dropwise at 0° C. After the mixture was stirred at 25° C. for 16 h, water (25 mL) was added dropwise at 0° C. The mixture was filtered and the filtrate was extracted with EtOAc (50 mL×3). Solvent was removed to give crude product 24-2 (11 g, 81.1%).

LCMS (ESI): m/z 385.3 [M+H$^+$].

Step 2

TMSCF$_3$ (3.55 g, 24.96 mmol) was added dropwise at −78° C. to a solution of 24-2 (6.4 g, 16.64 mmol) and TMAF (1.86 g, 19.97 mmol) in THF (30 mL). After the solution was stirred at −78° C. for 2 h, it was quenched slowly with water (2 mL), then diluted with water (50 mL). The mixture was extracted with EtOAc (60 mL×2). The organic layer was concentrated and the residue was purified by column chromatography on silica gel to give 24-3 (3.3 g, 44%).

$^1$H NMR (400 MHz, CDCl$_3$) δ 7.37-7.20 (m, 10H), 4.21-4.11 (m, 1H), 3.98-3.93 (m, 3H), 3.65-3.61 (m, 2H), 2.88-2.85 (m, 1H), 2.29-2.20 (m, 1H), 1.22 (s, 9H), 1.13-1.11 (m, 3H), 0.95-0.91 (m, 3H).

Step 3

A mixture of 24-3 (3.3 g, 7.26 mmol) and 4M HCl in MeOH (25 mL) was stirred at 25° C. for 6 h. Solvent was removed to give crude product of 24-4 (2.8 g).

LCMS (ESI): m/z 351.2 [M+H$^+$].

Step 4

To a solution of 24-4 (900 mg, 2.57 mmol), 2-oxopropanoic acid (905 mg, 10.28 mmol) and HOAc (617 mg, 10.28 mmol) in DCE (12 mL) was added NaBH(AcO)$_3$ (2.18 g, 10.28 mmol) at 25° C. After the mixture was stirred at 25° C. for 16 h, solvent was removed and the residue was purified by column chromatography to give 24-5 (700 mg, 64.5%).

LCMS (ESI): m/z 423.3 [M+H$^+$].

Step 5

To a solution of 24-5 (700 mg, 1.66 mmol) in MeOH (5 mL) was added SOCl$_2$ (395 mg, 3.32 mmol) dropwise at 0° C. After the solution was stirred at 50° C. for 16 h, it was cooled to 25° C. and solvent was removed under reduced pressure to give crude product of 24-6 (620 mg, crude).

LCMS (ESI): m/z 437.3 [M+H$^+$].

Step 6

To a solution of 24-6 (520 mg, 1.19 mmol) and Boc$_2$O (260 mg, 1.19 mmol) in MeOH (8 mL) was added Pd/C (100 mg). After the mixture was stirred at 25° C. for 16 h under H$_2$, it was filtered, solvent was removed and the residue was purified by column chromatography on silica gel (PE/EtOAc 5:1) to give 24-7 (390 mg, 92%).

LCMS (ESI): m/z 357.2 [M+H$^+$].

Step 7

To a solution of 24-7 (395 mg, 1.08 mmol) in MeOH (5 mL) was added 4M HCl in MeOH (5 mL, 20 mmol). After the solution was stirred at 25° C. for 2 h, solvent was removed and the residue was dissolved in DCM (8 mL). CbzCl (276 mg, 1.62 mmol) and Et$_3$N (219 mg, 2.16 mmol) were added at 0° C. and the mixture was stirred at 25° C. for 6 h. Solvent was removed and the residue was purified by prep-TLC to give compound 8 (110 mg, 26%).

LCMS (ESI): 391.1 [M+H$^+$].

Step 8

To a solution of compound 8 (110 mg, 0.282 mmol) in THF/MeOH/H$_2$O (0.5 mL: 0.5 mL: 0.5 mL) was added LiOH—H$_2$O (42 mg, 1 mmol) at 25° C. The solution was stirred at 25° C. for 2 h. Solvent Removed, and the residue was taken up with water (3 mL). The aqueous solution was acidified to pH 2 with 1M HCl and extracted with EtOAc (15 mL×3). The organic layer was dried over Na$_2$SO$_4$, filtered, concentrated to give compound 9 (100 mg, 94%).

LCMS (ESI): 377.1 m/z [M+H$^+$].

Step 9

To a solution of 24-9 (120 mg, 0.319 mmol) and (4-aminophenyl) methanol (79 mg, 0.638 mmol) in DCM (3 mL) was added EEDQ (158 mg, 0.638 mmol) at 0° C. under N$_2$. The mixture was stirred at r.t. for 6 h. After removal of the solvent, the residue was purified by prep-TLC, then SFC separation to give the major isomer (72 mg) 24-10 and minor isomer (26 mg). The absolute configuration of each isomer is not determined.

$^1$H NMR (400 MHz, MeOD) δ 7.65-7.63 (m, 2H), 7.37-7.27 (m, 7H), 5.14-5.07 (m, 2H), 4.56 (s, 2H), 3.81-3.79 (m, 1H), 3.59-3.57 (m, 1H), 3.37-3.35 (m, 1H), 2.11-2.10 (m, 1H), 1.33 (d, J=6.8 Hz, 3H), 0.93 (d, J=6.8 Hz, 3H), 0.87 (d, J=6.4 Hz, 3H).

LCMS (ESI): 482.2 m/z [M+H$^+$].

Step 10

To a solution of 24-10 (20 mg, 0.042 mmol) in THF (1.5 mL) was added PNP carbonate (38 mg, 0.125 mmol) and DIPEA (21 mg, 0.166 mmol) at 25° C. The mixture was heated at 50° C. for 18 h. Solvent was removed, and the residue was dissolved in DMF (1.5 mL). Norfloxacin (20 mg, 0.062 mmol) was added and the mixture was stirred at 25° C. for 2 h. The mixture was purified by prep-HPLC to give example 24 (11.2 mg, 33%).

$^1$H NMR (400 MHz, MeOD) δ 8.86 (s, 1H), 8.41 (s, 1H), 8.1-7.94 (m, 1H), 7.70-7.68 (m, 2H), 7.37-7.09 (m, 9H), 5.13-5.09 (m, 4H), 4.89-4.86 (m, 2H), 3.80-3.57 (m, 6H), 3.38-3.28 (m, 3H), 2.20-2.07 (m, 1H), 1.52 (s, 3H), 1.33 (t, J=6.8 Hz, 3H), 0.937 (d, J=6.8 Hz, 3H), 0.87 (d, J=6.8 Hz, 3H).

LCMS (ESI): 827.3 m/z [M+H$^+$].

Example 25: 7-(4-((4-(((2S,5R)-5-(benzyloxycarbonylamino)-2,6-dimethyl-4-oxoheptanamido)benzyloxy)carbonyl)piperazin-1-yl)-1-ethyl-6-fluoro-4-oxo-1,4-dihydroquinoline-3-carboxylic acid

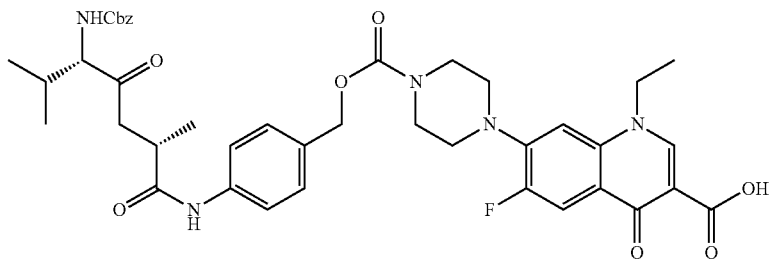

example 25

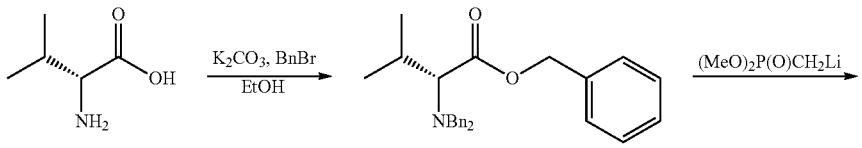

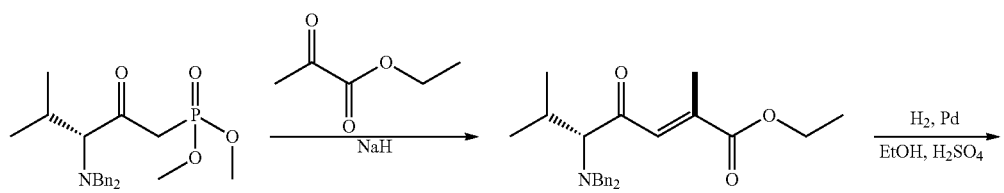

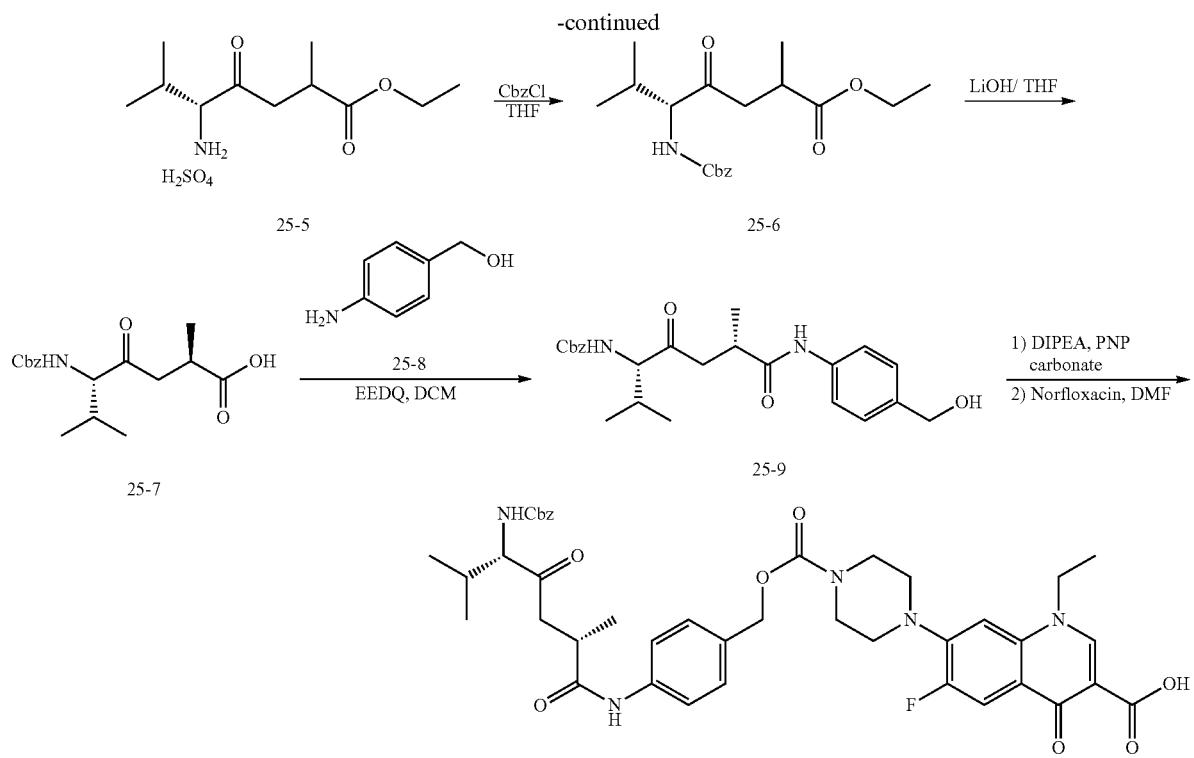

example 25

Step 1

To the solution of compound 25-1 (2 g, 17.07 mmol) and K$_2$CO$_3$ (7.066 g, 51.2 mmol) in EtOH (50 mL) was added benzyl bromide (8.7 g, 51.2 mmol). After the mixture was heated at reflux for 5 h, solid was filtered off and the filtrate was concentrated under reduced pressure and purified by flash chromatography on silica gel (EtOAc:hexane=1:10) to give 25-2 (3.52 g, 58.1%).

Step 2

To the solution of dimethyl methylphosphonate (6.78 g, 54.7 mmol) in dry THF (60 mL) was added dropwise LDA (2 mol/L, 27 mL) at −78° C. over 1 h. After it was stirred at −78° C. for 1 h, a solution of 25-2 (3.52 g, 9.12 mmol) in dry THF (10 mL) was added dropwise at −78° C. The mixture was stirred for 1 h and it was extracted with EtOAc (100 mL×3). The organic layer was washed with brine (60 mL) and concentrated to give the crude product of 25-3, which was used for next step without further purification (3.12 g, 84.9%).

LCMS (ESI): m/z 403.9 [M+H$^+$], 425.9 [M+Na$^+$]

Step 3

To a solution of 25-3 (3.12 g, 7.75 mmol) in dry THF (60 mL) was added sodium hydride (372 mg, 9.3 mmol, 60%) at 0° C. After it was stirred at 0° C. for 30 min, a solution of 2-oxo-propionic acid ethyl ester (1.349 g, 11.6 mmol) in dry THF (5 mL) was added dropwise. The mixture was stirred at r.t. for 16 h under N$_2$. Solvent was removed, the residue was purified by prep-HPLC to give 25-4 (2.85 g, 93.6%).

LCMS (ESI): m/z 394.2 [M+H$^+$].

Step 4

To the solution of 25-4 (2.85 g, 7.3 mmol) and sulfuric acid (750 mg, 7.3 mmol) in EtOH (60 mL) was added 10% palladium on activated carbon (1 g). After it was stirred under hydrogen for 6 h, the reaction mixture was filtered through a pad of celite and concentrated to give the desired product 25-5 (3.65 g, 100%).

Step 5

To the solution of 25-5 (3.65 g, 7.3 mmol) and triethylamine (2.21 g, 21.9 mmol) in CH$_2$Cl$_2$ (150 mL) was added dropwise a solution of CbzCl (1.36 g, 8.03 mmol) in ice bath. After the mixture was stirred at r.t. for 2 h, it was extracted with EtOAc (50 mL×3). The organic layer was washed with brine (50 mL), dried over Na$_2$SO$_4$, concentrated in vacuo to give the crude product 25-6.

LCMS (ESI): m/z 350.2 [M+H$^+$], 372.2 [M+Na$^+$].

Step 6

To the solution of 25-6 (1.6 g, 4.58 mmol) in a mixture of H$_2$O and THF (40 mL, 1:3) was added lithium hydroxide hydrate (1.93 g, 45.8 mmol). After the reaction mixture was stirred at r.t. for 16 h, it was extracted with EtOAc (50 mL×3). The organic layer was washed with brine (50 mL), dried over Na$_2$SO$_4$, concentrated in vacuo to give the crude product 25-7 (1.43 g, 97.3%).

LCMS (ESI): m/z 344.1 [M+Na$^+$].

Step 7

To a solution of compound 25-7 (1.0 g, 3.11 mmol) in dry DCM (20 mL) was added EEDQ (1.52 g, 6.22 mmol) and 25-8 (765 mg, 6.22 mmol). The mixture was stirred at 0° C. for 16 h under $N_2$. After the solvent was removed, the residue was purified by prep-HPLC and SFC to give 25-9, 25-10, 25-11, and 25-12.

$^1$H NMR (400 MHz, MeOD) δ 7.49 (d, J=8.8 Hz, 2H), 7.35-7.25 (m, 7H), 5.06 (s, 2H), 4.53 (s, 2H), 4.12 (d, J=5.6 Hz, 1H), 3.07-3.92 (m, 2H), 2.62-2.57 (m, 1H), 2.26-2.21 (m, 1H), 1.18 (d, J=6.8 Hz, 3H), 0.95 (d, J=6.8 Hz, 3H), 0.81 (d, J=6.8 Hz, 3H). LCMS (ESI): m/z 427.2 [M+H$^+$], 449.1 [M+Na$^+$], 409.2 [M-OH].

$^1$H NMR (400 MHz, MeOD) δ 7.49 (d, J=8.8 Hz, 2H), 7.33-7.20 (m, 7H), 5.07 (s, 2H), 4.53 (s, 2H), 4.12 (d, J=5.6 Hz, 1H), 3.28-2.92 (m, 2H), 2.63-2.57 (m, 1H), 2.27-2.19 (m, 1H), 1.18 (d, J=6.8 Hz, 3H), 0.95 (d, J=6.8 Hz, 3H), 0.81 (d, J=6.8 Hz, 3H). LCMS (ESI): m/z 427.2 [M+H$^+$], 449.1 [M+Na$^+$], 409.2 [M-OH].

$^1$H NMR (400 MHz, MeOD) δ 7.41 (d, J=6.8 Hz, 2H), 7.39-7.16 (m, 7H), 5.03-4.96 (m, 2H), 4.47 (s, 2H), 3.89 (d, J=6.4 Hz, 1H), 2.93-2.82 (m, 2H), 2.49-2.43 (m, 1H), 2.10-2.05 (m, 1H), 1.07 (d, J=6.8 Hz, 3H), 0.82 (d, J=6.8 Hz, 3H), 0.77 (d, J=6.8 Hz, 3H). LCMS (ESI): m/z 427.2 [M+H$^+$], 449.1 [M+Na$^+$], 409.2 [M-OH].

$^1$H NMR (400 MHz, MeOD) δ 8.02 (d, J=18.8 Hz, 2H), 7.79-7.29 (m, 7H), 5.16-5.08 (m, 2H), 4.56 (s, 2H), 4.01 (d, J=6.0 Hz, 1H), 3.32-2.94 (m, 2H), 2.60-2.55 (m, 1H), 2.24-2.12 (m, 1H), 1.19 (d, J=6.8 Hz, 3H), 0.95-0.88 (m, 6H). LCMS (ESI): m/z 409.0 [M-OH].

Step 8

To a solution of 25-9 (100 mg, 0.235 mmol) in dry DCM (2 mL) was added PNP carbonate (147 mg, 0.47 mmol) and DIPEA (61 mg). The mixture was heated at reflux for 16 h. After the solvent was removed, the residue was dissolved in DMF (3 mL). DIPEA (61 mg, 0.47 mmol) and norfloxacin (150 mg, 0.47 mmol) was added. The mixture was stirred at r.t. for 1 h. After solvent was removed, the residue was purified by prep-HPLC to give example 25 as a white solid.

$^1$H NMR (400 MHz, DMSO-d$_6$) δ 15.33 (s, 1H), 10.01 (s, 1H), 8.96 (s, 1H), 7.94 (d, J=12.8 Hz, 1H), 7.72 (d, J=8.0 Hz, 1H), 7.58 (d, J=8.4 Hz, 2H), 7.37-7.30 (m, 7H), 7.21 (d, J=7.2 Hz, 1H), 5.05-5.04 (m, 4H), 4.59-4.58 (m, 2H), 3.84-3.80 (m, 1H), 3.61 (s, 4H), 2.94-2.89 (m, 2H), 2.12-2.05 (m, 1H), 1.42-1.39 (m, 3H), 1.07 (d, J=6.0 Hz, 3H), 0.82 (d, J=6.4 Hz, 6H). LCMS (ESI): m/z 772.6 [M+H$^+$], 386.7 [M/2+H$^+$].

Example 26. 7-(4-((4-(2-(5-((S)-1-(benzyloxycarbonylamino)-2-methylpropyl)-1,3,4-oxadiazol-2-yl)propanamido)benzyloxy)carbonyl)piperazin-1-yl)-1-ethyl-4-oxo-1,4-dihydroquinoline-3-carboxylic acid

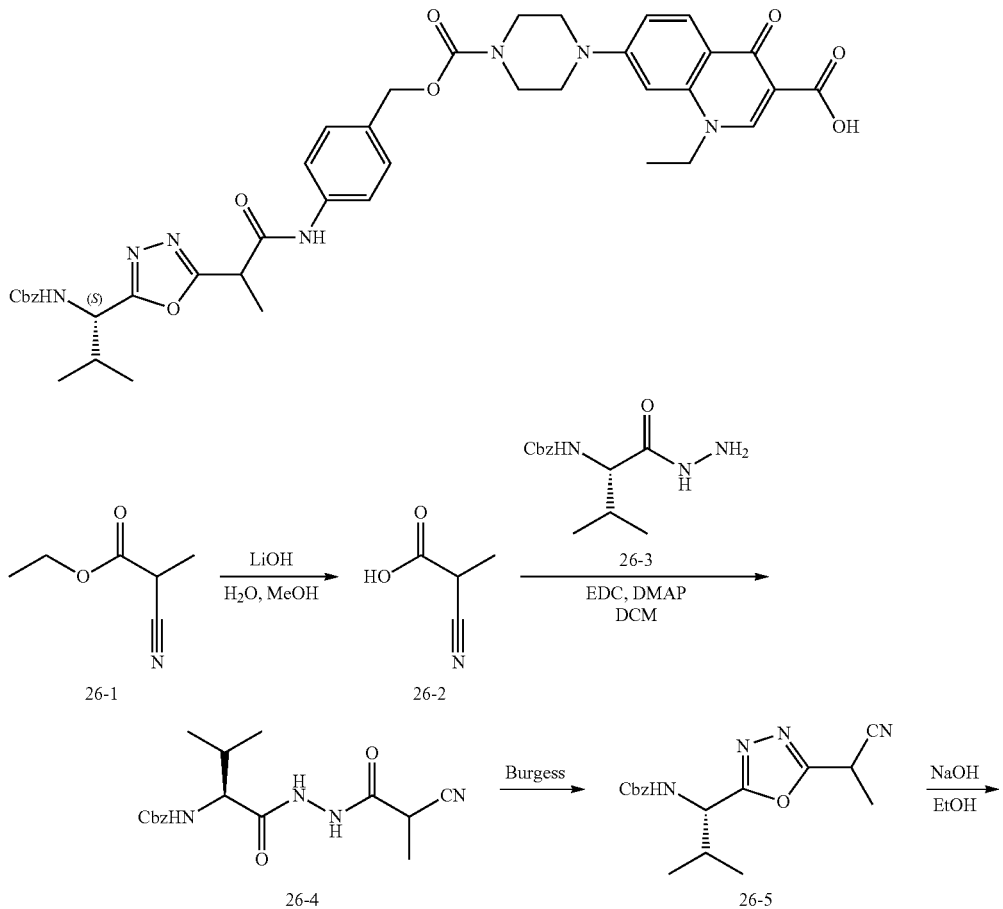

example 26

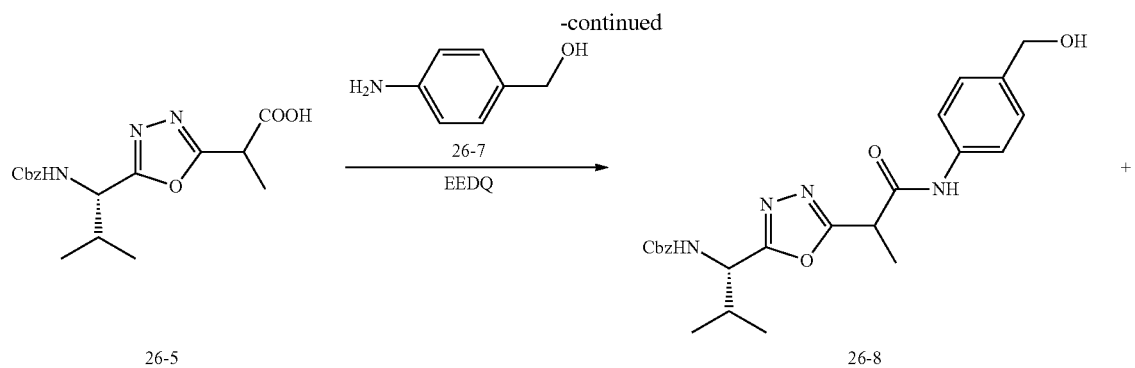

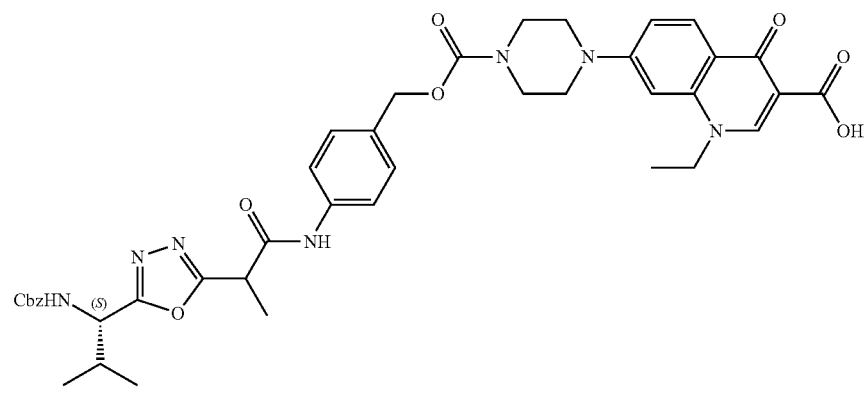

example 26

Step 1

To a solution of 26-1 (10.0 g, 78.7 mmol) in MeOH (180 mL) and H₂O (180 mL) was added LiOH.H₂O (16.9 g, 393.3 mmol). After the mixture was stirred at r.t. for 24 h, it was acidified with conc. HCl to pH=6. The crude was then extracted with (200 mL×3) and concentrated to give 26-2.

Step 2

To a stirred solution of 26-2 (2 g, 20.2 mmol) and DMAP (247 mg, 2.02 mmol) in DCM (400 mL) was added 26-3 (5.89 g, 22.2 mmol) and EDCI (4.26 g, 22.2 mmol). After the solution was stirred at r.t. for 2 h, it was washed successively with water (200 mL×3), brine (100 mL), dried over Na₂SO₄ and concentrated to give 26-4.

Step 3

A mixture of 26-4 (3 g, 8.7 mmol) and Burgess regent (3.1 g, 13.1 mmol) in THF (50 mL) was stirred at r.t. for 24 h. After removal of the solvent, the residue was extracted with EtOAc (100 mL×3). The organic layers were washed with brine (100 mL), concentrated and purified by column chromatography on silica gel (PE:EtOAc=2:1) to give 26-5.

Step 4

A mixture of 26-5 (1.67 g, 5.09 mmol) and a solution of NaOH (66 mmol) in EtOH (66 mL) and $H_2O$ (66 mL) was heated at 80° C. for 12 h. After it was cooled to r.t., the mixture was washed with EtOAc (50 mL) and the aqueous layer was adjusted to pH 5-6 and extracted with EtOAc (60 mL×3). The combined organic layers were dried over $Na_2SO_4$ and concentrated to give 26-6.

Step 5

A mixture of 26-6 (1.47 g, 4.23 mmol), 26-7 (1.56 g, 12.7 mmol) and EEDQ (3.14 g, 12.7 mmol) in DCM (50 mL) was stirred at r.t. for 2 h. Solvent was removed, and the residue was purified by prep-HPLC and SFC to give 26-8 and 26-9.

Step 6

A mixture of 26-8 (40 mg, 0.088 mmol), PNP (57 mg, 0.18 mmol) and DIPEA (34 mg, 0.26 mmol) in DCM (3 mL) was stirred at 50° C. for 12 h. It was concentrated and was mixed with Norfloxacin (82 mg, 0.26 mmol) and DIPEA (34 mg, 0.26 mmol) in DMF (5 mL). After it was stirred at r.t. for 2 h, solvent was removed, and the residue was purified by prep-HPLC to give example 26 (30.5 mg, 43.6%).

$^1$H NMR (400 MHz, DMSO-$d_6$) δ 15.33 (s, 1H), 10.44 (s, 1H), 8.97 (s, 1H), 8.12-8.08 (m, 1H), 7.95 (d, J=13.2 Hz, 1H), 7.58 (d, J=8.4 Hz, 2H), 7.37-7.34 (m, 7H), 7.21 (d, J=7.2 Hz, 1H), 5.05 (d, J=14.8 Hz, 4H), 4.59-4.58 (m, 3H), 4.19-4.17 (m, 1H), 3.61 (s, 4H), 3.38 (s, 4H), 2.10-2.07 (m, 1H), 1.58 (dd, J=2.0, 7.2 Hz, 3H), 1.40 (t, J=6.8 Hz, 3H), 0.93 (d, J=6.8 Hz, 3H), 0.82 (d, J=6.8 Hz, 3H).

LCMS (ESI): m/z 798.3 [M+H$^+$], 820.2 [M+Na$^+$].

Example 27. 7-(4-((4-((S)-2-(2-((S)-1-(benzyloxycarbonylamino)-2-methylpropyl)thiazol-5-yl)propanamido)benzyloxy)carbonyl)piperazin-1-yl)-1-ethyl-6-fluoro-4-oxo-1,4-dihydroquinoline-3-carboxylic acid

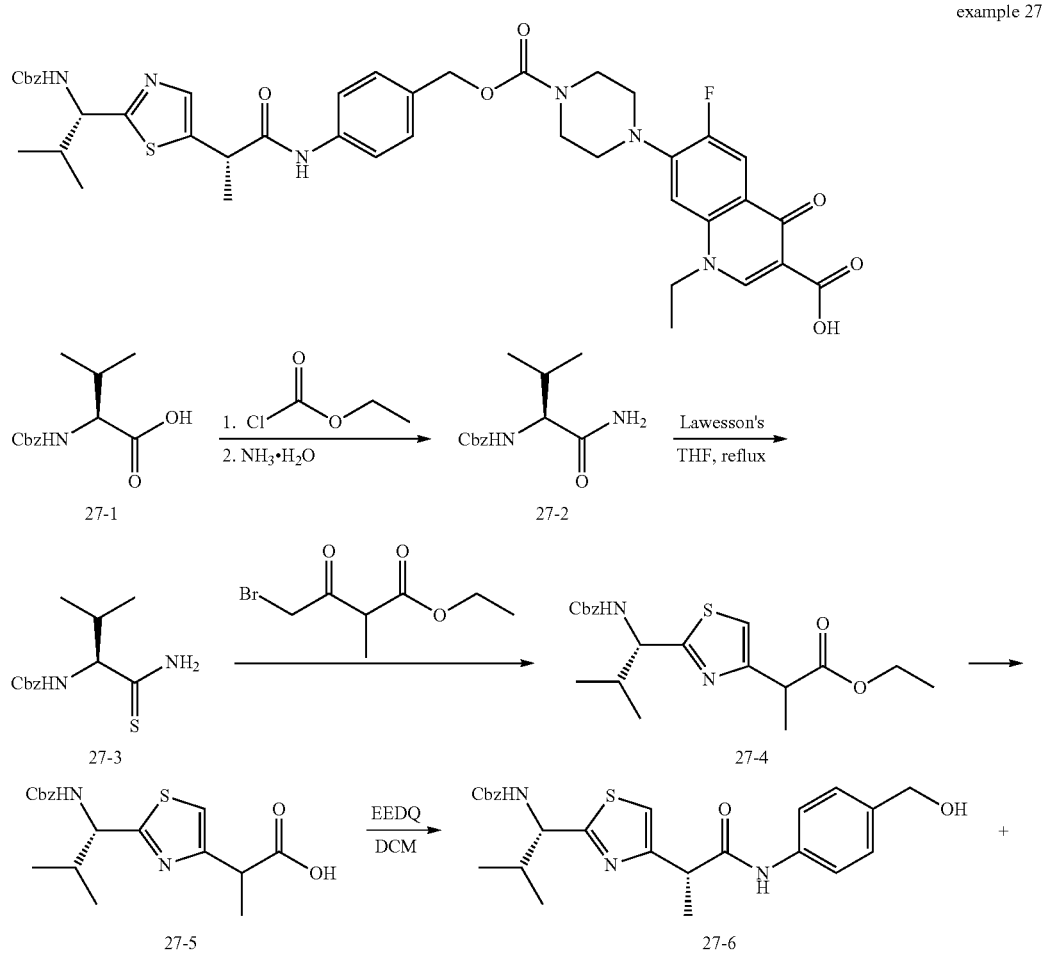

example 27

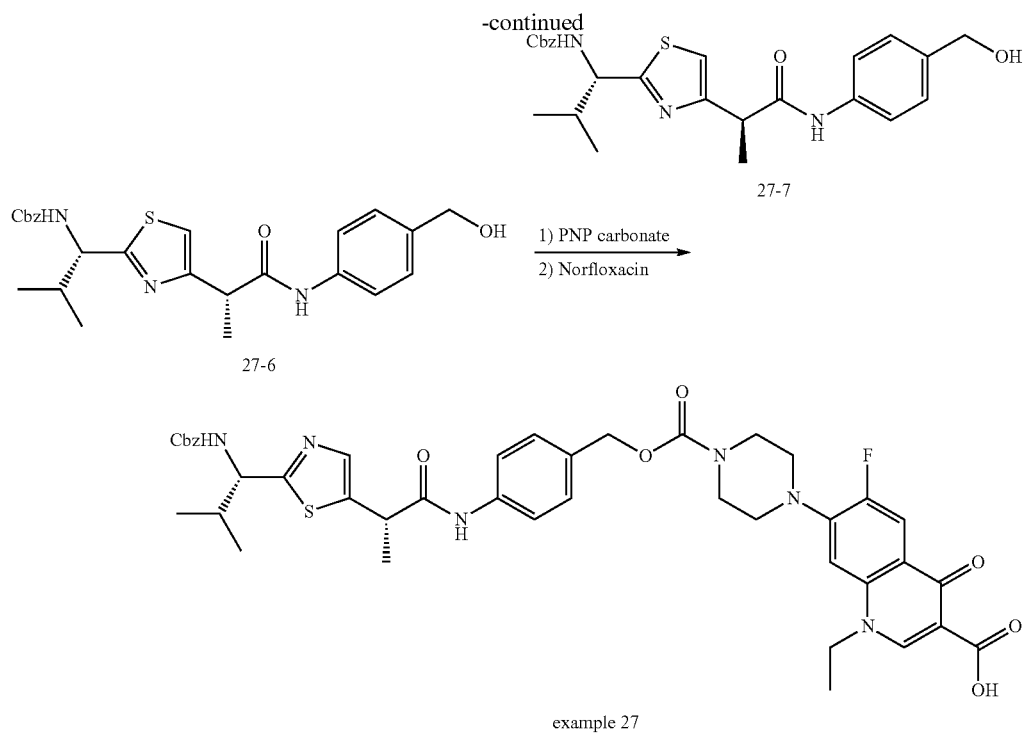

example 27

Step 1

To a solution of 27-1 (8 g, 31.8 mmol) and Et₃N (6.43 g, 63.6 mmol) in dry THF (100 mL) at −78° C. was added dropwise a solution of ethyl chloroformate (3.45 g, 31.8 mmol) in THF (10 mL). After the reaction was stirred at −78° C. for 1 h, NH₃·H₂O (5 mL) was added. The reaction was warmed to r.t. over 2 h. White solid was collected by filtration and dried to give 27-2 (5.1 g, 63.8%).

Step 2

A solution of 27-2 (3 g, 12 mmol) and Lawesson's Reagent (9.7 g, 24 mmol) in dry THF (60 mL) was stirred 70° C. for 16 h. Solvent was removed and residue was purified by column (EtOAc:henaxe=1:3) to give 27-3 (2.9 g, 90.6%).
LCMS (ESI): m/z 267.1 [M+H⁺], 289.1 [M+Na⁺].

Step 3

To the solution of 27-3 (3 g, 11.26 mmol), KHCO₃ (3.38 g, 33.8 mmol) in dry DME (40 mL) was added dropwise a solution of 27-3a (11.31 g, 22.52 mmol) in DME (10 mL). After the reaction was stirred at −40° C. for 16 h, water (50 mL) and EtOAc (100 mL) was added, and the organic layer was washed with brine, dried over Na₂SO₄, concentrated in vacuo. To the mixture of crude intermediate and 2, 6-dimethylpyridine (3.3 g, 30.4 mmol) in THF (20 mL) was added dropwise a solution of 2,2,2-trifluoroacetic anhydride (3.2 g, 15.2 mmol) at −40° C. slowly. After the reaction was stirred at −10° C. for 2 h, water (100 mL) and EtOAc (100 mL) was added. The organic layer was washed with brine, dried over Na₂SO₄, concentrated in vacuo. The crude product was purified by prep-HPLC to afford 27-4 (2 g, 67.7%).
LCMS (ESI): m/z 391.2 [M+H⁺].

Step 4

To the solution of 27-4 (2 g, 5.13 mmol) in a mixture of CH₃OH and H₂O (60 mL/20 mL) was added lithium hydroxide (2.15 g, 51.3 mmol). After the mixture was stirred at r.t. for 16 h, pH was adjusted to 5 with diluted HCl (5%) and the mixture was extracted with EtOAc (60 mL×2). The organic layer was washed with brine (60 mL), dried over Na₂SO₄, concentrated in vacuo to give 27-5.
LCMS (ESI): m/z 363.2 [M+H⁺].

Step 5

To the solution of 27-5 (1 g, 2.76 mmol) and EEDQ (750 mg, 5.52 mmol) in CH₂Cl₂ (20 mL) was added (4-aminophenyl)methanol (680 mg, 5.52 mmol) at 0° C. The reaction mixture was stirred at 0° C. for 2 h and then at r.t. for 16 h. The reaction mixture was diluted with CH₂Cl₂ (50 mL) and washed with brine (50 mL), dried over Na₂SO₄, filtered, concentrated, purified by prep-HPLC and SFC to give 27-6 and 27-7 (370 mg each, 28.7%).
¹H NMR (400 MHz, MeOD) δ 7.55 (d, J=8.4 Hz, 2H), 7.36-7.29 (m, 8H), 5.11 (s, 2H), 4.80 (d, J=6.8 Hz, 1H), 4.56 (s, 2H), 4.07-4.01 (m, 1H), 2.33-2.25 (m, 1H), 1.60 (d, J=6.8 Hz, 3H), 0.96-0.91 (m, 6H). LCMS (ESI): m/z 468.0 [M+H⁺], 490.2 [M+Na⁺].
¹H NMR (400 MHz, CDCl₃) δ 8.90 (s, 1H), 7.49-7.23 (m, 9H), 7.05 (s, 1H), 5.48-5.45 (m, 1H), 5.14-5.10 (m, 2H), 5.03-4.99 (m, 1H), 4.61 (s, 2H), 3.94-3.88 (m, 1H), 2.42-2.34 (m, 1H), 1.63 (d, J=7.2 Hz, 3H), 1.02-1.94 (m, 6H). LCMS (ESI): m/z 489.9 [M+Na⁺].

Step 6

To the solution of 27-6 (50 mg, 0.11 mmol) in dry DCM (2 mL) was added PNP carbonate (67 mg, 0.22 mmol) and DIPEA (28 mg). The mixture was heated at reflux for 16 h.

After the solvent was removed, the residue was dissolved in dry DMF (5 mL). DIPEA (60 mg, 047 mmol) and norfloxacin (60 mg, 0.188 mmol) was added. After the mixture was stirred at r.t. for 1 h, solvent was removed and the residue was purified by prep-HPLC to afford example 27.

¹H NMR (400 MHz, DMSO-d₆) δ 15.34 (s, 1H), 10.17 (s, 1H), 8.97 (s, 1H), 8.10 (d, J=8.4 Hz, 1H), 7.95 (d, J=8.4 Hz, 1H), 7.60 (d, J=8.4 Hz, 2H), 7.36-7.31 (m, 7H), 7.21 (d, J=7.2 Hz, 1H), 5.05 (s, 4H), 4.66-4.56 (m, 3H), 4.03-3.97 (m, 1H), 3.61 (s, 4H), 3.35 (s, 4H), 2.20-2.14 (m, 1H), 1.47-1.39 (m, 6H), 0.87-0.80 (m, 6H). LCMS (ESI): m/z 813.1, [M+H⁺], 407.1 [M/2+H⁺].

Example 28. 7-(4-((4-((R)-2-((S)-6-(benzyloxycarbonyl)-7-isopropyl-5-oxo-6,7-dihydro-5H-imidazo[5,1-c][2,4]triazol-3-yl)propanamido)benzyloxy)carbonyl)piperazin-1-yl)-1-ethyl-6-fluoro-4-oxo-1,4-dihydroquinoline-3-carboxylic acid

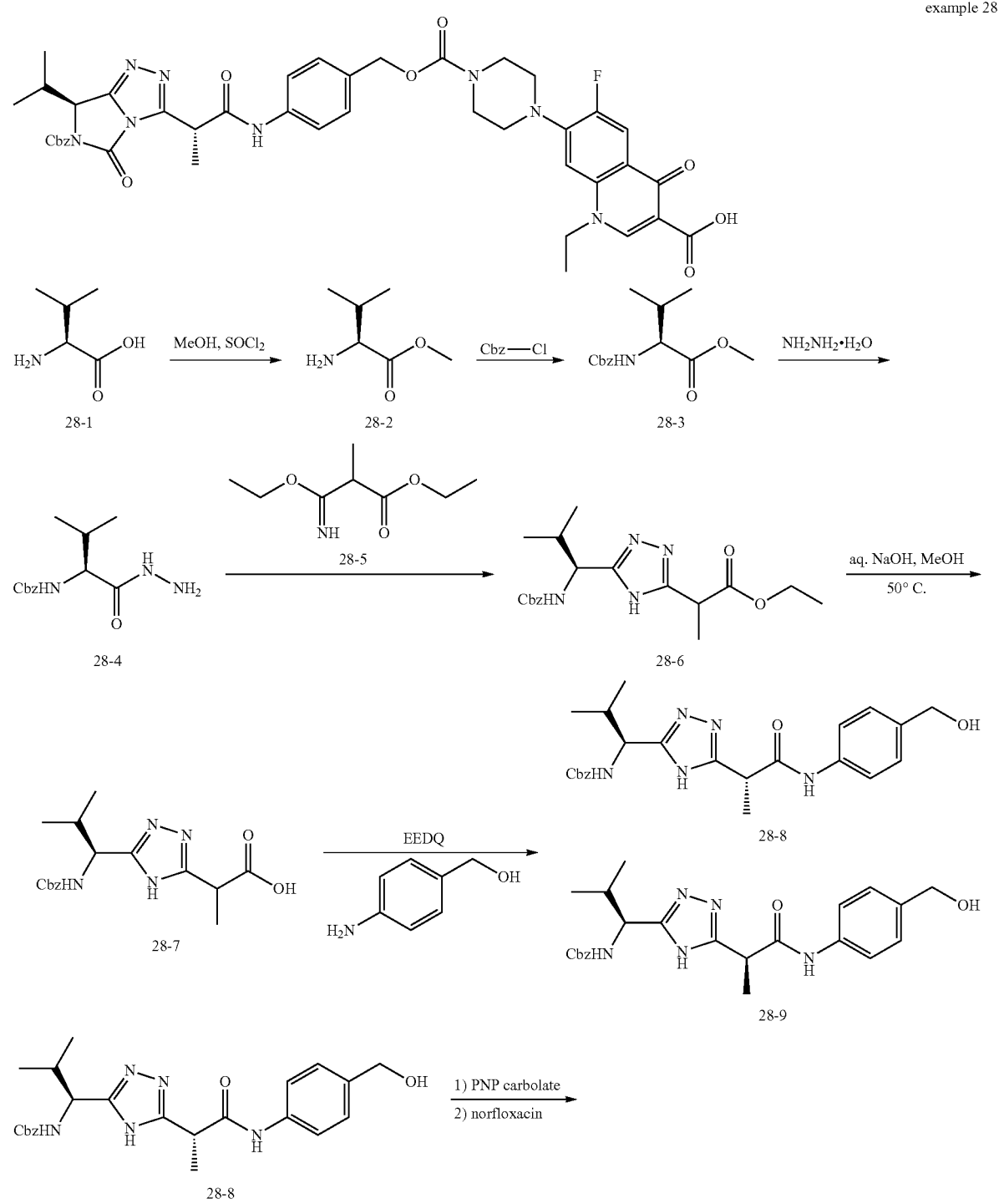

example 28

-continued

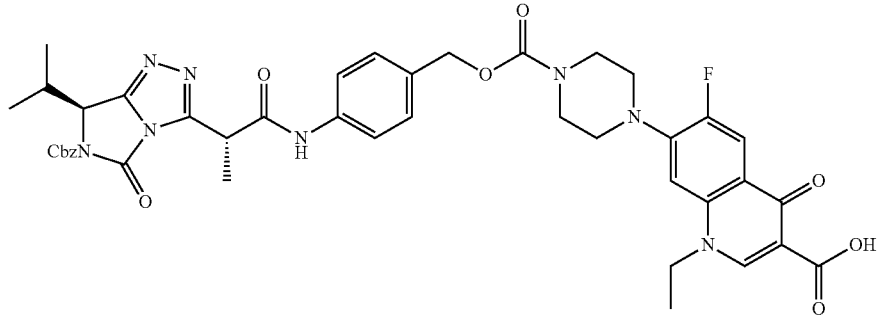

example 28

Step 1

To the solution of 28-1 (12 g, 0.1 mol) in MeOH (200 mL) was added SOCl$_2$ (10 mL) in 10 min at 0° C. After the mixture was stirred at r.t. for 12 h, solvent was removed, to give the desired product 28-2.

Step 2

To the solution of 28-2 (2.6 g, 5 mmol) in DCM (50 mL) was added TEA (2 mL) and stirred at 0° C. until the solution became clear. CbzCl (10.2 g, 6 mmol) was then added dropwise in 1 h and maintain the temperature below 5° C. The mixture was then stirred at r.t. for another 10 h. Solution was taken up with DCM (100 mL) and washed with aq. HCL aq. NaHCO$_3$ and water, organic layer was dried over anhydrous NaSO$_4$, and solvents were then evaporated to give 28-3.

LCMS (ESI): m/z 265.9 [M+H].

Step 3

To the solution of 28-3 (2.65 g, 10 mmol) in MeOH (25 mL) was added NH$_2$NH$_2$.H$_2$O (5 min, 80%). After the mixture was stirred at r.t. for 6 h, the solid was collected by filtration to give 28-4.

$^1$H NMR (400 MHz, MeOD) δ 7.36-7.30 (m, 5H), 5.07 (s, 2H), 4.59 (s, 1H), 3.84-3.82 (m, 1H), 0.94-0.91 (m, 6H).

Step 4

Compound 28-4 the solution of 28-2 (2.65 g, 10 mmol), 28-5 (4.2 g, 20.2 mmol) and dry MeOHd TEA (50 mL) was heated at 150° C. in a sealed container for 24 h. Solvent was removed to the desired product 28-6.

Step 5

To the solution of 28-6 (740 mg, 2 mmol) in EtOH (20 mL) and water (10 mL) was added NaOH (400 mg, 10 mmol). After the mixture was stirred at 50° C. for 1 h, solvent was removed, and the residue was purified by column to give 28-7.

$^1$H NMR (400 MHz, MeOD) δ 7.32-7.26 (m, 5H), 5.10-5.05 (s, 2H), 4.61-4.59 (m, 1H), 3.94-3.92 (m, 1H), 2.16-2.14 ((m, 1H), 1.55-1.53 (m, 3H), 0.99-0.82 (m, 6H).

Step 6

To the solution of 28-7 (100 mg, 0.28 mmol) in dry DCM (5 mL) was added (4-aminophenyl)methanol (250 mg, 2 mmol) and EEDQ (247 mg, 1 mmol). After the mixture was stirred at 0° C. for 2 h, solvent was removed, and the residue was purified by prep-HPLC and SFC to give 28-8 and 28-9.

$^1$H NMR (400 MHz, MeOD) δ 7.57 (d, J=8.4 Hz, 2H), 7.35-7.30 (m, 7H), 5.13-5.05 (m, 2H), 4.63 (d, J=7.6 Hz, 1H), 4.57 (s, 2H), 4.07-4.02 (m, 1H), 2.23-2.17 (m, 1H), 1.66 (d, J=7.2 Hz, 3H), 0.98 (d, J=6.8 Hz, 3H), 0.87 (d, J=6.8 Hz, 3H).

LCMS (ESI): m/z 452.0 [M+H$^+$].

$^1$H NMR (400 MHz, MeOD) δ 7.57 (d, J=8.4 Hz, 2H), 7.35-7.30 (m, 7H), 5.13-5.05 (m, 2H), 4.63 (d, J=7.6 Hz, 1H), 4.57 (s, 2H), 4.00-3.99 (m, 1H), 2.19-2.17 (m, 1H), 1.66 (s, 3H), 0.98 (d, J=5.6 Hz, 3H), 0.87 (d, J=6.8 Hz, 3H).

LCMS (ESI): m/z 473.9 [M+Na$^+$].

Step 7

To the solution of 28-8 (45 mg, 0.1 mmol) in dry DCM (30 mL) was added PNP carbonate (62 mg, 0.2 mmol) and DIPEA (1 mL). After the mixture was heated at reflux for 16 h, solvent was removed, and the residue was dissolved in DMF (5 mL). DIPEA (1.0 mL) and norfloxacin (65 mg, 0.2 mmol) were added. The mixture was stirred at r.t. for 1 h. After removal of the solvent, the residue was purified by prep-HPLC to give example 28.

$^1$H NMR (400 MHz, DMSO-d$_6$) δ 8.97 (s, 1H), 7.97-7.94 (m, 2H), 7.48-7.23 (m, 10H), 5.17 (s, 2H), 5.04 (s, 2H), 4.61-4.58 (m, 2H), 4.50-4.40 (m, 1H), 3.69-3.63 (m, 4H), 3.40-3.35 (m, 1H), 3.29-3.26 (m, 4H), 2.09-2.08 (m, 1H), 1.91-1.88 (m, 2H), 1.41 (t, J=7.2 Hz, 3H), 0.96-0.89 (m, 6H).

LCMS (ESI): 823.3 m/z [M+H$^+$].

Example 29. 7-(4-((4-((R)-2-(2-((S)-1-(benzyloxy-carbonylamino)-2-methylpropyl)thiazol-5-yl)propanamido)benzyloxy)carbonyl)piperazin-1-yl)-1-ethyl-6-fluoro-4-oxo-1,4-dihydroquinoline-3-carboxylic acid

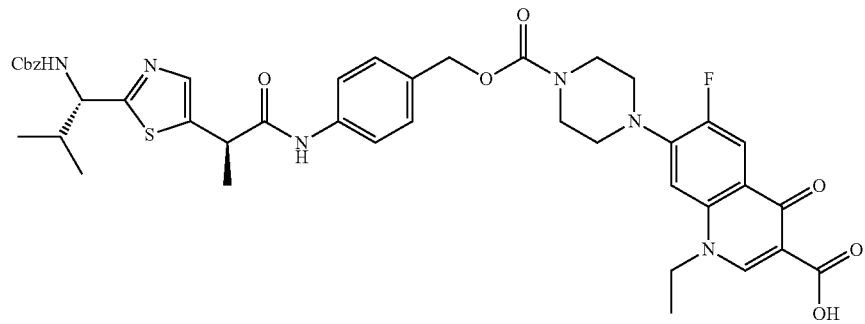

example 29

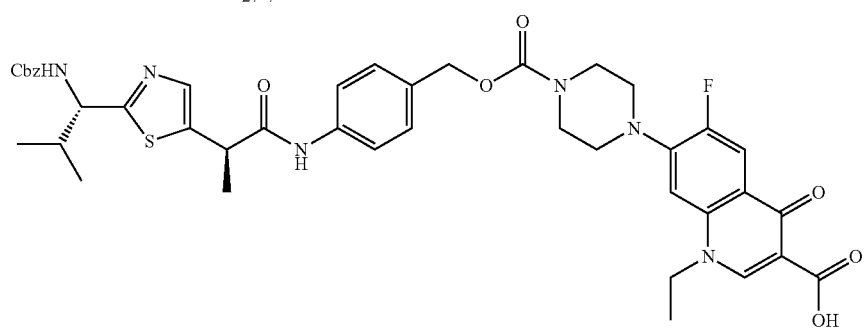

example 29

Example 29 was made using the procedure as Example 27.

$^1$H NMR (400 MHz, DMSO-d$_6$) δ 15.33 (brs, 1H), 10.17 (s, 1H), 8.96 (s, 1H), 8.10 (d, J=8.4 Hz, 1H), 7.95 (d, J=8.4 Hz, 1H), 7.60 (d, J=8.4 Hz, 2H), 7.36-7.31 (m, 7H), 7.21 (d, J=7.2 Hz, 1H), 5.05 (s, 4H), 4.66-4.56 (m, 3H), 4.03-3.97 (m, 1H), 3.61 (s, 4H), 3.35 (s, 4H), 2.20-2.14 (m, 1H), 1.47-1.39 (m, 6H), 0.87-0.80 (m, 6H). LCMS (ESI): m/z 813.1, [M+H$^+$], 407.3 [M/2+H$^+$].

Example 30. 7-(4-((4-((S)-2-((S)-6-(benzyloxycarbonyl)-7-isopropyl-5-oxo-6,7-dihydro-5H-imidazo[5,1-c][1,2,4]triazol-3-yl)propanamido)benzyloxy)carbonyl)piperazin-1-yl)-1-ethyl-6-fluoro-4-oxo-1,4-dihydroquinoline-3-carboxylic acid

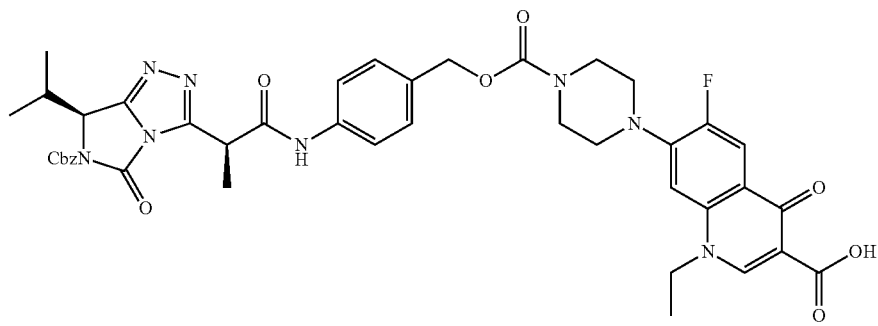

example 30

Example 30 was made using the procedure as Example 28.

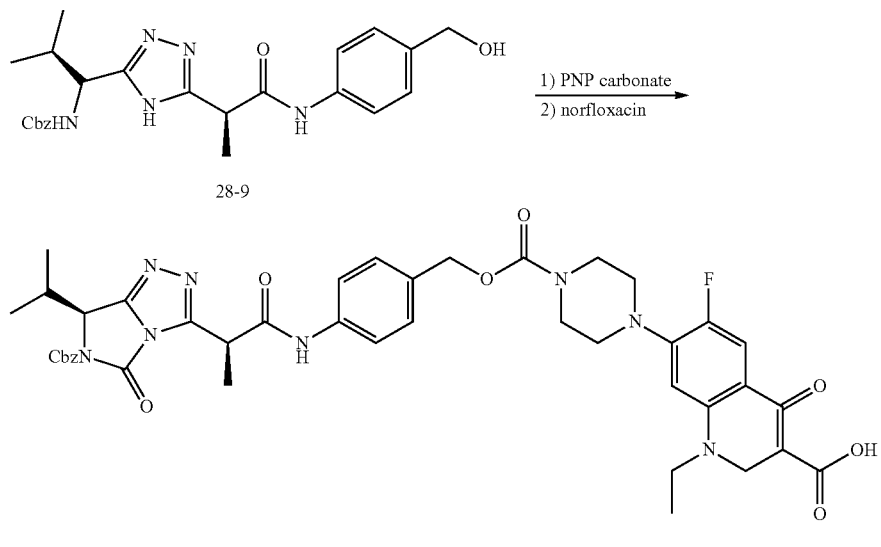

example 30

$^1$H NMR (400 MHz, DMSO-d$_6$) δ 8.99 (s, 1H), 8.14-7.93 (m, 2H), 7.57-7.19 (m, 10H), 5.19 (s, 2H), 5.11-5.03 (m, 2H), 4.62-4.56 (m, 2H), 4.51-4.47 (m, 1H), 3.67-3.57 (m, 4H), 3.52-3.50 (m, 1H), 3.40-3.35 (m, 4H), 2.25-2.15 (m, 1H), 1.90 (s, 2H), 1.41 (t, J=7.2 Hz, 3H), 0.98-0.84 (m, 6H).

Example 31: 7-(4-((4-((2S,5S)-5-(benzyloxycarbonylamino)-2,6-dimethyl-4-oxoheptanamido)benzyloxy) carbonyl)piperazin-1-yl)-1-ethyl-6-fluoro-4-oxo-1,4-dihydroquinoline-3-carboxylic acid

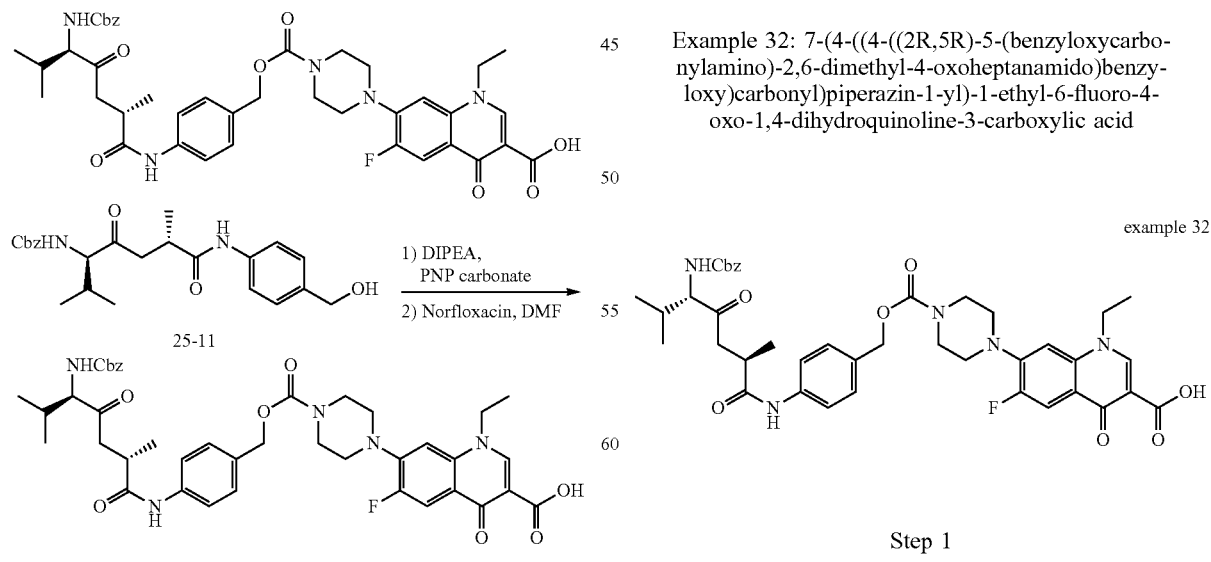

example 31

Step 1

Example 31 was made using the procedure as Example 25.

$^1$H NMR (400 MHz, DMSO-d$_6$) δ 15.29 (s, 1H), 9.98 (s, 1H), 8.92 (s, 1H), 7.90 (d, J=13.2 Hz, 1H), 7.57-7.54 (m, 3H), 7.32-7.24 (m, 7H), 7.17 (d, J=7.6 Hz, 1H), 5.05-4.97 (m, 4H), 4.56-4.54 (m, 2H), 3.95-3.92 (m, 1H), 3.58 (s, 4H), 3.26 (s, 4H), 2.93-2.83 (m, 2H), 2.57-2.52 (m, 1H), 2.16-2.08 (m, 1H), 1.45-1.35 (m, 3H), 1.07 (d, J=6.4 Hz, 3H), 0.85 (d, J=8.2 Hz, 3H), 0.75 (d, J=8.0 Hz, 3H). LCMS (ESI): m/z 772.1 [M+H$^+$].

Example 32: 7-(4-((4-((2R,5R)-5-(benzyloxycarbonylamino)-2,6-dimethyl-4-oxoheptanamido)benzyloxy)carbonyl)piperazin-1-yl)-1-ethyl-6-fluoro-4-oxo-1,4-dihydroquinoline-3-carboxylic acid example 32

Step 1

Example 32 was made using the procedure as Example 25, with the intermediate from the synthesis of Example 25.

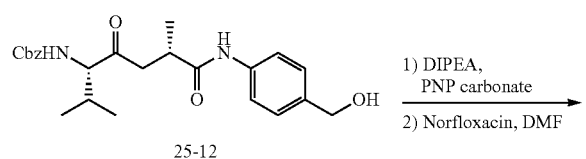

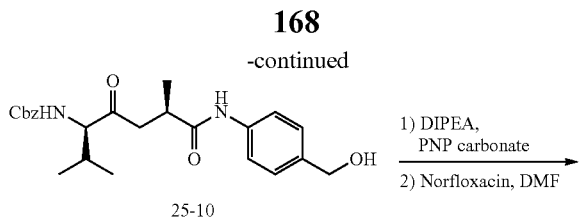

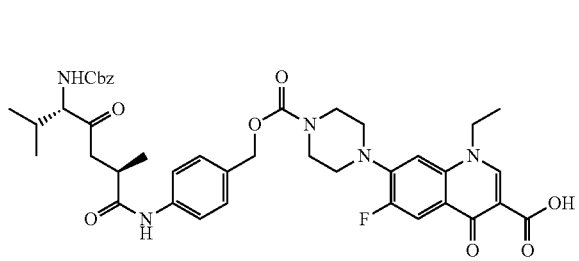

example 32

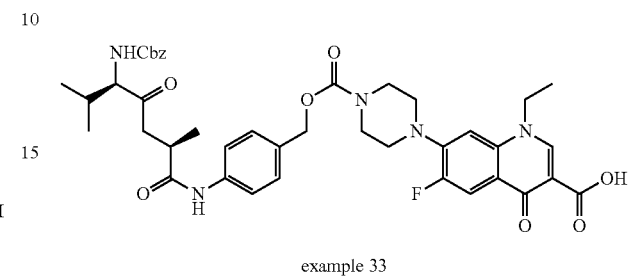

example 33

¹H NMR (400 MHz, DMSO-d₆) δ 15.30 (s, 1H), 10.03 (s, 1H), 8.97 (s, 1H), 7.95 (d, J=12.8 Hz, 1H), 7.74 (d, J=8.4 Hz, 1H), 7.58 (d, J=8.4 Hz, 2H) 7.37-7.31 (m, 7H), 7.21 (d, J=7.2 Hz, 1H) 5.09-5.02 (m, 4H), 4.60-4.56 (m, 2H), 3.84-3.80 (m, 1H), 3.61 (s, 4H), 3.34 (s, 4H), 2.92-2.85 (m, 2H), 2.12-2.08 (m, 1H), 2.05 (s, 1H), 1.42-1.39 (m, 3H), 1.07 (d, J=6.8 Hz, 3H), 0.82 (d, J=6.8 Hz, 6H). LCMS (ESI): m/z 772.4 [M+H⁺].

Example 33: 7-(4-((4-((2R,5S)-5-(benzyloxycarbonylamino)-2,6-dimethyl-4-oxoheptanamido)benzyloxy)carbonyl)piperazin-1-yl)-1-ethyl-6-fluoro-4-oxo-1,4-dihydroquinoline-3-carboxylic acid example 33

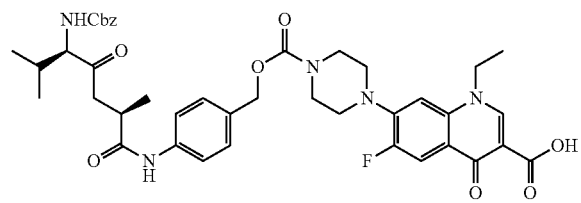

Step 1

Example 33 was made using the procedure as Example 25, with the intermediate from the synthesis of Example 25.

¹H NMR (400 MHz, DMSO-d₆) δ 15.34 (s, 1H), 10.02 (s, 1H), 8.97 (s, 1H), 7.95 (d, J=12.8 Hz, 1H), 7.58 (d, J=8.4 Hz, 3H), 7.36-7.29 (m, 7H), 7.21 (d, J=7.2 Hz, 1H), 5.08-5.00 (m, 4H), 4.61-4.56 (m, 2H), 3.99-3.95 (m, 1H), 3.61 (s, 4H), 3.31 (s, 4H), 2.96-2.85 (m, 2H), 2.50-2.47 (m, 1H), 2.19-2.13 (m, 1H), 1.42-1.39 (m, 3H), 1.08 (d, J=6.0 Hz, 3H), 0.90 (d, J=6.0 Hz, 3H), 0.82 (d, J=6.4 Hz, 3H). LCMS (ESI): m/z 772.0 [M+H⁺].

Example 34. 7-(4-((4-(2-(5-((R)-1-(benzyloxycarbonylamino)-2-methylpropyl)-1,3,4-oxadiazol-2-yl)propanamido)benzyloxy)carbonyl)piperazin-1-yl)-1-ethyl-6-fluoro-4-oxo-1,4-dihydroquinoline-3-carboxylic acid Example 34 was made using the procedure as Example 26, with the intermediate from the synthesis of Example 26.

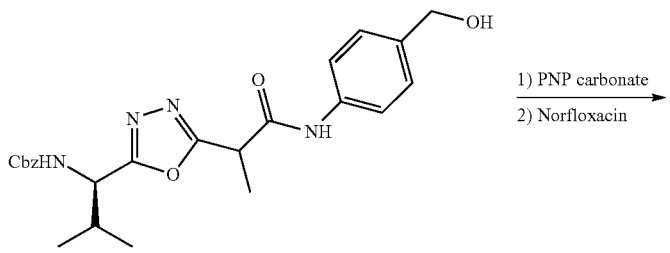

26-9

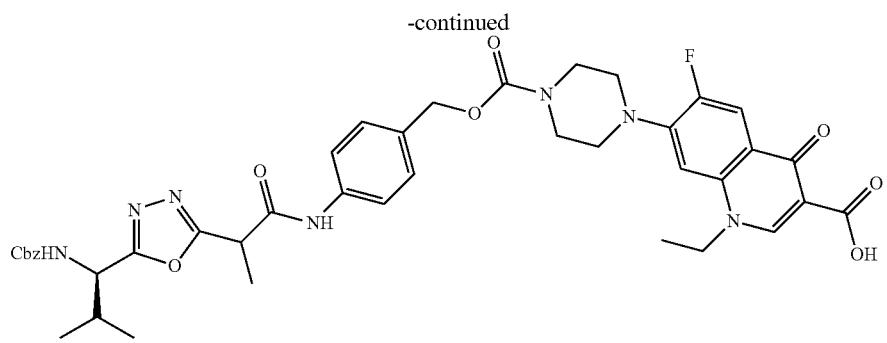

example 34

¹H NMR (400 MHz, DMSO-d₆) δ 15.32 (s, 1H), 10.46 (s, 1H), 8.95 (s, 1H), 8.09 (s, 1H), 7.94 (d, J=13.2 Hz, 1H), 7.58 (d, J=8.0 Hz, 2H), 7.36-7.33 (m, 7H), 7.20 (d, J=6.4 Hz, 1H), 5.04 (d, J=15.2 Hz, 4H), 4.62-4.57 (m, 3H), 4.22-4.21 (m, 1H), 3.61 (s, 4H), 3.35 (s, 4H), 2.13-2.11 (m, 1H), 1.58 (d, J=5.6 Hz, 3H), 1.40 (t, J=6.8 Hz, 3H), 0.93 (d, J=6.0 Hz, 3H), 0.81 (d, J=6.4 Hz, 3H).

LCMS (ESI): m/z 798.1 [M+H⁺].

Example 35: 7-(4-(((4-((2S,5S)-5-(benzyloxycarbonylamino)-4-hydroxy-2,6-dimethylheptanamide)benzyloxy)carbonyl)piperazin-1-yl)-1-ethyl-6-fluoro-4-oxo-1,4-dihydroquinoline-3-carboxylic acid Step 1

To the solution of example 25 (120 mg, 0.156 mmol) in dry CH₃OH (20 mL) was added NaBH₄ (6 mg, 0.158 mmol) in ice bath. After the mixture was stirred at r.t. for 2 h, the solvent was removed, and the residue was purified by prep-HPLC to give example 35 as a solid (40 mg).

¹H NMR (400 MHz, DMSO-d₆) δ 15.33 (s, 1H), 9.88 (s, 1H), 8.96 (s, 1H), 7.94 (d, J=12.8 Hz, 1H), 7.62 (d, J=8.4 Hz, 2H), 7.37-7.20 (m, 8H), 6.95 (d, J=10.0 Hz, 1H), 5.05-4.99 (m, 4H), 4.59-4.57 (m, 3H), 3.61 (s, 4H), 3.47-3.42 (m, 1H), 3.30 (s, 4H), 2.72-2.66 (m, 1H) 2.07-2.04 (m, 1H), 1.59-1.51 (m, 2H), 1.45-1.35 (m, 3H), 1.05 (d, J=8.0 Hz, 3H), 0.85-0.75 (m, 6H).

LCMS (ESI): m/z 387.7 [M/2+H⁺].

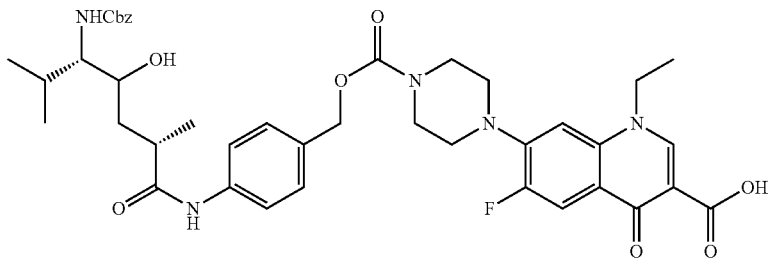

example 35

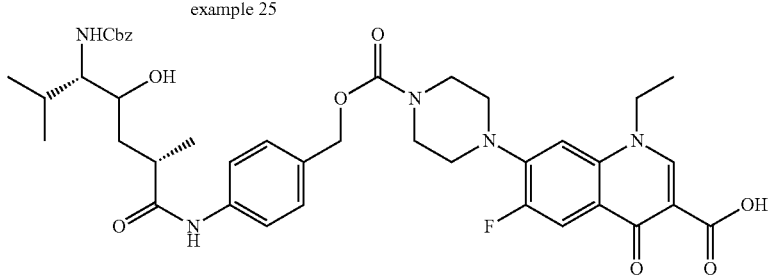

example 25 example 35

Example 36. 7-(4-((4-(2-(5-((S)-1-(benzyloxycarbonylamino)-2-methylpropyl)-4H-H-1,2,4-triazol-3-yl)propanamido)benzyloxy)carbonyl)piperazin-1-yl)-1-ethyl-6-fluoro-4-oxo-1,4-dihydroquinoline-3-carboxylic acid

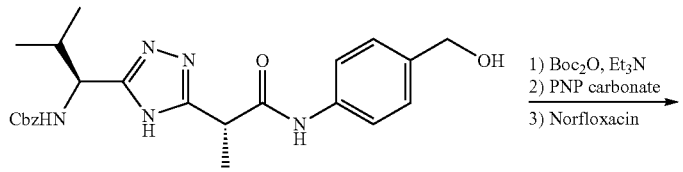

28-8

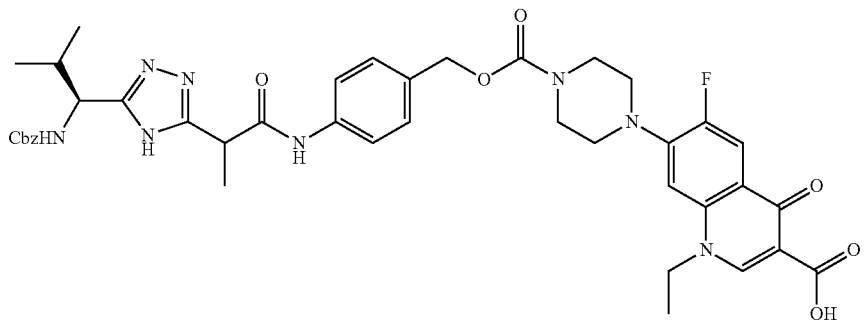

example 36

Step 1

To a solution of 28-8 (80 mg, 0.177 mmol) in DCM (3 mL) was added Boc$_2$O (232 mg, 1.062 mmol) and Et$_3$N (107 mg, 1.062 mmol) at 15° C. After the solution was stirred at 15° C. for 16 h, DCM was removed under reduced pressure and the residue was washed with petroleum ether (5 mL×3). The resulting solid was dissolved in DCM (3 mL), and PNP carbonate (108 mg, 0.354 mmol) DIPEA (92 mg, 0.708 mmol) were added. After the solution was stirred at 15° C. for 2 h, solvent was removed under reduced pressure and the residue was dissolved DMF (3 mL) and norfloxacin (170 mg, 0.531 mmol) and DIPEA (92 mg, 0.708 mmol) were added. It was stirred at 15° C. for 1 h. After the solvent was removed, the residue was purified by prep-HPLC to give a mixture of example 36 (37 mg, 26%).

$^1$H NMR (400 MHz, DMSO-d$_6$) δ 8.96 (s, 1H), 7.95 (d, J=13.2 Hz, 1H), 7.60 (d, J=8.4 Hz, 2H), 7.34-7.20 (m, 8H), 5.06-5.00 (m, 4H), 4.59-4.41 (m, 3H), 4.08-3.82 (m, 1H), 3.61 (s, 4H), 3.29 (s, 4H), 2.15-2.07 (m, 1H), 1.50-1.49 (m, 3H), 1.40 (t, J=7.2 Hz, 3H), 0.88-0.87 (m, 3H), 0.75-0.73 (m, 3H).

Example 37. 7-(4-((4-(2-(5-((S)-1-(benzyloxycarbonylamino)-2-methylpropyl)isoxazol-3-yl)propanamido)benzyloxy)carbonyl)piperazin-1-yl)-1-ethyl-6-fluoro-4-oxo-1,4-dihydroquinoline-3-carboxylic acid example 37

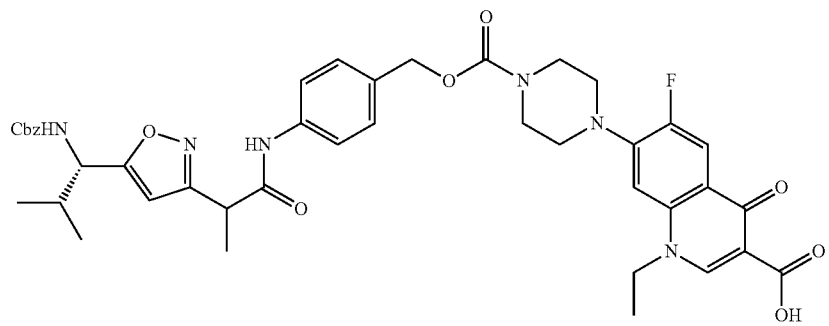

-continued

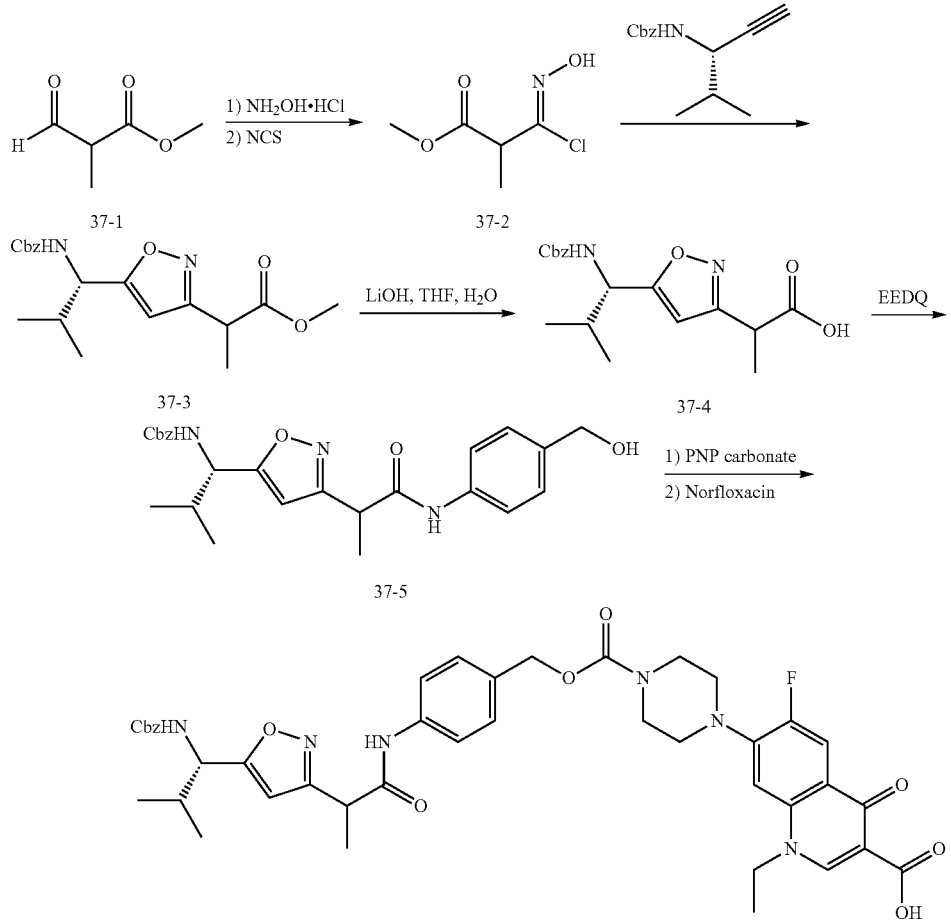

example 37

Step 1

A mixture of 37-1 (5 g, 43.1 mmol) and hydroxylamine hydrochloride (3.02 g, 43.1 mmol) in pyridine (50 mL) was stirred at 70° C. for 16 h. The solvent was removed and residue was dissolved in DMF (30 mL) and NCS (5.73 g, 43.1 mmol) was added at 0° C. The mixture was stirred at r.t. for 16 h. After the solvent was removed, the residue (37-2) was used directly in next step without purification.

Step 2

To a mixture of 37-2 (5 g, 30.2 mmol), $CuSO_4.5H_2O$ (250 mg, 1 mmol), sodium ascorbate (198 mg, 1 mmol), $Na_2CO_3$ (1.1 g, 10.4 mmol) in a mixture of t-BuOH and $H_2O$ (20 mL/20 mL) was added (1-isopropyl-prop-2-ynyl)-carbamic acid benzyl ester (1.2 g, 5.2 mmol) at 0° C. After the mixture was stirred at 60° C. for 16 h, it was extracted with EtOAc (80 mL×3). The organic layer was washed with brine (60 mL), dried over $Na_2SO_4$, concentrated in vacuo and purified by prep-HPLC to give 37-3.

LCMS (ESI): m/z 361.1 [M+H$^+$]

Step 3

To the solution of 37-3 (150 mg, 0.417 mmol) in a mixture of THF and $H_2O$ (8 mL/4 mL) was added lithium hydroxide hydrate (145 mg, 4.17 mmol) and the mixture was stirred at r.t. for 16 h. The solvent was removed and the mixture was washed with EtOAc. After it was acidified, it was extracted with EtOAc (30 mL×3). The organic layer was washed with brine (30 mL), dried over $Na_2SO_4$, concentrated to give the crude product 37-4, which was used in the next step without further purification (123 mg, 84.8%).

LCMS (ESI): m/z 347.2 [M+H$^+$].

Step 4

To a mixture of 37-4 (123 mg, 0.35 mmol) and (4-aminophenyl)methanol (87 mg, 0.71 mmol) in $CH_2Cl_2$ (5 mL) was added EEDQ (174 mg, 0.71 mmol) at 0° C. The mixture was stirred at r.t. for 16 h and extracted with EtOAc (30 mL×3). The organic layer was washed with brine (30 mL), dried over $Na_2SO_4$, concentrated and purified by prep-HPLC to give 37-5 (63 mg, 39.4%).

$^1$H NMR (400 MHz, MeOD) δ 7.44-7.42 (m, 2H), 7.23-7.19 (m, 7H), 6.23 (d, J=2.8 Hz, 1H), 4.99-4.98 (m, 2H), 4.58-4.54 (m, 1H), 4.46 (s, 2H), 3.90-3.85 (m, 1H), 2.10-2.01 (m, 1H), 1.45-1.43 (m, 3H), 089-0.79 (m, 6H). LCMS (ESI): m/z 434.1 [M-OH].

Step 5

To a solution of 37-5 (40 mg, 0.089 mmol) in dry DCM (2 mL) was added PNP carbonate (57 mg, 0.177 mmol) and DIPEA (23 mg). The mixture was heated at reflux for 16 h. After the solvent was removed, the residue was dissolved in DMF (2 mL), DIPEA (23 mg) and norfloxacin (54 mg, 0.178 mmol) was added. The mixture was stirred at r.t. for 1 h. After the solvent was removed, the residue was purified by prep-HPLC to give example 37.

$^1$H NMR (400 MHz, DMSO-$d_6$) δ 15.30 (s, 1H), 10.28 (s, 1H), 8.93 (s, 1H), 7.95-7.89 (m, 2H), 7.57 (d, J=8.8 Hz, 2H), 7.35-7.12 (m, 8H), 6.32 (d, J=4.4 Hz, 1H), 5.02 (d, J=11.6 Hz, 4H), 4.56-4.52 (m, 3H), 3.97-3.91 (m, 1H), 3.57 (s, 4H), 3.29 (s, 4H), 2.03-1.96 (m, 1H), 1.41-1.35 (m, 6H), 0.85-0.75 (m, 6H). LCMS (ESI): m/z 797.3 [M+H$^+$], 399.3 [M/2+H$^+$].

Example 38. 7-(4-((4-(2-(5-((S)-1-(benzyloxycarbonylamino)-2-methylpropyl)thiazol-2-yl)propanamido)benzyloxy)carbonyl)piperazin-1-yl)-1-ethyl-6-fluoro-4-oxo-1,4-dihydroquinoline-3-carboxylic acid

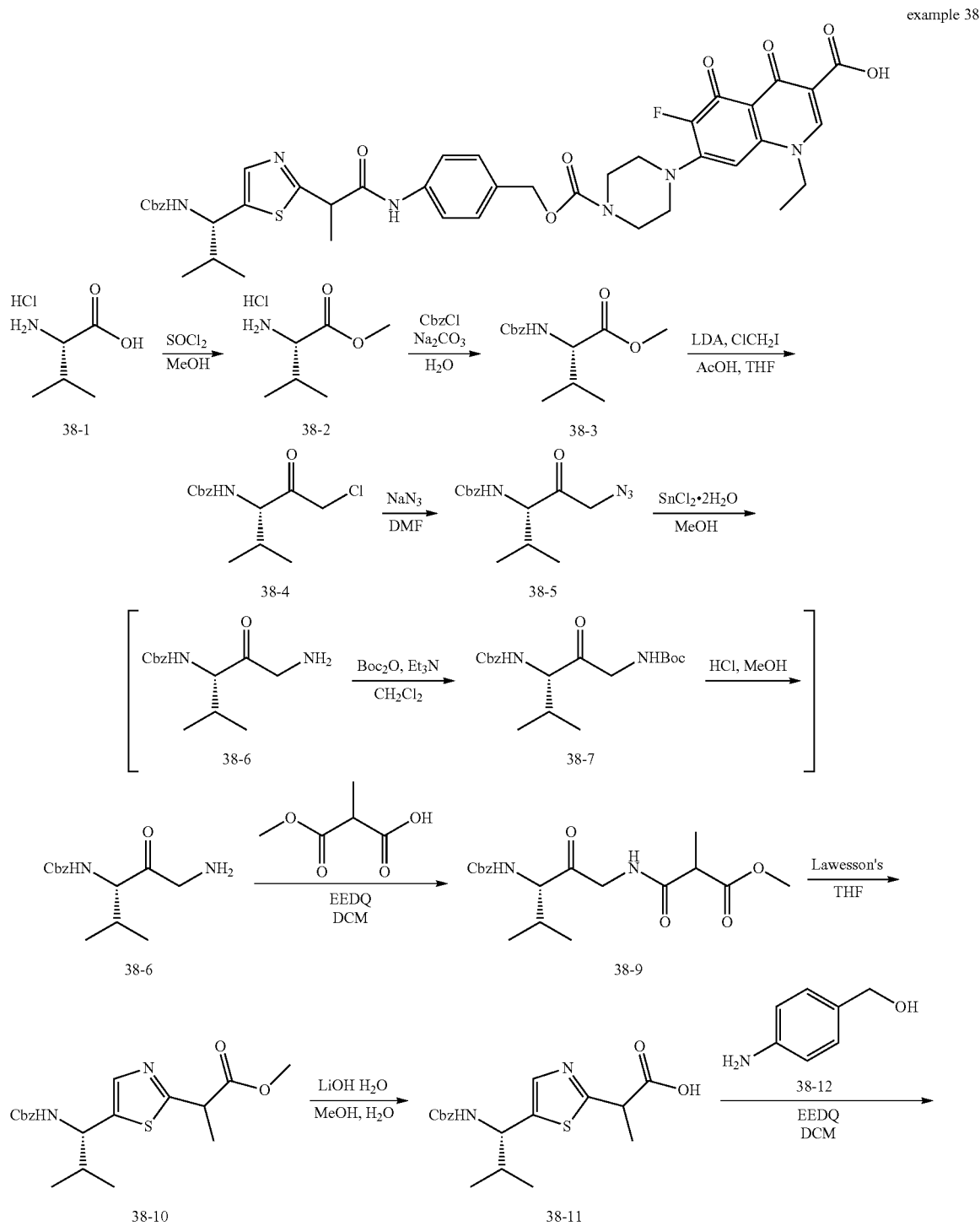

-continued

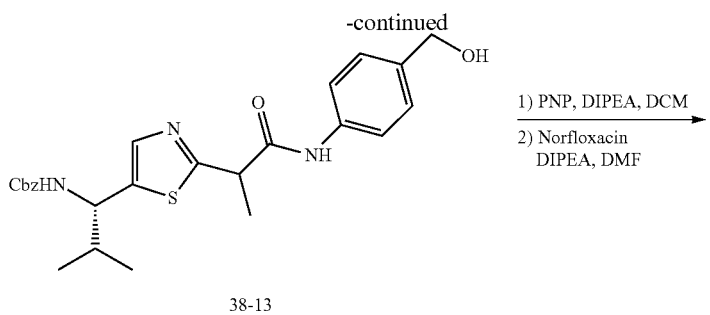

38-13

1) PNP, DIPEA, DCM
2) Norfloxacin DIPEA, DMF

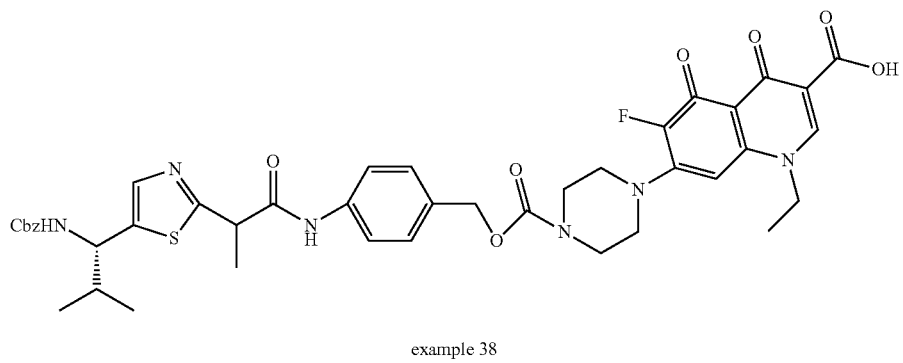

example 38

Step 1

To a solution of 38-1 (40 g, 0.34 mol) in MeOH (200 mL) at 0° C. was added the SOCl$_2$ (28 mL, 0.38 mol) under N$_2$. After the mixture was stirred at r.t. for 12 h, solvent was removed to give the crude product 38-2.

Step 2

CbzCl (53 mL, 0.37 mol) was added dropwise over 20 min to a mixture of 38-2 (57 g, 0.34 mol) and Na$_2$CO$_3$ (72 g, 0.68 mol) in water (300 mL). After the mixture was stirred at r.t. for 12 h, it was extracted with EtOAc (500 mL×3). The combined organic layers were dried over Na$_2$SO$_4$ and concentrated to give the crude product, which was purified by column chromatography on silica gel (PE:EtOAc=5:1) to give compound 38-3.

Step 3

To the solution of compound 38-3 (10 g, 37.7 mmol) in THF (20 mL) was added ClCH$_2$I (26.6 g, 151 mmol). After it was cooled to −78° C., LDA was added slowly in 2 h. After it was stirred at −78° C. for 30 min under N$_2$, HOAc (21 mL, 377 mmol) in THF was added under −70° C. It was warmed to r.t., and EtOAc (30 mL) was added and the mixture was poured to brine. It was extracted with EtOAc (80 mL×3), dried over Na$_2$SO$_4$, concentrated, and purified by column chromatography on silica gel (PE:EtOAc=5:1) to give compound 38-4.

Step 4

After a mixture of compound 38-4 (5 g, 17.6 mmol) and NaN$_3$ (1.8 g, 26.4 mmol) was stirred at r.t. for 1 h, it was poured to water and extracted with EtOAc (150 mL×3). The combined organic layers were dried over Na$_2$SO$_4$ and concentrated under pressure reduce to give the crude product of compound 38-5.

Step 5

To the solution of compound 38-5 (4.84 g, 16.7 mmol) in MeOH (50 mL) was added SnCl$_2$.2H$_2$O (7.5 g, 33.3 mmol) and the mixture was stirred at r.t. for 2 h. After the solvent was removed; the residue (38-6) was used directly in the next step.

Step 6

A mixture of compound 38-6 (3.75 g, 14.2 mmol), NaHCO$_3$ (11.93 g, 142 mmol), Boc$_2$O (3.41 g, 15.6 mmol) in H$_2$O (15 mL) and dioxane (15 mL) was stirred at r.t. for 1 h. The mixture was extracted with EtOAc (150 mL×3), dried over Na$_2$SO$_4$, concentrated and purified by column chromatography on silica gel (PE:EtOAc=5:1 to 2:1) to give compound 38-7. After a mixture of compound 38-7 (1.6 g, 4.43 mmol) and 4 M HCl in MeOH (20 mL) was stirred at r.t. for 1 h, it was evaporated to give compound 38-6, which was used for the next step without further purification.

Step 7

To the solution of compound 38-6 (1.17 g, 4.43 mmol) and compound 38-8 (643 mg, 4.87 mmol) in DCM (20 mL) was added EEDQ (1.31 g, 5.31 mmol). After the mixture was stirred at r.t. for 1 h, solvent was removed, and the residue was purified by prep-HPLC to give compound 38-9.

Step 8

To a solution of compound 38-9 (1 g, 2.64 mmol) in THF (20 mL) under N$_2$ was added Lawesson's reagent (1.18 g, 2.91 mmol). After the mixture was stirred at 60° C. for 1 h, solvent was removed, and the residue was purified by prep-HPLC to give compound 38-10.

Step 9

To a solution of compound 38-10 (630 mg, 1.67 mmol) in MeOH (5 mL) and H$_2$O (1 mL) was added LiOH—H$_2$O (105 mg, 2.51 mmol). After the suspension was stirred at r.t. for 1 h, it was acidified with conc. HCl to pH=6. The mixture was extracted with (50 mL×3) and concentrated under reduced pressure to give compound 38-11.

Step 10

A mixture of compound 38-11 (438 mg, 1.21 mmol), compound 38-12 (446 mg, 3.62 mmol), HATU (690 mg, 1.82 mmol), DIPEA (468 mg, 3.62 mmol) and EEDQ (895 mg, 3.62 mmol) in DCM (10 mL) was stirred at r.t. for 2 h. After the solvent was removed, it was purified by prep-HPLC to give 38-13 (200 mg, 35.4%).

$^1$H NMR (400 MHz, MeOD) δ 7.54 (d, J=8.4 Hz, 3H), 7.31-7.25 (m, 7H), 5.06-5.04 (m, 2H), 4.64 (d, J=8.0 Hz, 1H), 4.55 (s, 2H), 4.21 (m, 1H), 2.14-2.04 (m, 1H), 1.63 (d, J=6.8 Hz, 3H), 0.99 (d, J=6.8 Hz, 3H), 0.89-0.86 (m, 3H).

LCMS (ESI): m/z 467.9 [M+H$^+$].

Step 11

A mixture of 38-13 (50 mg, 0.107 mmol), PNP (65 mg, 0.214 mmol) and DIPEA (41 mg, 0.321 mmol) in DCM (5 mL) was stirred at 50° C. for 12 h. It was concentrated and added to a mixture of norfloxacin (102 mg, 0.321 mmol) and DIPEA (41 mg, 0.321 mmol) in DMF (5 mL). After it was stirred at r.t. for 2 h, solvent was removed and the residue was purified by prep-HPLC to give example 38 (24 mg, 27.6%).

$^1$H NMR (400 MHz, DMSO-d$_6$) δ 15.32 (s, 1H), 10.40 (s, 1H), 8.96 (s, 1H), 7.96-7.88 (m, 2H), 7.61 (d, J=8.4 Hz, 2H), 7.51 (s, 1H), 7.36-7.20 (m, 8H), 5.07 (s, 2H), 5.02-5.00 (m, 2H), 4.59-4.55 (m, 3H), 4.24-4.22 (m, 1H), 3.61 (s, 4H), 3.32 (s, 4H), 1.97-1.92 (m, 1H), 1.52 (d, J=6.8 Hz, 3H), 1.40 (t, J=6.8 Hz, 3H), 0.92 (d, J=6.0 Hz, 3H), 0.79-0.77 (m, 3H).

LCMS (ESI): m/z 813.2 [M+H$^+$].

Example 39. 7-(4-((4-((S)-2-((S)-2-(benzyloxycarbonylamino)-3-methylbutanamido)-5-guanidinopentanamido)benzyloxy)carbonyl)piperazin-1-yl)-1-ethyl-6-fluoro-4-oxo-1,4-dihydroquinoline-3-carboxylic acid

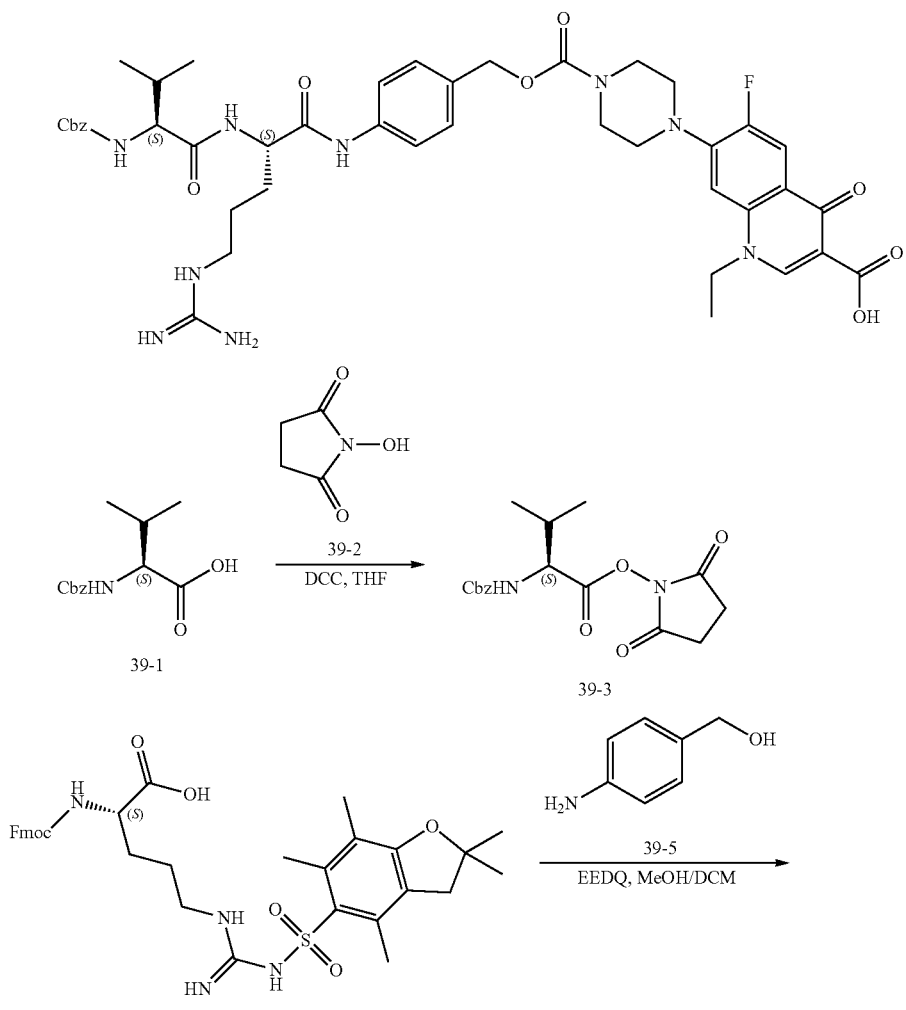

example 39

-continued
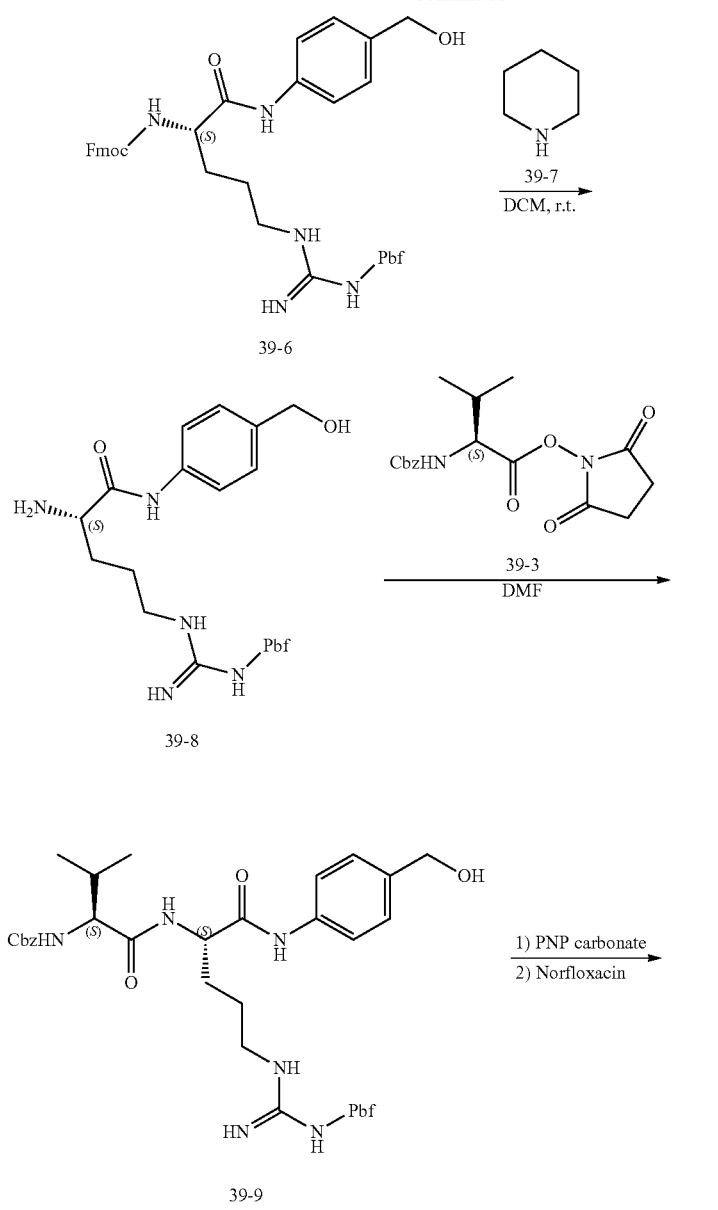
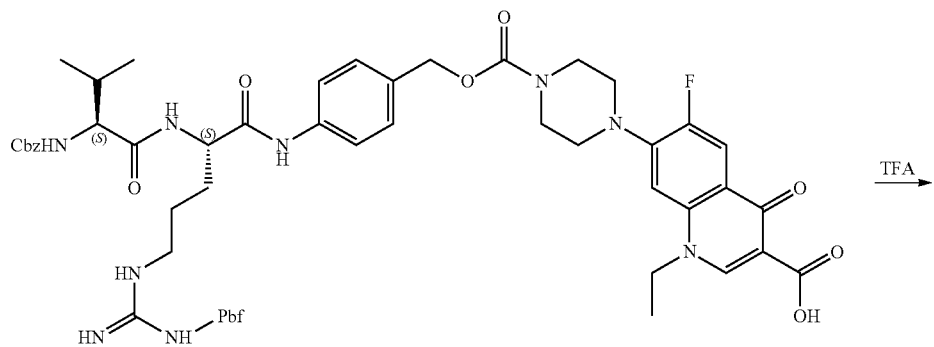

-continued

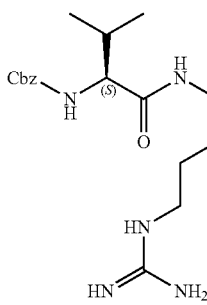
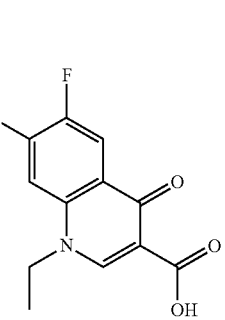

example 39

Step 1

To a stirred solution of compound 39-1 (1 g, 4 mmol), compound 39-2 (459 mg, 4 mmol) in THF (20 mL) was added DCC (908 mg, 4.4 mmol) at 0° C. The reaction mixture was stirred at r.t. for 16 h. The mixture was filtered and the filtrate was concentrated to give compound 39-3 (Yield: 90%).

Step 2

To a solution of compound 39-4 (2 g, 3.1 mmol) in DCM/MeOH (20 mL/20 mL) were added 4-amino-phenyl-methanol (39-60) (570 mg, 4.6 mmol) and EEDQ (1.532 mg, 6.2 mmol). The mixture was stirred at r.t. for 16 h and purified by column chromatography (PE/EtOAc=1/3) to give compound 39-6 (2 g, Yield: 86%).

Step 3

To a solution of compound 39-6 (2 g, 2.65 mmol) in DCM (50 mL) was added compound 39-7 (1.3 mL, 13.3 mmol) at r.t. After the mixture was stirred at r.t. for 16 h, it was concentrated and washed with MTBE, and filtrated to give compound 39-8 (Yield: 80%).

Step 4

To a solution of compound 39-8 (640 mg, 1.2 mmol) in DME (10 mL) was added a solution of compound 39-3 (640 mg, 1.8 mmol) and NaHCO$_3$ (304 mg, 3.6 mmol) in water (10 mL). After the mixture was stirred at r.t. for 16 h, it was washed with EtOAc and acidified to pH 3 with 10% HCl. The resulting suspension was extracted with EtOAc. The combined organic layer was concentrated and purified by column chromatography (PE/EtOAc=1/2) to give 39-9 (510 mg, Yield: 55%).

Step 5

To a solution of compound 39-9 (200 mg, 0.26 mmol), PNP carbonate (158 mg, 0.52 mmol) in DMF (4 mL) was added DIPEA (101 mg, 0.78 mmol) at 0° C. The mixture was stirred at r.t. for 16 h. To the mixture was added norfloxacin (170 mg, 0.52 mmol) at r.t. The mixture was stirred at r.t. for 1 h and was purified by prep-HPLC and SFC to give Compound 39-10 (Yield: 30% over two steps).

Step 6

To the compound 39-10 (100 mg, 0.1 mmol) was added a mixture of TFA and DCM (TFA/DCM=1/5) at 0° C. After the mixture was stirred at r.t. for 3 h, it was basified to pH=9 by NH$_3$.H$_2$O. The residue was purified by prep-HPLC and SFC to give example 39 (13.8 mg, 15%).

LCMS: (5-95, AB, 1.5 min, ESI), 0.826 min, MS=858.2 [M+1]

$^1$H NMR Methanol-d$_4$ 400 MHz, δ 8.80 (s, 1H), 8.55 (s, 1H), 7.98 (d, J=13.2 Hz, 1H), 7.58 (s, 2H), 7.36-7.27 (m, 9H), 7.15 (m, 1H), 5.11 (d, J=16.4 Hz, 4H), 4.57-4.50 (m, 4H), 3.94 (d, J=7.2 Hz, 1H), 3.71 (m, 4H), 3.22 (s, 2H), 2.07 (d, J=6.8 Hz, 1H), 1.95 (s, 1H), 1.83-1.79 (m, 1H), 1.70 (d, J=1.6 Hz, 2H), 1.51 (s, 3H), 0.97-0.96 (m, 6H).

Example 40. 7-(4-((4-((S)-6-amino-2-((S)-2-(benzyloxycarbonylamino)-3-(thiophen-2-yl)propanamido)hexanamido)benzyloxy)carbonyl)piperazin-1-yl)-1-ethyl-6-fluoro-4-oxo-1,4-dihydroquinoline-3-carboxylic acid

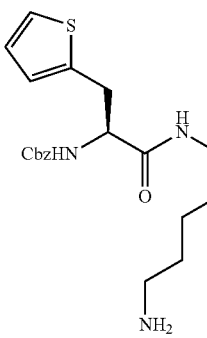
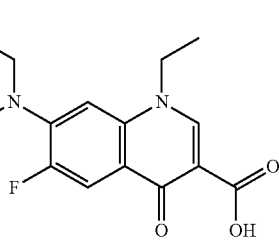

example 40

-continued
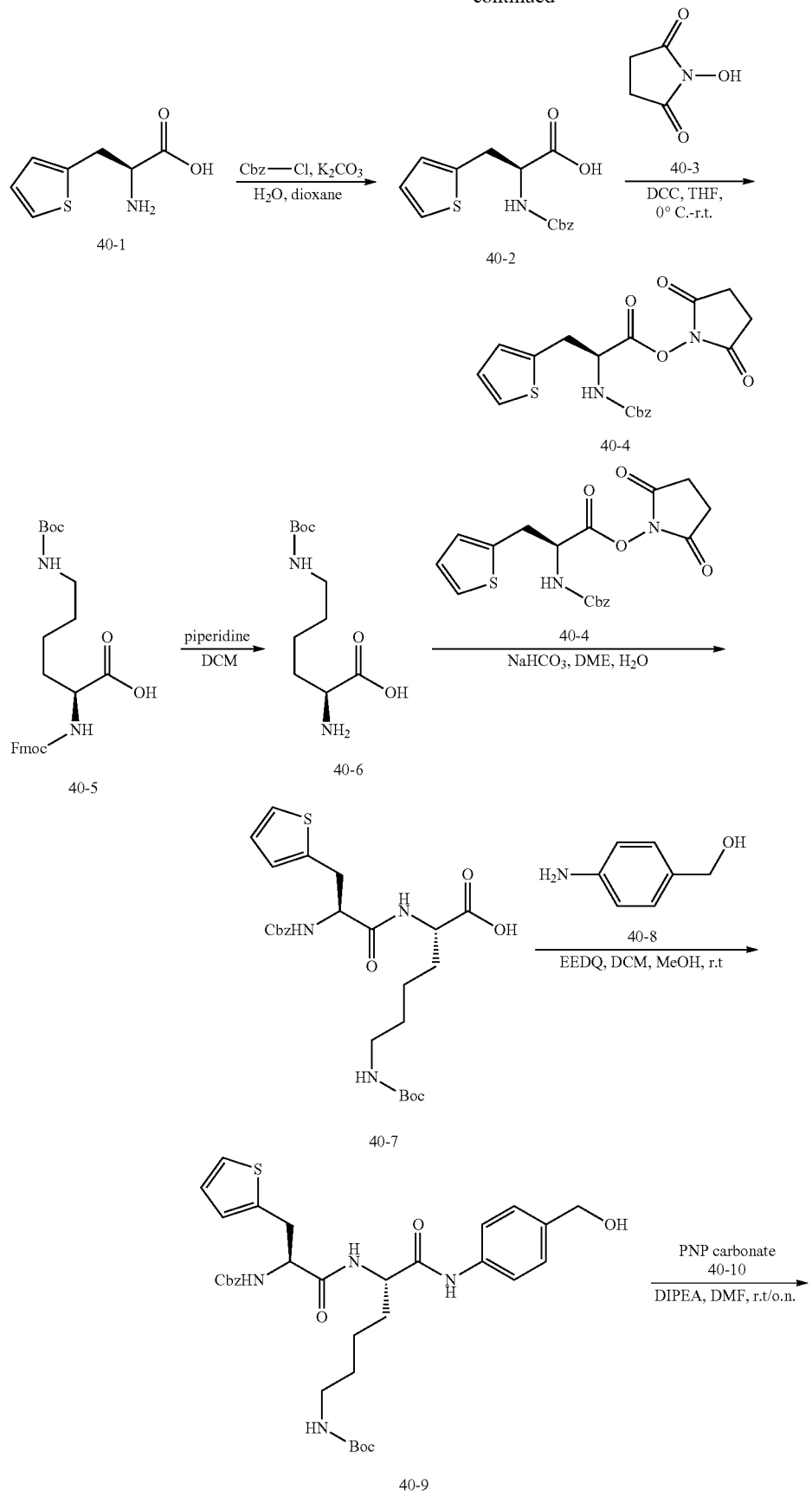

-continued

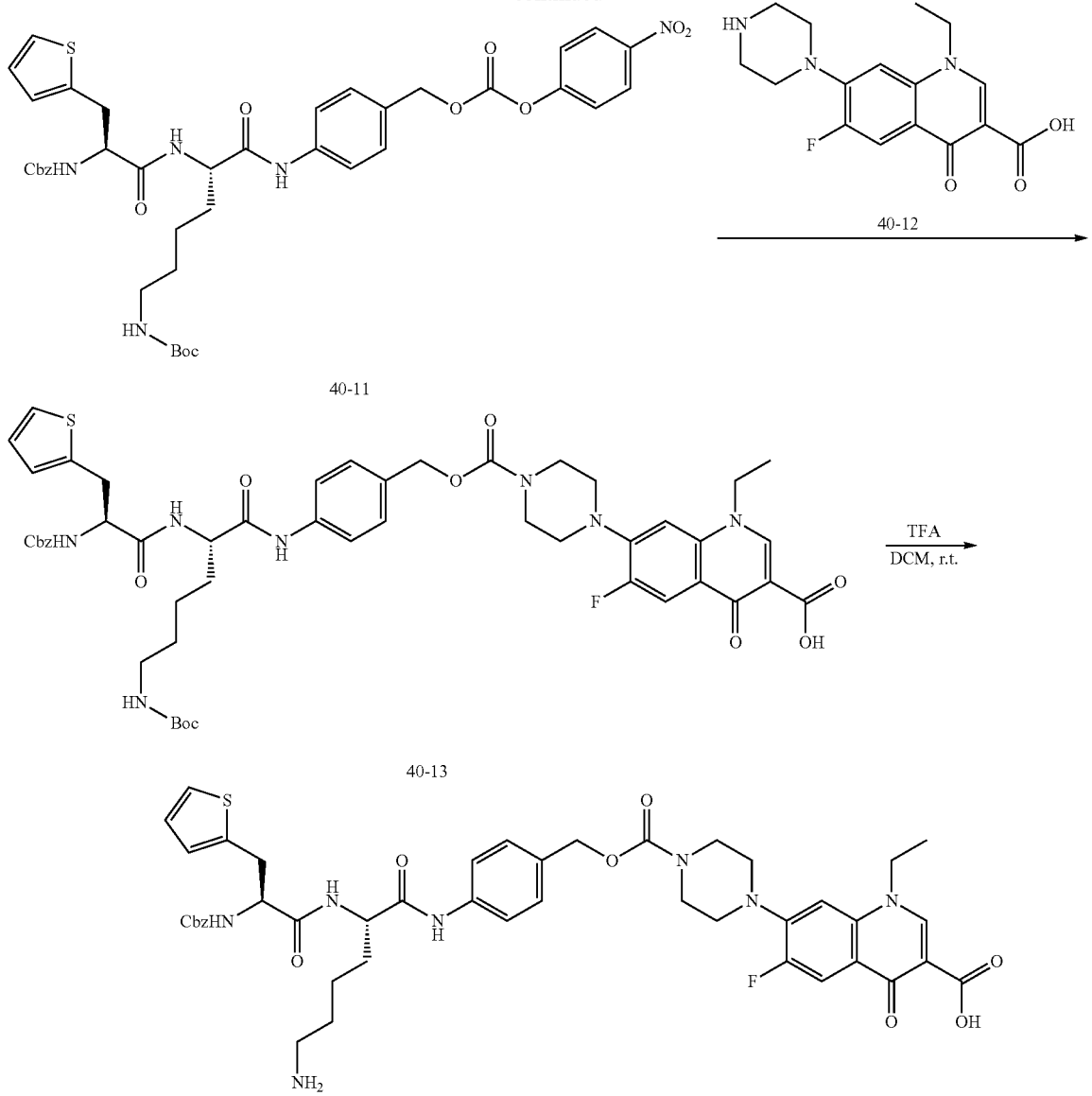

example 40

Step 1

To the mixture of compound 40-1 (1 g, 5.85 mmol) in H₂O (6 mL) and dioxane (9 mL) was added K₂CO₃ (2.02 g, 14.63 mmol), and Cbz-Cl (1.2 g, 7.01 mmol) at 0° C. The reaction mixture was stirred at r.t. for 2 h. The mixture was washed with EtOAc (20 mL). The aqueous phase was acidified with 1N HCl to pH=3 and was extracted with EtOAc (25 ml×2), the organic layers were dried over Na₂SO₄, filtered and concentrated under reduced pressure to give crude compound 40-2 as an oil (1.5 g, yield: 84.3%).

LCMS: (10-80, AB, 2 min, ESI), 0.954 min, MS=305.8 [M+1], 327.8 [M+Na⁺]

¹H NMR DMSO-d₆ 400 MHz δ 7.65-7.63 (d, J=8.0 Hz, 1H), 7.37-7.29 (m, 6H), 6.94-6.90 (m, 2H), 5.01 (s, 2H), 4.2-4.1 (m, 1H), 3.31-3.27 (m, 1H), 3.12-3.06 (m, 1H).

Step 2

To a solution of compound 40-2 (2.0 g, 6.55 mmol), compound 40-3 (829.15 mg, 7.2 mmol) in dry THF (25 mL) was added DCC (1.49 g, 7.21 mmol) at 0° C. The mixture was stirred at r.t. for 16 h under N₂. The mixture was filtered and the filtrate was concentrated to give crude compound 40-4 which was used for next step directly without further purification (2.2 g, Yield: 84.6%).

LCMS: (10-80, AB, 2 min, ESI), 1.040 min, MS=424.8 [M+Na⁺]

Step 3

To a stirred solution of compound 40-5 (5 g, 10.7 mmol) in DCM (80 mL) was added piperidine (4.5 g, 52.8 mmol) dropwise via syringe at r.t. After the mixture was stirred at r.t. for 30 min, it was concentrated under reduced pressure, and the residue was partitioned between EtOAc (30 mL) and H₂O (50 ml). The aqueous phase was concentrated to give crude compound 40-6 (2.0 g, 76%) as white solid which was used in the next step directly.

Step 4

To a solution of compound 40-4 (980 mg, 2.44 mmol) in DME (10 mL) was added a solution of compound 40-6 (500 mg, 2.03 mmol) and NaHCO₃ (374 mg, 4.46 mmol) in water (10 mL). After the mixture was stirred at r.t. for 16 h, it was washed with EtOAc (20 mL) and the aqueous phase was acidified to pH=3 with 15% citric acid solution. The resulting suspension was extracted with EtOAc (30 mL×2). The organic layer was purified by prep-HPLC to give compound 40-7 as white solid (200 mg, 18.4%).

LCMS: (10-80, AB, 2 min, ESI), 1.123 min, MS=434.1 [M+1-Boc⁺], 556.1 [M+Na⁺]

Step 5

To a solution of compound 40-7 (300 mg, 0.563 mmol) in DCM/MeOH (20 mL/10 mL) were added 4-amino-phenyl-methanol (40-8) (103.9 mg, 0.845 mmol) and EEDQ (208.82 mg, 0.845 mmol). After the mixture was stirred at r.t. for 16 h, it was concentrated. The residue was purified by column chromatography (PE:EtOAc=2:3) to give compound 40-9 as white solid (260 mg, Yield: 72.3%).

LCMS: (5-95, AB, 1.5 min, ESI), 0.880 min, MS=539.0 [M+1-Boc⁺], 661.0 [M+Na⁺]

¹H NMR CDCl₃ 400 MHz, δ 8.51 (s, 1H), 7.44 (d, J=8 Hz, 2H), 7.24-7.19 (m, 6H), 7.05-7.03 (m, 1H), 6.78-6.73 (m, 3H), 5.52 (d, J=3.2 Hz, 1H), 5.03 (s, 2H), 4.56 (s, 2H), 4.46-4.39 (m, 2H), 3.25 (d, J=5.6 Hz, 2H), 2.98 (s, 2H), 1.87-1.83 (m, 1H), 1.39 (d, J=7.6 Hz, 1H), 1.35 (s, 9H), 1.25-1.17 (m, 2H).

Step 6

To a solution of compound 40-9 (250 mg, 0.39 mmol) in dry DMF (5 mL) was added PNP carbonate (237.14 mg, 0.78 mmol) and DIPEA (251.6 mg, 1.95 mmol) at 0° C. The mixture was stirred at r.t. for 16 h. The mixture (40-11) was used for next step directly without further purification.

Step 7

To the mixture of 40-11 was added norfloxacin (249.1 mg, 0.78 mmol) at r.t. After the mixture was stirred at r.t. for 1 h, it was purified by prep-HPLC to give crude compound 40-13 (220 mg Yield: 57.3%).

LCMS: (5-95, AB, 1.5 min, ESI), 0.964 min, MS=442.6 [½M+1], 984.4 [M+1]

Step 8

To compound 40-13 (120 mg, 0.12 mmol) was added a mixture of DCM:TFA (5:1, 3 mL) at r.t. After the mixture was stirred at r.t. for 1 h, it was adjusted to pH=7 with ammonia, then concentrated, the residual was purified by prep-HPLC to give example 40 (29 mg, yield: 16.9%).

LCMS: (5-95, AB, 1.5 min, ESI), 0.826 min, MS=884.3 [M+1], 442.8 [½M+1]

¹H NMR DMSO-d₆ 400 MHz, δ 10.23 (s, 1H), 8.93 (s, 1H), 8.44 (s, 1H), 8.42 (s, 0.5H, HCOOH), 7.92 (d, J=13.2 Hz, 1H), 7.93-7.61 (m, 3H), 7.33-7.25 (m, 8H), 7.20-7.16 (m, 1H), 6.88-6.86 (m, 2H), 5.63 (s, 2H), 4.97 (s, 2H), 4.58-4.53 (m, 2H), 4.40-4.31 (m, 1H), 4.30-4.19 (m, 1H), 3.58 (s, 4H), 3.28-3.19 (m, 4H), 3.19-3.03 (m, 2H), 3.04-2.96 (m, 2H), 2.69-2.64 (m, 2H), 1.73-1.67 (m, 2H), 1.57-1.49 (m, 2H), 1.47-1.34 (m, 3H), 1.32-1.28 (m, 2H).

Example 41. 7-(4-((4-((S)-2-((S)-2-acetamido-3-methylbutanamido)-5-ureidopentanamido)benzyloxy) carbonyl)piperazin-1-yl)-1-ethyl-6-fluoro-4-oxo-1,4-dihydroquinoline-3-carboxylic acid

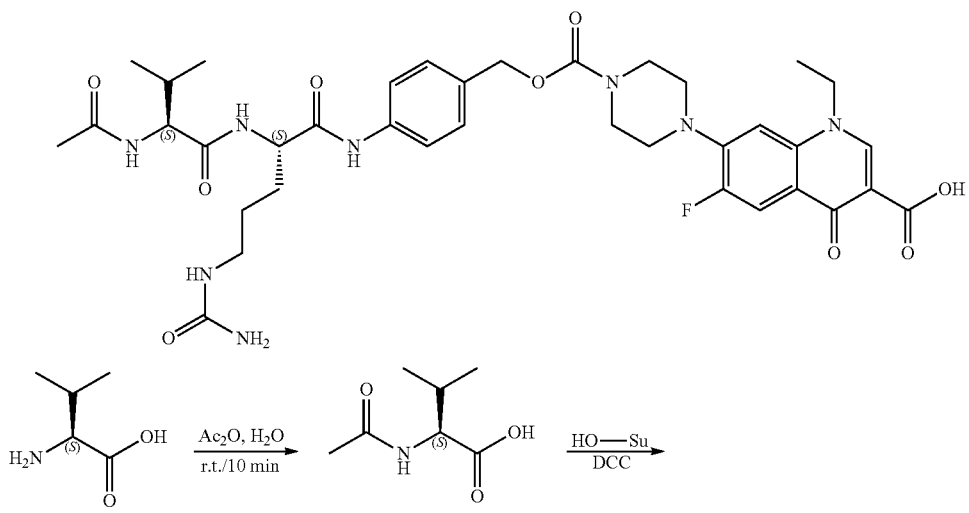

example 41

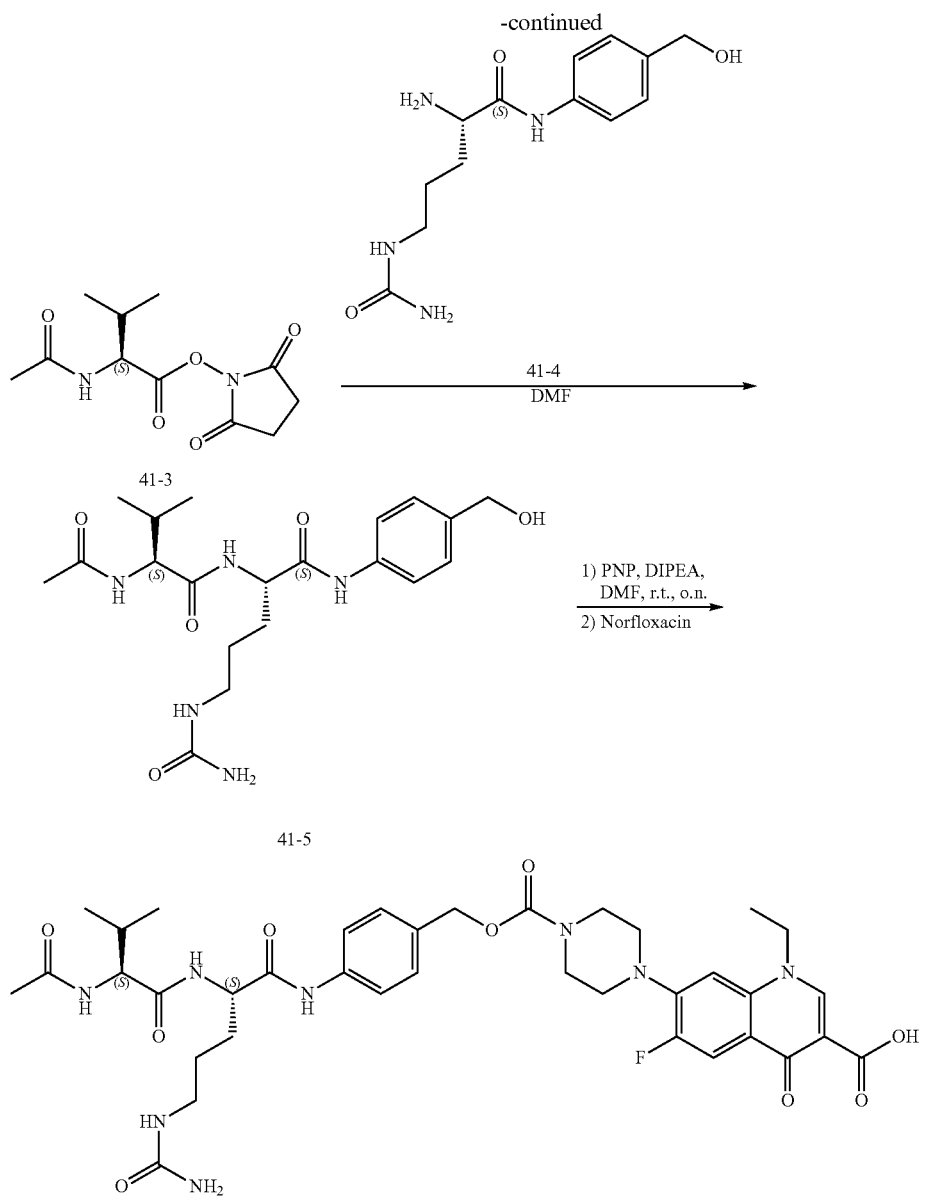

example 41

Step 1

After compound 41-1 (470.6 mg, 4 mmol) in water (10 mL) was sonicated for 6 min, Ac₂O was added over 4 min. The mixture was concentrated and the residue was dissolved in MeOH, filtered, concentrated to give crude 41-2 as a white solid (350 mg, 55%).

¹H NMR DMSO-d₆400 MHz, δ 7.94-7.92 (d, J=8.0 1H), 4.10-4.08 (m, 1H), 2.01-1.99 (m, 1H), 1.84 (s, 1H), 0.83-0.80 (m, 6H)

Step 2

To a solution of compound 41-2 (160 mg, 1 mmol) and HO—Su (122 mg, 1.05 mmol) in THF (10 mL) was added DCC (218 mg, 1.05 mmol) at r.t. The mixture was stirred at r.t. for 16 h under N₂. The mixture was filtered and the filtrate was concentrated to give 41-3 (242 mg, Yield: 95%).

Step 3

Compound 41-3 (242 mg, 0.94 mmol), 41-4 (265 mg, 0.94 mmol) were dissolved in DMF (15 mL). After the reaction mixture was stirred at r.t. for 3 h, it was filtered and purified by prep-HPLC to give 41-5 (70 mg, Yield: 17.7%).

Step 4

To a solution of compound 41-5 (60 mg, 0.142 mmol) in dry DMF (3 mL) was added PNP carbonate (87 mg, 0.285 mmol) and DIPEA (56 mg, 0.427 mmol) at r.t. The mixture was stirred at r.t. for 16 h. Norfloxacin (91 mg, 0.285 mmol) was added. The mixture was stirred at r.t. for another 1 h. The mixture was concentrated, filtered and purified by prep-HPLC (FA) to give example 41 (40 mg, yield: 37%).

LCMS: (5-95, AB, 1.5 min, ESI), 0.784 min, MS=767.1 [M+1]

¹H NMR DMSO-d₆ 400 MHz, δ 9.96 (s, 1H), 8.93 (s, 1H), 8.10 (d, J=7.6 Hz, 1H), 7.92 (d, J=12.4 Hz, 1H), 7.86 (d, J=8.8 Hz, 1H), 7.58 (d, J=8.4 Hz, 2H), 7.31 (d, J=8.8 Hz, 2H), 7.18 (d, J=7.2 Hz, 1H), 5.96-5.94 (m, 1H), 5.38 (s, 2H), 5.03 (s, 2H), 4.58-4.53 (m, 2H), 4.38-4.32 (m, 1H), 4.17-4.14 (m, 1H), 3.58 (s, 4H), 3.26 (s, 4H), 3.00-2.91 (m, 2H), 1.96-1.92 (m, 1H), 1.86 (s, 3H), 1.68-1.55 (m, 2H), 1.38 (m, 5H), 0.85-0.80 (m, 6H).
Example 42: 7-(4-{4-[(S)-6-Amino-2-((S)-2-benzyloxycarbonylamino-3-phenyl-propionylamino)-hexanoylamino]-benzyloxycarbonyl}-piperazin-1-yl)-1-ethyl-6-fluoro-4-oxo-1,4-dihydro-quinoline-3-carboxylic acid
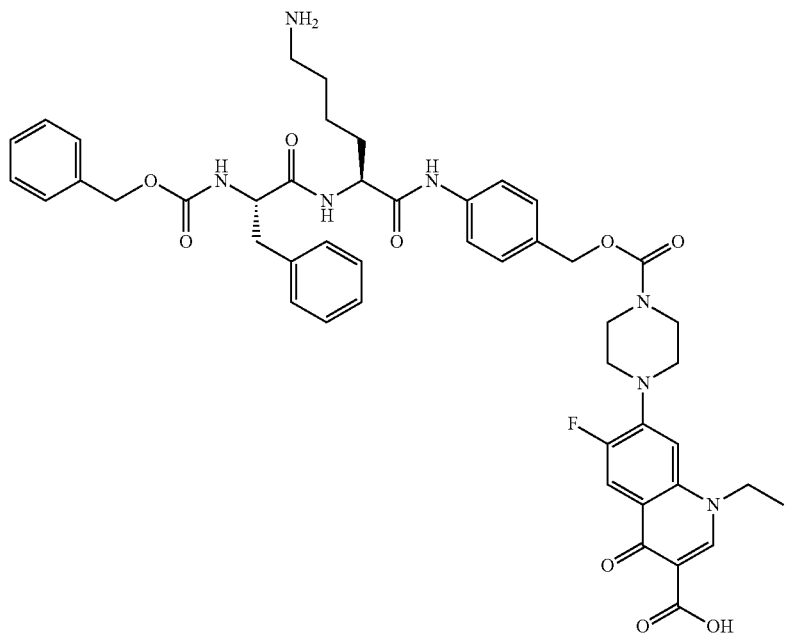
Example 42
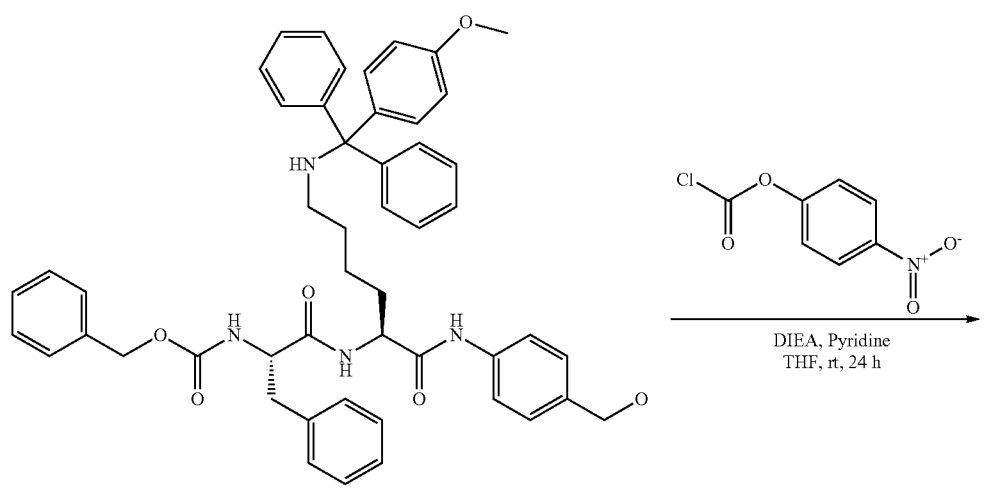
42-1

-continued

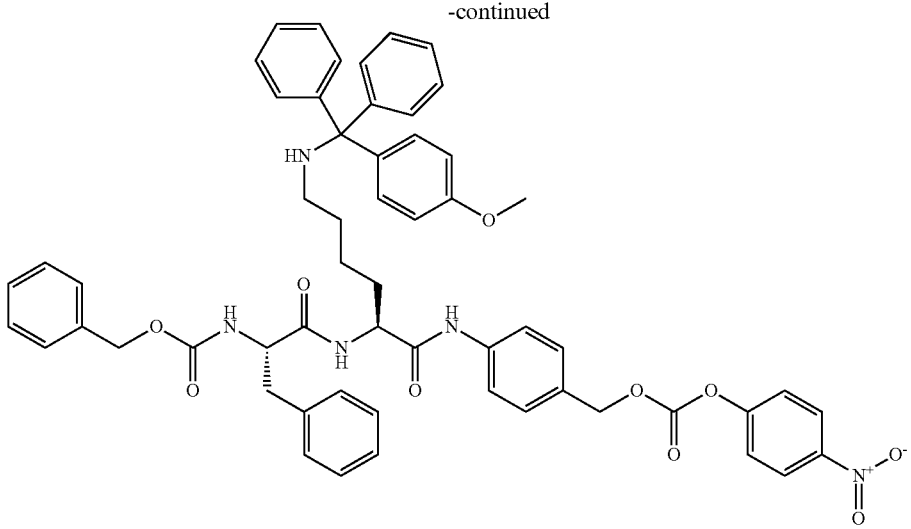

42-2

Step 1

To the 5 ml THF solution of 42-1 (200 mg, 0.25 mmol) was added DIEA (0.18 ml, 0.99 mmol), then added (4-nitrophenyl) carbonochloridate (150 mg, 0.75 mmol), followed by pyridine (0.03 ml, 0.32 mmol). The reaction mixture was stirred at 28° C. for overnight. The mixture was concentrated down to dry, dissolved into EtOAc, washed by Sat. NH4Cl, brine. The organic layer was dried over MgSO4, was concentrated down. The crude was triturated with ether, filtered to afford a light yellow solid 42-2 (190 mg, 79%).

LCMS (ESI): m/z 970.7 [M+H$^+$].

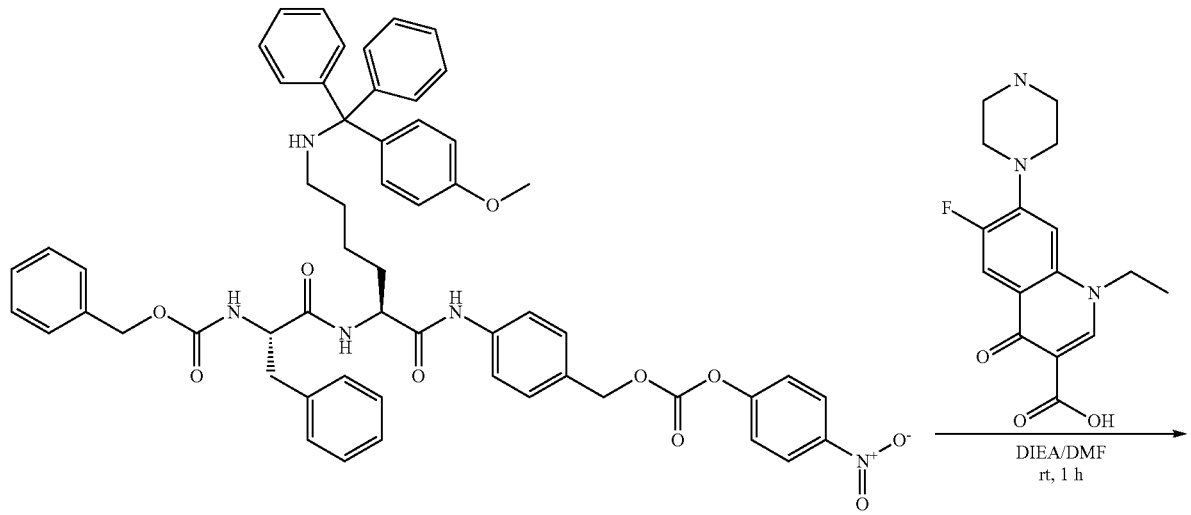

42-2

-continued

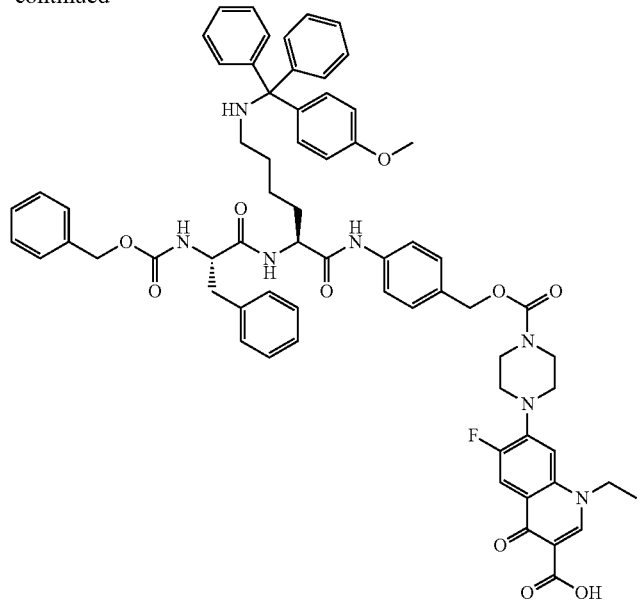

42-3

Step 2

To the suspension of 1-ethyl-6-fluoro-4-oxo-7-(piperazin-1-yl)-1,4-dihydroquinoline-3-carboxylic acid (59 mg, 0.18 mmol) in 2 ml DMF, was added DIEA (0.11 mL, 0.62 mmol), then added 42-2 (120 mg, 0.12 mmol) as one portion, slowly became yellow solution till reaction completed. The reaction mixture was poured into ice water, extracted with DCM. The organic layer washed by Sat. $NH_4Cl$, brine, dried over $MgSO_4$, was concentrated down to yield 42-3 (140 mg, 99%).

LCMS (ESI): m/z 1150.9 [M+H$^+$].

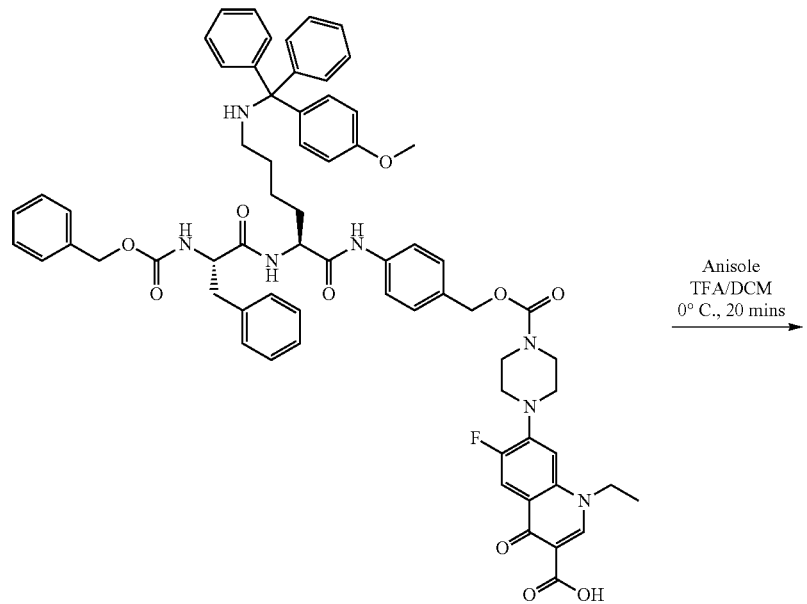

Anisole
TFA/DCM
0° C., 20 mins 42-3

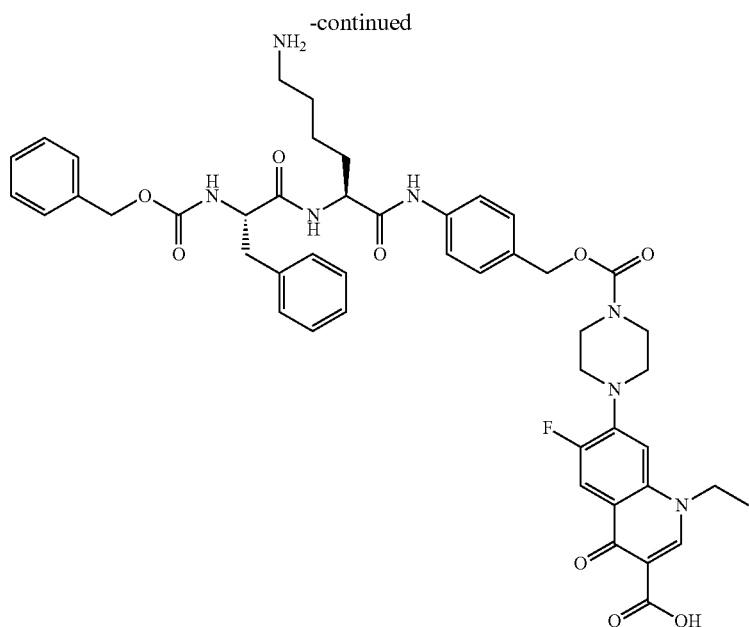

Example 42

Step 3

To the 10 ml DCM solution of 42-3 (145 mg, 0.13 mmol) was added anisole (0.05 ml, 0.50 mmol), cooled to ice bath, then dropwisely added TFA (0.1 ml, 1.00 mmol). After 10 mins the reaction was completed, removed the ice bath. The reaction mixture was concentrated down to dry, dissolved into DCM, washed by Sat. NaHCO3/water, brine. The organic layer was dried over MgSO4, was concentrated down. The crude was triturated with DCM, filtered to afford a light yellow solid 42 (38 mg, 34%).

LCMS (ESI): m/z 878.7 [M+H$^+$].

$^1$H NMR (400 MHz, DMSO-d$_6$) δ 10.13 (s, 1H), 8.86 (s, 1H), 8.26 (s, 1H), 7.91 (d, J=12.7 Hz, 1H), 7.62 (d, J=8.2 Hz, 2H), 7.48 (d, J=9.2 Hz, 1H), 7.38-7.10 (m, 13H), 5.07 (s, 2H), 4.95 (s, 2H), 4.51 (s, 2H), 4.40 (s, 1H), 4.33 (s, 1H), 3.61 (s, 4H), 3.03 (d, J=12.2 Hz, 2H), 1.69 (d, J=15.5 Hz, 3H), 1.39 (t, J=6.8 Hz, 8H).

Example 43. 7-(4-((4-((S)-2-((S)-2-(benzyloxycarbonylamino)-3-(thiophen-2-yl)propanamido)-5-ureidopentanamido)benzyloxy)carbonyl)piperazin-1-yl)-1-ethyl-6-fluoro-4-oxo-1,4-dihydroquinoline-3-carboxylic acid example 43

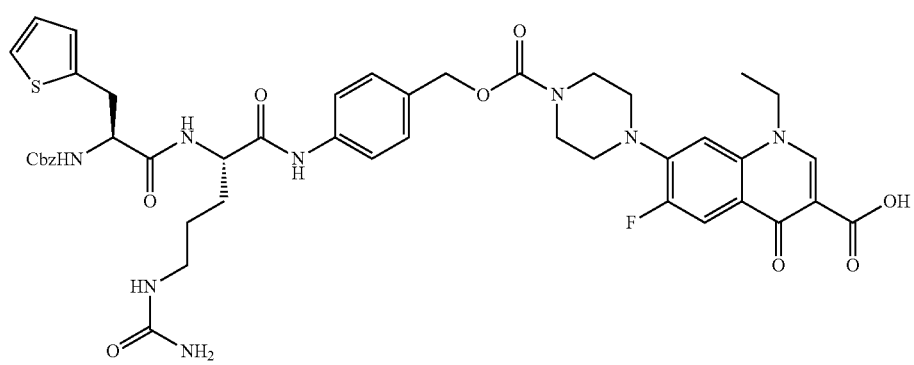

-continued
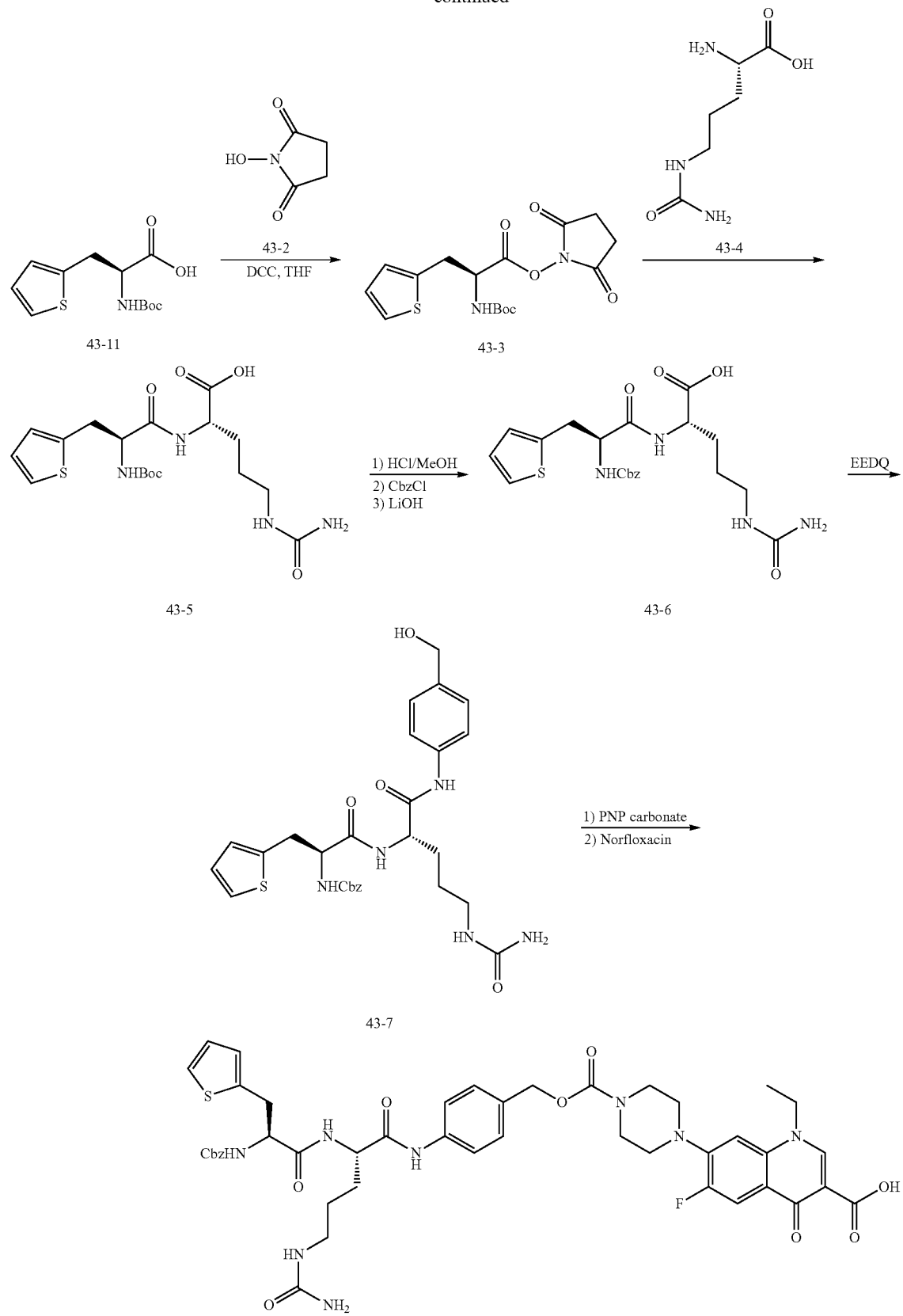
example 43

Step 1

To a solution of compound 43-1 (178 mg, 0.665 mmol) and compound 43-2 (79 mg, 0.688 mmol) in THF (3 mL) was added DCC (149 mg, 0.721 mmol) in THF (0.5 mL) at 10° C. The solution was stirred at 10° C. for 6 h. The solid was filtered, and solvent was removed. The residue was dissolved in DCM (5 mL). The mixture was allowed to stand for 1 h and was filtered to remove more DCU. The filtrate was evaporated to give crude compound 43-3 (245 mg).

$^1$H NMR (400 MHz, CDCl$_3$) δ 7.21 (d, J=5.2 Hz, 1H), 7.02-6.96 (m, 2H), 5.30-4.93 (m, 1H), 3.54-3.40 (m, 2H), 2.82 (s, 4H), 1.44 (s, 9H).

Step 2

To a solution of compound 43-3 (245 mg, 0.665 mmol) in DME (2 mL) was added a solution of compound 43-4 (175 mg, 0.998 mmol) in water (2 mL). The solution was stirred at 10° C. for 16 h. Saturated NaHCO$_3$ solution (3 mL) was added, and the mixture was washed with DCM (15 mL×2). The aqueous layer was acidified to pH 3 with 1M HCl solution, and extracted with EtOAc (15 mL×3). The organic layer was dried over Na$_2$SO$_4$, filtered, concentrated to give crude product 43-5 (270 mg).

LCMS (ESI): m/z 429.2 [M+H$^+$].

Step 3

A solution of compound 43-5 (270 mg, 0.63 mmol) in a MeOH of HCl (4 M, 5 mL) was stirred for 2 h at 10° C. Solvent was removed under reduced pressure and the residue was dissolved in H$_2$O/THF (v/v 1:1, 3 mL), then Na$_2$CO$_3$ (134 mg, 1.26 mmol) and CbzCl (167 mg, 0.979 mmol) were added. The mixture was stirred for 2 h at 10° C., then LiOH—H$_2$O (79 mg, 1.89 mmol) was added and the resulting solution was stirred for 1 h at 10° C. Organic solvent was removed and the aqueous solution was washed with DCM (15 mL×2). The aqueous layer was acidified to pH 2 with 1M HCl solution and extracted with EtOAc (15 mL×3). The organic layer was dried over Na$_2$SO$_4$, filtered, concentrated to give crude product (182 mg).

LCMS (ESI): m/z 463.2 [M+H$^+$].

Step 4

To a solution of compound 43-6 (180 mg, 0.389 mmol) and (4-aminophenyl) methanol (144 mg, 1.17 mmol) in DMF (4 mL) was added EEDQ (289 mg, 1.17 mmol) under N$_2$. The mixture was stirred at 30° C. for 16 h. The mixture was purified by prep-HPLC to give 43-6 (80 mg, 36%).

$^1$H NMR (400 MHz, MeOD) δ 7.55-7.53 (m, 2H), 7.32-7.27 (m, 7H), 7.17-7.15 (m, 1H), 6.88-6.84 (m, 2H), 5.11-5.03 (m, 2H), 4.55 (s, 2H), 4.50-4.39 (m, 2H), 3.38-3.36 (m, 1H), 3.19-3.05 (m, 3H), 1.89-1.50 (m, 4H).

LCMS (ESI): m/z 568.1 [M+H$^+$].

Step 5

To a solution of 43-7 (20 mg, 0.035 mmol) in DMF (2 mL) were added PNP carbonate (21 mg, 0.070 mmol) and DIPEA (18 mg, 0.141 mmol) at 10° C. After the mixture was stirred for 24 h at 10° C., norfloxacin (17 mg, 0.053 mmol) and DIPEA (9 mg, 0.0695 mmol) were added. The resulting solution was stirred at 10° C. for 1 h and purified by prep-HPLC to give example 43 (7 mg, 22%).

$^1$H NMR (400 MHz, DMSO-d$_6$) δ 10.16 (s, 1H), 8.95 (s, 1H), 8.33-8.32 (m, 1H), 7.94 (d, J=12.0 Hz, 1H), 7.63-7.57 (m, 3H), 7.35-7.19 (m, 10H), 6.91-6.90 (m, 2H), 6.04 (m, 1H), 5.44 (s, 2H), 5.06 (s, 2H), 5.00 (s, 2H), 4.59-4.29 (m, 4H), 3.61 (s, 4H), 3.21 (s, 4H), 3.04-2.94 (m, 4H), 1.71-1.61 (m, 2H), 1.45-1.38 (m, 5H).

LCMS (ESI): m/z 913.3 [M+H$^+$].

Example 44. 7-(4-((4-((S)-2-((S)-2-(2-(6-(2,5-dioxopyrrolidin-1-yl)hexanamido)acetamido)-3-methylbutanamido)-5-ureidopentanamido)benzyloxy)carbonyl)piperazin-1-yl)-1-ethyl-6-fluoro-4-oxo-1,4-dihydroquinoline-3-carboxylic acid example 44

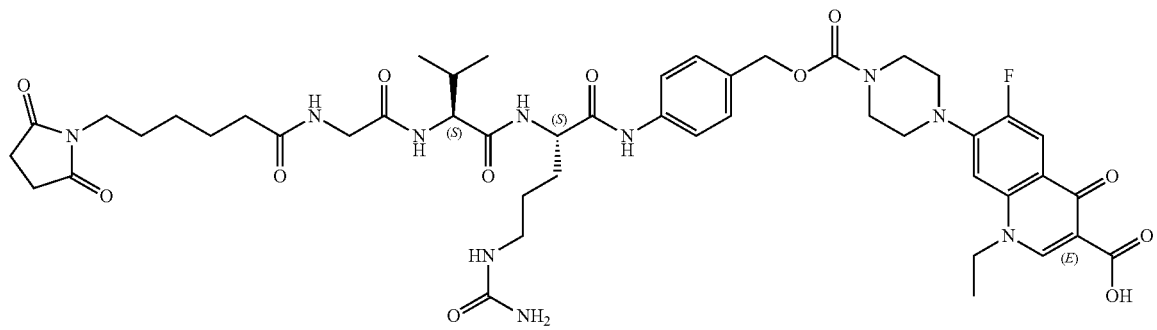

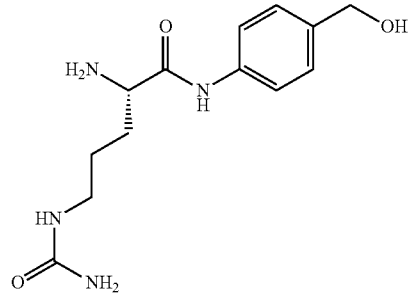
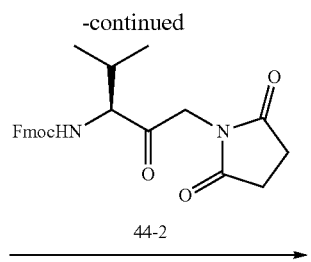
44-1
44-2
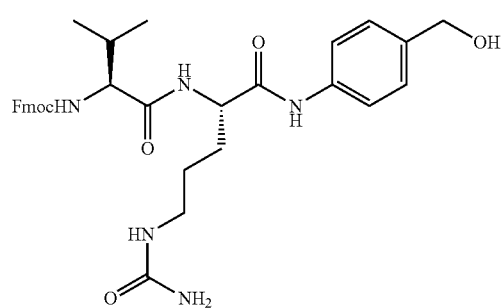
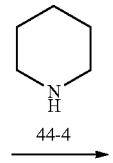
44-3
44-4
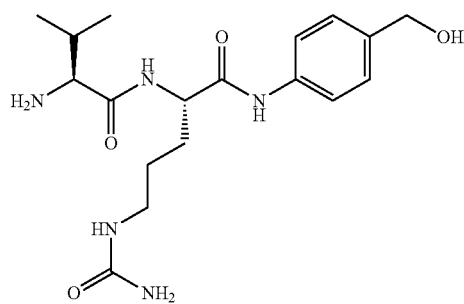
44-5
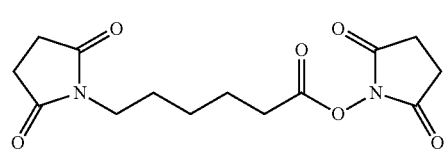
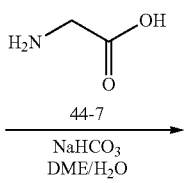
44-6
44-7
NaHCO₃
DME/H₂O
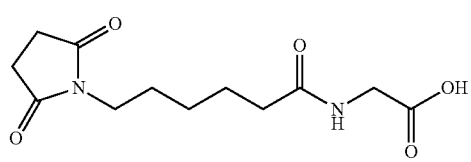
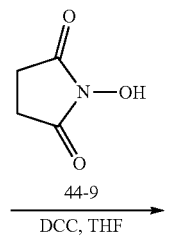
44-8
44-9
DCC, THF

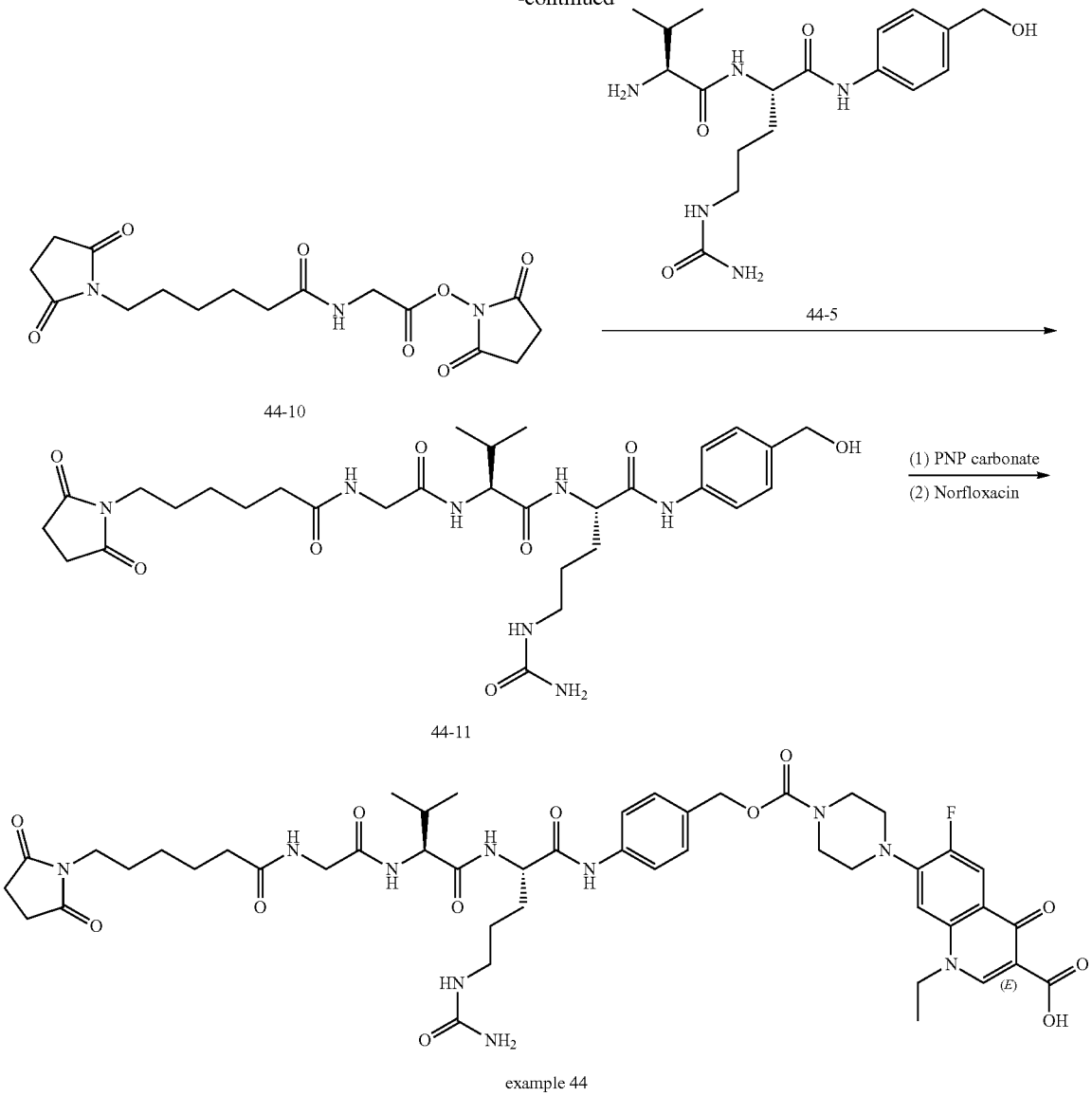

example 44

Step 1

Compound 44-1 (600 mg, 2.14 mmol) and compound 44-2 (936 mg, 2.14 mmol) were dissolved in DMF (5 mL) and stirred at r.t. for 3 h to give 44-3 as a mixture.

Step 2

To a solution of compound 44-3 (2.14 mmol) in DMF (10 mL) was added compound 44-4 (0.6 mL, 4.5 mmol) and stirred at r.t. for 1 h. The mixture was concentrated and washed with MTBE (30 mL×3), filtered and the filtrate was concentrated to give 44-5 (597 mg, Yield: 70%).

Step 3

To a solution of compound 44-7 (75 mg, 1 mmol) in DME (10 mL) was added a solution of compound 44-6 (340 mg, 1.1 mmol) and NaHCO$_3$ (252 mg, 3 mmol) in water (10 mL). The mixture was stirred at r.t. for 16 h. The mixture was washed with EtOAc and acidified to pH=3 with 10% HCl. The resulting suspension was extracted with EtOAc. The combined organic layer was concentrated to give crude compound 44-8 (350 mg)

Step 4

To a solution of 44-8 (350 mg, 1.3 mmol) and 44-9 (157 mg, 1.36 mmol) in THF (15 mL) was added DCC (281 mg, 1.36 mmol). After it was stirred for 16 h under nitrogen, it was concentrated to give 44-10 (480 mg, Yield: 100%).

Step 5

Compound 44-10 (404 mg, 1.1 mmol), compound 44-5 (835 mg, 2.2 mmol) were dissolved in DMF (6 mL). After the reaction mixture was stirred at r.t. for 3 h, it was filtered and purified by prep-HPLC to give compound 44-11 (110 mg, Yield: 16%).

Step 6

To a solution of compound 44-11 (85 mg, 0.135 mmol) in dry DMF (5 mL) was added PNP carbonate (82 mg, 0.27 mmol) and DIPEA (52 mg, 0.40 mmol) at r.t. It was stirred at r.t. for 16 h. Norfloxacin (85 mg, 0.27 mmol) was added and the mixture was stirred at r.t. for another 1 h. The mixture was concentrated, filtered and purified by prep-HPLC (FA) to give example 44 (70 mg, yield: 51%).

LCMS: (5-95, AB, 1.5 min, ESI), 0.794 min, MS=977.3 [M+1], 489.3 [½M+1]

$^{1}$H NMR DMSO-$d_6$ 400 MHz, δ 15.32 (s, 1H), 9.90 (s, 1H), 8.96 (s, 1H), 8.17 (s, 2H), 8.11 (s, 1H), 7.95 (d, J=13.6 Hz, 1H), 7.82 (d, J=8.4 Hz, 1H), 7.62 (d, J=8.8 Hz, 2H), 7.33 (d, J=8.4 Hz, 2H), 7.21 (d, J=9.6 Hz, 1H), 5.98 (s, 1H), 5.41 (s, 2H), 5.06 (s, 2H), 4.59 (d, J=7.2 Hz, 2H), 4.35 (s, 1H), 4.22 (d, J=14.8 Hz, 1H), 3.76-3.73 (m, 2H), 3.61 (s, 4H), 3.28 (s, 4H), 3.12-2.86 (m, 2H), 2.60 (s, 4H), 2.07 (d, J=6.8 Hz, 2H), 1.98 (s, 1H), 1.80-1.56 (m, 2H), 1.47-1.39 (m, 9H), 1.18 (s, 2H), 0.87-0.82 (m, 6H).

Example 45. 7-(4-((4-((S)-2-((S)-2-(benzyloxycarbonylamino)-3-(3-fluorophenyl)propanamido)-5-ureidopentanamido)benzyloxy)carbonyl)piperazin-1-yl)-1-ethyl-6-fluoro-4-oxo-1,4-dihydroquinoline-3-carboxylic acid

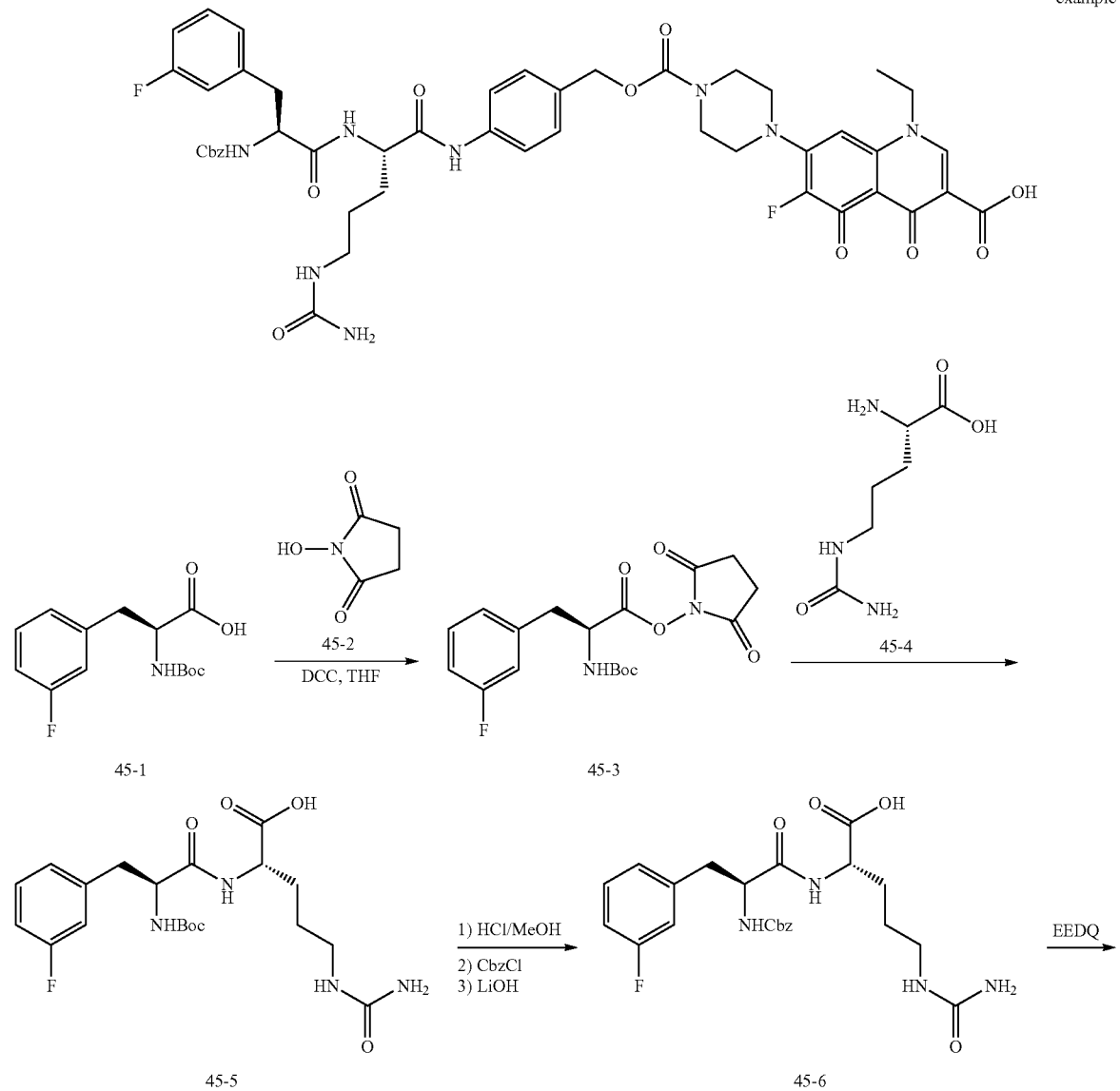

example 45

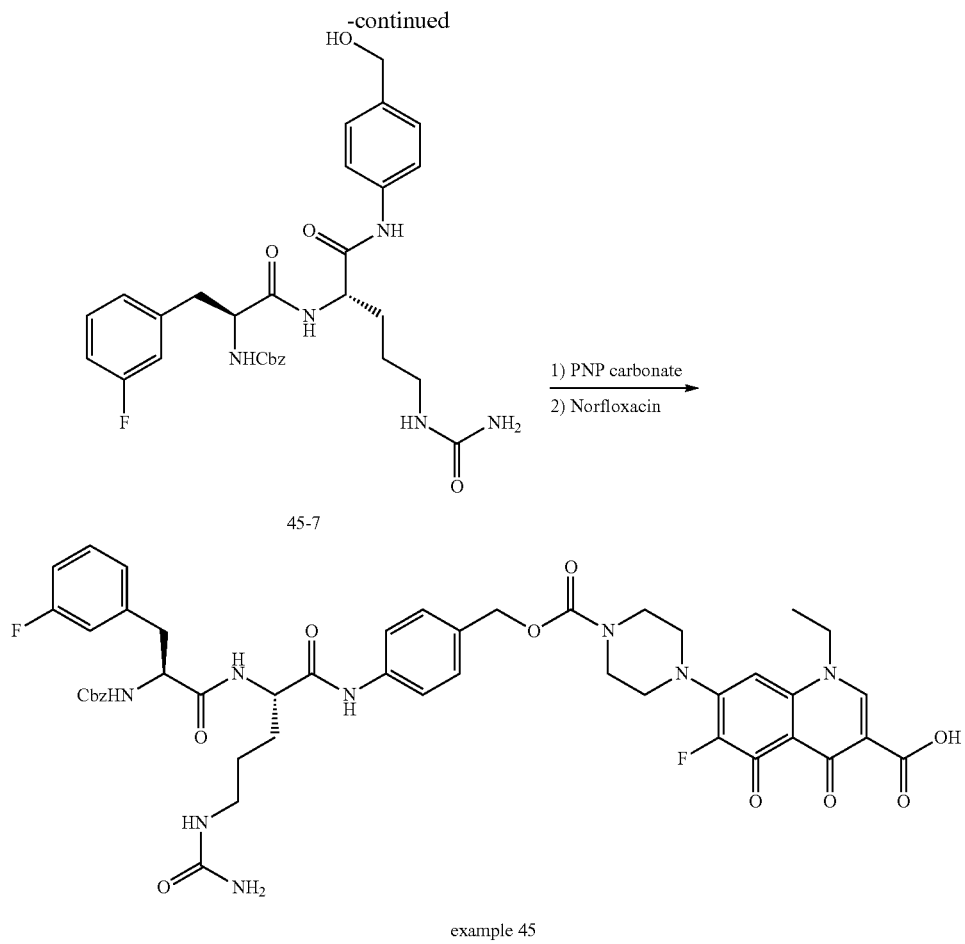

example 45

Step 1

To a solution of compound 45-1 (178 mg, 0.63 mmol) and compound 45-2 (76 mg, 0.662 mmol) in THF (3 mL) was added DCC (143 mg, 0.693 mmol) in THF (0.5 mL) at 10° C. After the solution was stirred at 10° C. for 3 h, solid was filtered, and solvent was removed. The residue was dissolved in DCM (5 mL). The mixture was allowed to stand for a 1 hour and then filtered to remove more DCU. The filtrate was evaporated to give crude compound 45-3 (250 mg).

$^1$H NMR (400 MHz, CDCl$_3$) δ 7.69-7.27 (m, 1H), 7.23-6.95 (m, 3H), 4.98-4.85 (m, 1H), 3.33-3.14 (m, 2H), 2.82 (s, 4H), 1.37 (s, 9H).

Step 2

To a solution of compound 45-3 (250 mg, 0.63 mmol) in DME (2 mL) was added a solution of compound 45-4 (173 mg, 0.986 mmol) in water (2 mL). The solution was stirred at 10° C. for 16 h. Saturated NaHCO$_3$ solution (3 mL) was added, and the mixture was washed with DCM (5 mL×2). The aqueous layer was acidified to pH 3 with 1M HCl solution, extracted with EtOAc (10 mL×3). The organic layer was dried over Na$_2$SO$_4$, filtered, concentrated to give the crude product 45-5 (280 mg).

LCMS (ESI): m/z 441.2 [M+H$^+$].

Step 3

After a solution of compound 45-5 (240 mg, 0.545 mmol) in 4M HCl in MeOH (5 mL) was stirred for 2 h at 10° C., solvent was removed under reduced pressure and the residue was dissolved in H$_2$O/THF (v/v 1:1, 3 mL). Na$_2$CO$_3$ (116 mg, 1.09 mmol) and CbzCl (139 mg, 0.817 mmol) was added. The mixture was stirred for 2 h at 10° C., then LiOH—H$_2$O (67 mg, 1.63 mmol) was added and the resulting solution was stirred for 1 h at 10° C. Solvent was removed, and the aqueous solution was washed with DCM (5 mL×2) and acidified to pH 2 with 1M HCl solution.

It was extracted with EtOAc (10 mL×3). The combined organic layer was dried over Na$_2$SO$_4$, filtered, concentrated to give of crude product 45-6 (198 mg).

LCMS (ESI): m/z 475.2 [M+H$^+$].

Step 4

To a solution of compound 45-6 (192 mg, 0.405 mmol) and (4-aminophenyl) methanol (150 mg, 1.21 mmol) in DMF (4 mL) was added EEDQ (300 mg, 1.21 mmol) under N$_2$. After the mixture was stirred at 30° C. for 16 h, it was purified by prep-HPLC to give 45-7 (70 mg, 30%).

$^1$H NMR (400 MHz, MeOD) δ 7.55-7.53 (m, 2H), 7.31-7.17 (m, 8H), 7.05-7.00 (m, 2H), 6.91-6.86 (m, 1H), 5.07-4.99 (m, 2H), 4.56 (s, 2H), 4.49-4.41 (m, 2H), 3.17-3.06 (m, 3H), 2.91-2.85 (m, 1H), 1.87-1.50 (m, 4H).

LCMS (ESI): m/z 580.2 [M+H$^+$].

Step 5

To a solution of 45-7 (20 mg, 0.0345 mmol) in DMF (2 mL) was added PNP carbonate (21 mg, 0.069 mmol) and DIPEA (18 mg, 0.139 mmol) at 10° C. After the mixture was stirred for 24 h at 10° C., norfloxacin (17 mg, 0.053 mmol) and DIPEA (9 mg, 0.0695 mmol) were added. The reaction mixture was stirred at 10° C. for 1 h and purified by prep-HPLC to give example 45 (17 mg, 53%).

$^1$H NMR (400 MHz, DMSO-$d_6$) δ 15.32 (br, 1H), 10.12 (s, 1H), 8.96 (s, 1H), 8.30-8.28 (m, 1H), 7.94 (d, J=13.2 Hz, 1H), 7.62 (d, J=8.4 Hz, 2H), 7.52 (d, J=8.8 Hz, 1H), 7.35-7.13 (m, 11H), 7.04-7.00 (m, 1H), 5.99 (m, 1H), 5.43 (s, 2H), 5.06 (s, 2H), 4.95 (s, 2H), 4.61-4.33 (m, 4H), 3.61 (s, 4H), 3.32 (s, 4H), 3.06-2.66 (m, 4H), 1.75-1.60 (m, 2H), 1.45-1.35 (m, 5H).

LCMS (ESI): m/z 925.5 [M+H$^+$].

Example 46. 7-(4-((4-((S)-2-((R)-2-(benzyloxycarbonylamino)-4,4,4-trifluorobutanamido)-5-ureidopentanamido)benzyloxy)carbonyl)piperazin-1-yl)-1-ethyl-6-fluoro-4-oxo-1,4-dihydroquinoline-2-carboxylic acid example 46

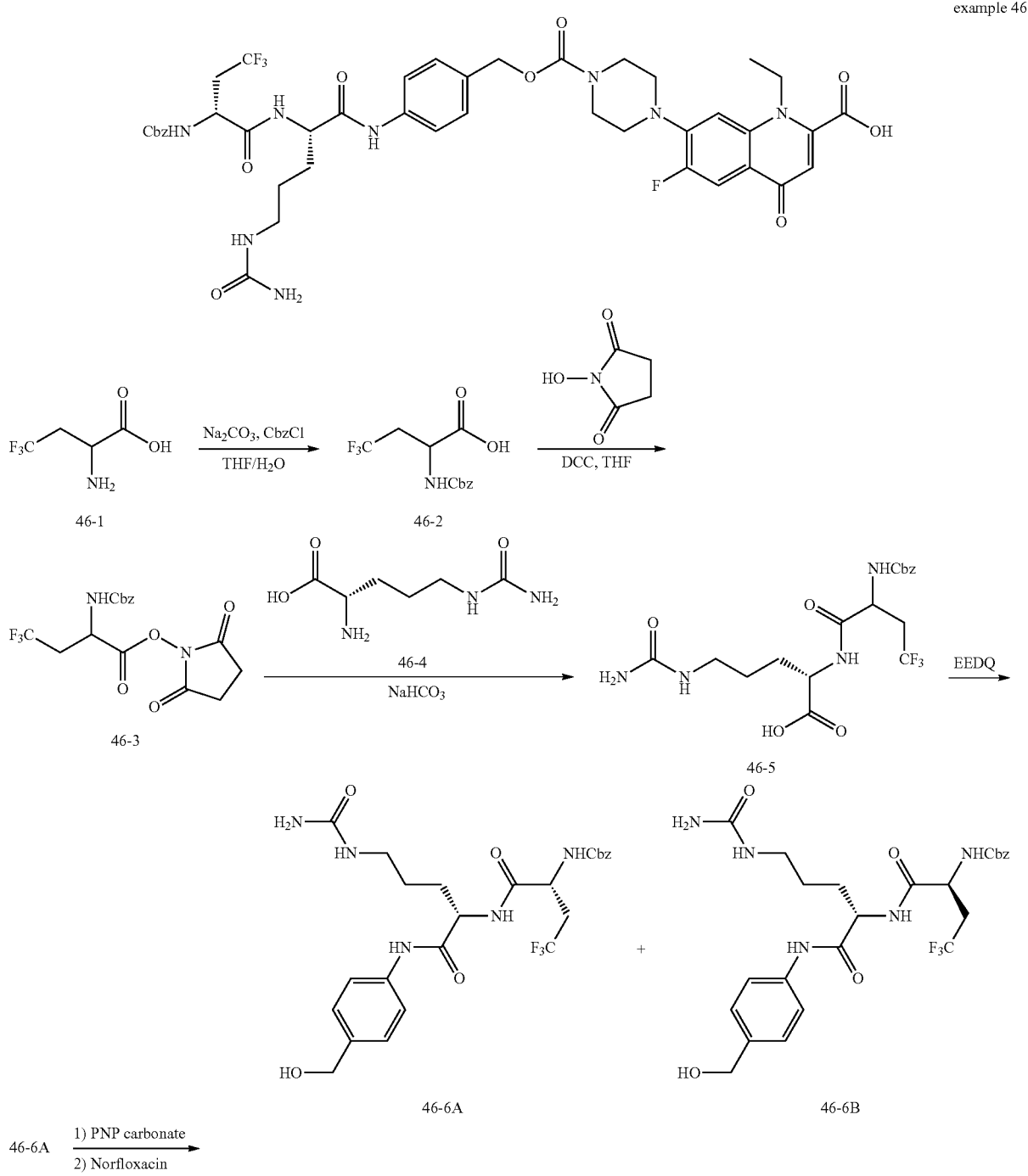

-continued

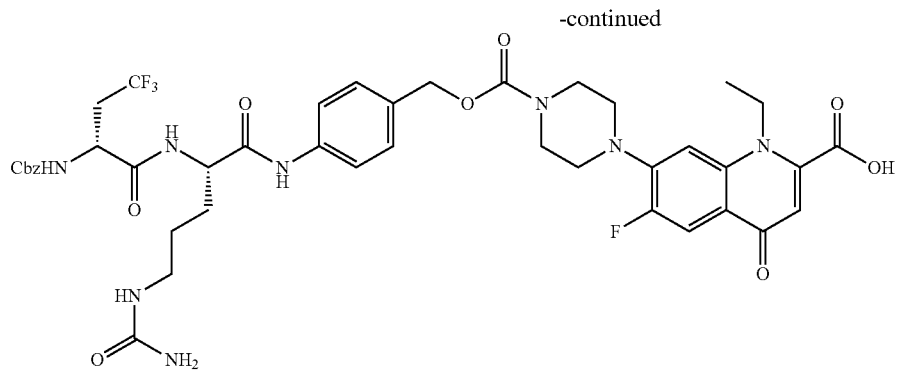

example 46

Step 1

To the solution of compound 46-1 (200 mg, 1.27 mmol) in THF (10 mL) was added benzyl carbonochloridate (226 mg, 1.33 mmol) in an ice bath. A solution of $Na_2CO_3$ (270 mg, 2.54 mmol) in water (10 mL) was added dropwise with vigorous stirred at 7° C. or lower. After mixture was stirred for 16 h, the organic layer was separated, washed with diluted HCl (0.1 M, 60 mL) and saturated $NaHCO_3$ solution (60 mL), dried over anhydrous $Na_2SO_4$, concentrated to afford compound 46-2 as a white solid (250 mg, 67.6%).

Step 2

To a mixture of compound 46-2 (250 mg, 0.887 mmol), 1-hydroxypyrrolidine-2, 5-dione (102 mg, 0.887 mmol) in dry THF (10 mL) was added DCC (183 mg, 0.887 mmol) at 0° C. The mixture was stirred at r.t. for 16 h, and filtered. The filtrate was concentrated in vacuo to give the crude product of compound 46-3, which was used for next step without further purification.

Step 3

To the solution of compound 46-3 (710 mg, 1.87 mmol) in a mixture of DME and $H_2O$ (10 mL/10 mL) was added compound 46-4 (327 mg, 1.87 mmol) and $NaHCO_3$ (236 mg, 2.8 mmol) at 0° C. After the mixture was stirred at r.t. for 16 h, it was extracted with EtOAc (50 mL×3). The organic layer was washed with brine (50 mL), dried over $Na_2SO_4$, and concentrated in vacuo. The crude product was purified by prep-HPLC to afford the desired product of compound 46-5 as a white solid (421 mg, 50.2%).
LCMS (ESI): m/z 449.2 [M+H$^+$].

Step 4

To the solution of compound 46-5 (410 mg, 0.915 mmol) in DCM (10 mL) was added EEDQ (448 mg, 1.83 mmol) and 4-aminophenyl-methanol (225 g, 1.83 mmol). After the mixture was stirred at 0° C. for 1 h, solvent was removed and the residue was purified with prep-HPLC and SFC separation to afford 46-6A and 46-6B.

46-6A $^1$H NMR (400 MHz, MeOD-d$_4$) δ 7.54 (d, J=8.4 Hz, 2H), 7.35-7.29 (m, 7H), 5.12 (s, 2H), 4.55-4.49 (m, 4H), 3.30-3.03 (m, 2H), 2.83-2.53 (m, 2H), 1.93-1.75 (m, 4H). LCMS: m/z 553.9 [M+H$^+$].

46-6B $^1$H NMR (400 MHz, DMSO-d$_6$) δ 10.94 (s, 1H), 9.31 (d, J=9.2 Hz, 1H), 8.53 (d, J=9.6 Hz, 1H), 8.26 (d, J=9.6 Hz, 2H), 8.00-7.96 (m, 5H), 7.90 (d, J=9.6 Hz, 2H), 6.45-6.44 (m, 1H), 5.81 (s, 1H), 5.48-5.36 (m, 3H), 4.77-4.69 (m, 4H), 3.09-2.95 (m, 2H), 2.79-2.64 (m, 2H), 1.64-1.20 (m, 4H). LCMS (ESI): m/z 553.9 [M+H$^+$].

Step 5

To the solution of 46-6A (20 mg, 0.036 mmol) in dry DCM (2 mL) was added PNP carbonate (22 mg, 0.072 mmol) and DIPEA (14 mg). The mixture was heated at reflux for 16 h. After solvent was removed, the residue was dissolved in DMF (5 mL). DIPEA (9 mg, 0.072 mmol) and norfloxacin (23 mg, 0.072 mmol) was added. The mixture was stirred at r.t. for 1 h. Solvent was removed and the residue was purified by prep-HPLC to afford example 46.

$^1$H NMR (400 MHz, DMSO-d$_6$) δ 15.33 (s, 1H), 10.11 (s, 1H), 8.97 (s, 1H), 8.34 (d, J=7.6 Hz, 1H), 7.95 (d, J=12.8 Hz, 1H), 7.78 (d, J=8.4 Hz, 1H), 7.60 (d, J=8.4 Hz, 2H), 7.37-7.21 (m, 8H), 6.00-5.98 (m, 1H), 5.97 (s, 2H), 5.43-5.03 (m, 4H), 4.61-4.37 (m, 4H), 3.61 (s, 4H), 3.31 (s, 4H), 3.04-2.49 (m, 4H), 1.70-1.20 (m, 7H). LCMS (ESI): m/z 450.3 [M/2+H$^+$].

Example 47. 7-(4-((4-((R)-3-(2-amino-2-oxoethyl-thio)-2-((S)-2-(benzyloxycarbonylamino)-3-methylbutanamido)propanamido)benzyloxy)carbonyl)piperazin-1-yl)-1-ethyl-6-fluoro-4-oxo-1,4-dihydroquinoline-3-carboxylic acid
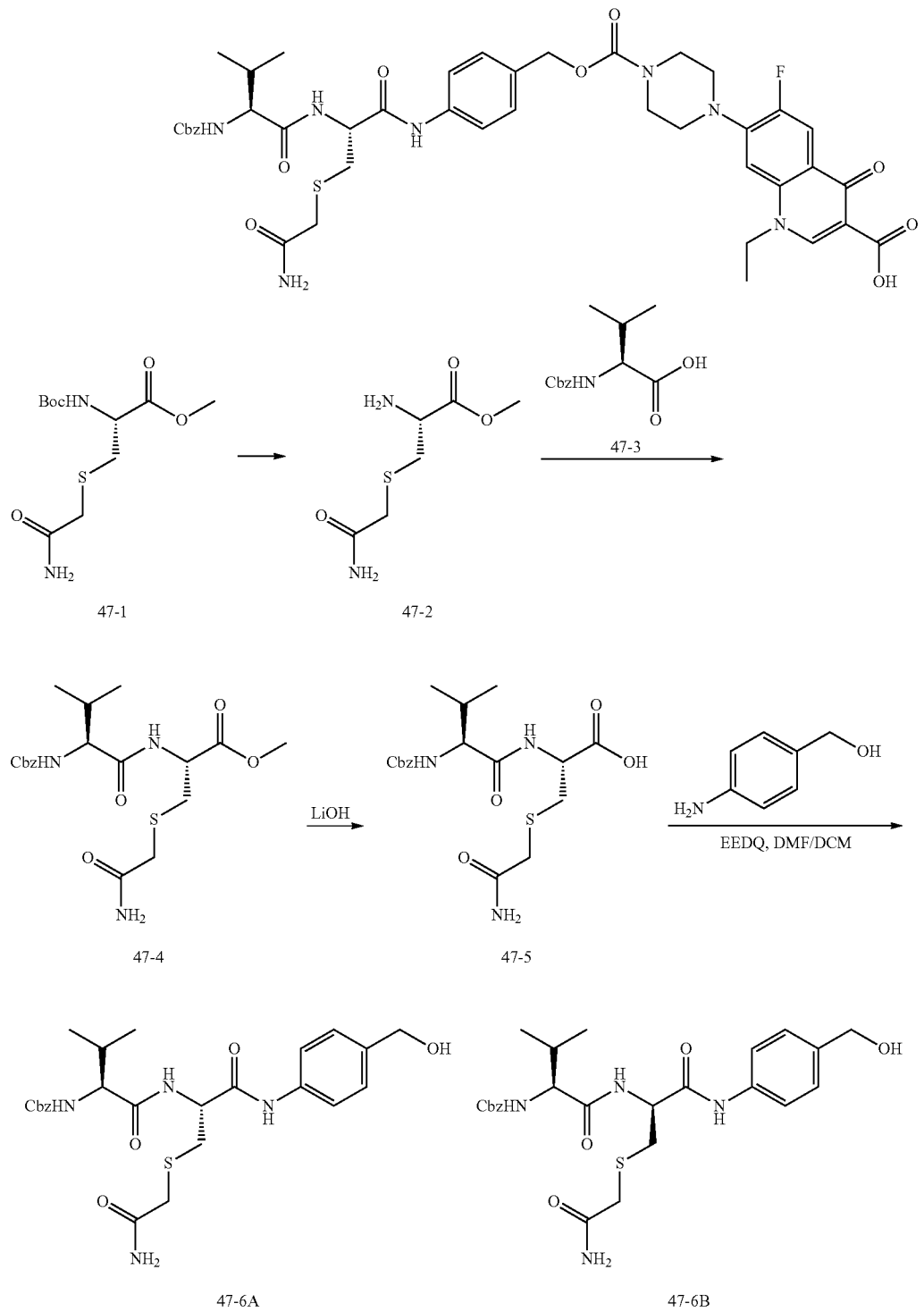

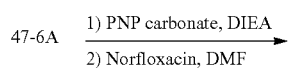

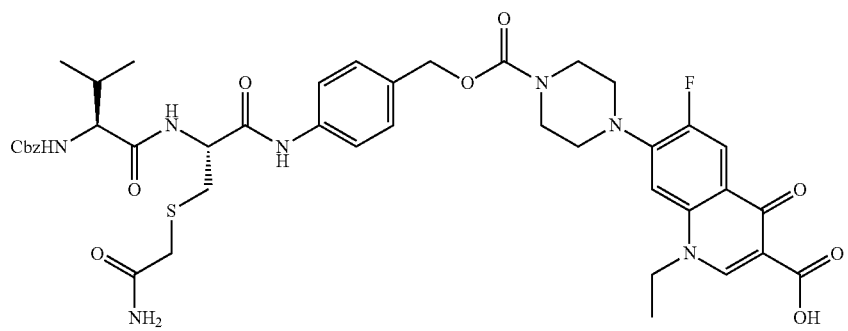

example 47

Step 1

The mixture of compound 47-1 (120 mg, 0.411 mmol) in 4 M HCl/1,4-dioxane (5 mL) was stirred at r.t. for 2 h. The mixture was concentrated to give 47-2.

LCMS (ESI): m/z 193.0 [M+H$^+$].

Step 2

To a solution of compound 47-2 (1.3 g, 6.85 mmol) in DCM (20 mL) was added compound 47-3 (2.065 g, 8.22 mmol), DIPEA (4.418 g, 34.25 mmol), HOBt (1.018 g, 7.535 mmol) and EDCI (1.7 g, 8.905 mmol). The mixture was stirred at r.t. for 16 h. The solution was filtered and the solid was used in next step without further purification (47-4).

LCMS (ESI): m/z 425.9 [M+H$^+$].

Step 3

To a solution of compound 47-4 (500 mg, 1.176 mmol) in THF/MeOH/H$_2$O (6 mL/2 mL/2 mL) was added LiOH (85 mg, 7.05 mmol). The mixture was stirred at r.t. for 1.5 h. The mixture was concentrated and the residue was purified by prep-HPLC to give compound 47-5.

LCMS (ESI): m/z 412.0 [M+H$^+$].

Step 4

To a solution of compound 47-5 (600 mg, 1.46 mmol) in DCM/DMF (10 mL/2 mL) were added 4-amino-phenyl-methanol (216 mg, 1.75 mmol) and EEDQ (541 mg, 2.19 mmol). The mixture was stirred at r.t. for 16 h. The mixture was quenched with H$_2$O. The residue was purified by prep-HPLC and then purified by SFC to give 47-6A and 47-6B.

47-6A $^1$H NMR (400 MHz, MeOD-d$_4$) δ 7.57 (d, J=8.4 Hz, 2H), 7.35-7.26 (m, 7H), 5.06 (s, 2H), 4.71-4.68 (m, 1H), 4.54 (s, 2H), 3.97 (d, J=6.4 Hz, 2H), 3.25 (m, 2H), 3.13-3.08 (m, 1H), 3.0-2.93 (m, 1H), 2.13-2.01 (m, 1H), 0.98-0.95 (m, 6H).

LCMS (ESI): m/z 517.2 [M+H$^+$].

47-6B $^1$H NMR (400 MHz, DMSO-d$_6$) δ 9.93 (m, 1H), 8.597-8.56 (m, 1H), 7.61-7.1 (m, 11H), 5.13-5.00 (m, 3H), 4.63-4.59 (m, 1H), 4.44-4.41 (m, 2H), 3.92-3.90 (m, 2H), 3.17-2.84 (m, 4H), 2.00-1.96 (m, 1H), 0.90-0.89 (m, 6H).

LCMS (ESI): m/z 517.1 [M+H$^+$].

Step 5

To a solution of 47-6A (40 mg, 0.0775 mmol) in DCM (3 mL) was added carbonic acid bis-(4-nitro-phenyl) ester (20 mg, 0.093 mmol) and DIPEA (15 mg, 0.116 mmol). The mixture was mixture was stirred at 45° C. for 16 h. The solution was concentrated and dissolved in DMF (3 mL), and norfloxacin (50 mg, 0.155 mmol) was added. The mixture was stirred at r.t. for 1 h. After removal of the solvent, the residue was purified by pre-HPLC to give example 47 (5.5 mg).

$^1$H NMR (400 MHz, DMSO-d$_6$) δ 10.25 (s, 1H), 8.93-8.89 (m, 1H), 8.40-8.34 (m, 2H), 7.63-7.61 (m, 4H), 7.36-7.35 (m, 8H), 7.13 (m, 2H), 5.06-5.03 (4H), 4.62-4.52 (m, 3H), 3.94-3.91 (m, 1 H), 3.36 (m, 4H), 3.19 (m, 4H), 3.00-2.86 (m, 3H), 2.03-1.95 (m, 1H), 1.38 (m, 3H), 0.88-0.83 (m, 6H).

LCMS (ESI): m/z 862.4 [M+H$^+$].

Example 48. 7-(4-((4-((S)-2-((S)-2-(benzyloxycarbonylamino)-3-(furan-2-yl)propanamido)-5-ureidopentanamido)benzyloxy)carbonyl)piperazin-1-yl)-1-ethyl-6-fluoro-4-oxo-1,4-dihydroquinoline-3-carboxylic acid
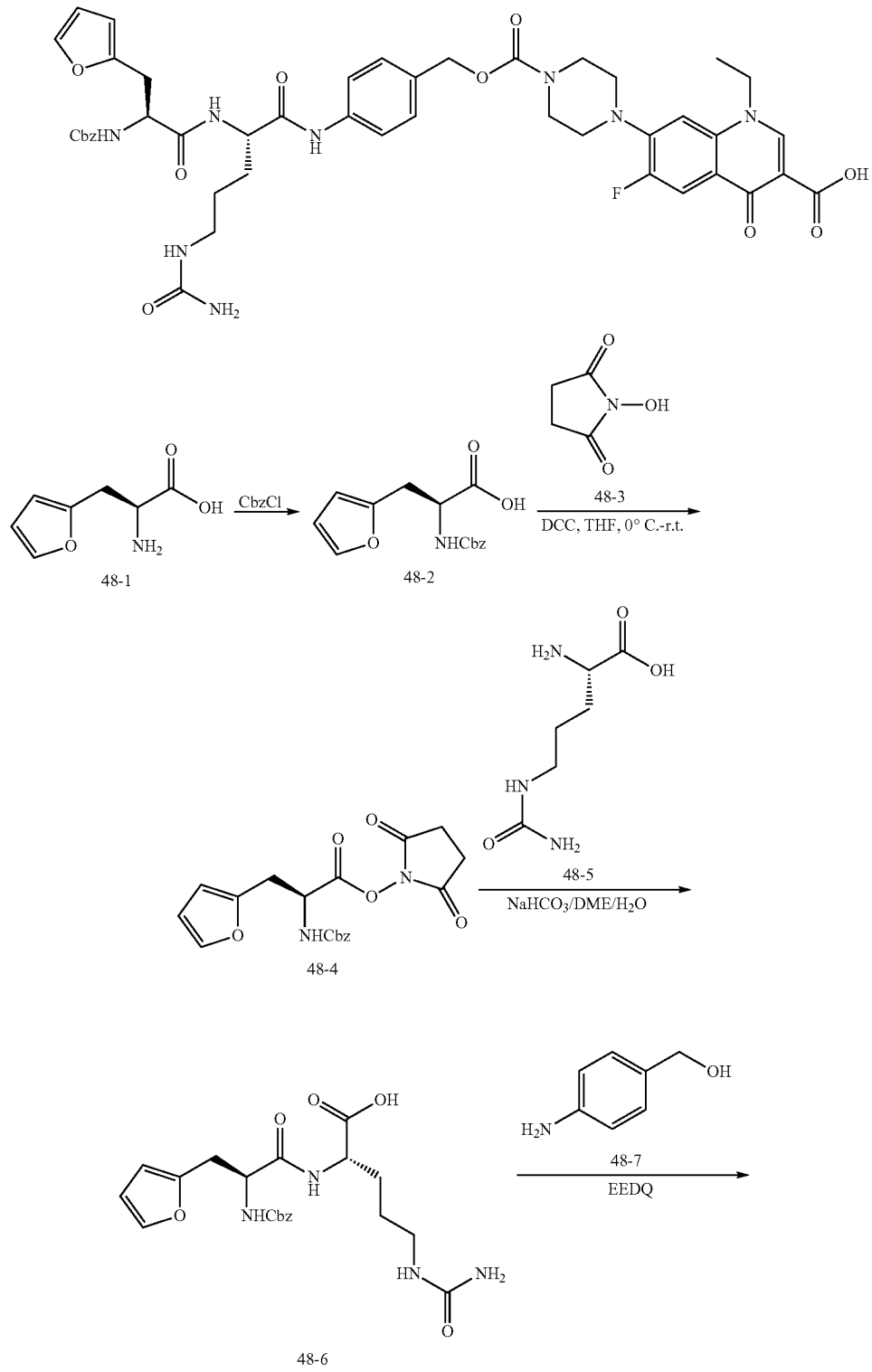
example 48

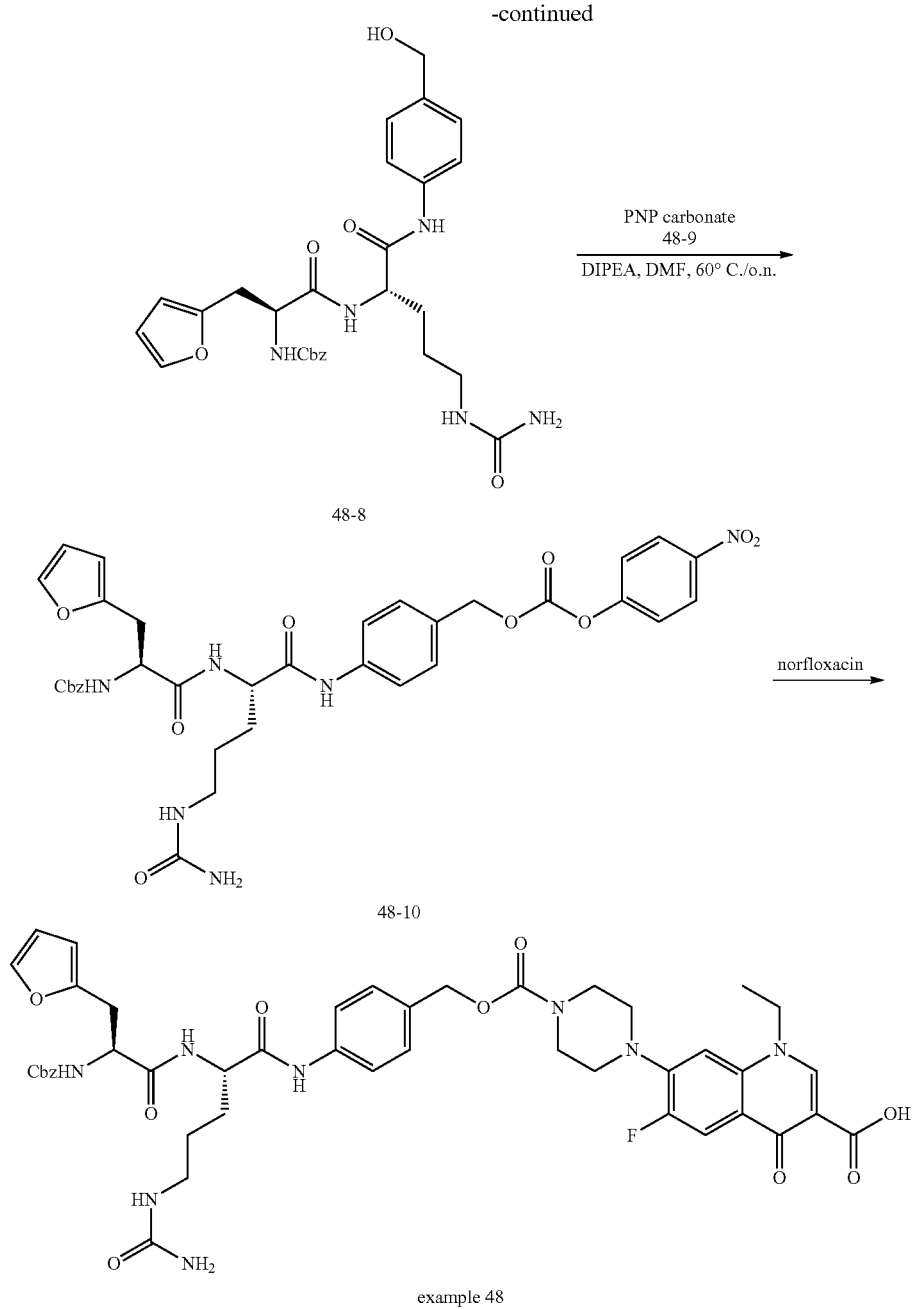

example 48

Step 1

To the mixture of compound 48-1 (1.0 g, 6.45 mmol) in THF and NaHCO₃ solution was added CbzCl via syring at 0° C. The reaction mixture was stirred at r.t. for 2 h and purified by prep-HPLC to give 48-2 (Yield: 32%).

Step 2

To a solution of compound 48-2 (380 mg, 1.31 mmol), compound 48-3 (151 mg, 1.31 mmol) in THF (25 mL) was added DCC (271 mg, 1.31 mmol) at 0° C. The mixture was stirred at r.t. for 16 h under N₂. The solution was filtered and the filtrate was concentrated to give 48-4 which used in the next step without further purification (Yield: 90%).

Step 3

To a solution of compound 48-4 (540 mg, 1.38 mmol) in DME (15 ml) was added a solution of compound 48-5 (364 mg, 2.07 mmol) and NaHCO₃ (174 mg, 2.07 mmol) in water (15 mL). The mixture was stirred at r.t. for 16 h. The mixture was washed with EtOAc and acidified to pH 3.0 with 10% HCl. The resulting suspension was extracted with EtOAc. The combined organic layer was concentrated to give compound 48-6 (Yield: 90%).

LCMS: (10-80, AB, 2 min, ESI), 0.826 min, MS=447.1 [M+1]

Step 4

To a solution of compound 48-6 (420 mg, 0.94 mmol) in DCM/MeOH (20 mL/10 mL) were added 4-amino-phenyl-methanol (174 mg, 1.4 mmol) and EEDQ (495 mg, 1.88 mmol). The mixture was stirred at r.t. for 16 h. The mixture was quenched with $H_2O$. The residue was purified by prep-HPLC and SFC to give 48-8 (Yield: 50%).

$^1$H NMR DMSO-$d_6$ 400 MHz, δ 9.98 (s, 1H), 8.20 (d, J=8 Hz, 1H), 7.56-7.49 (m, 3H), 7.37 (s, 1H), 7.35-7.30 (m, 5H), 7.24 (d, J=8.8 Hz, 3H), 6.33-6.32 (m, 1H), 6.13 (d, J=3.2 Hz, 1H), 5.98-5.95 (t, J=6.0 Hz, 1H), 5.41 (s, 2H), 5.11-5.08 (t, J=5.6 Hz, 1H), 4.99 (d, J=13.2 Hz, 2H), 4.44-4.35 (m, 3H), 3.33-2.83 (m, 4H), 1.71-1.58 (m, 2H), 1.44-1.34 (m, 2H).

Step 5

To a solution of compound 48-9 (30 mg, 0.06 mmol) in DMF (5 mL) was added a solution of PNP carbonate (37 mg, 0.12 mmol) and DIPEA (24 mg, 0.18 mmol) at 0° C. The mixture was stirred at r.t. for 16 h. The mixture (48-10) was used for next step without further purification (Yield: 95%)

LCMS: (10-80, AB, 2 min, ESI), 1.092 min, MS=717.1 [M+1]

Step 6.

A mixture of 48-10 from last step and norfloxacin was stirred at r.t. for 1 h. The residue was purified by prep-HPLC and then purified by SFC to give example 48. (Yield: 30%)

$^1$H NMR DMSO-$d_6$ 400 MHz δ 10.08 (s, 1H), 8.96 (s, 1H), 8.22 (d, J=7.2 Hz, 1H), 7.95 (d, J=13.2 Hz, 1H), 7.62 (s, 1H), 7.60 (s, 1H), 7.53 (d, J=8.4 Hz, 1H), 7.50 (s, 1H), 7.36-7.33 (m, 5H), 7.30 (d, J=7.6 Hz, 4H), 7.21 (d, J=7.2 Hz, 1H), 6.33-6.32 (m, 1H), 6.13 (d, J=2.4 Hz, 1H), 5.99-5.96 (m, 1H), 5.42 (s, 2H), 5.07 (s, 2H), 5.01 (d, J=1.6 Hz, 2H), 4.61-4.56 (m, 2H), 4.45-4.35 (m, 2H), 3.62 (d, J=10.4 Hz, 5H), 3.06-3.01 (m, 2H), 2.89-2.83 (m, 2H), 2.55-2.45 (m, 2H), 1.71-1.58 (m, 2H), 1.42 (s, 5H).

Example 49. 7-(4-((4-((S)-2-((S)-2-(benzyloxycarbonylamino)-3-methylbutanamido)-5-ureidopentanamido)benzyloxy)carbonyl)piperazin-1-yl)-1-ethyl-6-fluoro-4-oxo-1,4-dihydroquinoline-3-carboxylic acid

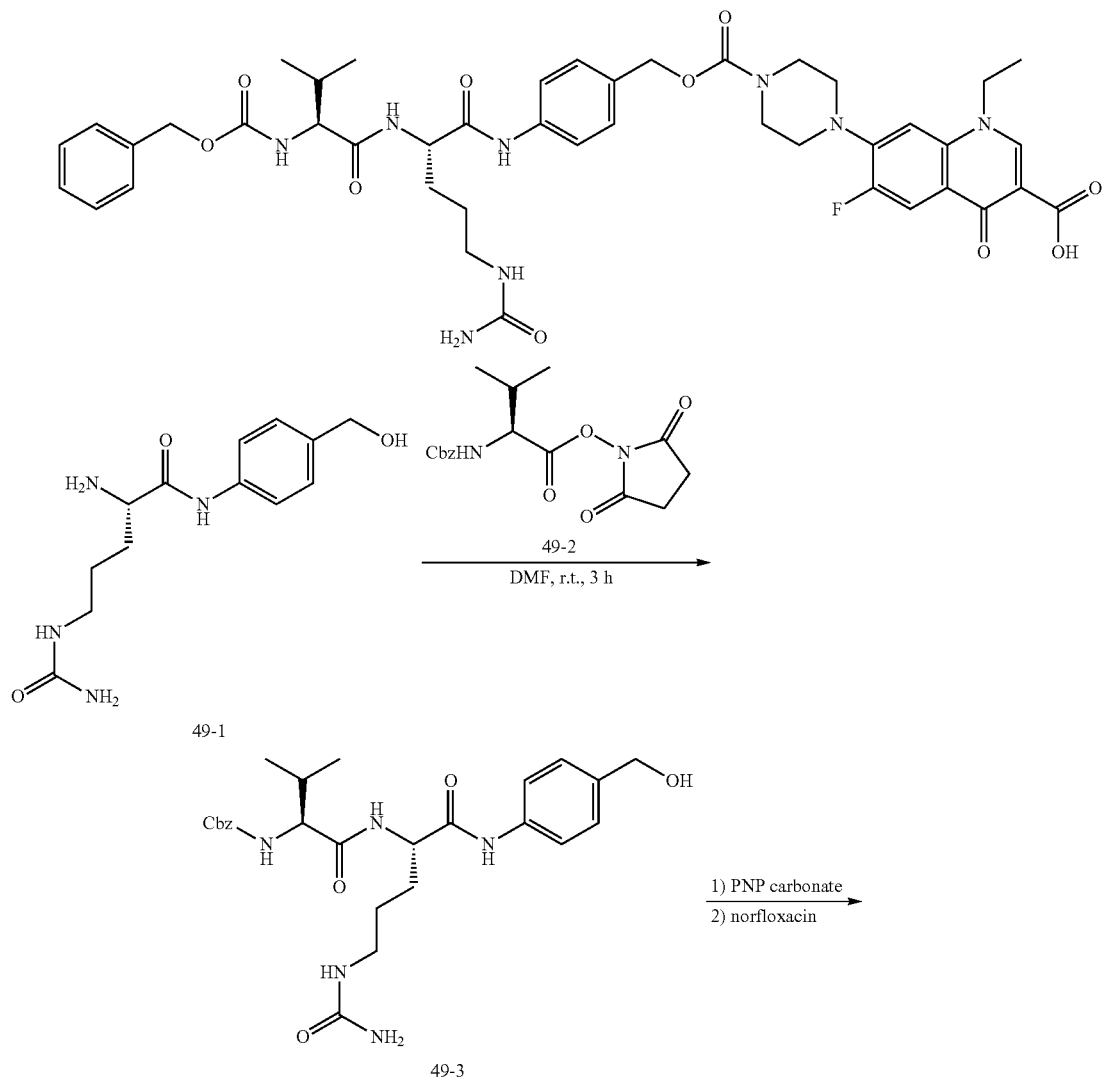

example 49

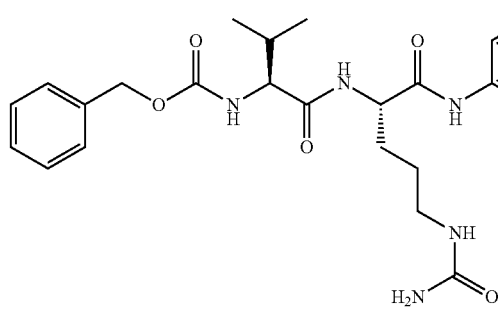
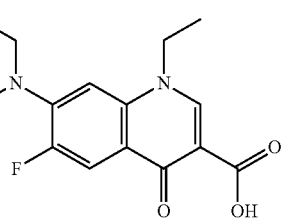

example 49

Step 1

Compound 49-1 (100 mg, 0.26 mmol) and compound 49-2 (138 mg, 0.38 mmol) were dissolved in DMF (5 mL) at r.t. The reaction mixture was stirred at r.t. for 3 h, filtered and purified by prep-HPLC to give 49-3 (100 mg, Yield: 54%).

Step 2

To a solution of compound 49-3 (60 mg, 0.142 mmol) in dry DMF (3 mL) was added PNP carbonate (87 mg, 0.285 mmol) and DIPEA (56 mg, 0.427 mmol) at r.t. The mixture was stirred at r.t. for 16 h. Norfloxacin (91 mg, 0.285 mmol) was added. The mixture was stirred at r.t. for another 1 h. The mixture was concentrated, filtered and purified by prep-HPLC (FA) to give example 49 (40 mg, yield: 37%).

LCMS: (5-95, AB, 1.5 min, ESI), 0.866 min, MS=859.2 [M+1]

$^1$H NMR DMSO-d$_6$ 400 MHz, δ 15.32-15.28 (m, 1H), 10.08 (s, 1H), 8.96 (s, 1H), 8.11 (d, J=7.2 Hz, 1H), 7.94 (d, J=13.2 Hz, 1H), 7.61 (d, J=8.4 Hz, 2H), 7.37-7.30 (m, 8H), 7.21 (d, J=7.2 Hz, 1H), 5.78 (d, J=4.8 Hz, 1H), 5.41 (s, 2H), 5.05 (d, J=9.6 Hz, 4H), 4.58 (d, J=7.2 Hz, 2H), 4.41 (d, J=5.6 Hz, 1H), 3.93 (s, 1H), 3.33 (s, 4H), 3.04-2.93 (m, 2H), 2.00-1.95 (m, 1H), 1.68 (s, 2H), 1.60-1.58 (m, 5H), 1.42 (d, J=7.2 Hz, 6H).

Example 50. 7-(4-(((4-((S)-2-((S)-2-(benzyloxycarbonylamino)-3-methylbutanamido)-3-(piperidin-4-yl)propanamido)benzyloxy)carbonyl)piperazin-1-yl)-1-ethyl-6-fluoro-4-oxo-1,4-dihydroquinoline-3-carboxylic acid

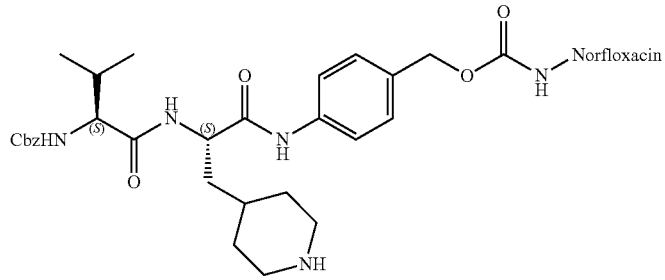

example 50

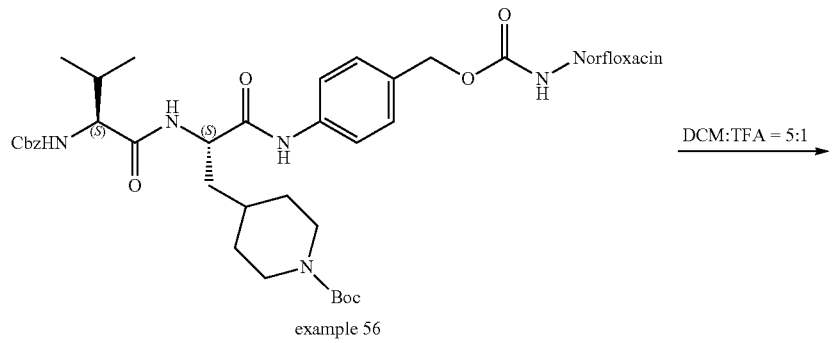

example 56

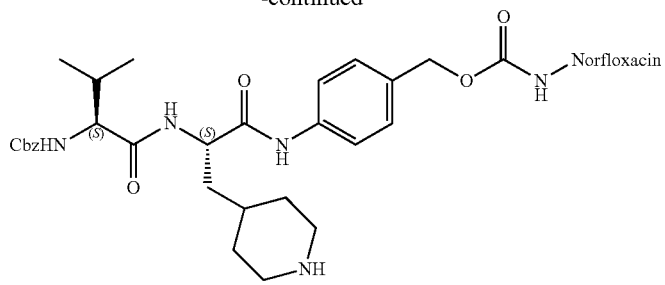

example 50

Step 1

A mixture of DCM/TFA (5:1, v:v) (1 mL) was added to example 56 (50 mg, 52 mmol) at 0° C. The mixture was allowed to stir at 0° C. for 1 h. LCMS showed 80% desired product and 20% STM. The mixture was purified by prep-HPLC (FA), to give example 50 (31.2 mg, 70%).

LCMS: (5-95, AB, 1.5 min, ESI), 0.811 min, MS=856.2 [M+1], 428.8 [½M+1]

$^1$H NMR Methanol-d$_4$ 400 MHz, δ 8.81 (s, 1H), 8.54 (s, 1H), 7.98-7.95 (m, 1H), 7.59-7.57 (m, 2H), 7.36-7.32 (m, 7H), 7.2-7.1 (m, 1H), 5.12-5.09 (m, 4H), 4.7-4.4 (m, 3H), 3.88-3.86 (m, 1H), 3.70 (m, 4H), 3.3 (m, 4H), 3.0-2.8 (m, 2H), 2.1-1.7 (m, 6H), 1.6-1.3 (m, 5H), 0.98-0.96 (m, 6H).

Example 51: 7-(4-{4-[(S)-2-((S)-2-Benzyloxycarbonylamino-3-methyl-butyrylamino)-propionylamino]-benzyloxycarbonyl}-piperazin-1-yl)-1-ethyl-6-fluoro-4-oxo-1,4-dihydro-quinoline-3-carboxylic acid

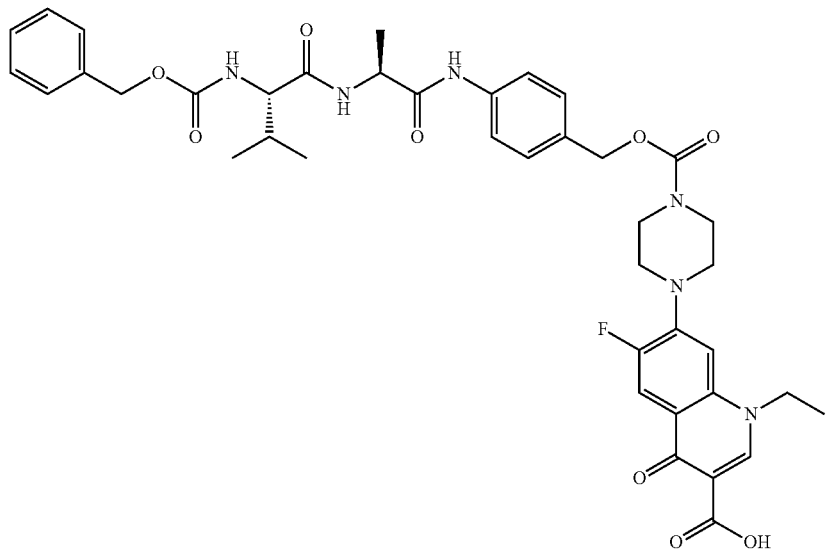

Example 51

Example 51 was made using the procedure as Example 42.

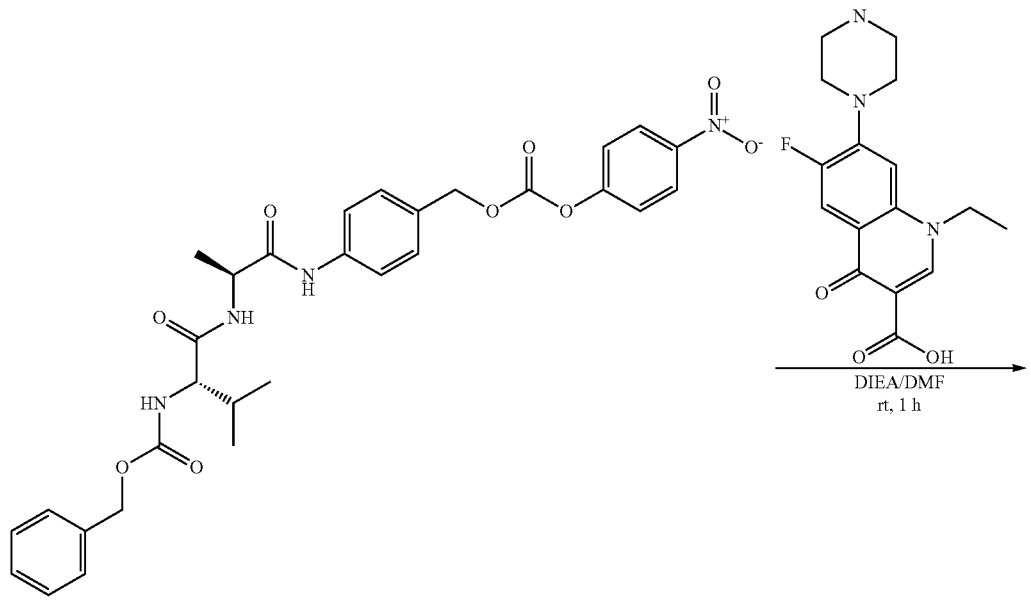

51-1

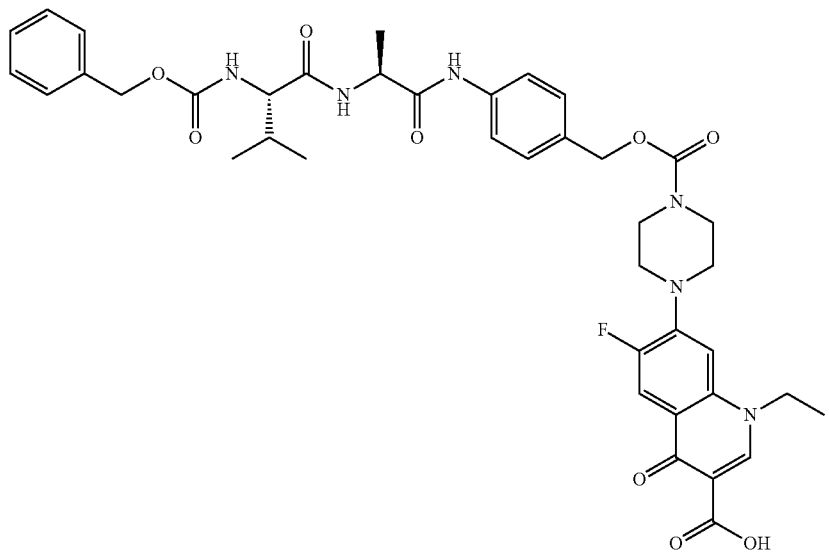

example 51

Step 1

To the suspension of 1-ethyl-6-fluoro-4-oxo-7-(piperazin-1-yl)-1,4-dihydroquinoline-3-carboxylic acid (129 mg, 0.40 mmol) in 2 ml DMF, was added DIEA (0.30 ml, 1.69 mmol), then added 51-1 (120 mg, 0.34 mmol) as one portion, slowly became yellow solution till reaction completed. The reaction mixture was poured into ice water, extracted with DCM. The organic layer washed by Sat. NH4Cl, brine, dried over MgSO4, was concentrated down, purified by Pre-HPLC to yield 51 (125 mg, 48%).

LCMS (ESI): m/z 773.3 [M+H$^+$].

$^1$H NMR (400 MHz, DMSO-d$_6$) δ 15.29 (s, 1H), 9.98 (s, 1H), 8.95 (s, 1H), 8.14 (d, J=6.8 Hz, 1H), 7.95 (d, J=13.1 Hz, 1H), 7.59 (d, J=8.3 Hz, 2H), 7.47-7.12 (m, 8H), 5.05 (d, J=9.9 Hz, 4H), 4.70-4.48 (m, 2H), 4.42 (t, J=7.0 Hz, 1H), 3.91 (t, J=7.8 Hz, 1H), 3.61 (s, 4H), 1.98 (d, J=6.8 Hz, 1H), 1.53-1.14 (m, 6H), 0.86 (dd, J=17.7, 6.7 Hz, 6H).

Example 52. 7-(4-((4-((S)-2-((R)-2-(benzyloxycarbonylamino)-3-(trimethylsilyl)propanamido)-5-ureidopentanamido)benzyloxy)carbonyl)piperazin-1-yl)-1-ethyl-6-fluoro-4-oxo-1,4-dihydroquinoline-3-carboxylic acid
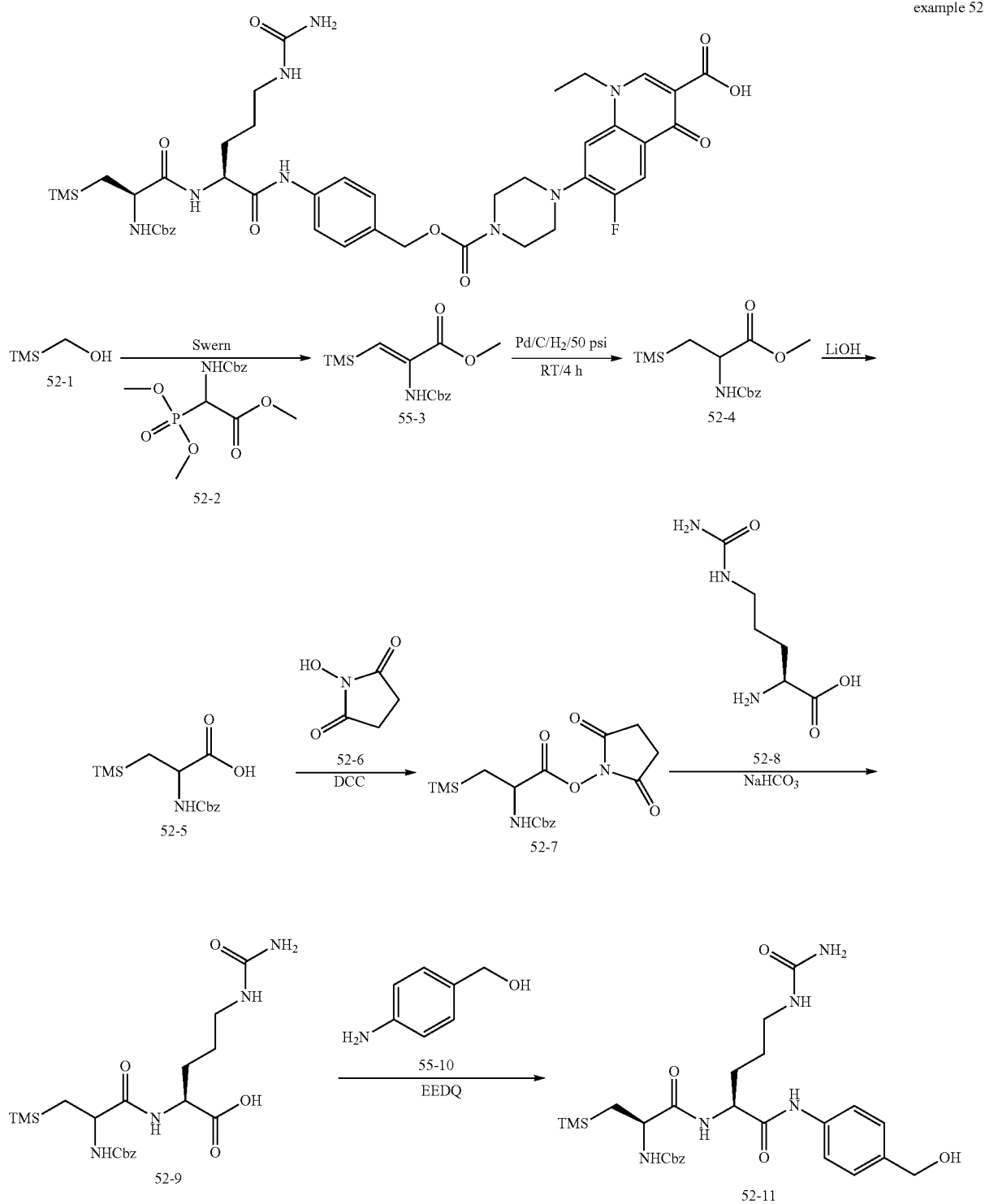
example 52

-continued

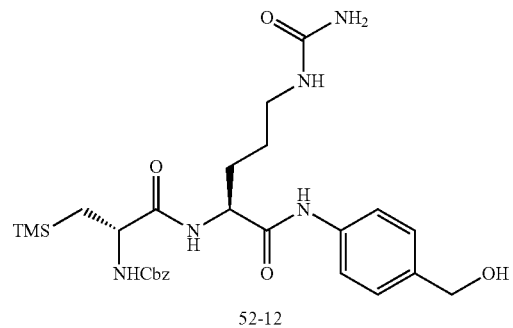
52-12

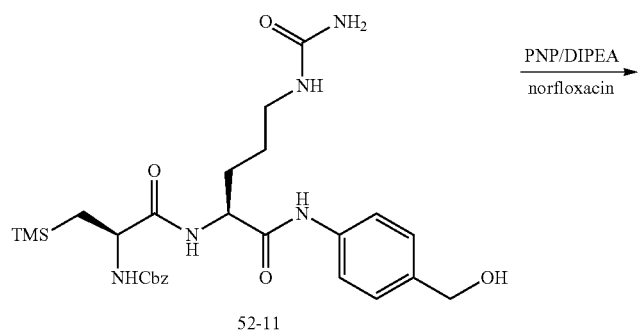
52-11

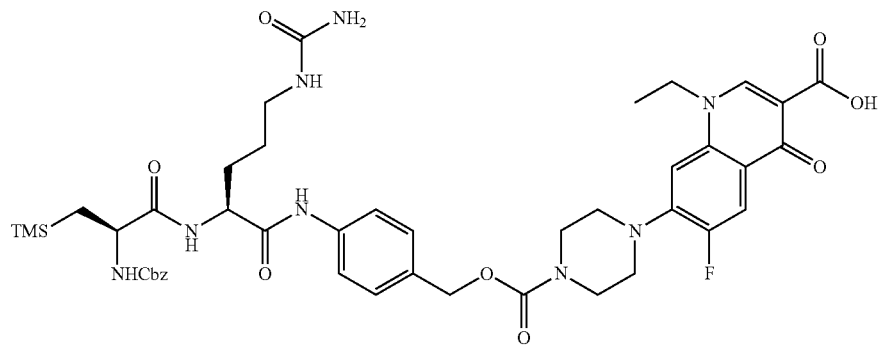
example 52

Step 1

To a stirred solution of 52-1 (3.31 g, 10.0 mmol) in DCM (10 mL) at 10° C. was added DBU (1.67 g, 11.0 mmol) and stirred at r.t. for 1 h. To a stirred solution of (COCl)$_2$ (1.83 g, 14.4 mmol) in DCM (30 mL) at −78° C. was added DMSO (1.28 g, 16.32 mmol). After 15 min, a mixture of compound 52-1 (1.0 g, 9.60 mmol) with DBU was added over 5 min. After 30 min, Et$_3$N (3.59 g, 35.52 mmol) was added and after 30 min, the ylide 52-2 was added at −78° C. After it was for 30 min, the reaction mixture was warmed to r.t. and stirred at r.t. for 6 h. The mixture was quenched with 1M HCl solution. After removal of the solvent, the residue was extracted with EtOAc (60 mL×3). The organic layer was washed with brine (60 mL), dried with Na$_2$SO$_4$ and concentrated. The residue was purified by prep-HPLC to give compound 52-3 (940 mg, 32%).

$^1$H NMR: 400 MHz, CDCl$_3$, δ 7.37-7.30 (m, 5H), 6.58 (s, 1H), 5.15 (s, 2H), 3.76 (s, 3H), 0.16-0.13 (s, 9H). LCMS (ESI): m/z 308.1 [M+H$^+$].

Step 2

Wet Pd/C (0.1 g) was added to the solution of compound 52-3 (0.5 g, 1.6 mmol) in MeOH (50 mL) at r.t. The reaction mixture was stirred under H$_2$ (50 psi) at r.t. for 4 h. The reaction mixture was filtered and the filtrate was concentrated to afford compound 52-4, which was used directly in the next step without further purification.

$^1$H NMR: CDCl$_3$, 400 MHz, δ 7.36-7.30 (m, 5H), 5.10 (s, 2H), 4.42-4.36 (m, 1H), 3.72 (s, 3H), 1.17-1.11 (dd, J=6.4, 14.8 Hz, 1H), 0.99-0.93 (dd, J=9.2, 14.8 Hz, 1H), 0.04 (s, 9H).

LCMS (ESI): m/z 310.1 [M+H$^+$].

Step 3

To a solution of compound 52-4 (220 mg, 0.7 mmol) in THF/H$_2$O (5 mL/5 mL) was added LiOH (44 mg, 1 mmol) at 0° C. The reaction mixture was warmed to r.t. and stirred for 20 h. After removal of the solvent, the residue was extracted with EtOAc (20 mL) and the aqueous layer was acidified with 1 M HCl to pH=2 and extracted with EtOAc (30 mL×2). The organic layer was washed with brine (20 mL×2), dried over sodium sulfate and concentrated. The residue was purified by prep-HPLC to afford compound 52-5.

LCMS (ESI): m/z 280.1 [M+H$^+$].

Step 4

To a solution of compound 52-5 (145 mg, 0.49 mmol) and 52-6 (57 mg, 0.495 mmol) in dry THF (20 mL) was added a solution of DCC (102.3 mg, 0.495 mmol) in dry THF (10 mL) dropwise at 0° C. The reaction mixture was stirred at 0-5° C. for 3 h. After removal of the solvent, the residue was dissolved in DCM (20 mL). The precipitate was filtered and the filtrate was concentrated to afford the crude product 52-7 as a white solid, which was used in next step without further purification.

Step 5

To the solution of compound 52-7 (obtained above, 0.49 mmol) in DME (15 mL) and H$_2$O (15 mL) was added compound 52-8 (129.5 mg, 0.74 mmol) and NaHCO$_3$ (61.8 mg, 0.74 mmol). The mixture was stirred at r.t. for 16 h under N$_2$. After removal of the solvent, the residue (52-9) was used in next step without further purification.

$^1$H NMR: DMSO-d$_6$, 400 MHz, δ 7.97 (dd, J=7.6, 29.2 Hz, 1H), 7.35-7.29 (m, 5H), 5.93-5.92 (m, 1H), 5.36 (s, 2H), 5.07-4.98 (m, 2H), 4.15-4.07 (m, 2H), 2.95-2.90 (m, 2H), 1.75-1.64 (m, 1H), 1.58-1.49 (m, 1H), 0.98-0.87 (m, 2H), −0.01 (s, 9H).

Step 6

To the solution of compound 52-9 (160 mg, 0.35 mmol) and (4-aminophyl)methanol (65.2 mg, 0.53 mmol) in dry DCM (10 mL) was added EEDQ (175 mg, 0.71 mmol) at 0° C. under N$_2$. The reaction mixture was warmed to r.t. and stirred for 1 h under N$_2$. After removal of the solvent, the residue was purified by prep-HPLC and SFC to give 52-10 and 52-11.

LCMS: (10-80, AB, 2 min, ESI), 1.151 min, MS=558.1 [M+1]

$^1$H NMR Methanol-d$_4$, 400 MHz, δ 9.99 (s, 1H), 7.92 (d, J=8.0 Hz, 1H), 7.55 (d, J=8.8 Hz, 1H), 7.45-7.24 (m, 8H), 6.01-5.98 (m, 1H), 5.41 (s, 2H), 5.11 (t, J=5.2 Hz, 1H), 5.05 (d, J=4.8 Hz, 2H), 4.44 (d, J=5.6 Hz, 3H), 4.15-4.08 (m, 1H), 3.08-2.87 (m, 2H), 1.72-1.41 (m, 4H), 1.02-0.90 (m, 2H), 0 (s, 9H).

LCMS: (10-80, AB, 2 min, ESI), 1.130 min, MS=558.1 [M+1]

$^1$H NMR Methanol-d$_4$, 400 MHz, δ 9.89 (s, 1H), 8.16 (d, J=8.0 Hz, 1H), 7.59-7.57 (d, J=8.8 Hz, 2H), 7.45-7.24 (m, 8H), 6.01-5.95 (m, 1H), 5.41 (s, 2H), 5.11 (t, J=5.6 Hz, 1H), 5.03 (d, J=11.2 Hz, 2H), 4.43 (d, J=5.6 Hz, 2H), 4.42-4.38 (m, 1H), 4.20-4.12 (m, 1H), 3.05-2.87 (m, 2H), 1.72-1.41 (m, 4H), 0.95 (d, J=8.0 Hz, 2H), 0 (s, 9H).

Step 7

To the solution 52-11 (30 mg, 0.066 mmol) in dry DCM (5 mL), was added PNP carbonate (40.4 mg, 0.13 mmol) and DIPEA (0.5 mL). The mixture was heated at reflux for 20 h. After removal of the solvent, the residue was dissolved in DMF (3 mL). DIPEA (0.5 mL) and norfloxacin (63.5 mg, 0.2 mmol) were added. The mixture was stirred at r.t. for 2 h. The reaction mixture was purified by prep-HPLC to give example 52.

LCMS: (10-80, AB, 2 min, ESI), 1.269 min, MS=903.0 [M+1]

$^1$H NMR DMSO-d$_6$, 400 MHz, δ 10.00 (s, 1H), 8.97 (s, 1H), 8.18 (d, J=10.4 Hz, 1H), 7.94 (d, J=13.2 Hz, 1H), 7.63 (d, J=8.4 Hz, 2H), 7.40 (d, J=8.4 Hz, 1H), 7.35-7.30 (m, 7H), 7.21 (d, J=7.6 Hz, 1H), 5.96 (t, J=6.4 Hz, 1H), 5.41 (s, 2H), 5.06 (s, 2H), 5.02 (d, J=9.6 Hz, 2H), 4.61-4.55 (m, 2H), 4.41-4.36 (m, 1H), 4.21-4.12 (m, 1H), 3.61 (s, 4H), 3.33 (s, 4H), 3.03-2.90 (m, 2H), 1.71-1.68 (m, 1H), 1.58-1.53 (m, 1H), 1.41 (t, J=7.2 Hz, 4H), 1.42-1.31 (m, 1H), 0.93 (d, J=6.8 Hz, 2H), −0.01 (s, 9H).

Example 53. 7-(4-((4-((S)-2-((S)-2-(benzyloxycarbonylamino)-4,4,4-trifluorobutanamido)-5-ureidopentanamido)benzyloxy)carbonyl)piperazin-1-yl)-1-ethyl-6-fluoro-4-oxo-1,4-dihydroquinoline-2-carboxylic acid

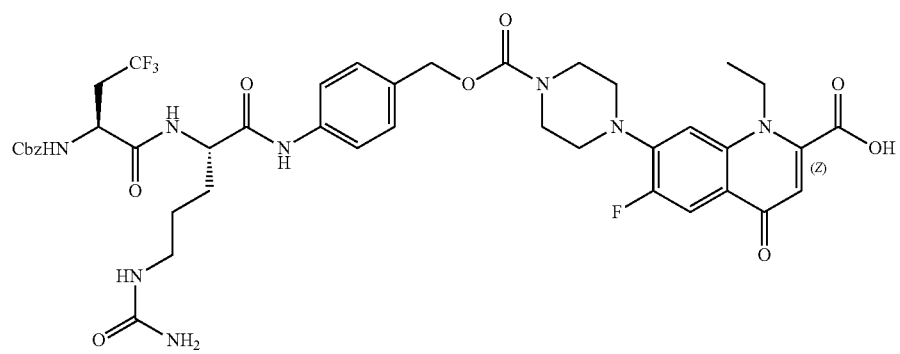

example 53

Example 53 was made using the procedure as Example 46, with the intermediate from the synthesis of Example 46.

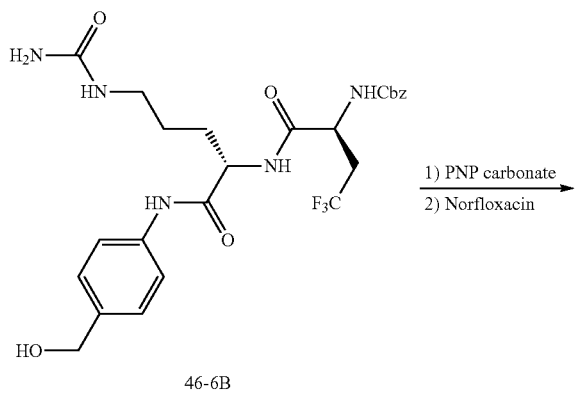

46-6B

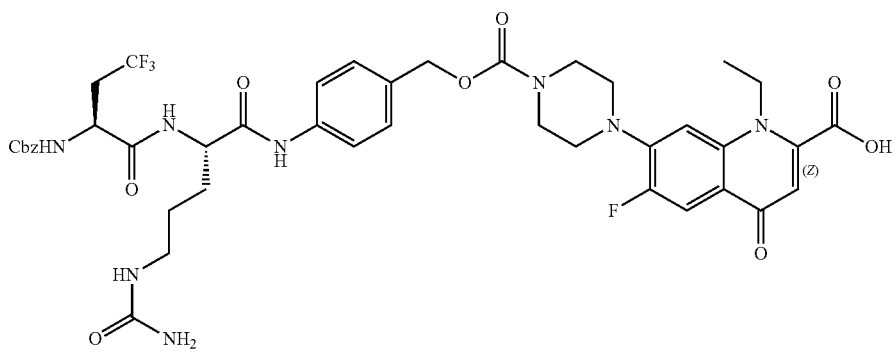

example 53

Step 1

To the solution of 46-6B (23 mg, 0.041 mmol) in dry DCM (2 mL) was added PNP carbonate (25 mg, 0.082 mmol) and of DIPEA (16 mg). The mixture was heated at reflux for 16 h. After the solvent was removed, the residue was dissolved in of DMF (5 mL). DIPEA (16 mg, 0.123 mmol) and norfloxacin (26 mg, 0.082 mmol) was added, and the mixture was stirred at r.t. for 1 h. Solvent was removed and the residue was purified by prep-HPLC to afford example 53.

$^1$H NMR (400 MHz, DMSO-$d_6$) δ 15.33 (s, 1H), 10.03 (s, 1H), 8.97 (s, 1H), 8.51 (d, J=8.0 Hz, 1H), 7.45 (d, J=13.2 Hz, 1H), 7.79 (d, J=8.4 Hz, 1H), 7.63 (d, J=8.4 Hz, 2H), 7.36-7.21 (m, 8H), 5.98-5.96 (m, 1H), 5.41 (s, 2H), 5.07-5.01 (m, 4H), 4.59-4.42 (m, 4H), 3.61 (s, 4H), 3.31 (s, 4H), 3.17-2.50 (m, 4H), 1.71-1.60 (m, 7H). LCMS (ESI): m/z 898.8 [M+H$^+$], 450.3 [M/2+H$^+$].

Example 54. 7-(4-((4-(((S)-2-((S)-2-(benzyloxycarbonylamino)-3-(trimethylsilyl)propanamido)-5-ureidopentanamido)benzyloxy)carbonyl)piperazin-1-yl)-1-ethyl-6-fluoro-4-oxo-1,4-dihydroquinoline-3-carboxylic acid

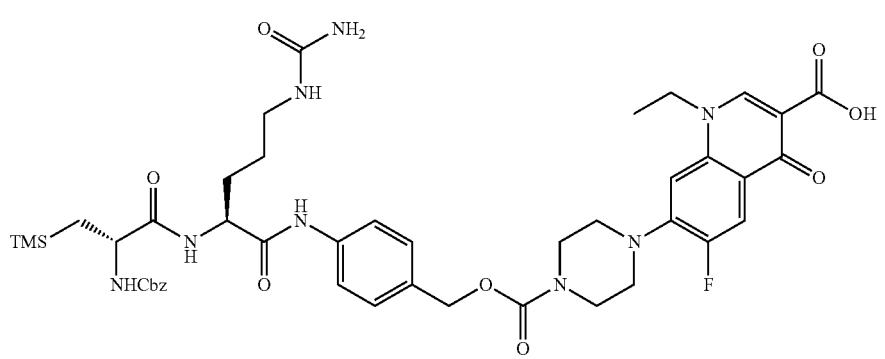

example 54

Example 54 was made using the procedure as Example 52, with the intermediate from the synthesis of Example 52.

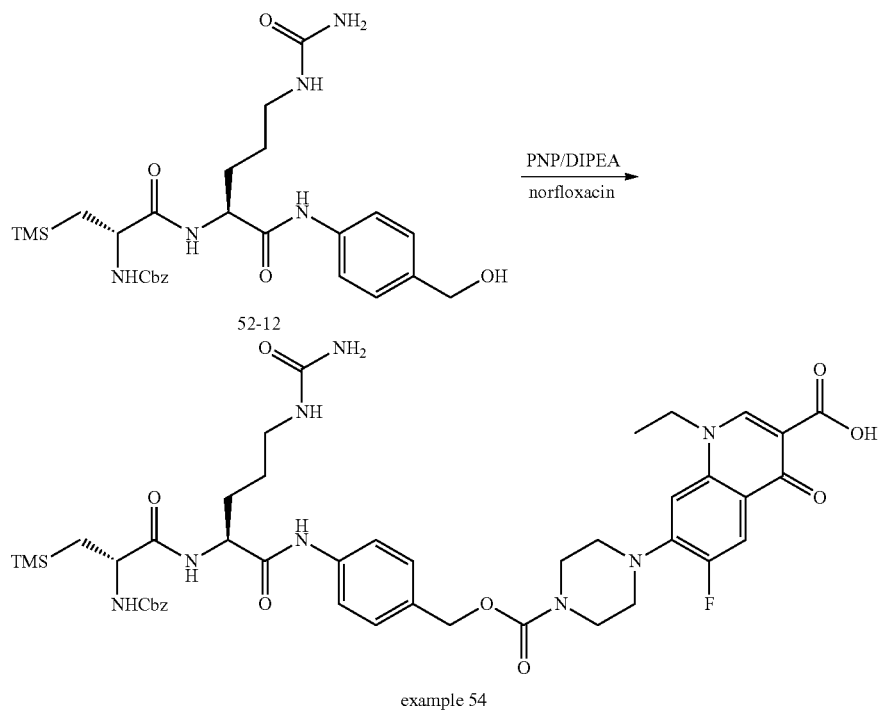
example 54
LCMS: (10-80, AB, 2 min, ESI), 1.274 min, MS=903.0 [M+1]
¹H NMR (400 MHz, DMSO-d₆) δ 10.10 (s, 1H), 8.97 (s, 1H), 7.95 (d, J=13.2 Hz, 2H), 7.61 (d, J=8.4 Hz, 2H), 7.40 (d, J=8.4 Hz, 1H), 7.37-7.29 (m, 7H), 7.21 (d, J=10.8 Hz, 1H), 5.98 (t, J=6.4 Hz, 1H), 5.05 (d, J=8.8 Hz, 2H), 5.01 (d, J=13.2 Hz, 2H), 4.62-4.56 (m, 2H), 4.43-4.40 (m, 1H), 4.14-4.08 (m, 1H), 3.61 (s, 4H), 3.33 (s, 4H), 3.05-2.91 (m, 2H), 1.76-1.52 (m, 2H), 1.48-1.39 (m, 5H), 1.01-0.89 (m, 2H), −0.01 (s, 9H).
Example 55. 7-(4-((4-((R)-3-(2-aminoethylthio)-2-((S)-2-(benzyloxycarbonylamino)-3-methylbutanamido) propanamido)benzyloxy)carbonyl)piperazin-1-yl)-1-ethyl-6-fluoro-4-oxo-1,4-dihydroquinoline-3-carboxylic acid
example 55
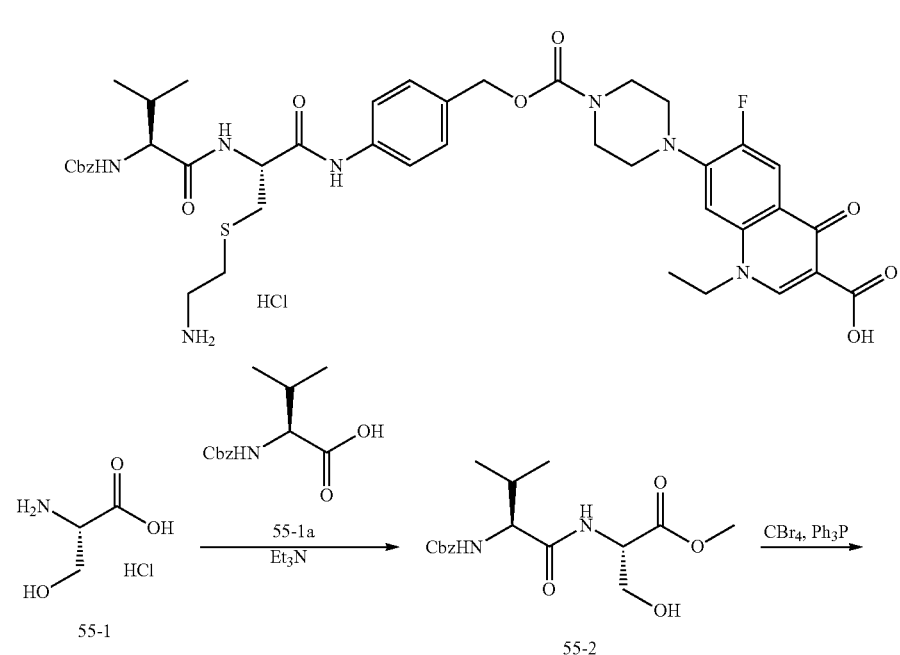

-continued
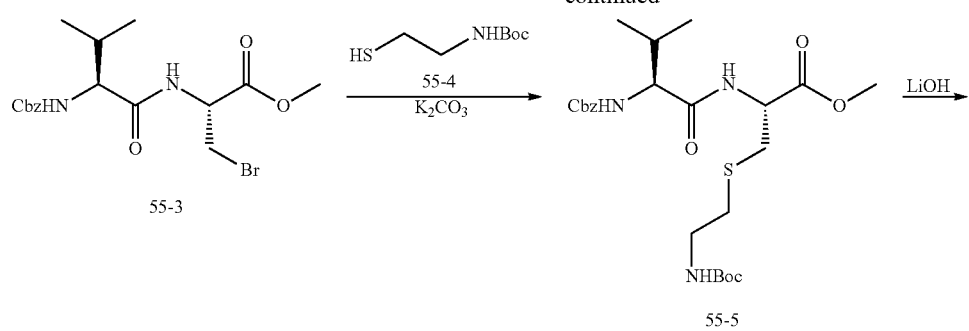
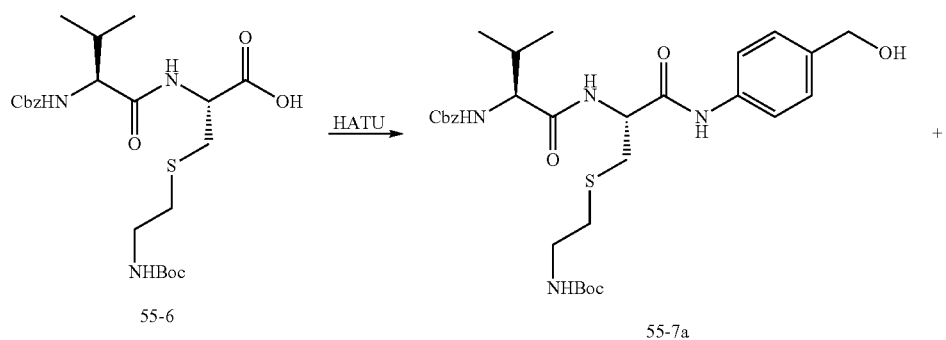
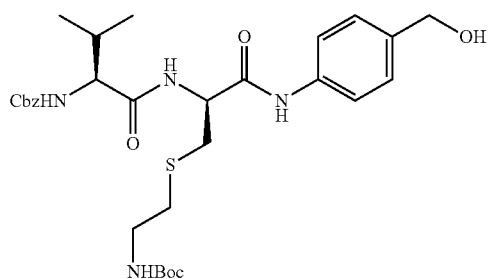
55-7b
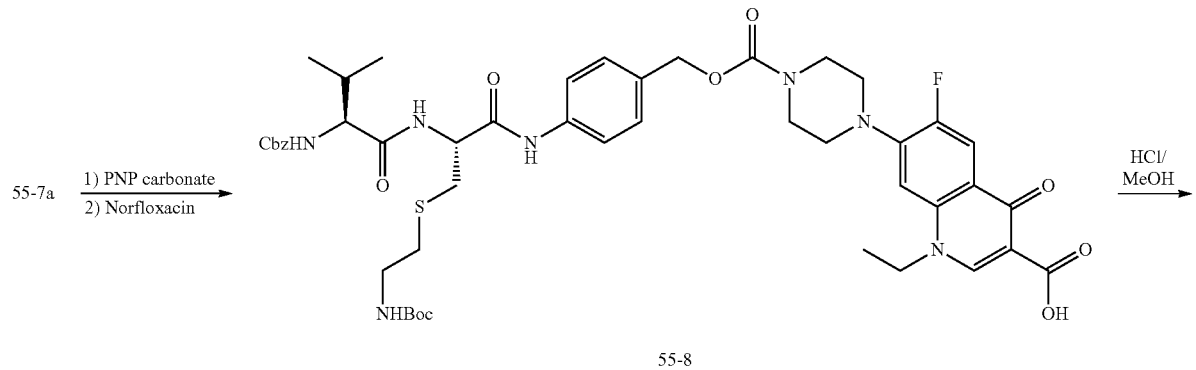

-continued

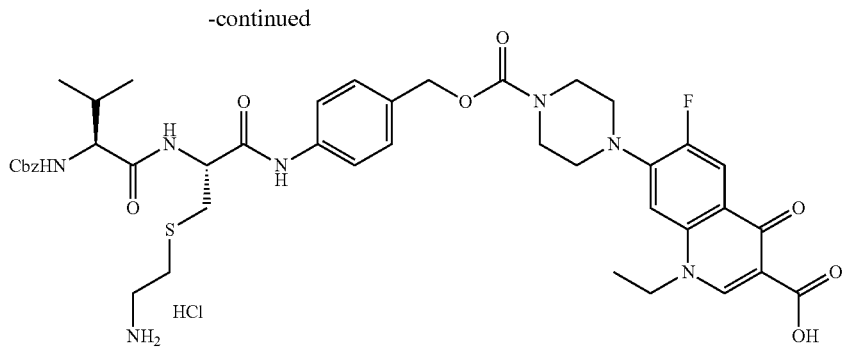

example 55

Step 1

To a mixture of compound 55-1 (1.55 g, 10 mmol), 55-1a (2.51 g, 10 mmol) and Et₃N (3.03 g, 30 mmol) in DMF (20 mL) was added HATU (3.8 g, 10 mmol). After the mixture was stirred at r.t. for 3 h, it was extracted with EtOAc (60 mL×3). The organic layer was washed with brine (60 mL×3), dried over NaSO₄, concentrated in vacuo and purified by column (20% EtOAc in hexane) to give compound 55-2 (3.21 g, 91.2%).

LCMS (ESI): m/z 353.1 [M+H⁺].

Step 2

Triphenylphosphine (2.87 g, 10.94 mmol) in dry DCM (60 mL) was added dropwise over 10-15 min to a well stirred solution of compound 55-2 (3.21 g, 9.12 mmol) and tetrabromomethane (4.54 g, 13.68 mmol) in dry DCM at 0° C. After the mixture was stirred at r.t. for 9-10 h, it was treated with pentane (200 mL) and the resulting precipitate was removed by filtration and washed several times with pentane. The combined pentane solution was washed with 5% NaHCO₃, water, brine and dried over Na₂SO₄. The solvent was evaporated and the oil was purified by column chromatography on silica gel (hexane:EtOAc=4:1) to give compound 55-3 (3.43 g, 90.7%).

LCMS (ESI): m/z 414.9 [M+H⁺].

Step 3

To the solution of compound 55-3 (3.43 g, 8.3 mmol) in DMF (5 mL) was added compound 55-4 (1.12 g, 4.0 mmol) and K₂CO₃ (1.15 g, 8.3 mmol). After the mixture was stirred at r.t. for 16 h, it was extracted with EtOAc (100 mL×2). The organic layer was washed with brine (60 mL), dried over Na₂SO₄, and concentrated to give the crude product of compound 55-5 (3.67 g, 86.4%).

LCMS (ESI): m/z 412.0 [M-BOC+H⁺], 534.1 [M+Na⁺].

Step 4

To a solution of compound 55-5 (3.67 g, 6.22 mmol) in THF/H₂O (30 mL/10 mL) was added LiOH.H₂O (2.6 g, 62.2 mmol). After the mixture was stirred at r.t. for 16 h, solvent was removed, and water (30 mL) was added. It was extracted with EtOAc (80 mL×3). The organic layer was washed with brine (60 mL), dried over Na₂SO₄, concentrated in vacuo to give compound 55-6, which was used for next step without further purification (3 g, 96.9%).

LCMS (ESI): m/z 398.2 [M-BOC+H⁺].

Step 5

To a solution of compound 55-6 (500 mg, 1.0 mmol), (4-amino-phenyl)-methanol (246 mg, 2 mmol) and DIPEA (258 mg, 2 mmol) in DCM (10 mL) was added HATU (380 mg, 1.0 mmol) at 0° C. After the mixture was stirred at 0° C. for 2 h, solvent was removed, and the residue was purified with prep-HPLC and SFC separation to afford 55-7a and 55-7b.

55-7a

¹H NMR (400 MHz, MeOD) δ 7.60 (d, J=8.8 Hz, 2H), 7.31-7.24 (m, 7H), 5.06 (s, 2H), 4.67-4.64 (m, 1H), 4.53 (s, 2H), 3.88 (d, J=7.6 Hz, 1H), 3.28-3.11 (m, 3H), 2.89-2.84 (m, 1H), 2.67-2.57 (m, 2H), 2.08-1.99 (m, 1H), 1.41 (s, 9H), 1.01-1.99 (m, 6H). LCMS (ESI): m/z 503.0 [M+H⁺-BOC].

55-7b

¹H NMR (400 MHz, MeOD) δ 7.56 (d, J=8.8 Hz, 2H), 7.34-7.25 (m, 7H), 5.08 (s, 2H), 4.66-4.63 (m, 1H), 4.54 (s, 2H), 3.96 (d, J=7.6 Hz, 1H), 3.22-3.04 (m, 3H), 2.90-2.80 (m, 1H), 2.69-2.57 (m, 2H), 2.13-2.03 (m, 1H), 1.40 (s, 9H), 0.98-0.94 (m, 6H). LCMS (ESI): m/z 502.9 [M+H⁺-BOC], 624.5 [M+Na⁺].

Step 6

To a solution of 55-7a (28 mg, 0.047 mmol) in dry DCM (2 mL) was added PNP carbonate (30 mg, 0.094 mmol) and DIPEA (0.2 mL). The mixture was heated at reflux for 16 h. After solvent was removed, residue was dissolved in of DMF (2 mL). DIPEA (0.2 mL) and norfloxacin (29 mg, 0.094 mmol) was added. The mixture was stirred at r.t. for 1 h. Solvent was removed, and the residue was purified by prep-HPLC to give compound 55-8 (38 mg, 84.4%).

LCMS (ESI): m/z 948.4 [M+H⁺].

Step 7

To a solution of compound 55-8 (38 mg, 0.04 mmol) in dry DCM (10 mL) was added HCl/CH₃OH (4 mol/L) at 0° C. over 10 min. After the mixture was stirred at r.t. for 1 h, solvent was removed and the residue was purified by prep-HPLC to give example 55 as a white solid.

¹H NMR (400 MHz, MeOD) δ 8.86 (s, 1H), 7.97 (d, J=13.2 Hz, 1H), 7.66 (d, J=8.4 Hz, 2H), 7.34 (d, J=8.8 Hz, 2H), 7.27-7.22 (m, 5H), 7.14 (d, J=7.2 Hz, 1H), 5.08 (d, J=21.6 Hz, 4H), 4.73-4.51 (m, 1H), 4.50-4.48 (m, 2H), 3.81

(d, J=8.0 Hz, 1H), 3.69 (s, 4H), 3.34 (s, 4H), 3.25-2.91 (m, 3H), 2.90-2.79 (m, 3H), 2.09-2.00 (m, 1H), 1.55-1.45 (m, 3H), 1.09-1.00 (m, 6H).
LCMS (ESI): m/z 848.1 [M+H$^+$].

Example 56. 7-(4-((4-((S)-2-((S)-2-(benzyloxycarbonylamino)-3-methylbutanamido)-3-(1-(tert-butoxycarbonyl)piperidin-4-yl)propanamido)benzyloxy)carbonyl)piperazin-1-yl)-1-ethyl-6-fluoro-4-oxo-1,4-dihydroquinoline-3-carboxylic acid Step 1

To a solution of compound 56-2 (150 mg, 0.551 mmol) in THF/H$_2$O (10 mL/2 mL) were added NaHCO$_3$ (138 mg, 1.653 mmol) and compound 56-1 (287 mg, 0.827 mmol). After the mixture was stirred at 25° C. overnight, it was acidified to pH=6 with HCl (1 N), extracted with EtOAc (50 mL×3). The organic layers were dried and concentrated to give 56-3, which was purified by column chromatography on silica gel (PE/EtOAc=10/1 to 1/10).

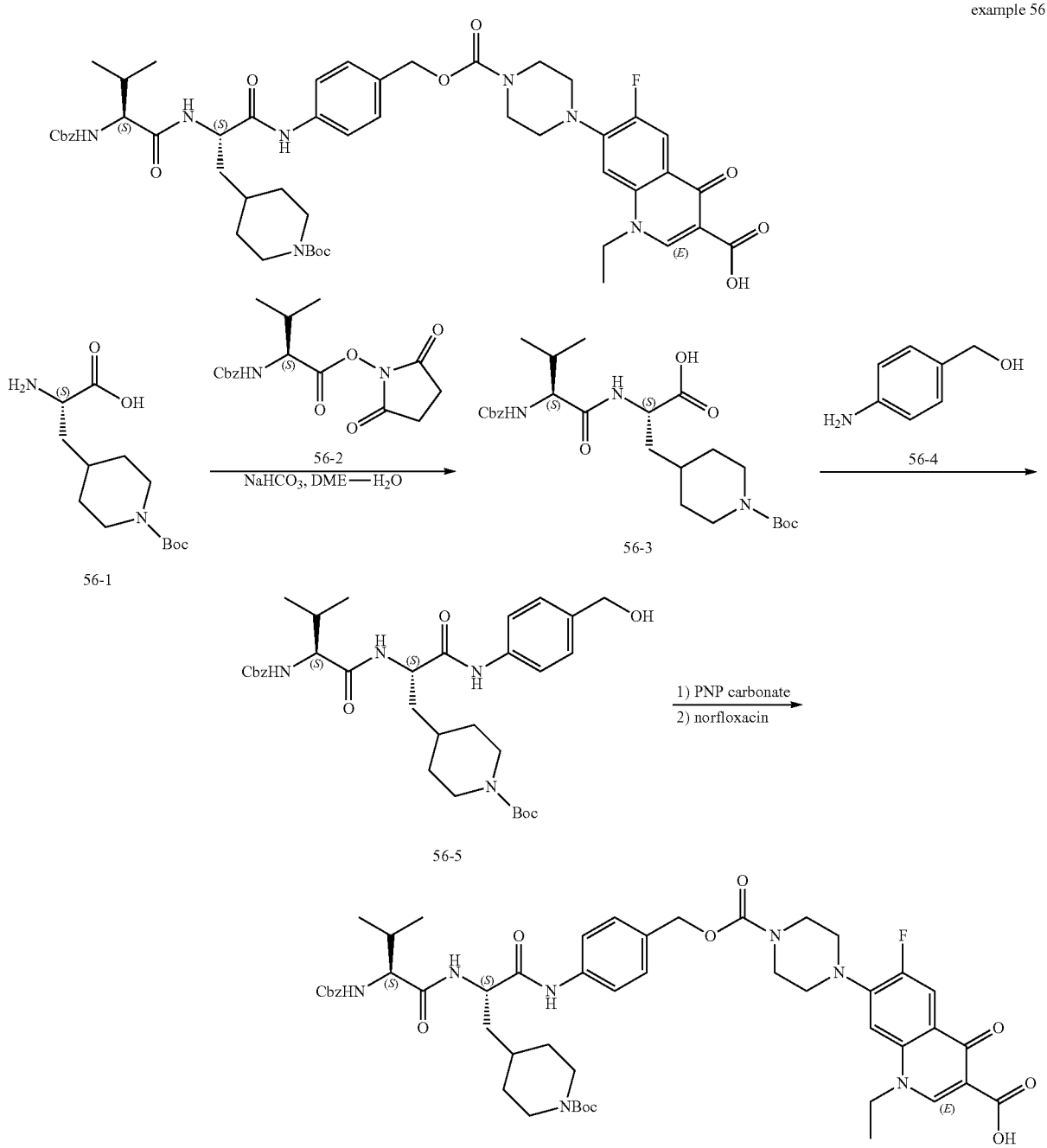

example 56

LCMS: (0-60, AB, 2 min, ESI), 1.309 min, MS=406.3 [M+1-Boc⁺]

Step 2

To a solution of compound 56-3 (1.2 g, 2.376 mmol) in DCM (20 mL) were added compound 56-4 (439 mg, 3.56 mmol), and HATU (1.7 g, 5.064 mmol). The mixture was stirred at 25° C. overnight. The solution was quenched with H₂O, and extracted with DCM (50 mL×3). The organic layers were dried, and concentrated and purified by column chromatography on silica gel (PE/EtOAc=10/1 to 1/10) to give 56-5.

LCMS: (0-60, AB, 2 min, ESI), 1.413 min, MS=511.2 [M+1-Boc⁺]

Step 3

To compound 56-5 (100 mg, 0.16 mmol) in dry DMF (2 mL) at 0° C., was added DIPEA (0.5 mL, 3 mmol) and PNP carbonate (200 mg, 0.66 mmol, 4.1 eq) under N₂. The mixture was stirred at r.t. overnight. To the mixture was added norfloxacin (102 mg, 0.32 mmol, 2 eq), and stirred for 1 h. The mixture was purified by prep-HPLC (FA), to give example 56 (60 mg, 40%).

LCMS: (5-95, AB, 1.5 min, ESI), 1.064 min, MS=956.3 [M+1]

¹H NMR: MeOH-d₄ 400 MHz, δ 8.84 (s, 1H), 7.97-7.93 (dd, J=16, 1H), 7.59-7.57 (m, 2H), 7.35-7.27 (m, 7H), 7.20-7.10 (m, 1H), 5.11-5.07 (m, 4H), 4.6-4.5 (m, 1H), 4.55-4.45 (m, 2H), 4.10-3.90 (m, 3H), 3.75-3.65 (m, 4H), 3.3 (m, 4H), 2.80-2.50 (m, 2H), 2.1-2.0 (m, 1H), 1.8-1.6 (m, 5H), 1.6-1.5 (m, 3H), 1.43 (s, 9H), 1.2-1.0 (m, 2H), 0.96-0.94 (d, J=6.8 Hz, 6H).

example 57

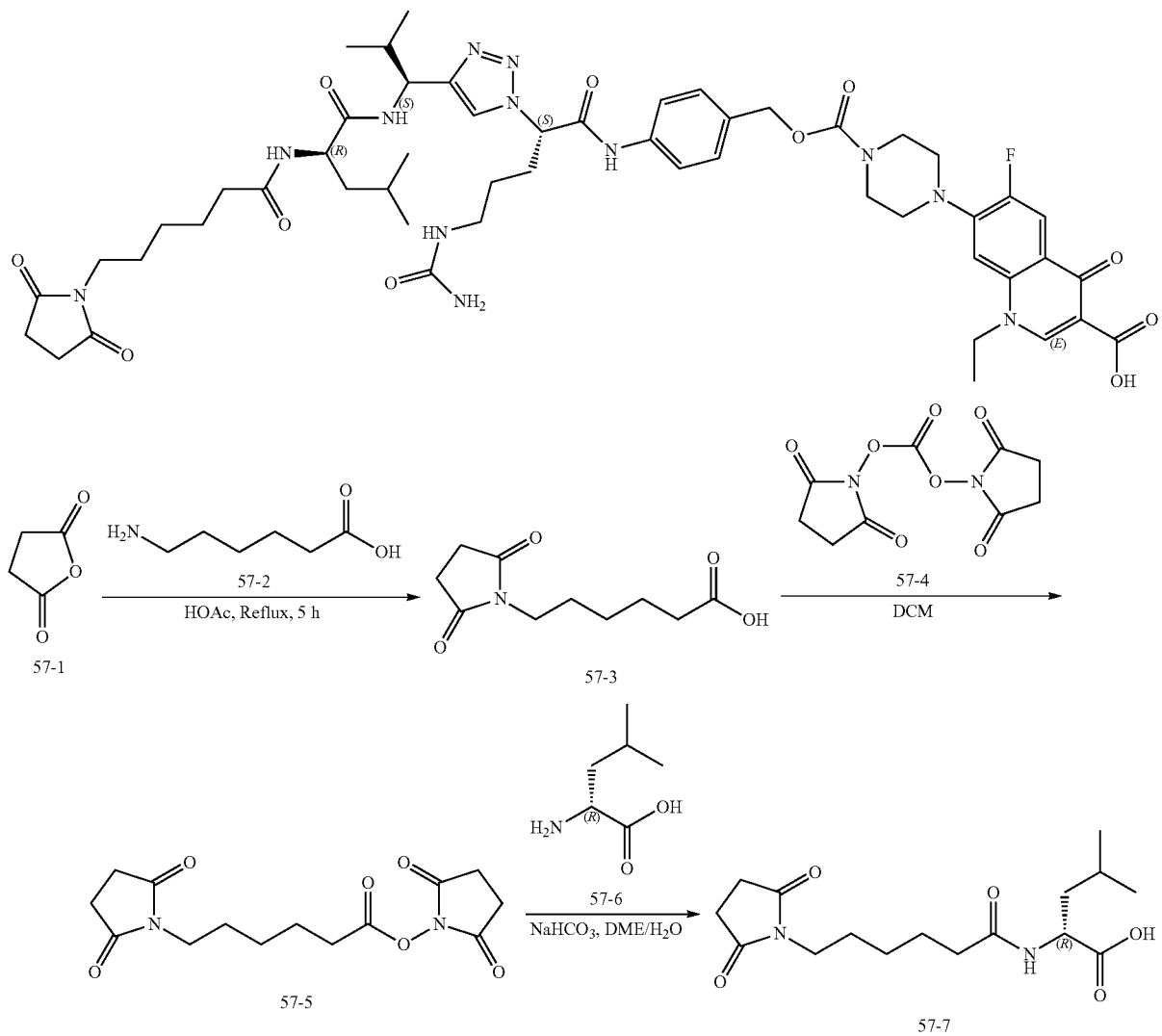

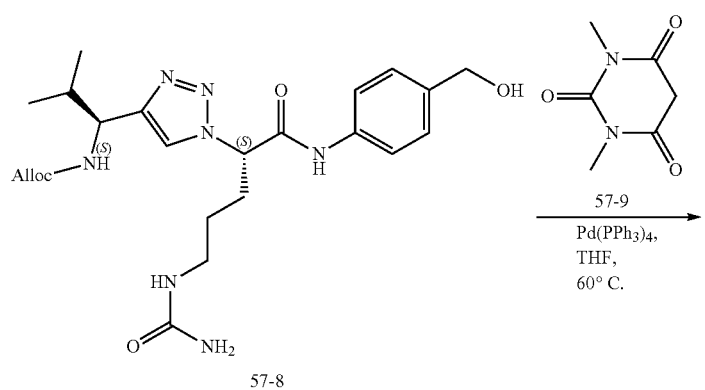
-continued
57-9
Pd(PPh₃)₄,
THF,
60° C.
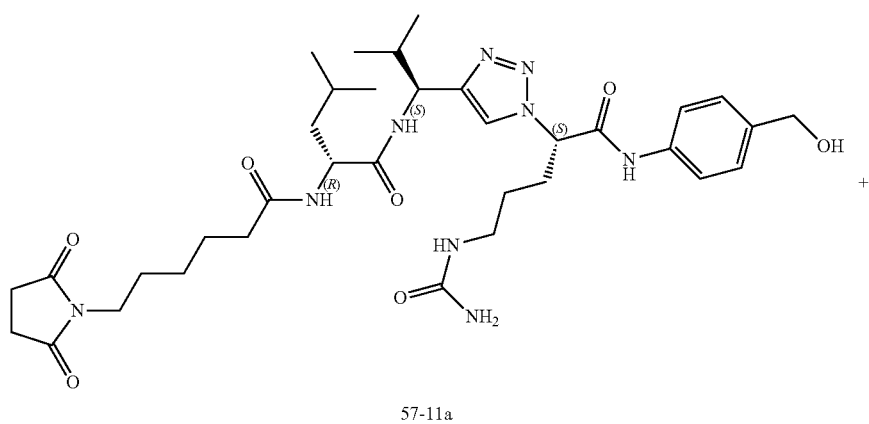
57-7
HATU, DIPEA, DMF
57-11a → PNP carbonate / Norfloxacin

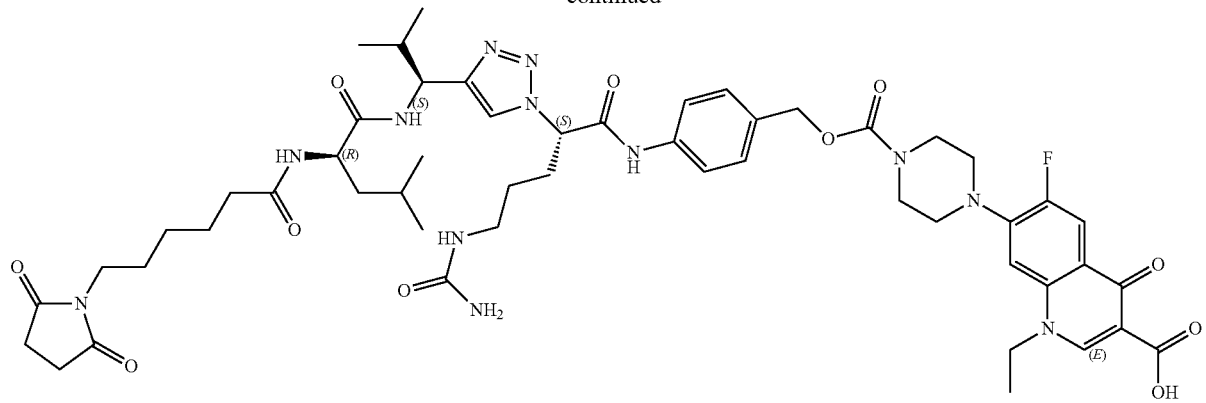

example 57

Step 1

A solution of compound 57-2 (10 g, 100 mmol) in glacial acid (30 mL) was added to a solution of compound 57-1 (13.1 g, 100 mmol) in glacial acid (150 mL) under $N_2$ over a period of 15 min. After it was stirred at r.t. for 1 h, the white heterogeneous reaction mixture was heated at reflux for 5 h. Most of the acetic acid was removed under vacuum. The residual was partitioned between water and DCM. DCM was removed and the brown oil was dissolved in small amount of EtOAc and poured to PE. White precipitate was collected by filtration to give 57-3 (12 g, Yield: 56%).

$^1$H NMR DMSO-$d_6$ 400 MHz, δ 11.98 (s, 1H), 3.34-3.31 (m, 2H), 2.61 (m, 4H), 2.19-2.16 (m, 2H), 1.50-1.43 (m, 4H), 1.23 (d, J=7.2 Hz, 2H).

Step 2

To a solution of compound 57-3 (12 g, 56.3 mmol) and excess of triethylamine (25 mL, 168.9 mmol) in DCM (100 mL) was added excess of compound 57-4 (36 g, 140.8 mmol) over 15 min. The mixture was stirred at r.t. for 6 h under $N_2$. The mixture became homogeneous and stirred at 40° C. for 3 h. It was concentrated, washed with water and brine, dried over anhydrous $MgSO_4$. It was concentrated and purified by column chromatography (EtOAc), to give 57-5 (4 g, Yield: 23%).

$^1$H NMR MeOD-$d_4$ 400 MHz, δ 3.54-3.50 (m, 2H), 2.86 (d, J=3.2 Hz, 4H), 2.71 (d, J=2.8 Hz, 4H), 2.66-2.63 (m, 2H), 1.79-1.75 (m, 2H), 1.65-1.59 (m, 2H), 1.45-1.41 (m, 2H).

Step 3

To a solution of compound 57-6 (375 mg, 2.86 mmol) in DME (10 mL) was added a solution of compound 57-5 (800 mg, 2.6 mmol) and $NaHCO_3$ (656 mg, 7.8 mmol) in water (10 mL). The mixture was stirred at r.t. for 16 h. The mixture was washed with EtOAc and acidified to pH=3 with 10% HCl. The resulting suspension was extracted with EtOAc. The combined organic layers was concentrated to give crude compound 57-7 (1.2 g, contains impurity).

Step 4

To a mixture of compound 57-8 (2.0 g, 4.10 mmol) in THF (50 mL) was added compound 57-9 (3.8 g, 24.34 mol) and $Pd(PPh_3)_4$ (946 mg, 0.82 mmol). The reaction mixture was stirred at 60° C. for 3 h. The mixture was cooled to r.t. and filtered, the filtrate cake was purified by prep-HPLC to give 57-10 (1.0 g, 60.4%).

Step 5

Compound 57-7 (100 mg, 0.3 mmol), HATU (175 mg, 0.46 mmol), DIPEA (119 mg, 0.92 mmol) were dissolved in DMF (10 ml). The reaction mixture was stirred at r.t. for 30 min. Then compound 57-10 (124 mg, 119 mmol) was added. The reaction mixture was stirred at r.t. for 3 h. Then the mixture was concentrated and purified by prep-HPLC to give 57-11a and 57-11b (30 mg each, 5%).

Step 6

To a solution of compound 57-11a (30 mg, 0.042 mmol) and PNP carbonate (26 mg, 0.084 mmol) in DMF (2 mL) was added DIPEA (17 mg, 0.127 mmol) at 0° C. The mixture was stirred at r.t. for 16 h and norfloxacin (27 mg, 0.084 mmol) was added at r.t. The mixture was stirred at r.t. for 1 h. The residue was purified by prep-HPLC to give example 57 (14 mg, Yield: 15%).

LCMS: (5-95, AB, 1.5 min, ESI), 0.832 min, MS=529.4. [½M+1]

$^1$H NMR Methanol-$d_4$ 400 MHz, δ 8.89 (s, 1H), 8.33 (d, J=4.6 Hz, 1H), 8.06-8.01 (m, 2H), 7.63 (d, J=8.4 Hz, 2H), 7.50-7.40 (m, 1H), 7.39 (d, J=8.4 Hz, 2H), 7.21 (s, 1H), 5.55-5.51 (m, 1H), 5.15 (s, 2H), 4.92 (s, 1H), 4.58 (s, 6H), 3.74 (s, 4H), 3.49-3.46 (m, 2H), 3.35-3.33 (m, 4H), 2.69 (s, 4H), 2.26-2.22 (m, 4H), 1.65-1.57 (m, 9H), 1.56-1.29 (m, 5H), 1.01 (d, J=6.8 Hz, 3H), 0.93 (d, J=6.4 Hz, 3H), 0.92-0.81 (m, 6H)

Example 58. 7-(4-((4-((S)-6-amino-2-(4-((S)-1-(benzyloxycarbonylamino)-2-methylpropyl)-1H-1,2,3-triazol-1-yl)hexanamido)benzyloxy)carbonyl)piperazin-1-yl)-1-ethyl-6-fluoro-4-oxo-1,4-dihydroquinoline-3-carboxylic acid
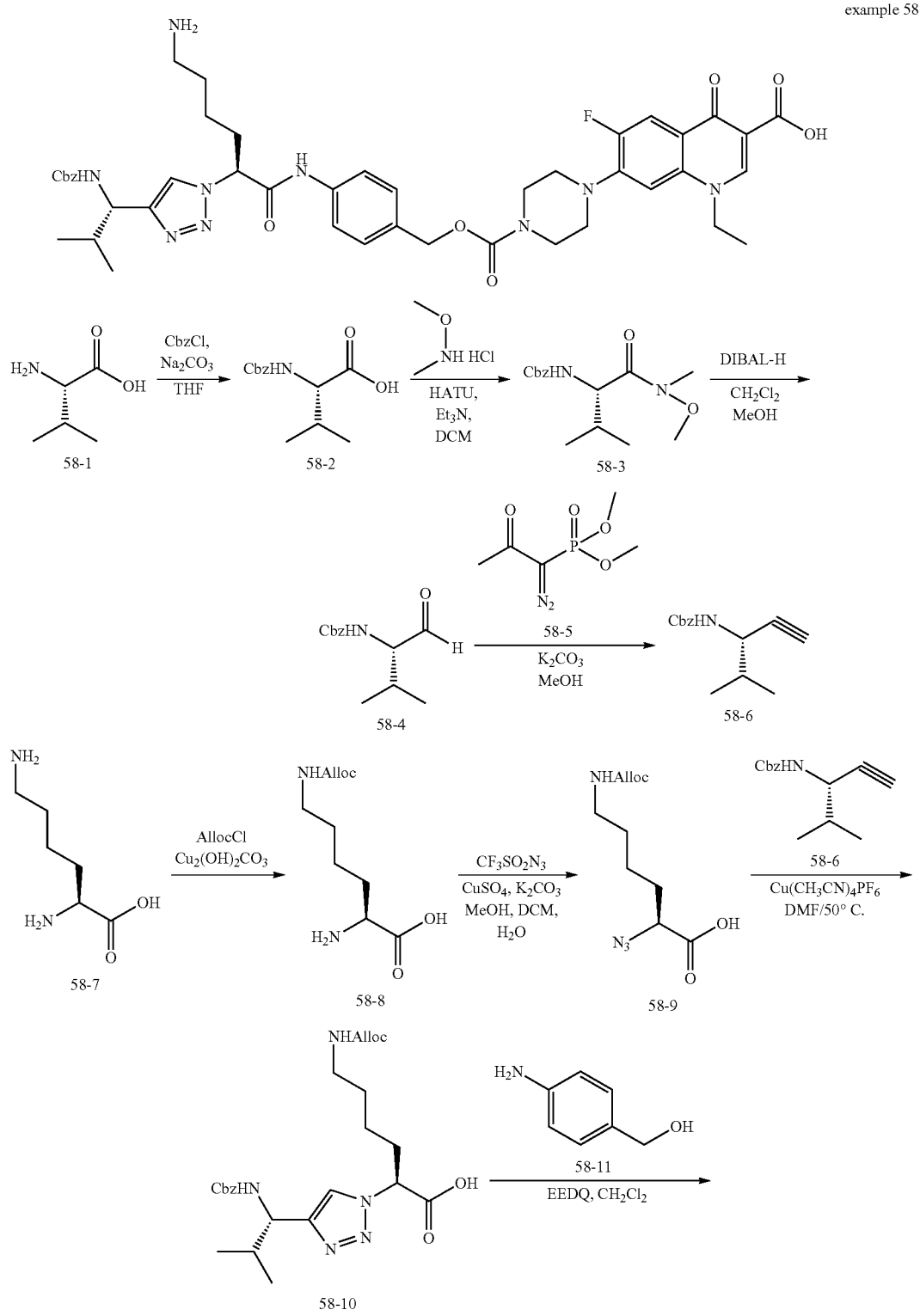
example 58

-continued

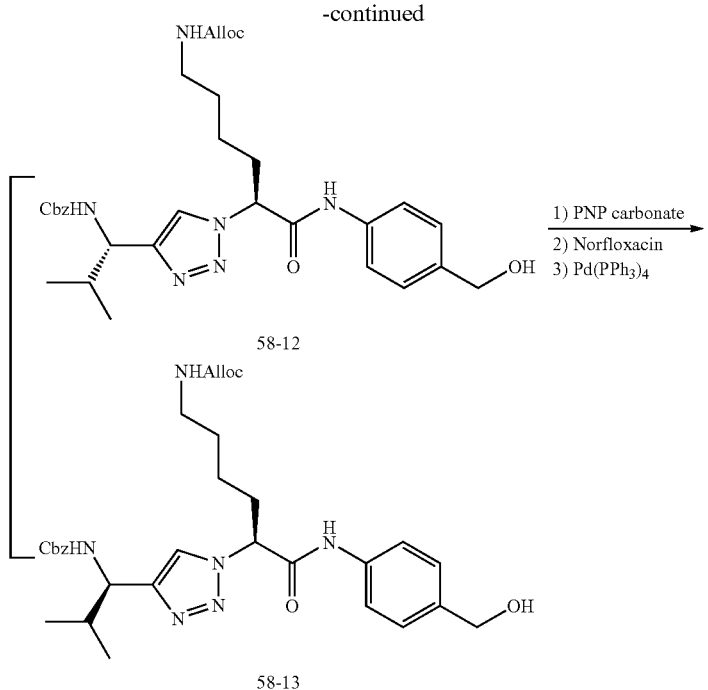

58-12

58-13

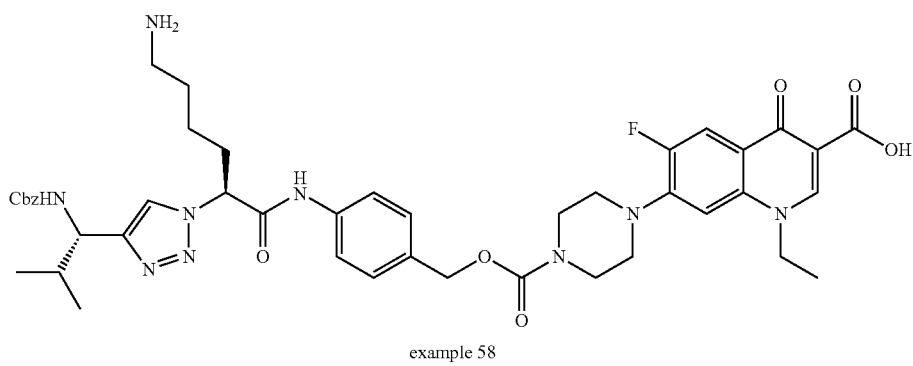

example 58

Step 1

CbzCl (26.7 mL, 0.19 mol) was added dropwise over 20 min to a mixture of 58-1 (20 g, 0.17 mol) and Na$_2$CO$_3$ (36 g, 0.34 mol) in water (100 mL). After it was stirred at r.t. for 12 h, it was washed with EtOAc (200 mL×2). The aqueous layer was adjusted to pH=2 and extracted with EtOAc (200 mL×4). The combined organic layers were dried over Na$_2$SO$_4$ and concentrated to give 58-2.

Step 2

To a solution of 58-2 (20 g, 79.3 mmol), N,O-dimethylhydroxylamine (8.4 g, 87.2 mmol) and HATU (45.2 g, 118.9 mmol) in DCM (200 mL) was added Et$_3$N (45.8 mL, 317.1 mmol). The mixture was stirred at r.t. for 1 h. After removal of the solvent, the residue was extracted with EtOAc (200 mL×3). The organic layer was washed with conc. HCl, aqueous NaHCO$_3$, saturated NaCl and concentrated. The crude was purified by column chromatography on silica gel (PE:EtOAc=2:1) to give 58-3.

Step 3

Compound 58-3 (6.0 g, 20.4 mmol) in DCM (100 mL) was cooled to −78° C. in a dry ice/acetone bath. DIBAL-H (30.6 mL, 30.6 mmol) was added dropwise and the mixture was stirred at −78° C. for 4 h. Excess hydride was quenched with MeOH (5 mL) and the solution was warmed to r.t. After solvent was removed, 58-4 was used in next step without further purification.

Step 4

The mixture of 58-4 (4.80 g, 20.4 mmol), compound 5 (4.70 g, 24.5 mmol) and K$_2$CO$_3$ (5.64 g, 40.8 mmol) in MeOH (60 mL) was stirred at r.t. for 12 h. After removal of the solvent, the residue was extracted with EtOAc (100 mL×3). The organic layer was washed with brine (60 mL) and dried over Na$_2$SO$_4$. The solvent was removed and the crude was purified by column chromatography on silica gel (PE:EtOAc=10:1) to give 58-6.

Step 5

A solution of 58-7 (10 g, 68.4 mmol) and Cu(OH)$_2$CO$_3$ (15.12 g, 68.4 mmol) in H$_2$O (100 mL) was heated at reflux for 30 min. Solids formed during reflux were removed by filtration while hot. The filtrate was cooled to 0° C. and was adjusted to pH 9 by addition of solid Na$_2$CO$_3$ (1.0 g). AllocCl (10.8 mL, 102.6 mmol) was added dropwise, while the solution stirred at 0° C. During the addition, the reaction mixture was maintained at pH 9 by the addition of solid Na$_2$CO$_3$ (20 g). The reaction mixture was allowed to warm to room temperature and stirred for 12 h. The blue solid product formed during the reaction was collected by filtration in quantitative yield. The solid copper salt of Orn(Alloc) collected above was suspended in H$_2$O (200 mL) and two equivalents of thioacetamide (6.511 g, 86.66 mmol) were added to. The alkaline suspension was stirred at 50° C. for 3 h, during which time, the solid slowly dissolved. The solution was then acidified to pH 2 with 2M HCl and was further boiled for 5 min. The precipitated CuS was removed by filtration. The filtrate was concentrated under vacuum to about 100 mL, at which point the product hydrochloride salt of Orn(Alloc) 58-8 precipitated as a white solid in quantitative yield.

Step 6

A solution of NaN$_3$ (8.5 g, 129.7 mmol) in distilled H$_2$O (45 mL) and CH$_2$Cl$_2$ (75 mL) was cooled on an ice bath. Tf$_2$O (4.4 mL, 25.94 mmol) was added slowly over 5 min with stirring continued for 2 h. The mixture was place in a separator funnel and the CH$_2$Cl$_2$ phase was removed. The aqueous portion was extracted with CH$_2$Cl$_2$ (35 mL×2). The organic fractions, containing the triflyl azide were pooled and washed once with saturated Na$_2$CO$_3$ and used without further purification. Compound 58-8 (2.99 g, 12.97 mmol) was combined with K$_2$CO$_3$ (2.69 g, 19.46 mmol) and CuSO$_4$-5H$_2$O (486 mg, 1.94 mmol) in distilled H$_2$O (90 mL) and MeOH (180 mL). The triflyl azide in CH$_2$Cl$_2$ (150 mL) was added and the mixture was stirred at r.t. for 12 h. Subsequently, the organic solvents were removed under pressure and the aqueous slurry was diluted with 0.2 M pH 6.2 phosphate buffers (100 mL) and extracted with EtOAc (200 mL×2) to remove sulfonamide byproduct. The aqueous phase was then acidified to pH 2 with conc.HCl. The product was obtained from another round of EtOAc extractions (400 mL×3). The EtOAc extracts were combined, dried over Na$_2$SO$_4$ and evaporated to give 58-9, which was used for next step without further purification.

Step 7

The mixture of 58-9 (3.32 g, 12.97 mmol), 58-6 (1.50 g, 6.48 mmol) and Cu(CH$_3$CN)$_4$PF$_6$ (362 mg, 0.97 mmol) in DMF (10 mL) was stirred at 50° C. for 2 h. After removal of the solvent, the residue was purified by prep-HPLC to give 58-10 (2.3 g, 36.4%).

Step 8

The mixture of 58-10 (2.33 g, 4.78 mmol), 58-11 (1.76 mg, 14.3 mmol) and EEDQ (3.55 g, 14.3 mmol) in DCM (50 mL) was stirred at r.t. for 1 h. After removal of the solvent, the residue was purified by prep-HPLC and SFC separation to afford 58-12 (326 mg) and 58-13 (30 mg).

$^1$H NMR (400 MHz, MeOD) δ 8.04 (s, 1H), 7.55-7.53 (m, 2H), 7.33-7.30 (m, 7H), 5.91-5.87 (m, 1H), 5.45-5.41 (m, 1H), 5.27-5.23 (m, 1H), 5.15-5.11 (m, 1H), 5.07 (d, J=2.8 Hz, 2H), 4.70-4.68 (m, 1H), 4.55 (s, 2H), 4.48-4.46 (m, 2H), 3.34-3.32 (m, 1H), 3.09-3.07 (m, 2H), 2.28-2.22 (m, 3H), 1.54-1.50 (m, 2H), 1.44-1.35 (m, 2H), 0.93 (d, J=6.8 Hz, 3H), 0.87 (d, J=6.8 Hz, 3H).

LCMS (ESI): m/z 593.0 [M+H$^+$].

$^1$H NMR (400 MHz, MeOD) δ 8.04 (s, 1H), 7.55-7.52 (m, 2H), 7.32-7.27 (m, 7H), 5.91-5.87 (m, 1H), 5.43-5.42 (m, 1H), 5.27-5.22 (m, 1H), 5.15-5.12 (m, 1H), 5.07 (d, J=3.6 Hz, 2H), 4.70-4.68 (m, 1H), 4.55 (s, 2H), 4.47 (d, J=5.2 Hz, 2H), 3.07-3.05 (m, 2H), 2.22-2.14 (m, 3H), 1.54-1.50 (m, 2H), 1.44-1.20 (m, 2H), 0.92 (d, J=6.8 Hz, 3H), 0.87 (d, J=6.8 Hz, 3H).

LCMS (ESI): m/z 593.0 [M+H$^+$].

Step 9

The mixture of 58-12 (100 mg, 0.169 mmol), PNP (103 mg, 0.338 mmol) and DIPEA (66 mg, 0.507 mmol) in DCM (5 mL) was stirred at 50° C. for 12 h and solvent was removed. A mixture of the above crude product (128 mg, 0.169 mmol), Norfloxacin (160 mg, 0.507 mmol) and DIPEA (66 mg, 0.507 mmol) in DMF (5 mL) was stirred at r.t. for 2 h. After removal of the solvent, the residue was purified by prep-HPLC to give 100 mg of intermediate. To the intermediate (50 mg, 0.053 mmol) and 1,3-dimethylbarbituric acid (67 mg, 0.426 mmol) in THF (5 mL) was added Pd(PPh$_3$)$_4$ (12 mg, 0.0106 mmol). The mixture was stirred at 50° C. for 12 h. After removal of the solvent, the residue was purified by prep-HPLC to give example 58 (20.6 mg).

$^1$H NMR (400 MHz, DMSO-d$_6$) δ 8.96 (s, 1H), 8.47-8.43 (m, 1H), 8.09 (s, 1H), 7.96-7.93 (m, 1H), 7.74-7.72 (m, 1H), 7.62-7.60 (m, 2H), 7.38-7.29 (m, 7H), 7.22-7.20 (m, 1H), 5.52-5.49 (m, 1H), 5.07 (s, 2H), 5.02 (d, J=4.8 Hz, 2H), 4.62-4.58 (m, 3H), 3.62 (s, 4H), 3.15 (s, 4H), 2.67-2.66 (m, 2H), 2.15-2.09 (m, 3H), 1.54-1.52 (m, 2H), 1.40 (t, J=7.2 Hz, 3H), 1.23-1.18 (m, 2H), 0.84 (d, J=6.4 Hz, 3H), 0.78 (d, J=6.4 Hz, 3H).

LCMS (ESI): m/z 854.1 [M+H$^+$].

Example 59. 7-(4-((4-((S)-2-(4-((S)-1-((R)-2-(6-(2,5-dioxopyrrolidin-1-yl)hexanamido)-3-phenylpropanamido)-2-methylpropyl)-1H-1,2,3-triazol-1-yl)-5-ureidopentanamido)benzyloxy) carbonyl) piperazin-1-yl)-1-ethyl-6-fluoro-4-oxo-1,4-dihydroquinoline-3-carboxylic acid
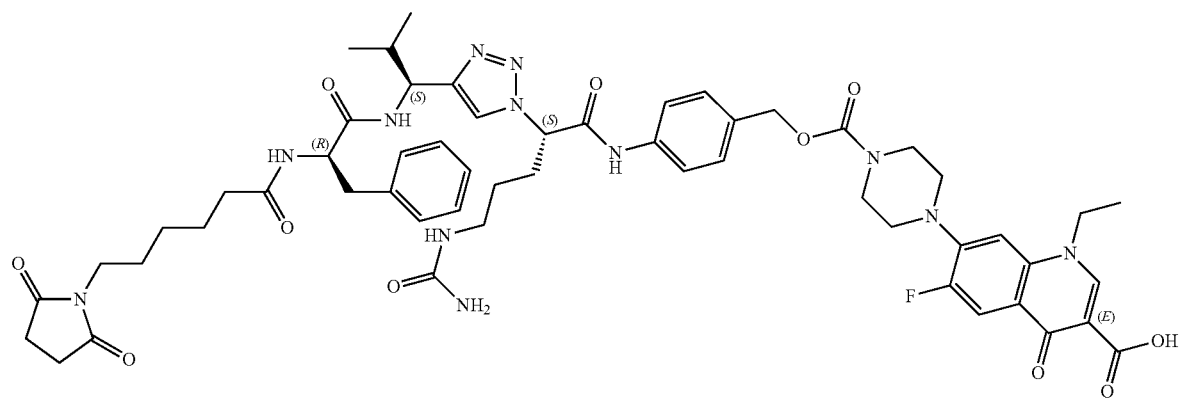
example 59
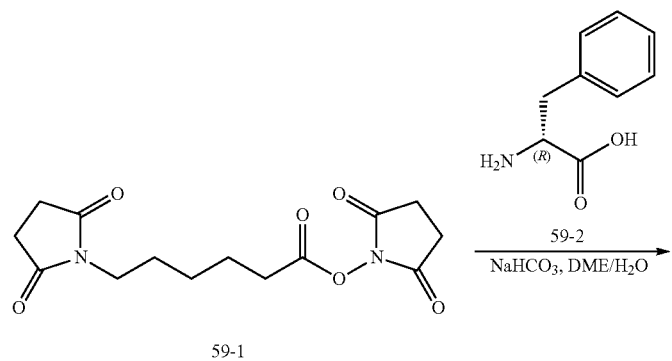
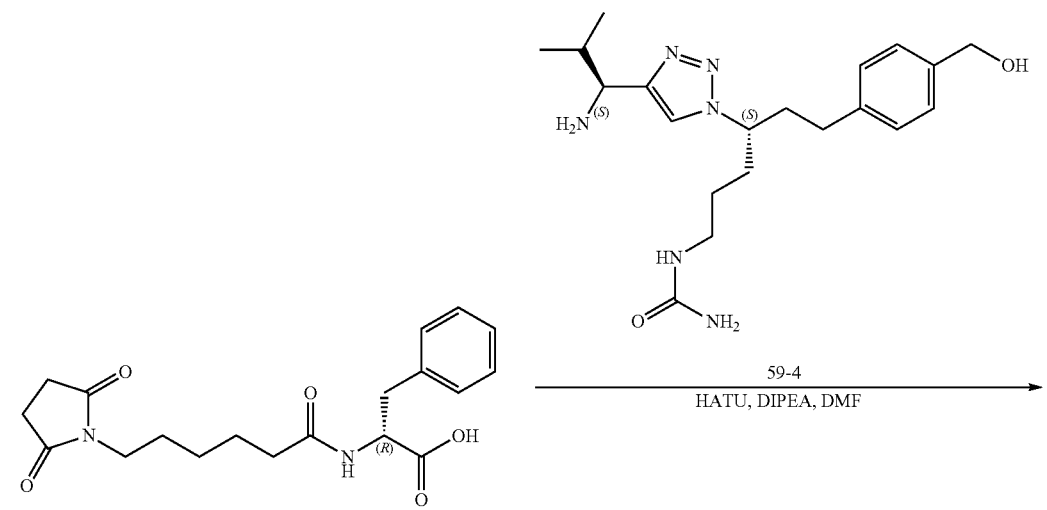

-continued

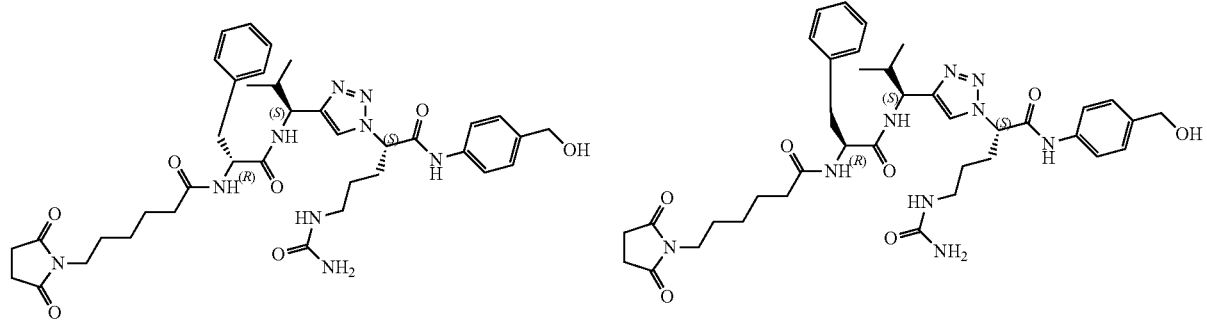

59-5a 59-5b 59-5a →[PNP carbonate / Norfloxacin]

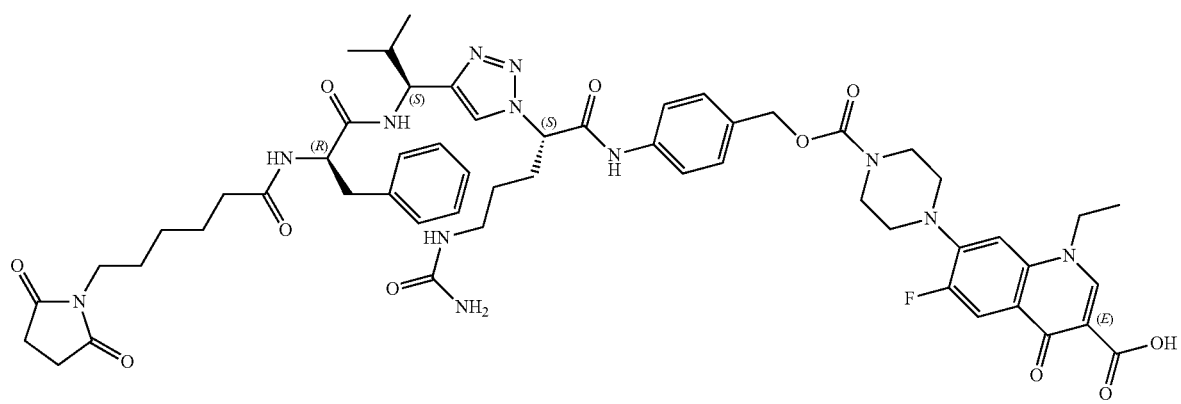

example 59

Step 1

To a solution of compound 59-2 (118 mg, 0.71 mmol) in DME (5 mL) was added a solution of compound 59-1 (200 mg, 0.71 mmol) and NaHCO$_3$ (122 mg, 1.42 mmol) in water (5 mL). The mixture was stirred at r.t. for 16 h. The mixture was washed with EtOAc and acidified to pH=3 with 10% HCl. The resulting suspension was extracted with EtOAc. The combined organic layer was concentrated to give crude compound 59-3 (240 mg).

Step 2

Compound 59-3 (240 mg, 0.67 mmol), HATU (506 mg, 1.34 mmol), DIPEA (258 mg, 2.01 mmol) were dissolved in DMF (5 mL) and stirred at r.t. for 30 min. Then compound 59-4 (269 mg, 0.67 mmol) was added. The reaction mixture was stirred at r.t. for 3 h. The mixture was concentrated and purified by prep-HPLC to give 59-5a and 59-5b (40 mg each, 8%)

Step 3

To a solution of compound 59-5a (40 mg, 0.054 mmol) in dry DMF (3 mL) was added PNP carbonate (34 mg, 0.11 mmol) and DIPEA (21 mg, 0.162 mmol) at r.t. and stir at r.t. for 1.5 h. Norfloxacin (35 mg, 0.11 mmol) was added. The mixture was stirred at r.t. for another 1 h and concentrated, filtered and purified by prep-HPLC (FA) (14 mg, Yield: 20%).

LCMS: (5-95, AB, 1.5 min, ESI), 0.838 min, MS=546.5. [½M+1]

$^1$H NMR DMSO-d$_6$ 400 MHz, δ 10.64 (s, 1H), 8.96 (s, 1H), 8.22 (d, J=9.2 Hz, 1H), 8.04 (d, J=8.4 Hz, 1H), 8.04-7.92 (m, 2H), 7.61 (d, J=8.4 Hz, 2H), 7.36 (d, J=8.4 Hz, 2H), 7.22-7.20 (m, 5H), 7.14 (s, 1H), 6.06 (d, J=6 Hz, 1H), 5.50-5.47 (m, 1H), 5.44 (s, 2H), 5.07 (s, 2H), 4.90-4.86 (m, 1H), 4.61-4.58 (m, 3H), 3.61 (s, 4H), 3.34-3.25 (m, 4H), 3.04-2.91 (m, 4H), 2.75-2.71 (m, 2H), 2.60 (s, 4H), 2.14-2.11 (m, 2H), 2.09-2.00 (m, 2H), 1.42-1.29 (m, 10H), 1.40 (d, J=7.2 Hz, 2H), 0.85-0.79 (m, 6H).

Example 60. 7-(4-((4-((S)-2-(4-((S)-1-((R)-2-(6-(2,5-dioxopyrrolidin-1-yl)hexanamido)-3-methylbutanamido)-2-methylpropyl)-1H-1,2,3-triazol-1-yl)-5-ureidopentanamido)benzyloxy)carbonyl)piperazin-1-yl)-1-ethyl-6-fluoro-4-oxo-1,4-dihydroquinoline-3-carboxylic acid
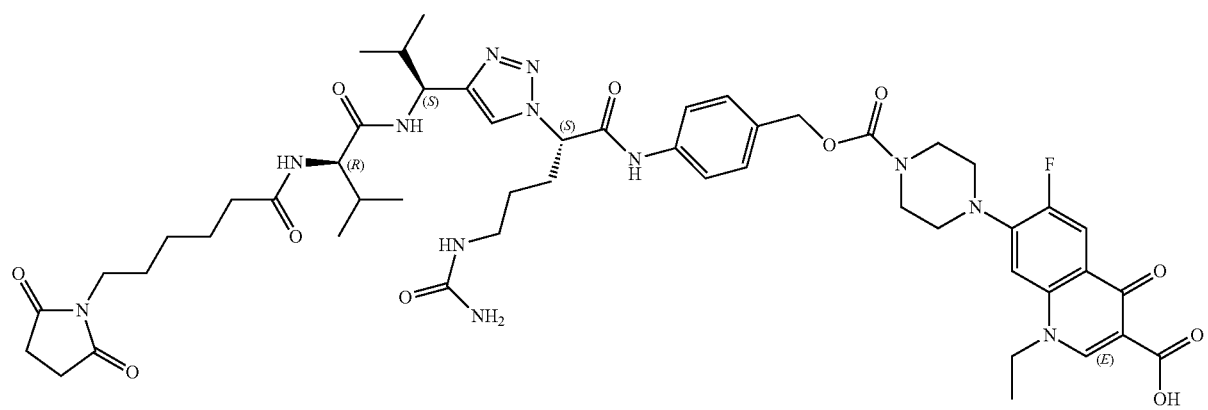
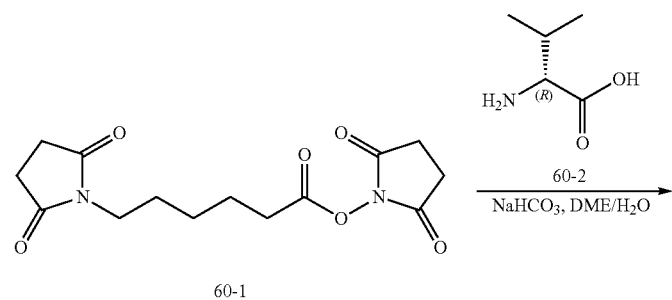
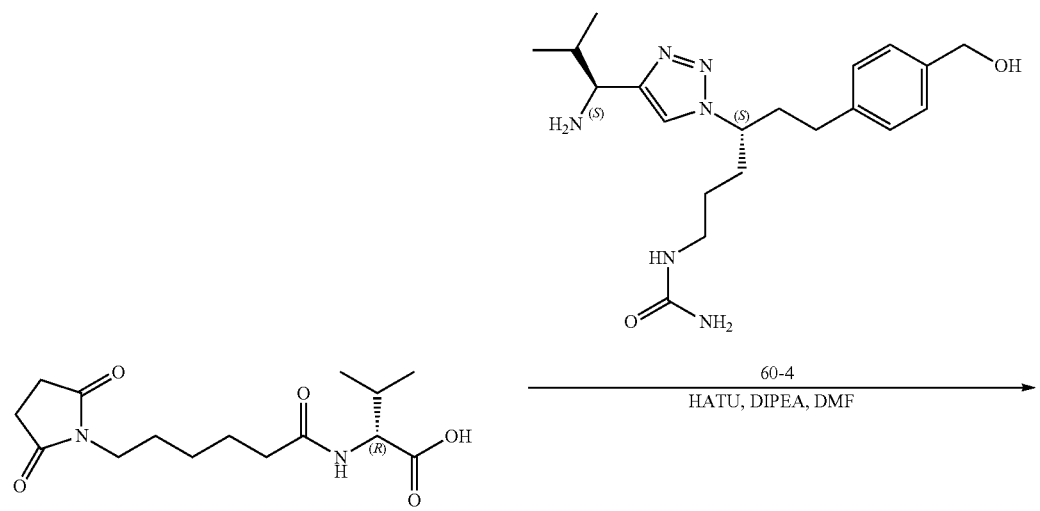

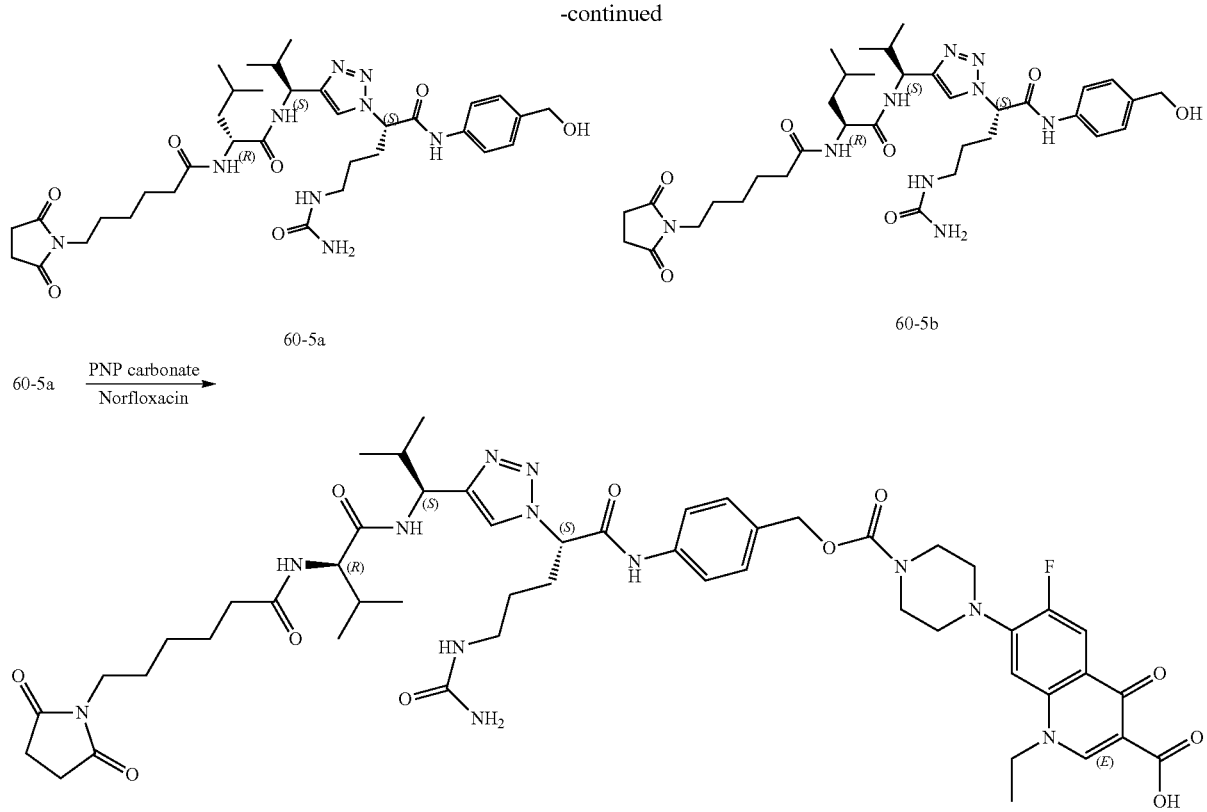

60-5a 60-5b 60-5a $\xrightarrow{\text{PNP carbonate}}$ Norfloxacin example 60

Step 1

To a solution of compound 60-2 (83 mg, 0.71 mmol) in DME (5 mL) was added a solution of compound 60-1 (200 mg, 0.71 mmol) and NaHCO$_3$ (122 mg, 1.42 mmol) in water (5 mL). After the mixture was stirred at r.t. for 16 h, it was washed with EtOAc and acidified to pH 3 with 10% HCl. The resulting suspension was extracted with EtOAc. The combined organic layer was concentrated to give compound 60-3 (160 mg, with impurity, Yield: 80%.

Step 2

Compound 60-3 (160 mg, 0.5 mmol), HATU (390 mg, 1.02 mmol), DIPEA (200 mg, 0.68 mmol) were dissolved in DMF (5 mL) and stirred at r.t. for 30 min. Then compound 60-4 (207 mg, 0.51 mmol) was added. The reaction mixture was stirred at r.t. for 3 h. Then the mixture was concentrated and purified by prep-HPLC to give 60-5a and 60-5b (60 mg and 60 mg, 8% and 8%, respectively)

Step 3

To a solution of compound 60-5a (60 mg, 0.086 mmol) in dry DMF (3 mL) was added PNP carbonate (60 mg, 0.2 mmol) and DIPEA (0.5 mL, 3 mmol) at r.t., and the mixture was stirred at r.t. for 1.5 h. Norfloxacin (60 mg, 0.19 mmol) was added. The mixture was stirred at r.t. for additional 1 h. The mixture was concentrated, filtered and purified by prep-HPLC (FA) to give example 60 (47.9 mg, yield: 54%).
LCMS: (5-95, AB, 1.5 min, ESI), 0.824 min, MS=522.4. [½M+1]

$^1$H NMR DMSO-d$_6$ 400 MHz, δ 10.1 (s, 1H), 8.93 (s, 1H), 8.15-8.13 (d, 1H), 7.99 (s, 1H), 7.93-7.90 (d, 1H), 7.81-7.79 (d, 1H), 7.57-7.55 (d, J=8.0 Hz, 2H), 7.35-7.33 (d, J=8.0 Hz, 2H), 7.20-7.18 (m, 1H), 6.0 (m, 1H), 5.5 (m, 1H), 5.40 (s, 2H), 5.04 (s, 2H), 4.8 (m, 1H), 4.6-4.5 (m, 2H), 4.2-4.1 (m, 1H), 3.6 (s, 4H), 3.2 (m, 6H), 3.05-2.9 (m, 2H), 2.57 (s, 4H), 2.15-2.0 (m, 5H), 1.9-1.8 (m, 1H), 1.5-1.35 (m, 7H), 1.3-1.1 (m, 4H), 0.82-0.80 (m, J=8.0 Hz, 3H), 0.76-0.70 (m, 9H).

Example 61. 7-(4-((4-((S)-2-(4-((S)-1-((R)-2-(6-(2,5-dioxopyrrolidin-1-yl)hexanamido)propanamido)-2-methylpropyl)-1H-1,2,3-triazol-1-yl)-5-ureidopentanamido)benzyloxy)carbonyl)piperazin-1-yl)-1-ethyl-6-fluoro-4-oxo-1,4-dihydroquinoline-3-carboxylic acid
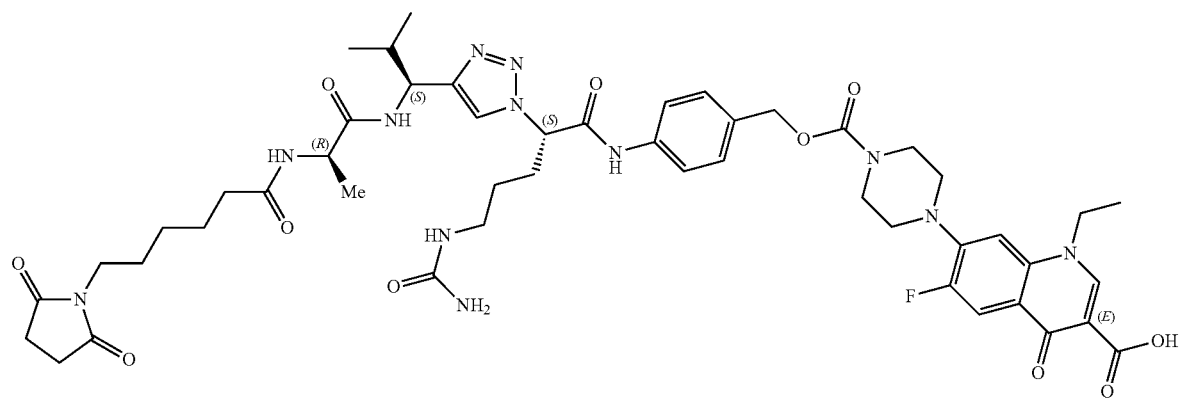
example 61
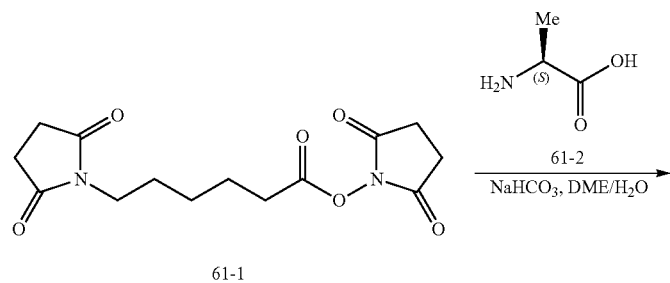
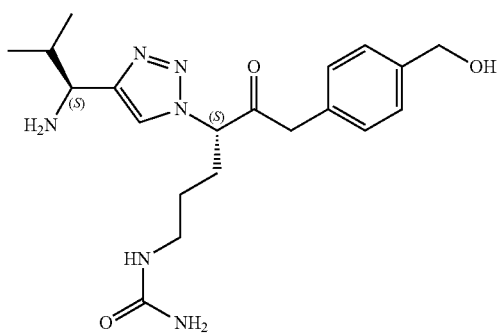
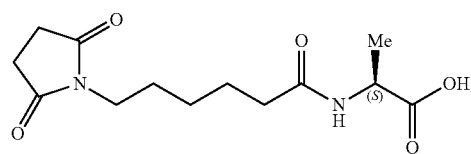

-continued

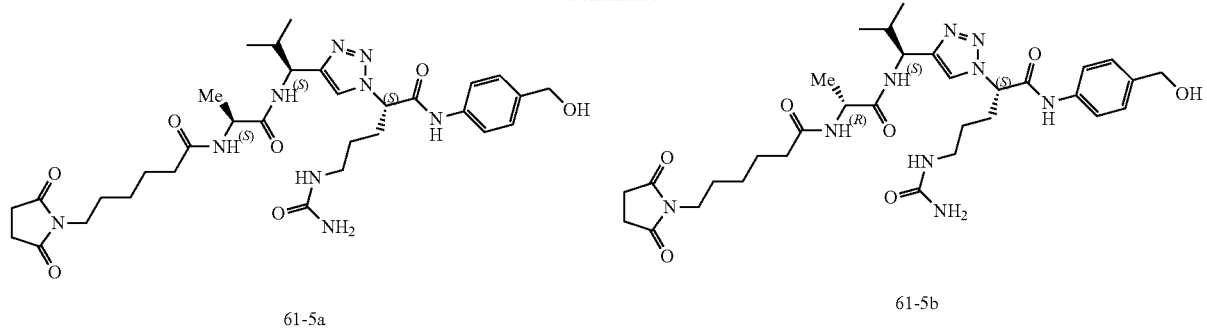

61-5a 61-5b

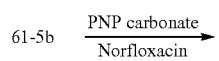

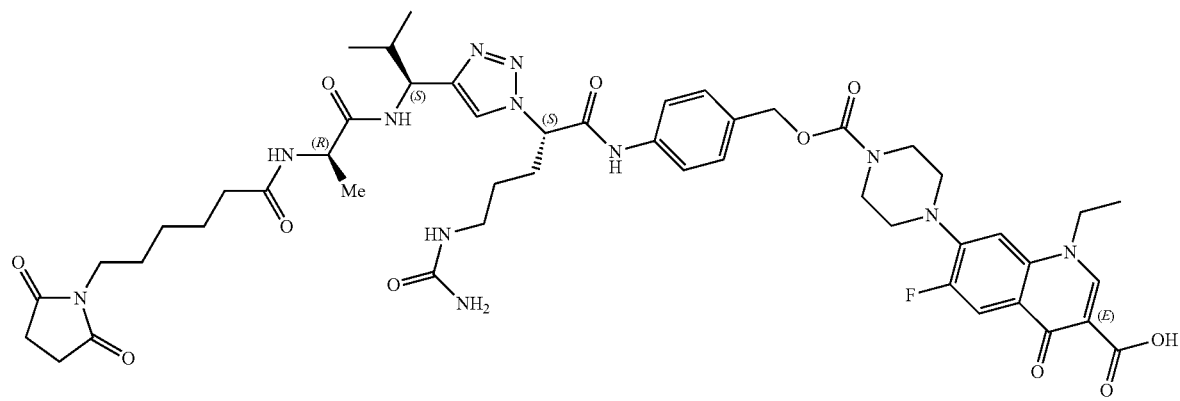

example 61

Step 1

To a solution of compound 61-2 (64 mg, 0.71 mmol) in DME (5 mL) was added a solution of compound 61-1 (200 mg, 0.71 mmol) and NaHCO$_3$ (122 mg, 1.42 mmol) in water (5 mL). After the mixture was stirred at r.t. for 16 h, it was washed with EtOAc and acidified to pH=3 with 10% HCl. The resulting suspension was extracted with EA. The combined organic layer was concentrated to give compound 61-3. (100 mg, contains impurity, Yield: 60%)

Step 2

Compound 61-3 (100 mg, 0.35 mmol), HATU (267 mg, 0.7 mmol), DIPEA (136 mg, 1.05 mmol) were dissolved in DMF (5 mL) and stirred at r.t. for 30 min. Compound 61-4 (142 mg, 0.35 mmol) was added and the reaction mixture was stirred at r.t. for 3 h. The mixture was concentrated and purified by prep-HPLC to give 61-5a and 61-5b (43 mg, 22 mg, 6%, 3%, respectively)

Step 3

To a solution of compound 61-5b (22 mg, 0.033 mmol) in dry DMF (2 mL) was added PNP carbonate (20 mg, 0.066 mmol) and DIPEA (0.2 mL, 1.2 mmol) at r.t., and the mixture was stirred at r.t. for 1.5 h. Norfloxacin (20 mg, 0.066 mmol) was added. The mixture was stirred at r.t. for another 1 h. The mixture was concentrated, filtered and purified by prep-HPLC (FA), to give example 61 (14.6 mg yield: 43%).

LCMS: (5-95, AB, 1.5 min, ESI), 0.805 min, MS=508.3. [½M+1]

$^1$H NMR methanol-d$_4$+CDCl$_3$ 400 MHz, δ 8.83 (s, 1H), 8.02-7.99 (m, 2H), 7.77 (solvent:CDCl$_3$), 7.59-7.57 (d, J=8.0 Hz, 2H), 7.36-7.34 (d, J=8.0 Hz, 2H), 7.15-7.13 (m, 1H), 5.5 (m, 1H), 5.11 (s, 2H), 4.95-4.9 (m, 1H), 4.55-4.45 (m, 2H), 4.4-4.35 (m, 1H), 3.7 (s, 4H), 3.45 (m, 2H), 3.4 (s, 4H), 3.25-3.05 (m, 2H), 2.66 (s, 4H), 2.3-2.1 (m, 5H), 1.6-1.5 (m, 7H), 1.5-1.3 (m, 2H), 1.3-1.2 (m, 5H), 0.96-0.94 (d, J=8.0 Hz, 3H), 0.87-0.85 (d, J=8.0 Hz, 3H).

Example 62. 7-(4-((4-((S)-2-(4-((S)-1-(benzyloxy-carbonylamino)-2,2-dimethylpropyl)-1H-1,2,3-triazol-1-yl)-5-ureidopentanamido)benzyloxy)carbonyl)piperazin-1-yl)-1-ethyl-6-fluoro-4-oxo-1,4-dihydroquinoline-3-carboxylic acid
example 62
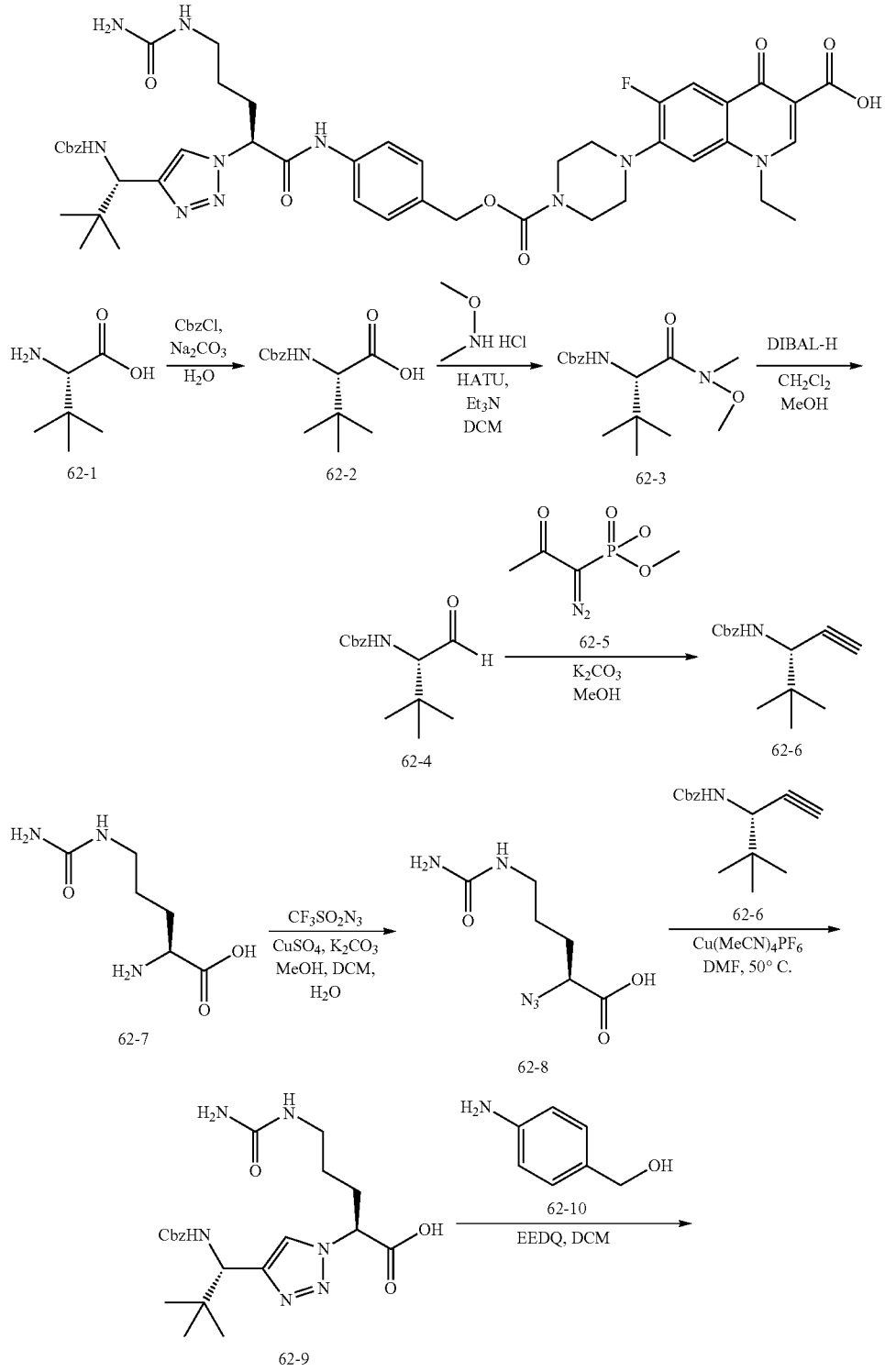

-continued

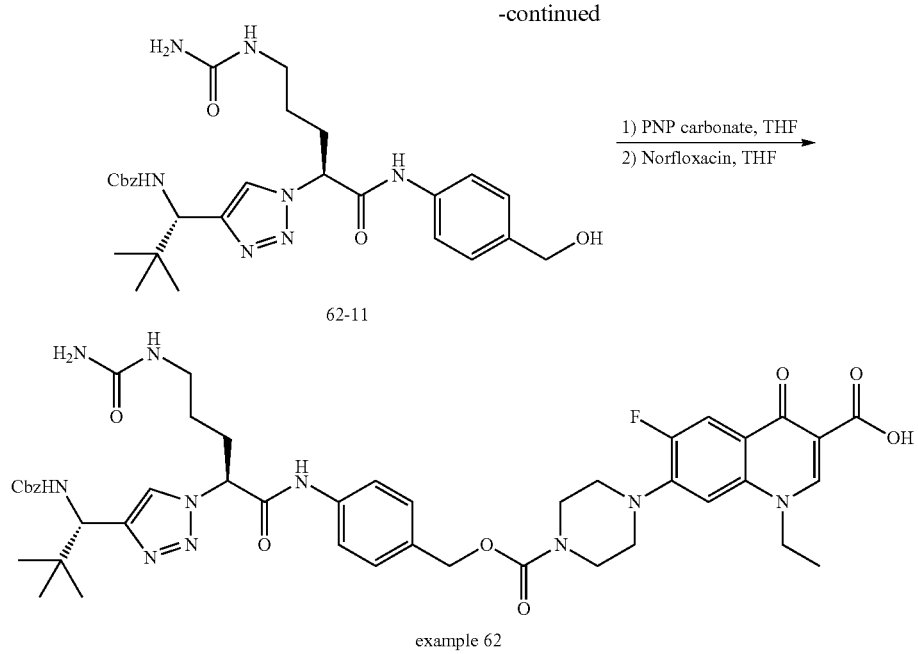

example 62

Step 1

CbzCl (24 mL, 0.17 mol) was added to dropwise over 20 min to a mixture of 62-1 (20 g, 0.15 mol) and $Na_2CO_3$ (32 g, 0.30 mol) in water (100 mL). After the reaction mixture was stirred for 12 h, it was washed with EtOAc (200 mL×2). The aqueous layer was adjusted to pH=2 and extracted with EtOAc (200 mL×4). The combined organic layers were dried over $Na_2SO_4$ and concentrated under reduced pressure to give 62-2, which was used for next step without further purification.

Step 2

To a mixture of 62-2 (10 g, 37.7 mmol), N,O-dimethylhydroxylamine (4.0 g, 41.5 mmol) and HATU (21.3 g, 56.0 mmol) in DCM (100 mL) was added $Et_3N$ (21.8 mL, 150.8 mmol). After the mixture was stirred at r.t. for 1 h, the solvent was removed and the crude was taken up with water (200 mL). The aqueous layer was extracted with EtOAc (200 mL×3). The extracts were washed with conc. HCl, aq. $NaHCO_3$, saturated NaCl. It was concentrated and purified by column chromatography on silica gel (PE:EtOAc=2:1) to give the 62-3.

Step 3

DIBAL-H (19.5 mL, 19.46 mmol) was added dropwise to a solution of compound 3 (4 g, 12.97 mmol) in DCM (60 mL) at −78° C. After the mixture was stirred at −78° C. for 4 h, excess hydride was quenched with MeOH (5 mL) and the resulting solution was warmed to r.t. The solution was concentrated to give compound 4, which was used for next step without further purification.

Step 4

After a mixture of 62-4 (3.23 g, 12.97 mmol), 62-5 (2.99 g, 15.56 mmol) and $K_2CO_3$ (3.58 g, 25.94 mmol) in MeOH (40 mL) was stirred at r.t. for 12 h, solvent was removed, and the residue was extracted with EtOAc (60 mL×3). The organic layers were washed with brine, dried over $Na_2SO_4$, concentrated and purified by column (PE:EtOAc=10:1) to give the 62-6.

Step 5

$Tf_2O$ (4.4 mL, 25.94 mmol) was added slowly over 5 min to a solution of $NaN_3$ (8.3 g, 129.7 mmol) in a mixture of $H_2O$ (45 mL) and DCM (75 mL) at 0° C. After it was stirred for 2 h, DCM layer was separated and the aqueous portion was extracted with DCM (35 mL×2). The organic fractions, containing the triflyl azide were pooled and washed once with saturated $Na_2CO_3$ and added to a mixture of 62-7 (2.27 g, 12.97 mmol), $K_2CO_3$ (2.69 g, 19.46 mmol) and $CuSO_4.5H_2O$ (323 mg, 1.30 mmol) in $H_2O$ (90 mL) and MeOH (180 mL). After the mixture was stirred for 12 h, organic solvents were removed under pressure and the aqueous slurry was diluted with phosphate buffers (0.2M, pH 6.2, 100 mL) and extracted with EtOAc (200 mL×2). The aqueous phase was then acidified to pH=2 with conc. HCl, and extracted with (400 mL×3). The organic layers were combined, dried over $Na_2SO_4$ and concentrated to give 62-8, which was used for next step without further purification.

Step 6

After a mixture of 62-8 (2.61 g, 12.97 mmol), 62-6 (1.59 g, 6.48 mmol) and $Cu(CH_3CN)_4PF_6$ (362 mg, 0.97 mmol) in DMF (5 mL) was stirred at 50° C. for 2 h, solvent was removed, and the residue was purified by prep-HPLC to give 62-9.

Step 7

After a mixture of 62-9 (968 mg, 2.17 mmol), 62-10 (801 mg, 6.50 mmol) and EEDQ (1.61 g, 6.50 mmol) in DCM (50 mL) was stirred at r.t. for 2 h, solvent was removed, and the residue was purified by prep-HPLC to give 62-11 (395.9 mg, 33.1%).

¹H NMR (400 MHz, MeOD) δ 8.11 (s, 1H), 7.59-7.56 (m, 2H), 7.37-7.27 (m, 7H), 5.55-5.51 (m, 1H), 5.13-5.05 (m, 2H), 4.79 (s, 1H), 4.58 (s, 2H), 3.34-3.32 (m, 1H), 3.25-3.11 (m, 1H), 2.28-2.22 (m, 2H), 1.48-1.41 (m, 2H), 0.96 (s, 9H).
LCMS (ESI): m/z 551.9 [M+H⁺].

Step 8

After a mixture of 62-11 (190 mg, 0.34 mmol), PNP carbonate (126 mg, 0.41 mmol) and DIPEA (132 mg, 1.02 mmol) in DCM (5 mL) was stirred at 50° C. for 12 h, solvent was removed and added to a mixture of norfloxacin (323 mg, 1.02 mmol) and DIPEA (132 mg, 1.02 mmol) in DMF (5 mL). After it was stirred at r.t. for 2 h solvent was removed, and the residue was purified by prep-HPLC to give example 62 (6.2 mg).

¹H NMR (400 MHz, DMSO-d₆) δ 15.31 (s, 1H), 10.66 (s, 1H), 8.96 (s, 1H), 8.15 (s, 1H), 7.94 (d, J=13.2 Hz, 1H), 7.72-7.70 (m, 1H), 7.60 (d, J=8.0 Hz, 2H), 7.38-7.28 (m, 8H), 6.04-6.03 (m, 1H), 5.52-5.51 (m, 1H), 5.42 (s, 2H), 5.07 (s, 2H), 5.03-5.01 (m, 2H), 4.66 (d, J=9.6 Hz, 1H), 4.58-4.56 (m, 2H), 3.61 (s, 4H), 3.41 (s, 4H), 3.02-2.98 (m, 2H), 2.12-2.02 (m, 2H), 1.42-1.39 (m, 3H), 1.26-1.23 (m, 2H), 0.84 (s, 9H).
LCMS (ESI): m/z 897.1 [M+H⁺].

Example 63. 7-(4-((4-((S)-2-(4-((S)-1-((S)-2-(6-(2,5-dioxopyrrolidin-1-yl)hexanamido)propanamido)-2-methylpropyl)-1H-1,2,3-triazol-1-yl)-5-ureidopentanamido)benzyloxy)carbonyl)piperazin-1-yl)-1-ethyl-6-fluoro-4-oxo-1,4-dihydroquinoline-3-carboxylic acid

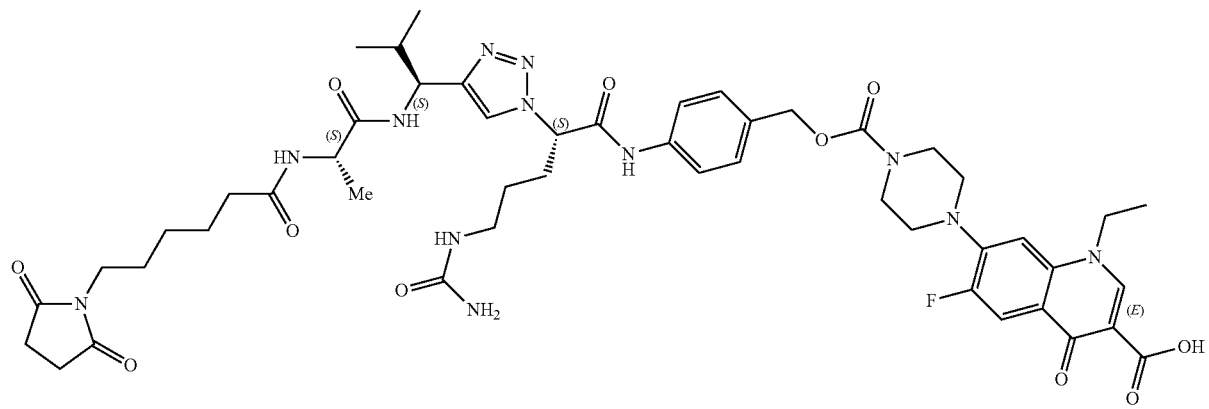

example 63

Example 63 was made using the procedure as Example 61, with intermediate from the synthesis of Example 61.

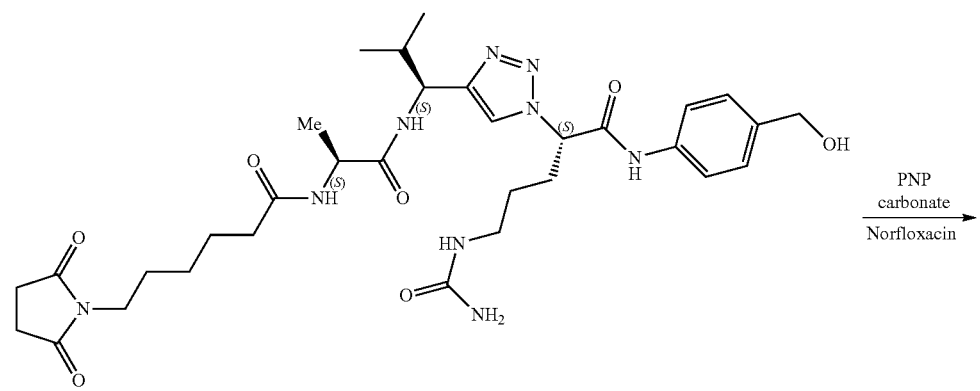

61-5a

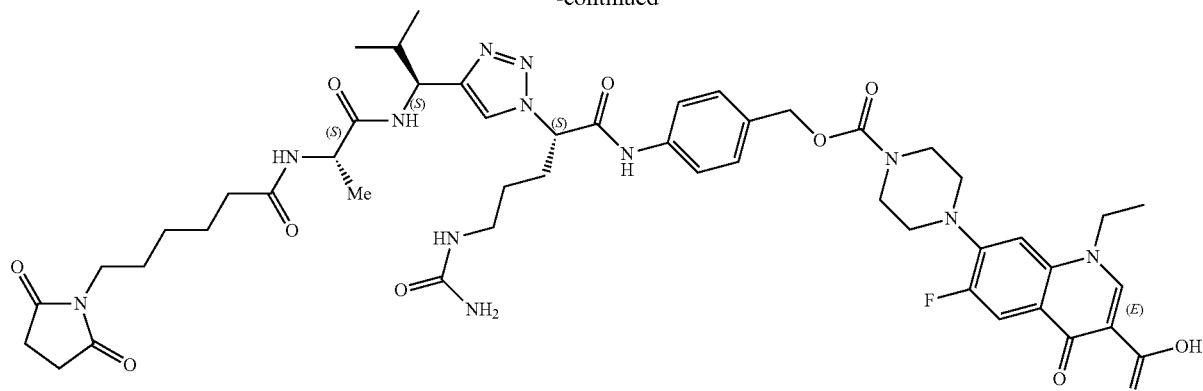

example 63

Step 1

To a solution of compound 61-5a (43 mg, 0.064 mmol) in dry DMF (3 mL) was added PNP carbonate (40 mg, 0.128 mmol) and DIPEA (0.4 ml, 2.4 mmol) at r.t., and the mixture was allowed to stir at r.t. for 1.5 h. Norfloxacin (40 mg, 0.128 mmol) was added. The mixture was stirred at r.t. for another 1 h. The mixture was concentrated, filtered and purified by prep-HPLC (FA), to give example 63 (33.8 mg, yield: 52%).

LCMS: (5-95, AB, 1.5 min, ESI), 0.803 min, MS=508.4 [½M+1]

$^1$H NMR Methanol-$d_4$ 400 MHz, δ 8.86 (s, 1H), 8.15-8.12 (d, 1H), 8.10-8.05 (m, 1H), 8.05-7.98 (d, 1H), 7.62-7.60 (d, J=8.0 Hz, 2H), 7.37-7.35 (d, J=8.0 Hz, 2H), 7.20-7.18 (m, 1H), 5.5 (m, 1H), 5.12 (s, 2H), 4.95-4.9 (m, 1H), 4.6-4.5 (m, 2H), 4.42-4.38 (m, 1H), 3.7 (s, 4H), 3.41 (m, 2H), 3.3 (s, 4H), 3.25-3.1 (m, 2H), 2.63 (s, 4H), 2.35-2.2 (m, 5H), 1.6-1.5 (m, 7H), 1.5-1.3 (m, 2H), 1.35-1.33 (d, J=8.0 Hz, 3H), 1.3-1.2 (m, 2H), 0.95-0.93 (d, J=8.0 Hz, 3H), 0.91-0.88 (d, J=8.0 Hz, 3H).

Example 64. 7-(4-(((4-((S)-2-(4-(((S)-1-acetamido-2-methylpropyl)-1H-1,2,3-triazol-1-yl)-5-ureidopentanamido)benzyloxy)carbonyl)piperazin-1-yl)-1-ethyl-6-fluoro-4-oxo-1,4-dihydroquinoline-3-carboxylic acid example 64

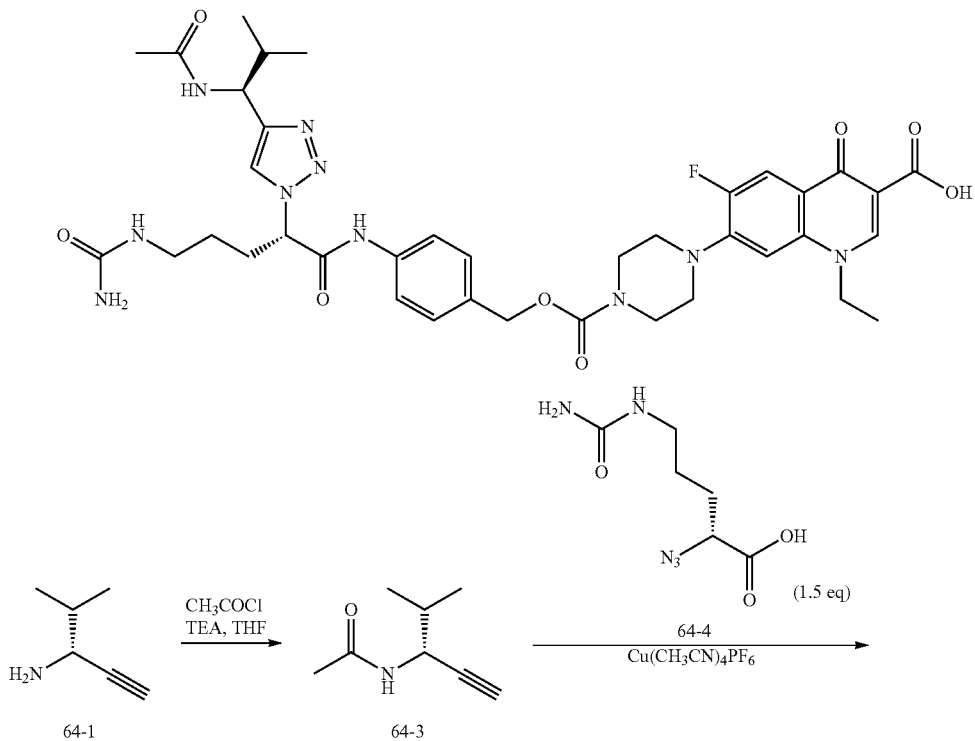

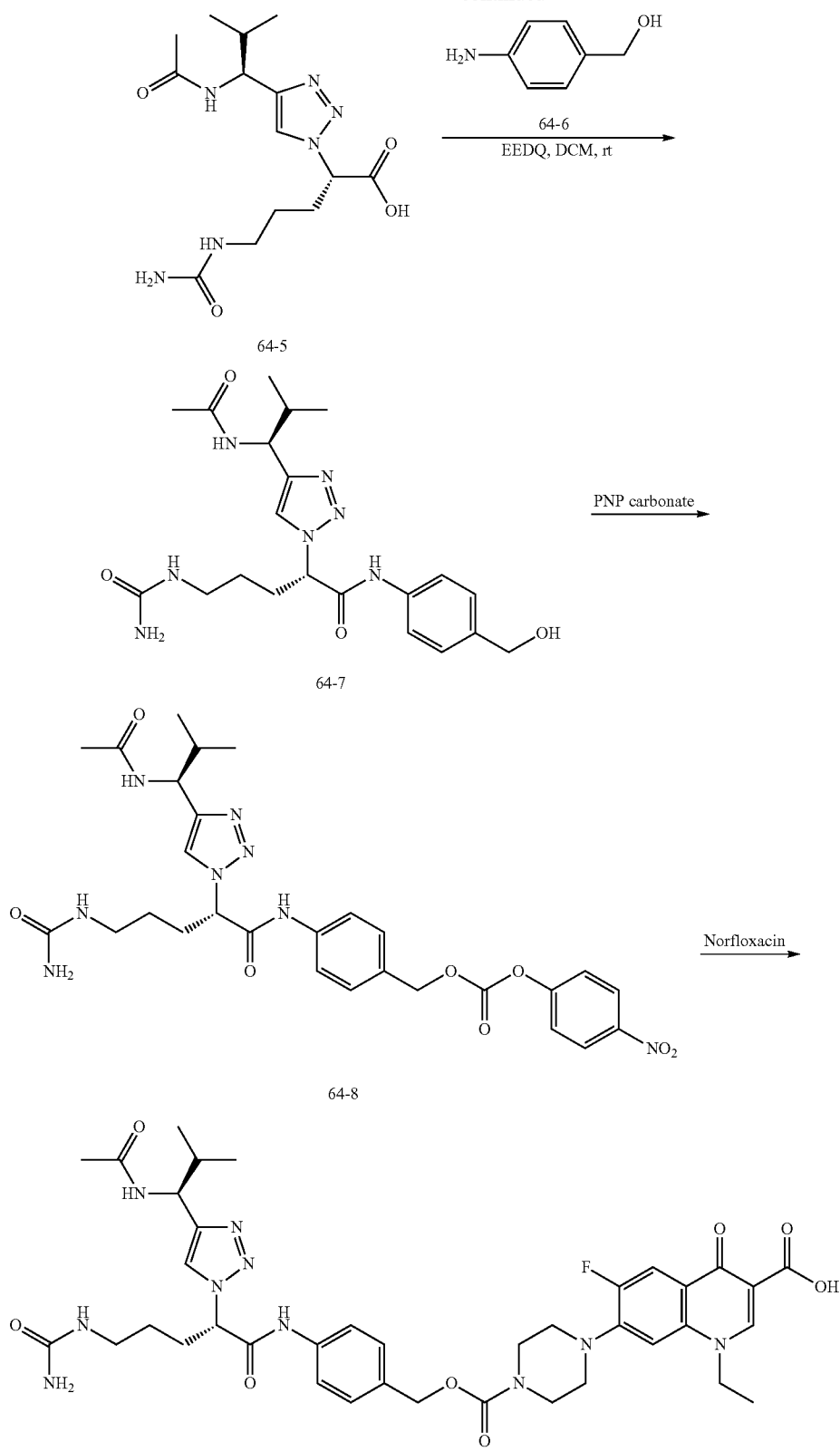

Step 1

To a stirred solution of 64-1 (1.1 g, 11.4 mmol) in THF was added 64-2 (4.5 mL, 57 mmol), TEA (9 mL, 62.7 mmol) at 0° C. The mixture was stirred at r.t. for 3 h under $N_2$. The reaction mixture was poured into water (30 mL) and extracted with DCM, the combined organic layers were washed with aqueous NaCl and concentrated to give the 64-3 (Yield: 95%).

Step 2

Compound 64-3 (139 mg, 1 mmol), 64-4 (302 mg, 1.5 mmol), $Cu(CH_3CN)_4PF_6$ (75 mg, 0.2 mmol) was dissolved in DMF (8 mL) at r.t. The mixture was stirred at 60° C. for 2 h. The mixture 64-5 was used for next step without further purification.

Step 3

To the crude mixture of 64-5 was added 64-6 (1.123 g, 9.12 mmol) and EEDQ (3 g, 12.2 mmol) at r.t. The mixture was stirred at r.t. for 16 h under $N_2$ atmosphere. The residue was purified by prep-HPLC and then purified by SFC to give 64-7. (Yield: 80%)
LCMS (ESI): m/z 446.0 [M+H$^+$].

Step 4

To a solution of 64-7 (30 mg, 0.068 mmol) in DMF (2 mL) was added PNP carbonate (42 mg, 0.136 mmol) and DIPEA (27 mg, 0.21 mmol) at 0° C. The mixture was stirred at r.t. for 16 h. The mixture 64-8 was used for next step without further purification. (Yield: 95%)
LCMS (ESI): m/z 611.2 [M+H$^+$].

Step 5

To the mixture that 64-8 was added norfloxacin (44 mg, 0.136 mmol) at r.t. The mixture was stirred at r.t. for 1 h. The residue was purified by prep-HPLC and then purified by SFC to give example 64 (Yield: 30%).
$^1$H NMR (400 MHz, DMSO-d$_6$) δ 10.62 (s, 1H), 8.96 (s, 1H), 8.17 (d, J=9.2 Hz, 1H), 8.06 (d, J=6.8 Hz, 1H), 7.94 (d, J=13.2 Hz, 1H), 7.60 (d, J=8.4 Hz, 2H), 7.36 (d, J=8.0 Hz, 2H), 7.21 (d, J=6.0 Hz, 1H), 6.02 (d, J=4.4 Hz, 1H), 5.51-5.42 (m, 3H), 5.07 (s, 2H), 4.90-4.86 (m, 1H), 4.59-4.57 (m, 2H), 3.65-3.61 (m, 4H), 3.06-2.96 (m, 2H), 2.12-1.87 (m, 3H), 1.86 (s, 3H), 1.48-1.35 (m, 3H), 1.28 (s, 2H), 0.89-0.72 (m, 6H).

Example 65: 7-(4-((4-((S)-2-(4-((S)-1-(benzyloxy-carbonylamino)-2-methylpropyl)-1H-1,2,3-triazol-1-yl)-5-ureidopentanamido)benzyloxy)carbonyl)piper-azin-1-yl)-1-ethyl-6-fluoro-4-oxo-1,4-dihydroquinoline-3-carboxylic acid

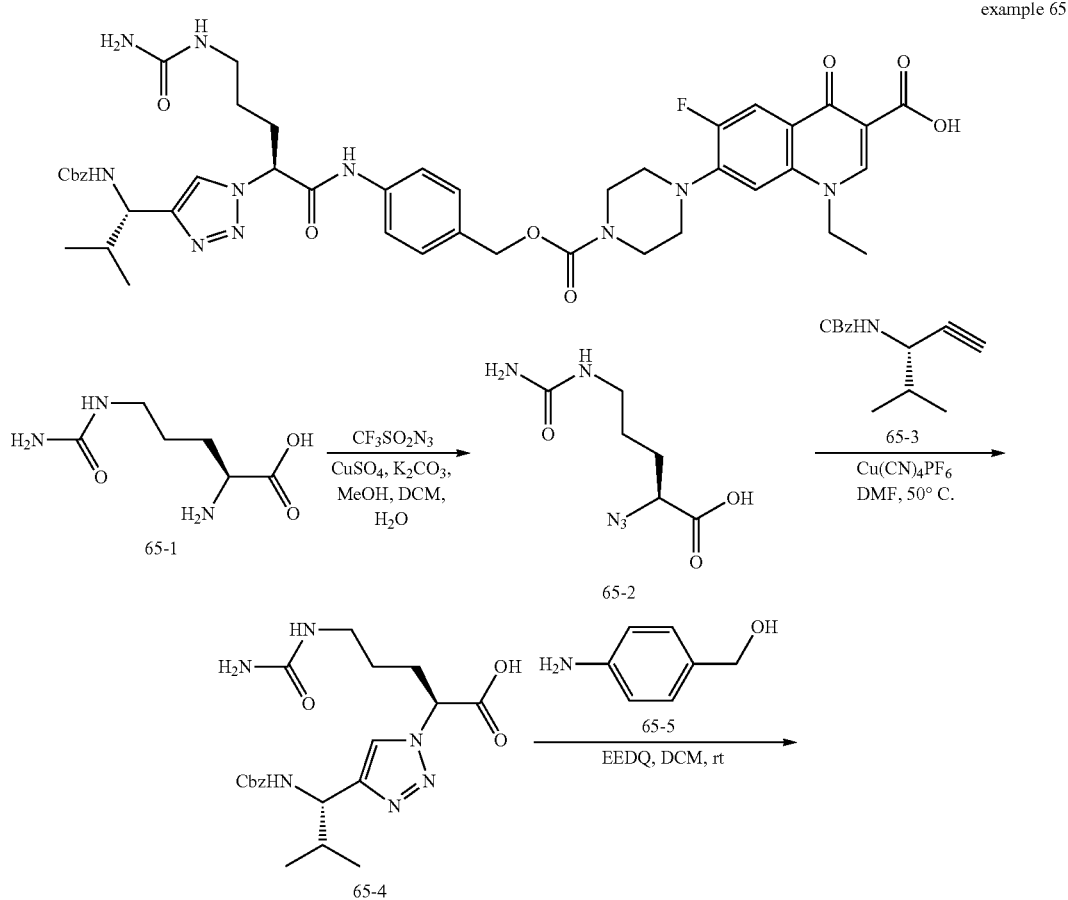

example 65

-continued

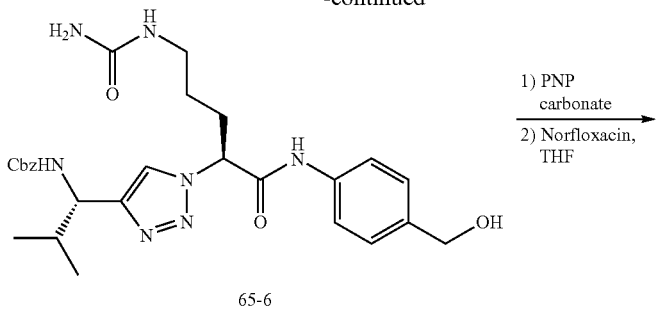

65-6

1) PNP carbonate
2) Norfloxacin, THF

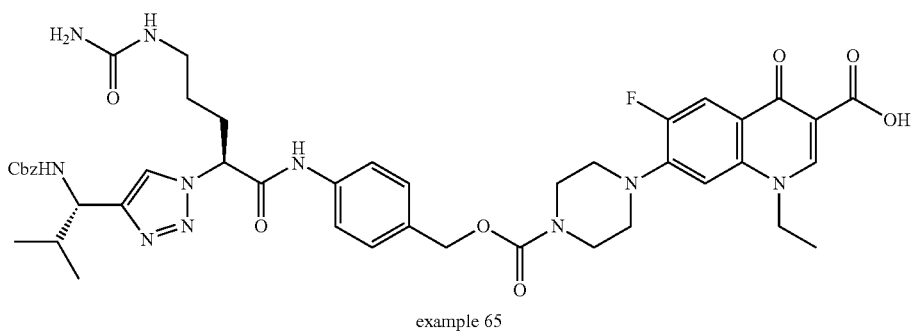

example 65

Step 1

Tf$_2$O (8.8 mL, 51.9 mmol) was added slowly over 5 min to a solution of NaN$_3$ (16.9 g, 259.4 mmol) in a mixture of distilled H$_2$O (30 mL) and CH$_2$Cl$_2$ (45 mL) at 0° C. After it was stirred for 2 h, the organic phase was separate and aqueous portion was extracted with CH$_2$Cl$_2$ (40 mL×2). The organic fractions, containing the triflyl azide, were pooled and washed once with saturated Na$_2$CO$_3$ and added to a mixture of 65-1 (2.3 g, 12.97 mmol), K$_2$CO$_3$ (2.69 g, 19.46 mmol) and CuSO$_4$.5H$_2$O (65 mg, 0.26 mmol) in H$_2$O (90 mL) and MeOH (180 mL). After the mixture was stirred at 26° C. for 12 h, the organic solvents were removed under reduced pressure and the aqueous slurry was diluted with H$_2$O (50 mL). The mixture was acidified to pH=6 with conc. HCl and then diluted with phosphate buffers (0.2 M, pH 6.2, 50 mL). The mixture was washed with EtOAc (100 mL×2) and the aqueous phase was then acidified to pH=2 with conc.HCl. The mixture was extracted with EtOAc (200 mL×3). The organic layer was dried over Na$_2$SO$_4$ and concentrated to give 65-2, which was used for next step without further purification.

Step 2

After a mixture of 65-2 (2.6 g, 12.97 mmol), 65-3 (1.5 g, 6.48 mmol) and Cu(MeCN)$_4$PF$_6$ (304 mg, 0.97 mmol) in DMF (10 mL) was stirred at 50° C. for 2 h, solvent was removed, and the residue was purified by prep-HPLC to give 65-4 (516 mg, 18%).

Step 3

After a mixture of 65-4 (285 mg, 0.66 mmol), 65-5 (244 mg, 1.98 mmol) and EEDQ (490 mg, 1.98 mmol) in DCM (30 mL) was stirred at 24° C. for 2 h, solvent was removed, and the residue was purified by prep-HPLC to give 65-6 (250 mg, 70.4%).

$^1$H NMR (400 MHz, MeOD) δ 8.10 (s, 1H), 7.58 (s, 2H), 7.45-7.20 (m, 7H), 5.55-5.52 (m, 1H), 5.10-5.05 (m, 2H), 4.77-4.58 (m, 3H), 3.22-3.21 (m, 2H), 2.33-2.15 (m, 3H), 1.49-1.47 (m, 2H), 0.97 (s, 3H), 0.90 (s, 3H).

LCMS (ESI): m/z 538.3 [M+H$^+$].

Step 4

After a mixture of 65-6 (127 mg, 0.24 mmol), PNP (143 mg, 0.47 mmol) and DIPEA (92 mg, 0.71 mmol) in DCM (10 mL) was stirred at 50° C. for 12 h, solvent was removed and the residue was mixed with DIPEA (93 mg, 0.72 mmol) and norfloxacin (230 mg, 0.72 mmol) in DMF (10 mL). After it was stirred at 24° C. for 4 h, solvent was removed, and the residue was purified by prep-HPLC to give example 65 (30 mg, 14.1%).

$^1$H NMR (400 MHz, DMSO-d$_6$) δ 15.32 (s, 1H), 10.63 (s, 1H), 8.96 (s, 1H), 8.08 (s, 1H), 7.94 (d, J=13.2 Hz, 1H), 7.71 (d, J=9.2 Hz, 1H), 7.60 (d, J=8.4 Hz, 2H), 7.38-7.29 (m, 8H), 7.21 (d, J=7.6 Hz, 1H), 6.02 (s, 1H), 5.48-5.47 (m, 1H), 5.42 (s, 2H), 5.06 (s, 2H), 5.02 (s, 2H), 4.62-4.60 (m, 3H), 3.61 (s, 4H), 3.44 (s, 4H), 3.02-2.99 (m, 2H), 2.12-2.02 (m, 3H), 1.40 (t, J=6.8 Hz, 3H), 1.27-1.24 (m, 2H), 0.84 (d, J=6.8 Hz, 3H), 0.78 (d, J=6.8 Hz, 3H).

LCMS (ESI): m/z 883.7 [M+H$^+$].

Example 66. 7-(4-((4-((S)-2-(4-((S)-(benzyloxycarbonylamino)(cyclopropyl)methyl)-1H-1,2,3-triazol-1-yl)-5-ureidopentanamido)benzyloxy)carbonyl)piperazin-1-yl)-1-ethyl-6-fluoro-4-oxo-1,4-dihydroquinoline-3-carboxylic acid
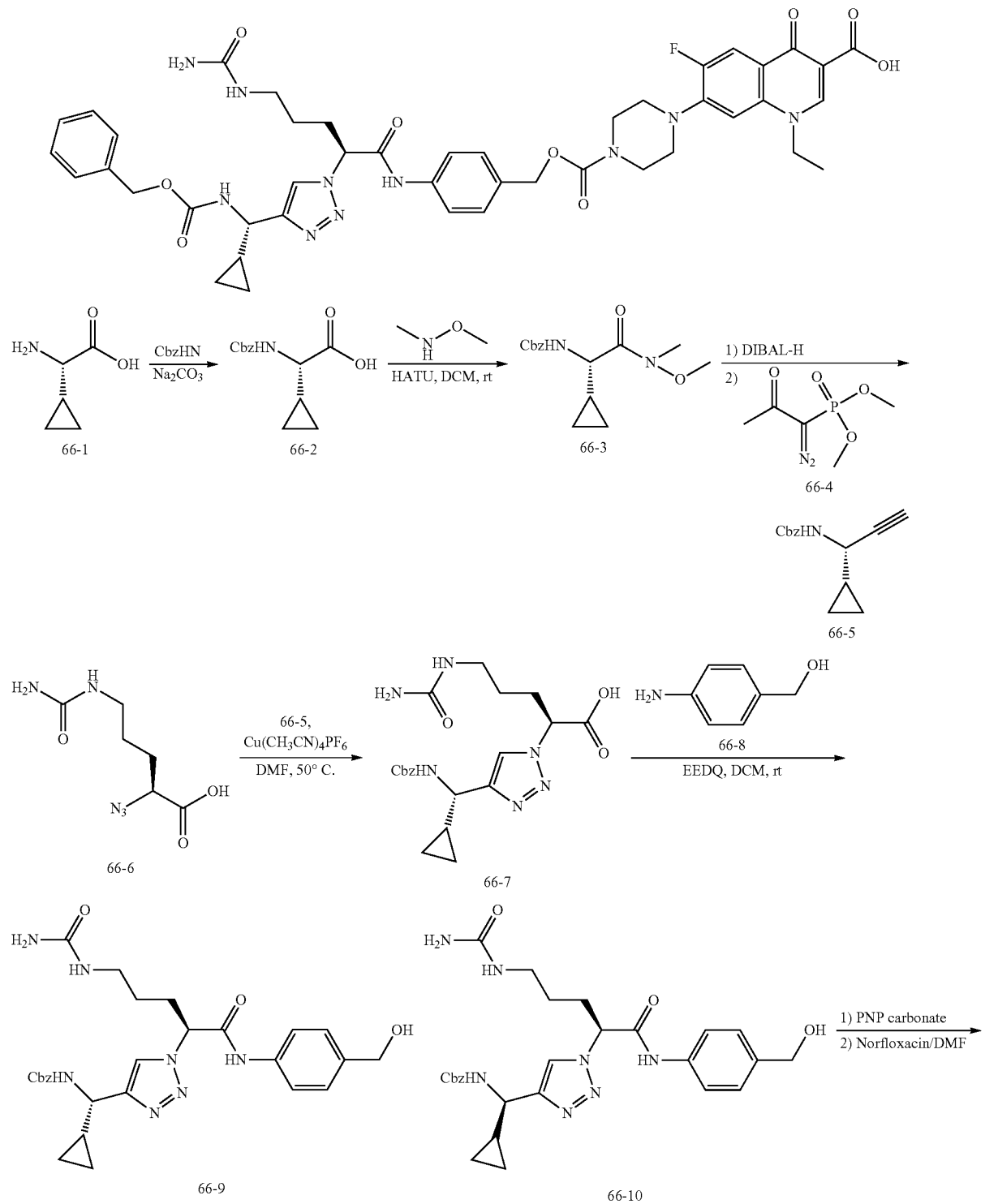

-continued

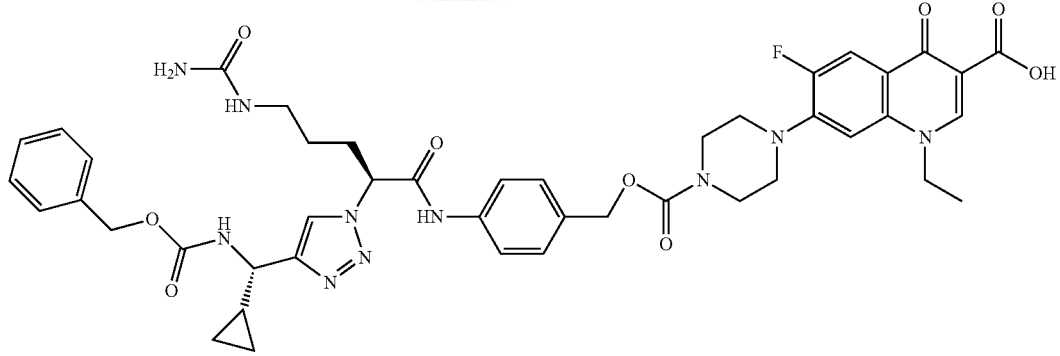

example 66

Step 1

To a mixture of 66-1 (5.0 g, 43.43 mmol) and $Na_2CO_3$ (6.9 g, 65.15 mmol) in $H_2O$ (50 mL) was added CbzCl (8.89 g, 52.12 mmol) dropwise at 0° C. After the reaction mixture was stirred at 25° C. for 16 h, it was washed with EtOAc (30 mL×2). The aqueous phase was acidified to pH 2 with conc. HCl, and extracted with EtOAc (50 mL×2). The combined organic layer was dried over $Na_2SO_4$ and concentrated under reduced pressure to give 66-2 (11 g, crude).

$^1$H NMR (400 MHz, $CDCl_3$) δ 7.38-7.29 (m, 5H), 5.13-5.08 (m, 2H), 4.72-4.68 (m, 1H), 1.12-1.09 (m, 1H), 0.61-0.43 (m, 4H).

Step 2

To a mixture of 66-2 (500 mg, 2.006 mmol), N, O-dimethylhydroxylamine hydrochloride (235 mg, 2.407 mmol) and $Et_3N$ (609 mg, 6.018 mmol) in DCM (10 mL) was added HATU (1.14 g, 3.009 mmol) at 25° C. After it was stirred at 25° C. for 2 h, solvent was removed and the residue was taken up with water (10 mL). The aqueous layer was extracted with EtOAc (8 mL×2). The organic layer was washed with saturated $Na_2CO_3$ solution (10 mL), 1N HCl solution (10 mL), then water (10 mL). The organic layer was dried over $Na_2SO_4$, filtered and concentrated. The crude was purified by column chromatography on silica gel (PE/EtOAc=2:1) to give 66-3 (400 mg, 68%).

LCMS (ESI): m/z 293.1 [M+H$^+$].

Step 3

DIBAL-H in toluene (1M, 18 mL, 18 mmol) was added to a mixture of 66-3 (3.5 g, 11.97 mmol) in DCM (30 mL) at −78° C. After the mixture was stirred at −78° C. for 3 h, MeOH (5 mL) was added dropwise. The mixture was warmed to 25° C. Solvent was removed and it was dissolved in MeOH (25 mL) and $K_2CO_3$ (3.31 g, 23.94 mmol) and 66-4 (2.76 g, 14.36 mmol) was added at 0° C. The mixture was stirred at 25° C. for 16 h. After solvent was removed, the crude was taken up with 1N HCl solution (30 mL), extracted with EtOAc (20 mL×3). The organic layer was dried over $Na_2SO_4$, concentrated and purified by column chromatography on silica gel (PE/EtOAc=5:1-2:1) to give 66-5 (1.5 g, 55%).

$^1$H NMR (400 MHz, $CDCl_3$) δ 7.41-7.30 (m, 5H), 5.12-5.05 (m, 3H), 4.47 (m, 1H), 2.24 (s, 1H), 1.18-1.11 (m, 1H), 0.56-0.47 (m, 4H).

Step 4

$Cu(CH_3CN)_4PF_6$ (366 mg, 0.981 mmol) was added to a solution of 66-6 (2.63 g, 13.08 mmol) and 66-5 (1.5 g, 6.54 mmol) in DMF (10 mL) at 25° C. The reaction mixture was stirred at 50° C. for 2 h under $N_2$. Solvent was removed and the residue was purified by prep-HPLC to give 66-7 (3.0 g, 53%).

$^1$H NMR (400 MHz, DMSO-$d_6$) δ 8.01 (s, 1H), 7.83-7.81 (m, 1H), 7.37-7.14 (m, 5H), 5.97 (br, 1H), 5.40-5.38 (m, 1H), 5.03-4.99 (m, 2H), 4.32-4.28 (m, 1H), 2.94 (s, 2H), 2.17-2.07 (m, 2H), 1.30-1.10 (m, 3H), 0.50-0.26 (m, 4H).

Step 5

A solution of 66-7 (1.0 g, 2.32 mmol), 66-8 (571 mg, 4.64 mmol) and EEDQ (1.15 g, 4.64 mmol) in DCM (15 mL) was stirred at 25° C. for 2 h. After removal of the solvent, the residue was purified by prep-HPLC and SFC to give 66-9 (500 mg) and of 66-10 (112 mg).

$^1$H NMR (400 MHz, DMSO-$d_6$) δ 10.60 (s, 1H), 8.10 (s, 1H), 7.82 (d, J=9.2 Hz, 1H), 7.56-7.54 (m, 2H), 7.36-7.25 (m, 7H), 6.08-6.05 (m, 1H), 5.51-5.43 (m, 3H), 5.14 (t, J=5.6 Hz, 1H), 5.03 (s, 2H), 4.44 (d, J=5.6 Hz, 2H), 4.31 (t, J=8.4 Hz, 1H), 3.04-2.97 (m, 2H), 2.15-2.08 (m, 2H), 1.30-1.23 (m, 3H), 0.49-0.30 (m, 4H).

LCMS (ESI): m/z 536.3 [M+H$^+$].

$^1$H NMR (400 MHz, DMSO-$d_6$) δ 10.54 (s, 1H), 8.09 (s, 1H), 7.82-7.80 (m, 1H), 7.56-7.54 (m, 2H), 7.36-7.26 (m, 7H), 6.03-6.01 (m, 1H), 5.49-5.42 (m, 3H), 5.13 (t, J=5.6 Hz, 1H), 5.03 (s, 2H), 4.44 (d, J=5.6 Hz, 2H), 4.29 (t, J=8.4 Hz, 1H), 3.04-2.97 (m, 2H), 2.14-2.05 (m, 2H), 1.30-1.25 (m, 3H), 0.49-0.30 (m, 4H).

LCMS (ESI): m/z 536.4 [M+H$^+$].

Step 6

To a solution of 66-9 (80 mg, 0.149 mmol) in DCM (2 mL) were added PNP carbonate (136 mg, 0.447 mmol) and DIPEA (77 mg, 0.596 mmol) at 25° C. The mixture was heated at reflux for 20 h. Solvent was removed and residue was dissolved in DMF (2 mL) and norfloxacin (72 mg, 0.224 mmol) and DIEA (96 mg, 0.745 mmol) were added at 25° C., and mixture was stirred at 25° C. for 2 h. After removal of the solvent, the residue was purified by prep-TLC (DCM/MeOH=10:1) to give example 66 (23 mg, 18%).

$^1$H NMR (400 MHz, MDSO-$d_6$) δ 15.33 (s, 1H), 10.65 (s, 1H), 8.96 (s, 1H), 8.14 (s, 1H), 8.09 (s, 1H), 7.96-7.81 (m, 2H), 7.62-7.60 (m, 2H), 7.38-7.20 (m, 8H), 6.04-6.00 (m, 1H), 5.48-5.43 (m, 1H), 5.07 (s, 2H), 5.02 (s, 2H), 4.59-4.57 (m, 2H), 4.40-4.31 (m, 1H), 3.61 (s, 4H), 3.32 (s, 4H), 3.03-2.99 (m, 2H), 2.20-2.11 (m, 2H), 1.40 (t, J=7.2 Hz, 3H), 1.30-1.23 (m, 3H), 0.48-0.23 (m, 4H).

LCMS (ESI): m/z 881.4 [M+H$^+$].

Example 67. 7-(4-((4-((S)-2-(4-((S)-1-(2-(6-(2,5-dioxopyrrolidin-1-yl)hexanamido)acetamido)-2-methylpropyl)-1H-1,2,3-triazol-1-yl)-5-ureidopentanamido)benzyloxy)carbonyl)piperazin-1-yl)-1-ethyl-6-fluoro-4-oxo-1,4-dihydroquinoline-3-carboxylic acid
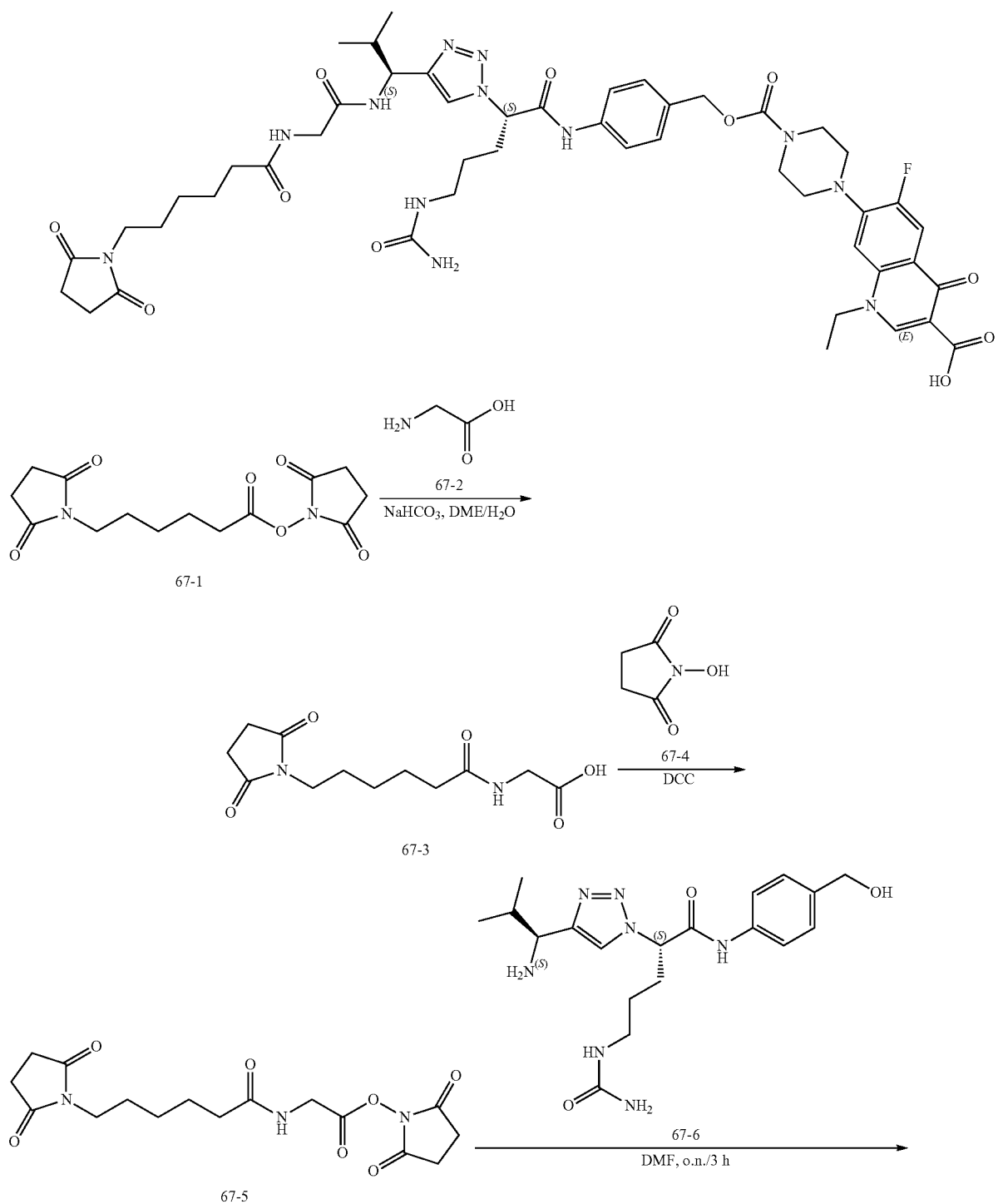

-continued

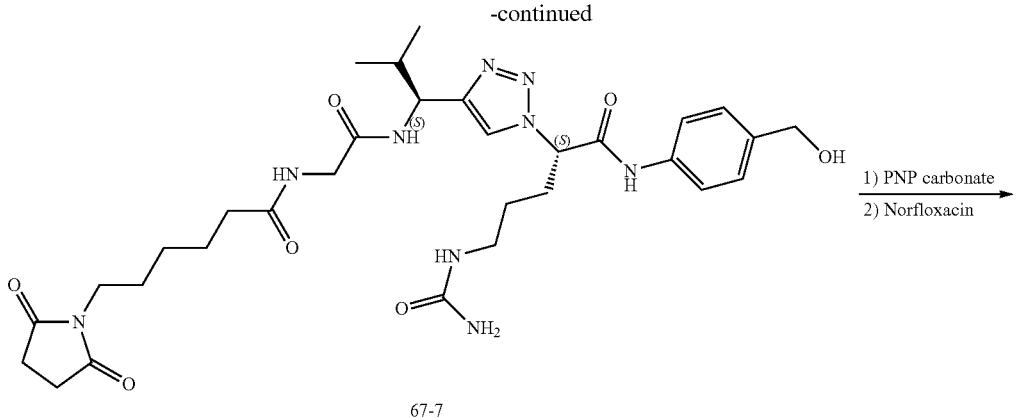

67-7

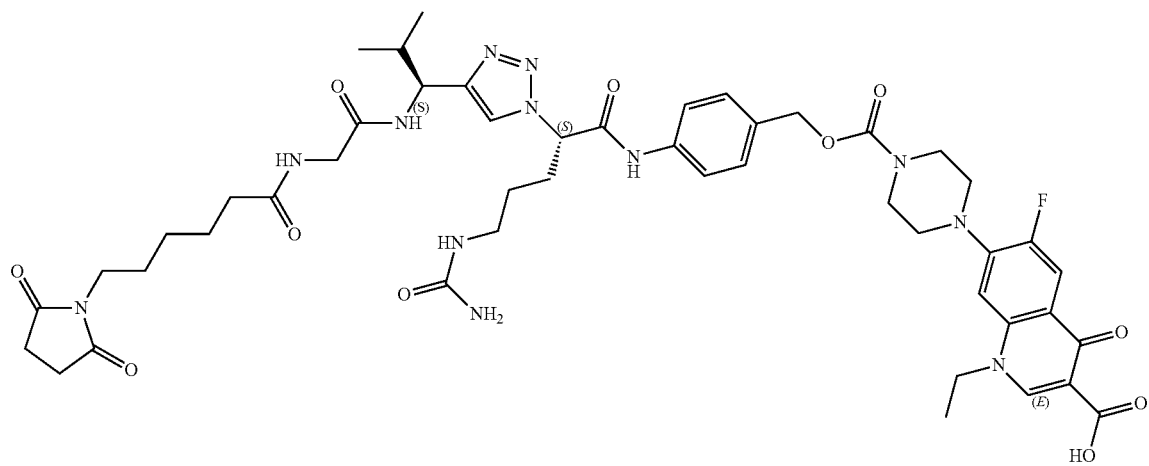

example 67

Step 1

To a solution of compound 67-2 (75 mg, 1 mmol) in DME (10 mL) was added a solution of compound 67-1 (310 mg, 1 mmol) and NaHCO$_3$ (252 mg, 3 mmol) in water (10 mL). The mixture was stirred at r.t. for 16 h. The mixture was washed with EtOAc and acidified to pH=3 with 10% HCl. The resulting suspension was extracted with EtOAc. The combined organic layer was concentrated to give compound 67-3 (270 mg, contains impurity).

Step 2

To a solution of compound 67-3 (200 mg, 0.74 mmol) and compound 67-4 (90 mg, 0.777 mmol) in THF (10 mL) was added DCC (161 mg, 0.777 mmol) at r.t. The mixture was stirred at r.t. for 16 h under N$_2$. It was concentrated and the filtrate was concentrated to give 67-5 (200 mg, Yield: 74%).

Step 3

Compound 67-5 (200 mg, 0.53 mmol), compound 67-6 (107 mg, 0.265 mmol) were dissolved in DMF (6 mL) and the reaction mixture was stirred at r.t. for 3 h. The mixture was filtered and purified by prep-HPLC to give 67-7 (25 mg, Yield: 6.3%) Step 4. To a solution of compound 67-7 (25 mg, 0.038 mmol) in dry DMF (3 mL) was added PNP carbonate (25 mg, 0.076 mmol) and DIPEA (15 mg, 0.114 mmol) at r.t. The mixture was stirred at r.t. for 1.5 h. Norfloxacin (30 mg, 0.076 mmol) was added. The mixture was stirred at r.t. for another 1 h. The mixture was concentrated, filtered and purified by prep-HPLC (FA), to give example 67 (20 mg, yield: 48%).

LCMS: (5-95, AB, 1.5 min, ESI), 0.802 min, MS=501.3. [½M+1]

$^1$H NMR Methanol-d$_4$+CDCl$_3$ 400 MHz, δ 8.83 (s, 1H), 7.99 (d, J=13.2 Hz, 2H), 7.59 (d, J=6.8 Hz, 2H), 7.35 (d, J=8.0 Hz, 2H), 7.11 (s, 1H), 5.51 (s, 1H), 5.12 (s, 2H), 4.95 (s, 1H), 4.47 (s, 2H), 3.86 (s, 2H), 3.71 (s, 4H), 3.48-3.44 (m, 2H), 3.31 (s, 4H), 3.25 (s, 1H), 3.15 (s, 1H), 2.67 (s, 4H), 2.26-2.20 (m, 5H), 1.65-1.61 (m, 6H), 1.58-1.52 (m, 1H), 1.33-1.29 (m, 4H), 0.95 (d, J=6.8 Hz, 3H), 0.88 (d, J=6.4 Hz, 3H).

Example 68. 7-(4-((4-((S)-2-(4-((S)-1-(6-(2,5-dioxo-2,5-dihydro-1H-pyrrol-1-yl)hexanamido)-2-methyl-propyl)-1H-1,2,3-triazol-1-yl)-5-ureidopentanamido)benzyloxy)carbonyl)piperazin-1-yl)-1-ethyl-6-fluoro-4-oxo-1,4-dihydroquinoline-3-carboxylic acid
example 68
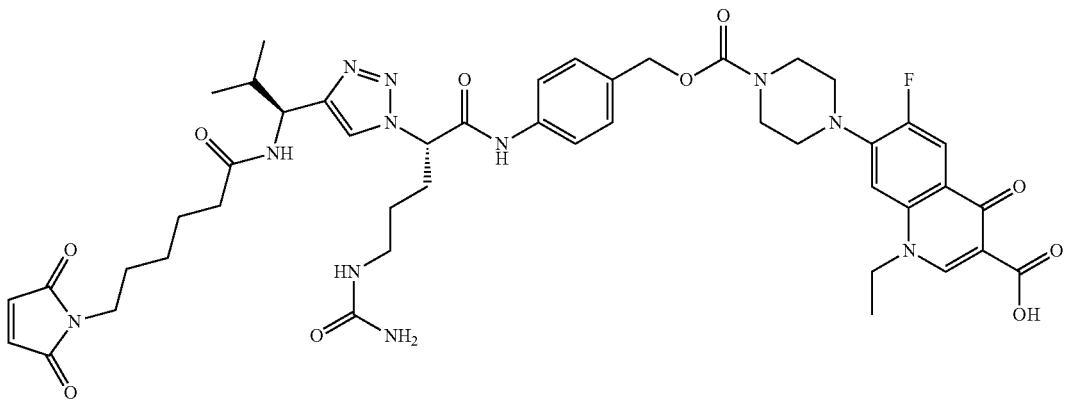
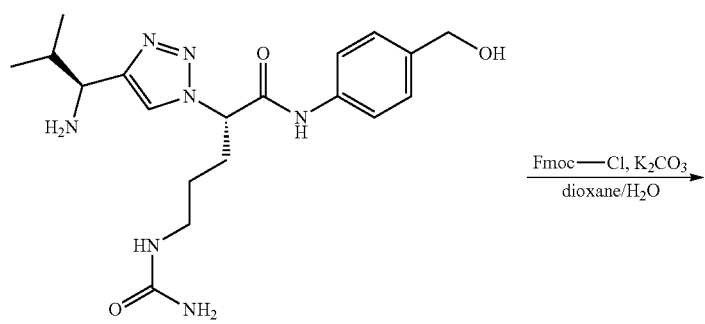
68-1
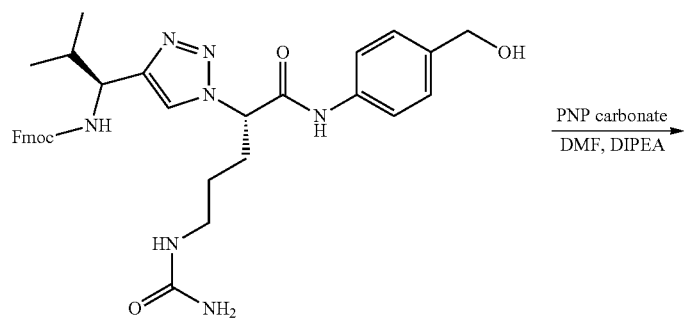
68-2

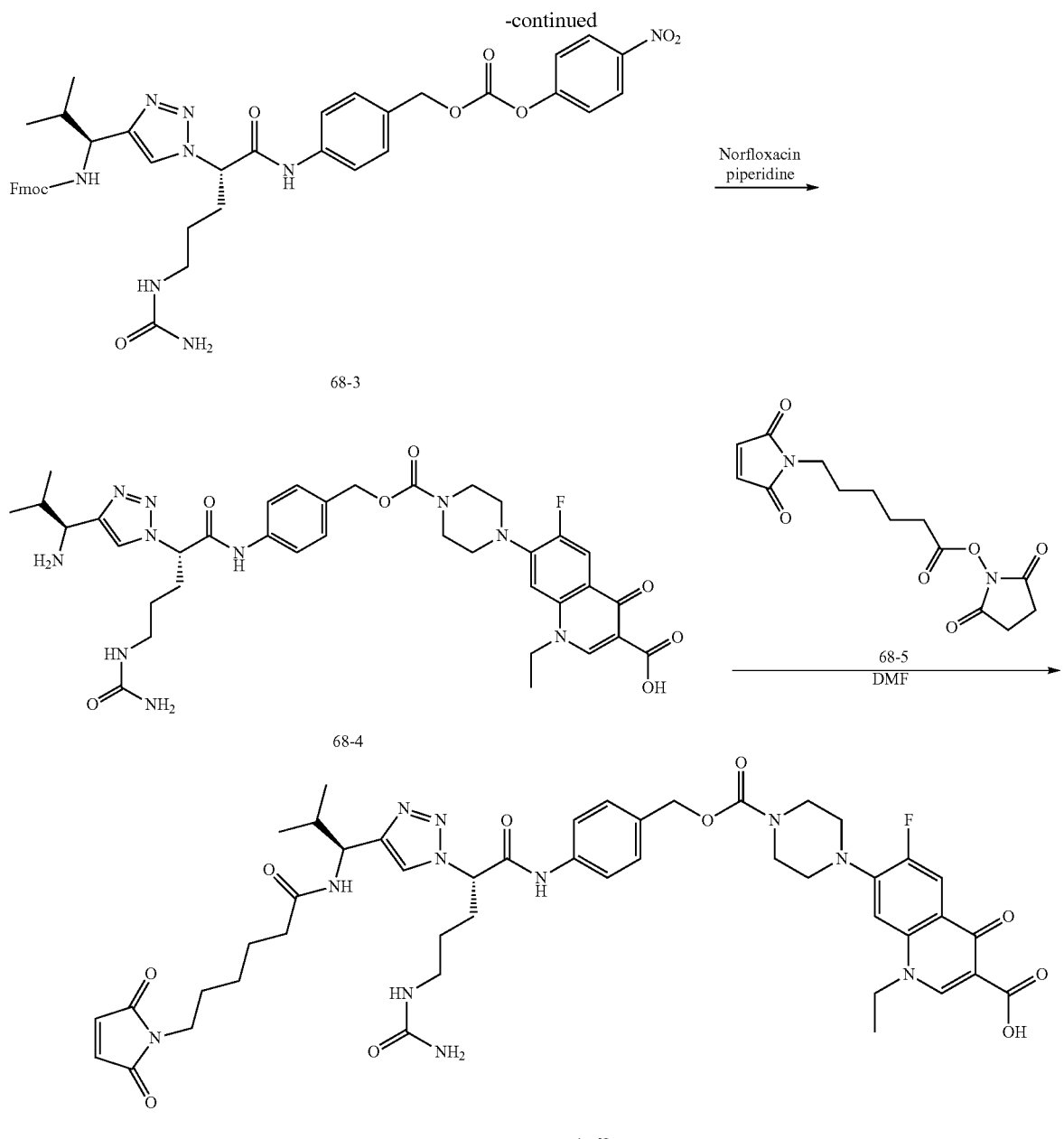

example 68

Step 1

To a solution of crude compound 68-1 (500 mg, 1.24 mmol) in 1,4-dioxane/H₂O (10 mL/5 mL) was added K₂CO₃ (428 mg, 3 mmol) and Fmoc-Cl (416 mg, 1.6 mmol) in dioxane (10 mL) dropwise. After the mixture was stirred at r.t. for 16 h, it was concentrated and purified by column chromatography (15%-20% MeOH in DCM) to give compound 68-2 (286 mg, 37%).

LCMS: (5-95, AB, 1.5 min, ESI), 0.709 min, MS=626.1 [M+1]

$^1$H NMR Methanol-$d_4$ 400 MHz, δ 8.06 (s, 1H), 7.80-7.78 (d, J=7.2 Hz, 2H), 7.67-7.63 (t, J=6.8 Hz, 2H), 7.58-7.56 (d, J=8.4 Hz, 2H), 7.39-7.27 (m, 6H), 5.6-5.5 (m, 1H), 4.69-4.67 (d, J=7.2 Hz, 1H), 4.57 (s, 2H), 4.40-4.36 (m, 2H), 4.25-4.15 (m, 1H), 3.3-3.2 (m, 1H), 3.2-3.1 (m, 1H), 2.35-2.15 (m, 3H), 1.55-1.35 (m, 2H), 0.98-0.97 (d, J=6.8 Hz, 3H), 0.90-0.88 (d, J=6.8 Hz, 3H).

Step 2

To a solution of compound 68-2 (200 mg, 0.31 mmol) in dry DMF (5 mL) was added PNP carbonate (185 mg, 0.62 mmol) and DIPEA (0.5 mL, 3.0 mmol) at r.t., and the mixture was stirred at r.t. for 1.5 h under nitrogen. Norfloxacin (197 mg, 0.62 mmol) was added. The mixture was stirred at r.t. for another 1 h. Then piperidine (0.1 mL, 1 mmol) was added. After 30 min, the mixture was purified by prep-HPLC to give compound 68-4 (250 mg, contained 4-nitrophenol). It was used in next step without further purification.

Step 3

To a solution of compound 68-4 (100 mg, 0.134 mmol) in dry DMF (2 mL) was added compound 5 (50 mg, 0.162 mmol). The mixture stirred at 23° C. for 2 h. The mixture was purified by prep-HPLC to give example 68 (20 mg, yield 16%).

LCMS: (5-95, AB, 1.5 min, ESI), 0.803 min, MS=942.4 [M+1], 471.8 [½M+1]

$^1$H NMR DMSO-$d_6$ 400 MHz, δ 15.3 (s, 1H), 10.60 (s, 1H), 8.94 (s, 1H), 8.1 (d, 1H) 8.01 (s, 1H), 7.94-7.90 (dd, J=12.8 Hz, 1H), 7.58-7.56 (d, J=8.8 Hz, 2H), 7.34-7.32 (d, J=8.8 Hz, 2H), 7.2 (d, 1H), 6.97 (s, 2H), 6.0 (m, 1H), 5.5-5.4 (m, 1H), 5.40 (s, 2H), 5.04 (s, 2H), 4.9-4.85 (m, 1H), 4.6-4.5 (m, 2H), 3.58 (s, 4H), 3.4-3.3 (m, 6H), 3.1-2.9 (m, 2H), 2.2-2.0 (m, 5H), 1.6-1.4 (m, 7H), 1.3-1.2 (m, 4H), 0.80-0.78 (d, J=6.8 Hz, 3H), 0.76-0.74 (d, J=6.8 Hz, 3H).

Example 69. 7-(4-((4-((S)-2-(4-((S)-1-(benzyloxy-carbonylamino)pentyl)-1H-1,2,3-triazol-1-yl)-5-ureidopentanamido)benzyloxy)carbonyl)piperazin-1-yl)-1-ethyl-6-fluoro-4-oxo-1,4-dihydroquinoline-3-carboxylic acid

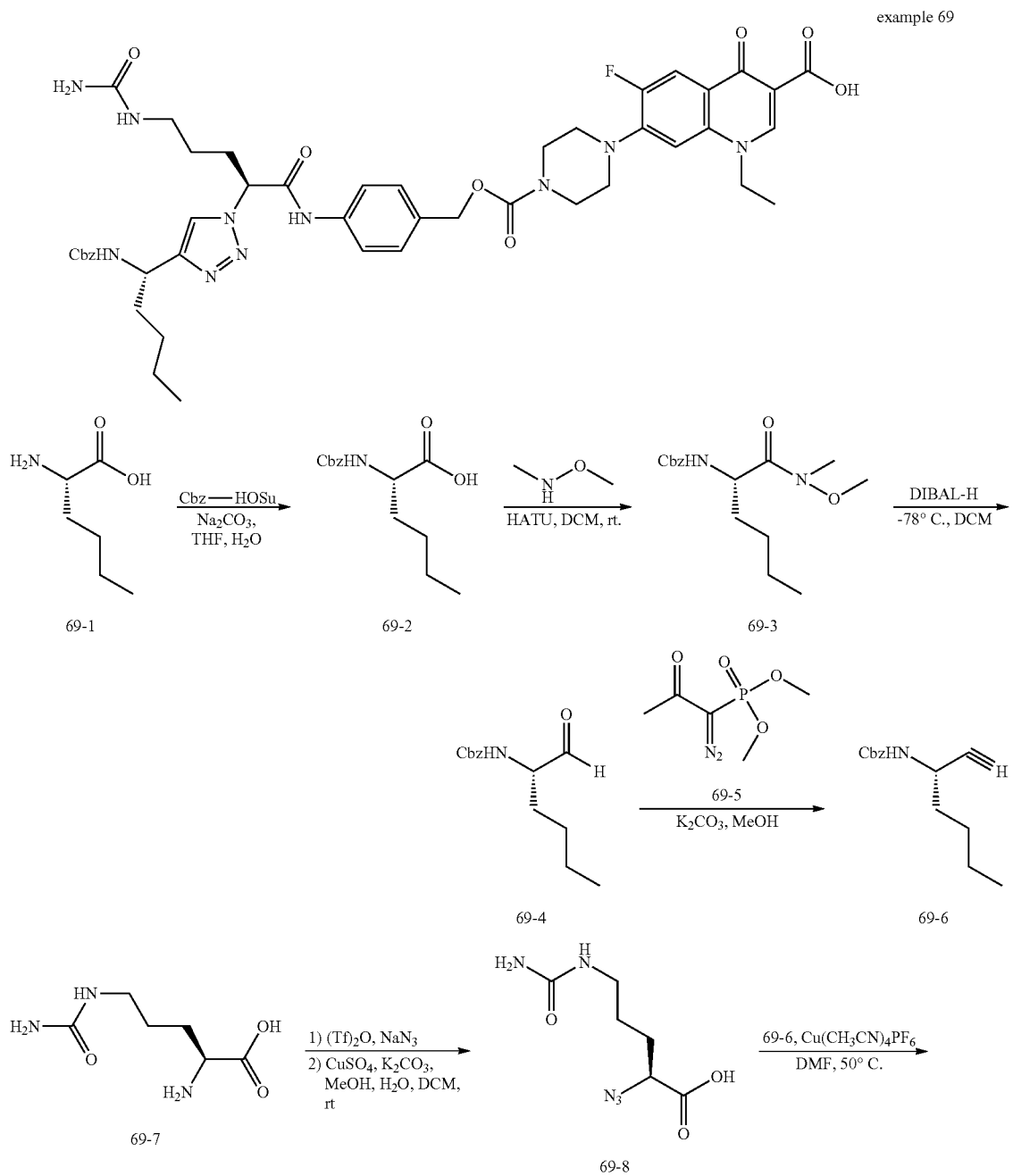

-continued
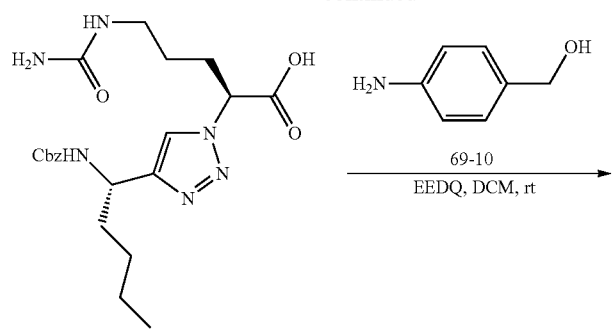
69-9
69-10
EEDQ, DCM, rt
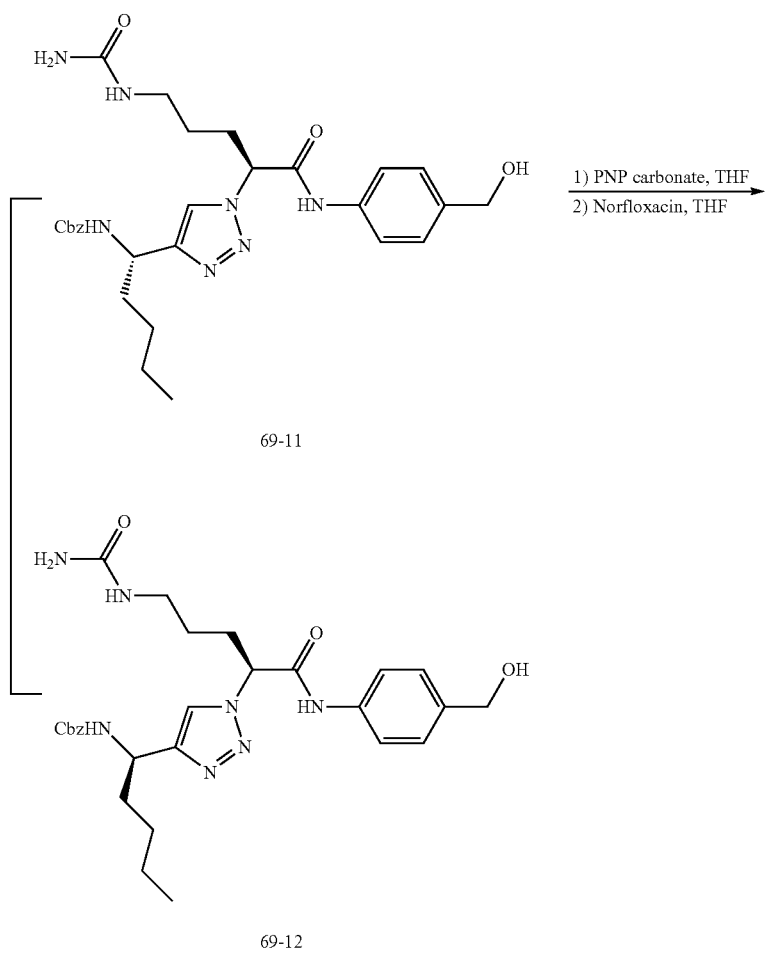
69-11
69-12
1) PNP carbonate, THF
2) Norfloxacin, THF

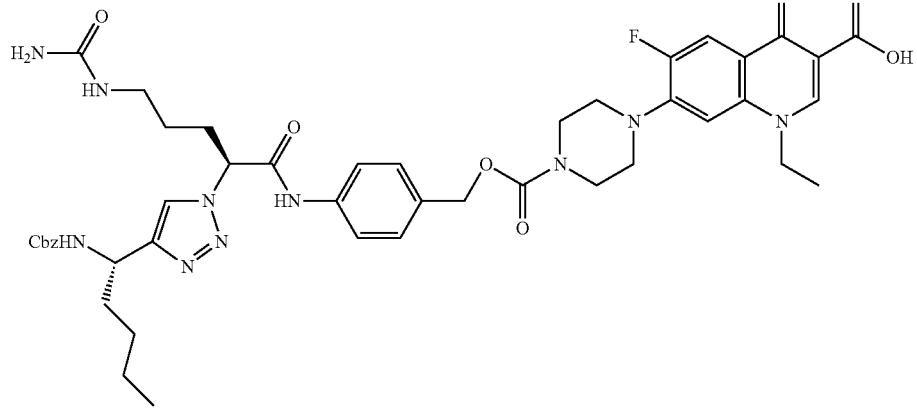

example 69

Step 1

To a mixture of aq Na₂CO₃ (16 g, 152.5 mmol) and 69-1 (5 g, 38.1 mmol) was added Cbz-OSu (11.4 g, 45.7 mmol) in THF (40 mL). After the mixture was stirred at r.t. for 16 h, it was adjusted to pH>10 and washed with EtOAc (100 mL×2). The aqueous layer was acidified to pH<1 with conc. HCl. The solution was extracted with EtOAc (200 mL×3). The organic layer was dried over Na₂SO₄ and concentrated to give 69-2 (9.7 g, 95.9%), which was used for next step without further purification.

Step 2

To a mixture of 69-2 (9.7 g, 36.6 mmol), N,O-dimethylhydroxylamine hydrochloride (3.9 g, 40.2 mmol) and HATU (20.8 g, 54.8 mmol) in DCM (100 mL) was added Et₃N (21 mL, 146.2 mmol). After the mixture was stirred at r.t. for 2 h, solvent was removed, and the crude was taken up with water (150 mL) and extracted with EtOAc (150 mL×3). The organic layer was washed with saturated NaHCO₃, conc. HCl, saturated NaCl and concentrated. The residue was purified by column chromatography on silica gel (PE:EtOAc=2:1) to give 69-3 (10.1 g, 89.6%).

Step 3

DIBAL-H (19.5 mL, 1M in Tol) was added dropwise to a solution of 69-3 (4.0 g, 13.0 mmol) in anhydrous CH₂Cl₂ (50 mL) at −78° C. After the reaction mixture was stirred at −78° C. for 2 h, excess DIBAL was quenched by anhydrous MeOH (15 mL) and the mixture was warmed to r.t. It was concentrated to give 69-4 (3.2 g, crude), which was used for next step without further purification.

Step 4

After a mixture of 69-4 (3.2 g, 13.0 mmol), 69-5 (3.0 g, 15.6 mmol) and K₂CO₃ (3.6 g, 26.0 mmol) in MeOH (60 mL) was stirred at r.t. for 16 h, solvent was removed, and the residue was extracted with EtOAc (80 mL×3). The organic layers were washed with brine (60 mL) and dried over anhydrous Na₂SO₄, concentrated, and purified by column chromatography on silica gel (PE:EtOAc=10:1) to give 69-6 (1.9 g, 60.3%).

Step 5

Tf₂O (3.3 mL, 19.6 mmol) was added slowly to a solution of NaN₃ (6.3 g, 97.8 mmol) in H₂O (30 mL) and CH₂Cl₂ (48 mL) at 0° C. After it was stirred for 2 h, the organic phase was separated and the aqueous phase was extracted with CH₂Cl₂ (24 mL×2). The organic fractions, containing the triflyl azide, were pooled and washed once with saturated Na₂CO₃ and used without further purification. The triflyl azide solution in CH₂Cl₂ was added to a mixture of 69-7 (1.71 g, 13.9 mmol), K₂CO₃ (2.03 g, 14.67 mmol) and CuSO₄.5H₂O (245 mg, 0.98 mmol) in H₂O (54 mL) and MeOH (108 mL). After the mixture was stirred at 26° C. for 12 h, the organic solvents were removed under reduced pressure and the aqueous slurry was diluted with H₂O (200 mL). The mixture was acidified to pH 6 with conc. HCl and diluted with phosphate buffers (0.2M, pH 6.2, 200 mL) and washed with EtOAc (300 mL×2). The aqueous phase was then acidified to pH=2 with conc. HCl. It was extracted with (300 mL×3), and the extracts were dried over Na₂SO₄ and concentrated to give 69-8, which was used for next step without further purification.

Step 6

After a mixture of 69-8 (2.0 g, 9.78 mmol), 69-6 (1.2 g, 4.89 mmol) and Cu(CH₃CN)₄PF₆ (273 mg, 0.73 mmol) in DMF (5 mL) was stirred at 50° C. for 2 h, solvent was removed, and the residue was purified by prep-HPLC to give 69-9 (600 mg, 27.5%).

Step 7

After a mixture of 69-9 (600 mg, 1.34 mmol), 69-10 (496 mg, 4.03 mmol) and EEDQ (996 mg, 4.03 mmol) in DCM (15 mL) was stirred at 23° C. for 4 h, solvent was removed, and the residue was purified by prep-HPLC and SFC to give 69-11 (350 mg, 47.4%) and 69-12 (23.1 mg).

¹H NMR (400 MHz, MeOD) δ 8.02 (s, 1H), 7.54 (d, J=6.8 Hz, 2H), 7.34-7.25 (m, 7H), 5.49-5.46 (m, 1H), 5.08 (s, 2H), 4.55 (s, 2H), 3.37-3.33 (m, 1H), 3.24-3.16 (m, 1H), 2.24-1.80 (m, 3H), 1.45-1.43 (m, 7H), 1.41 (s, 3H).

LCMS (ESI): m/z 552.1 [M+H⁺].

¹H NMR (400 MHz, MeOD) δ 10.53 (s, 1H), 8.03 (s, 1H), 7.55 (d, J=9.2 Hz, 1H), 7.35 (d, J=4.0 Hz, 2H), 7.31-7.26 (m, 7H), 6.04 (s, 1H), 5.50-5.43 (m, 3H), 5.12-5.03 (m, 3H), 4.77-4.73 (m, 1H), 4.44 (d, J=3.2 Hz, 2H), 3.08-2.91 (m, 2H), 2.24-2.16 (m, 2H), 1.90-1.71 (m, 2H), 1.35-1.20 (m, 6H), 0.86-0.83 (m, 3H).

LCMS (ESI): m/z 552.2 [M+H⁺].

Step 8

A mixture of 69-11 (100 mg, 0.18 mmol), PNP carbonate (109 mg, 0.36 mmol) and DIPEA (70 mg, 0.54 mmol) in DCM (5 mL) was stirred at 50° C. for 12 h. It was concentrated and added to a mixture of DIPEA (70 mg, 0.54 mmol) and norfloxacin (172 mg, 0.54 mmol) in DMF (5 mL). After it was stirred at 23° C. for 4 h, solvent was removed, and the residue was purified by prep-HPLC to give example 69 (69.3 mg, 43%).

¹H NMR (400 MHz, DMSO-d₆) δ 15.32 (s, 1H), 10.63 (s, 1H), 8.96 (s, 1H), 8.02 (s, 1H), 7.94 (d, J=12.8 Hz, 1H), 7.70 (d, J=8.0 Hz, 1H), 7.60 (d, J=8.8 Hz, 2H), 7.38-7.20 (m, 8H), 6.03 (s, 1H), 5.49-5.42 (m, 3H), 5.07 (s, 2H), 5.04 (d, J=4.0 Hz, 2H), 4.72-4.71 (m, 1H), 4.58-4.57 (m, 2H), 3.67 (s, 4H), 3.61 (s, 4H), 3.06-3.01 (m, 2H), 2.12-2.07 (m, 2H), 1.80-1.68 (m, 2H), 1.42-1.38 (m, 3H), 1.34 (s, 6H), 0.84 (s, 3H).

LCMS (ESI): m/z 897.4 [M+H⁺].

Example 70: 7-(4-((4-((S)-2-(4-((S)-1-(benzyloxy-carbonylamino)-2-methylpropyl)-1H-1,2,3 triazol-1-yl)propanamido)benzyloxy)carbonyl)piperazin-1-yl)-1-ethyl-6-fluoro-4-oxo-1,4,4a,8a-tetrahydroquinoline-3-carboxylic acid

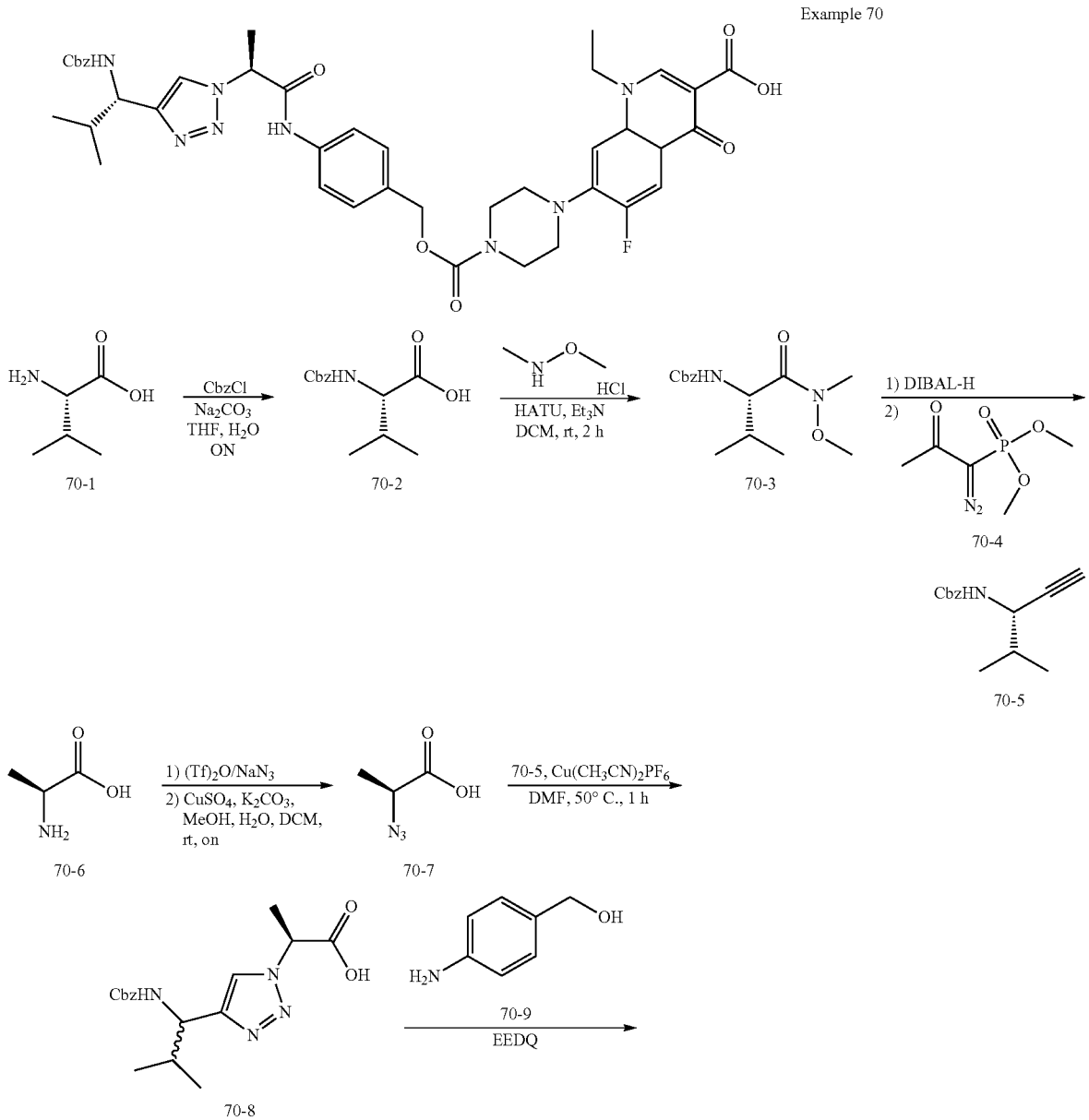

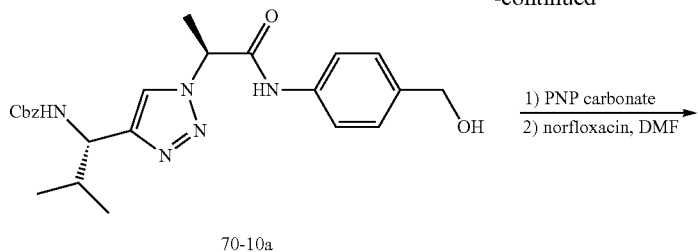

70-10a

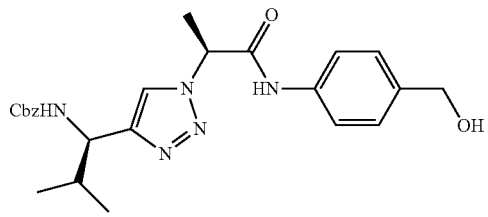

70-10b

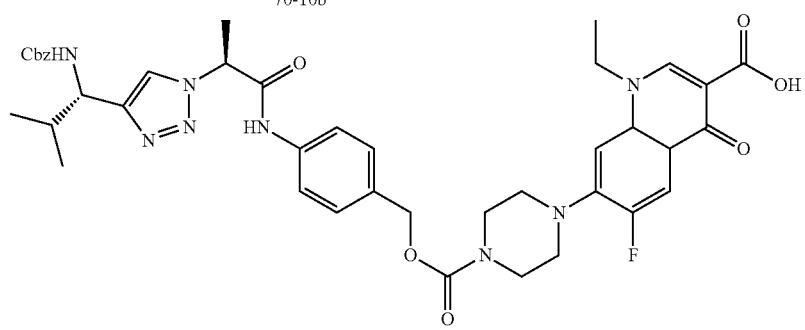

example 70

Step 1

To a mixture of compound 70-1 (3.0 g, 25.61 mmol) in water (20 mL) was added Na₂CO₃ (2.71 g, 25.61 mmol). CbzCl (4.81 g, 28.17 mmol) was added and the reaction mixture was stirred at 28° C. for 16 h. The mixture was filtered and extracted with EtOAc (15 mL×2). The combined organic layer was dried over Na₂SO₄ and concentrated under reduced pressure to give compound 70-2 (5.9 g, 92%).

$^1$H NMR (400 MHz, CDCl₃) δ 8.21-7.30 (m, 5H), 5.86 (br, 1H), 5.15 (s, 2H), 4.37-4.34 (m, 1H), 2.28-2.21 (m, 1H), 1.01-0.84 (m, 6H).

Step 2

To a solution of compound 70-2 (5.9 g, 23.48 mmol), N-methoxymethanamine hydrochloride (2.52 g, 25.83 mmol) and Et₃N (7.13 g, 70.44 mmol) in DCM (60 mL) was added HATU (13.4 g, 35.22 mmol) at 28° C. After the mixture was stirred at 28° C. for 3 h, solvent was removed and the residue was dissolved in water (30 mL). The aqueous layer was extracted with EtOAc (80 mL×3). The organic layers were combined, dried over Na₂SO₄ and concentrated. The crude was purified by column chromatography on silica gel (PE/EtOAc=2:1) to give compound 70-3 (4.5 g, 65%).

LCMS (ESI): m/z 295.1 [M+H⁺].

Step 3

To a mixture of compound 70-3 (588 mg, 2.0 mmol) in DCM (8 mL) at −78° C. was added dropwise DIBAL-H in toluene (1M, 2.4 mL, 2.4 mmol). After the mixture was stirred at −78° C. for 2 h, MeOH (1 mL) was added dropwise. The mixture was allowed to warm up to r.t. Solvent was removed and the crude was used directly in the next step.

To a solution of the above crude in MeOH (5 mL) was added K₂CO₃ (553 mg, 4.0 mmol) and compound 70-4 (461 mg, 2.4 mmol). The reaction mixture was stirred at 26° C. for 8 h. Solvent was removed and the residue was purified by column chromatography on silica gel (PE/EtOAc=20:1) to give compound 70-5 (300 mg, 65.2%).

LCMS (ESI): m/z 232.1 [M+H⁺].

Step 4

To mixture of NaN₃ (2.0 g, 30.76 mmol) in distilled H₂O (4.5 mL) and DCM (7.5 mL) was added Tf₂O (1.57 g, 5.55 mmol) dropwise at 0° C. The mixture was stirred at 0° C. for 3 h. The aqueous layer was extracted with DCM (4 mL×2), and washed with saturated Na₂CO₃ solution (8 mL). To a mixture of compound 70-6 (249 mg, 2.79 mmol), K₂CO₃ (578 mg, 4.19 mmol) and CuSO₄·5H₂O (7 mg, 27.9 umol) in H₂O (9 mL) and MeOH (18 mL) was added the triflyl azide in DCM (15.5 mL) dropwise. After the mixture was stirred at 26° C. overnight, the organic solvents were removed under reduced pressure and the aqueous slurry was diluted with H₂O (50 mL). It was acidified to pH 6 with conc. HCl, diluted with phosphate buffers (0.2 M, pH 6.2, 50 mL), and exacted with EtOAc (50 mL×2). The aqueous phase was then acidified to pH 2 with conc. HCl and extracted with EtOAc (80 mL×3). The organic layer was dried over $Na_2SO_4$ and evaporated to give 70-7, which was used for next step without further purification.

Step 5

To a solution of compound 70-7 (321 mg, 2.79 mmol) and compound 70-5 (278 mg, 1.2 mmol) in DMF (3 mL), was added $Cu(CH_3CN)_4PF_6$ (67 mg, 0.18 mmol). The reaction mixture was heated at 50° C. for 2 h under $N_2$. After removal of the solvent, the residue was purified by column chromatography on silica gel (2.5-5% of MeOH in DCM) to give compound 70-8 (90 mg, 22%).
$^1$H NMR (400 MHz, DMSO-$d_6$) δ 7.65 (s, 1H), 7.37-7.32 (m, 5H), 5.05 (s, 2H), 4.64 (s, 1H), 3.35 (s, 4H), 2.02 (s, 1H), 0.85-0.67 (m, 6H).

Step 6

To a solution of compound 70-8 (1.4 g, 4.04 mmol) and compound 70-9 (1.49 g, 12.12 mmol) in DCM (15 mL) was added EEDQ (3.0 g, 12.12 mmol) at 25° C. After the reaction mixture was stirred at 25° C. for 2 h, the solvent was removed, the residue was purified by prep-HPLC to give a mixture (1.1 g). The two isomers were purified by SFC separation to give 70-10a (250 mg) and other enantiomer 70-10b (116 mg).
$^1$H NMR (400 MHz, MeOD) δ 8.03 (s, 1H), 7.57-7.54 (m, 2H), 7.35-7.28 (m, 7H), 5.57 (q, J=7.2 Hz, 1H), 5.13-5.06 (m, 2H), 4.72-4.65 (m, 1H), 4.58 (s, 2H), 2.21-2.17 (m, 1H), 1.87 (d, J=7.2 Hz, 3H), 0.97 (d, J=6.8 Hz, 3H), 0.90 (d, J=6.8 Hz, 3H). LCMS (ESI): m/z 452.2 [M+H$^+$].

Step 7

To a solution of 70-10a (100 mg, 0.221 mmol) in THF (3 mL) were added PNP carbonate (202 mg, 0.663 mmol) and DIPEA (114 mg, 0.884 mmol) at 25° C. After the mixture was heated at reflux for 24 h, solvent was removed, and the residue was purified by column chromatography on silica gel (DCM/MeOH=20:1) to give the intermediate (90 mg). To a norfloxacin solution (70 mg, 0.219 mmol) in DMF (2 mL) was added DIPEA (94 mg, 0.73 mmol). After the solution was stirred at 25° C. for 15 min, the above intermediate (90 mg, 0.219 mmol) was added. The mixture was stirred at 25° C. for 2 h. Solvent was removed and the residue was purified by prep-TLC (DCM/MeOH=10:1) to give example 70 (26.5 mg, 23%).
$^1$H NMR (400 MHz, DMSO-$d_6$) δ 15.32 (s, 1H), 10.61 (s, 1H), 8.98 (s, 1H), 8.07 (s, 1H), 7.95-7.92 (m, 1H), 7.71-7.58 (m, 3H), 7.38-7.16 (m, 8H), 5.52 (m, 1H), 5.10-5.00 (m, 4H), 4.63-4.52 (m, 3H), 3.60 (s, 4H), 3.30 (s, 4H), 2.10-2.00 (m, 1H), 1.75 (d, J=7.6 Hz, 3H), 1.42 (t, J=7.6 Hz, 3H), 0.88-0.75 (m, 6H). LCMS (ESI): m/z 797.6 [M+H$^+$].

Example 71. 7-(4-((4-((2S)-6-amino-2-(4-(1-(benzyloxycarbonylamino)-2-(thiophen-2-yl)ethyl)-1H-1,2,3-triazol-1-yl)hexanamido)benzyloxy)carbonyl)piperazin-1-yl)-1-ethyl-6-fluoro-4-oxo-1,4-dihydroquinoline-3-carboxylic acid

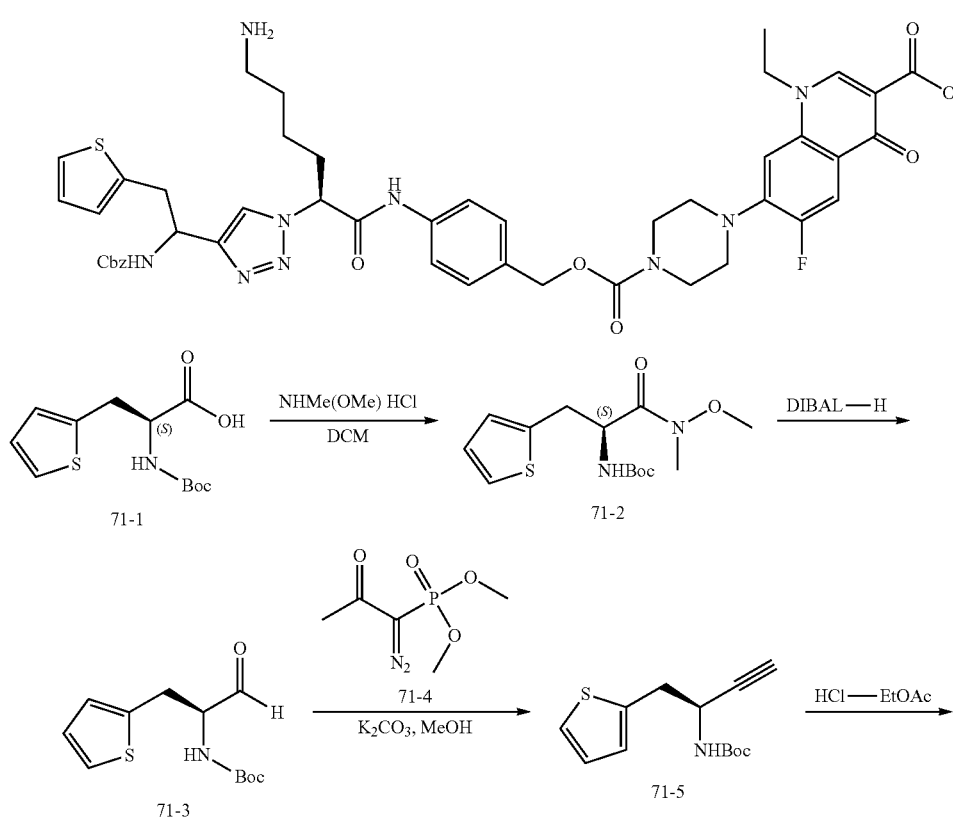

example 71

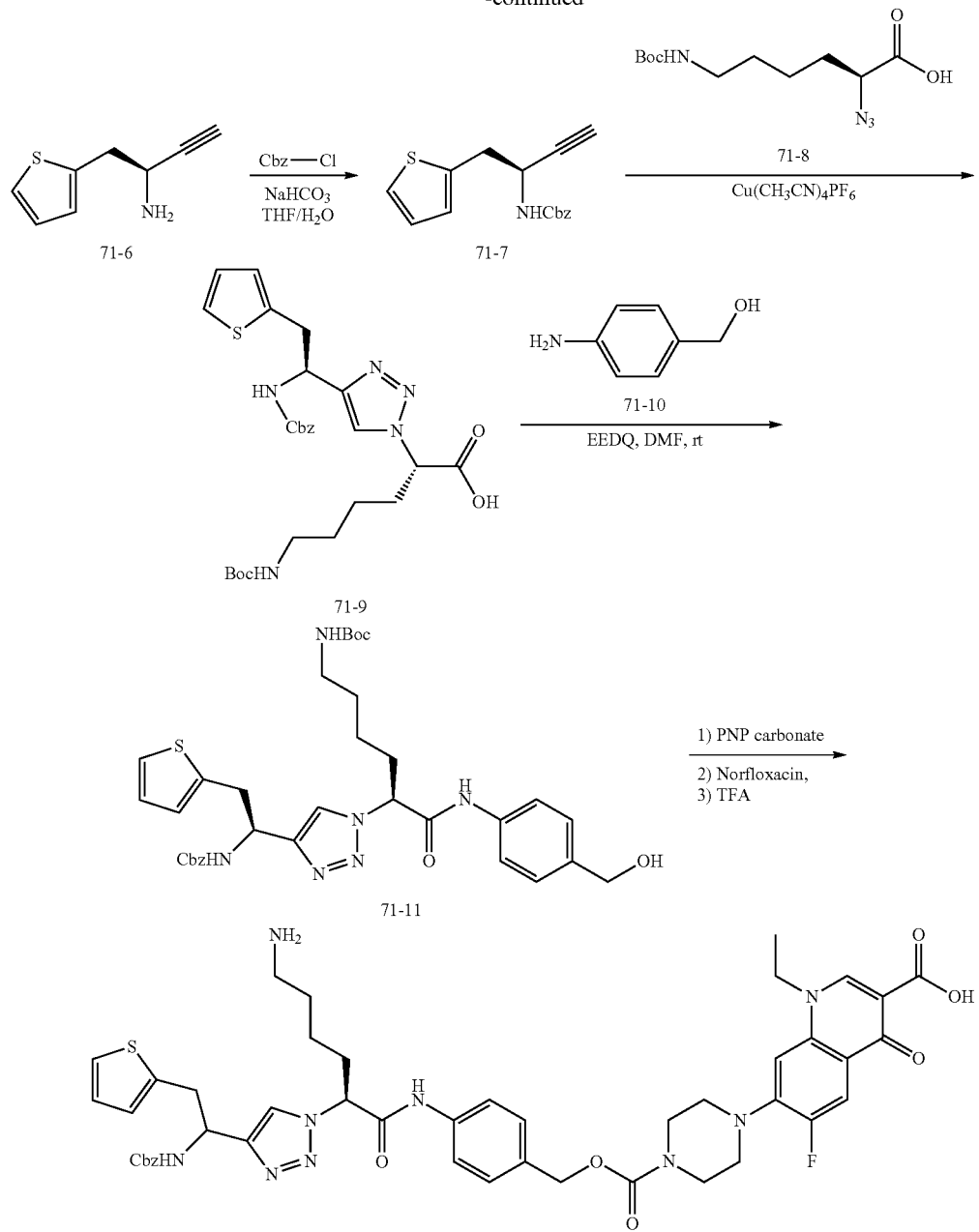

example 71

Step 1

To a mixture of compound 71-1 (500 mg, 1.84 mmol) in anhydrous DCM (20 mL) was added Et₃N (559 mg, 5.52 mmol) and HATU (1.049 g, 2.76 mmol). The mixture was stirred at r.t. for 15 min, then NHMe(OMe)HCl (269 mg, 2.76 mmol) was added. The reaction mixture was stirred at r.t. overnight. The mixture was extracted with EtOAc (30 mL×3) and water (30 mL), The combined organic layer was dried, concentrated, and purified by column chromatography on silica gel (PE:EtOAc=2:1) to give 71-2 (500 mg, 86.4%).

$^1$H NMR (400 MHz, DMSO-$d_6$) δ 7.34 (d, J=4.8 Hz, 1H), 7.22 (d, J=9.2 Hz, 1H), 6.94-6.89 (m, 2H), 4.56 (s, 1H), 3.70 (s, 3H), 3.11 (s, 3H), 3.09-2.95 (m, 2H), 1.35 (s, 9H).

Step 2

Compound 71-2 (500 mg, 1.59 mmol) was dissolved in anhydrous CH₂Cl₂ (5 mL) and was cooled to −78° C. in a dryice/acetone bath. DIBAL-H (4.8 mL, 4.77 mmol, 1.0 M in toluene) was added dropwise and the resulting solution was stirred at −78° C. for 3 h. Excess hydride was quenched with MeOH (5 mL) and the resulting solution was warmed to r.t. The solution was evaporated to give the compound 71-3 without further purification.

Step 3

To a solution of crude compound 71-3 (406 mg, 1.59 mmol), compound 71-4 (611 mg, 3.18 mmol) in MeOH (20 mL) was added K₂CO₃ (659 mg, 4.77 mmol). The reaction mixture was stirred at r.t overnight. The mixture was concentrated in vacuum, and purified by column chromatography on silica gel (PE:EtOAc=5:1) to give 71-5 (250 mg, 62.3%).

¹H NMR (400 MHz, DMSO-d₆) δ 7.45 (d, J=8.4 Hz, 1H), 7.35 (dd, J=4.8, 1.2 Hz, 1H), 6.96-6.92 (m, 2H), 4.35-4.31 (m, 1H), 3.19 (d, J=1.2 Hz, 1H), 3.10-3.08 (m, 2H), 1.36 (s, 9H).

Step 4

To a solution of compound 71-5 (250 mg, 0.99 mmol) in DCM (5 mL) was added HCl-EtOAc (5 mL, 4.0 M, 20.00 mmol) dropwise at 0° C. The reaction mixture was stirred at 0° C. for 1 h. The mixture was concentrated in vacuum at 25° C. to give 71-6 as a HCl salt (180 mg, 96.9%)

Step 5

Cbz-Cl (287 mg, 1.68 mmol) in THF (2 mL) was added dropwise into a solution of compound 71-6 (170 mg, 0.91 mmol) in saturated aq. NaHCO₃ solution (2 mL). The reaction mixture was stirred at 0° C. for 1 h. The mixture was extracted with EtOAc (10 mL×3) and H₂O (10 mL). The combined organic layer was dried over Na₂SO₄, filtered and concentrated. The residue was purified by column chromatography on silica gel (PE:EtOAc=5:1) to give compound 71-7 (250 mg, 96.3%).

¹H NMR (400 MHz, DMSO-d₆) δ 7.93 (d, J=8.4 Hz, 1H), 7.38-7.31 (m, 6H), 6.96-6.93 (m, 2H), 5.02 (s, 2H), 4.45-4.39 (m, 1H), 3.26 (d, J=2.0 Hz, 1H), 3.13 (dd, J=6.8, 2.0 Hz, 2H).

Step 6

To the solution of compound 71-7 (280 mg, 0.98 mmol) and Compound 71-8 (400 mg, 1.47 mmol) in DMF (5 mL) was added Cu(CH₃CN)₄PF₆ (37 mg, 0.1 mmol). The reaction mixture was stirred at 50° C. for 2 h to give 71-9 which was used directly for next step.

Step 7

To the mixture of crude compound 71-9 (547 mg, 0.98 mmol) in DMF (5 mL) was added EEDQ (484 mg, 1.96 mmol) and compound 71-10 (181 mg, 1.47 mmol). The reaction mixture was stirred at r.t. under N₂ overnight. The mixture was purified by prep-HPLC to give the 71-11 (100 mg, 15.4%).

¹H NMR (400 MHz, DMSO-d₆) δ 10.54 (s, 1H), 8.11-8.06 (m, 1H), 7.90 (t, J=8.4 Hz, 1H), 7.53 (d, J=8.8 Hz, 2H), 7.36-7.26 (m, 8H), 6.92-6.89 (m, 1H), 6.85 (d, J=3.2 Hz, 1H), 6.79 (t, J=4.8 Hz, 1H), 5.44-5.40 (m, 1H), 5.14 (t, J=6.0 Hz, 1H), 5.06-4.93 (m, 3H), 4.44 (d, J=5.6 Hz, 2H), 3.43-3.38 (m, 1H), 3.01-3.24 (m, 1H), 2.90-2.85 (m, 2H), 2.12-2.07 (m, 2H), 1.43-1.39 (m, 2H), 1.37 (s, 9H), 1.18-1.10 (m, 2H).

Step 8

To the solution of compound 71-11 (100 mg, 0.15 mmol) in anhydrous DMF (2 mL) was added DIPEA (116 mg, 0.90 mmol), PNP carbonate (91 mg, 0.30 mmol) 0° C. After the reaction mixture was stirred at 0° C. for 2 h, norfloxacin was added. The mixture was stirred at ° C. for another 1 h, and it was purified by prep-HPLC to give compound 71-12 (120 mg, 79.4%).

Step 9

To the mixture of compound 71-12 (100 mg, 0.10 mmol) in anhydrous DCM (2.5 mL) was added TFA (0.5 mL). The reaction mixture was stirred at 0° C. for 1 h. Then the mixture was diluted with DMF, and was adjusted to pH 8 with NH₃H₂O dropwise. The resulting mixture was purified by prep-HPLC to give example 71 (63 mg, 69.4%) was obtained.

LCMS (ESI): RT=0.830 min, M/2+H⁺=454.8. method=5-95/2 min.

¹H NMR (400 MHz, DMSO-d₆) δ 10.84 (bs, 1H), 8.96 (s, 1H), 8.46 (s, 1H), 8.13-8.09 (m, 1H), 7.96-7.89 (m, 2H), 7.61 (d, J=8.8 Hz, 2H), 7.38-7.30 (m, 8H), 7.21 (d, J=7.2 Hz, 1H), 6.92-6.90 (m, 1H), 6.86 (d, J=2.0 Hz, 1H), 5.49-5.45 (m, 1H), 5.08-4.92 (m, 5H), 4.60-4.55 (m, 2H), 3.61 (s, 4H), 3.34-3.26 (m, 6H), 2.70-2.66 (m, 2H), 2.19-2.08 (m, 2H), 1.57-1.49 (m, 2H), 1.42-1.37 (m, 3H), 1.23-1.16 (m, 2H).

Example 72. 7-(4-((4-((S)-6-amino-2-(4-((S)-1-(benzyloxycarbonylamino)-2-phenylethyl)-1H-1,2,3-triazol-1-yl)hexanamido)benzyloxy)carbonyl)piperazin-1-yl)-1-ethyl-6-fluoro-4-oxo-1,4-dihydroquinoline-3-carboxylic acid

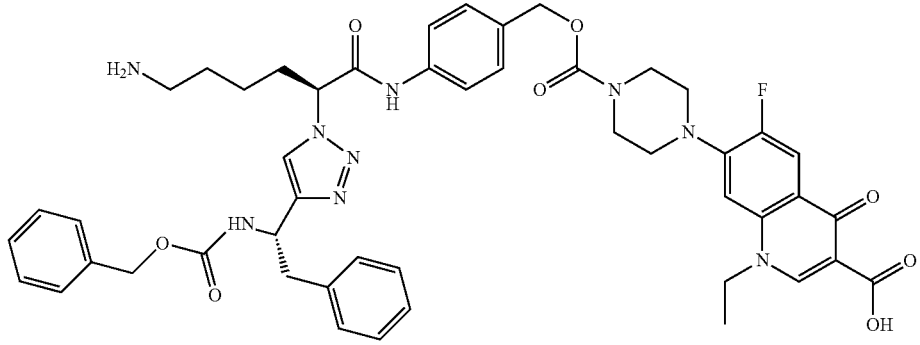

example 21

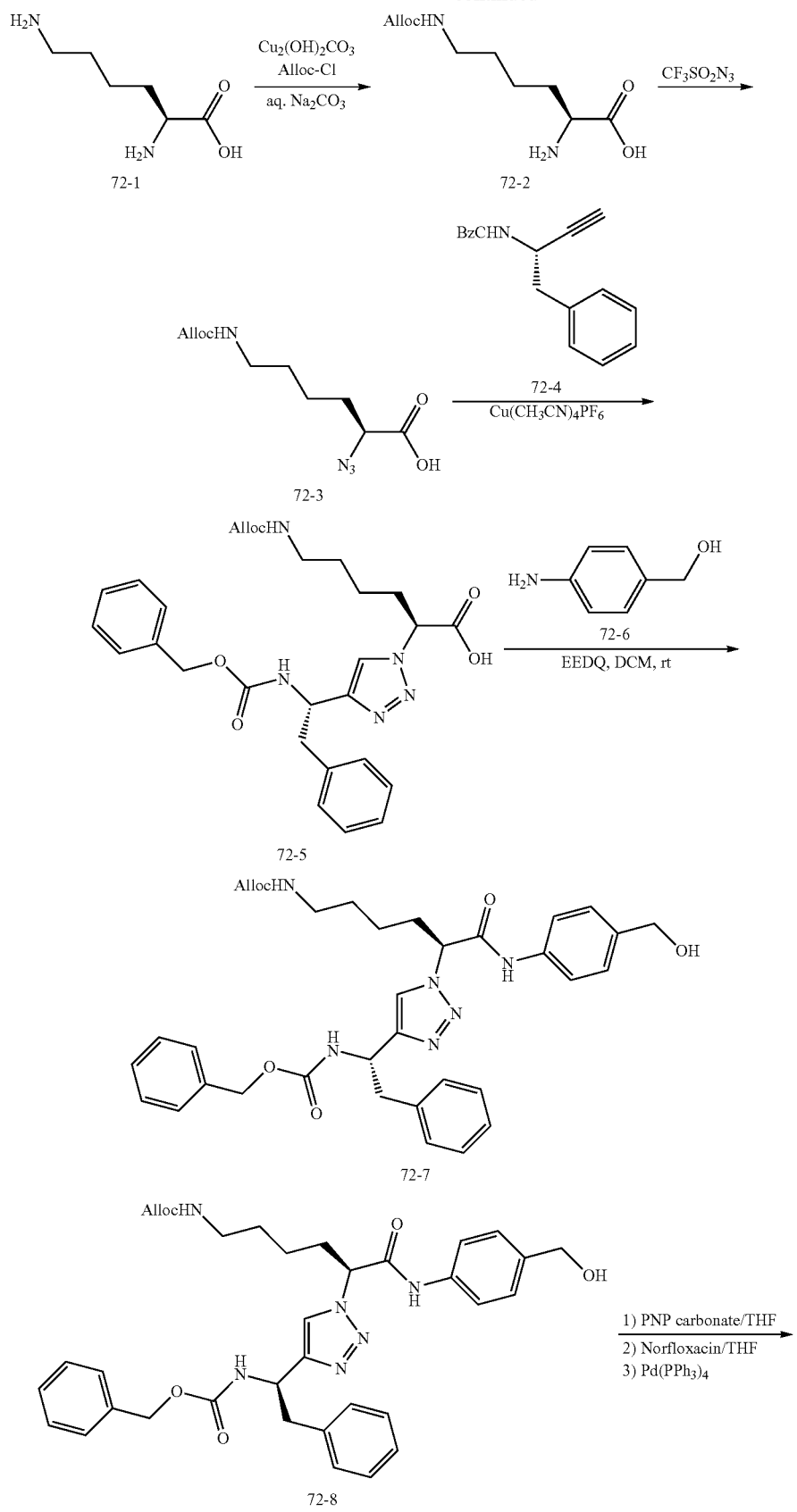

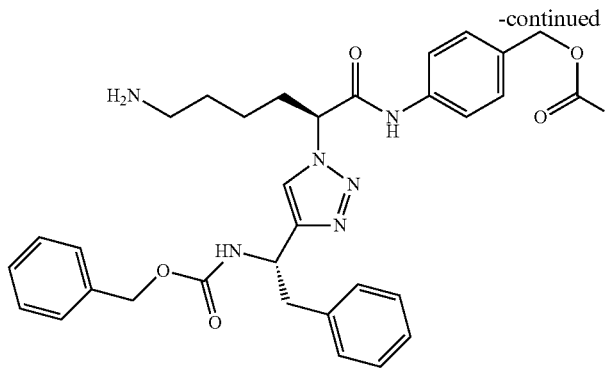

example 72

Step 1

To a solution of compound 72-1 (14.7 g, 0.1 mol) in water (300 mL) was added Cu$_2$(OH)$_2$CO$_3$ (38 g, 0.1 mol). It was heated at reflux for 1 h. Solid was filtered off, and the pH of filtrate was adjusted to 9.0 by addition of Na$_2$CO$_3$. Alloc-Cl (14.4 g, 0.12 mmol) was added dropwise at 0° C., while pH was maintained at 9.0 by addition of Na$_2$CO$_3$. The mixture was stirred for 12 h at r.t. The blue solid was collected by filtration and re-dissolved in water (300 mL). Thioacetamide (20 mmol) was added to and the solution was stirred at 50° C. for 3 h. The solution was acidified with HCl to pH 2.0 and boiled for 10 min. CuS was filtered off, and the solution was concentrated to 100 mL, and 72-2 was collected by filtration.

$^1$H NMR (400 MHz, MeOD) δ 5.94-5.88 (m, 1H), 5.30-5.26 (m, 1H), 5.18-5.15 (m, 1H), 4.55-4.93 (m, 1H), 3.50 (brs, 1H), 3.13-3.09 (m, 2H), 2.00-1.70 (m, 2H), 1.54-1.41 (m, 4H).

Step 2

To the solution of NaN$_3$ (1.78 g, 27.45 mmol) in a mixture of H$_2$O (5 mL) and DCM (7.5 mL) was added Tf$_2$O (0.93 mL, 5.55 mmol). After the mixture was stirred at r.t. for 2 h, it was extracted with DCM (50 mL×3). The organic layer was washed with aq. Na$_2$CO$_3$ and concentrated to 10 mL. Compound 72-2 (640 mg, 2.8 mmol) was added, followed by K$_2$CO$_3$ (577 mg, 4.19 mmol), CuSO$_4$ (7 mg, 0.028 mmol), H$_2$O (9 mL) and MeOH (18 mL). The mixture was stirred at r.t. for 12 h. The organic solvents were evaporated, solution was diluted with water, and pH was adjust to 6.0 with HCl and diluted with phosphate buffers (0.25 M, pH 6.2, 50 mL). The mixture was extracted with EtOAc (50 mL×3). The organic layer was dried to give compound 72-3, which was used for next step without further purification.

Step 3

To the solution of 72-3 (560 mg, 2 mmol) in DMF (5 mL) was added 72-4 (1.12 g, 4.0 mmol) and cat. Cu(CH$_3$CN)$_4$PF$_6$. The mixture was stirred at 50° C. for 3 h under N$_2$. After the solvent was removed, the residue was purified by prep-HPLC to give 72-5.

LCMS (ESI): m/z 536.2 [M+H$^+$]

Step 4

To the solution of 72-5 (480 mg, 1.0 mmol) in DCM (10 mL) was added EEDQ (247 mg, 1.0 mmol) and 72-6 (123 g, 1.0 mmol), and the mixture was stirred at 0° C. for 1 h under N$_2$. After the solvent was removed, the residue was purified with prep-HPLC and SFC separation to give 72-7 and 72-8.

$^1$H NMR (400 MHz, CDCl$_3$) δ 7.91 (s, 1H), 7.55-7.52 (m, 2H), 7.33-7.15 (m, 12H), 5.89-5.87 (m, 1H), 5.42-5.38 (m, 1H), 5.28-5.23 (m, 1H), 5.15-5.02 (m, 3H), 4.58 (s, 2H), 4.51-4.47 (m, 2H), 3.31-3.05 (m, 4H), 2.20-2.15 (m, 2H), 1.53-1.50 (m, 2H), 1.31-1.21 (m, 2H). LCMS (ESI): m/z 641.1 [M+H$^+$].

$^1$H NMR (400 MHz, CDCl$_3$) δ 7.95 (s, 1H), 7.56 (d, J=8.4 Hz, 2H), 7.35-7.17 (m, 12H), 5.95-5.88 (m, 1H), 5.45-5.41 (m, 1H), 5.30-5.26 (m, 1H), 5.18-5.03 (m, 3H), 4.58 (s, 2H), 4.51-4.50 (m, 2H), 3.31-3.23 (m, 1H), 3.15-3.01 (m, 3H), 2.23-2.15 (m, 2H), 1.56-1.53 (m, 2H), 1.32-1.22 (m, 2H). LCMS: m/z 641.1 [M+H$^+$].

Step 5

To the solution of 72-7 (59 mg, 0.1 mmol) in dry DCM (30 mL) was added PNP carbonate (62 mg, 0.2 mmol) and DIPEA (1 mL). The mixture was heated at reflux for 16 h. After the solvent was removed, the residue was dissolved in DMF (5 mL). DIPEA (0.2 mL) and norfloxacin (65 mg, 0.2 mmol) were added. The mixture was stirred at r.t. for 1 h. After the solvent was removed, the residue was purified by column. To the intermediate in dry THF (10 mL) was added Pd(PPh$_3$)$_4$ (116 mg, 0.1 mmol). The mixture was stirred at r.t. for 12 h under N$_2$. After the solvent was removed, the residue was purified by column on silica gel to give example 72.

$^1$H NMR (400 MHz, CDCl$_3$) δ 8.86 (s, 1H), 8.47 (s, 1H), 8.01-7.93 (m, 2H), 7.59-7.57 (m, 2H), 7.39-7.37 (m, 2H), 7.27-7.14 (m, 11H), 5.41 (s, 1H), 5.14 (s, 2H), 5.09-4.92 (m, 3H), 4.59-4.50 (m, 2H), 3.72-3.71 (m, 4H), 3.30 (s, 4H), 3.21-3.19 (m, 2H), 2.89-2.85 (m, 2H), 2.25-2.23 (m, 2H), 1.69-1.67 (m, 2H), 1.52-1.49 (m, 3H), 1.40-1.20 (m, 2H). LCMS (ESI): m/z 902.5 [M+H$^+$].

Example 73: 7-(4-((4-((S)-2-(4-((S)-2-(benzyloxycarbonylamino)-3-methylbutan-2-yl)-1H-1,2,3-triazol-1-yl)propanamido)benzyloxy)carbonyl)piperazin-1-yl)-1-ethyl-6-fluoro-4-oxo-1,4,4a,8a-tetrahydroquinoline-3-carboxylic acid
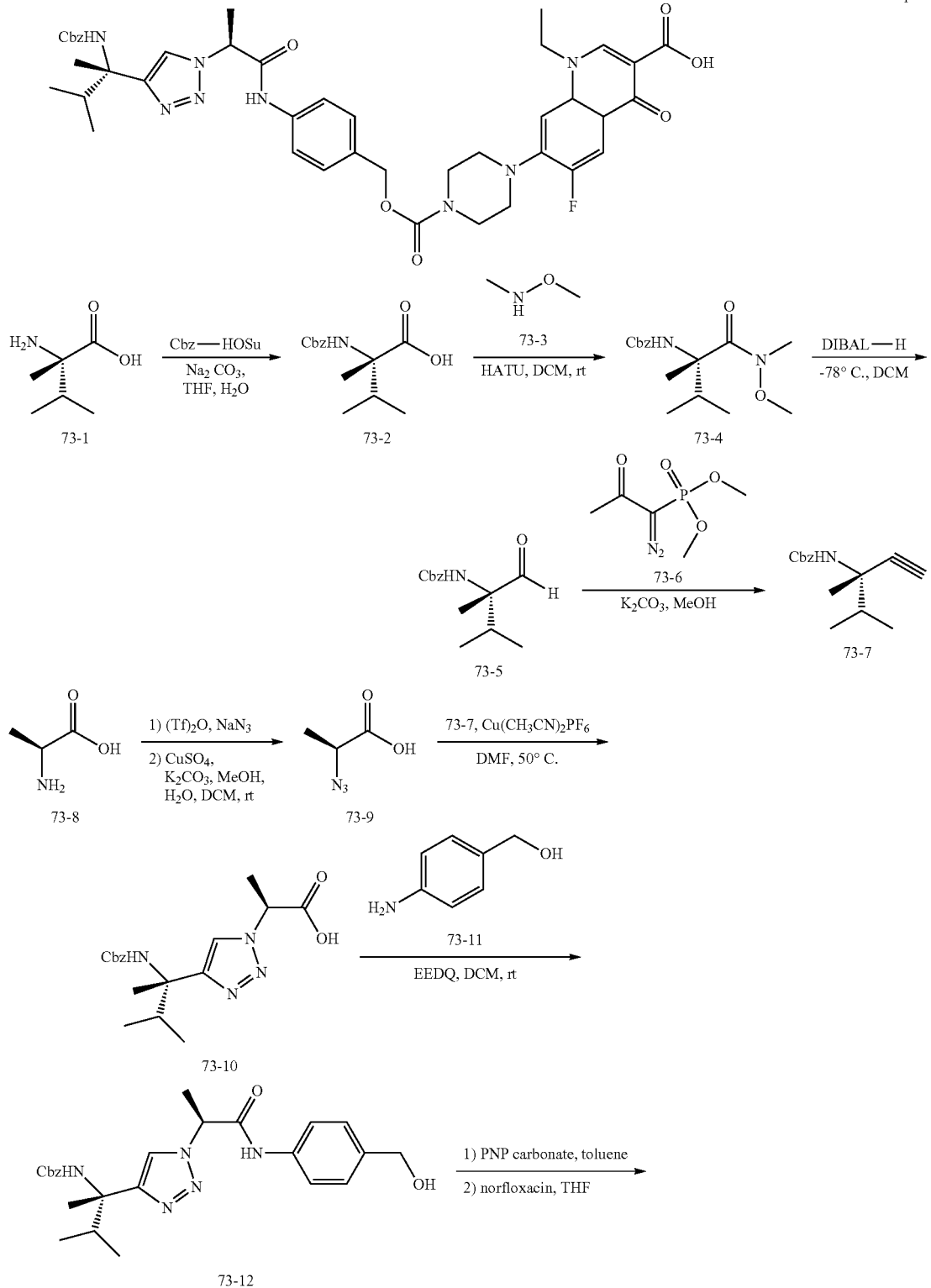

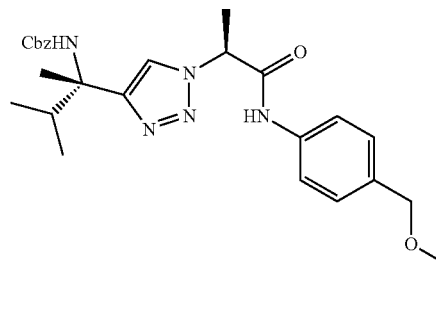
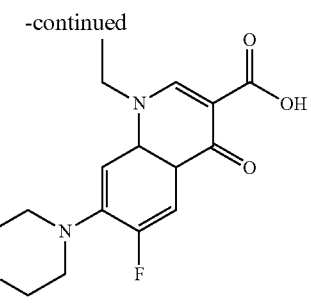

example 73

Step 1

To a mixture of aq Na$_2$CO$_3$ (82 g, 0.78 mol) and compound 73-1 (20 g, 0.19 mol) was added Cbz-OSu (57 g, 0.23 mol) in THF (150 mL). After the mixture was stirred at r.t. for 16 h, it was adjusted to pH>10 and the solution was extracted with EtOAc (400 mL×2). The aqueous layer was acidified to pH<1 with conc.HCl and the solution was extracted with EtOAc (500 mL×2). The organic layers were dried over Na$_2$SO$_4$ and concentrated to give compound 73-2 (45 g, 0.19 mol), which was used for next step without further purification.

Step 2

To a mixture of compound 73-2 (20 g, 84.3 mmol), N,O-dimethylhydroxylamine Hydrochloride (8.9 g, 92.7 mmol) and HATU (48.1 g, 126.4 mmol) in DCM (200 mL) was added Et$_3$N (48.7 mL, 337.2 mmol). After the mixture was stirred at r.t. for 2 h, solvent was removed and the residue was taken up with water (300 mL). The aqueous layer was extracted with EtOAc (300 mL×3). The organic layer was washed with saturated NaHCO$_3$ (100 mL), conc.HCl (100 mL), saturated NaCl (100 mL). Solvent was removed and the residue was purified by column chromatography on silica gel (PE:EtOAc=2:1) to give compound 73-4 (12.9 g, 46.0 mmol).

Step 3

DIBAL (17.8 mL, 1M in Tol) was added dropwise to a solution of compound 73-4 (4.15 g, 14.8 mmol) in anhydrous CH$_2$Cl$_2$ (100 mL) at −78° C. The resulting solution was stirred at −78° C. for 2 h and excess DIBAL was quenched with anhydrous MeOH (5 mL) and the resulting solution was warmed to r.t. The solution was concentrated to give compound 73-5 (3.27 g, 14.8 mmol), which was used for next step without further purification.

Step 4

After a mixture of compound 75-5 (3.27 g, 14.8 mmol), 73-6 (2.96 g, 17.8 mmol) and K$_2$CO$_3$ (4.1 g, 29.7 mmol) in MeOH (60 mL) was stirred at r.t. for 16 h, solvents were removed under reduced pressure and the crude residue was partitioned between EtOAc (200 mL) and water (100 mL). The organic layer was washed with brine and dried over anhydrous Na$_2$SO$_4$. After removal of the solvent, the residue was purified by column chromatography on silica gel (PE:EtOAc=10:1) to give compound 73-7 (606 mg, 2.79 mmol).

Step 5

To a mixture of NaN$_3$ (3.2 g, 49.3 mmol) in distilled H$_2$O (10 mL) and CH$_2$Cl$_2$ (16 mL) was added Tf$_2$O (1.7 mL, 9.9 mmol) slowly over 5 min at 0° C. After it was stirred for 2 h the organic phase was separated and the aqueous phase was extracted with CH$_2$Cl$_2$ (8 mL×2). The organic fractions, containing the triflyl azide, were washed once with saturated Na$_2$CO$_3$ and added to a mixture of Compound 73-8 (0.86 g, 4.93 mmol), K$_2$CO$_3$ (1.02 g, 7.40 mmol) and CuSO$_4$.5H$_2$O (25 mg, 0.099 mmol) in distilled H$_2$O (18 mL) and MeOH (36 mL). After the mixture was stirred at 26° C. for 12 h, the organic solvents were removed under reduced pressure and the aqueous slurry was diluted with H$_2$O (50 mL) and acidified to pH 6 with conc.HCl and diluted with 0.2M pH 6.2 phosphate buffers (50 mL). It was washed with EtOAc (100 mL×2), and the aqueous phase was then acidified to pH 2 with conc. HCl. It was extracted with EtOAc (200 mL×3) and the combined layers were dried over Na$_2$SO$_4$ concentrated and used for next step without further purification.

Step 6

A mixture of compound 73-9 (0.99 g, 4.93 mmol), compound 73-7 (0.54 g, 2.46 mmol) and Cu(CH$_3$CN)$_2$PF$_6$ (115 mg, 0.37 mmol) in DMF (5 mL) was stirred at 50° C. for 2 h. Solvent was removed and the residue was purified by prep-HPLC to give compound 73-10 (250 mg, 23%).

Step 7

A mixture of compound 73-10 (199 mg, 0.55 mmol), compound 73-11 (176 mg, 1.43 mmol) and EEDQ (353 mg, 1.43 mmol) in DCM (10 mL) was stirred at 24° C. for 2 h. Solvent was removed and the residue was purified by prep-HPLC to give 73-12 (100 mg, 39.1%).

$^1$H NMR (400 MHz, MeOD) δ 7.98 (s, 1H), 7.54 (d, J=8.4 Hz, 2H), 7.33-7.31 (m, 6H), 7.10 (s, 1H), 5.55-5.49 (m, 1H), 4.98 (s, 2H), 4.55 (s, 3H), 2.35 (s, 1H), 1.84 (d, J=6.4 Hz, 3H), 1.69 (s, 3H), 0.94 (d, J=6.8 Hz, 3H), 0.79 (d, J=6.8 Hz, 3H).

LCMS (ESI): m/z 465.9 [M+H$^+$].

Step 8

A mixture of 73-12 (150 mg, 0.29 mmol), PNP (173 mg, 0.57 mmol) and DIPEA (111 mg, 0.86 mmol) in DCM (5 mL) was stirred at 50° C. for 12 h. Solvent was removed and the residue was used in next step without further purification. The mixture (200 mg, 0.29 mmol), DIPEA (112 mg, 0.87 mmol) and norfloxacin (316 mg, 0.87 mmol) in DMF (5 mL) was stirred at 25° C. for 4 h. Solvent was removed and the residue was purified by prep-HPLC to give example 73 (38.9 mg, 14.8%).

$^1$H NMR (400 MHz, CDCl$_3$) δ 8.69 (s, 1H), 8.11 (d, J=12.8 Hz, 1H), 7.94 (s, 1H), 7.59 (s, 1H), 7.50 (d, J=8.0 Hz, 2H), 7.32-7.27 (m, 6H), 6.82 (d, J=6.4 Hz, 1H), 5.45 (s, 1H), 5.38-5.37 (m, 1H), 5.10 (s, 2H), 4.97 (s, 2H), 4.34-4.29 (m, 2H), 3.71 (d, J=2.4 Hz, 4H), 3.25 (s, 4H), 2.52-2.46 (m, 1H), 1.94-1.91 (m, 3H), 1.74 (s, 3H), 1.58-1.56 (m, 3H), 0.93 (d, J=7.2 Hz, 3H), 0.82 (d, J=6.8 Hz, 3H).

LCMS (ESI): m/z 811.2 [M+H$^+$].

Example 74. 7-(4-((4-((S)-2-(4-((S)-1-(benzyloxy-carbonylamino)-2-(4-fluorophenyl)ethyl)-1H-1,2,3-triazol-1-yl)-5-ureidopentanamido)benzyloxy)carbonyl)piperazin-1-yl)-1-ethyl-6-fluoro-4-oxo-1,4,4a,8a-tetrahydroquinoline-3-carboxylic acid example 74

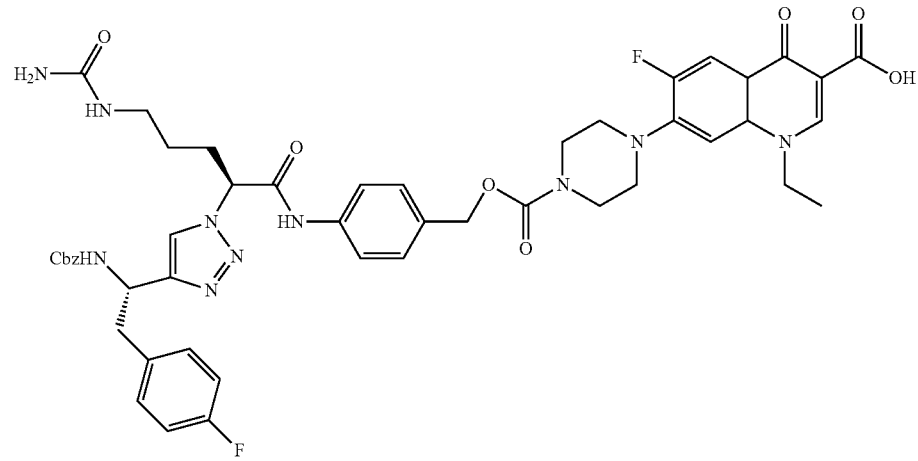

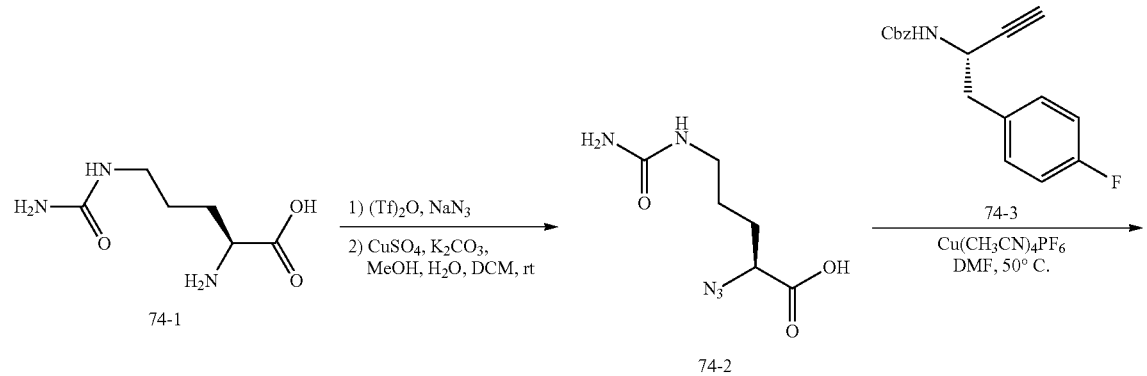

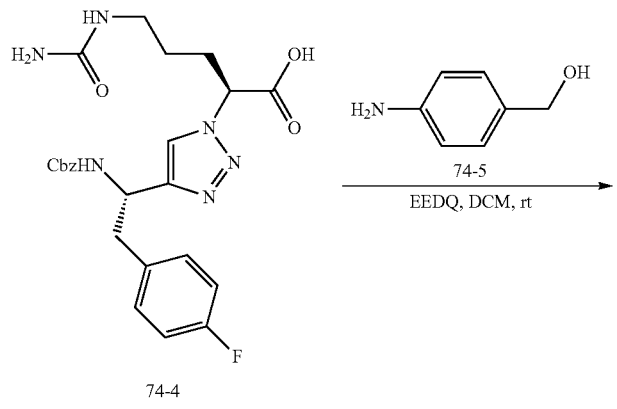

-continued

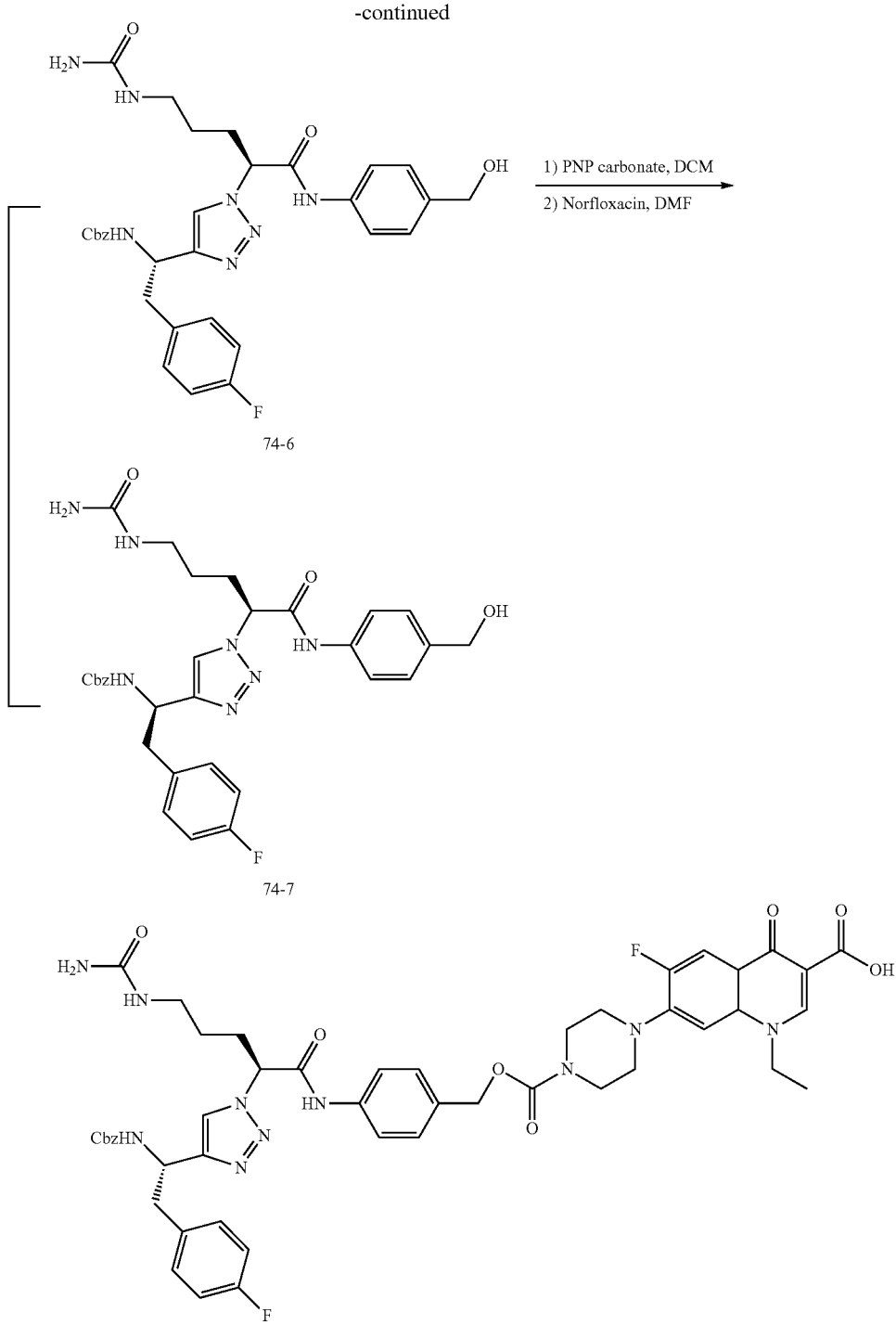

example 74

Step 1

Tf$_2$O (3.15 mL, 18.4 mmol) was added slowly over 5 min with stirring to a solution of NaN$_3$ (5.93 g, 91.3 mmol) in H$_2$O (18 mL) and DCM (30 mL) in icebath. After it was stirred at 0° C. for 2 h, the organic phase was separated. The aqueous portion was extracted with DCM (30 mL×2). The organic fractions, containing the triflyl azide were pooled and washed once with saturated Na$_2$CO$_3$ and used without further purification. Compound 74-1 (1.6 g, 9.14 mmol), K$_2$CO$_3$ (1.90 g, 13.7 mmol) and CuSO$_4$.5H$_2$O (46 mg, 0.183 mmol) were mixed in H$_2$O (33 mL) and MeOH (66 mL). The triflyl azide in DCM was added and the mixture was stirred at 20° C. for 12 h. Organic solvents were removed under reduced pressure and the aqueous slurry was diluted with H$_2$O (60 mL), acidified to pH 6 with conc.HCl and diluted with 0.2 M pH 6.2 phosphate buffers (60 mL). It was exacted with EtOAc (150 mL×2) to remove sulfonamide by-product. The aqueous phase was then acidified to pH 2 with conc. HCl. It was extracted with EtOAc (200 mL×3) and the organic layers were combined, dried over $Na_2SO_4$ and evaporated to give 74-2, which was used for next step without further purification.

Step 2

The mixture of 74-2 (1.84 g, 9.14 mmol), 74-3 (1.36 g, 4.57 mmol) and $Cu(CN)_4PF_6$ (213 mg, 0.687 mmol) in DMF (10 mL) was stirred at 50° C. for 2 h. After removal of the solvent, the residue was purified by prep-HPLC to give 74-4 (470 mg, 20.6%).
LCMS (ESI): m/z 499.2 [M+H$^+$].

Step 3

The mixture of 74-4 (300 mg, 0.602 mmol), 74-5 (148 mg, 1.20 mmol) and EEDQ (294 mg, 1.20 mmol) in DCM (10 mL) was stirred at 20° C. for 10 h. After removal of the solvent, the residue was purified by prep-HPLC and SFC to give 74-6 (160 mg, 44.1%) and 74-7 (95 mg, 26.2%).
$^1$H NMR (400 MHz, DMSO-d$_6$) δ 10.5 (s, 1H), 8.07 (s, 1H), 7.80 (d, J=9.2 Hz, 1H), 7.53 (d, J=6.8 Hz, 2H), 7.51-7.18 (m, 8H), 7.05-7.00 (m, 2H), 6.03-6.00 (m, 1H), 5.47-5.41 (m, 3H), 5.12-5.09 (m, 1H), 4.99-4.88 (m, 3H) 4.42 (d, J=5.6 Hz, 2H), 3.17-2.92 (m, 4H), 2.14-2.05 (m, 2H), 1.28-1.22 (m, 2H).
LCMS (ESI): m/z 604.1 [M+H$^+$].
$^1$H NMR (400 MHz, DMSO-d$_6$) δ 10.56 (s, 1H), 8.03 (s, 1H), 7.81 (d, J=9.2 Hz, 1H), 7.51 (d, J=6.8 Hz, 2H), 7.28-7.18 (m, 8H), 7.04-7.00 (m, 2H), 6.06-6.03 (m, 1H), 5.49-5.41 (m, 3H), 5.13-5.10 (m, 1H), 4.99-4.87 (m, 3H) 4.42 (d, J=5.6 Hz, 2H), 3.18-2.92 (m, 4H), 2.13-2.02 (m, 2H), 1.24-1.23 (m, 2H).
LCMS (ESI): m/z 604.1 [M+H$^+$].

Step 4

The mixture of 74-6 (50 mg, 0.082 mmol), PNP (53 mg, 0.166 mmol) and DIPEA (32 mg, 0.246 mmol) in DCM (5 mL) was stirred at 50° C. for 12 h. After removal of the solvent, the residue was used without further purification. The mixture of above crude product (110 mg, crude, 0.082 mmol), DIPEA (32 mg, 0.246 mmol) and norfloxacin (51 mg, 0.166 mmol) in DMF (5 mL) was stirred at 20° C. for 2 h. After removal of the solvent, the residue was purified by prep-HPLC to give example 74 (25 mg, 32.1%).
$^1$H NMR (400 MHz, DMSO-d$_6$) δ 15.64-15.33 (m, 1H), 10.67 (s, 1H), 8.96 (s, 1H), 8.21-7.03 (m, 17H), 6.08 (s, 1H), 5.47 (s, 3H), 5.08 (s, 2H), 5.01-4.91 (m, 3H), 4.58 (s, 2H). 3.61 (s, 4H), 3.31 (s, 4H), 3.20-2.96 (m, 4H), 2.12 (s, 2H), 1.41-1.24 (m, 5H).
LCMS (ESI): m/z 949.1 [M+H$^+$], 475.3 [M/2+H$^+$].

Example 75. 7-(4-((4-(((S)-2-(4-((S)-1-amino-3-methylbutyl)-1H-1,2,3-triazol-1-yl)-5-ureidopentanamido)benzyloxy)carbonyl)piperazin-1-yl)-1-ethyl-6-fluoro-4-oxo-1,4-dihydroquinoline-3-carboxylic acid

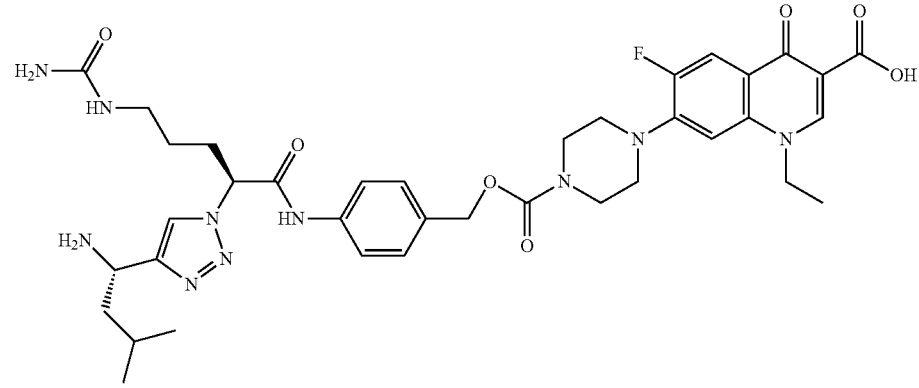

example 75

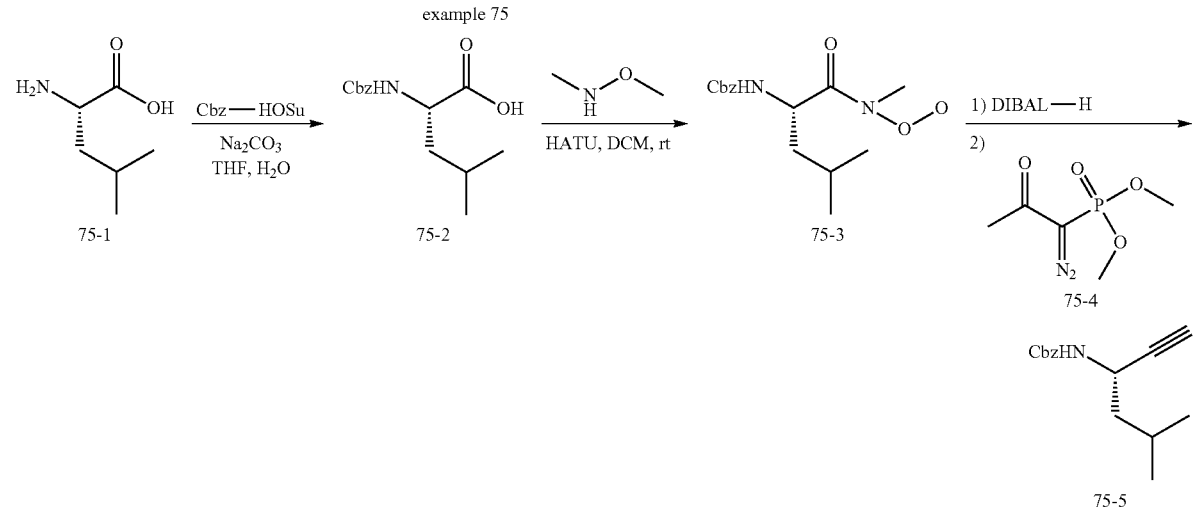

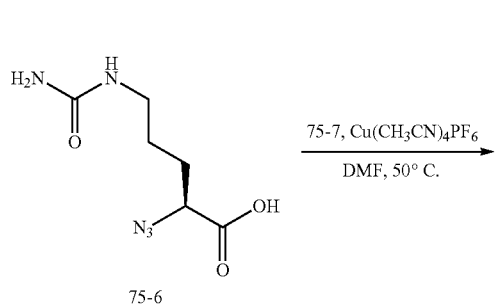
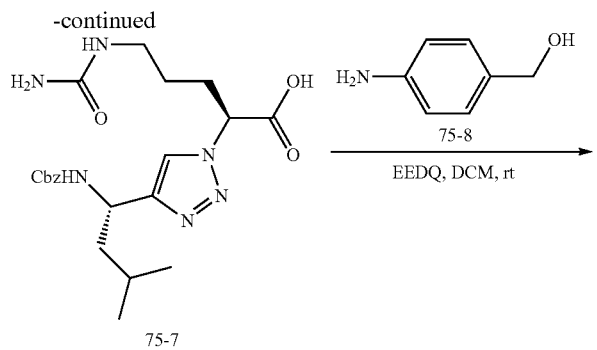
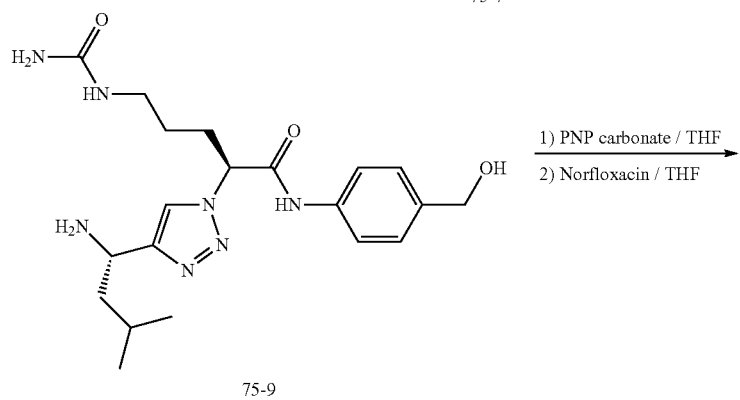
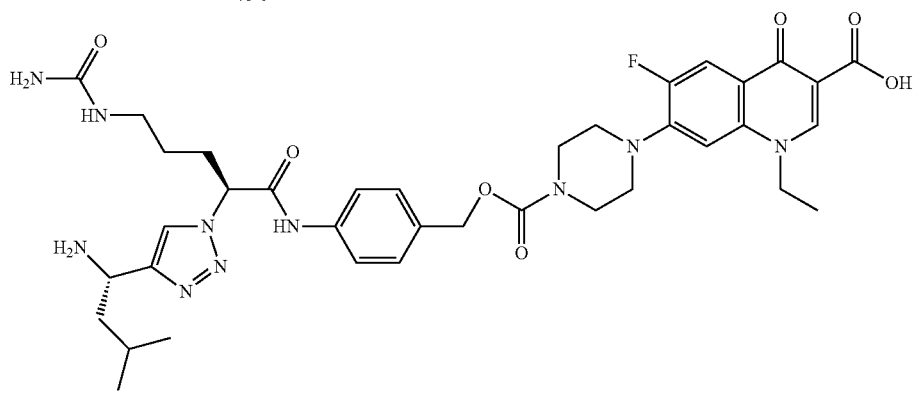

example 75

Step 1

Cbz-HOSu (22.8 g, 91.4 mmol) in THF (60 mL) was added dropwise over 15 min to a mixture of 75-1 (10.0 g, 76.2 mmol) in a mixture of water (60 mL) and THF (30 mL). The mixture was treated with $Na_2CO_3$ (24.2 g, 228.6 mmol). After the reaction mixture was stirred at 25° C. for 16 h, solvent was removed and the residue was extracted with EtOAc (150 mL×3). The aqueous phase was acidified to pH=2 with conc.HCl, and extracted with EtOAc (60 mL×3). The combined organic layer was dried over $Na_2SO_4$ and concentrated under reduced pressure to give 75-2 (21.0 g crude).

LCMS (ESI): m/z 288.1 [M+Na$^+$].

Step 2

To a solution of 75-2 (5.0 g, 18.85 mmol), N, O-dimethylhydroxylamine hydrochloride (2.2 g, 22.62 mmol) and $Et_3N$ (5.7 g, 56.55 mmol) in DCM (150 mL) was added HATU (10.8 g, 28.28 mmol) at 25° C. After the mixture was stirred at 25° C. for 2 h, solvent was removed and the residue was taken up with water (80 mL). The aqueous layer was extracted with EtOAc (80 mL×2). The organic layer was washed with 2N HCl solution (80 mL) and dried over $Na_2SO_4$, filtered and concentrated. The crude was purified by column chromatography on silica gel (PE/EtOAc=2:1) to give 75-3 (4.1 g, 71%).

LCMS (ESI): m/z 309.2 [M+H$^+$].

Step 3

DIBAL-H in toluene (1M, 16 mL, 16 mmol) was added dropwise to a mixture of 75-3 (4.1 g, 13.3 mmol) in DCM (25 mL) at −78° C. After the mixture was stirred at −78° C. for 2 h, MeOH (1 mL) was added dropwise. The mixture was warmed to 25° C., solvent was removed, and dissolved in MeOH (40 mL). To this solution $K_2CO_3$ (3.68 g, 26.6 mmol) and 75-4 (3.07 g, 16.0 mmol) were added at 0° C. After the solution was stirred at 25° C. for 16 h, solvent was removed, and the crude was taken up with 1N HCl solution (30 mL) and extracted with EtOAc (360 mL×3). The organic layer was dried over $Na_2SO_4$, filtered and concentrated in vacuo. The crude was purified by column chromatography on silica gel (PE/EtOAc=20:1) to give 75-5 (1.9 g, 58%).

LCMS (ESI): m/z 246.1 [M+H$^+$].

Step 4

Cu(CH$_3$CN)$_4$PF$_6$ (432 mg, 1.16 mmol) was added to a solution of 75-6 (3.11 g, 15.48 mmol) and compound 5 (1.9 g, 7.74 mmol) in DMF (15 mL) at 25° C. After the reaction mixture was heated at 50° C. for 2 h under N$_2$, solvent was removed and the residue was purified by prep-HPLC to give 75-7 (2.1 g, 61%).

$^1$H NMR (400 MHz, DMSO-d$_6$) δ 7.95 (s, 1H), 7.69 (d, J=8.8 Hz, 1H), 7.36-7.29 (m, 5H), 5.96 (br, 1H), 5.38-5.35 (m, 1H), 5.07-4.99 (m, 2H), 4.82-4.77 (m, 1H), 2.94 (s, 2H), 2.16-2.06 (m, 2H), 1.68-1.56 (m, 3H), 1.28-1.05 (m, 2H), 0.92-0.80 (m, 6H).

Step 5

A mixture of 75-7 (500 mg, 1.12 mmol), 75-8 (414 mg, 3.36 mmol) and EEDQ (831 mg, 3.36 mmol) in DCM (10 mL) was stirred at 25° C. for 2 h. Solvent was removed and the residue was purified by column chromatography on silica gel (DCM/MeOH=5:1) to give 75-9 (350 mg, 57%).

$^1$H NMR (400 MHz, MeOD) δ 8.02 (s, 1H), 7.56-7.54 (m, 2H), 7.33-7.27 (m, 7H), 5.50-5.46 (m, 1H), 5.07 (s, 2H), 4.95-4.91 (m, 1H), 4.55 (s, 2H), 3.25-3.07 (m, 2H), 2.25-2.21 (m, 2H), 1.77-1.64 (m, 3H), 1.44-1.40 (m, 2H), 0.96-0.95 (m, 6H).

LCMS (ESI): m/z 552.2 [M+H$^+$].

Step 6

To a solution of 75-9 (120 mg, 0.218 mmol) in THF (3 mL) was added PNP carbonate (199 mg, 0.654 mmol) and DIPEA (113 mg, 0.872 mmol) at 25° C. After the mixture was heated at 50° C. for 18 h, solvent was removed, and the residue was dissolved in DMF (3 mL). Norfloxacin (104 mg, 0.327 mmol) and DIPEA (141 mg, 1.09 mmol) was added and the mixture was stirred at 25° C. for 6 h. Solvent was removed, and the residue was purified by prep-HPLC to give example 75 (90 mg, 46%).

$^1$H NMR (400 MHz, DMSO-d$_6$) δ 15.34 (s, 1H), 10.64 (s, 1H), 8.97 (s, 1H), 8.13 (s, 1H), 8.04 (s, 1H), 7.97-7.93 (m, 1H), 7.73-7.70 (m, 1H), 7.61-7.59 (m, 2H), 7.38-7.20 (m, 8H), 6.03 (m, 1H), 5.47-5.43 (m, 1H), 5.07-5.03 (m, 4H), 4.82-4.74 (m, 1H), 4.59-4.57 (m, 2H), 3.61 (s, 4H), 3.34 (s, 4H), 2.90-3.01 (m, 2H), 2.10-2.07 (m, 2H), 1.62-1.56 (m, 3H), 1.42-1.38 (m, 3H), 1.27 (m, 2H), 0.90-0.89 (m, 6H).

LCMS (ESI): m/z 897.4 [M+H$^+$].

Example 76. 7-(4-((4-((S)-2-(4-((S)-1-((S)-2-(6-(2,5-dioxopyrrolidin-1-yl)hexanamido)-4-methylpentanamido)-2-methylpropyl)-1H-1,2,3-triazol-1-yl)-5-ureidopentanamido)benzyloxy)carbonyl)piperazin-1-yl)-1-ethyl-6-fluoro-4-oxo-1,4-dihydroquinoline-3-carboxylic acid example 76

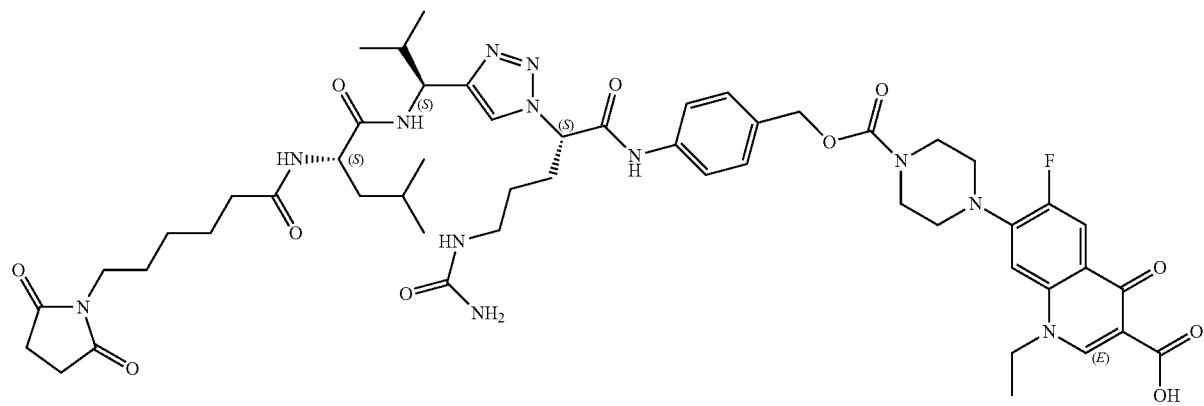

Example 76 was made using the procedure as Example 57, with the intermediate from the synthesis of Example 57.

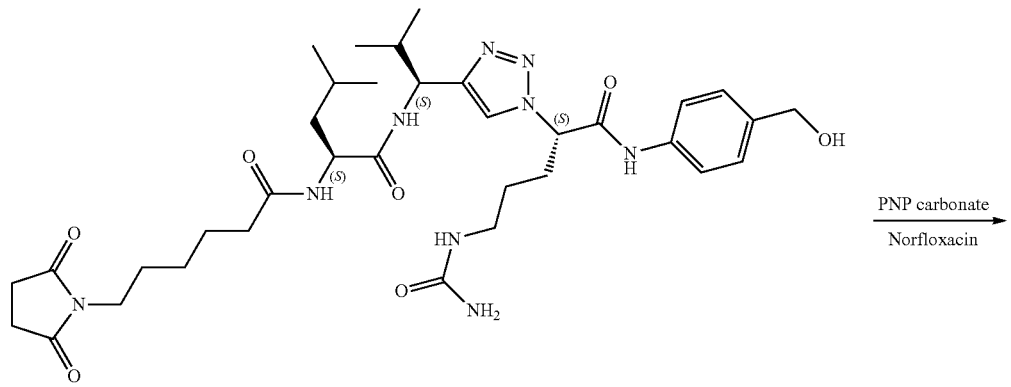

57-11b

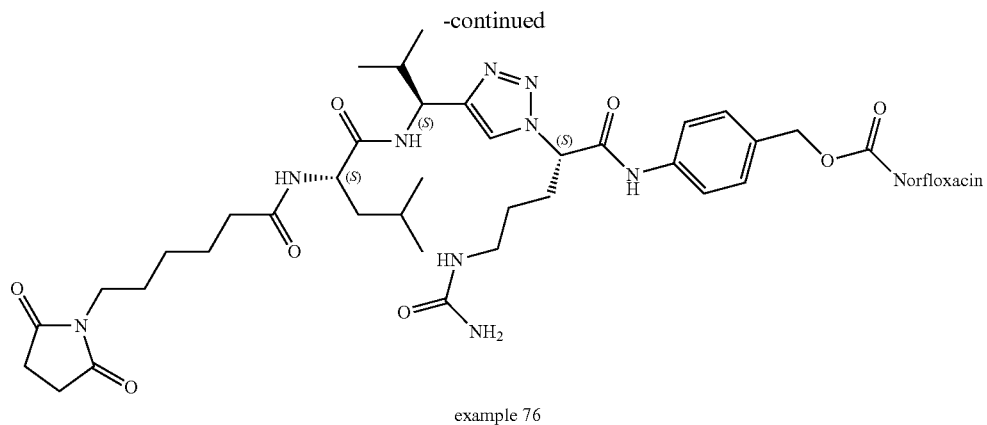

example 76

LCMS: (5-95, AB, 1.5 min, ESI), 0.828 min, MS=529.4. [½M+1]

¹H NMR Methanol-d₄ 400 MHz, δ 8.89 (s, 1H), 8.09 (s, 1H), 8.00 (d, J=13.2 Hz, 1H), 7.62 (d, J=8 Hz, 2H), 7.38 (d, J=8 Hz, 2H), 7.20 (s, 1H), 5.51 (d, J=5.2 Hz, 1H), 5.15 (s, 2H), 4.96 (d, J=6.8 Hz, 1H), 4.88 (s, 2H), 4.60 (s, 4H), 3.73 (s, 4H), 3.46-3.42 (m, 2H), 3.35 (s, 4H), 2.65 (s, 4H), 2.30-2.22 (m, 4H), 1.65-1.56 (m, 9H), 1.54-1.28 (m, 5H), 1.00-0.97 (m, 12H).

Example 77. 7-(4-((4-((S)-2-(4-((S)-1-((S)-2-(6-(2,5-dioxopyrrolidin-1-yl)hexanamido)-3-phenylpropanamido)-2-methylpropyl)-1H-1,2,3-triazol-1-yl)-5-ureidopentanamido)benzyloxy) carbonyl)piperazin-1-yl)-1-ethyl-6-fluoro-4-oxo-1,4-dihydroquinoline-3-carboxylic acid example 77

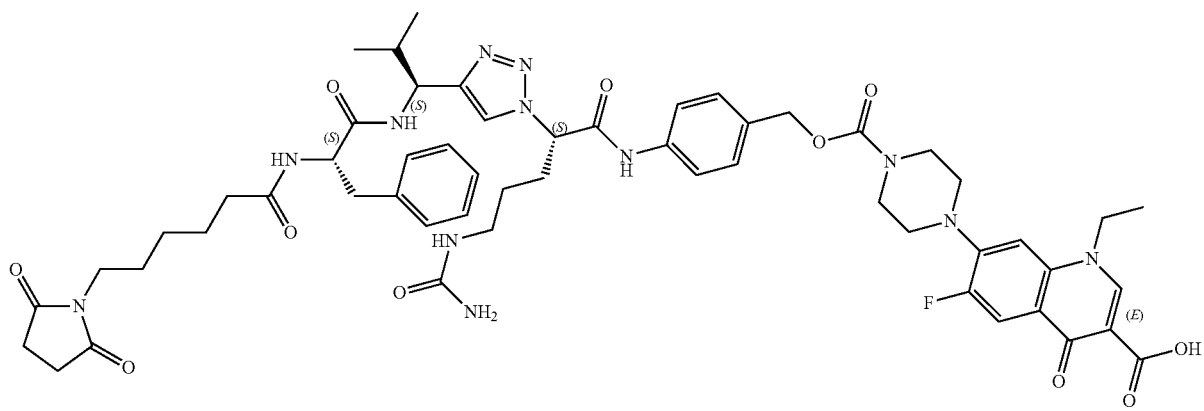

Example 77 was made using the procedure as Example 59, with intermediates from the synthesis of Example 59.

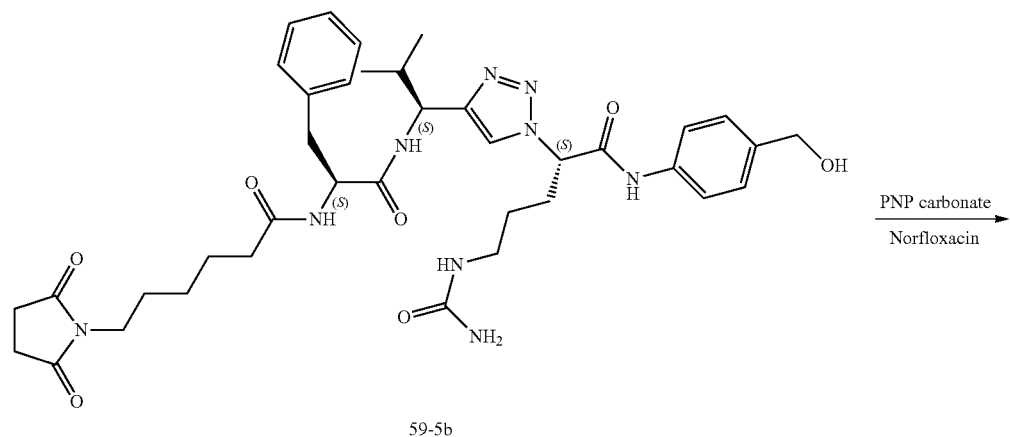

59-5b

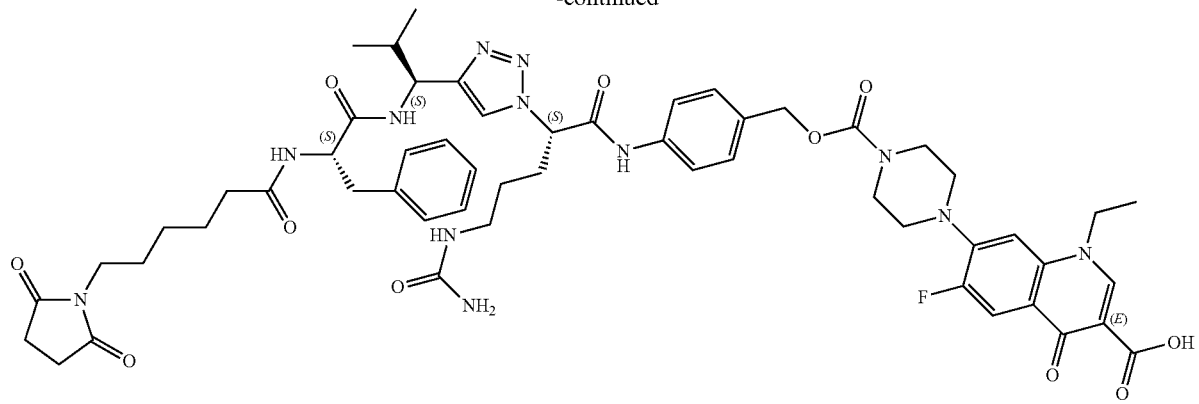

example 77

LCMS: (5-95, AB, 1.5 min, ESI), 0.841 min, MS=546.5 [½M+1]

$^1$H NMR DMSO-d$_6$ 400 MHz, δ 10.66 (s, 1H), 8.96 (s, 1H), 8.34 (d, J=9.2 Hz, 1H), 8.09 (s, 1H), 8.04 (d, J=8.8 Hz, 1H), 7.95 (d, J=12.8 Hz, 1H), 7.61 (d, J=8.4 Hz, 2H), 7.36 (d, J=8.8 Hz, 2H), 7.28-7.17 (m, 6H), 6.05 (s, 1H), 5.55-5.48 (m, 1H), 5.43 (s, 2H), 5.07 (s, 2H), 4.90-4.86 (m, 1H), 4.59-4.58 (m, 3H), 3.61 (s, 4H), 3.34-3.23 (m, 4H), 3.04-2.95 (m, 4H), 2.78 (s, 1H), 2.59 (s, 4H), 2.05-1.98 (m, 4H), 1.43-1.22 (m, 10H), 1.04 (d, J=7.2 Hz, 2H), 0.77 (d, J=6.8 Hz, 3H), 1.42 (d, J=6.8 Hz, 3H).

Example 78. 7-(4-((4-((S)-2-(4-((S)-1-((S)-2-(6-(2, 5-dioxopyrrolidin-1-yl)hexanamido)-3-methylbutanamido)-2-methylpropyl)-1H-1,2,3-triazol-1-yl)-5-ureidopentanamido) benzyloxy)carbonyl)piperazin-1-yl)-1-ethyl-6-fluoro-4-oxo-1,4-dihydroquinoline-3-carboxylic acid example 78

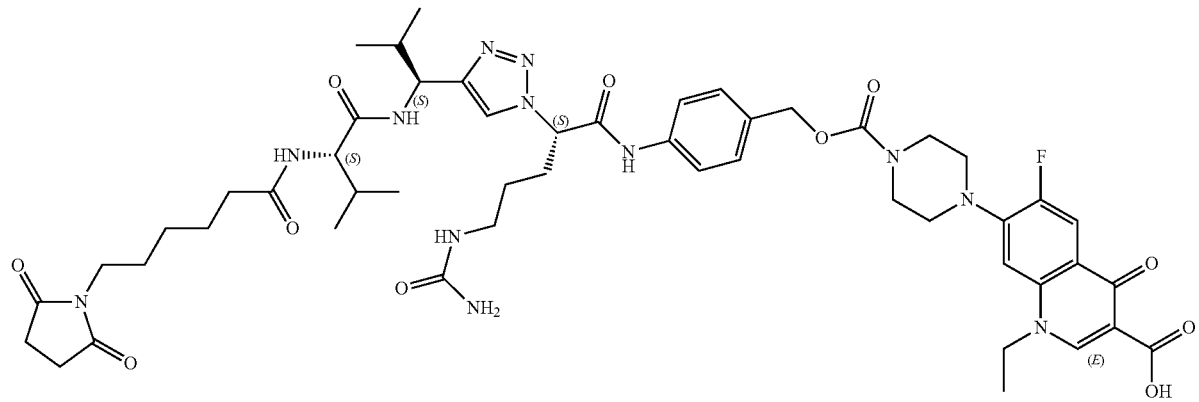

Example 78 was made using the procedure as Example 60, with intermediate from the synthesis of Example 60.

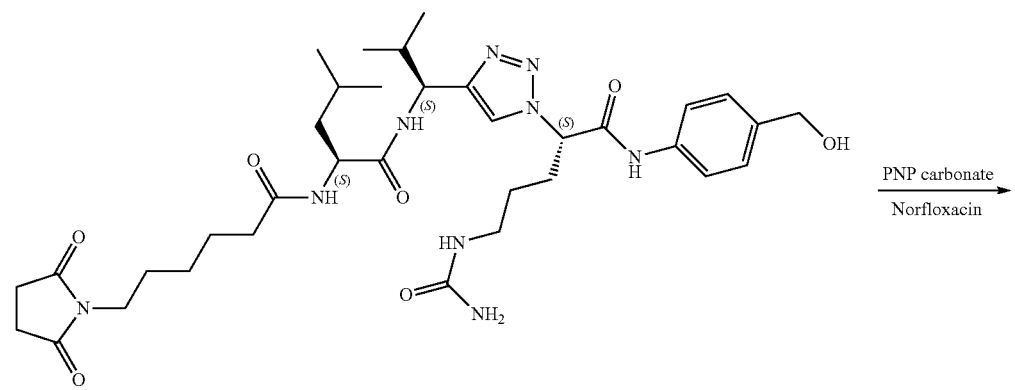

60-5b

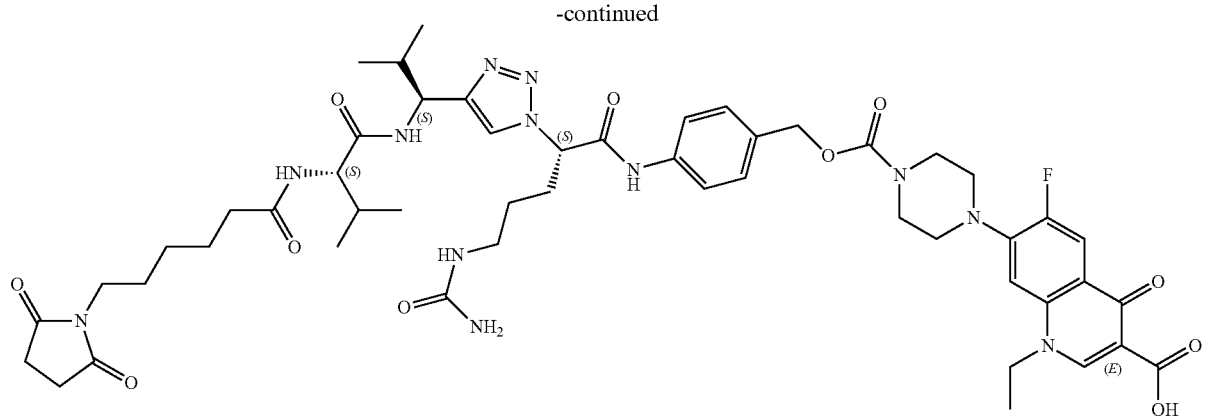

example 78

Step 1

To a solution of compound 60-5b (50 mg, 0.072 mmol) in dry DMF (3 mL) was added PNP carbonate (50 mg, 0.16 mmol) and DIPEA (0.5 mL, 3 mmol) at r.t., and the mixture was stirred at r.t. for 1.5 h. Norfloxacin (50 mg, 0.16 mmol) was added. The mixture was stirred at r.t. for additional 1 h. The mixture was concentrated, filtered and purified by prep-HPLC (FA), to give example 78 (38.8 mg, yield: 52%).

LCMS: (5-95, AB, 1.5 min, ESI), 0.833 min, MS=522.4. [½M+1]

$^1$H NMR DMSO-$d_6$ 400 MHz, δ 10.1 (s, 1H), 8.93 (s, 1H), 8.25-8.22 (d, 1H), 8.04 (s, 1H), 7.93-7.90 (d, 1H), 7.81-7.79 (d, 1H), 7.58-7.56 (d, J=8.0 Hz, 2H), 7.35-7.33 (d, J=8.0 Hz, 2H), 7.20-7.18 (m, 1H), 6.0 (m, 1H), 5.5 (m, 1H), 5.40 (s, 2H), 5.04 (s, 2H), 4.9-4.87 (m, 1H), 4.6-4.5 (m, 2H), 4.2-4.1 (m, 1H), 3.6 (s, 4H), 3.2 (m, 6H), 3.05-2.9 (m, 2H), 2.55 (s, 4H), 2.18-2.0 (m, 5H), 1.9-1.8 (m, 1H), 1.5-1.35 (m, 7H), 1.3-1.05 (m, 4H), 0.84-0.77 (m, 12H).

Example 79. 7-(4-(((4-((S)-2-(4-((S)-1-(benzyloxy-carbonylamino)-2-methylpropyl)-1H-1,2,3-triazol-1-yl)-5-guanidinopentanamido)benzyloxy)carbonyl)piperazin-1-yl)-1-ethyl-6-fluoro-4-oxo-1,4-dihydroquinoline-3-carboxylic acid

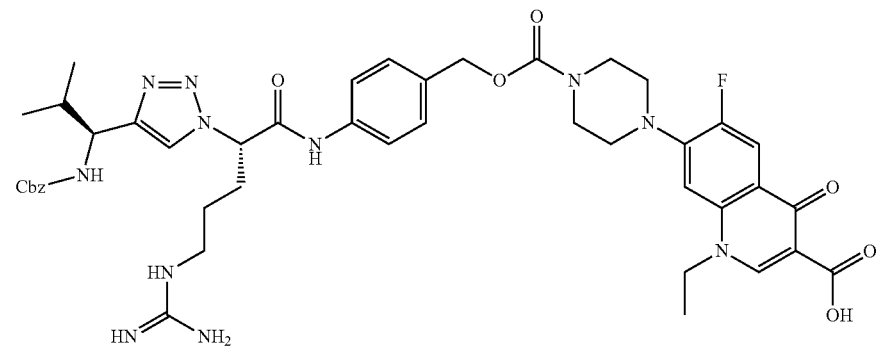

example 79

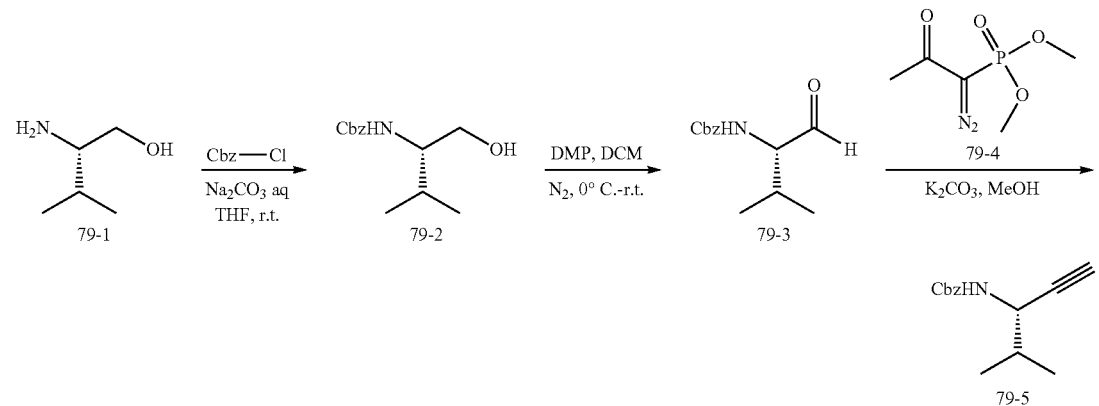

339
-continued
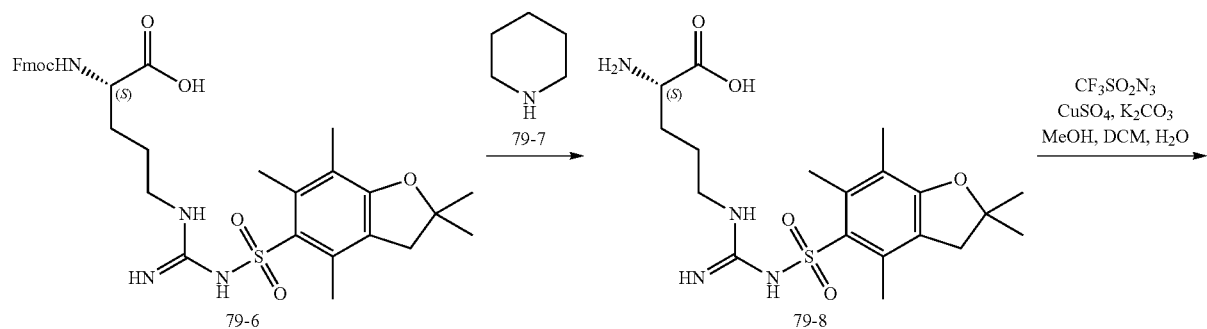
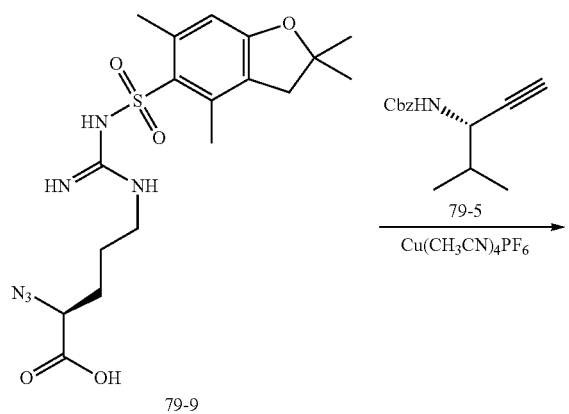
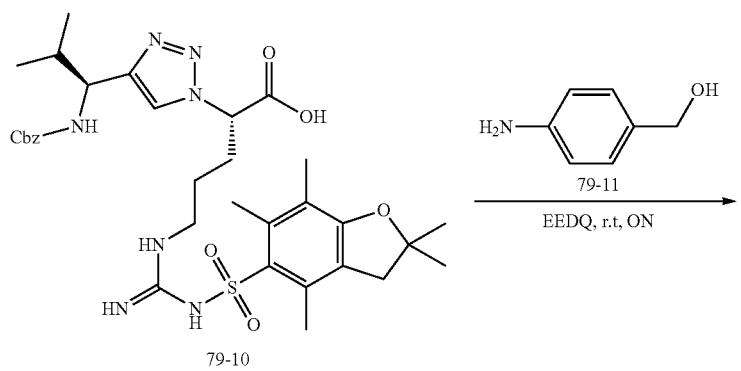
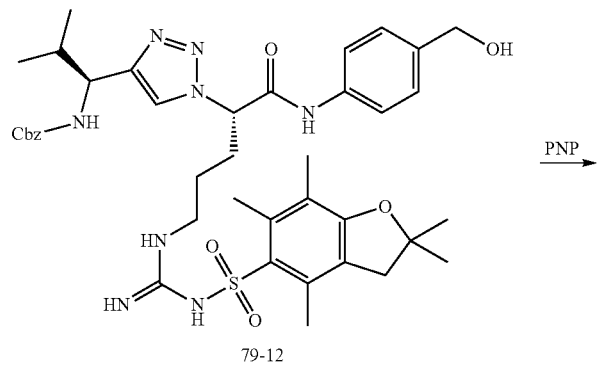

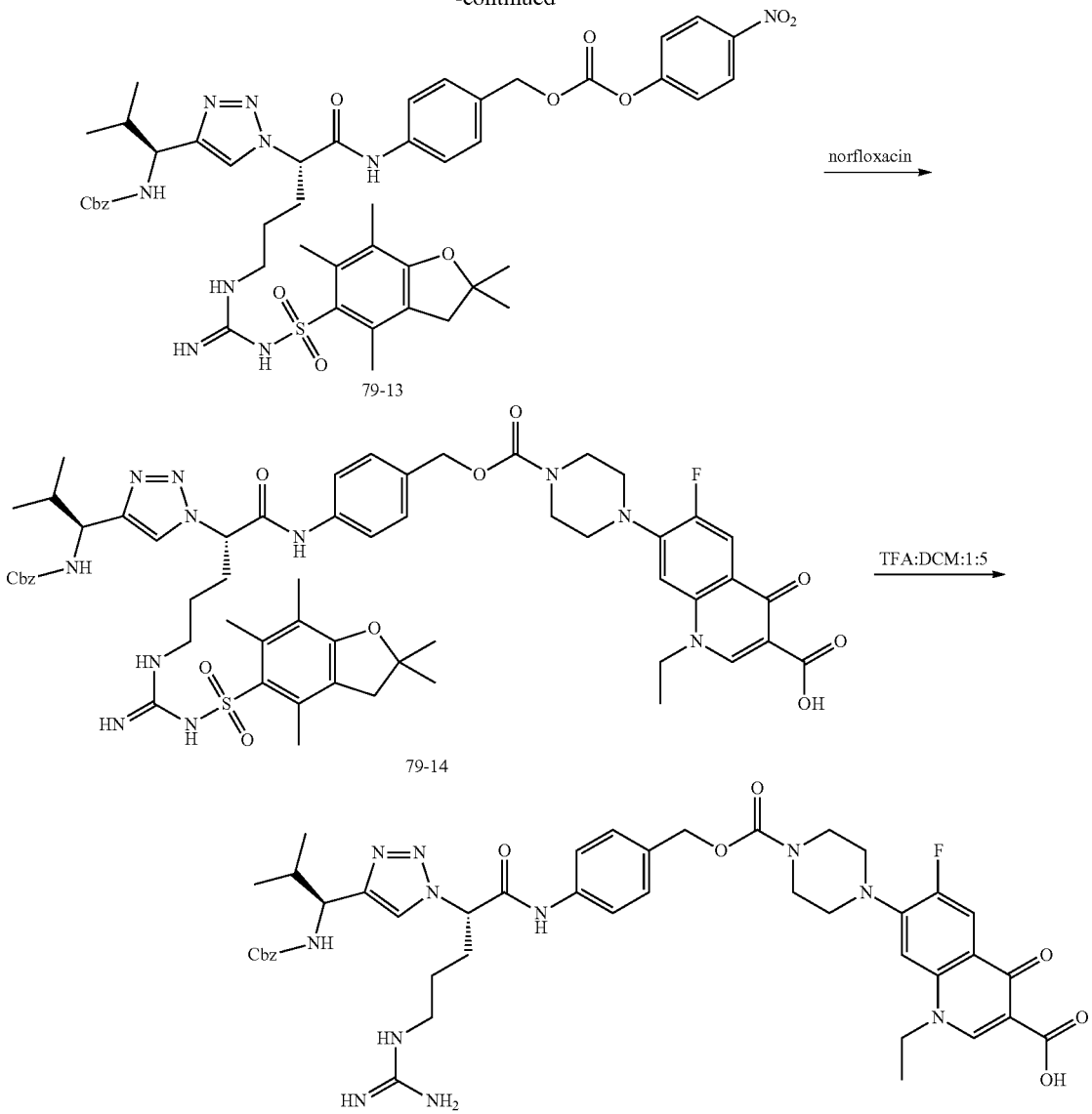

example 79

Step 1

To a solution of compound 79-1 (2 g, 19.4 mmol) in THF (4 mL) was added sat. aq. K$_2$CO$_3$ (30 mL), followed by Cbz-Cl (3.958 g, 23.2 mmol) at 0° C. After the reaction mixture was stirred at 28° C. for 1 h, it was extracted with EtOAc (20 mL×3) and H$_2$O (20 mL). The combined organic layer was dried over Na$_2$SO$_4$, filtered and concentrated to give compound 79-2 (5 g, 100%) which was used in the next step without further purification.

$^1$H NMR (400 MHz, DMSO-d$_6$) δ 7.36-7.31 (m, 5H), 6.92 (d, J=8.8 Hz, 1H), 5.01 (s, 2H), 3.39-3.32 (m, 3H), 1.80-1.76 (m, 1H), 0.85-0.80 (m, 6H).

Step 2

To a solution of compound 79-2 (6.8 g, 28.7 mmol) in DCM (100 mL) under N$_2$ was added DMP (14.59 mg, 343.4 mmol) at 0° C. After 5 min, the reaction mixture was warmed to r.t. and stirred at r.t. for 1 h. The reaction mixture was cooled to 0° C. and washed with a saturated solution of NaHCO$_3$/Na$_2$SO$_3$ (1:1). After separation, the organic layer was washed once more. The combined aqueous layers were extracted with DCM (30 mL×2). It was dried over Na$_2$SO$_4$, filtered and concentrated to give compound 79-3 (5.3 g, 79%), which was use in the next step without further purification.

$^1$H NMR (400 MHz, DMSO-d$_6$) δ 9.51 (d, J=0.8 Hz, 1H), 7.72-7.61 (m, 1H), 7.43-7.30 (m, 5H), 5.04 (s, 2H), 3.91-3.88 (m, 1H), 2.18-2.13 (m, 6H), 0.94-0.82 (m, 6H).

Step 3

To a solution of compound 79-3 (crude, 4.9 g, 12.76 mmol), compound 79-4 (4.9 g, 25.5 mmol) in MeOH (50 mL) was added K$_2$CO$_3$ (5.28 g, 38.28 mmol). The reaction mixture was stirred at r.t. for overnight. The mixture was concentrated and purified by column chromatography on silica gel (PE:EtOAc=10:1) to give the desired product 79-5 (1.30 g, 44%).

$^1$H NMR (400 MHz, DMSO-d$_6$) δ 7.74 (d, J=8.8 Hz, 1H), 7.37-7.29 (m, 5H), 5.01 (s, 2H), 4.09-4.05 (m, 1H), 3.16 (d, J=2.4 Hz, 1H), 1.76 (d, J=6.8 Hz, 1H), 0.91 (d, J=6.8 Hz, 3H), 0.87 (d, J=6.8 Hz, 3H).

Step 4

To a solution of compound 79-6 (2 g, 3.09 mmol) in DCM (30 mL) was added compound 79-7 (1.6 mL, 15.4 mmol). After the reaction mixture was stirred at r.t. for 16 h, it was concentrated in vacuum, and washed with MTBE, filtered to give the desired product 79-8 (1.315 g, 100%).

Step 5

A mixture of NaN$_3$ (1.6 g, 15.45 mmol) in distilled H$_2$O (5 mL) and CH$_2$Cl$_2$ (10 mL) was cooled on an ice bath. Tf$_2$O (1.1 mL, 6.18 mmol) was added slowly over 5 min and stirred for 2 h. The CH$_2$Cl$_2$ phase was removed and the aqueous phase was extracted with CH$_2$Cl$_2$ (5 mL×2). The organic fractions, containing the triflyl azide were pooled and washed once with saturated Na$_2$CO$_3$ (40 mL) and used without further purification. Compound 79-8 (1.315 g, 3.09 mmol), K$_2$CO$_3$ (641 mg, 4.635 mmol) and CuSO$_4$.5H$_2$O (155 mg, 0.618 mmol) was added to distilled H$_2$O (10 mL) and MeOH (20 mL). The triflyl azide solution in CH$_2$Cl$_2$ (50 mL) was added and the mixture was stirred at r.t for overnight. Organic solvents were removed under reduced pressure and the aqueous slurry was diluted with H$_2$O (50 mL) and acidified to pH 6 with conc. HCl then diluted with 0.2 M pH 6.2 phosphate buffer (50 mL) and exacted with EtOAc (3×100 mL) to remove sulfonamide by-product. The aqueous phase was then acidified to pH 2 with conc. HCl. The product was obtained from another round of EtOAc/MeOH (20:1) extractions (4×100 mL). These EtOAc/MeOH extracts were combined, dried over Na$_2$SO$_4$ and evaporated to give compound 79-9 without further purification (600 mg, 43%).

Step 6

To the solution of compound 79-9 (500 mg, 1.1 mmol) and 79-5 (307 g, 1.33 mmol) in DMF (5 mL) was added Cu(CH$_3$CN)$_4$PF$_6$ (165 mg, 0.44 mmol). The reaction mixture was stirred at 50° C. for 2 h, the mixture (79-10) was used directly for next step.

Step 7

To the mixture of compound 79-10 (crude, 752 mg, 1.1 mmol) in DMF (5 mL) was added EEDQ (544 mg, 2.2 mmol) and compound 79-11 (203 g, 1.65 mmol). The reaction mixture was stirred at 0° C. and warmed to r.t. under N$_2$ overnight. The mixture was purified by prep-HPLC and SFC separation to give compound 79-12 (250 mg, 30%).

Step 8

To the solution of compound 79-12 (90 mg, 0.114 mmol) and PNP carbonate (69 mg, 0.228 mmol) in DMF (3 mL) was added DIPEA (45 mg, 0.342 mmol). The reaction mixture was stirred at 21° C. for 3 h under N$_2$. The mixture (79-13) was used directly for next step without purification.

Step 9

To the solution from previous step was added norfloxacin (75 mg, 0.228 mmol). The reaction mixture was stirred at 21° C. for 1 h. The mixture was purified by prep-HPLC to give compound 79-14 (80 mg, 62%).

Step 10

To the solution of compound 79-14 (60 mg, 0.053 mmol) in DCM (5 mL) was added TFA (1 mL) at 0° C. The reaction mixture was stirred at 16° C. for 5 h. The mixture was purified by prep-HPLC and SFC to give example 79 (30 mg, 64%).

LCMS (ESI): RT=0.837 min, M+H$^+$=882.2. method=5-95/1.5 min.

$^1$H NMR (400 MHz, DMSO-d$_6$) δ 8.94 (s, 1H), 8.48 (s, 1H), 8.12 (s, 1H), 7.92 (d, J=12.4 Hz, 1H), 7.76 (d, J=8.8 Hz, 1H), 7.61 (s, 1H), 7.34 (m, 10H), 5.07-4.99 (m, 5H), 4.59 (d, J=7.2 Hz, 1H), 3.61 (s, 4H), 3.17 (m, 6H), 3.12 (s, 2H), 2.18-2.03 (m, 4H), 1.39 (s, 5H), 0.84 (d, J=6.4 Hz, 3H), 0.78 (d, J=6.0 Hz, 3H).

Example 80. (S)-7-(4-((4-(2-(4-(2-(benzyloxycarbonylamino)propan-2-yl)-1H-1,2,3-triazol-1-yl)-5-ureidopentanamido)benzyloxy)carbonyl)piperazin-1-yl)-1-ethyl-6-fluoro-4-oxo-1,4-dihydroquinoline-3-carboxylic acid

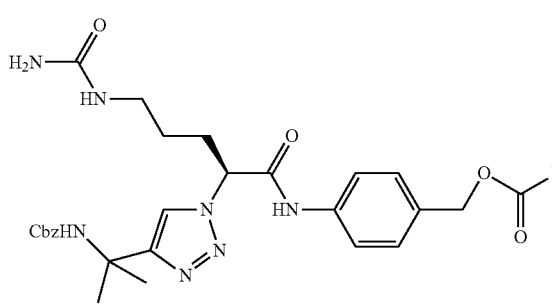
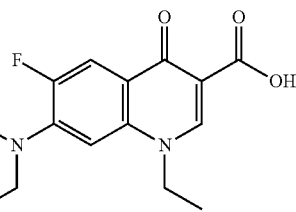

example 80

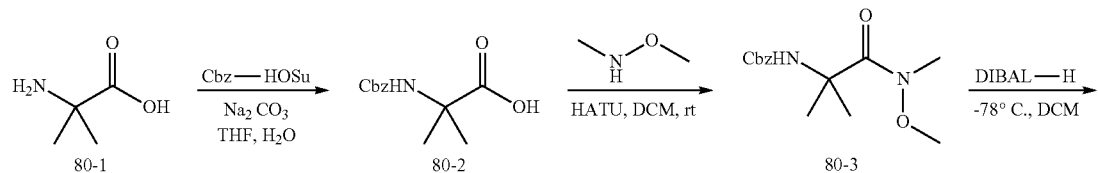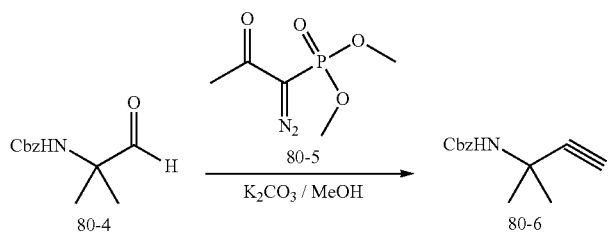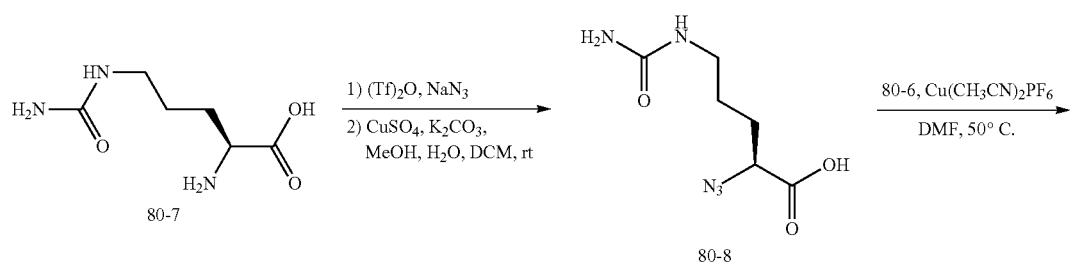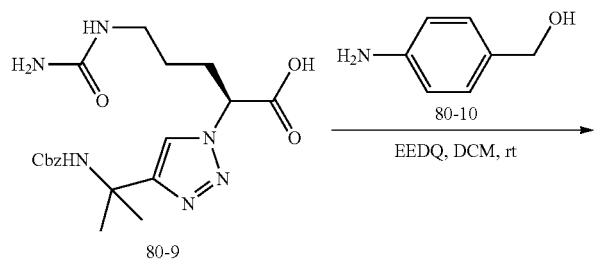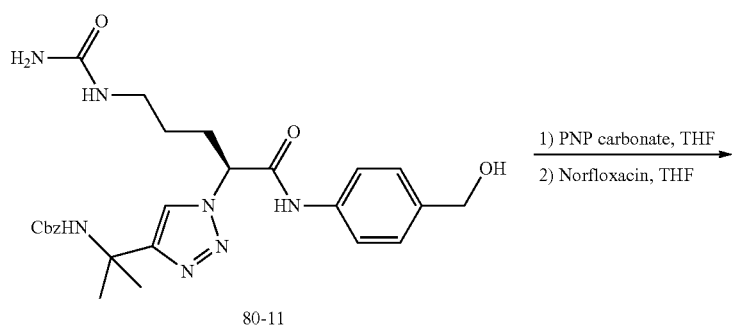

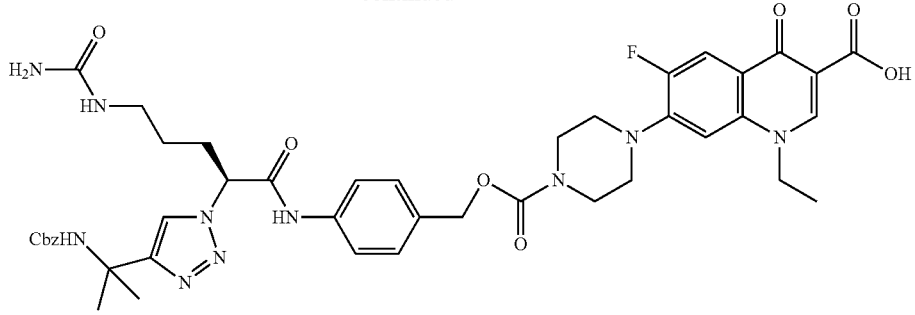

example 80

Step 1

Cbz-OSu (57 g, 0.23 mol) in THF (150 mL) was added a mixture of aq Na$_2$CO$_3$ (82 g, 0.78 mol) and 80-1 (20 g, 0.19 mol). After it was stirred at r.t. for 16 h, it was adjusted to pH>10 and washed with EtOAc (400 mL×2). The aqueous layer was pooled and acidified to pH<1 with conc. HCl. It was extracted with EtOAc (500 mL×2). The organic layer was dried over Na$_2$SO$_4$ and evaporated to give 80-2 (45 g, 97.8%).

Step 2

To a mixture of 80-2 (20 g, 84.3 mmol), N, O-dimethyl-hydroxylamine hydrochloride (8.9 g, 92.7 mmol) and HATU (48.1 g, 126.4 mmol) in DCM (200 mL) was added Et$_3$N (48.7 mL, 337.2 mmol). The mixture was stirred at r.t. for 2 h. After the solvent was removed, the residue was taken up with water (300 mL). The aqueous layer was extracted with EtOAc (300 mL×3) and the organic layers were washed with saturated NaHCO$_3$ (150 mL), conc.HCl (100 mL) and saturated NaCl (100 mL). The organic layer was dried over Na$_2$SO$_4$, concentrated and purified by column chromatography on silica gel (PE:EtOAc=2:1) to give 80-3 (12.9 g, 54.6%).

Step 3

DIBAL-H (17.8 mL, 1M in toluene) was added dropwise to a solution of 80-3 (4.15 g, 14.8 mmol) in anhydrous CH$_2$Cl$_2$ (100 mL) at −78° C. and the resulting solution was stirred at −78° C. for 2 h. Excess DIBAL was quenched by anhydrous MeOH (5 mL) and the solution was warmed to r.t. The solution was concentrated to give 80-4 (3.27 g), which was used in next step without further purification.

Step 4

A mixture of 80-4 (3.27 g, 14.8 mmol), 80-5 (2.96 g, 17.8 mmol) and K$_2$CO$_3$ (4.1 g, 29.7 mmol) in MeOH (60 mL) was stirred at r.t. for 16 h. The solvents were removed under reduced pressure and the crude residue was partitioned in EtOAc (200 mL) and water (100 mL). The organic layer was washed with brine (50 mL) and dried over anhydrous Na$_2$SO$_4$. The solvent was removed under reduced pressure and purified by column chromatography on silica gel (PE: EtOAc=10:1) to give 80-6 (606 mg, 18.9%).

Step 5

Tf$_2$O (1.7 mL, 9.9 mmol) was added slowly over 5 min to a solution of NaN$_3$ (3.2 g, 49.3 mmol) in distilled H$_2$O (10 mL) and CH$_2$Cl$_2$ (16 mL) at 0° C. After it was for 2 h, the organic phase was separated, and the aqueous was extracted with CH$_2$Cl$_2$ (20 mL×2). The combined organic fractions, containing the triflyl azide were pooled and washed once with saturated Na$_2$CO$_3$ and used without further purification.

To a mixture of 80-7 (0.86 g, 4.93 mmol) and K$_2$CO$_3$ (1.02 g, 7.40 mmol), CuSO$_4$.5H$_2$O (25 mg, 0.099 mmol) in H$_2$O (18 mL) and MeOH (36 mL) was added the triflyl azide in CH$_2$Cl$_2$ (32 mL) and the mixture was stirred at 26° C. for 12 h. The organic solvents were removed under reduced pressure and the aqueous slurry was diluted with H$_2$O (50 mL). It was acidified to pH 6 with conc. HCl and diluted with phosphate buffers (0.2M, pH 6.2, 50 mL) and washed with EtOAc (100 mL×2). The aqueous phase was then acidified to pH 2 with conc. HCl and extracted with EtOAc (100 mL×2), dried over Na$_2$SO$_4$ and concentrated to give 80-8, which was used in next step without further purification.

Step 6

A mixture of 80-8 (0.99 g, 4.93 mmol), 80-6 (0.54 g, 2.46 mmol) and Cu(CH$_3$CN)$_4$PF$_6$ (115 mg, 0.37 mmol) in DMF (5 mL) was stirred at 50° C. for 2 h. After solvent was removed, the residue was purified by prep-HPLC to give 80-9 (250 mg, 23%).

Step 7

The mixture of 80-9 (199 mg, 0.48 mmol), 80-10 (176 mg, 1.43 mmol) and EEDQ (353 mg, 1.43 mmol) in DCM (10 mL) was stirred at 24° C. for 2 h. After removal of the solvent, the residue was purified by prep-HPLC to give 80-11 (211 mg, 84%).

$^1$H NMR (400 MHz, MeOD) δ 8.00 (s, 1H), 7.56 (dd, J=1.6, 8.4 Hz, 2H), 7.33-7.31 (m, 7H), 5.48-5.44 (m, 2H), 4.99 (s, 2H), 4.56 (s, 2H), 3.23-3.16 (m, 1H), 3.09-3.03 (m, 1H), 2.26-2.20 (m, 2H), 1.68 (s, 6H), 1.51-1.45 (m, 1H), 1.39-1.29 (m, 1H).

LCMS (ESI): m/z 524.3 [M+H$^+$].

Step 8

After a mixture of 80-11 (150 mg, 0.29 mmol), PNP carbonate (173 mg, 0.57 mmol) and DIPEA (111 mg, 0.86 mmol) in DCM (5 mL) was stirred at 50° C. for 12 h solvent was removed and added to a solution of DIPEA (112 mg, 0.87 mmol) and norfloxacin (316 mg, 0.87 mmol) in DMF (5 mL), and stirred at 25° C. for 4 h. Solvent was removed and the residue was purified by prep-HPLC to give example 80 (113 mg, 45%).

$^1$H NMR (400 MHz, DMSO-d$_6$) δ 10.65 (s, 1H), 8.96 (s, 1H), 7.98-7.93 (m, 2H), 7.63-7.60 (m, 3H), 7.38-7.20 (m, 9H), 6.05 (s, 1H), 5.44 (s, 3H), 5.07 (s, 2H), 4.93 (s, 2H), 4.59-4.57 (m, 2H), 3.61 (s, 4H), 3.02-2.98 (m, 2H), 2.12-2.02 (m, 2H), 1.57 (d, J=4.0 Hz, 6H), 1.42-1.38 (m, 3H), 1.28-1.23 (m, 2H).

LCMS (ESI): m/z 869.3 [M+H$^+$].

Example 81. 7-(4-((4-((S)-2-(4-((S)-1-(benzyloxy-carbonylamino)-2-phenylethyl)-1H-1,2,3-triazol-1-yl)-5-ureidopentanamido)benzyloxy)carbonyl)piper-azin-1-yl)-1-ethyl-6-fluoro-4-oxo-1,4,4a,8a-tetrahydroquinoline-3-carboxylic acid
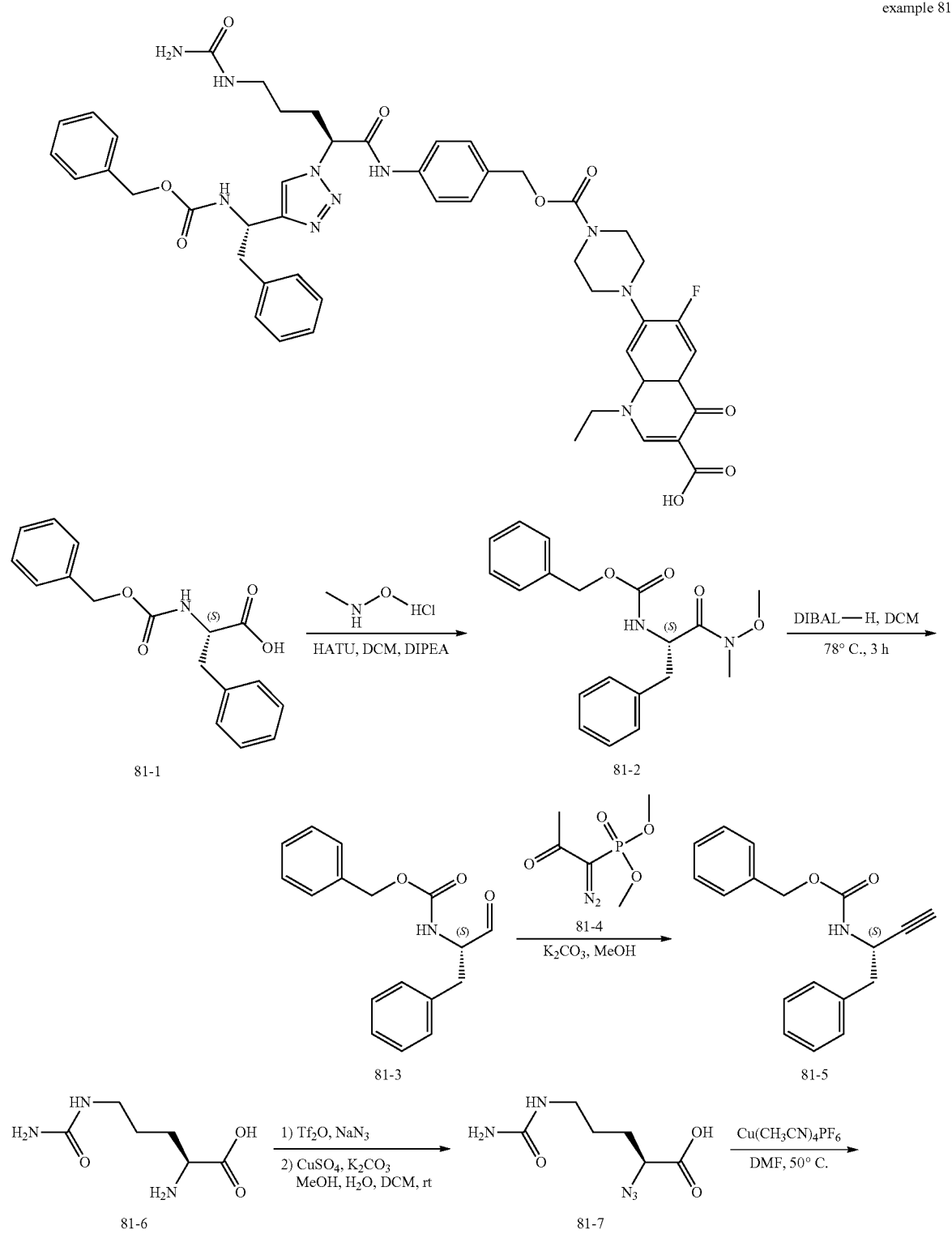
example 81

-continued
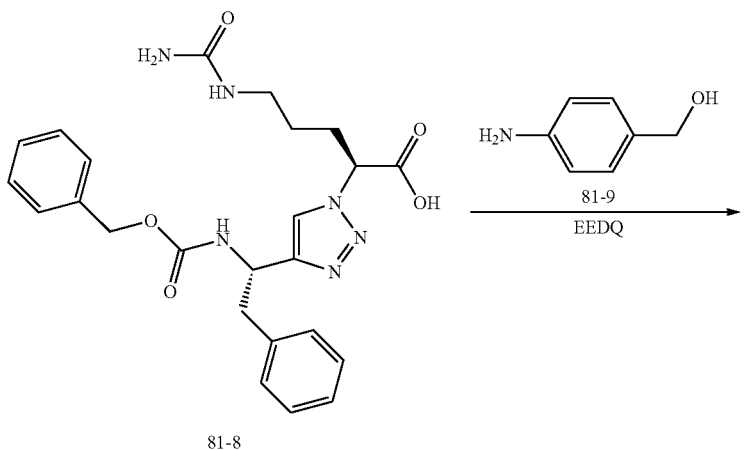
81-8
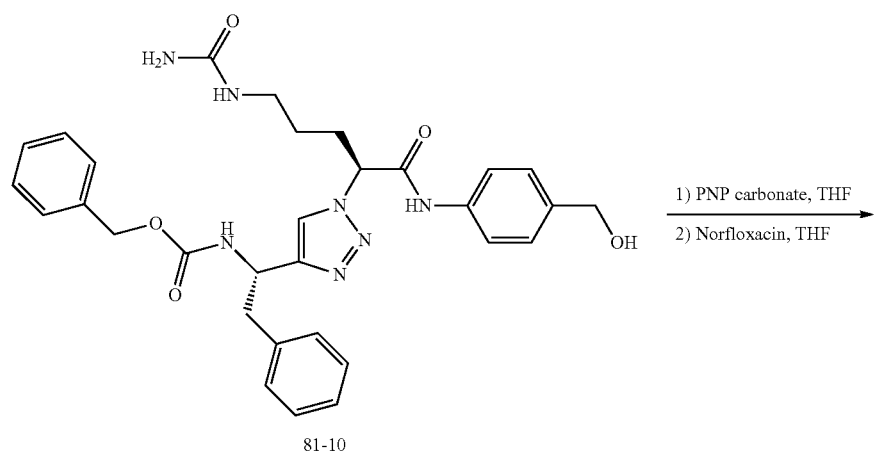
81-10
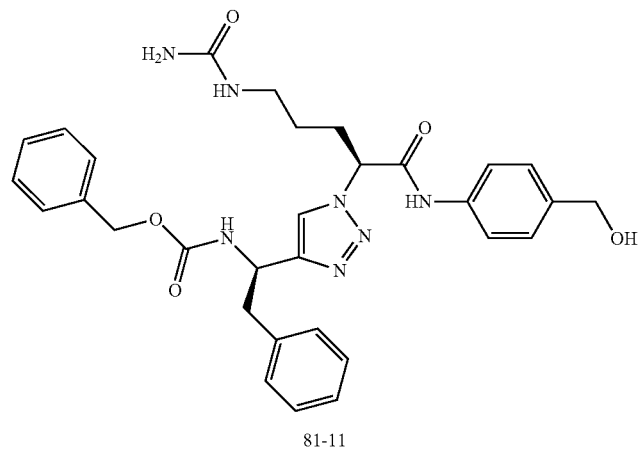
81-11

-continued

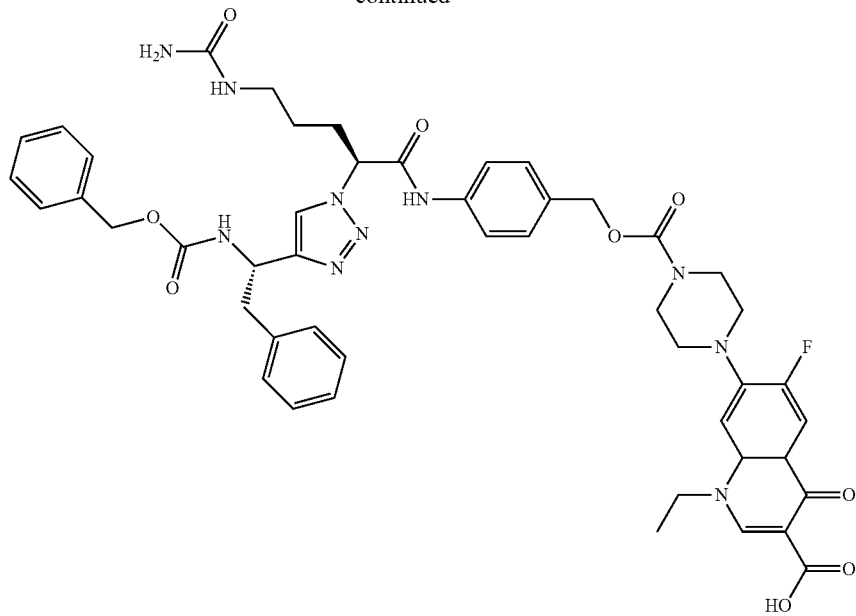

example 81

Step 1

To the solution of Cbz-L-phenylalanine (3.0 g, 10 mmol) in DCM (100 mL) was added HATU (4.57 g, 12.0 mmol) and DIPEA (3.87 g, 30.0 mmol). After it was stirred at r.t. for 15 min, N-methoxymethanamine hydrochloride (1.2 g, 12 mmol) was added. After the solution was stirred for another 1 h, it was extracted with DCM (60 mL×3), washed with 10% aq. HCl (60 mL) and water (60 mL). The organic layer was dried over $Na_2SO_4$, concentrated and purified by the column chromatography on silica gel to give 81-2 (3.2 g, 94%).

$^1$H NMR (400 MHz, $CDCl_3$) δ 7.36-7.14 (m, 10H), 5.42-5.40 (m, 1H), 5.13-5.02 (m, 3H), 3.69 (s, 3H), 3.18 (s, 3H), 3.11-3.06 (m, 1H), 2.94-2.89 (m, 1H).

Step 2

DIBAL-H (20 mL, 1M in toluene) was added to a solution of 81-2 (3.4 g, 10 mmol) in dry DCM (150 mL) at −78° C. under $N_2$. After the solution was stirred at −78° C. for 6 h, the mixture was quenched with MeOH (50 mL) and water (50 mL). It was filtered and the filtrate was dried over $Na_2SO_4$, concentrated and 81-3 used directly in the next step without further purification.

LCMS (ESI): m/z 284.1 [M+H$^+$].

Step 3

To the solution of 81-3 (10 mmol) in MeOH (100 mL) was added $K_2CO_3$ (2.76 g, 20 mmol) and 81-4 (2.31 g, 12 mmol) at 0° C. After the reaction was stirred at 0° C. for 12 h, solvent was removed and the residue was purified by column chromatography on silica gel to give 81-5.

LCMS (ESI): m/z 280.1 [M+H$^+$].

Step 4

To a solution of $NaN_3$ (1.78 g, 27.45 mmol) in a mixture of $H_2O$ (5 mL) and DCM (7.5 mL) was added $Tf_2O$ (0.93 mL, 5.55 mmol). After the mixture was stirred for 2 h at r.t., it was extracted with DCM (60 mL×3). The organic layer was washed with aq. $Na_2CO_3$ and concentrated to 10 mL. 81-6 (500 mg, 2.8 mmol) was then added, followed by $K_2CO_3$ (577 mg, 4.19 mmol), $CuSO_4$ (7 mg, 0.028 mmol), $H_2O$ (9 mL) and MeOH (18 mL). The mixture was stirred at r.t. for 12 h. After the organic solvents were evaporated, it was diluted with water (20 mL) and pH was adjusted to 6.0 with HCl and then diluted with phosphate buffers (0.25 M, pH 6.2, 50 mL). The mixture was extracted with EtOAc (50 mL×3). The organic layer was dried over $Na_2SO_4$ to afford 81-7, which was used directly in the next step.

Step 5

To the solution of 81-5 (560 mg, 2 mmol) in DMF (5 mL) was added 81-7 (804 mg, 4.0 mmol) and cat. $Cu(CH_3CN)_4PF_6$. The mixture was stirred at 50° C. for 3 h under $N_2$. After the solvent was removed, the residue was purified by prep-HPLC to give 81-8.

$^1$H NMR (400 MHz, MeOD) δ 8.00 (s, 1H), 7.57 (d, J=8.4 Hz, 2H), 7.35-7.18 (m, 12H), 5.50-5.45 (m, 1H), 5.14-5.11 (m, 1H), 5.05-5.03 (m, 2H), 4.58 (s, 2H), 3.26-3.24 (m, 2H), 3.13-3.12 (m, 2H), 2.35-2.15 (m, 2H), 1.55-1.35 (m, 2H).

Step 6

To a solution of 81-8 (480 mg, 1.0 mmol) in DCM (10 mL) was added EEDQ (247 mg, 1.0 mmol) and 81-9 (123 g, 1.0 mmol) under $N_2$ and the mixture was stirred at 0° C. for 1 h. After the solvent was removed, the residue was purified by prep-HPLC and SFC separation to give 81-10 and 81-11.

$^1$H NMR (400 MHz, MeOD) δ 8.00-7.95 (m, 1H), 7.58-7.56 (m, 2H), 7.35-7.18 (m, 12H), 5.51-5.47 (m, 1H), 5.15-5.09 (m, 1H), 5.55-5.00 (m, 2H), 4.58 (s, 2H), 3.33-3.20 (m, 2H), 3.16-3.09 (m, 2H), 2.25-2.18 (m, 2H), 1.43-1.38 (m, 2H). LCMS (ESI): m/z 586.0 [M+H$^+$].

355

¹H NMR (400 MHz, MeOD) δ 7.96 (s, 1H), 7.57 (d, J=8.8 Hz, 2H), 7.35-7.18 (m, 12H), 5.52-5.48 (m, 1H), 5.13-4.87 (m, 3H), 4.58 (s, 2H), 3.33-3.15 (m, 2H), 3.14-3.07 (m, 2H), 2.27-2.14 (m, 2H), 1.46-1.31 (m, 2H). LCMS (ESI): m/z 586.1 [M+H⁺].

Step 7

To a solution of 81-10 (59 mg, 0.1 mmol) in dry DCM (30 mL) was added PNP carbonate (62 mg, 0.2 mmol) and DIPEA (1 mL). The mixture was heated at reflux for 16 h. After the solvent was removed, the residue was dissolved in DMF (5 mL) and DIPEA (0.3 mL) and norfloxacin (65 mg, 0.2 mmol) were added. The mixture was stirred at r.t. for 1 h. After the solvent was removed, the residue was purified by prep-HPLC to give example 81.

356

¹H NMR (400 MHz, DMSO-d₆) δ 15.35 (br s, 1H), 10.66 (s, 1H), 8.97 (s, 1H), 8.10 (s, 1H), 7.95 (d, J=12.8 Hz, 1H), 7.85-7.83 (m, 1H), 7.62 (d, J=8.4 Hz, 2H), 7.39-7.19 (m, 13H), 6.07-6.02 (m, 1H), 5.51-5.45 (m, 3H), 5.07 (s, 2H), 5.01-4.92 (m, 3H), 4.59 (d, J=7.6 Hz, 2H), 3.61 (s, 4H), 3.44-3.38 (m, 4H), 3.21-3.16 (m, 1H), 3.06-2.98 (m, 3H), 2.12-2.00 (m, 2H), 1.45-1.15 (m, 5H). LCMS (ESI): m/z 931.2 [M+H⁺].

Example 82. (S)-7-(4-((4-(2-(4-(1-(benzyloxycarbonylamino)cyclopropyl)-1H-1,2,3-triazol-1-yl)-5-ureidopentanamido)benzyloxy)carbonyl)piperazin-1-yl)-1-ethyl-6-fluoro-4-oxo-1,4-dihydroquinoline-3-carboxylic acid

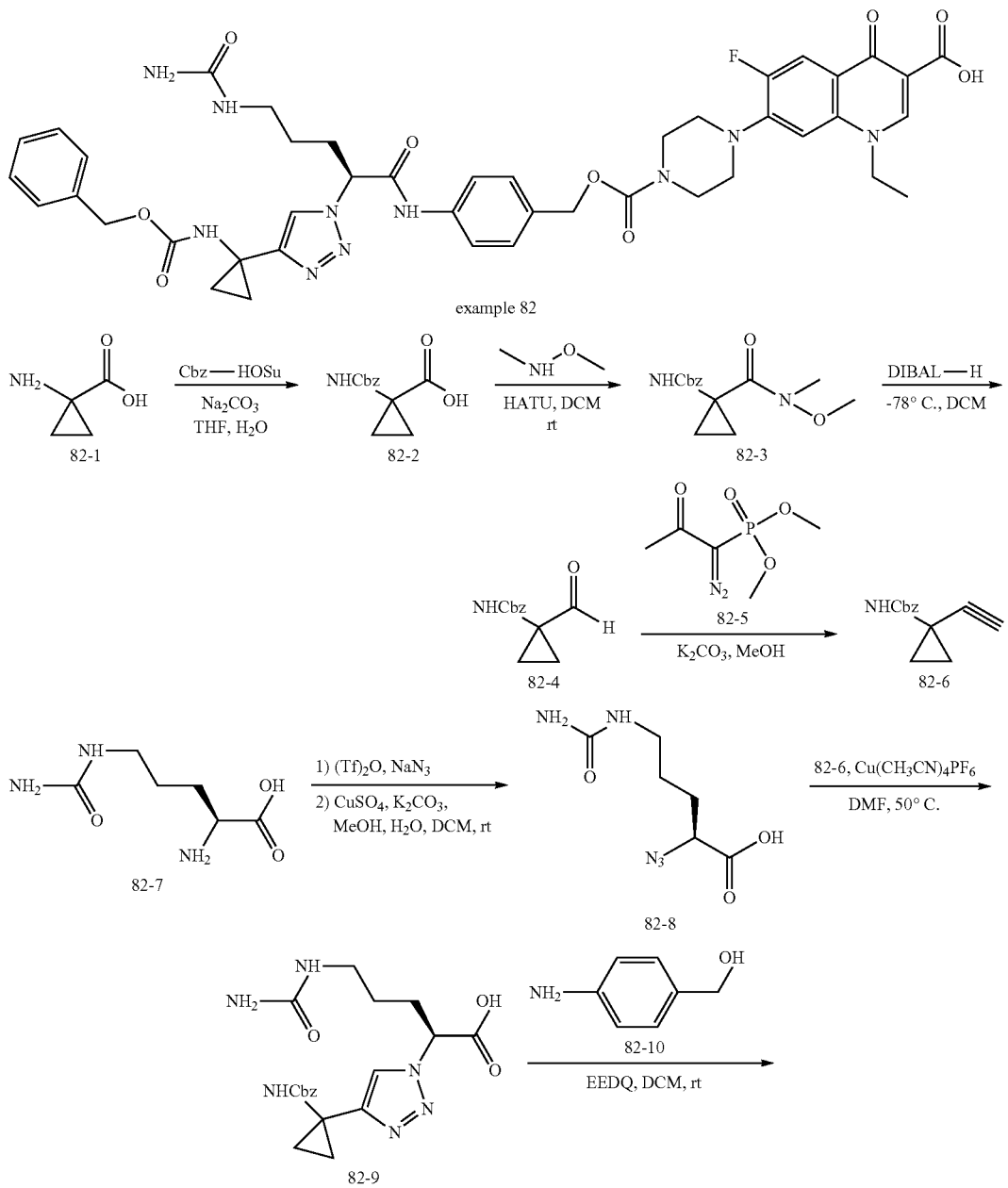

-continued

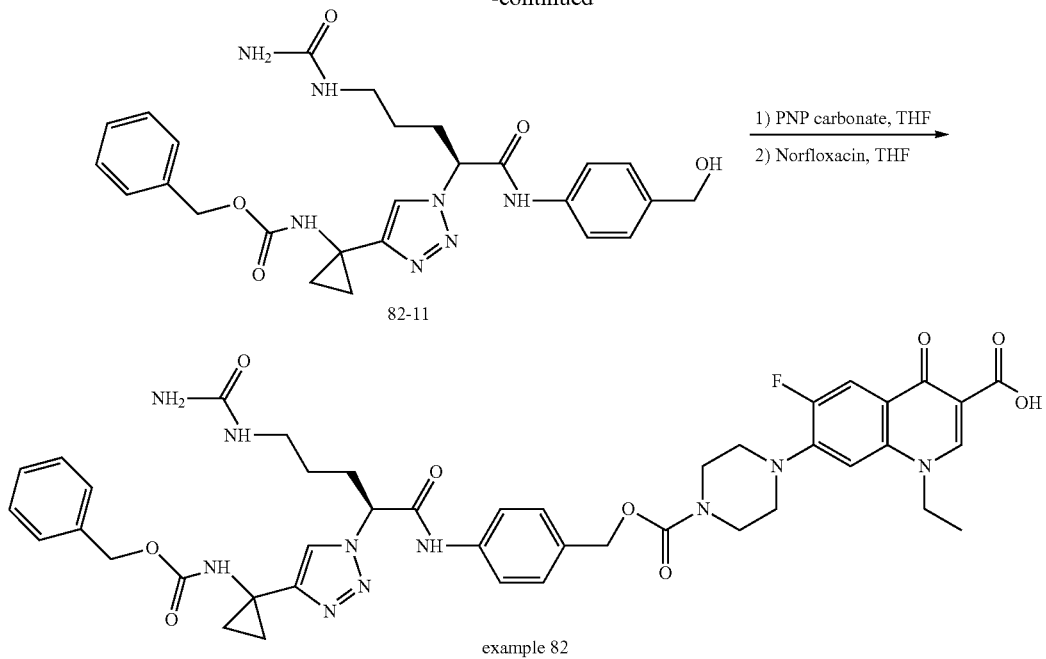

example 82

Step 1

To a mixture of 82-1 (10 g, 98.9 mmol) in aq. solution Na₂CO₃ (41.9 g, 395.6 mmol) and was added Cbz-OSu (29.6 g, 118.7 mmol) in THF (150 mL). After the mixture was stirred at r.t. for 16 h, it was adjusted to pH>10 and the solution was washed with EtOAc (200 mL×2). The aqueous layer was acidified to pH<1 with conc. HCl and the solution was extracted with EtOAc (250 mL×2). The organic layer was dried over Na₂SO₄ and concentrated to give 82-2 (23 g, crude), which was used for next step without further purification.

Step 2

To a solution of 82-2 (10 g, 42.5 mmol), N,O-dimethyl-hydroxylamine Hydrochloride (4.5 g, 46.8 mmol) and HATU (24.2 g, 63.8 mmol) in DCM (100 mL) was added Et₃N (24.6 mL, 170.0 mmol). After the mixture was stirred at r.t. for 2 h, solvent was removed, and the crude was taken up with water (300 mL). The aqueous layer was extracted with EtOAc (300 mL×3). The organic layer was washed with saturated NaHCO₃, diluted HCl, saturated NaCl, concentrated and purified by column chromatography on silica gel (PE:EtOAc=2:1) to give 82-3 (10.8 g, 91.3%).

Step 3

DIBAL-H (22.5 mL, 1M in toluene) was added to dropwise to a solution of 82-3 (4.2 g, 15.0 mmol) in anhydrous CH₂Cl₂ (50 mL) −78° C. After the mixture was stirred at −78° C. for 2 h, excess DIBAL was quenched by anhydrous MeOH (15 mL) and the resulting solution was warmed to r.t. The solution was concentrated to give 82-4 (3.3 g, crude), which was used for next step without further purification.

Step 4

After a mixture of 82-4 (3.3 g, 15.0 mmol), 82-5 (3.0 g, 18.1 mmol) and K₂CO₃ (4.1 g, 30 mmol) in MeOH (60 mL) was stirred at r.t. for 16 h, solvents were removed under reduced pressure and the crude residue was partitioned between EtOAc (200 mL) and water (100 mL). The organic layer was washed with brine and dried over anhydrous Na₂SO₄. After removal of the solvent, the residue was purified by column chromatography on silica gel (PE:EtOAc=10:1) to give 82-6 (1.8 g, 55.6%).

Step 5

Tf₂O (4.7 mL, 27.9 mmol) was added slowly to mixture of NaN₃ (9.2 g, 139.3 mmol) in distilled H₂O (30 mL) and DCM (48 mL) at 0° C. After it was stirred for 2 h, DCM layer was separated and the aqueous portion was extracted with CH₂Cl₂ (24 mL×2). The organic fractions, containing the triflyl azide were pooled and washed once with saturated Na₂CO₃ and used without further purification.

The triflyl azide in CH₂Cl₂ (96 mL) was added to a mixture of 82-7 (2.44 g, 13.9 mmol), K₂CO₃ (2.89 g, 20.9 mmol) and CuSO₄.5H₂O (347 mg, 1.39 mmol) in H₂O (54 mL) and MeOH (108 mL). After the mixture was stirred at 26° C. for 12 h, organic solvents were removed under reduced pressure and the aqueous slurry was diluted with H₂O (200 mL). The mixture was acidified to pH=6 with conc. HCl and diluted with phosphate buffers (0.2 M, pH 6.2, 200 mL) and washed with EtOAc (300 mL×2). The aqueous phase was then acidified to pH=2 with conc. HCl. It was extracted with EtOAc (300 mL×3). The organic layer was dried over Na₂SO₄ and concentrated to give 82-8, which was used for next step without further purification.

Step 6

After a mixture of 82-8 (2.8 g, 14.0 mmol), 82-6 (1.5 g, 7.0 mmol) and Cu(CN)₄PF₆ (779 mg, 2.1 mmol) in DMF (20 mL) was stirred at 50° C. for 2 h, solvent was removed and the residue was purified by prep-HPLC to give 82-9 (200 mg, 6.9%).

Step 7

After a mixture of 82-9 (410 mg, 0.98 mmol), 82-10 (364 mg, 2.95 mmol) and EEDQ (730 mg, 2.95 mmol) in DCM (10 mL) was stirred at 24° C. for 2 h, solvent was removed, and the residue was purified by prep-HPLC to give 82-11 (350 mg, 68%).

<sup>1</sup>H NMR (400 MHz, MeOD) δ 7.96 (s, 1H), 7.60 (d, J=8.4 Hz, 2H), 7.42-7.35 (m, 7H), 5.50-5.46 (m, 1H), 5.14 (s, 2H), 4.61 (s, 2H), 3.24-3.22 (m, 1H), 3.15-3.13 (m, 1H), 2.30-2.15 (m, 2H), 1.46-1.40 (m, 4H), 1.29 (s, 2H).

LCMS (ESI): m/z 522.0 [M+H$^+$].

Step 8

After a mixture of 82-11 (200 mg, 0.38 mmol), PNP (234 mg, 0.77 mmol) and DIPEA (149 mg, 1.15 mmol) in DCM (10 mL) was stirred at 50° C. for 12 h, it was concentrated and added to a solution of DIPEA (149 mg, 1.15 mmol) and Norfloxacin (367 mg, 1.15 mmol) in DMF (8 mL). After it was stirred at 23° C. for 4 h, solvent was removed, and the residue was purified by prep-HPLC to give example 82 (50 mg, 15.2%).

<sup>1</sup>H NMR (400 MHz, DMSO-d$_6$) δ 10.62 (s, 1H), 8.96 (s, 1H), 8.18 (s, 1H), 7.96-7.89 (m, 2H), 7.62-7.60 (m, 2H), 7.38-7.36 (m, 7H), 7.22-7.20 (m, 1H), 6.04 (s, 1H), 5.43 (s, 3H), 5.07 (s, 2H), 5.03 (s, 2H), 4.59-4.57 (m, 2H), 3.67 (s, 6H), 3.30-2.98 (m, 4H), 2.20-2.09 (m, 2H), 1.42-1.38 (m, 3H), 1.25-1.22 (s, 4H), 1.13 (s, 2H).

MS (ESI): m/z 867.05 [M+H$^+$], 889.16 [M+Na$^+$].

Example 83. 7-(4-((4-((S)-5-amino-2-(4-((S)-1-(benzyloxycarbonylamino)-2-methylpropyl)-1H-1,2,3-triazol-1-yl)pentanamido)benzyloxy)carbonyl)piperazin-1-yl)-1-ethyl-6-fluoro-4-oxo-1,4-dihydroquinoline-3-carboxylic acid Example 83 was made using the procedure as Example 58.

Example 83

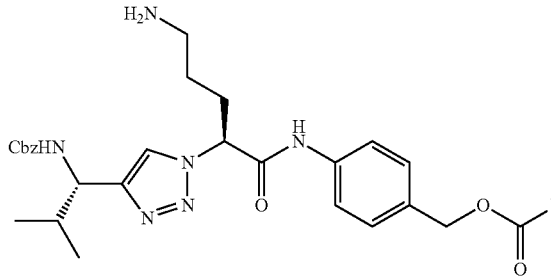
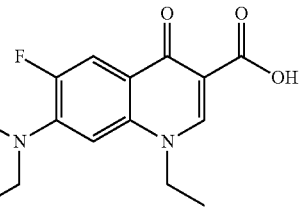

<sup>1</sup>H NMR (400 MHz, DMSO-d$_6$) δ 8.96 (s, 1H), 8.47-8.39 (m, 1H), 8.08 (s, 1H), 7.94 (d, J=13.2 Hz, 1H), 7.74 (d, J=9.2 Hz, 1H), 7.61 (d, J=8.4 Hz, 2H), 7.38-7.29 (m, 8H), 7.22-7.20 (m, 1H), 5.49-5.47 (m, 1H), 5.07 (s, 2H), 5.02 (d, J=6.0 Hz, 2H), 4.62-4.55 (m, 3H), 3.60 (s, 4H), 3.16 (s, 4H), 2.77-2.70 (m, 2H), 2.20-2.15 (m, 2H), 2.09-2.00 (m, 1H), 1.40 (t, J=6.8 Hz, 5H), 1.23 (s, 1H), 0.85 (d, J=6.8 Hz, 3H), 0.78 (d, J=6.8 Hz, 3H).

LCMS (ESI): m/z 840.2 [M+H$^+$].

Method of Preparing Linker-Drug Compounds

Preparation of CBI-PBD LD1

(11aS)-4-((S)-6-amino-2-(1-(5-(2,5-dioxo-2,5-dihydro-1H-pyrrol-1-yl)pentylcarbamoyl)cyclobutanecarboxamido)hexanamido)benzyl 8-(6-((S)-1-(chloromethyl)-5-(phosphonooxy)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate Synthetic Scheme

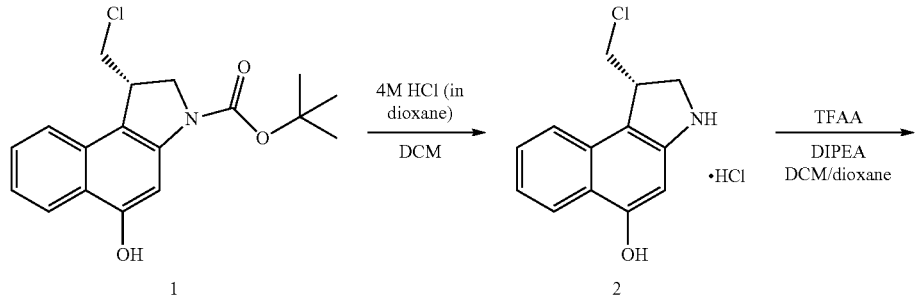

-continued
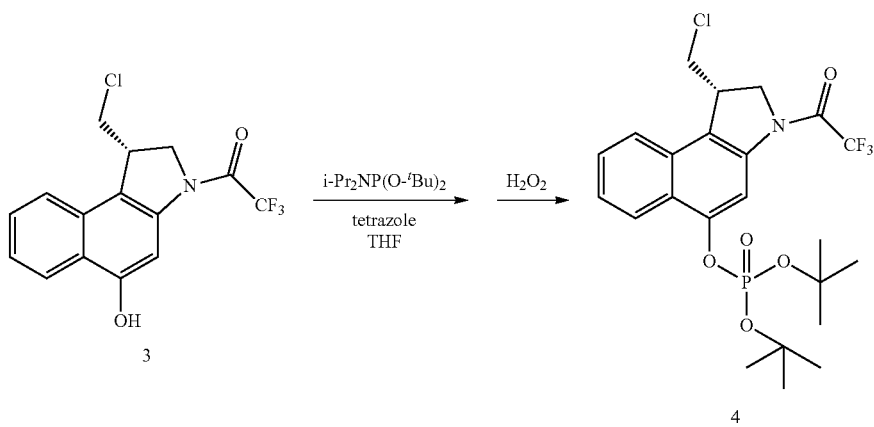
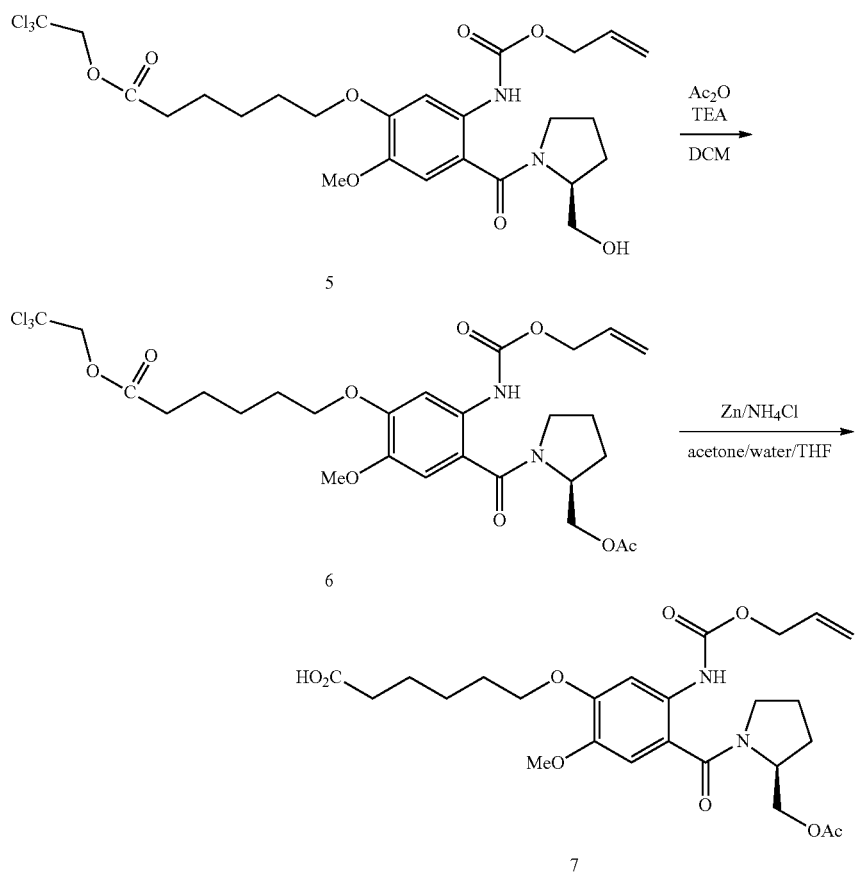
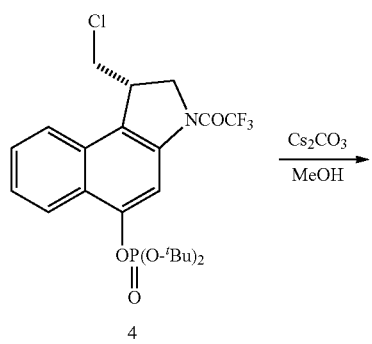

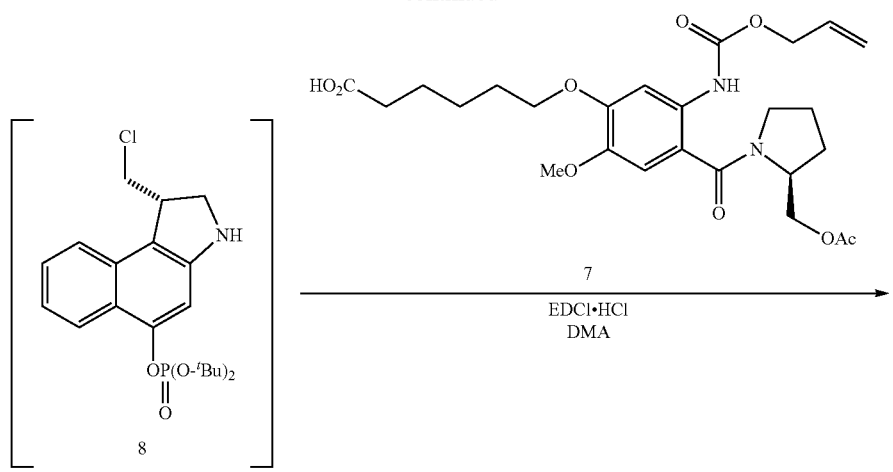
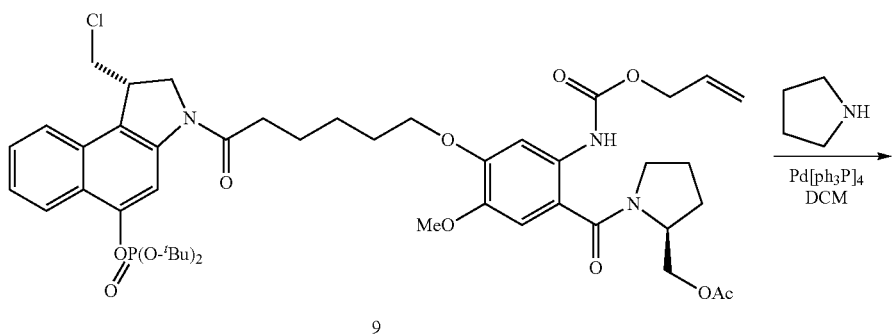
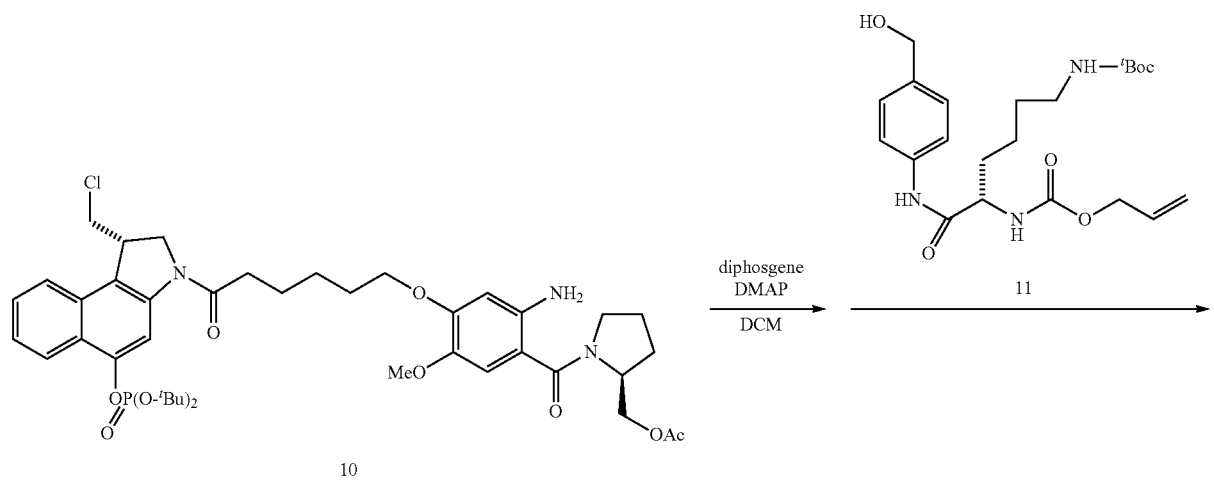

-continued
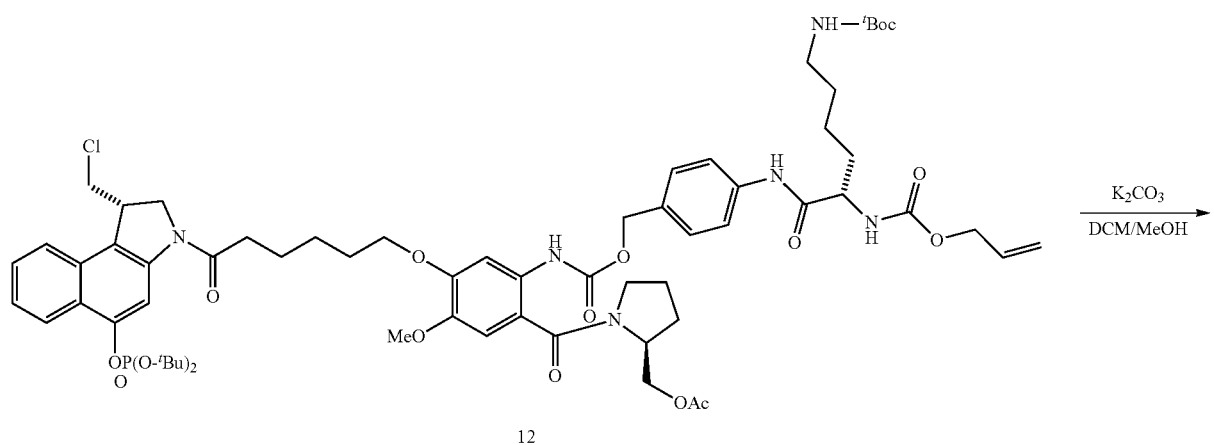
12
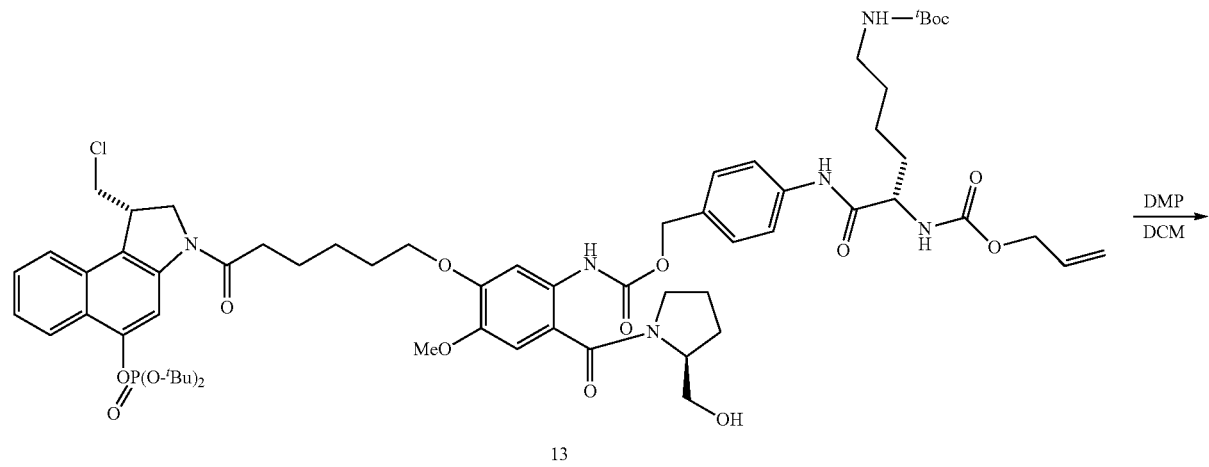
13
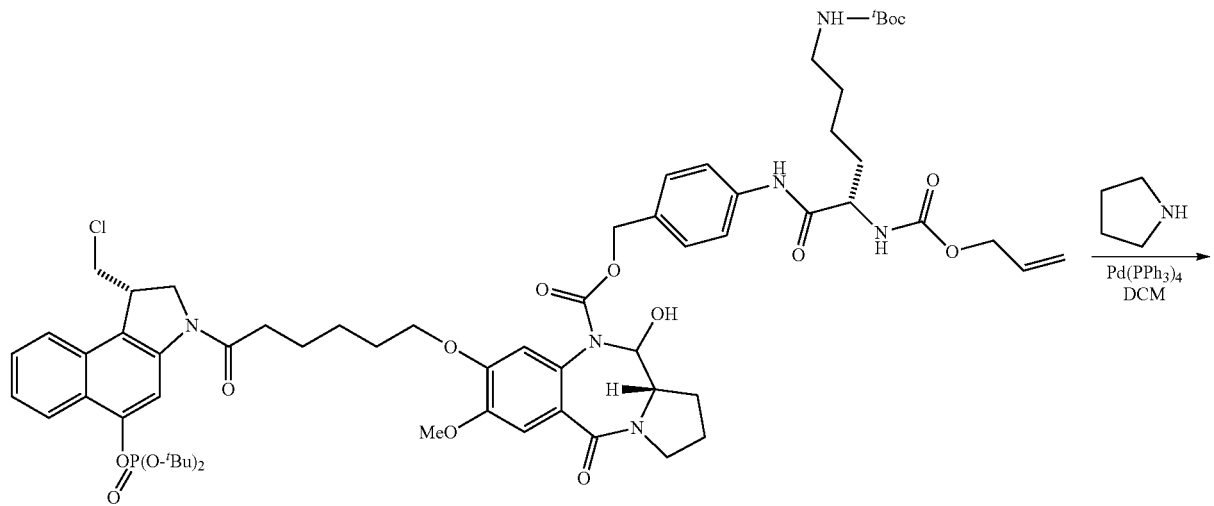
14

-continued
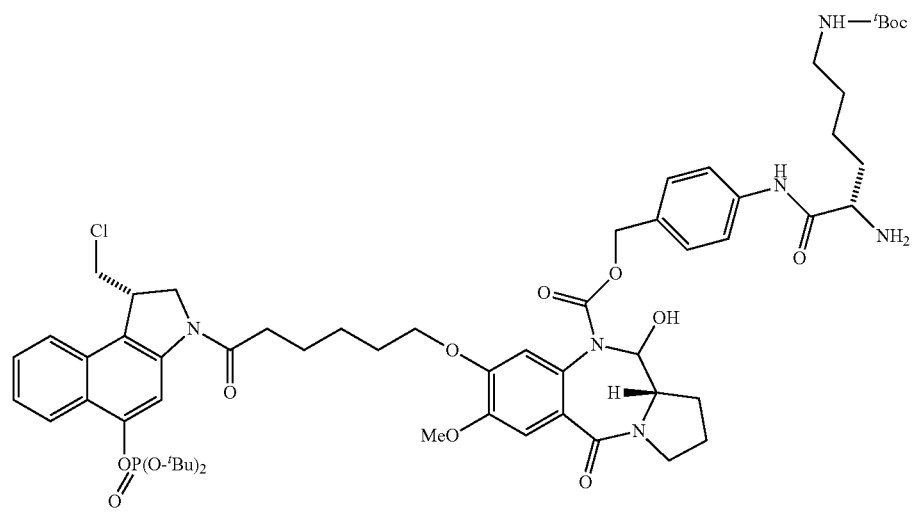
15
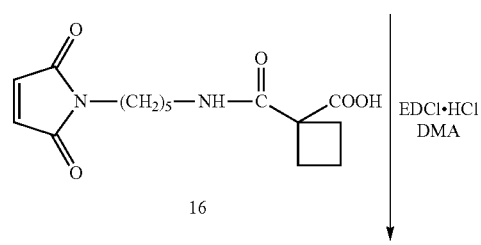
16
EDCl·HCl
DMA
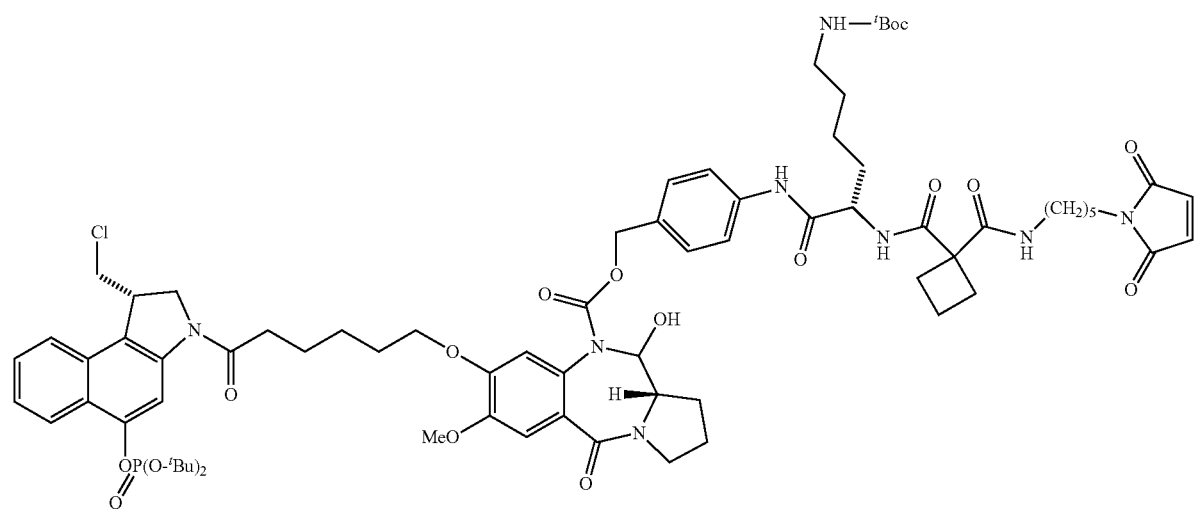
17
TFA/DCM (1:1)

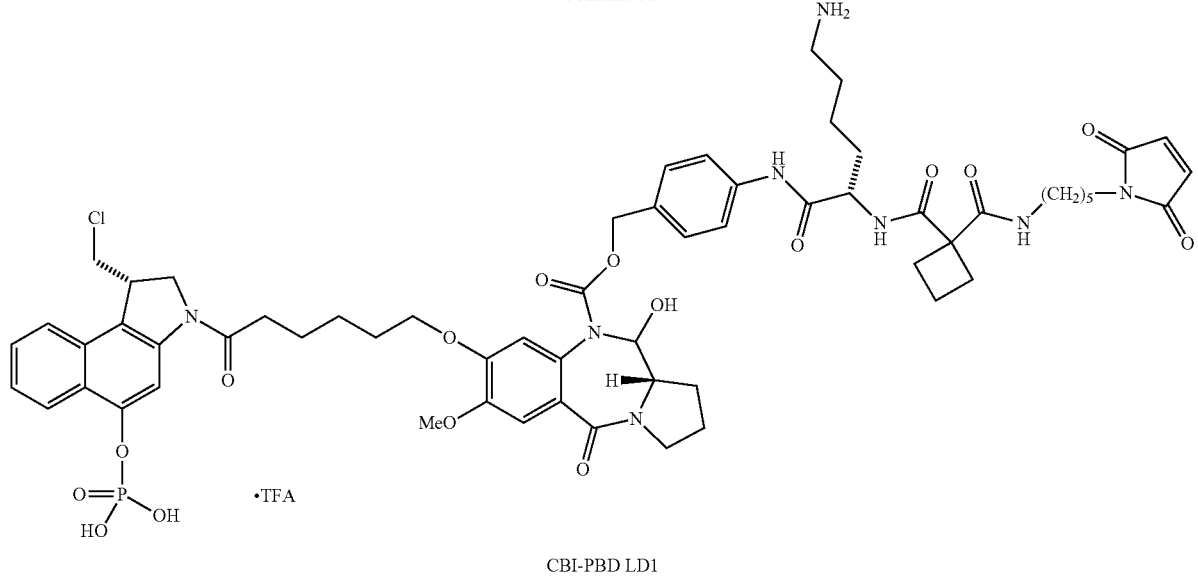

CBI-PBD LD1

Example 1. 2,2,2-Trifluoroacetic acid compound with (11aS)-4-((S)-6-amino-2-(1-((5-(2,5-dioxo-2,5-dihydro-1H-pyrrol-1-yl)pentyl)carbamoyl) cyclobutanecarboxamido)hexanamido)benzyl 8-((6-((S)-1-(chloromethyl)-5-(phosphonooxy)-1H-benzo[e]indol-3(2H)-yl)-6-oxohexyl)oxy)-11-hydroxy-7-methoxy-5-oxo-2,3,11,11a-tetrahydro-1H-benzo[e]pyrrolo[1,2-a][1,4]diazepine-10(5H)-carboxylate (1:1) (CBI-PBD LD1)

To a stirred homogeneous solution of phenol 1 (3.34 g, 10.0 mmol) in dry DCM (25 mL) at 20° C. under a nitrogen atmosphere was added 4M HCl in dioxane (12.5 mL, 50.0 mmol). After addition the reaction mixture was stirred at 20° C. under nitrogen for a further 20 h. The mixture was diluted with petroleum ether (250 mL) and stirred at 20° C. under nitrogen for 20 min. Solvents were decanted and the procedure was repeated once more with petroleum ether (250 mL). The resulting solid was dried under vacuum at 25° C. for 1 h to give compound 2 (2.7 g, 100%); $^1$H NMR [(CD$_3$)$_2$SO]δ 10.80 (s, 1H), 8.15 (d, J=8.3 Hz, 1H), 7.87 (d, J=8.2 Hz, 1H), 7.58 (br t, J=7.5 Hz, 1H), 7.43 (br t, J=7.4 Hz, 1H), 6.81 (s, 1H), 4.27-4.17 (m, 1H), 4.01 (dd, J=11.0, 3.2 Hz, 1H), 3.93-3.74 (m, 3H), 2 protons not observed. The crude product was used for the next step without further purification.

To a stirred heterogeneous mixture of amine 2 (2.7 g, 10.0 mmol) in dry DCM (10 mL) and dioxane (30 mL) at 0° C. under a nitrogen atmosphere was added trifluoroacetic anhydride (TFAA) (3.4 mL, 24.0 mmol), followed by diisopropylethylamine (DIPEA) (8.71 mL, 50.0 mmol). After addition the reaction mixture was stirred at 0° C. under nitrogen for a further 50 min. Ethyl acetate (400 mL) was added and 1N HCl (200 mL) were added at 0° C. and the mixture stirred for 20 min under nitrogen. The ethyl acetate layer was separated, washed successively with 1N HCl (200 mL) and water (2×200 mL), and then dried (MgSO$_4$) and evaporated under reduced pressure at a bath temperature of 25° C. to give 3 (3.3 g, 100%) as a green-grey solid. This material was used for the next step without further purification.

To a stirred homogeneous solution of phenol 3 (3.3 g, 10.0 mmol) in dry THF (40 mL) at 20° C. under a nitrogen atmosphere was added di-tert-butyl-N,N-diisopropylphosphoramidite (4.31 mL, 13.0 mmol). After addition the reaction mixture was stirred at 20° C. under nitrogen for 5-10 min and then tetrazole (3% solution in CH$_3$CN, 38.0 mL, 13.0 mmol) was added dropwise over 17 min. The final reaction mixture was stirred further at 20° C. under nitrogen for 19 h. The mixture was cooled in an ice-bath and 30% H$_2$O$_2$ (11.3 mL, 100.0 mmol) was added. After addition the reaction mixture was stirred at 20° C. for a further 1 h 30 min. The mixture was diluted with ethyl acetate (300 mL) and 10% aqueous Na$_2$S$_2$O$_3$ (500 mL) at stirred at 0° C. for 20 min. The ethyl acetate layer was separated and washed successively with water (200 mL), saturated NaHCO$_3$ (200 mL), and water (200 mL) and then dried (MgSO$_4$) and evaporated under reduced pressure at a bath temperature of 25° C. to give an amber oil. Purification by chromatography on a silica gel (eluting with ethyl acetate:petroleum ether 1:3) gave compound 4 (4.7 g, 90%) as a colorless foamy solid, mp 39-42° C.; [α]$_D$−61.8 (c 1.02, CHCl$_3$). Anal. (C$_{23}$H$_{28}$ClF$_3$NO$_5$P) Calc: C, 52.93; H, 5.41; N, 2.68. Found: C, 53.05; H, 5.43; N, 2.80.

To a stirred solution of alcohol 5 (4.14 g, 6.95 mmol) (J. Med. Chem. 2003, 46, 2132-2151) in dry DCM (25 mL) was added acetic anhydride (3.30 mL, 34.8 mmol) and triethylamine (5.81 mL, 41.7 mmol). The mixture was stirred at 20° C. for 3 h 30 min. Dry MeOH (4.0 mL) was added and the mixture was stirred for 30 min. The mixture was partitioned between EtOAc (400 mL) and water (400 mL). The EtOAc layer was separated, washed with water (2×200 mL), and then dried (MgSO$_4$) and evaporated to give acetate 6 (4.28 g, 96%) as an oil; [α]$_D$−57.4° (c 0.21, CHCl$_3$); $^1$H NMR [(CD$_3$)$_2$SO]δ 9.10 (s, 1H), 7.17 (s, 1H), 6.87 (s, 1H), 6.01-5.87 (m, 1H), 5.32 (dd, J=17.2, 1.5 Hz, 1H), 5.21 (dd, J=10.4, 1.4 Hz, 1H), 4.89 (s, 2H), 4.54 (d, J=5.4 Hz, 2H), 4.39-4.20 (m, 3H), 3.93 (t, J=6.4 Hz, 2H), 3.75 (s, 3H), 3.46-3.27 (m, 2H), 2.13-1.90 (m, 4H), 1.89-1.60 (m, 7H), 1.54-1.40 (m, 2H), 2 protons obscured by DMSO peak. HRMS (ESI) m/z calc. for C$_{27}$H$_{36}$Cl$_3$N$_2$O$_9$: 637.1481. found: 637.1475 [MH$^+$]; calc. for C$_{27}$H$_{35}$Cl$_3$N$_2$NaO$_9$:

659.1300. found: 659.1303 [MNa+]; calc. for $C_{27}H_{35}Cl_3KN_2O_9$: 675.1040. found: 675.1035 [MK+].

To a stirred solution of acetate 6 (4.27 g, 6.69 mmol) in acetone (75 mL), water (50 mL), and THF (30 mL) was added zinc powder (17.5 g, 268 mmol) and NH$_4$Cl (28.6 g, 535 mmol). The mixture was stirred at 20° C. under a nitrogen atmosphere for 42 h. Acetone (100 mL) was added, the mixture was stirred for 10 min, and the supernatant was decanted. The procedure was repeated twice and the combined supernatants were evaporated under reduced pressure to remove acetone and THF. The residue was diluted with water (50 mL) and acidified with aqueous 1N HCl to pH ca. 1. The acidic mixture was washed with petroleum ether (2×200 mL) and extracted with EtOAc (400 mL). The EtOAc extract was washed with water (200 mL) and dried (MgSO$_4$) and the solvent was evaporated to give acid 7 (2.72 g, 80%) as an oil; $[\alpha]_D$ −73.5° (c 1.12, CHCl$_3$); $^1$H NMR [(CD$_3$)$_2$SO]δ 11.99 (s, exchangeable with D$_2$O, 1H), 9.10 (s, exchangeable with D$_2$O, 1H), 7.17 (s, 1H), 6.87 (s, 1H), 6.00-5.86 (m, 1H), 5.32 (dd, J=17.2, 1.5 Hz, 1H), 5.20 (dd, J=10.4, 1.5 Hz, 1H), 4.57-4.52 (m, 2H), 4.37-4.03 (m, 3H), 3.93 (t, J=6.5 Hz, 2H), 3.75 (s, 3H), 3.40-3.10 (m, 2H), 2.23 (t, J=7.3 Hz, 2H), 2.07-1.93 (m, 4H), 1.89-1.66 (m, 5H), 1.62-1.49 (m, 2H), 1.47-1.34 (m, 2H). HRMS (ESI) m/z calc. for $C_{25}H_{35}N_2O_9$: 507.2337. found: 507.2340 [MH+]; calc. for $C_{25}H_{34}KN_2O_9$: 545.1896. found: 545.1906 [MK+]; calc. for $C_{25}H_{34}N_2NaO_9$: 529.2157. found: 529.2169 [MNa+].

To a stirred solution of trifluoroacetamide 4 (1.38 g, 2.64 mmol) in MeOH (10 mL) at 0° C. under a nitrogen atmosphere was added Cs$_2$CO$_3$ (1.03 g, 3.17 mmol). The mixture was stirred at 0° C. for 2 h 30 min and then partitioned between EtOAc (200 mL) and water (150 mL). The EtOAc layer was separated and washed again with water (100 mL), and then dried (MgSO$_4$) and evaporated under reduced pressure at a bathe temperature of 25° C. to give the unstable amine 8 (1.17 g) as a pale yellow foamy solid.

This crude material was treated with acid 7 (1.24 g, 2.45 mmol), EDCI.HCl (1.41 g, 7.35 mmol) and p-toluenesulfonic acid (84 mg, 0.49 mmol) in dry DMA (14 mL) at 0-20° C. for 22 h. The mixture was partitioned between EtOAc (400 mL) and water (300 mL). The EtOAc layer was separated and washed again with water (100 mL), and then dried (MgSO$_4$) and evaporated. Purification by chromatography on silica gel (eluting with EtOAc:petroleum ether 2:1) gave amide 9 (1.49 g, 66%) as a pale yellow foamy solid, mp 55-59° C.; $[\alpha]_D$ −68.0° (c 1.00, CHCl$_3$); $^1$H NMR [(CD$_3$)$_2$SO]δ 9.10 (s, exchangeable with D$_2$O, 1H), 8.56 (s, 1H), 8.03 (d, J=8.1 Hz, 1H), 7.92 (d, J=8.4 Hz, 1H), 7.57 (t, J=8.1 Hz, 1H), 7.47 (t, J=7.6 Hz, 1H), 7.19 (s, 1H), 6.86 (s, 1H), 5.99-5.86 (m, 1H), 5.32 (dd, J=17.2, 1.6 Hz, 1H), 5.20 (dd, J=10.4, 1.5 Hz, 1H), 4.53 (d, J=5.4 Hz, 2H), 4.45-3.84 (m, 10H), 3.74 (s, 3H), 3.44-3.26 (m, 2H), 2.68-2.47 (m, 2H), 2.02 (br s, 3H), 1.93-1.43 (m, 10H), 1.474 and 1.469 (2 s, 18H). HRMS (ESI) m/z calc. for $C_{46}H_{62}ClN_3O_{12}P$: 914.3754. found: 914.3749 [MH+]; calc. for: $C_{46}H_{61}ClKN_3O_{12}P$: 952.3313. found: 952.3381 [MK+]; calc. for $C_{46}H_{61}ClN_3NaO_{12}P$: 936.3574. found: 936.3589 [MNa+].

To a stirred solution of carbamate 9 (548 mg, 0.60 mmol) in DCM (8 mL) at 20° C. under a nitrogen atmosphere was added Pd(Ph$_3$P)$_4$ (17.1 mg; 9.8% Pd) and pyrrolidine (0.49 mL, 6.00 mmol). The mixture was stirred at 20° C. for 30 min and then partitioned between EtOAc (200 mL) and water (150 mL). The EtOAc layer was separated and washed again with water (50 mL), and then dried (MgSO$_4$) and evaporated under reduced pressure at a bath temperature of 25° C. The crude product was purified by chromatography on silica gel (eluting with EtOAc:MeOH 50:1) to give aniline 10 (323 mg, 65%) as a pale yellow foamy solid, mp 46-49° C.; $[\alpha]_D$ −85.2° (c 0.36, CHCl$_3$); $^1$H NMR [(CD$_3$)$_2$SO]δ 8.56 (s, 1H), 8.04 (d, J=8.3 Hz, 1H), 7.93 (d, J=8.4 Hz, 1H), 7.58 (t, J=8.2 Hz, 1H), 7.47 (t, J=8.1 Hz, 1H), 6.67 (s, 1H), 6.37 (s, 1H), 5.09 (s, exchangeable with D$_2$O, 2H), 4.46-3.85 (m, 10H), 3.63 (s, 3H), 3.52-3.34 (m, 2H), 2.69-2.50 (m, 2H), 2.08-1.94 (m, 1H), 2.01 (s, 3H), 1.91-1.61 (m, 7H), 1.58-1.44 (m, 2H), 1.476 and 1.470 (2 s, 18H). HRMS (ESI) m/z calc. for $C_{42}H_{58}ClN_3O_{10}P$: 830.3522. found: 830.3543 [MH+].

To a stirred solution of aniline 10 (293 mg, 0.35 mmol) and DMAP (202 mg, 1.65 mmol) in dry DCM (7 mL) at 20° C. under a nitrogen atmosphere was added a solution of diphosgene in dry DCM (0.05 M, 6.7 mL, 0.33 mmol). The mixture was stirred for 25 min and then a solution of alcohol 11 (1.54 g, 3.54 mmol) in dry DCM (20 mL) was added. The mixture was stirred at 20° C. under a nitrogen atmosphere for 68 h and then partitioned between EtOAc (300 mL) and water (200 mL). The EtOAc layer was separated, washed again with water (100 mL) and then dried (MgSO$_4$) and evaporated at a bath temperature of 30° C. The resulting orange oil was purified by chromatography on silica gel (eluting with EtOAc:MeOH:petroleum ether 30:0.5:10) to afford carbamate 12 (385 mg, 84%) as a foamy solid, mp 72-75° C.; $[\alpha]_D$ −55.2° (c 0.53, CHCl$_3$); $^1$H NMR [(CD$_3$)$_2$SO]δ 10.04 (s, exchangeable with D$_2$O, 1H), 9.12 (br s, exchangeable with D$_2$O, 1H), 8.56 (s, 1H), 8.03 (d, J=8.3 Hz, 1H), 7.92 (d, J=8.4 Hz, 1H), 7.65-7.52 (m, 3H, reduced to 2H after D$_2$O), 7.46 (t, J=7.8 Hz, 2H), 7.31 (d, J=8.5 Hz, 2H), 7.20 (br s, 1H), 6.86 (s, 1H), 6.75 (poorly resolved t, exchangeable with D$_2$O, 1H), 5.97-5.83 (m, 1H), 5.30 (br d, J=17.3 Hz, 1H), 5.17 (br d, J=10.6 Hz, 1H), 5.18-4.97 (m, 2H), 4.51-3.85 (m, 13H), 3.74 (s, 3H), 3.43-3.23 (m, 2H, partially obscured by water peak), 2.94-2.83 (m, 2H), 2.65-2.50 (m, 2H, partially obscured by DMSO peak), 2.07-1.91 (m, 1H), 2.01 (br s, 3H), 1.88-1.43 (m, 11H), 1.473-1.468 (2 s, 18H), 1.43-1.20 (m, 4H), 1.35 (s, 9H). HRMS (ESI) m/z calc. for $C_{65}H_{89}ClN_6O_{17}P$: 1291.5665. found: 1291.5705 [MH+]; calc. for $C_{65}H_{88}ClKN_6O_{17}P$: 1329.5262. found: 1329.5264 [MK+]; calc. for $C_{65}H_{88}ClN_6NaO_{17}P$: 1313.5554. found: 1313.5524 [MNa+].

A mixture of acetate 12 (366 mg, 0.28 mmol) and K$_2$CO$_3$ (1.14 g, 8.24 mmol) in DCM (9 mL) and MeOH (9 mL) was stirred at 0° C. for 3 h 30 min. The mixture was stirred with cold EtOAc (200 mL) and ice-water (150 mL) for 10 min. The EtOAc layer was separated, washed again with water (100 mL), and then dried (MgSO$_4$) and evaporated at a bath temperature of 25° C. to give alcohol 13 (343 mg, 97%) as a colorless foamy solid, mp 71-75° C.; $[\alpha]_D$ −58.2° (c 0.57, CHCl$_3$); $^1$H NMR [(CD$_3$)$_2$SO]δ 10.04 (s, exchangeable with D$_2$O, 1H), 9.11 (br s, exchangeable with D$_2$O, 1H), 8.56 (s, 1H), 8.03 (d, J=8.3 Hz, 1H), 7.92 (d, J=8.4 Hz, 1H), 7.65-7.53 (m, 3H, reduced to 2H after D$_2$O), 7.46 (t, J=7.6 Hz, 2H), 7.32 (d, J=8.6 Hz, 2H), 7.27 (br s, 1H), 6.93 (s, 1H), 6.75 (poorly resolved t, exchangeable with D$_2$O, 1H), 5.97-5.82 (m, 1H), 5.29 (br d, J=17.2 Hz, 1H), 5.17 (br d, J=10.5 Hz, 1H), 5.03 (br s, 2H), 4.73 (t, J=5.8 Hz, exchangeable with D$_2$O, 1H), 4.50-3.82 (m, 11H), 3.74 (s, 3H), 3.62-3.44 (m, 2H), 3.40-3.21 (m, 2H, partially obscured by water peak), 2.95-2.80 (m, 2H), 2.65-2.50 (m, 2H, partially obscured by DMSO peak), 1.93-1.21 (m, 16H), 1.473-1.468 (2 s, 18H), 1.35 (s, 9H). HRMS (ESI) m/z calc. for $C_{63}H_{86}ClKN_6O_{16}P$: 1287.5158. found: 1287.5113 [MK+]; calc. for $C_{63}H_{86}ClN_6NaO_{16}P$: 1271.5419. found: 1271.5381 [MNa+].

To a stirred solution of alcohol 13 (322 mg, 0.26 mmol) in dry DCM (14 mL) at 0° C. was added Dess-Martin periodinane (DMP) (131 mg, 0.31 mmol) portionwise over 3 min. The reaction mixture was stirred at 0° C. for a further 2 h, then at 20° C. for 50 h. The mixture was diluted with DCM (40 mL) and 10% Na$_2$S$_2$O$_3$ (40 mL), stirred at 20° C. for 10 min, and then partitioned between DCM (200 mL) and saturated NaHCO$_3$ solution (150 mL). The DCM layer was separated and the aqueous layer was further extracted with DCM (2×50 mL). The combined DCM extracts were washed with saturated NaHCO$_3$ solution (2×100 mL) and water (2×100 mL), and then dried (MgSO$_4$) and evaporated at a bath temperature of 25° C. The resulting orange oil was purified by chromatography on silica gel (eluting with CHCl$_3$:MeOH 40:1) to give 14 (228 mg, 71%) as a pale brown foamy solid, mp 98° C. (decomp); [α]$_D$+74.5° (c 0.26, CHCl$_3$); $^1$H NMR [(CD$_3$)$_2$SO]δ 10.02 (s, exchangeable with D$_2$O, 1H), 8.56 (s, 1H), 8.04 (d, J=8.3 Hz, 1H), 7.92 (d, J=8.4 Hz, 1H), 7.65-7.47 (m, 5H, reduced to 4H after D$_2$O), 7.25-7.12 (m, 2H, br s and 1H on D$_2$O exchange), 7.03 (s, 1H), 6.83-6.64 (m, 2H), 6.48 (br s, exchangeable with D$_2$O, 1H), 5.96-5.80 (m, 1H), 5.52-5.39 (m, d on D$_2$O exchange, J=9.6 Hz, 1H), 5.27 (br d, J=16.8 Hz, 1H), 5.21-5.10 (m, 2H), 4.81 (br d, J=12.3 Hz, 1H), 4.54-3.85 (m, 8H), 3.83-3.70 (m, 5H), 3.53-3.21 (m, 3H, partially obscured by water peak), 2.93-2.82 (m, 2H), 2.64-2.47 (m, 2H, partially obscured by DMSO peak), 2.10-1.20 (m, 16H), 1.470 and 1.464 (2 s, 18H), 1.34 (s, 9H). HRMS (ESI) m/z calc. for C$_{63}$H$_{84}$ClKN$_6$O$_{16}$P: 1285.5002. found: 1285.4938 [MK$^+$]; calc. for C$_{63}$H$_{84}$ClN$_6$NaO$_{16}$P: 1269.5262. found: 1269.5220 [MNa$^+$].

To a stirred solution of 14 (125 mg, 0.10 mmol) in DCM (2 mL) at 20° C. under a nitrogen atmosphere was added Pd(Ph$_3$P)$_4$ (2.9 mg; 9.8% Pd) and pyrrolidine (0.08 mL, 1.00 mmol). The mixture was stirred at 20° C. and monitored by TLC (EtOAc:MeOH 20:1). After 40 min more Pd(Ph$_3$P)$_4$ (5.8 mg; 9.8% Pd) and pyrrolidine (0.16 mL, 2.00 mmol) were added and the mixture was stirred for another 3 h. The mixture was partitioned between EtOAc (100 mL) and water (100 mL). The EtOAc layer was separated and washed again with water (50 mL), and then dried (MgSO$_4$) and evaporated at a bath temperature of 25° C. The crude product 15 (94 mg, 81%) was used for the next step without further purification. HRMS (ESI) m/z calc. for C$_{59}$H$_{81}$ClN$_6$O$_{14}$P: 1163.5231. found: 1163.5188 [MH$^+$].

A solution of 15 (91 mg, 0.078 mmol) in dry DMA (1.0 mL) was treated with a pre-formed (at 20° C. for 10 min) mixture of acid 16 (36 mg, 0.12 mmol), EDCI.HCl (34 mg, 0.18 mmol), and TsOH (4.0 mg, 0.023 mmol) in dry DMA (0.5 mL) at 20° C. under a nitrogen atmosphere. After 10 min DIPEA (0.016 mL, 0.078 mmol) was added and the reaction mixture was stirred for 23 h. The mixture was partitioned between EtOAc (100 mL) and water (100 mL). The EtOAc layer was separated and washed further with saturated NaHCO$_3$ (50 mL), water (50 mL), and then dried (MgSO$_4$). Evaporation of solvent at a bath temperature of 25° C. gave a crude product which was purified by chromatography on silica gel (eluting with CHCl$_3$:EtOAc: MeOH 30:10:2) to give 17 (63 mg, 56%) as a pale brown foamy solid; mp 67-70° C.; [α]$_D$+23.9° (c 2.09, CHCl$_3$); $^1$H NMR [(CD$_3$)$_2$SO]δ 10.05 (s, exchangeable with D$_2$O, 1H), 8.56 (s, 1H), 8.03 (d, J=8.3 Hz, 1H), 7.92 (d, J=8.4 Hz, 1H), 7.84-7.71 (m, 2H, exchangeable with D$_2$O), 7.62-7.52 (m, 3H), 7.46 (t, J=7.7 Hz, 1H), 7.22-7.13 (m, 2H), 7.03 (br s, 1H), 6.96 (s, 2H), 6.71 (br s, 2H, reduced to 1H after D$_2$O), 6.49 (br s, exchangeable with D$_2$O, 1H), 5.51-5.41 (m, but d on D$_2$O exchange with J=9.5 Hz, 1H), 5.15 (d, J=12.2 Hz, 1H), 4.82 (br d, J=12.4 Hz, 1H), 4.47-3.85 (m, 8H), 3.77 (br s, 3H), 3.52-3.20 (m, 3H, partially obscured by water peak), 3.12-3.20 (m, but t on D$_2$O exchange with J=6.7 Hz, 2H), 2.92-2.80 (m, 2H), 2.65-2.50 (m, 2H, partially obscured by DMSO peak), 2.39 (t, J=7.9 Hz, 2H), 2.07-1.24 (m, 28H), 1.469 and 1.463 (2 s, 18H), 1.33 (s, 9H). HRMS (ESI) m/z calc. for C$_{74}$H$_{98}$ClN$_8$NaO$_{18}$P: 1475.6317. found: 1475.6267 [MNa$^+$].

To a stirred solution of 17 (45 mg, 0.031 mmol) in DCM (1.0 mL) at 20° C. under nitrogen was added TFA (1.0 mL) and the mixture was stirred for 15 min. Petroleum ether (20 mL) was added and the mixture was stirred for 30 min. The supernatant was decanted and the procedure was repeated using EtOAc:petroleum ether (1:5) (2×20 mL). The resulting solid was collected and purified by preparative HPLC [Synergi PolarRP column; aqueous TFA (pH=2.56; 90% to 2%)/10% water in CH$_3$CN (10% to 98%); gradient elution over 23 min with a flow rate of 12 mL/min] to give pure CBI-PBD LD1 (17.5 mg, 38%) as a beige solid, purity (HPLC): 99.1%; [α]$_D$+54.9° (c 0.18, MeOH); $^1$H NMR [(CD$_3$)$_2$SO]δ 10.20 (s, exchangeable with D$_2$O, 1H), 8.50 (s, 1H), 8.20-7.78 (m, 7H, reduced to 1H after D$_2$O), 8.12 (d, J=9.1 Hz, 1H), 7.72-7.47 (m, 4H, reduced to 3H after D$_2$O), 7.40 (t, J=7.5 Hz, 1H), 7.17 (br d, J=7.3 Hz, 2H), 7.03 (br s, 1H), 6.97 (s, 2H), 6.66 (br s, exchangeable with D$_2$O, 1H), 5.51 (br s, 1H), 5.48 (br d, J=9.7 Hz, 1H), 5.32-5.18 (m, but d after D$_2$O, J=12.6 Hz, 1H), 4.75 (br d, J=12.4 Hz, 1H), 4.44-3.81 (m, 8H), 3.77 (s, 3H), 3.52-3.21 (m, 5H, partially obscured by water peak), 3.04 (q, but t after D$_2$O with J=6.8 Hz, 2H), 2.80-2.68 (m, 2H), 2.39 (t, J=7.7 Hz, 2H), 2.12-1.08 (m, 28H). HRMS (ESI) m/z calc. for C$_{61}$H$_{75}$ClN$_8$O$_{16}$P: 1241.4722. found: 1241.4700 [MH$^+$]; calc. for C$_{61}$H$_{74}$ClN$_8$NaO$_{16}$P: 1263.4541. found: 1263.4531 [MNa$^+$].

Synthesis of CBI-CBI LD4

4-((S)-2-(1-(5-(2,5-dioxo-2,5-dihydro-1H-pyrrol-1-yl)pentylcarbamoyl)cyclobutanecarboxamido)-5-ureidopentanamido)benzyl (S)-1-(chloromethyl)-3-(5-((S)-1-(chloromethyl)-5-(phosphonooxy)-1H-benzo[e]indol-3(2H)-yl)-5-oxopentanoyl)-2,3-dihydro-1H-benzo[e]indol-5-ylcarbamate Synthetic Scheme

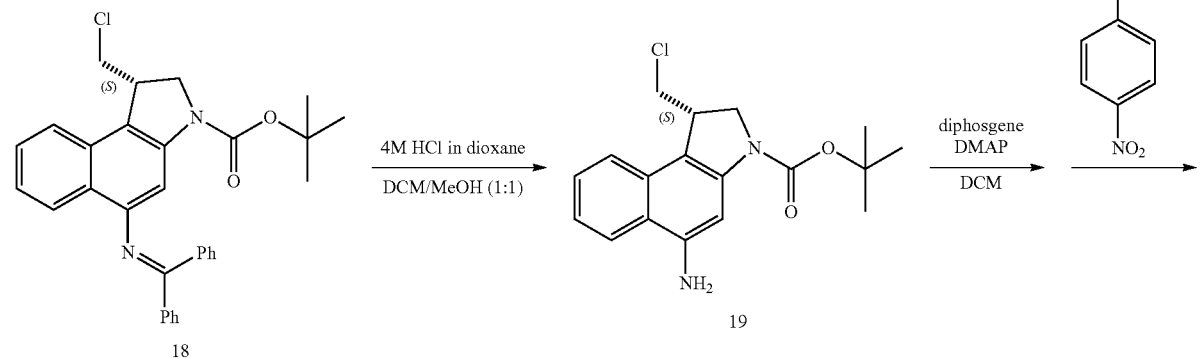

-continued
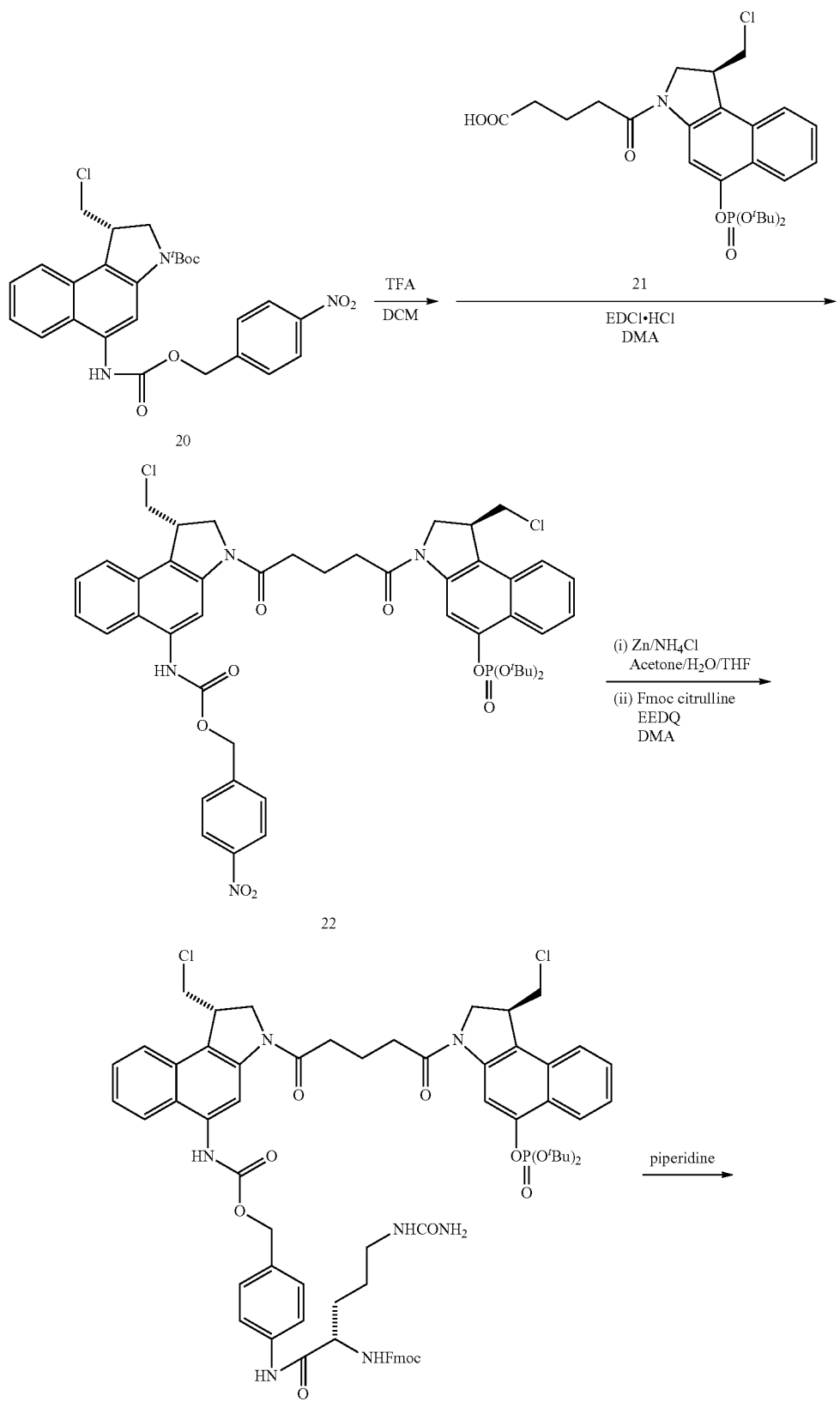

377
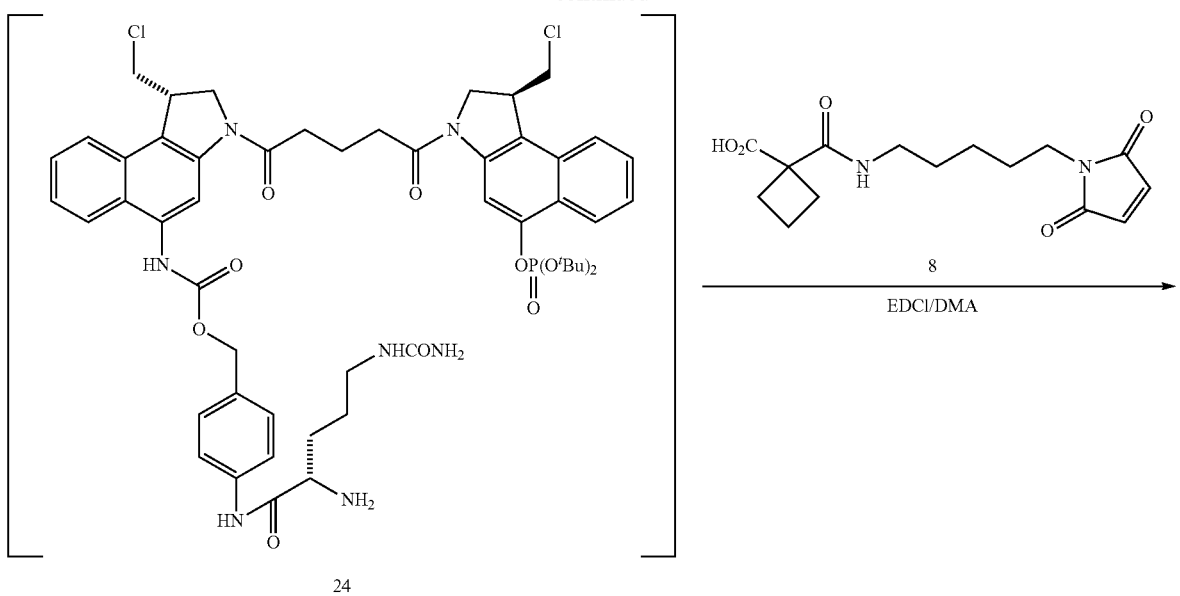
378
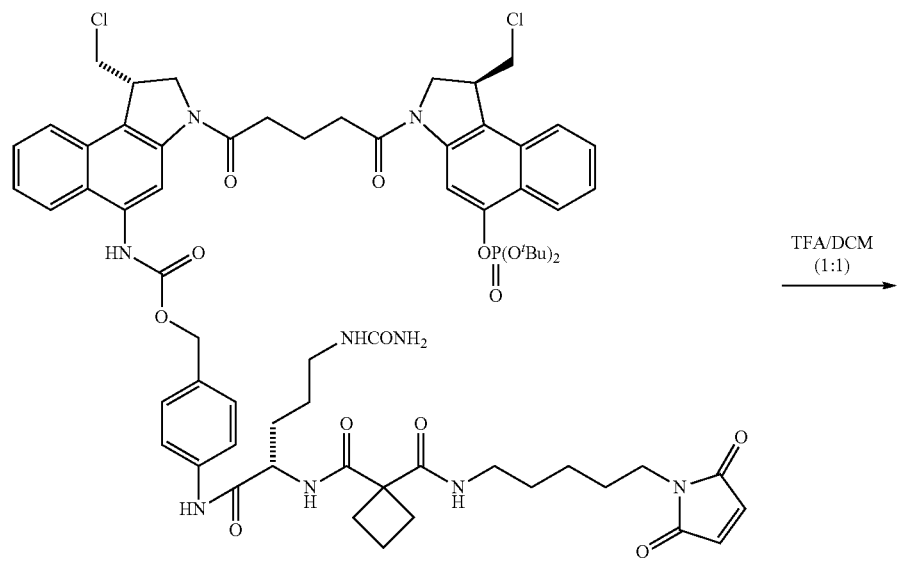

-continued

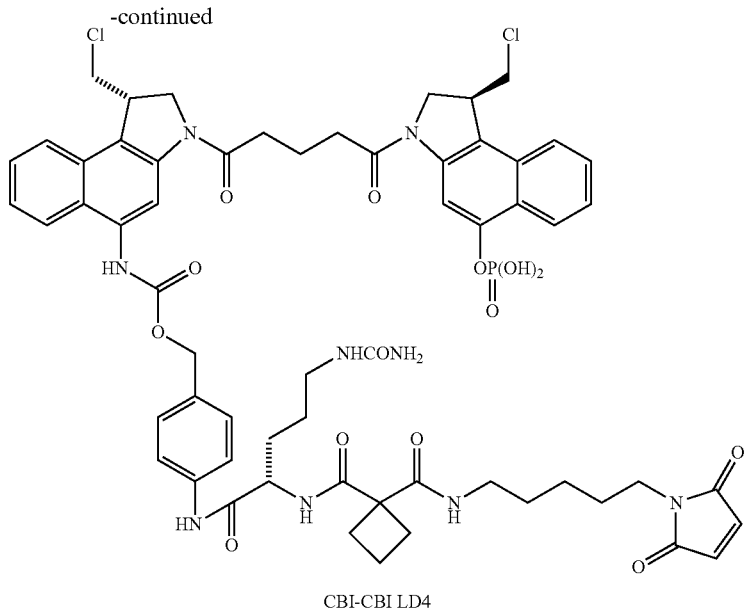

CBI-CBI LD4

Example 2. 4-((S)-2-(1-((5-(2,5-dioxo-2,5-dihydro-1H-pyrrol-1-yl)pentyl)carbamoyl)cyclobutanecarboxamido)-5-ureidopentanamido)benzyl ((S)-1-(chloromethyl)-3-(5-((S)-1-(chloromethyl)-5-(phosphonooxy)-1H-benzo[e]indol-3(2H)-yl)-5-oxopentanoyl)-2,3-dihydro-1H-benzo[e]indol-5-yl)carbamate (CBI-CBI LD4)

To a stirred solution of imine 18 (497 mg, 1.00 mmol) in dry DCM (10 mL) and MeOH (10 mL) at 20° C. under nitrogen was added 4M HCl in dioxane (0.63 mL, 2.5 mmol). After addition the reaction mixture was stirred at 20° C. for 1 h. The volatiles were evaporated under reduced pressure at 20° C. to give a yellow solid which was stirred with a mixture of EtOAc and petroleum ether (1:10) (200 mL) at 20° C. for 30 min. The supernatant was decanted and the procedure was repeated. The resulting solid was stirred with a mixture of aqueous $Na_2CO_3$ (2N, 200 mL) and DCM (200 mL) at 0° C. for 15 min. The DCM layer was separated, washed with water (100 mL), and then dried ($MgSO_4$) and evaporated at 25° C. to give aniline 19 (322 mg, 97%) as an unstable solid; $^1$H NMR [$(CD_3)_2SO$]δ 8.01 (d, J=8.4 Hz, 1H), 7.94-7.78 (m, 2H), 7.52 (t, J=7.3 Hz, 1H), 7.39 (t, J=7.5 Hz, 1H), 4.20-3.72 (m, 5H), 1.54 (s, 9H), 2 protons not observed. HRMS (ESI) m/z calc. for $C_{18}H_{22}ClN_2O_2$: 333.1364. found: 333.1355 [MH$^+$]; calc. for $C_{18}H_{21}ClKN_2O_2$: 371.0923. found: 371.0920 [MK$^+$]; calc. for $C_{18}H_{21}ClN_2NaO_2$: 355.1184. found: 355.1179 [MNa$^+$]. This material was used for the next step without further purification.

To a stirred homogeneous mixture of aniline 19 (322 mg, 0.97 mmol) and DMAP (730 mg, 6.00 mmol) in dry DCM (30 mL) at 20° C. under nitrogen was added a solution of diphosgene in dry DCM (0.10 M, 11 mL, 1.10 mmol). The mixture was stirred for 20 min and then solid p-nitrobenzyl alcohol (1.53 g, 10.0 mmol) was added. The final reaction mixture was stirred at 20° C. under nitrogen for 18 h and then partitioned between EtOAc (300 mL) and water (300 mL). The EtOAc layer was separated, washed with brine (200 mL) and dried ($MgSO_4$). Evaporation of solvent at 30° C. gave a soft yellow solid which was purified by chromatography on silica gel (eluting with DCM:EtOAc:petroleum ether 20:1:10) to afford carbamate 20 (411 mg, 83%) as a pale yellow solid, mp 141-142° C.; $[α]_D$–15.0° (c 0.20, CHCl$_3$); $^1$H NMR [$(CD_3)_2SO$]δ 9.85 (s, 1H), 8.36-8.15 (m, 3H), 8.05 (d, J=8.4 Hz, 1H), 7.88 (d, J=8.3 Hz, 1H), 7.72 (d, J=8.6 Hz, 2H), 7.57-7.49 (m, 1H), 7.45-7.36 (m, 1H), 5.35 (s, 2H), 4.27-4.12 (m, 2H), 4.10-3.96 (m, 2H), 3.94-3.81 (m, 1H), 1.52 (s, 9H). Anal. ($C_{26}H_{26}ClN_3O_6$) Calc: C, 61.00; H, 5.12; N, 8.21. Found: C, 61.27; H, 5.05; N, 8.25.

To a stirred solution of 20 (282 mg, 0.55 mmol) in DCM (6 mL) at 0° C. under nitrogen was added trifluoroacetic acid (TFA) (3 mL). After addition the reaction mixture was stirred at 0° C. for 1 h 15 min and then partitioned between DCM (300 mL) and cold aqueous $Na_2CO_3$ (2N, 300 ml). The DCM layer was separated, washed with cold aqueous $Na_2CO_3$ (2N, 100 mL) and water (100 mL) and then dried ($MgSO_4$) and evaporated at 25° C. to give an orange solid. This solid was dissolved in dry DMA (4 mL) and treated with acid 21 (297 mg, 0.55 mmol), EDCI.HCl (317 mg, 1.65 mmol) and TsOH (19 mg, 0.11 mmol). The mixture was stirred at 20° C. under nitrogen for 22 h and then partitioned between EtOAc (300 mL) and water (300 mL). The EtOAc layer was separated, washed with water (200 mL), and dried ($MgSO_4$). Evaporation of solvent at 25° C. gave an oil which was purified by chromatography on silica gel (eluting with DCM:EtOAc 2:1) to afford amide 22 (181 mg, 35%) as a sticky solid, $[α]_D$–26.8° (c 0.37, CHCl$_3$); $^1$H NMR [$(CD_3)_2SO$]δ 9.84 (s, 1H), 8.62 (s, 1H), 8.59 (s, 1H), 8.28 (d, J=8.5 Hz, 2H), 8.04 (d, J=8.5 Hz, 2H), 7.92 (d, J=8.2 Hz, 2H), 7.72 (d, J=8.3 Hz, 2H), 7.63-7.57 (m, 2H), 7.51-7.39 (m, 2H), 5.34 (s, 2H), 4.48-4.17 (m, 6H), 4.10-3.97 (m, 2H), 3.97-3.84 (m, 2H), 2.82-2.54 (m, 4H), 2.04-1.91 (m, 2H), 1.49 (s, 18H). HRMS (ESI) m/z calc. for $C_{47}H_{51}Cl_2KN_4O_{10}P$: 971.2351. found: 971.2344 [MK$^+$]; calc. for $C_{47}H_{51}Cl_2N_4NaO_{10}P$: 955.2612. found: 955.2621 [MNa$^+$].

To a stirred solution of nitro compound 22 (47 mg, 0.05 mmol) in acetone:water:THF (10:5:1) (6 mL) at 0° C. under nitrogen was added Zn powder (65.4 mg, 1.00 mmol) and $NH_4Cl$ (107 mg, 2.00 mmol). After addition the reaction mixture was stirred at 0° C. for 40 min. The reaction mixture was filtered through celite, washing several times with cold DCM. The combined filtrates were washed with cold water (50 mL), and then dried ($MgSO_4$) and evaporated at 25° C. to give a yellow foamy solid. This solid was dissolved in dry DMA (1 mL) and added to a preformed (10 min at 20° C.)

mixture of Fmoc-L-citrulline (29.8 mg, 0.075 mmol) and EEDQ (18.5 mg, 0.075 mmol) in DMA (0.3 mL). The reaction mixture was stirred at 20° C. under nitrogen for 48 h and then partitioned between EtOAc (100 mL) and water (100 mL). The EtOAc layer was separated, washed with water (50 mL), and dried (MgSO$_4$). Evaporation of solvent at 25° C. gave an oil which was purified by chromatography on silica gel (EtOAc:MeOH 10:1) to give 23 (24 mg, 38%) as a sticky solid, [α]$_D$–31.9° (c 0.28, CHCl$_3$); $^1$H NMR [(CD$_3$)$_2$SO]δ 10.09 (s, 1H), 9.66 (s, 1H), 8.62 (s, 1H), 8.59 (s, 1H), 8.10-7.25 (m, 21H), 6.04-5.94 (m, 1H), 5.53-5.29 (m, 2H), 5.13 (s, 2H), 4.51-4.08 (m, 10H), 4.08-3.82 (m, 4H), 3.11-2.90 (m, 2H), 2.80-2.54 (m, 4H), 2.04-1.92 (m, 2H), 1.80-1.30 (m, 4H), 1.49 (s, 18H). HRMS (ESI) m/z calc. for C$_{68}$H$_{75}$Cl$_2$N$_7$O$_{12}$P: 1282.4583. found: 1282.4536 [MH$^+$]; calc. for C$_{68}$H$_{74}$Cl$_2$KN$_7$O$_{12}$P: 1320.4142. found: 1320.4119 [MK$^+$]; calc. for C$_{68}$H$_{74}$Cl$_2$N$_7$NaO$_{12}$P: 1304.4402. found: 1304.4388 [MNa$^+$].

To a stirred solution of 23 (86 mg, 0.067 mmol) in dry DMA (3 mL) at 0° C. under nitrogen was added a solution of piperidine in DMA (1.00 M, 0.58 mL, 0.58 mmol) and the mixture was stirred at 0° C. for 1 h 30 min. A mixture of EtOAc and petroleum ether (1:10, 60 mL) was added and the mixture was stirred at 0° C. for 40 min. The supernatant was decanted and the procedure was repeated with more EtOAc-petroleum ether (1:3, 50 mL then 30 mL). The residual oil was dried in vacuum at 20° C. for 1 h to give intermediate amine 24 (67 mg, 94%) as a sticky solid. This solid was used for the next step without further purification.

A mixture of acid 8 (30.4 mg, 0.098 mmol), EDCI.HCl (25.3 mg, 0.13 mmol) and TsOH (2.2 mg, 0.013 mmol) in dry DMA (0.7 mL) was stirred at 20° C. under nitrogen for 10 min. To this mixture was added a solution of the above amine 24 (67 mg, 0.060 mmol), followed by DIPEA (0.011 mL, 0.065 mmol). The reaction mixture was stirred at 20° C. under nitrogen for 20 h. Ice-water (30 mL) was added and the mixture was stirred at 0° C. for 30 min. The separated solid was filtered off, dried, and purified by chromatography on silica gel (eluting with DCM:EtOAc;MeOH 10:10:1) to give 25 (44 mg, 54%) as a sticky solid, [α]$_D$–51.6° (c 0.16, CHCl$_3$); $^1$H NMR [(CD$_3$)$_2$SO]δ 10.15 (s, exchangeable with D$_2$O, 1H), 9.66 (s, exchangeable with D$_2$O, 1H), 8.62 (s, 1H), 8.59 (s, 1H), 8.08-7.76 (m, 6H, reduced to 4H after D$_2$O exchange), 7.69-7.34 (m, 8H), 6.97 (s, 2H), 5.96 (t, J=5.7 Hz, exchangeable with D$_2$O, 1H), 5.40 (s, exchangeable with D$_2$O, 2H), 5.11 (s, 2H), 4.50-4.15 (m, 7H), 4.02-3.82 (m, 4H), 3.25 (t, partially obscured by water peak, J=6.8 Hz, 2H), 3.13-2.86 (m, 4H), 2.81-2.56 (m, 4H), 2.45-2.33 (m, 4H), 2.05-1.91 (m, 2H), 1.83-1.09 (m, 12H), 1.49 (s, 18H). HRMS (ESI) m/z calc. for C$_{68}$H$_{83}$Cl$_2$N$_9$O$_{14}$P: 1350.5169. found: 1350.5170 [MH$^+$]; calc. for C$_{68}$H$_{82}$Cl$_2$KN$_9$O$_{14}$P: 1388.4727. found: 1388.4771 [MK$^+$]; calc. for C$_{68}$H$_{82}$Cl$_2$N$_9$NaO$_{14}$P: 1372.4988. found: 1372.4992 [MNa$^+$].

To a stirred solution of 25 (30.3 mg, 0.022 mmol) in DCM (1.0 mL) at 20° C. under nitrogen was added TFA (1.0 mL). After addition the mixture was stirred at this temperature for 1 min. Cold petroleum ether (20 mL) was added and the mixture was stirred at 0° C. for 15 min. The supernatant was decanted and the procedure was repeated with EtOAc-petroleum ether (1:3, 2×20 mL). The resulting solid was collected and dried in vacuum at 20° C. to give CBI-CBI LD4 (25.3 mg, 93%) as a beige solid, [α]$_D$–186° (c 0.059, MeOH); $^1$H NMR [(CD$_3$)$_2$SO]δ 10.13 (s, exchangeable with D$_2$O, 1H), 9.66 (s, exchangeable with D$_2$O, 1H), 8.62 (s, 1H), 8.51 (s, 1H), 8.10 (d, J=8.4 Hz, 1H), 8.00 (d, J=8.5 Hz, 1H), 7.94-7.73 (m, 4H, reduced to 2H after D$_2$O exchange), 7.65 (d, J=8.4 Hz, 2H), 7.60-7.32 (m, 6H), 6.97 (s, 2H), 6.00 (t, J=5.5 Hz, exchangeable with D$_2$O, 1H), 5.45 (br s, exchangeable with D$_2$O, 2H), 5.13 (s, 2H), 4.52-4.15 (m, 7H), 4.10-3.82 (m, 4H), 3.28 (t, partially obscured by water peak, J=6.9 Hz, 2H), 3.13-2.84 (m, 4H), 2.81-2.56 (m, 4H), 2.47-2.34 (m, 4H), 2.08-1.89 (m, 2H), 1.84-1.53 (m, 4H), 1.53-1.09 (m, 8H), 2H not observed. HRMS (ESI) m/z calc. for C$_{60}$H$_{65}$Cl$_2$N$_9$O$_{14}$P: 1236.3771. found: 1236.3772 [M–H]$^-$.

Preparation of (11aS)-4-((S)-6-amino-2-(1-((5-(2,5-dioxo-2,5-dihydro-1H-pyrrol-1-yl)pentyl)carbamoyl)cyclobutanecarboxamido)hexanamido)benzyl 8-((6-((S)-1-(chloromethyl)-5-((4-methylpiperazine-1-carbonyl)oxy)-1H-benzo[e]indol-3(2H)-yl)-6-oxohexyl)oxy)-11-hydroxy-7-methoxy-5-oxo-2,3,11,11a-tetrahydro-1H-benzo[e]pyrrolo[1,2-a][1,4]diazepine-10(5H)-carboxylate bis(2,2,2-trifluoroacetate) (CBI-PBD LD2) and (11aS)-4-((S)-6-amino-2-(1-((5-(2,5-dioxo-2,5-dihydro-1H-pyrrol-1-yl)pentyl)carbamoyl)cyclobutanecarboxamido)hexanamido)benzyl 8-((6-((S)-1-(chloromethyl)-5-((4-methylpiperazine-1-carbonyl)oxy)-1H-benzo[e]indol-3(2H)-yl)-6-oxohexyl)oxy)-7,11-dimethoxy-5-oxo-2,3,11,11a-tetrahydro-1H-benzo[e]pyrrolo[1,2-a][1,4]diazepine-10(5H)-carboxylate bis(2,2,2-trifluoroacetate) (CBI-PBD LD3)

Step A

Synthesis of Compound 15 (65j in PCT/US2014/042560)

(S)-4-((S)-2-(allyloxycarbonylamino)-6-(tert-butoxycarbonylamino)hexanamido)benzyl 8-(6-((S)-1-(chloromethyl)-5-(4-methylpiperazine-1-carbonyloxy)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate Scheme -continued
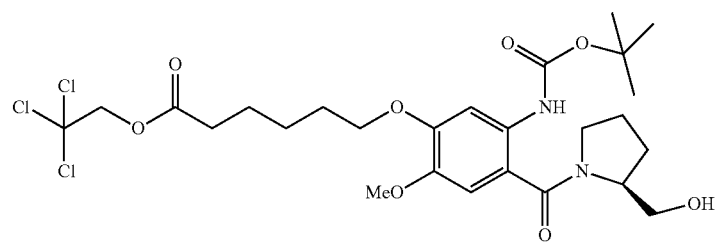
54c
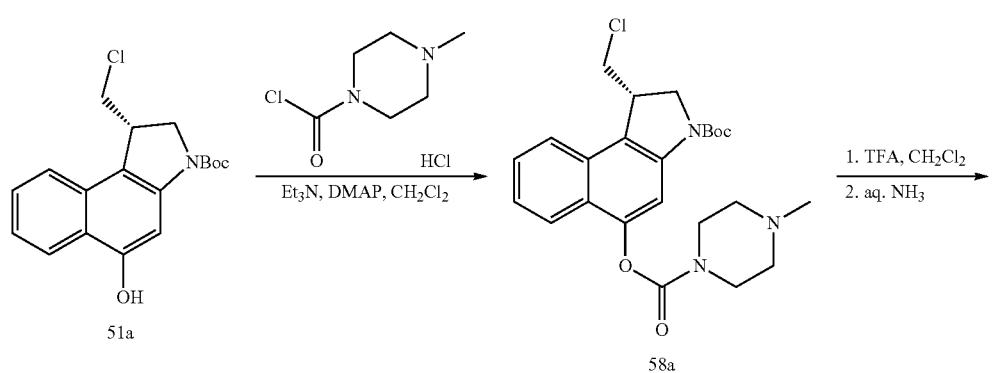
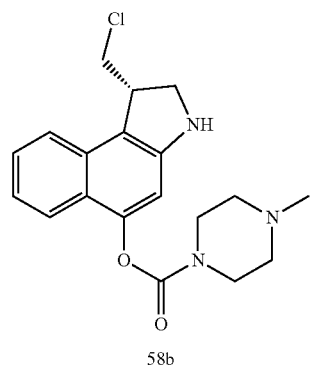
58b
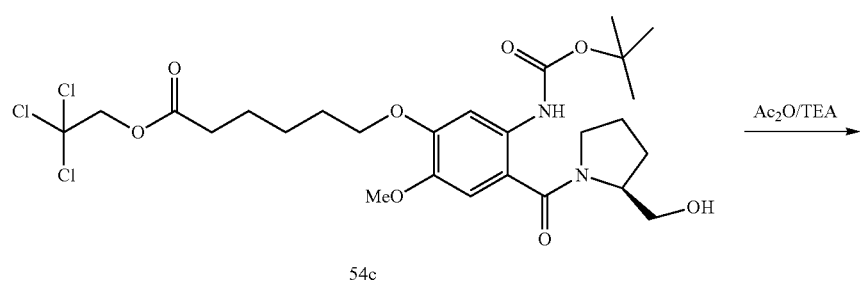
54c
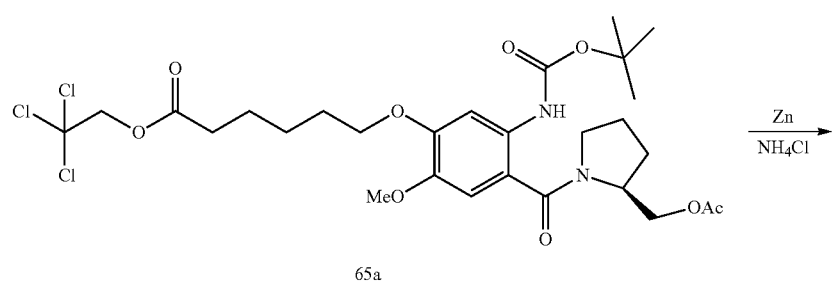
65a -continued
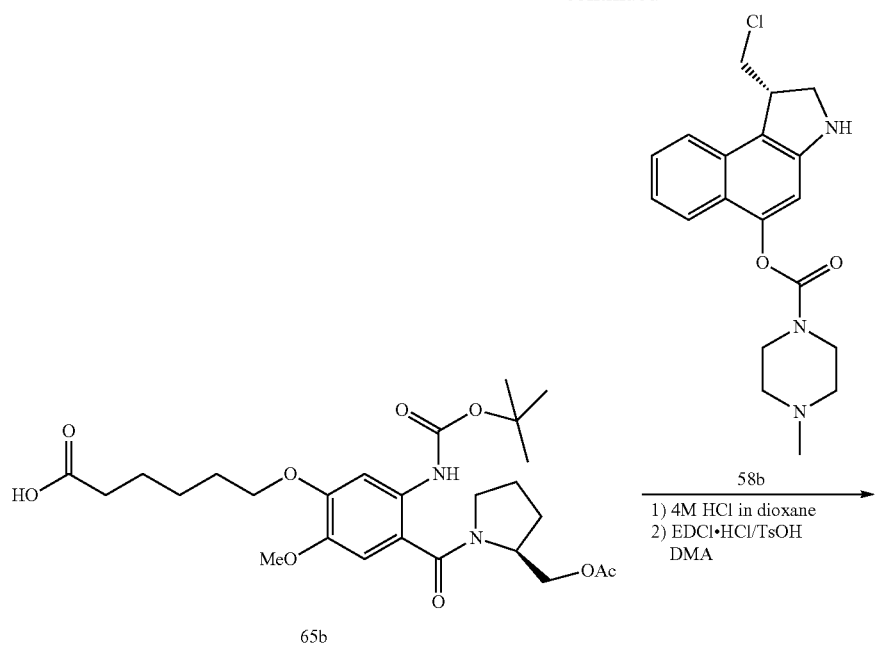
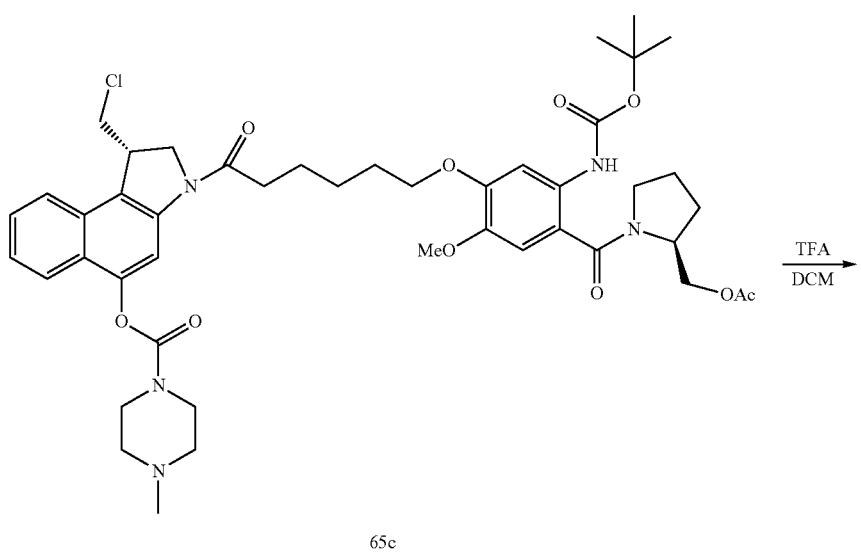
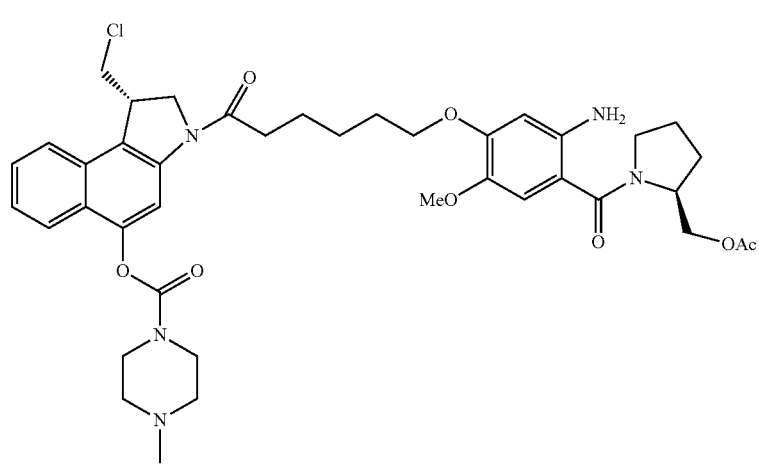

-continued
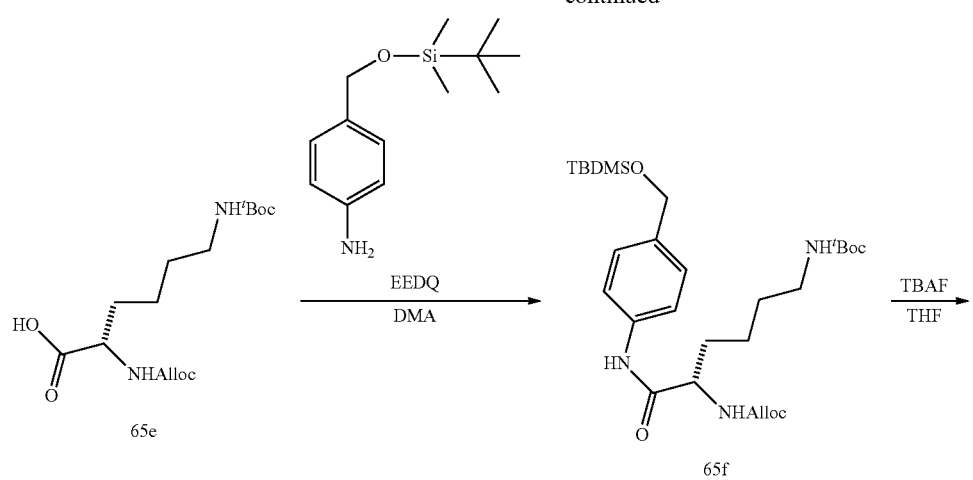
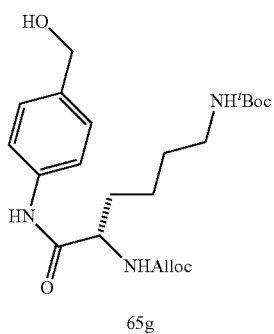
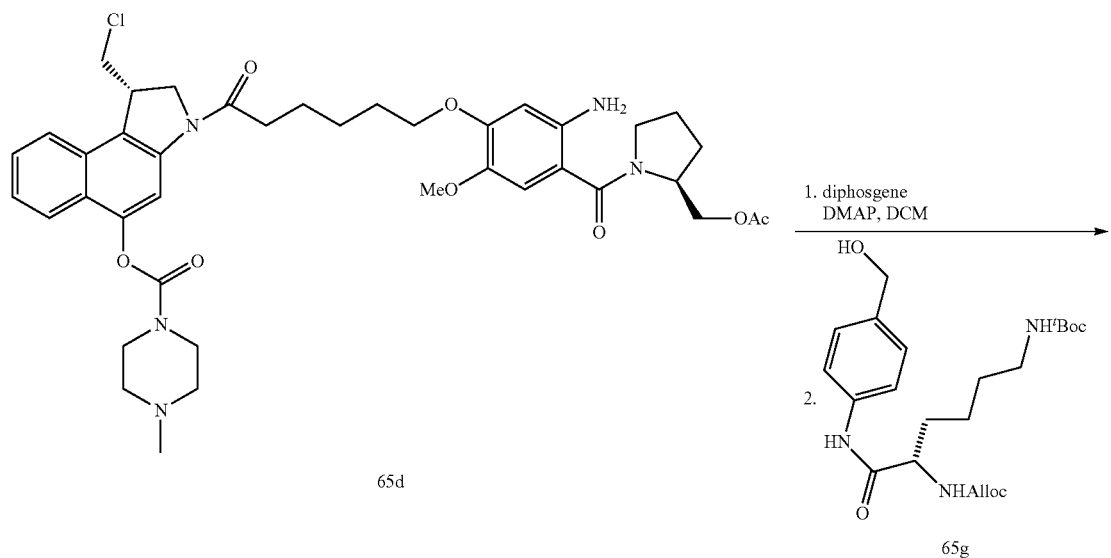

389 390
-continued
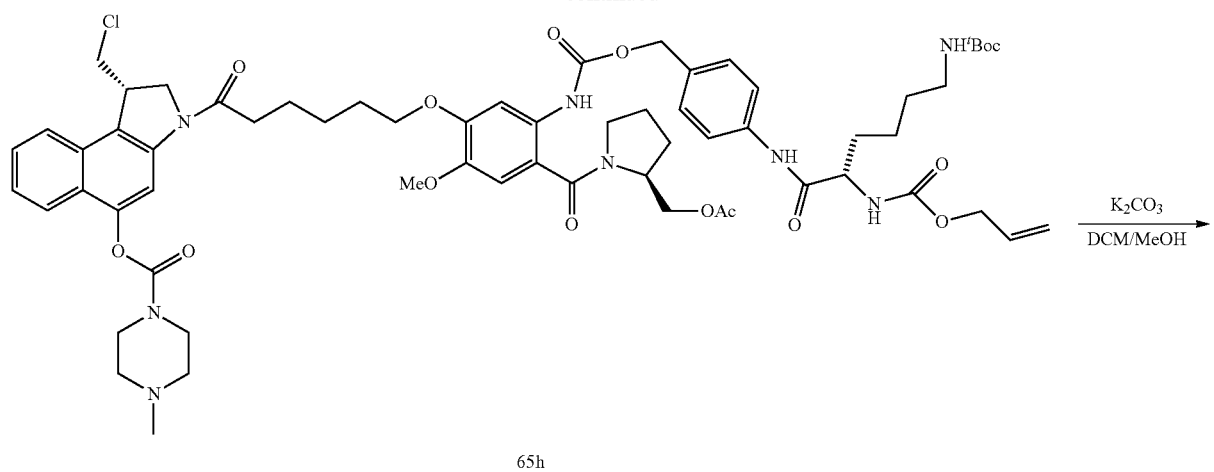
65h
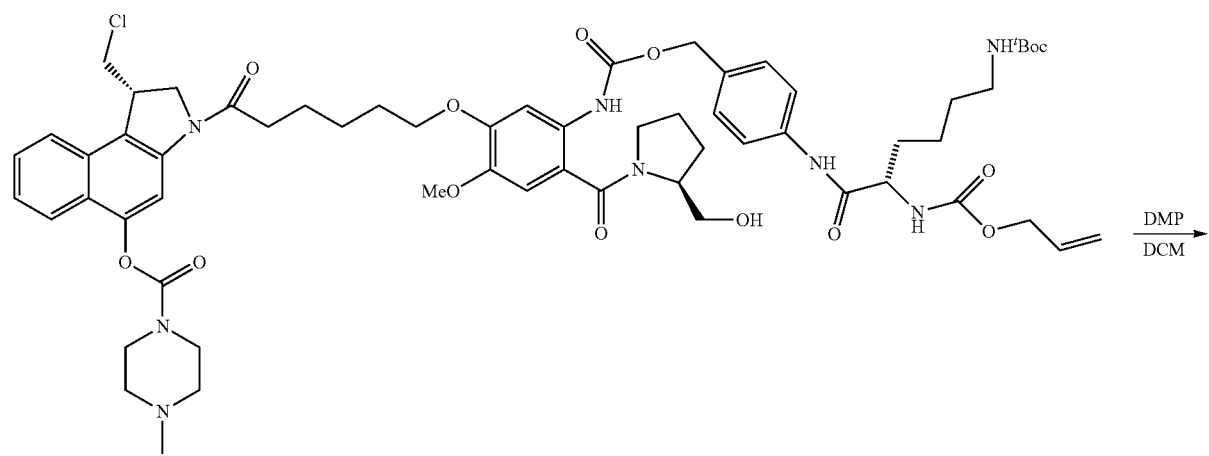
65i
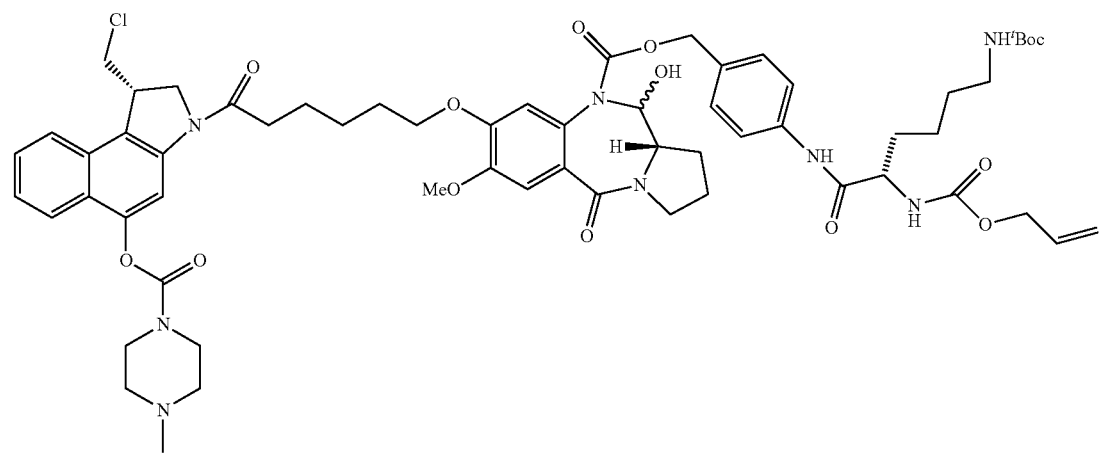
65j

Step 1. (S)-2,2,2-trichloroethyl 6-(5-(tert-butoxycarbonylamino)-4-(2-(hydroxymethyl)pyrrolidine-1-carbonyl)-2-methoxyphenoxy)hexanoate 54c A mixture of (S)-(2-amino-4-hydroxy-5-methoxyphenyl)(2-(hydroxymethyl)pyrrolidin-1-yl)methanone 54a (7.6 g, 28.6 mmol), prepared by the procedures of Tercel et al (2003) J. Med. Chem 46:2132-2151, and di-t-butyl dicarbonate (12.48 g, 57.2 mmol) in anhydrous THF (140 mL) was stirred under reflux in a nitrogen atmosphere for 18 h. The reaction mixture was cooled to r.t. and 2N NaOH (57.2 mL, 114 mmol) and MeOH (70 mL) were added. The mixture was stirred at r.t. for 6 h. Volatiles were evaporated under reduced pressure at 35-40° C. (bath temperature). Ice water (250 mL) was added and the pH was adjusted to 8-9 at 0° C. The mixture was stirred with petroleum ether-ethyl acetate (20:1) (2×400 mL) at r.t. for 15 min. The organic layer was separated and discarded. The aqueous layer was extracted with DCM (4×300 mL) and the combined extracts were dried (MgSO$_4$) and evaporated under reduced pressure to give (S)-tert-butyl 5-hydroxy-2-(2-(hydroxymethyl)pyrrolidine-1-carbonyl)-4-methoxyphenylcarbamate 54b as a pink-white solid (9.36 g, 89%); mp 154-156° C.; $^1$H NMR [(CD$_3$)$_2$SO]δ 9.51 (s, 1H), 8.90 (s, 1H), 7.27 (s, 1H), 6.91 (s, 1H), 4.73 (t, J=5.8 Hz, 1H), 4.16-4.02 (m, 1H), 3.73 (s, 3H), 3.64-3.34 (m, 4H), 1.99-1.60 (m, 4H), 1.43 (s, 9H). Anal. (C$_{18}$H$_{26}$N$_2$O$_6$) Calc: C, 59.00; H, 7.15; N, 7.65. Found: C, 58.94; H, 7.31; N, 7.39.

To a solution of 54b (2.88 g, 7.87 mmol) and 2,2,2-trichloroethyl 6-bromohexanoate (3.86 g, 11.8 mmol), prepared by the procedures in Tercel et al (2003) J. Med. Chem 46:2132-2151, in dry DMA (7 mL) was added anhydrous K$_2$CO$_3$ (2.61 g, 18.9 mmol). The resulting mixture was stirred at r.t. for 68 h. It was poured into ice-water (600 mL) and the product was extracted into ethyl acetate (600 mL). The extracts were washed successively with cold (0° C.) aqueous 2N Na$_2$CO$_3$ solution (2×400 mL) and water (400 mL) and then dried (MgSO$_4$). Evaporation of the solvent gave a brown oil which was purified by SiO$_2$ column chromatography (DCM-ethyl acetate=2:1) to give pure (S)-2,2,2-trichloroethyl 6-(5-(tert-butoxycarbonylamino)-4-(2-(hydroxymethyl)pyrrolidine-1-carbonyl)-2-methoxyphenoxy)hexanoate 54c (3.62 g, 76%) as a pale yellow foam; mp 36-39° C.; $^1$H NMR [(CD$_3$)$_2$SO]δ 9.90 (s, 1H), 7.33 (s, 1H), 6.93 (s, 1H), 4.89 (s, 2H), 4.74 (t, J=5.8 Hz, 1H), 4.17-4.02 (m, 1H), 3.94 (t, J=6.4 Hz, 2H), 3.73 (s, 3H), 3.63-3.26 (m, 4H), 2.55-2.46 (m, 2H, partially obscured by DMSO peak), 2.00-1.55 (m, 8H), 1.53-1.36 (m, 11H). Anal. (C$_{26}$H$_{37}$N$_2$O$_8$) Calc: C, 51.03; H, 6.09; N, 4.58. Found: C, 51.33; H, 6.21; N, 4.35.

Step 2: (S)-1-(chloromethyl)-2,3-dihydro-1H-benzo[e]indol-5-yl 4-methylpiperazine-1-carboxylate 58b A mixture of (S)-tert-butyl 1-(chloromethyl)-5-hydroxy-1H-benzo[e]indole-3(2H)-carboxylate 51a (3.338 g, 10 mmol), 4-methylpiperazine-1-carbonyl chloride hydrochloride (5.98 g, 30 mmol), Et$_3$N (3.5 g, 35 mmol) and DMAP (1.34 g, 11 mmol) in CH$_2$Cl$_2$ (80 mL) was stirred at room temperature for 2 days. See FIG. 12. The mixture was washed with water and the solvent was dried and removed under vacuum, to give (S)-tert-butyl 1-(chloromethyl)-5-(4-methylpiperazine-1-carbonyloxy)-1H-benzo[e]indole-3(2H)-carboxylate 58a (Boger D. L. et al, Synthesis, (1999), 1505-1509) in quantitative yield: mp 98° C.; $^1$H NMR (CDCl$_3$) δ 8.11 (br, 1H), 7.84 (d, J=8.4 Hz, 1H), 7.70 (d, J=8.4 Hz, 1H), 7.50 (ddd, J=8.2, 6.9, 1.1 Hz, 1H), 7.37 (ddd, J=8.1, 6.9, 1.0 Hz, 1H), 4.34-4.20 (m, 1H), 4.17-4.10 (m, 1H), 4.01-3.98 (m, 1H), 3.94 (dd, J=9.6, 2.4 Hz, 1H), 3.87-3.80 (br, 2H), 3.68-3.60 (br, 2H), 3.47 (t, J=10.8 Hz, 1H), 2.57-2.48 (m, 4H), 2.83 (s, 3H), 1.58 (s, 9H); MS (APCI+) m/z 461.2 MH$^+$. Anal. Calcd for C$_{24}$H$_{30}$ClN$_3$O$_4$: C, 62.7; H, 6.6; N, 9.1. Found: C, 62.5; H, 6.8; N, 9.2%.

A solution of 58a (2.30 g, 5 mmol) in CH$_2$Cl$_2$ (50 mL) was treated with excess trifluoroacetic acid (TFA) at 0° C. for 4 h, and the mixture was neutralized with cold aq. NH$_3$. Dilution with hexanes resulted in the precipitation of a solid which was collected by filtration, washed with water and hexane, and dried to give (S)-1-(chloromethyl)-2,3-dihydro-1H-benzo[e]indol-5-yl 4-methylpiperazine-1-carboxylate 58b (1.60 g, 89%): mp 144-147° C.; $^1$H NMR (CDCl$_3$) δ 7.69 (d, J=8.4 Hz, 1H), 7.63 (d, J=8.4 Hz, 1H), 7.45 (ddd, J=8.3, 6.9, 1.2 Hz, 1H), 7.25 (ddd, J=8.4, 6.8, 1.2 Hz, 1H), 6.82 (s, 1H), 5.30 (s, 1H), 4.17-4.05 (m, 2H), 4.03-3.96 (m, 2H), 3.89-3.77 (m, 4H), 3.54 (t, J=10.9 Hz, 1H), 3.20-2.90 (m, 4H), 2.76 (s, 3H). Anal. Calcd for C$_{19}$H$_{22}$ClN$_3$O$_2$: C, 63.4; H, 6.2; N, 11.7. Found: C, 63.2; H, 6.2; N, 11.5%.

Step 3: (S)-3-(6-(4-((S)-2-(acetoxymethyl)pyrrolidine-1-carbonyl)-5-amino-2-methoxyphenoxy)hexanoyl)-1-(chloromethyl)-2,3-dihydro-1H-benzo[e]indol-5-yl 4-methylpiperazine-1-carboxylate 65d To a stirred solution of (S)-2,2,2-trichloroethyl 6-(5-(tert-butoxycarbonylamino)-4-(2-(hydroxymethyl)pyrrolidine-1-carbonyl)-2-methoxyphenoxy)hexanoate 54c (1.66 g, 2.71 mmol) in dry DCM (10 mL) at r.t. was added acetic anhydride (1.29 mL, 13.6 mmol) and triethylamine (2.27 mL, 16.3 mmol). See FIG. 17. The reaction mixture was stirred for a further 4 h. Dry MeOH (1.5 mL) was added and the mixture was stirred for 30 min. Ethyl acetate (200 mL) was added and the ethyl acetate layer was separated and then washed with water several times. The ethyl acetate solution was dried (MgSO$_4$) and evaporated to give (S)-2,2,2-trichloroethyl 6-(4-(2-(acetoxymethyl)pyrrolidine-1-carbonyl)-5-(tert-butoxycarbonylamino)-2-methoxyphenoxy)hexanoate 65a (1.8 g, 100%) as a pale yellow glue; $^1$H NMR [(CD$_3$)$_2$SO]δ 8.82 (br s, 1H), 7.27 (s, 1H), 6.86 (s, 1H), 4.89 (s, 2H), 4.39-4.20 (m, 3H), 3.93 (t, J=6.4 Hz, 2H), 3.74 (s, 3H), 3.50-3.33 (m, 2H), 2.10-1.94 (m, 4H), 1.92-1.61 (m, 7H), 1.53-1.42 (m, 2H), 1.43 (s, 9H), 2H obscured by DMSO peak. HRMS (ESI) m/z calc. for C$_{28}$H$_{39}$Cl$_3$N$_2$NaO$_9$: 675.1613. found: 675.1603 [MNa$^+$]. Calc. for C$_{28}$H$_{40}$Cl$_3$N$_2$O$_9$: 653.1794. found: 653.1778 [MH$^+$].

To a stirred solution of 65a (1.76 g, 2.69 mmol) in a mixture of acetone (30 mL), water (20 mL), and THF (12 mL) under nitrogen was added Zn (7.06 g, 108 mmol) and NH$_4$Cl (11.6 g, 216 mmol). The mixture was stirred at r.t. for 23 h. Ethyl acetate (100 mL) was added and the mixture was stirred for 15 min. The organic layer was decanted. The extraction was repeated with more ethyl acetate (2×100 mL). The combined organic solution was washed with water (2×100 mL), dried (MgSO$_4$), filtered through celite and evaporated to give (S)-6-(4-(2-(acetoxymethyl)pyrrolidine-1-carbonyl)-5-(tert-butoxycarbonylamino)-2-methoxyphenoxy)hexanoic acid 65b (1.36 g, 96%) as a sticky colorless foam; $^1$H NMR [(CD$_3$)$_2$SO]δ 11.49 (very br s, 1H), 8.83 (s, 1H), 7.27 (s, 1H), 6.86 (br s, 1H), 4.39-4.02 (m, 3H), 3.93 (t, J=6.4 Hz, 2H), 3.74 (s, 3H), 3.51-3.33 (m, 2H, partially obscured by water peak), 2.21 (t, J=7.1 Hz, 2H), 2.11-1.93 (m, 4H), 1.90-1.66 (m, 5H), 1.62-1.50 (m, 2H), 1.50-1.35 (m, 2H), 1.43 (s, 9H). Anal. (C$_{26}$H$_{38}$N$_2$O$_9$.) Calc: C, 59.76; H, 7.33; N, 5.36. Found: C, 59.66; H, 7.49; N, 5.29.

To a stirred solution of 65b (0.87 g, 2.41 mmol) and (S)-1-(chloromethyl)-2,3-dihydro-1H-benzo[e]indol-5-yl 4-methylpiperazine-1-carboxylate 58b (1.26 g, 2.41 mmol) in dry DMA (5 mL) at 0° C. under a nitrogen atmosphere was added 4M HCl in p-dioxane (1.21 mL, 4.82 mmol), followed by EDCI.HCl (1.39 g, 7.23 mmol), and anhydrous TsOH (83 mg, 0.48 mmol). The reaction mixture was stirred at 0° C. under nitrogen for 21 hours then partitioned between ethyl acetate (500 mL) and water (500 mL). The ethyl acetate layer was separated and the aqueous layer was further extracted with more ethyl acetate (200 mL). The combined ethyl acetate extracts were washed successively with water (200 mL), saturated NaHCO$_3$ solution (2×200 mL) and water (200 mL). The ethyl acetate layer was dried and evaporated to give (S)-3-(6-(4-((S)-2-(acetoxymethyl)pyrrolidine-1-carbonyl)-5-(tert-butoxycarbonylamino)-2-methoxyphenoxy)hexanoyl)-1-(chloromethyl)-2,3-dihydro-1H-benzo[e]indol-5-yl 4-methylpiperazine-1-carboxylate 65c (1.66 g, 80%) as a beige solid-foam; mp 84-87° C.; $^1$H NMR [(CD$_3$)$_2$SO]δ 8.84 (br s, 1H), 8.21 (s, 1H), 7.95 (d, J=8.3 Hz, 1H), 7.81 (d, J=8.3 Hz, 1H), 7.58 (br t, J=7.7, 1H), 7.46 (br t, J=8.1 Hz, 1H), 7.29 (s, 1H), 6.86 (s, 1H), 4.40 (t, J=10.0 Hz, 1H), 4.36-3.86 (m, 10H), 3.83-3.74 (m, 1H), 3.73 (s, 3H), 3.54-3.36 (m, 4H), 2.67-2.34 (m, 6H, partially obscured by DMSO peak), 2.26 (s, 3H), 2.02 (br s, 3H), 1.93-1.62 (m, 8H), 1.60-1.47 (m, 2H), 1.42 (s, 9H). Anal. (C$_{45}$H$_{58}$ClN$_5$O$_{10}$.1½H$_2$O) Calc: C, 60.63; H, 6.90; N, 7.86. Found: C, 60.39; H, 6.66; N, 8.08.

To a stirred solution of 65c (2.17 g, 2.51 mmol) in DCM (20 mL) at 0° C. under a nitrogen atmosphere was added TFA (20 mL). After addition, the mixture was stirred further at this temperature for 2.5 h. The mixture was poured into a cold (0° C.) mixture of NaHCO$_3$ (50 g), water (700 mL), and DCM (500 mL) and stirred for 15 min. (pH ca. 8). The DCM layer was separated and washed with more aqueous NaHCO$_3$ (200 mL) and water (200 mL) and then dried (MgSO$_4$).

The solvent was evaporated to give (S)-3-(6-(4-((S)-2-(acetoxymethyl)pyrrolidine-1-carbonyl)-5-amino-2-methoxyphenoxy)hexanoyl)-1-(chloromethyl)-2,3-dihydro-1H-benzo[e]indol-5-yl 4-methylpiperazine-1-carboxylate 65d as a pale brown solid-foam (1.76 g, 92%); mp 62° C.; $^1$H NMR [(CD$_3$)$_2$SO]δ 8.21 (s, 1H), 7.95 (d, J=8.3 Hz, 1H), 7.81 (d, J=8.3 Hz, 1H), 7.57 (br t, J=7.6 Hz, 1H), 7.46 (br t, J=7.2 Hz, 1H), 6.67 (s, 1H), 6.37 (s, 1H), 5.09 (s, 2H), 4.41 (t, J=9.7 Hz, 1H), 4.36-4.20 (m, 3H), 4.17-4.00 (m, 3H), 3.97-3.86 (m, 3H), 3.81-3.70 (m, 2H), 3.63 (s, 3H), 3.54-3.32 (m, 5H), 2.66-2.34 (m, 6H, partially obscured by DMSO peak), 2.26 (s, 3H), 2.08-1.96 (m, 1H), 2.10 (s, 3H), 1.93-1.63 (m, 7H), 1.57-1.45 (m, 2H). Anal. (C$_{40}$H$_{50}$ClN$_5$O$_8$.½H$_2$O) Calc: C, 62.13; H, 6.65; N, 9.06. Found: C, 62.12; H, 6.76; N, 8.77.

Step 4: 65g

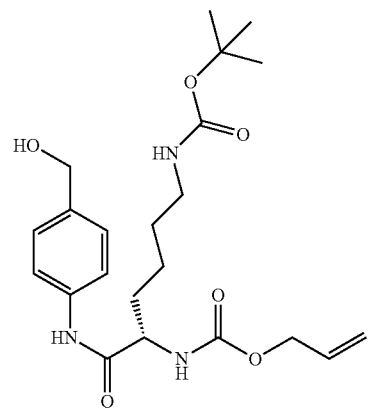 [SMILES: C=CCOC(=O)N[C@@H](CCCCNC(=O)OC(C)(C)C)C(=O)Nc1ccc(CO)cc1]

A mixture of (S)-2-(allyloxycarbonylamino)-6-(tert-butoxycarbonylamino)hexanoic acid 65e (3.30 g, 10.0 mmol) and EEDQ (3.71 g, 15.0 mmol) in dry DMA (10 mL) was stirred at r.t. under nitrogen for 15 min. See FIG. 18. To this preformed mixture was added a solution of 4-((tert-butyldimethylsilyloxy)methyl)aniline (prepared from the corresponding p-nitrobenzyl alcohol and TBDMSCl in DMF; followed by reduction using Zn/NH$_4$Cl) (2.37 g, 10.0 mmol) in dry DMA (3 mL). The final reaction mixture was stirred further at r.t. under a nitrogen atmosphere for 23 h. The mixture was partitioned between ethyl acetate (500 mL) and water (500 mL). The ethyl acetate layer was separated and washed successively with saturated NaHCO$_3$ (2×300 mL) and water (300 mL) and then dried (MgSO$_4$). Evaporation of the solvent gave an orange oil which was purified by a silica column chromatography (petroleum ether-ethyl acetate gradient from 10-35%) to afford the TBDMS-protected lysine 65f (4.87 g, 89%) as a sticky beige solid-foam; $^1$H NMR [(CD$_3$)$_2$SO]δ 9.97 (s, 1H), 7.55 (d, J=8.50 Hz, 2H), 7.44 (d, J=7.8 Hz, 1H), 7.21 (d, J=8.5 Hz, 2H), 6.75 (t, J=5.3 Hz, 1H), 5.99-5.82 (m, 1H), 5.28 (br d, J=17.2 Hz, 1H), 5.17 (br d, J=10.5 Hz, 1H), 4.64 (s, 2H), 4.46 (d, J=5.2 Hz, 2H), 4.12-4.02 (m, 1H), 2.93-2.83 (m, 2H), 1.70-1.52 (m, 2H), 1.46-1.20 (m, 4H), 1.35 (s, 9H), 0.89 (s, 9H), 0.06 (s, 6H). HRMS (ESI) m/z calc. for C$_{28}$H$_{47}$N$_3$NaO$_6$Si: 572.3126. found: 572.3136 [MNa$^+$].

To a stirred solution of 65f (4.81 g, 8.75 mmol) in THF (30 mL) at r.t. was added a 1M solution of tetrabutylammonium fluoride in THF (17.5 mL, 17.5 mmol). After addition, the mixture was stirred at this temperature for a further 2.5 h. Aqueous NH$_4$Cl (300 mL) was added and product was extracted into ethyl acetate (500 mL). The ethyl acetate was washed with water (2×100 mL) and dried (MgSO$_4$). The solvent was evaporated to give benzyl alcohol lysine 65g (3.81 g, 100%) as a beige solid; mp 101-103° C.; $^1$H NMR [(CD$_3$)$_2$SO]δ 9.94 (s, 1H), 7.52 (d, J=8.4 Hz, 2H), 7.44 (d, J=7.8 Hz, 1H), 7.23 (d, J=8.4 Hz, 2H), 6.76 (t, J=5.4 Hz, 1H), 5.97-5.84 (m, 1H), 5.29 (br d, J=17.2 Hz, 1H), 5.17 (br d, J=10.4 Hz, 1H), 5.08 (t, J=5.7 Hz, 1H), 4.47

Step 5: (S)-3-(6-(4-((S)-2-(acetoxymethyl)pyrrolidine-1-carbonyl)-5-((4-((S)-2-(allyloxycarbonylamino)-6-(tert-butoxycarbonylamino)hexanamido)benzyloxy)carbonylamino)-2-methoxyphenoxy)hexanoyl)-1-(chloromethyl)-2,3-dihydro-1H-benzo[e]indol-5-yl 4-methylpiperazine-1-carboxylate 65h To a stirred solution of 65d (764 mg, 1.00 mmol) and DMAP (367 mg, 3.00 mmol) in dry DCM (15 mL) at r.t. under nitrogen was added a solution of diphosgene in dry DCM (0.05 mmol per mL, 12 mL, 0.60 mmol) and the mixture was stirred for a further 20 min. See FIG. 19. To this mixture was added a solution of 65g (3.97 g, 9.13 mmol) in dry DCM (80 mL). The final reaction mixture was stirred further at r.t. under a nitrogen atmosphere for 48 h. The mixture was partitioned between ethyl acetate (500 mL) and water (300 mL). The ethyl acetate layer was separated and the aqueous layer was further extracted with ethyl acetate (2×200 mL). The combined ethyl acetate solution was washed with more water (2×200 mL) and dried (MgSO$_4$). Evaporation of the solvent at 30° C. (bath temperature) gave an orange oil which was purified by silica column chromatography (ethyl acetate-MeOH=10:1) to afford (S)-3-(6-(4-((S)-2-(acetoxymethyl)pyrrolidine-1-carbonyl)-5-((4-((S)-2-(allyloxycarbonylamino)-6-(tert-butoxycarbonylamino)hexanamido)benzyloxy)carbonylamino)-2-methoxyphenoxy)hexanoyl)-1-(chloromethyl)-2,3-dihydro-1H-benzo[e]indol-5-yl 4-methylpiperazine-1-carboxylate 65h (1.04 g, 85%) as a pale orange solid; mp 90-93° C.; $^1$H NMR [(CD$_3$)$_2$SO]δ 10.04 (s, 1H), 9.10 (br s, 1H), 8.21 (s, 1H), 7.95 (d, J=8.3 Hz, 1H), 7.81 (d, J=8.3 Hz, 1H), 7.63-7.53 (m, 3H), 7.51-7.42 (m, 2H), 7.32 (d, J=8.5 Hz, 2H), 7.21 (br s, 1H), 6.85 (br s, 1H), 6.79-6.72 (m, 1H), 5.97-5.83 (m, 1H), 5.29 (br d, J=17.2 Hz, 1H), 5.17 (br d, J=10.4 Hz, 1H), 5.08-4.96 (m, 2H), 4.52-4.37 (m, 3H), 4.37-3.85 (m, 10H), 3.83-3.66 (m, 2H), 3.74 (s, 3H), 3.54-3.41 (m, 2H), 3.41-3.23 (m, 2H, partially obscured by water peak), 2.95-2.83 (m, 2H), 2.66-2.34 (m, 6H, partially obscured by DMSO peak), 2.25 (s, 3H), 2.07-1.92 (m, 4H), 1.87-1.45 (m, 11H), 1.45-1.20 (m, 4H), 1.35 (s, 9H). HRMS (ESI) m/z calc. for C$_{63}$H$_{82}$ClN$_8$O$_{15}$: 1225.5583. found: 1225.5557 [MH$^+$]; calc. for C$_{63}$H$_{81}$ClN$_8$NaO$_{15}$: 1247.5402. found: 1247.5401 [MNa$^+$]; calc. for C$_{63}$H$_{81}$ClKN$_8$O$_{15}$: 1263.5142. found: 1263.5141 [MK$^+$].

A mixture of 65h (1.01 g, 0.824 mmol) and K$_2$CO$_3$ (1.14 g, 8.24 mmol) in DCM (20 mL) and MeOH (10 mL) was stirred at r.t. for 1 hour and 40 min. The mixture was diluted with DCM (200 mL) and stirred with ice-water (200 mL) for 10 min. The DCM layer was separated and the aqueous layer was further extracted with DCM (2×100 mL). The combined DCM solution was washed with more water (200 mL) and dried (MgSO$_4$). Evaporation of solvent at 25° C. (bath temperature) gave (S)-3-(6-(5-((4-((S)-2-(allyloxycarbonylamino)-6-(tert-butoxycarbonylamino)hexanamido)benzyloxy)carbonylamino)-4-((S)-2-(hydroxymethyl)pyrrolidine-1-carbonyl)-2-methoxyphenoxy)hexanoyl)-1-(chloromethyl)-2,3-dihydro-1H-benzo[e]indol-5-yl 4-methylpiperazine-1-carboxylate 65i (0.94 g, 96%) as a beige solid; mp 104-107° C.; $^1$H NMR [(CD$_3$)$_2$SO]δ 10.04 (s, 1H), 9.17 (br s, 1H), 8.21 (s, 1H), 7.95 (d, J=8.4 Hz, 1H), 7.80 (d, J=8.3 Hz, 1H), 7.63-7.53 (m, 3H), 7.51-7.42 (m, 2H), 7.38-7.21 (m, 3H), 6.93 (s, 1H), 5.32 (t, J=5.4 Hz, 1H), 5.98-5.83 (m, 1H), 5.30 (br d, J=17.2 Hz, 1H), 5.17 (br d, J=11.7 Hz, 1H), 5.03 (s, 2H), 4.73 (t, J=5.7 Hz, 1H), 4.52-4.36 (m, 3H), 4.36-4.17 (m, 2H), 4.17-3.85 (m, 6H), 3.83-3.66 (m, 2H), 3.73 (s, 3H), 3.61-3.40 (m, 4H), 3.40-3.20 (m, 2H, partially obscured by water peak), 2.94-2.83 (m, 2H), 2.67-2.34 (m, 6H, partially obscured by DMSO peak), 2.25 (s, 3H), 1.96-1.45 (m, 12H), 1.45-1.20 (m, 4H), 1.35 (s, 9H). HRMS (ESI) m/z calc. for C$_{61}$H$_{80}$ClN$_8$O$_{14}$: 1183.5477. found: 1183.5445 [MH$^+$]; calc. for C$_{61}$H$_{79}$ClN$_8$NaO$_{14}$: 1205.5296. found: 1205.5256 [MNa$^+$]; calc. for C$_{61}$H$_{79}$ClKN$_8$O$_{14}$: 1221.5036. found: 1221.5026 [MK$^+$].

To a stirred solution of 65i (0.92 g, 0.78 mmol) in dry DCM (20 mL) at 0° C. was added Dess-Martin periodinane (DMP, 1,1,1-triacetoxy-1,1-dihydro-1,2-benziodoxol-3(1H)-one, CAS Reg. No. 87413-09-0, 492 mg, 1.16 mmol) portionwise (over 8 min). After addition was complete the reaction mixture was stirred further at 0° C. for 2 h, then at r.t. for 45 h. The mixture was diluted with DCM (100 mL) and stirred with 10% Na$_2$S$_2$O$_3$ (100 mL) at r.t. for 10 min. The resulting mixture was partitioned between DCM (400 mL) and saturated NaHCO$_3$ solution (400 mL). The DCM layer was separated and the aqueous layer was further extracted with DCM (2×100 mL). The combined DCM solution was further washed with saturated NaHCO$_3$ solution (200 mL) and water (200 mL) and then dried (MgSO$_4$). Evaporation of solvent at 25° C. (bath temperature) gave a pale brown solid which was purified by SiO$_2$ column chromatography (DCM-ethyl acetate-MeOH=15:15:1, gradient to 15:15:3) to give (S)-4-((S)-2-(allyloxycarbonylamino)-6-(tert-butoxycarbonylamino)hexanamido)benzyl 8-(6-((S)-1-(chloromethyl)-5-(4-methylpiperazine-1-carbonyloxy)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate 65j (0.64 g, 70%) as a pale yellow solid; mp 137° C. (dec.); $^1$H NMR [(CD$_3$)$_2$SO]δ 10.02 (s, 1H), 8.21 (s, 1H), 7.95 (d, J=8.4 Hz, 1H), 7.80 (d, J=8.3 Hz, 1H), 7.65-7.38 (m, 5H), 7.18 (d, J=7.0 Hz, 2H), 7.03 (s, 1H), 6.82-6.63 (m, 2H), 6.49 (poorly resolved d, J=4.7 Hz, exchangeable with D$_2$O, 1H), 5.96-5.82 (m, 1H), 5.46 (poorly resolved dd, J=9.8, 4.7 Hz, became a d after D$_2$O, J=10.1 Hz, 1H), 5.27 (br d, J=17.1 Hz, 1H), 5.21-5.10 (m, 2H), 4.81 (br d, J=12.3 Hz, 1H), 4.51-4.17 (m, 5H), 4.13-3.84 (m, 4H), 3.84-3.67 (m, 2H), 3.77 (s, 3H), 3.55-3.20 (m, 6H, partially obscured by water peak), 2.66-2.30 (m, 6H, partially obscured by DMSO peak), 2.26 (s, 3H), 2.10-1.20 (m, 16H), 1.35 (s, 9H). HRMS (ESI) m/z calc. for C$_{61}$H$_{78}$ClN$_8$O$_{14}$: 1181.5321. found: 1181.5286 [MH$^+$]; calc. for C$_{61}$H$_{77}$ClN$_8$NaO$_{14}$: 1203.5140. found: 1203.5130 [MNa$^+$]; calc. for C$_{61}$H$_{77}$ClKN$_8$O$_{14}$: 1219.4879. found: 1219.4861 [MK$^+$].

Step B (11aS)-4-((S)-6-amino-2-(1-((5-(2,5-dioxo-2,5-dihydro-1H-pyrrol-1-yl)pentyl)carbamoyl)cyclobutanecarboxamido)hexanamido)benzyl 8-((6-((S)-1-(chloromethyl)-5-((4-methylpiperazine-1-carbonyl)oxy)-1H-benzo[e]indol-3(2H)-yl)-6-oxohexyl)oxy)-11-hydroxy-7-methoxy-5-oxo-2,3,11,11-tetrahydro-1H-benzo[e]pyrrolo[1,2-a][1,4]diazepine-10(5H)-carboxylate bis(2,2,2-trifluoroacetate) (CBI-PBD LD2) and (11aS)-4-((S)-6-amino-2-(1-((5-(2,5-dioxo-2,5-dihydro-1H-pyrrol-1-yl)pentyl)carbamoyl)cyclobutanecarboxamido)hexanamido)benzyl 8-((6-((S)-1-(chloromethyl)-5-((4-methylpiperazine-1-carbonyl)oxy)-1H-benzo[e]indol-3(2H)-yl)-6-oxohexyl)oxy)-7,11-dimethoxy-5-oxo-2,3,11,11a-tetrahydro-1H-benzo[e]pyrrolo[1,2-a][1,4]diazepine-10(5H)-carboxylate bis(2,2,2-trifluoroacetate) (CBI-PBD LD3)

Synthesis of CBI-PBD LD2 and CBI-PBD LD3

Synthetic Scheme

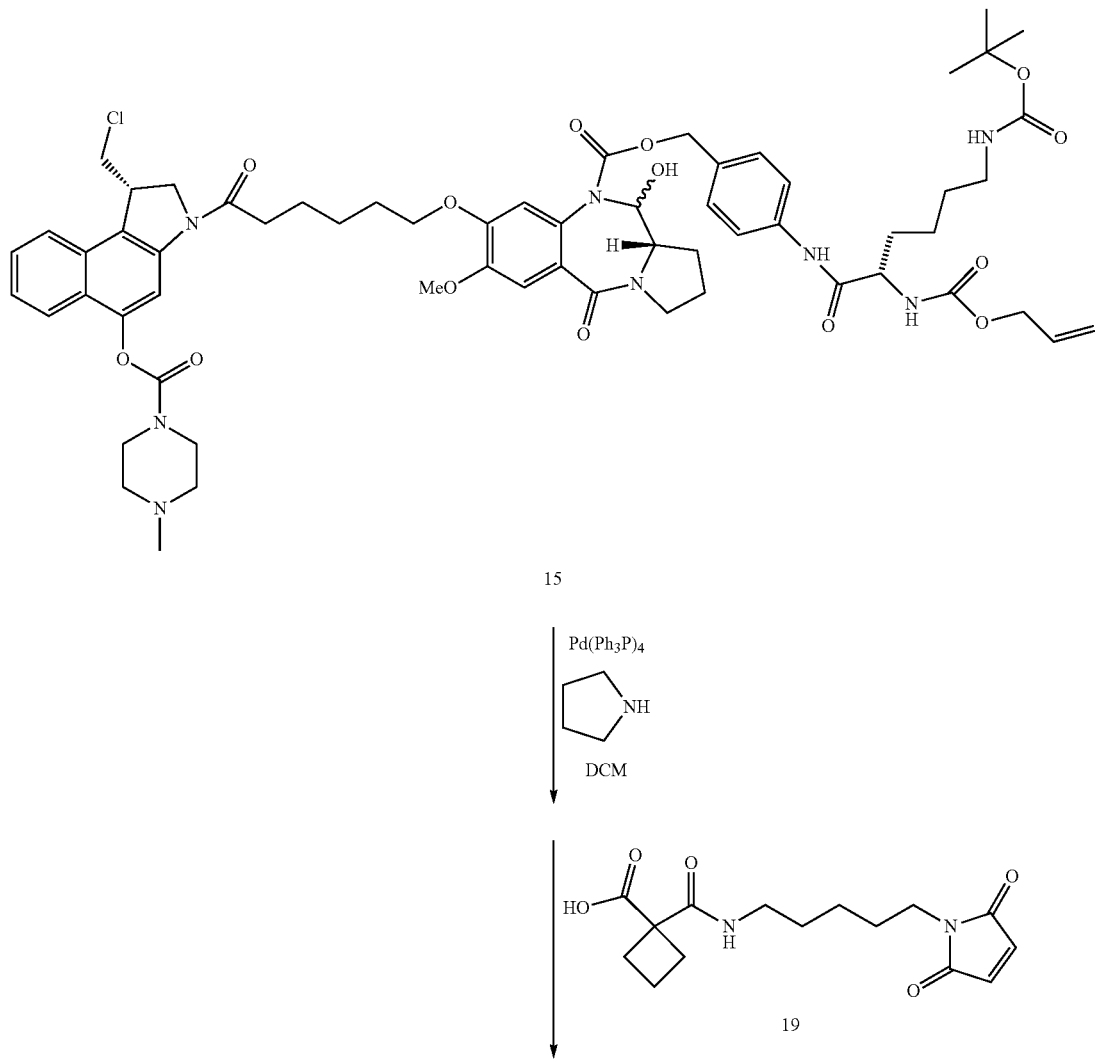

-continued
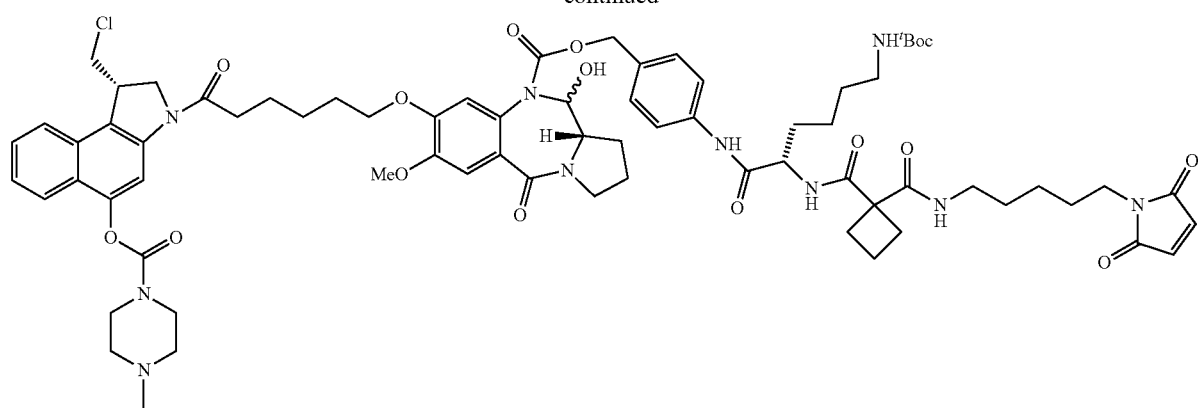
20
Synthesis of CBI-PBD LD2 and CBI-PBD LD3
Synthetic Scheme (cont'd)
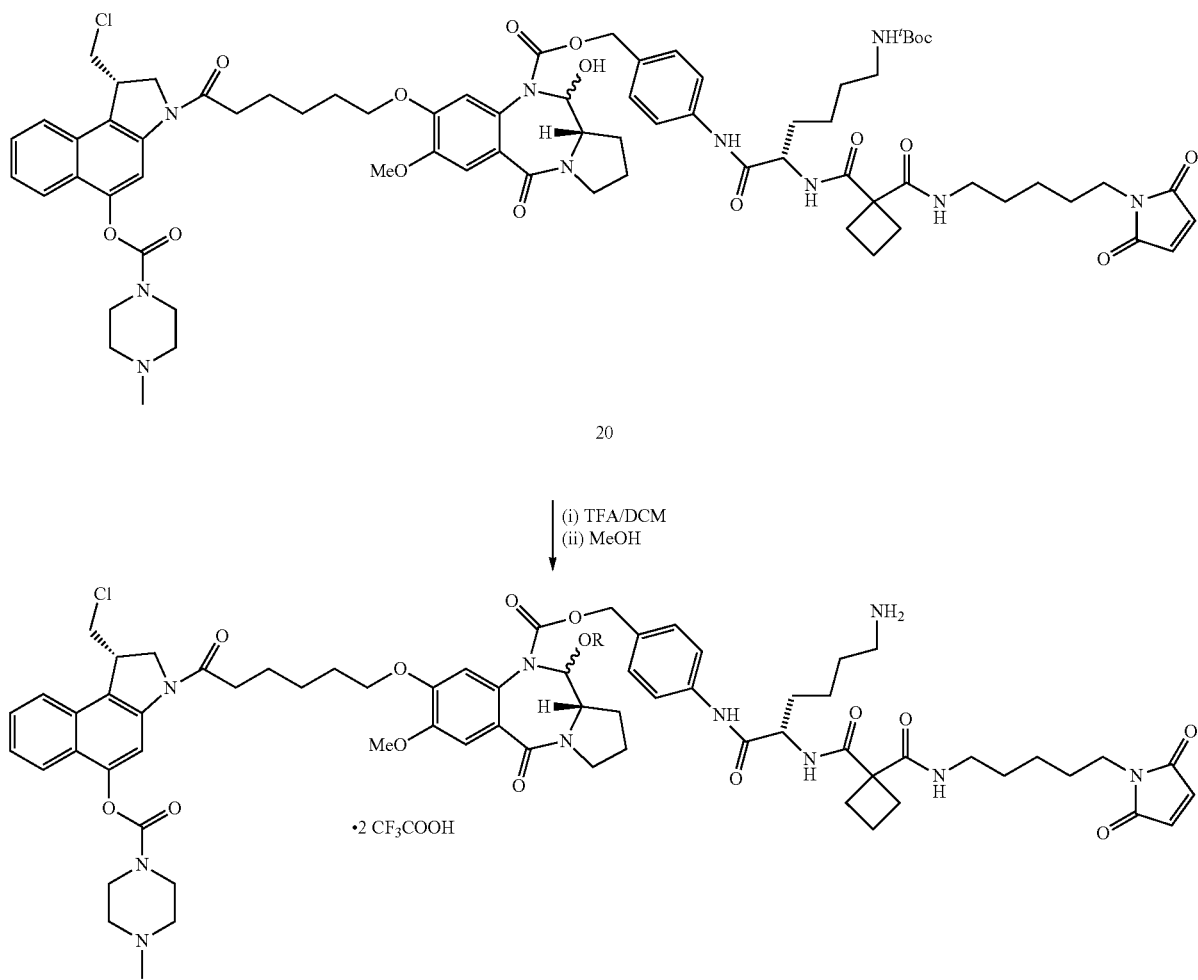
CBI-PBD LD2 (R = H)
CBI-PBD LD3 (R = Me)

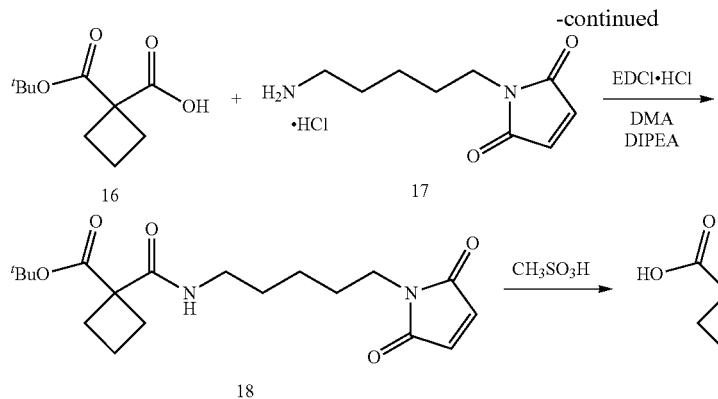
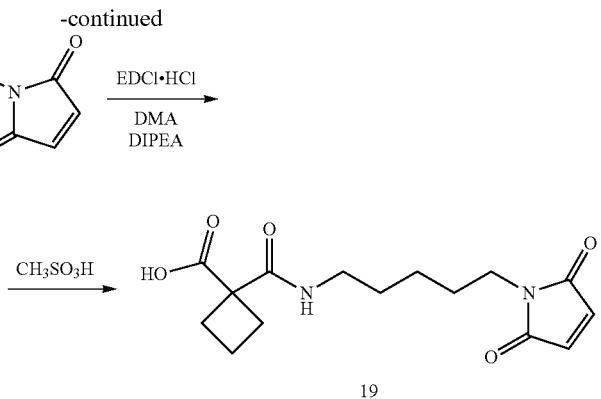

To a mixture of 1-(tert-butoxycarbonyl)cyclobutanecarboxylic acid (16) (200 mg, 1.00 mmol) (PCT Int. Appl. 2002, WO 2002076968 A1), 1-(5-aminopentyl)-1H-pyrrole-2,5-dione hydrochloride (17) (218 mg, 1.00 mmol) (J. Med. Chem. 2013, 56, 7890-7901), EDCI.HCl (576 mg, 3.00 mmol) and TsOH (35 mg, 0.20 mmol) was added DMA (2 mL). The mixture was stirred at 20° C. for 15 min and DIPEA (0.17 mL, 1.00 mmol) was added. The reaction mixture was stirred further for 20 h and partitioned between EtOAc (200 mL) and water (100 mL). The EtOAc layer was separated and washed successively with cold 1N HCl (100 mL), saturated NaHCO$_3$ (100 mL), and water (100 mL), and then dried (MgSO$_4$). Evaporation of solvent gave tert-butyl 1-((5-(2,5-dioxo-2,5-dihydro-1H-pyrrol-1-yl)pentyl)carbamoyl)cyclobutanecarboxylate (18) (290 mg, 80%) as a pale yellow solid, mp 63-65° C.; $^1$H NMR [(CD$_3$)$_2$SO]δ 7.58 (t, J=5.6 Hz, 1H), 7.00 (s, 2H), 3.37 (t, J=7.0 Hz, 2H), 3.03 (q, J=6.0 Hz, 2H), 2.40-2.23 (m, 4H), 1.85-1.64 (m, 2H), 1.55-1.32 (m, 4H), 1.38 (s, 9H), 1.26-1.01 (m, 2H). HRMS (ESI) m/z calc. for C$_{19}$H$_{29}$N$_2$O$_5$: 365.2071. found: 365.2071 [MH$^+$]; calc. for C$_{19}$H$_{28}$N$_2$NaO$_5$: 387.1890. found: 387.1898 [MNa$^+$]; calc. for C$_{19}$H$_{28}$KN$_2$O$_5$: 403.1630. found: 403.1629 [MK$^+$].

To a stirred solution of 18 (794 mg, 2.18 mmol) in DCM (50 mL) was added methanesulfonic acid (2.83 mL, 43.6 mmol). The cloudy mixture was stirred at 20° C. for 2 h 30 min. The mixture was diluted with DCM (200 mL) and washed with water (2×50 mL). The DCM solution was dried (MgSO$_4$) and evaporated at 25° C. (bath temperature) to give 1-((5-(2,5-dioxo-2,5-dihydro-1H-pyrrol-1-yl)pentyl)carbamoyl)cyclobutanecarboxylic acid (19) (636 mg, 95%) as a pale yellow solid, mp 100-102° C.; $^1$H NMR [(CD$_3$)$_2$SO]δ 12.46 (br s, 1H), 7.63 (t, J=5.4 Hz, 1H), 7.00 (s, 2H), 3.37 (t, J=7.0 Hz, 2H), 3.02 (q, J=5.9 Hz, 2H), 2.42-2.28 (m, 4H), 1.89-1.63 (m, 2H), 1.55-1.32 (m, 4H), 1.29-1.11 (m, 2H). Anal. (C$_{15}$H$_{20}$N$_2$O$_5$) Calc: C, 58.43; H, 6.54; N, 9.09. Found: C, 58.54; H, 6.39; 8.84.

To a stirred homogeneous solution of (11aS)-4-((S)-2-(((allyloxy)carbonyl)amino)-6-((tert-butoxycarbonyl)amino)hexanamido)benzyl 8-((6-((S)-1-(chloromethyl)-5-((4-methylpiperazine-1-carbonyl)oxy)-1H-benzo[e]indol-3(2H)-yl)-6-oxohexyl)oxy)-11-hydroxy-7-methoxy-5-oxo-2,3,11,11a-tetrahydro-1H-benzo[e]pyrrolo[1,2-a][1,4]diazepine-10(5H)-carboxylate (15) (177 mg, 0.15 mmol) (refer filed patent: GENENLAW-#446508) in dry DCM (2 mL) at 20° C. and under a nitrogen atmosphere was added pyrrolidine (0.122 mL, 1.50 mmol), followed by Pd(Ph$_3$P)$_4$ (4.28 mg, 9.8% Pd). After addition the reaction mixture was stirred further at 20° C. (N$_2$) for 25 min. The mixture was diluted with petroleum ether (50 mL) and stirred at 20° C. (N$_2$) for 10 min. Solvents were decanted and the procedure was repeated with DCM-petroleum ether (1:10) (2×30 mL). The solid left behind was dissolved in DCM (100 mL) and washed with water (50 mL), brine (50 mL), and then dried (MgSO$_4$). Evaporation of solvent at 25° C. (bath temperature) gave the free amine as a beige solid (140 mg, 85%). Some of this material (110 mg, 0.10 mmol) was treated with a pre-formed (at 20° C. for 10 min) mixture of 19 (34 mg, 0.11 mmol), EDCI.HCl (58 mg, 0.30 mmol), and TsOH (3.4 mg, 0.02 mmol) in dry DMA (1 mL) at 20° C. (under a nitrogen atmosphere). After 10 min DIPEA (0.02 mL, 0.10 mmol) was added and the reaction mixture stirred further for 22 h. The mixture was partitioned between EtOAc (200 mL) and water (100 mL). The EtOAc layer was separated and washed further with saturated NaHCO$_3$ (100 mL), water (100 mL), and then dried (MgSO$_4$). Evaporation of solvent at 25° C. (bath temperature) gave a crude product which was purified by SiO$_2$ column chromatography (DCM-EtOAc-MeOH=20:10:3) to give 20 (92 mg, 66%) as a pale yellow solid; mp 106-109° C.; [α]$_D$+43.1° (c 0.418, CHCl$_3$); $^1$H NMR [(CD$_3$)$_2$SO]δ 10.06 (s, exchangeable with D$_2$O, 1H), 8.21 (s, 1H), 7.95 (d, J=8.4 Hz, 1H), 7.85-7.77 (m, 2H, reduced to 1H after D$_2$O), 7.75 (d, J=8.0 Hz, exchangeable with D$_2$O, 1H), 7.65-7.51 (m, 3H), 7.46 (t, J=7.6 Hz, 1H), 7.24-7.11 (m, 2H), 7.03 (s, 1H), 6.96 (s, 2H), 6.79-6.66 (m, 2H, reduced to 1H after D$_2$O), 6.54-6.43 (m, exchangeable with D$_2$O, 1H), 5.52-5.41 (m, but d after D$_2$O with J=9.5 Hz, 1H), 5.15 (d, J=12.0 Hz, 1H), 4.81 (d, J=12.0 Hz, 1H), 4.47-4.18 (m, 5H), 4.08-3.98 (m, 1H), 3.97-3.86 (m, 2H), 3.84-3.67 (m, 5H), 3.56-3.21 (m, 8H, partially obscured by water peak), 3.12-3.02 (m, but t after D$_2$O with J=6.2 Hz, 2H), 2.92-2.80 (m, 2H), 2.65-2.33 (m, 10H, partially obscured by DMSO peak), 2.25 (s, 3H), 2.15-1.12 (m, 23H), 1.33 (s, 9H). HRMS (ESI) m/z calc. for C$_{72}$H$_{92}$ClN$_{10}$O$_{16}$: 1387.6376. found: 1387.6319 [MH$^+$]; calc. for C$_{72}$H$_{91}$ClN$_{10}$NaO$_{16}$: 1409.6195. found: 1409.6146 [MNa$^+$]; calc. for C$_{72}$H$_{91}$ClKN$_{10}$O$_{16}$: 1425.5935. found: 1425.5875 [MK$^+$].

To a stirred solution of 20 (79 mg, 0.057 mmol) in DCM (5 mL) at 20° C. and under nitrogen was added TFA (5 mL). After addition the mixture was stirred further at this temperature for 20 min. Petroleum ether (100 mL) was added and the mixture was stirred at 20° C. for 30 min. Solvent was removed and the oil left behind was stirred with more EtOAc-petroleum ether (1:10) (3×50 mL). The residual oil was dissolved in MeOH and the solution was evaporated to give a glassy solid (76 mg) which was purified by preparative HPLC [SynergiMaxRP column, 4μ, 21×250 mm; water- TFA (pH=2.56; 95% to 55%)/10% H₂O in CH₃CN (5% to 45%); gradient time 30 min; flow rate: 12 mL/min] to give (i) CBI-PBD LD2 (26.2 mg, 30%) as a pale amber solid; HPLC purity: 98.5%; [α]$_D$+30.0° (c 0.233, MeOH); ¹H NMR [(CD₃)₂SO]δ 10.08 (s, exchangeable with D₂O, 1H), 9.82 (br s, exchangeable with D₂O, 1H), 8.27 (s, 1H), 7.97 (d, J=8.4 Hz, 1H), 7.92-7.79 (m, 3H, reduced to 1H after D₂O), 7.67-7.52 (m, 5H, reduced to 3H after D₂O), 7.46 (t, J=8.0 Hz, 1H), 7.21-7.11 (m, 2H), 7.04 (s, 1H), 6.97 (s, 2H), 6.75 (s, 1H), 6.50 (br s, 1H, exchangeable with D₂O), 5.45 (br d, but d after D₂O with J=9.0 Hz, 1H), 5.10 (br d, J=13 Hz, 1H), 4.87 (br d, J=12 Hz, 1H), 4.55-4.10 (m, 5H), 4.50 (dd, J=11.4, 3.4 Hz, 1H), 4.01-3.88 (m, 2H), 3.76 (s, 3H), 3.39-3.22 (m, 4H), 3.14-3.03 (m, 2H), 2.89 (s, 3H), 2.81-2.69 (m, 2H), 2.65-2.55 (m, 1H), 2.47-2.34 (m, 4H), 2.07-1.13 (m, 23H), remaining 12H obscured by water and DMSO peaks. HRMS (ESI) m/z calc. for C₆₇H₈₄ClN₁₀O₁₄: 1287.5852. found: 1287.5845 [MH⁺]; calc. for C₆₇H₈₃ClN₁₀NaO₁₄: 1309.5671. found: 1309.5654 [MNa⁺].

Also purified was (ii) CBI-PBD LD3 (11.2 mg, 15%) as a beige solid; HPLC purity: 92.6%; ¹H NMR [(CD₃)₂SO]δ 10.07 (s, exchangeable with D₂O, 1H), 9.90 (br s, exchangeable with D₂O, 1 H), 8.27 (s, 1H), 7.96 (d, J=8.5 Hz, 1H), 7.93-7.76 (m, 3H, reduced to 1H after D₂O), 7.73-7.51 (m, 5H, reduced to 3H after D₂O), 7.46 (t, J=8.2 Hz, 1H), 7.16-7.08 (m, 2H), 7.04 (s, 1H), 6.97 (s, 2H), 6.85 (s, 1H), 5.33 (br d, J=7.8 Hz, 1H), 5.07 (br d, J=12 Hz, 1H), 4.93 (br d, J=13 Hz, 1H), 4.56-4.10 (m, 5H), 3.77 (s, 3H), 3.62-3.23 (m, 6H), 3.44 (s, 3H), 3.15-3.01 (m, 2H), 2.89 (s, 3H), 2.82-2.69 (m, 2H), 2.66-2.55 (m, 1H), 2.46-2.34 (m, 4H), 2.11-1.12 (m, 23H), remaining 13H obscured by water and DMSO peaks. HRMS (ESI) m/z calc. for C₆₈H₈₆ClN₁₀O₁₄: 1301.6008. found: 1301.5952 [MH⁺]; calc. for C₆₈H₈₅ClN₁₀NaO₁₄: 1323.5827. found: 1323.5778 [MNa⁺].

Preparation of
(2E,2'E)-3,3'-(2-(3-((S)-2-(1-(5-(2,5-dioxo-2,5-dihydro-1H-pyrrol-1-yl)pentylcarbamoyl)cyclobutanecarboxamido)-5-ureidopentanamido)propanamido)-1,4-phenylene)diacrylic acid

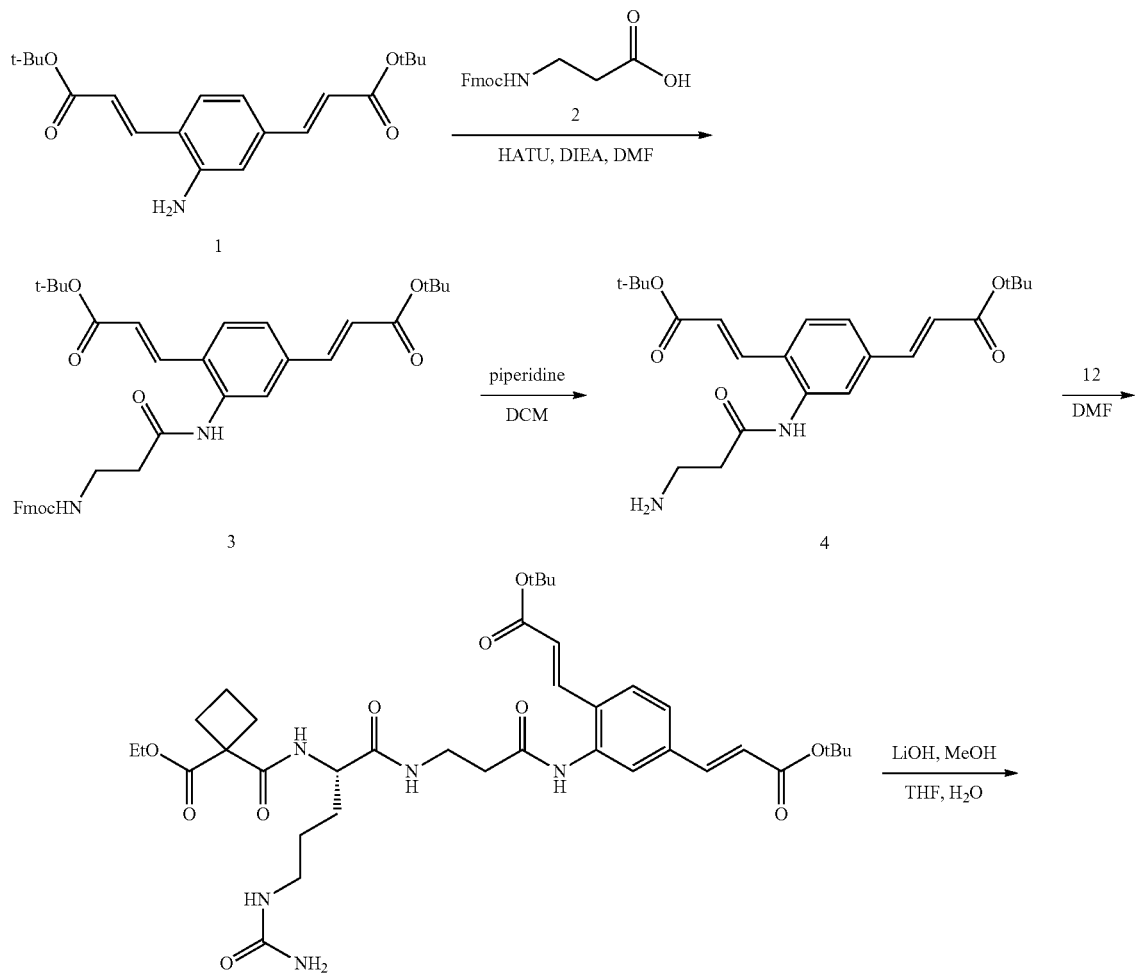

405
-continued
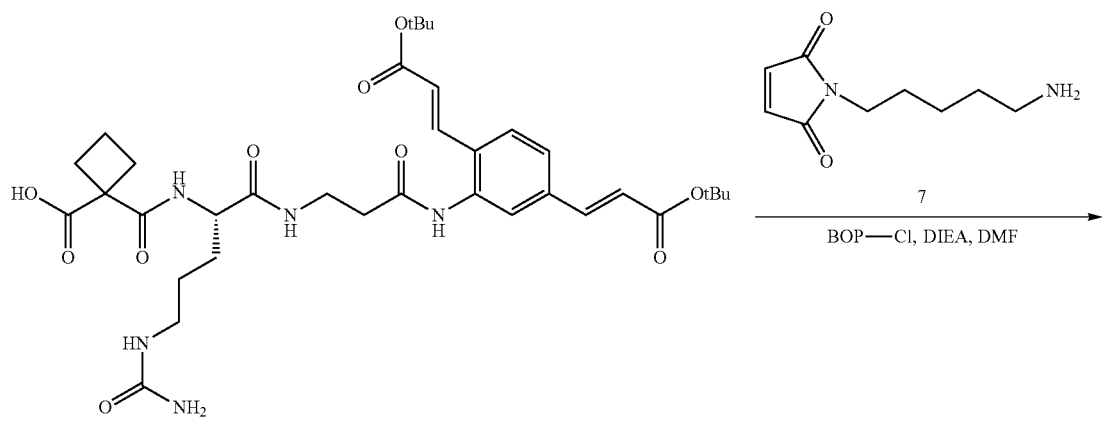
6
406
BOP—Cl, DIEA, DMF
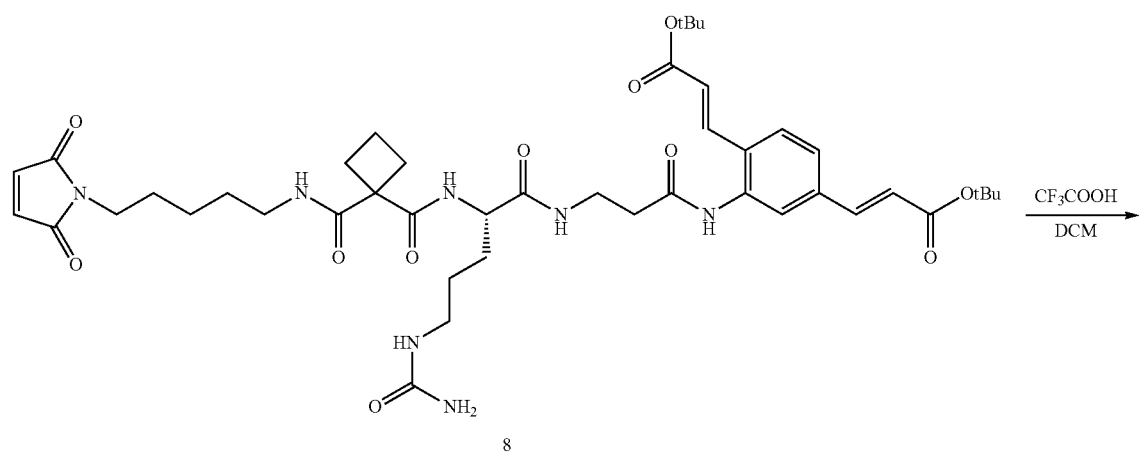
8
CF₃COOH
DCM
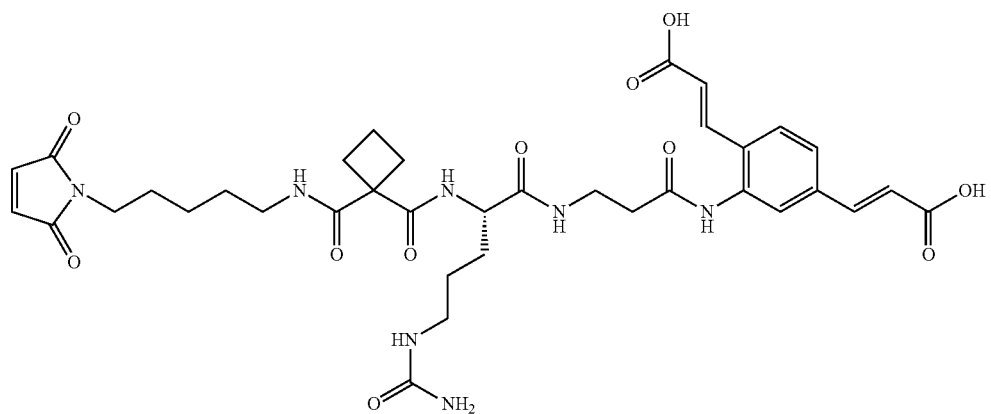

Synthesis of INT 12:

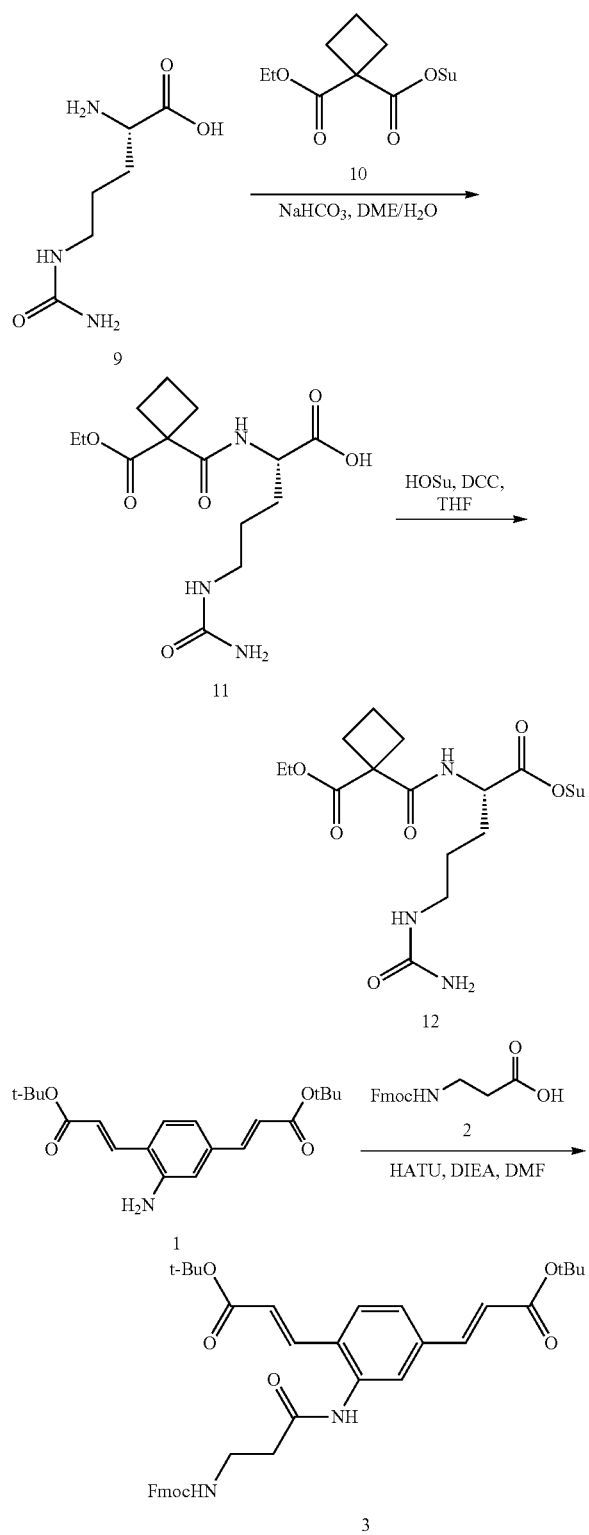

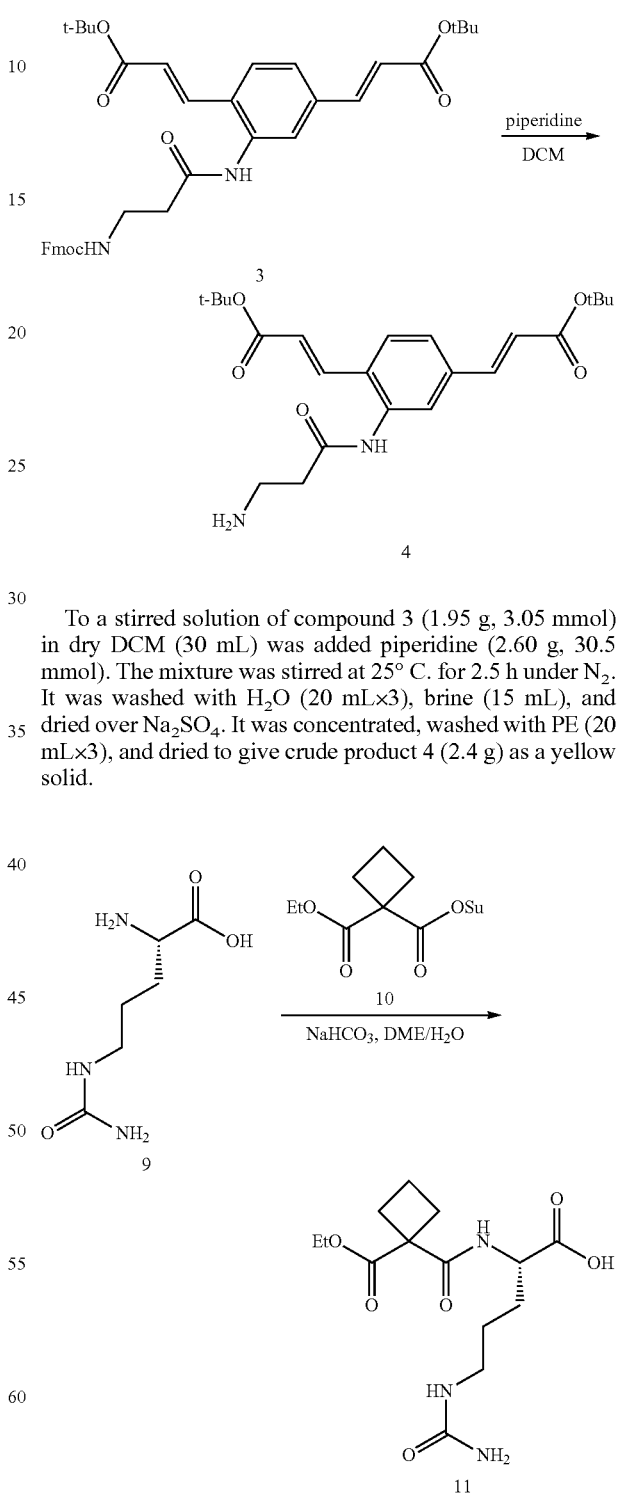

To a stirred solution of 2 (1.35 g, 4.34 mmol) in dry DMF (20 mL) was added HATU (2.20 g, 5.79 mmol), DIEA (1.12 g, 8.68 mmol). After the mixture was stirred at 25° C. for 10 min, compound 1 (1.0 g, 2.89 mmol) was added. The reaction mixture was stirred at 25° C. for 15 h under $N_2$.

Water (20 mL) was added and it was extracted with EtOAc (30 mL×3). The combined the organic phase was washed with brine, dried over $Na_2SO_4$, and concentrated. It was purified by flash column (PE:EtOAc=1:1) to give crude product 3 (2.25 g) as yellow solid. LCMS: (5-95 AB, 1.5 min), 1.075 min, $[M-114]^+=527.0$.

To a stirred solution of compound 3 (1.95 g, 3.05 mmol) in dry DCM (30 mL) was added piperidine (2.60 g, 30.5 mmol). The mixture was stirred at 25° C. for 2.5 h under $N_2$. It was washed with $H_2O$ (20 mL×3), brine (15 mL), and dried over $Na_2SO_4$. It was concentrated, washed with PE (20 mL×3), and dried to give crude product 4 (2.4 g) as a yellow solid.

To a solution of compound 9 (3.0 g, 17.1 mmol) in DME/$H_2O$ (40 mL/20 mL) was added NaHCO$_3$ (2.88 g, 34.3 mmol). After the mixture was stirred at 25° C. for 15 min, compound 10 (5.54 g, 20.6 mmol) was added. The mixture was stirred at 25° C. for 16 h under N₂. Solvents was removed and H₂O (5 mL) was added. It was extracted with EtOAc (30 mL×3). The pH of water phase was adjusted to 3 with HCl solution, and it was extracted with EtOAc (120 mL×3). The combined organic phase was dried over Na₂SO₄, and concentrated to give crude product 11 as colorless oil.

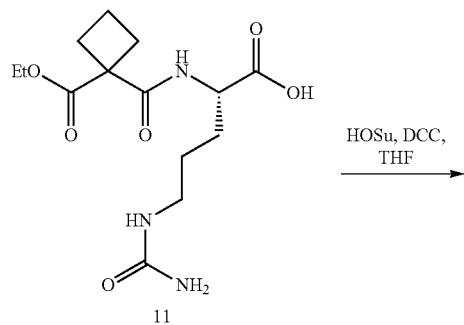

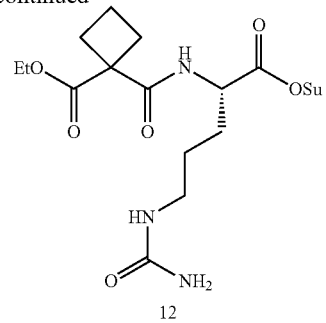

To a solution of compound 11 (5.64 g, 17.1 mmol) in dry THF (120 mL) was added HOSu (2.07 g, 17.98 mmol) and DCC (3.70 g, 17.98 mmol). The mixture was stirred at 25° C. for 15 h under N₂. It was filtered and concentrated. The residue was washed the with PE (30 mL×3), dried and concenrated to give crude product 12 (8.30 g) as white solid.

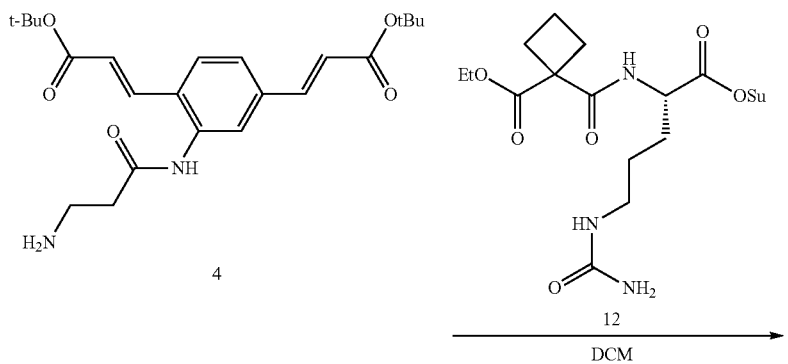

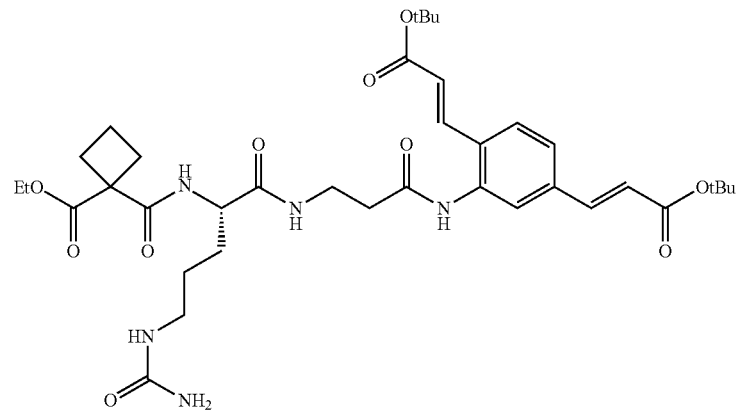

To a solution of compound 4 (1.65 g, 3.96 mmol) in dry DMF (20 mL) was added compound 12 (2.03 g, 4.75 mmol). The mixture was stirred at 25° C. for 15 h under N$_2$. Water (30 mL) was added and it was extracted with EtOAc (30 mL×3). The combined organic phase was washed with brine (30 mL), and dried over Na$_2$SO$_4$. It was concentrated to give crude product, which was washed the with PE (30 mL×4) and MTBE/PE (15 mL/45 mL×2), and dried to give product 5 (0.96 g, yield: 33%) as light yellow solid.

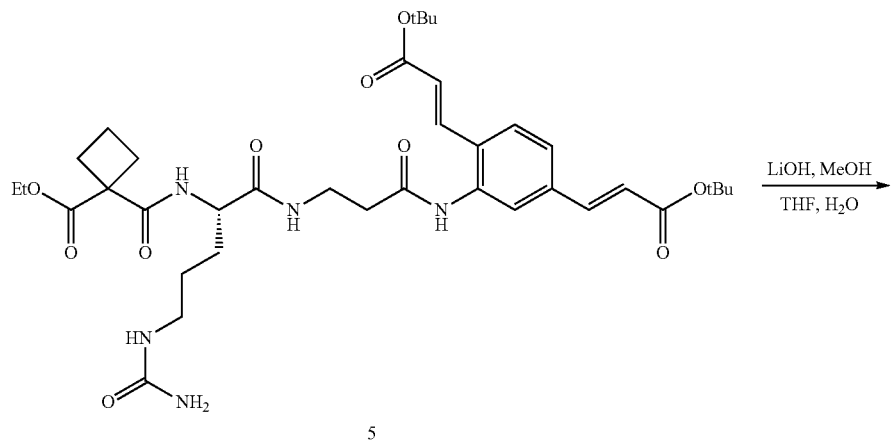

5

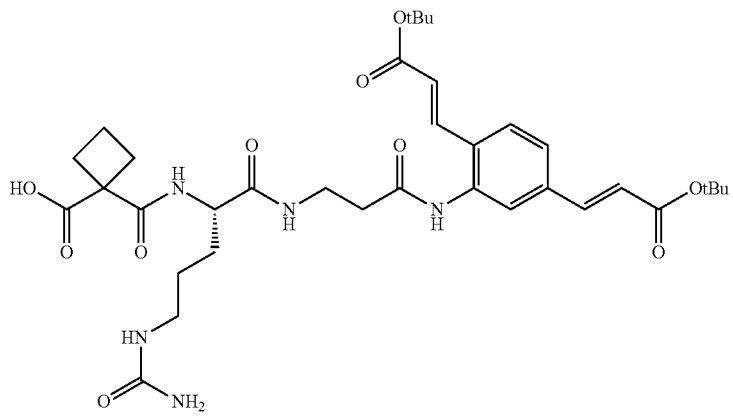

6

To a solution of compound 5 (0.96 g, 1.32 mmol) in MeOH (4 mL), THF (8 mL) and H$_2$O (8 mL) was added LiOH—H$_2$O (111 mg, 2.64 mmol). The mixture was stirred at 25° C. for 30 min under N$_2$. Organic solvents was removed under reduced pressure and H$_2$O (10 mL) was added. HCl solution was added to adjust pH to 3-4. It was extracted with EtOAc (50 mL×4), dried over Na$_2$SO$_4$, and concentrated to give crude product. The crude product was washed with PE (30 mL) and MTBE (10 mL×3), and dried to give product 6 (620 mg, yield: 67%) as white solid.

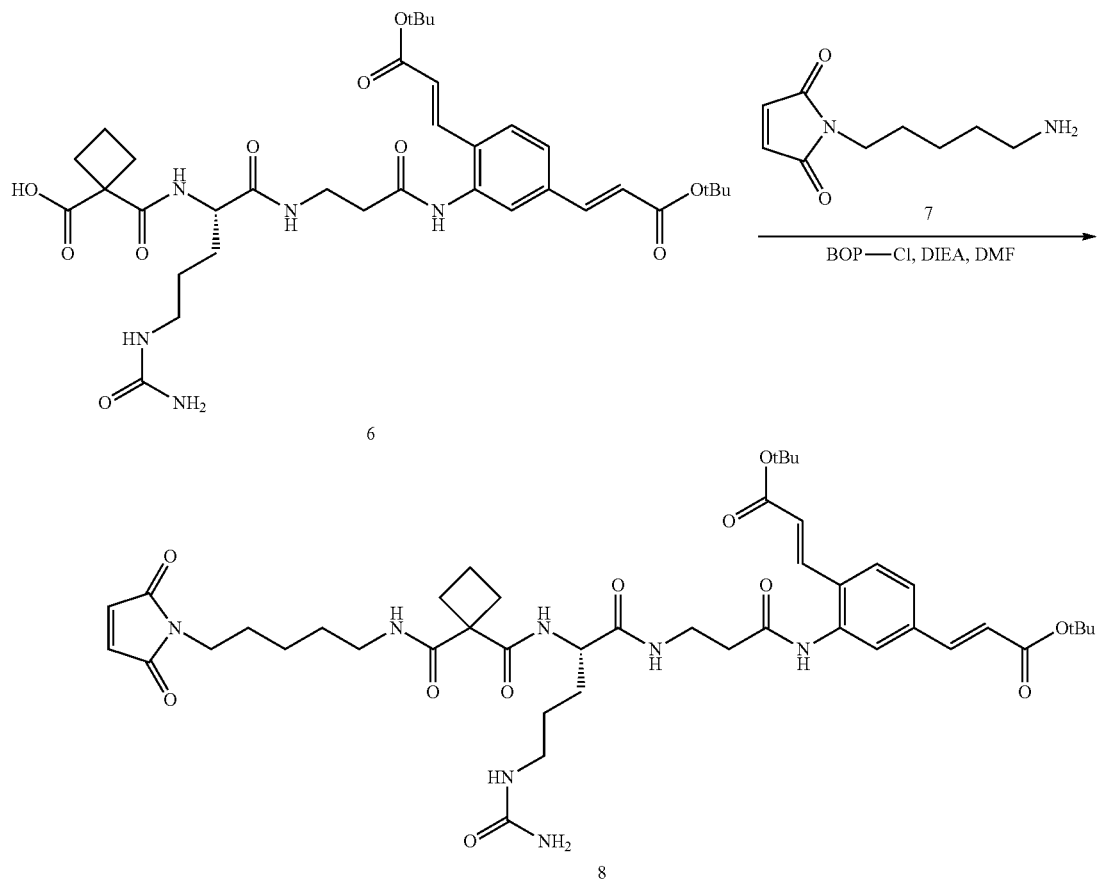

To a solution of compound 6 (620 mg, 0.89 mmol) in dry DMF (10 mL) was added DIEA (573 mg, 4.43 mmol) and Bop-Cl (248 mg, 0.97 mmol) at 0° C. Compound 7 (177.59 mg, 0.97 mmol) was added. After the mixture was stirred at 0° C. for 30 min under N₂, H₂O (20 mL) was added and it was extracted with EtOAc (30 mL×3). The combined organic phase was washed with brine (30 mL), dried over Na₂SO₄, and concentrated to give crude product. It was washed with MTBE (10 mL×2) and PE (50 mL×3), and dried to give product 8 (690 mg, yield: 90%) as white solid.

LCMS: (5-95 AB, 1.5 min), 0.875 min, MS=864.2 [M+1];

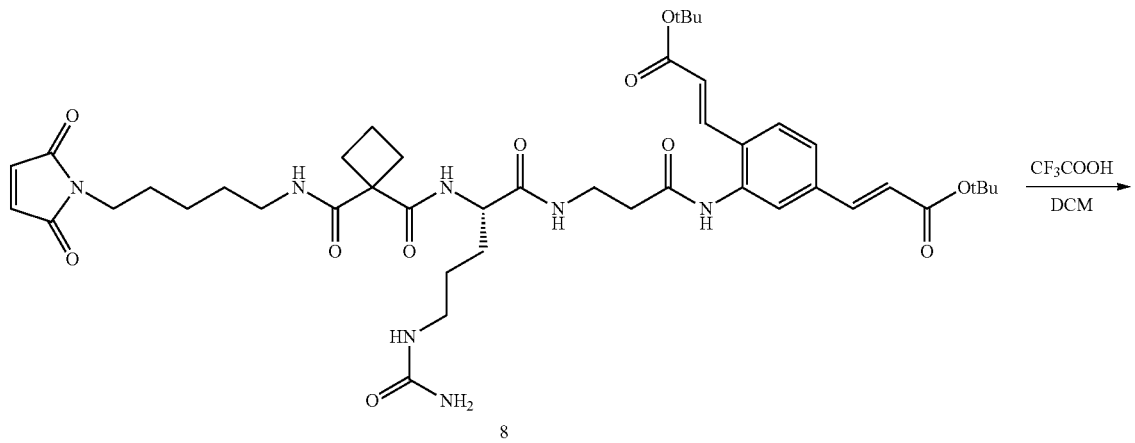

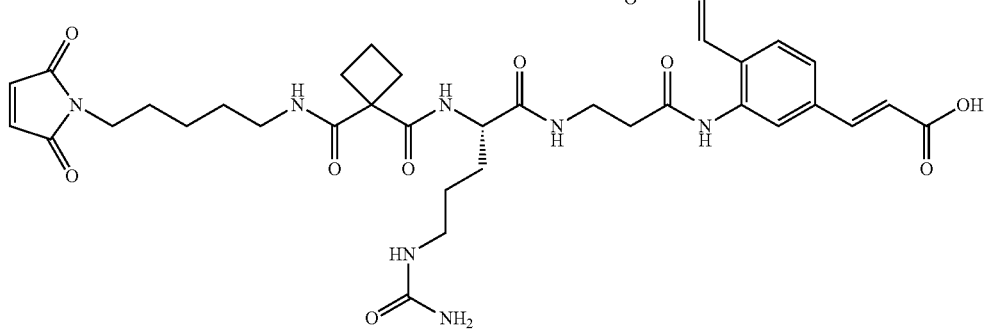

To a stirred solution of compound 8 (300 mg, 0.347 mmol) in dry DCM (4.0 mL) was added dropwise TFA (2.0 mL). After the mixture was stirred at 25° C. for 30 min under $N_2$, solvent was removed. The residue was dissolved in DMF and purified by prep-HPLC (HCOOH) to give product (2E,2'E)-3,3'-(2-(3-((S)-2-(1-(5-(2,5-dioxo-2,5-dihydro-1H-pyrrol-1-yl)pentylcarbamoyl)cyclobutanecarboxamido)-5-ureidopentanamido)propanamido)-1,4-phenylene)diacrylic acid
(81.4 mg, yield: 31%) as light yellow powder. $^1$H NMR (400 MHz, DMSO-d6) δ 9.93 (s, 2H), 6.13 (s, 1H), 7.82-7.46 (m, 8H), 6.98 (s, 2H), 6.55-6.51 (d, J=16.0 Hz, 2H), 5.98 (s, 1H), 5.41 (s, 2H), 4.22 (s, 1H), 3.03-2.90 (m, 6H), 2.67-2.50 (m, 4H), 2.36 (s, 4H), 1.69 (s, 3H), 1.46-1.33 (m, 7H), 1.23-1.16 (d, J=28 Hz, 2H).

Preparation of CBI-CBI LD5

4-((S)-2-(1-(5-(2,5-dioxo-2,5-dihydro-1H-pyrrol-1-yl)pentylcarbamoyl)cyclobutanecarboxamido)-5-ureidopentanamido)benzyl 2,5-bis((E)-3-((S)-1-(chloromethyl)-5-(phosphonooxy)-1H-benzo[e]indol-3(2H)-yl)-3-oxoprop-1-enyl)phenylcarbamate

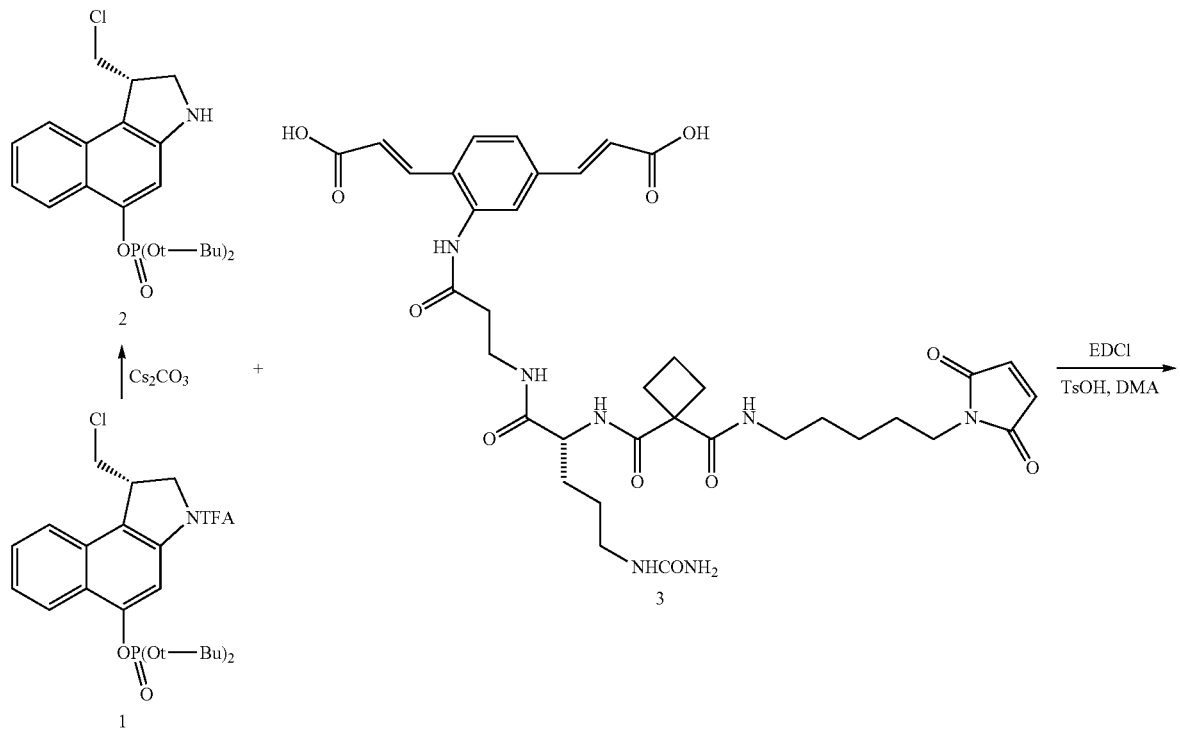

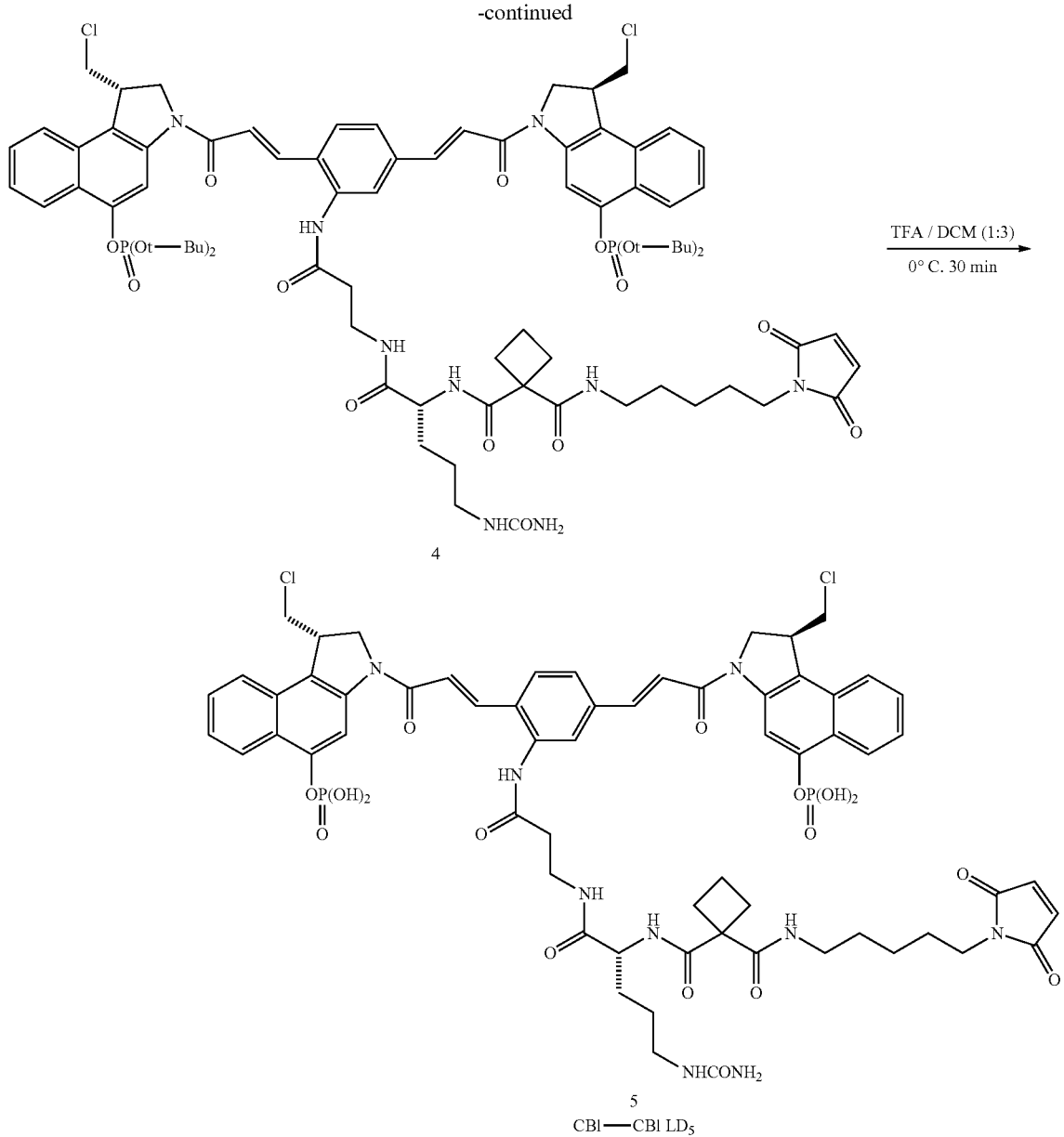

5
CBI—CBI LD$_5$

To a solution of 1 (230 mg, 0.44 mmol) in MeOH (2 mL) cooled in an ice bath was added Cs$_2$CO$_3$ (287 mg, 0.88 mmol) and several drops of water. The mixture was stirred in the ice bath for 1 h and then redistributed between ethyl acetate and water. The aqueous phase was extracted with ethyl acetate three times. The combined organic extracts were washed with water and brine, dried over anhydrous Na$_2$SO$_4$, filtered through celite, and the solvent was removed. The resultant residue was dissolved in ethyl acetate and filtered through a pad of Florisil to give crude 2 as an off-white gum (188 mg, 100%) which was used directly without further purification.

4

To 180 mg (0.42 mmol) of 2 (freshly made by the procedure mentioned above) was added (2E,2'E)-3,3'-(2-(3-((S)-2-(1-(5-(2,5-dioxo-2,5-dihydro-1H-pyrrol-1-yl)pentyl-carbamoyl)cyclobutanecarboxamido)-5-ureidopentanamido)propanamido)-1,4-phenylene)diacrylic acid 3 (100 mg, 0.12 mmol), EDCI.HCl (185 mg, 0.96 mmol), toluene-sulfonic acid (2.1 mg, 0.012 mmol) and DMA (0.5 mL). After the mixture was stirred overnight, most of the DMA was removed under vacuum and the residue was redistributed between ethyl acetate and aq. NaHCO$_3$. The aqueous phase was extracted with ethyl acetate three times. The combined organic extracts were washed with water followed by brine, dried over anhydrous Na$_2$SO$_4$, and filtered through a pad of Celite. The solvent was removed and the resultant residue was dissolved in the minimum DCM and precipitated by adding heptane to give crude product (207 mg), which was further purified by preparative HPLC [Column: Synergi-Max RP 4μ, 250×21.20 mm; Mobile phase: A/B=from 20% to 1% (A: ammonium formate pH 3.45, B: 90% acetonitrile in water); flow rate 12 mL/min] to give 4 (65 mg, 33%) as a yellow solid. $^1$H NMR (CDCl$_3$) δ 9.67 (br s, 1H), 8.67 (br s, 2H), 8.18-7.98 (m, 4H), 7.90-7.72 (m, 3H), 7.66-7.58 (m, 6H), 7.50-7.28 (m, 8H), 6.84-6.62 (m, 4H), 6.66 (s, 2H, maleimide), 6.00 (br s, 1H), 5.23-5.13 (m, 2H), 4.80-4.70 (m, 1H), 4.40-3.85 (m, 6H), 3.50-3.40 (m, 6H), 3.20-3.14 (m, 2H), 2.90-2.75 (m, 2H), 2.60-2.45 (m, 4H), 1.92-1.80 (m, 2H), 1.62, 1.60, 1.57, 1.56 (4s, 36H), 1.55-1.40 (m, 6H), 1.30-1.20 (m, 3H). $^{31}$P NMR (CDCl$_3$) δ −15.44 (s), 15.82 (s). HRMS (ESI) found m/z 1666.6051 (M+Na). C$_{83}$H$_{101}$Cl$_2$N$_9$NaO$_{18}$P$_2$ requires 1666.6009.

5

To a solution of 4 (25 mg, 0.015 mmol) in DCM (0.6 mL) cooled in an ice bath was added TFA (0.2 mL, 2.61 mmol). The mixture was stirred in an ice bath for 0.5 h. All the volatile components were pumped off at 0° C. and the resultant residue was triturated with ethyl acetate, then washed with THF and petroleum ether to give 5 (CBI-CBI LD5) as a yellow solid (19 mg, 88%). $^1$H NMR (DMSO) δ 10.33 (br s, 1H), 9.63 (s, 1H), 8.70 (s, 1H), 8.95 (s, 1H), 8.14-8.11 (m, 4H), 7.96-7.90 (m, 4H), 7.81-7.69 (m, 6H), 7.64-7.54 (m, 2H), 7.50-7.39 (m, 4H), 7.33-7.26 (m, 2H), 6.97 (s, 2H, maleimide), 6.13 (br s, 2H), 5.14 (s, 2H), 4.58 (s, 4H), 4.40-4.30 (m, 4H), 4.08-3.95 (m, 4H), 3.29 (t, J=6.9 Hz, 2H), 2.99-2.94 (m, 4H), 2.39-2.33 (m, 2H), 1.71-1.67 (m, 4H), 1.40-1.35 (m, 6H), 1.12-1.10 (m, 3H). $^{31}$P NMR (DMSO) δ −5.91 (s). HRMS (ESI) found m/z 1442.3438 (M+Na). C$_{67}$H$_{69}$Cl$_2$N$_9$NaO$_{18}$P$_2$ requires 1442.3505.

CBI-CBI LD6

4-((S)-2-(1-(5-(2,5-dioxo-2,5-dihydro-1H-pyrrol-1-yl)pentylcarbamoyl)cyclobutanecarboxamido)-5-ureidopentanamido)benzyl 2,5-bis((E)-3-((S)-1-(chloromethyl)-5-(phosphonooxy)-1H-benzo[e]indol-3(2H)-yl)-3-oxoprop-1-enyl)phenylcarbamate Step A: (S)—N-(5-(2,5-dioxo-2,5-dihydro-1H-pyrrol-1-yl)pentyl)-N-(1-(4-(hydroxymethyl)phenylamino)-1-oxo-5-ureidopentan-2-yl)cyclobutane-1,1-dicarboxamide Scheme

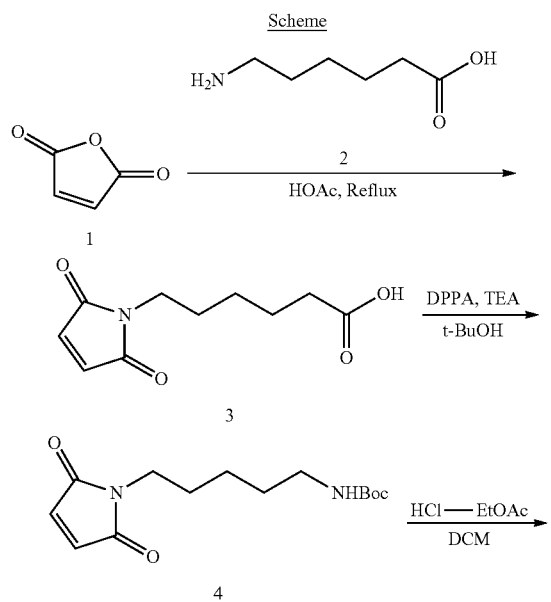

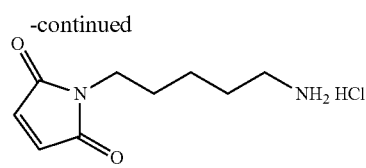

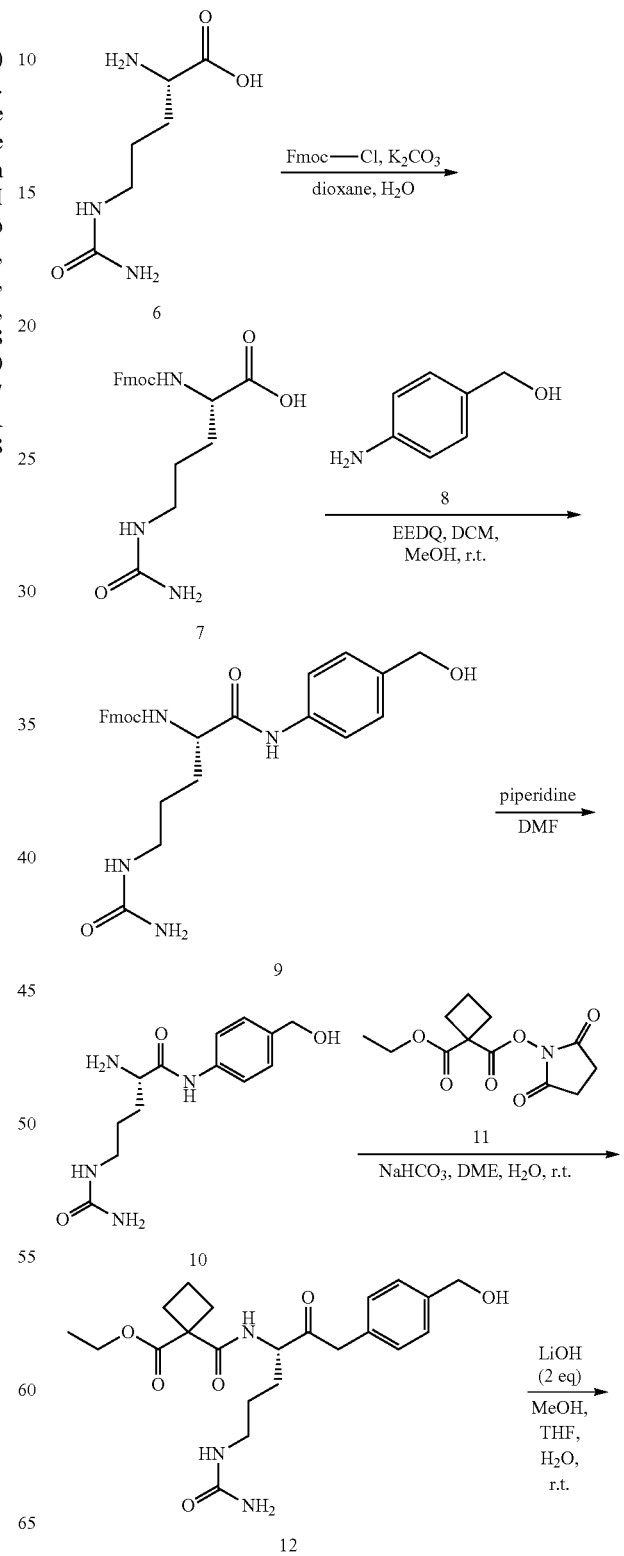

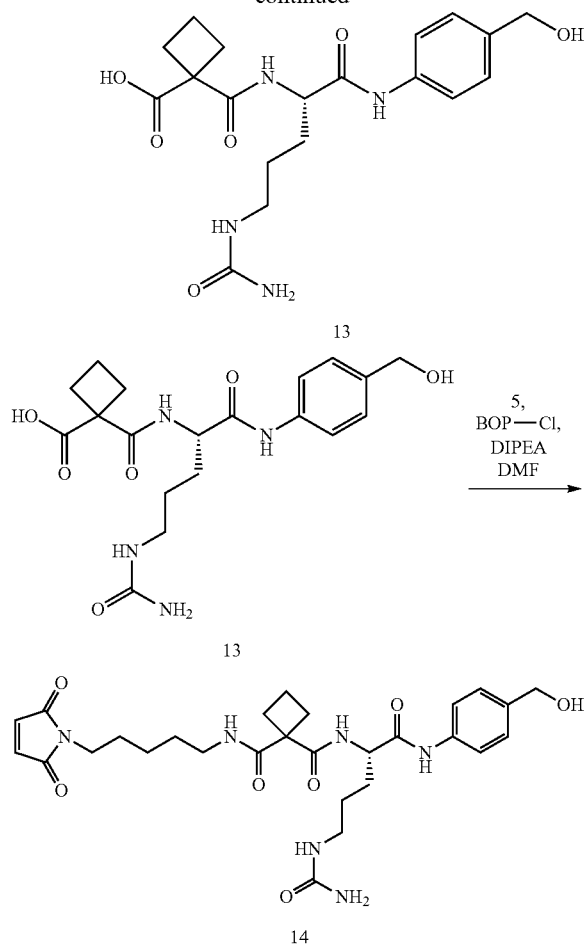

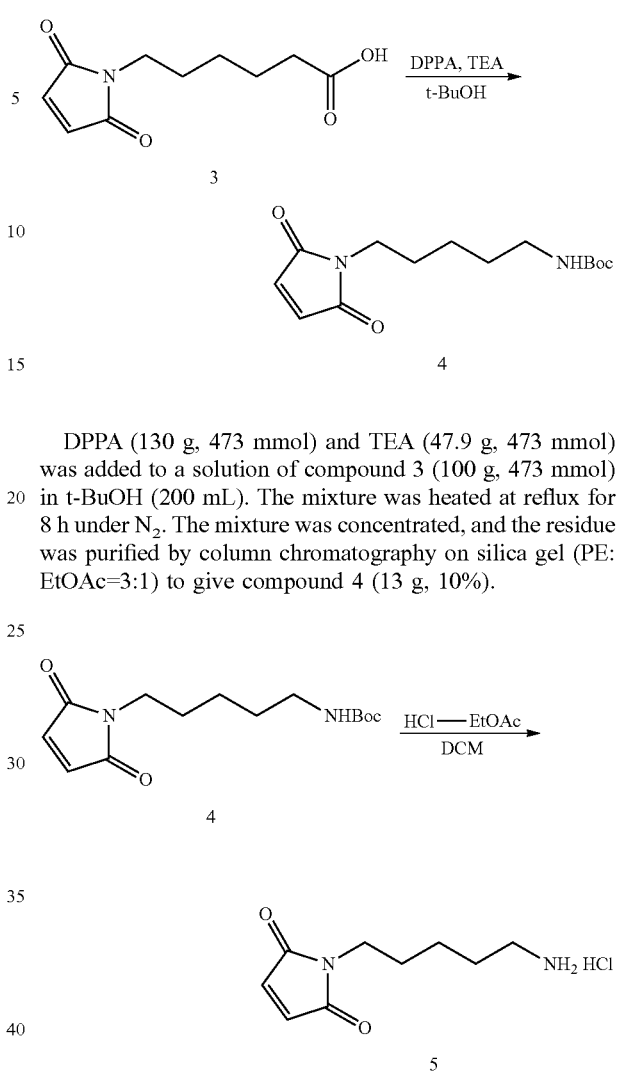

DPPA (130 g, 473 mmol) and TEA (47.9 g, 473 mmol) was added to a solution of compound 3 (100 g, 473 mmol) in t-BuOH (200 mL). The mixture was heated at reflux for 8 h under $N_2$. The mixture was concentrated, and the residue was purified by column chromatography on silica gel (PE: EtOAc=3:1) to give compound 4 (13 g, 10%).

To a solution of compound 4 (28 g, 992 mmol) in anhydrous EtOAc (30 mL) was added HCl/EtOAc (50 mL) dropwise. After the mixture was stirred at r.t. for 5 h, it was filtered and the solid was dried to give compound 5 (16 g, 73.7%).

$^1$H NMR (400 MHz, DMSO-$d_6$): δ 8.02 (s, 2H), 6.99 (s, 2H), 3.37-3.34 (m, 2H), 2.71-2.64 (m, 2H), 1.56-1.43 (m, 4H), 1.23-1.20 (m, 2H).

Procedure

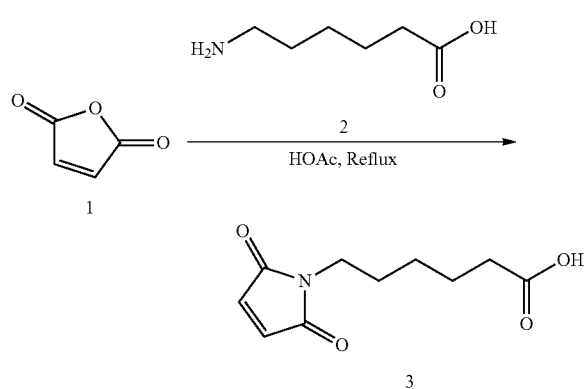

Compound 1 (150 g, 1.53 mol) was added to a stirred solution of Compound 2 (201 g, 1.53 mol) in HOAc (1000 mL). After the mixture was stirred at r.t. for 2 h, it was heated at reflux for 8 h. The organic solvents were removed under reduced pressure and the residue was extracted with EtOAc (500 mL×3), washed with $H_2O$. The combined organic layers was dried over $Na_2SO_4$ and concentrated to give the crude product. It was washed with petroleum ether to give compound 3 as white solid (250 g, 77.4%).

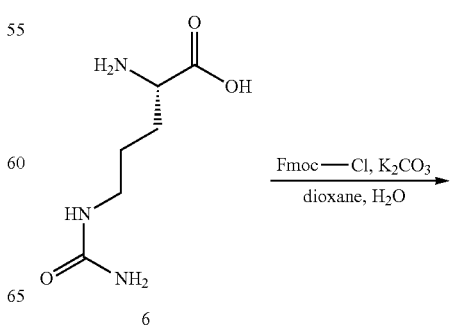

-continued

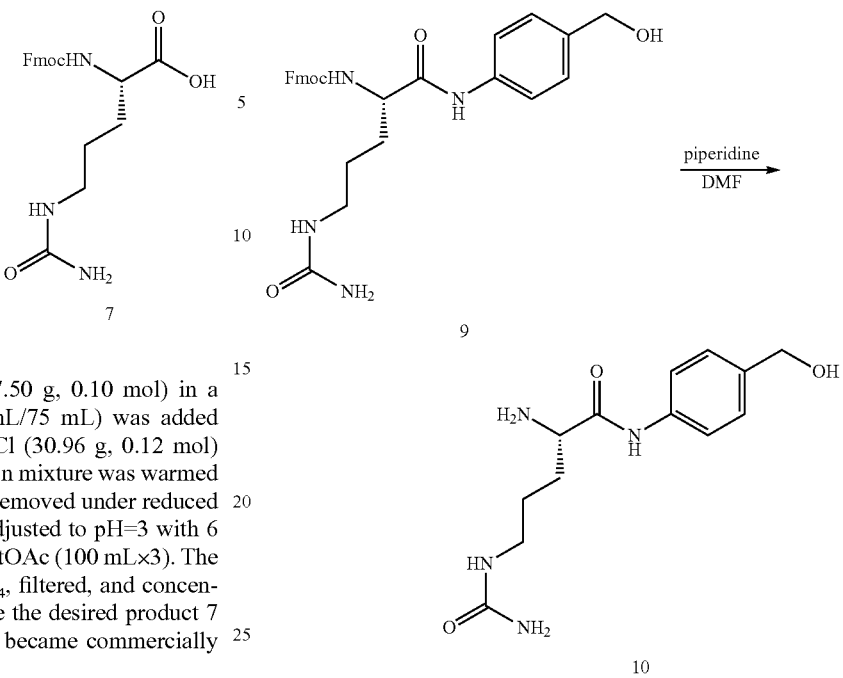

To a mixture of compound 6 (17.50 g, 0.10 mol) in a mixture of dioxane and H$_2$O (50 mL/75 mL) was added K$_2$CO$_3$ (34.55 g, 0.25 mol). Fmoc-Cl (30.96 g, 0.12 mol) was added slowly at 0° C. The reaction mixture was warmed to r.t. over 2 h. Organic solvent was removed under reduced pressure, and the water slurry was adjusted to pH=3 with 6 M HCl solution, and extracted with EtOAc (100 mL×3). The organic layer was dried over Na$_2$SO$_4$, filtered, and concentrated under reduced pressure to give the desired product 7 (38.0 g, 95.6%). (Compound 7 later became commercially available.)

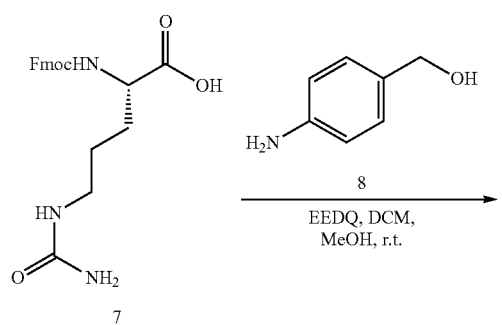

To a stirred solution of compound 9 (4.2 g, 8.3 mmol) in dry DMF (20 ml) was added piperidine (1.65 mL, 17 mmol, 2 eq) dropwise at r.t. The mixture was stirred at r.t. for 30 min, and solid precipitate formed. Dry DCM (50 mL) was added, and the mixture became transparent immediately. The mixture was stirred at r.t. for another 30 min, and LCMS showed compound 9 was consumed. It was concentrated to dryness under reduced pressure (make sure no piperidine remained), and the residue was partitioned between EtOAc and H$_2$O (50 mL/20 mL). Aqueous phase was washed with EtOAc (50 mL×2) and concentrated to give 10 as an oily residual (2.2 g, 94%) (contained small amount of DMF).

To a solution of compound 7 (4 g, 10 mmol) in a mixture of DCM and MeOH (100 mL/50 mL) were added 4-aminophenyl-methanol (8) (1.6 g, 13 mmol, 1.3 eq) and EEDQ (3.2 g, 13 mmol, 1.3 eq). After the mixture was stirred at r.t. for 16 h under N$_2$, it was concentrated to give a brown solid. MTBE (200 mL) was added and it was stirred at 15° C. for 2 h. The solid was collected by filtration, washed with MTBE (50 mL×2) to give the crude product 9 as an orange solid (4.2 g, 84%).

LCMS (ESI): m/z 503.0 [M+1].

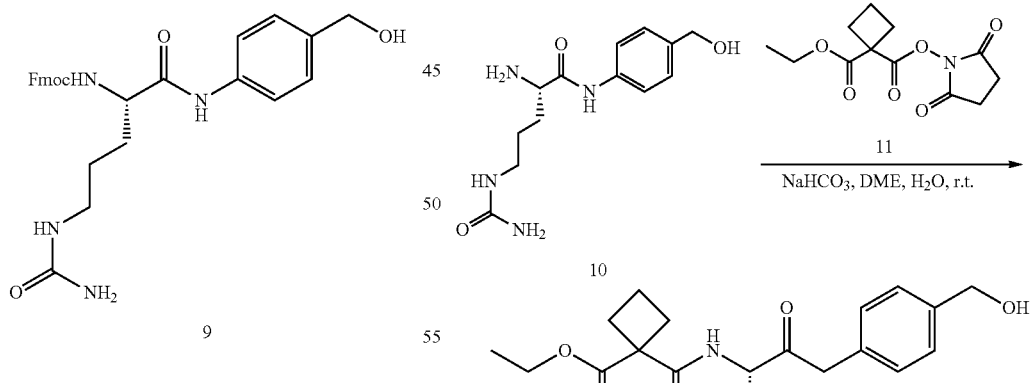

To a solution of compound 11 (8 g, 29.7 mmol) in DME (50 mL) was added a solution of compound 10 (6.0 g, 21.4 mmol) and NaHCO₃ (7.48 g, 89.0 mmol) in water (30 mL). After the mixture was stirred at r.t. for 16 h, it was concentrated to dryness under reduced pressure and the residue was purified by column chromatography (DCM:MeOH=10:1) to give crude compound 12 as white solid (6.4 g, 68.7%).

LCMS (ESI): m/z 435.0 [M+1].

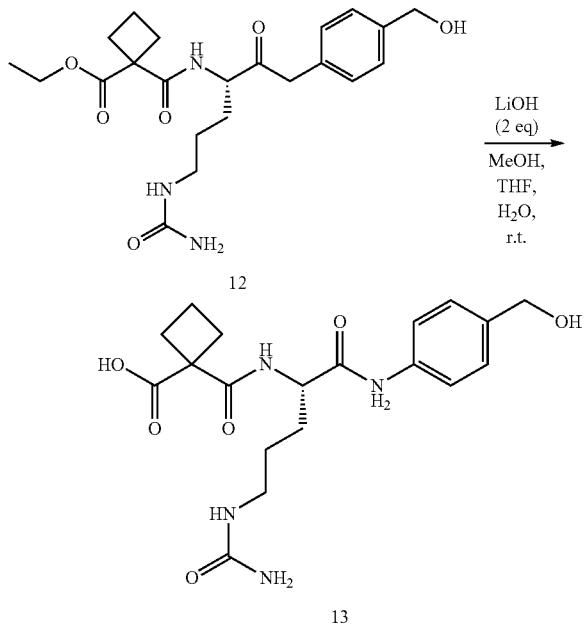

To a stirred solution of compound 12 (6.4 g, 14.7 mmol) in a mixture of THF and MeOH (20 mL/10 mL) was added a solution of LiOH*H₂O (1.2 g, 28.6 mmol) in H₂O (20 mL) at r.t. After the reaction mixture was stirred at r.t. for 16 h, solvent was removed under reduced pressure, the residue obtained was purified by prep-HPLC to give compound 13 (3.5 g, yield: 58.5%).

LCMS (ESI): m/z 406.9 [M+1].

¹H NMR (400 MHz, Methanol-d₄) δ 8.86 (d, J=8.4 Hz, 2H), 8.51 (d, J=8.4 Hz, 2H), 5.88-5.85 (m, 1H), 5.78 (s, 2H), 4.54-4.49 (m, 3H), 4.38-4.32 (m, 1H), 3.86-3.75 (m, 1H), 3.84-3.80 (m, 2H), 3.28-3.21 (m, 1H), 3.30-3.24 (m, 1H), 3.00-2.80 (m, 1H), 2.37-2.28 (m, 2H).

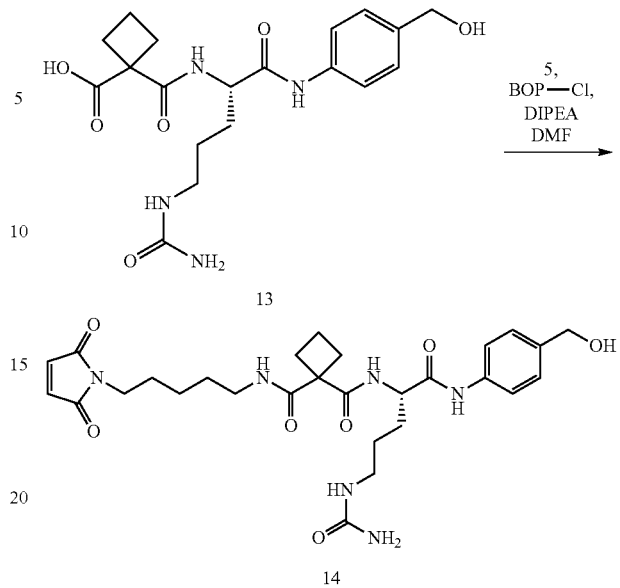

DIPEA (1.59 g, 12.3 mmol) and BOP—Cl (692 mg, 2.71 mmol) was added to a solution of compound 13 (1.0 g, 2.46 mmol) in DMF (10 mL) at 0° C., followed by compound 5 (592 mg, 2.71 mmol). The mixture was stirred at 0° C. for 0.5 h. The reaction mixture was quenched with a citric acid solution (10 mL), extracted with DCM/MeOH (10:1). The organic layer was dried and concentrated, and the residue was purified by column chromatography on silica gel (DCM:MeOH=10:1) to give compound 14 (1.0 g, 71%).

¹H NMR (400 MHz, DMSO-d₆): δ 10.00 (s, 1H), 7.82-7.77 (m, 2H), 7.53 (d, J=8.4 Hz, 2H), 7.19 (d, J=8.4 Hz, 2H), 6.96 (s, 2H), 5.95 (t, J=6.4 Hz, 1H), 5.39 (s, 2H), 5.08 (t, J=5.6 Hz, 1H), 4.40-4.35 (m, 3H), 4.09 (d, J=4.8 Hz, 1H), 3.01 (d, J=3.2 Hz, 2H), 3.05-2.72 (m, 4H), 2.68-2.58 (m, 3H), 2.40-2.36 (m, 4H), 1.72-1.70 (m, 3H), 1.44-1.42 (m, 1H), 1.40-1.23 (m, 6H), 1.21-1.16 (m, 4H).

Step B: Synthesis of (2E,2'E)-3,3'-(2-((4-((S)-2-(1-(5-(2,5-dioxo-2,5-dihydro-1H-pyrrol-1-yl)pentylcarbamoyl)cyclobutanecarboxamido)-5-ureidopentanamido)benzyloxy)carbonylamino)-1,4-phenylene)diacrylic acid Scheme

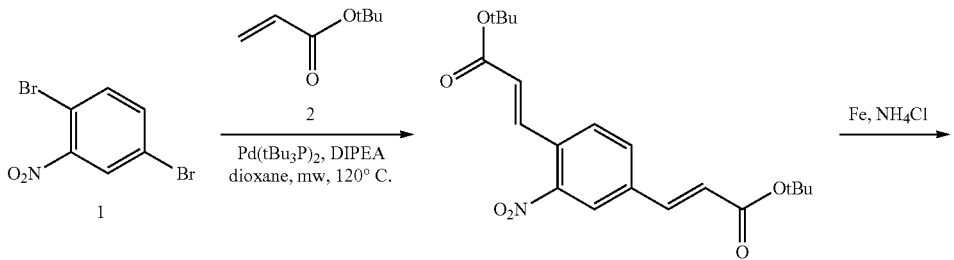

-continued
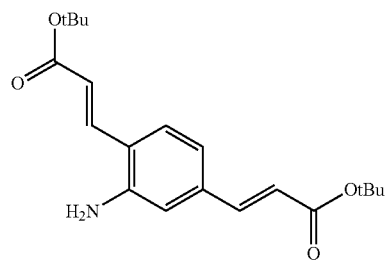
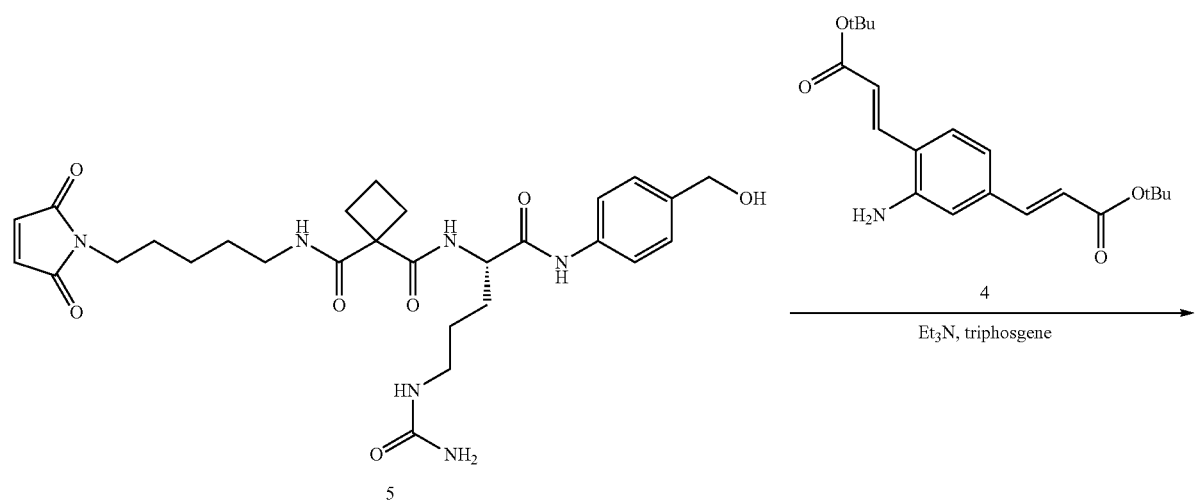
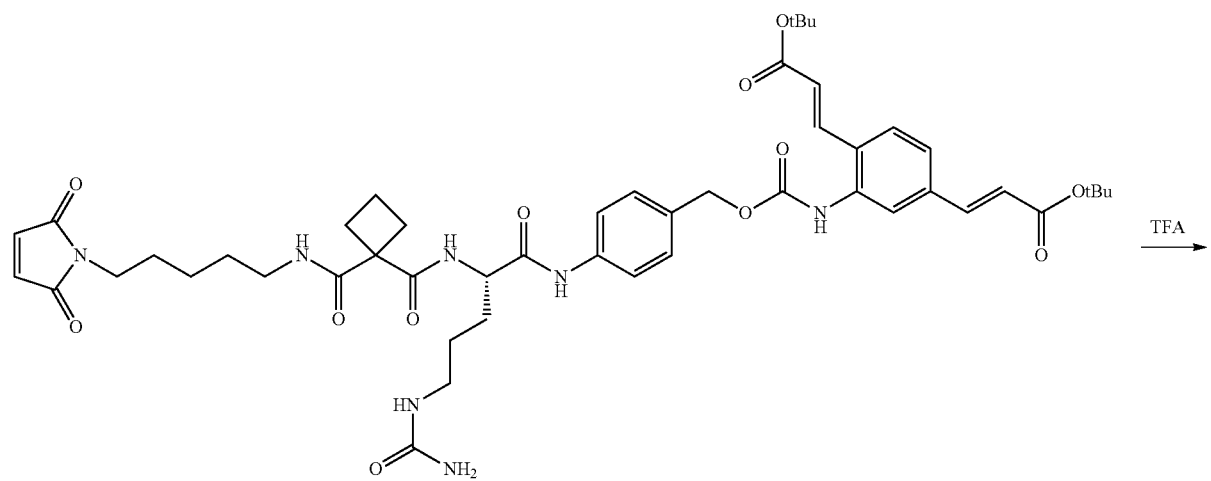

-continued

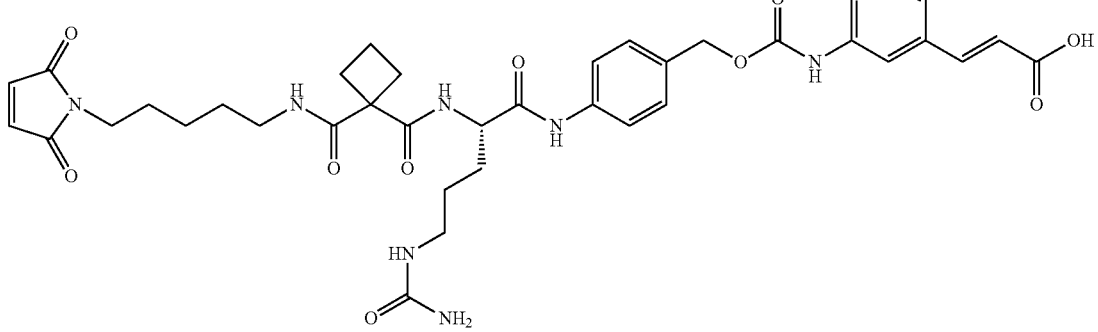

Procedure

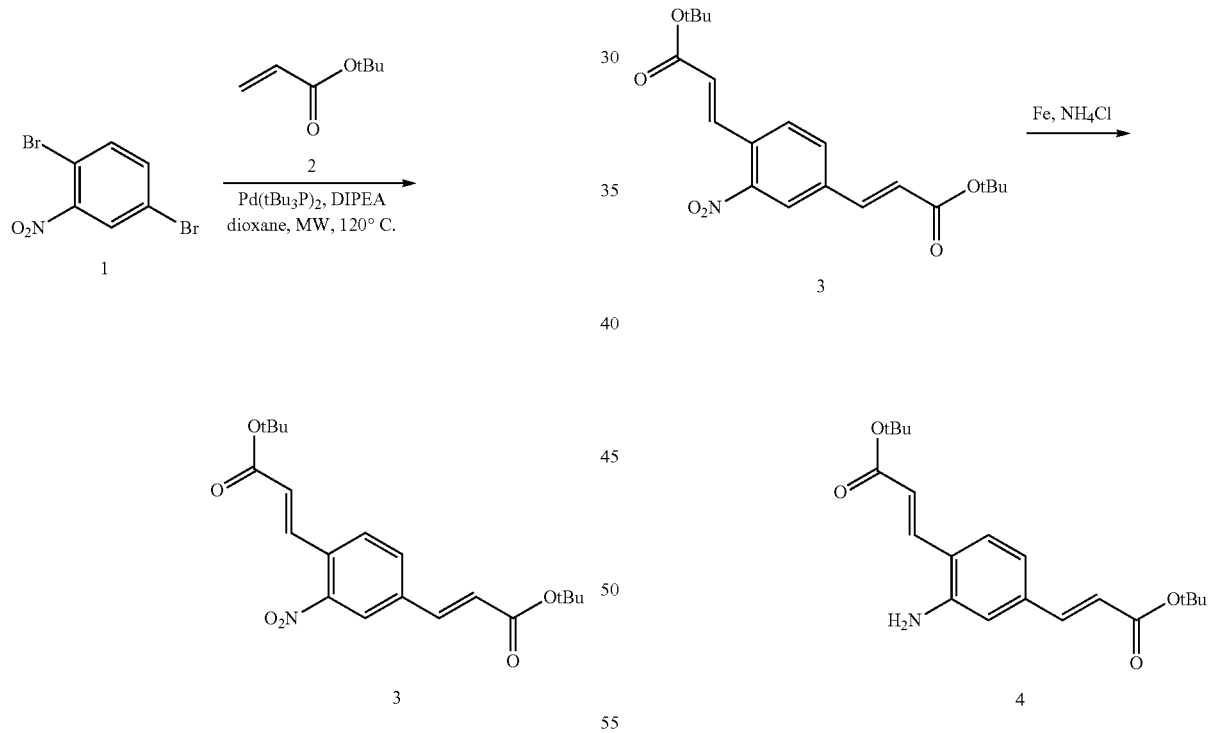

To a solution of compound 1 (1.5 g, 21.4 mmol) in dioxane (4.0 mL) was added compound 2 (2.74 g, 85.6 mmol), DIPEA (3.45 g, 107 mmol) and Pd(t-Bu$_3$P)$_2$ (0.55 g, 4.30 mmol). The reaction was stirred at 120° C. for 2.0 h under microwave irradiation. The reaction was repeated 4 times (total 6.0 g of 1 was used). The combined reaction mixture was concentrated, diluted with water (20 mL) and extracted with EtOAc (100.0 mL×3). The organic layer was combined, dried over Na$_2$SO$_4$. It was concentrated and purified by column (PE:EtOAc=10:1) to give the desired product (3.8 g, 47%).

To a solution of compound 3 (3.8 g, 10.1 mmol) in EtOH/H$_2$O (120.0 mL) was added Fe (2.83 g, 50.7 mmol), and NH$_4$Cl (5.4 g, 101 mmol), and the reaction mixture was stirred at 100° C. for 2.0 h. The reaction mixture was filtered and the filtrate was concentrated and extracted with EtOAc (60.0 mL×3). The organic layer was combined, dried over Na$_2$SO$_4$ and concentrated to give product (2.5 g, 72%).

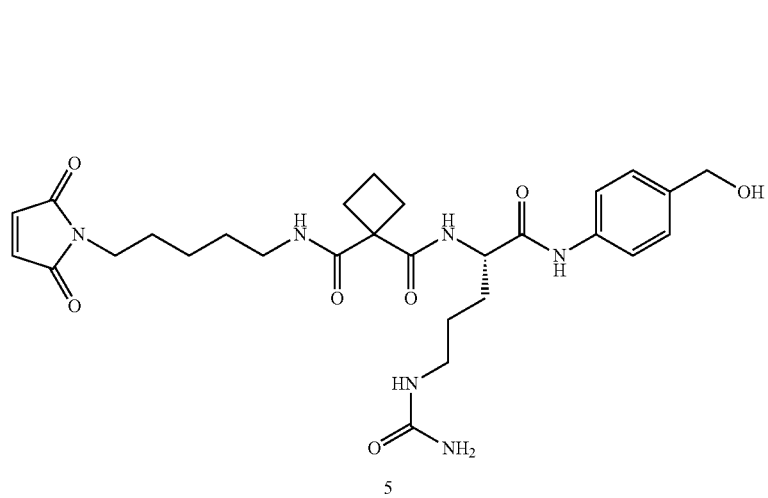

5

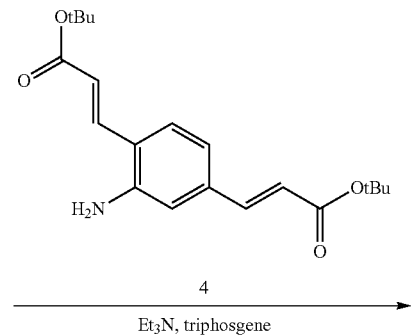

$\xrightarrow[\text{Et}_3\text{N, triphosgene}]{4}$

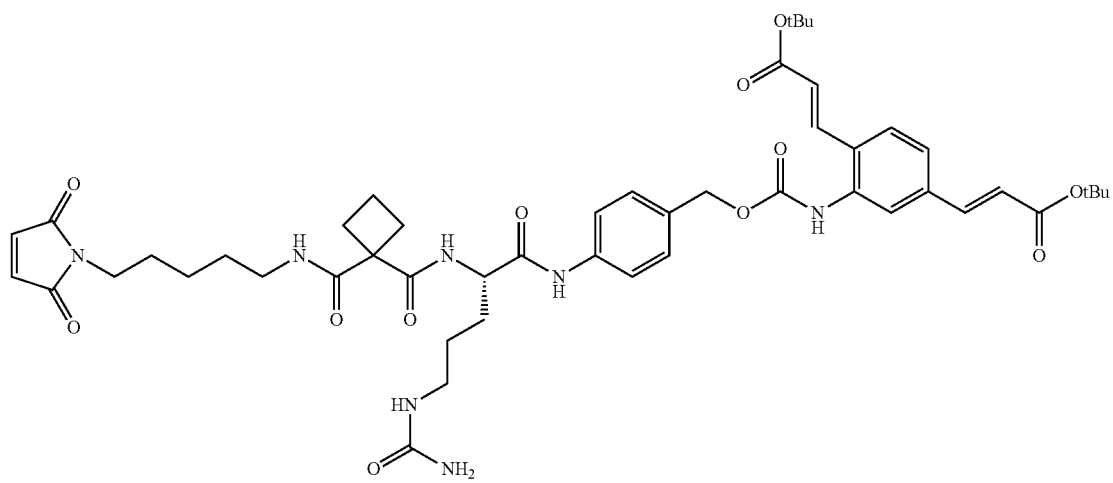

6

To a solution of triphosgene (224 mg, 0.76 mmol) was added a solution of compound 4 (725 mg, 2.1 mmol) and Et$_3$N (530.3 mg, 5.25 mmol) in DCM (5.0 mL) dropwise in ice-bath. The reaction mixture was stirred at 21° C. for 1.0 h until there was no starting material left. The reaction mixture was washed with water (5.0 mL×2), and dried over Na$_2$SO$_4$. It was concentrated and dissolved in DCM (5.0 mL). A solution of the compound 5 (1.0 g, 1.75 mmol) was added and the reaction mixture was stirred at 21° C. for 3.0 h. The reaction was quenched with MeOH (2.0 mL), and purified by column (DCM:MeOH=10:1) to give the desired product (380 mg, 23%).

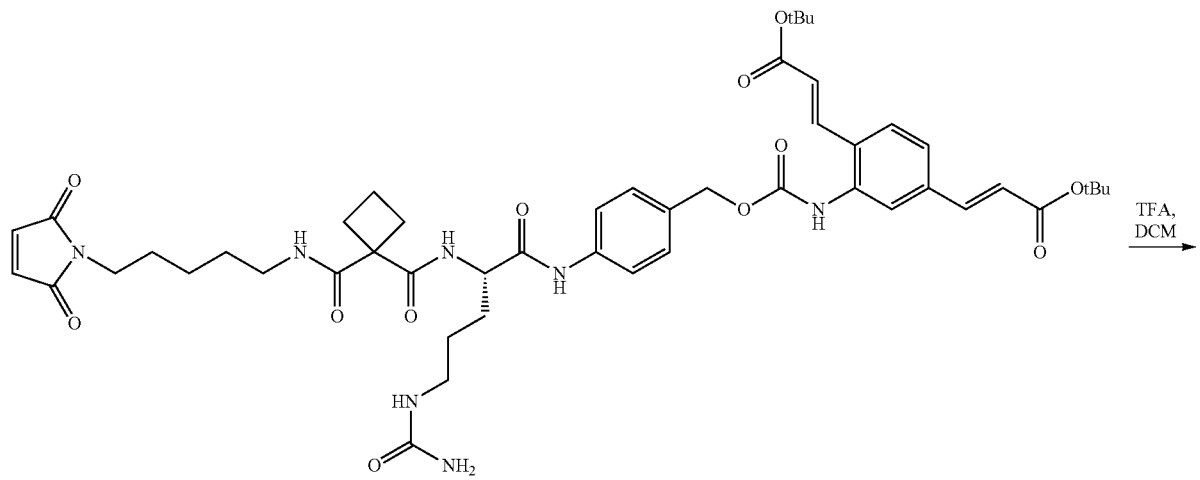

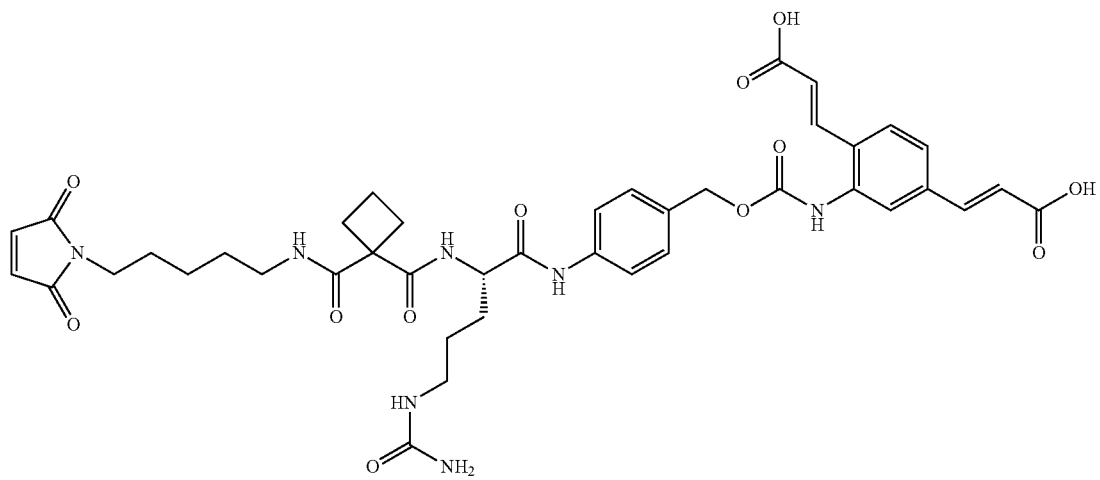 [SMILES: NC(=O)NCCC[C@H](NC(=O)C1(C(=O)NCCCCCN2C(=O)C=CC2=O)CCC1)C(=O)Nc1ccc(COC(=O)Nc2cc(/C=C/C(=O)O)ccc2/C=C/C(=O)O)cc1]

To a solution of compound 6 (300.0 mg, 0.32 mmol) in DCM (10.0 mL) was added TFA (2.0 mL), and the mixture was stirred at 21° C. for 30.0 min. The mixture was adjusted to pH 6 with NH₃.H₂O. The precipitation was collected by filtration to give the product (2E,2'E)-3,3'-(2-((4-((S)-2-(1-(5-(2,5-dioxo-2,5-dihydro-1H-pyrrol-1-yl)pentylcarbamoyl)cyclobutanecarboxamido)-5-ureidopentanamido)benzyloxy)carbonylamino)-1,4-phenylene)diacrylic acid (112.0 mg, yield 42

LCMS (10-80, AB, 2.0 min) RT=0.962 min, [M+1]⁺=830.0;

¹H NMR (400 MHz, DMSO-d₆) δ 12.45 (br, 2H), 10.10 (s, 1H), 9.55 (s, 1H), 7.50-7.81 (m, 8H), 7.34 (m, 2H), 6.95 (s, 2H), 6.47-6.57 (m, 2H), 5.96 (s, 1H), 5.40 (s, 2H), 5.05 (s, 2H), 4.36-4.39 (m, 1H), 2.98-3.06 (m, 6H), 2.35-2.39 (m, 4H), 1.15-1.73 (m, 13H).

Step C
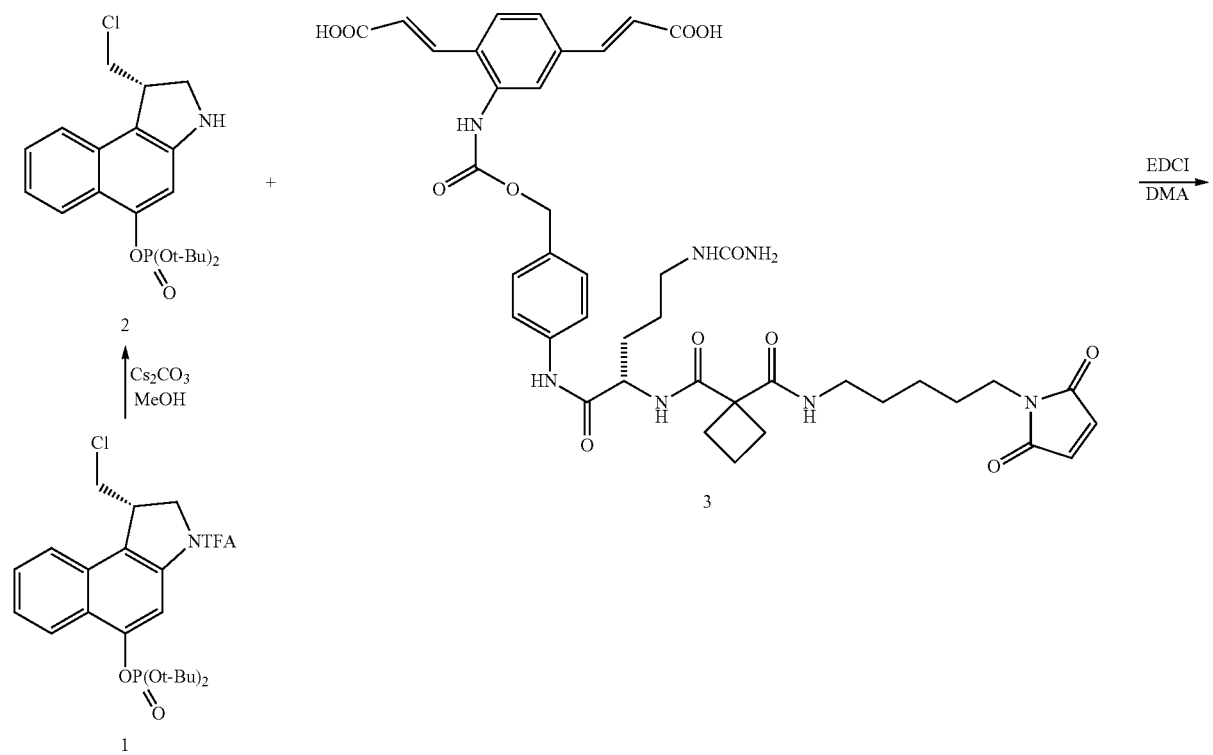
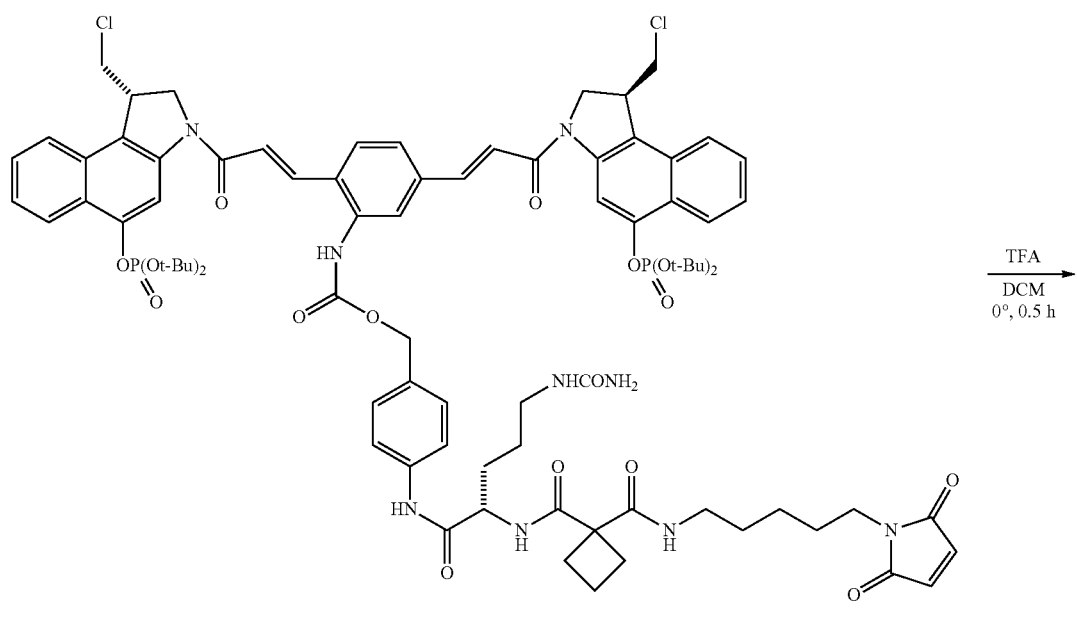

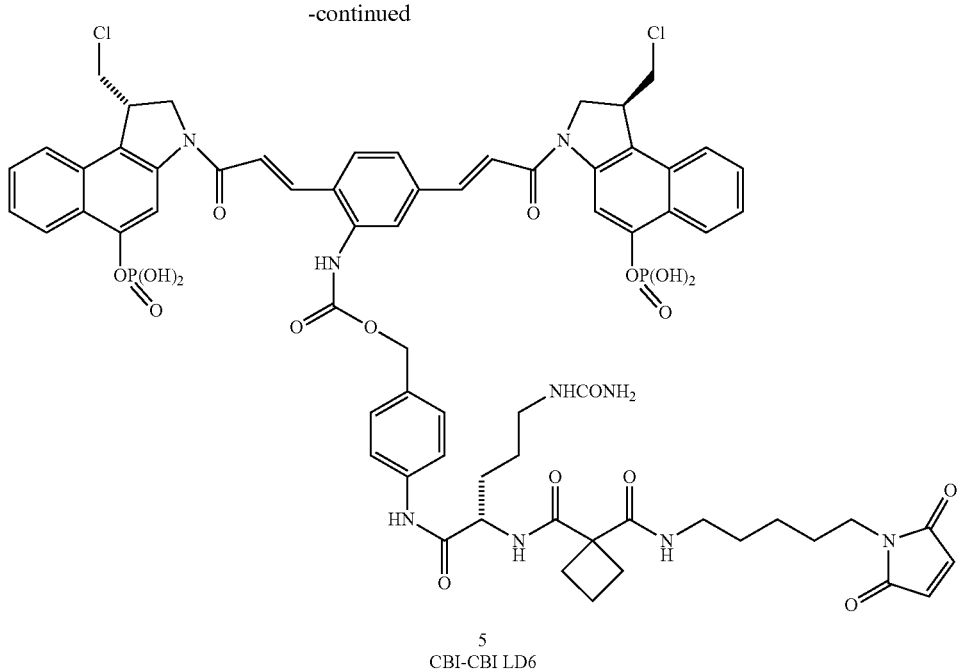

5
CBI-CBI LD6

To 184 mg (0.43 mmol) of 2 (freshly made by the procedure mentioned above) was added 3 (80 mg, 0.11 mmol), EDCI.HCl (165 mg, 0.86 mmol), toluenesulfonic acid (2.0 mg, 0.011 mmol) and DMA (0.5 mL). After the mixture was stirred overnight, most of the DMA was removed under vacuum and the residue was redistributed between ethyl acetate and aq. NaHCO$_3$. The aqueous phase was extracted with ethyl acetate three times. The combined organic extracts were washed with water followed by brine, dried over anhydrous Na$_2$SO$_4$, and filtered through a pad of Celite.

The solvent was removed and the resultant residue was dissolved in the minimum DCM and precipitated by adding heptane to give crude product (195 mg), which was further purified by preparative HPLC [Column: Synergi-Max RP 4μ, 250×21.20 mm; Mobile phase: A/B=from 90% to 2% (A: ammonium formate pH 3.45, B: 90% acetonitrile in water); flow rate 12 mL/min] to give 4 (56 mg, 34%) as a yellow solid. $^1$H NMR (DMSO) δ 10.02 (s, 1H), 8.67 (s, 2H), 8.14-8.06 (m, 4H), 7.97 (d, J=8.4 Hz, 2H), 7.86-7.76 (m, 4H), 7.70 (d, J=15.2 Hz, 1H), 7.63-7.59 (m, 2H), 7.53-7.49 (m, 2H), 7.29-7.23 (m, 2H), 6.96 (s, 2H, maleimide), 5.91 (br s, 1H), 5.36 (br s, 2H), 4.65-4.50 (m, 4H), 4.44-4.37 (m, 2H), 4.28-4.22 (m, 2H), 4.05-3.95 (m, 4H), 3.60 (t, J=6.6 Hz, 1H), 3.07-3.00 (m, 2H), 2.95-2.88 (m, 2H), 2.68-2.58 (m, 2H), 2.42-2.32 (m, 3H), 1.78-1.62 (m, 4H), 1.51, 1.50, 1.49, 1.48 (4s, 36H), 1.49-1.28 (m, 11H). $^{31}$P NMR (CDCl$_3$) δ −15.44 (s), 15.46 (s). HRMS (ESI) found m/z 1588.5827 (M+Na). C$_{78}$H$_{99}$Cl$_2$N$_9$NaO$_{17}$P$_2$ requires 1588.5903.

5

To a solution of 4 (25 mg, 0.015 mmol) in DCM (0.6 mL) cooled in an ice bath was added TFA (0.2 mL, 2.61 mmol). The mixture was stirred in an ice bath for 0.5 h. Ether was added and the resultant precipitate was collected by filtration and washed with ethyl acetate, THF and petroleum ether to give 5 (CBI-CBI LD6) as a brown solid (18 mg, 86%). $^1$H NMR (DMSO) δ 10.01 (br s, 1H), 8.60 (br s, 2H), 8.16-8.09 (m, 4H), 7.96-7.93 (m, 2H), 7.88-7.58 (m, 8H), 7.46 (t, J=7.7 Hz, 2H), 7.30-7.25 (m, 2H), 6.97 (s, 2H, maleimide), 6.10 (br s, 1H), 5.35 (br s, 2H), 4.60-4.18 (m, 6H), 4.05-3.95 (m, 4H), 3.45-3.29 (m, 5H), 3.04-2.87 (m, 4H), 2.68-2.60 (m, 2H), 2.40-2.30 (m, 4H), 1.72-1.57 (m, 4H), 1.43-1.28 (m, 5H), 1.20-1.07 (m, 3H). $^{31}$P NMR (DMSO) δ −5.82 (s). HRMS (ESI) found m/z 1342.3562 (M+H). C$_{62}$H$_{68}$Cl$_2$N$_9$O$_{17}$P$_2$ requires 1342.3580.

Method of Preparing ADCs

Preparation of Cysteine Engineered Antibodies for Conjugation by Reduction and Reoxidation Under certain conditions, the cysteine engineered antibodies may be made reactive for conjugation with linker-drug intermediates of the invention by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Full length, cysteine engineered monoclonal antibodies (ThioMabs) expressed in CHO cells (Gomez et al (2010) Biotechnology and Bioeng. 105(4): 748-760; Gomez et al (2010) Biotechnol. Prog. 26:1438-1445) were reduced, for example with about a 50 fold excess of DTT overnight at room temperature to reduce disulfide bonds which may form between the newly introduced cysteine residues and the cysteine present in the culture media.

Light chain amino acids are numbered according to Kabat (Kabat et al., Sequences of proteins of immunological interest, (1991) 5th Ed., US Dept of Health and Human Service, National Institutes of Health, Bethesda, Md.). Heavy chain amino acids are numbered according to the EU numbering system (Edelman et al (1969) Proc. Natl. Acad. of Sci. 63(1):78-85), except where noted as the Kabat system. Single letter amino acid abbreviations are used.

Full length, cysteine engineered monoclonal antibodies (ThioMabs) expressed in CHO cells bear cysteine adducts (cystines) or glutathionylated on the engineered cysteines due to cell culture conditions. To liberate the reactive thiol groups of the engineered cysteines, the ThioMabs are dissolved in 500 mM sodium borate and 500 mM sodium chloride at about pH 8.0 and reduced with about a 50-100 fold excess of 1 mM TCEP (tris(2-carboxyethyl)phosphine hydrochloride (Getz et al (1999) Anal. Biochem. Vol 273: 73-80; Soltec Ventures, Beverly, Mass.) for about 1-2 hrs at 37° C. Alternatively, DTT can be used as reducing agent. The formation of inter-chain disulfide bonds was monitored either by non-reducing SDS-PAGE or by denaturing reverse phase HPLC PLRP column chromatography. The reduced ThioMab is diluted and loaded onto a HiTrap SP FF column in 10 mM sodium acetate, pH 5, and eluted with PBS containing 0.3M sodium chloride, or 50 mM Tris-Cl, pH 7.5 containing 150 mM sodium chloride.

Disulfide bonds were reestablished between cysteine residues present in the parent Mab by carrying out reoxidation. The eluted reduced ThioMab is treated with 15x or 2 mM dehydroascorbic acid (dhAA) at pH 7 for 3 hours or for 3 hrs in 50 mM Tris-Cl, pH 7.5, or with 2 mM aqueous copper sulfate ($CuSO_4$) at room temperature overnight. Other oxidants, i.e. oxidizing agents, and oxidizing conditions, which are known in the art may be used. Ambient air oxidation may also be effective. This mild, partial reoxidation step forms intrachain disulfides efficiently with high fidelity. The buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm.

Liquid chromatography/Mass Spectrometric Analysis was performed on a TSQ Quantum Triple Quadrupole™ mass spectrometer with extended mass range (Thermo Electron, San Jose Calif.). Samples were chromatographed on a PRLP-S®, 1000 A, microbore column (50 mm×2.1 mm, Polymer Laboratories, Shropshire, UK) heated to 75° C. A linear gradient from 30-40% B (solvent A: 0.05% TFA in water, solvent B: 0.04% TFA in acetonitrile) was used and the eluent was directly ionized using the electrospray source. Data were collected by the Xcalibur® data system and deconvolution was performed using ProMass® (Novatia, LLC, New Jersey). Prior to LC/MS analysis, antibodies or drug conjugates (50 micrograms) were treated with PNGase F (2 units/ml; PROzyme, San Leandro, Calif.) for 2 hours at 37° C. to remove N-linked carbohydrates.

Hydrophobic Interaction Chromatography (HIC) samples were injected onto a Butyl HIC NPR column (2.5 micron particle size, 4.6 mm×3.5 cm) (Tosoh Bioscience) and eluted with a linear gradient from 0 to 70% B at 0.8 ml/min (A: 1.5 M ammonium sulfate in 50 mM potassium phosphate, pH 7, B: 50 mM potassium phosphate pH 7, 20% isopropanol). An Agilent 1100 series HPLC system equipped with a multi wavelength detector and Chemstation software was used to resolve and quantitate antibody species with different ratios of drugs per antibody. Cysteine engineered antibodies of the present invention can be prepared according the general method described above.

Conjugation of Linker-Drug Intermediates to Antibodies (Procedure 1)

Engineered antibody cysteines were blocked as mixed disulfides with glutathione and/or cysteine as expressed in CHO cells. These cysteines had to be "deblocked" prior to conjugation.

Deblocked antibody (5-12 mg/mL) in 20 mM succinate, 150 mM NaCl, 2 mM EDTA was brought to 75-100 mM Tris, pH 7.5-8 (using 1M Tris). Co-solvent (DMSO, DMF, or DMA) was added to the antibody solution, followed by linker-drug (in DMSO or DMF) to give a final %-organic solvent of 10-13% and final concentration of linker-drug 2.5-10x relative to antibody concentration. Reactions were allowed to proceed at room temperature for 1-12 hours (until maximum conjugation was achieved). Conjugation reactions were purified via cation exchange chromatography and/or gel filtration using disposable columns (S maxi or Zeba, respectively). Additional purification by preparative gel filtration (S200 columns) was performed if the crude conjugate was significantly aggregated according to analytical SEC (e.g., >10%). Conjugates were subsequently exchanged into formulation buffer (20 mM His-acetate, pH 5.5, 240 mM sucrose) using either gel filtration or dialysis. Tween-20 was subsequently added to the purified conjugate to reach a final concentration of 0.02%. Final conjugate concentrations ranged from 2.4 to 7.5 mg/mL (% Yield: 34-81% from deblocked antibody). Conjugates were analyzed by LCMS to obtain a measurement of the drug-antibody ratio (DAR), which ranged from 1.3 to 2.1 (average: 1.8). Conjugates were also analyzed for presence of high-molecular weight aggregates using analytical SEC (Zenix or Shodex columns); final, purified conjugates displayed aggregation ranging from 0-10%. Conjugates were also assessed for endotoxin contamination, which, in all cases, did not exceed 1.3 EU/mg. Free, unconjugated drug did not exceed 1% of the final conjugate.

Conjugation of Linker-Drug Intermediates to Antibodies (Procedure 2, Alternative Procedure)

After the reduction and reoxidation procedures of the above example, the antibody is dissolved in PBS (phosphate buffered saline) buffer and chilled on ice. An excess, from about 1.5 molar to 20 equivalents of a linker-drug intermediate with a thiol-reactive functional group such as maleimido or bromo-acetamide, is dissolved in DMSO, diluted in acetonitrile and water, and added to the chilled reduced, reoxidized antibody in PBS. After about one hour, an excess of maleimide is added to quench the reaction and cap any unreacted antibody thiol groups. The conjugation mixture may be loaded and eluted through a HiTrap SP FF column to remove excess drug-linker intermediate and other impurities. The reaction mixture is concentrated by centrifugal ultrafiltration and the cysteine engineered antibody drug conjugate is purified and desalted by elution through G25 resin in PBS, filtered through 0.2 μm filters under sterile conditions, and frozen for storage.

The ADCs of the present invention can be prepared according to the procedure described in the above section.

Assays

Select linkers were then tested and found active in in vitro and in vivo assays. The cleavage data is shown in the table below Cathepsin B Cleavage Assay Like peptide linkers, non-peptide linkers for ADC is expect to be cleavable in lysosome in order for proper drug release. As a digestive organelle of the cell, lysosome is enriched with some proteases which show optimal hydrolytic activity at an acidic pH. Cathepsin B is a representative lysosomal protease and has been shown to contribute to the activation of ADC peptide linkers (ref). As an initial screen, an assay was developed using purified cathepsin B to identify cleavable linker-drug constructs that are suitable for conjugation with antibody. Norfloxacin was used to represent the drug component of the linker-drug. The percentage of cleavage relative to the control peptides (such as Val-Cit) was measured at a given time point as well as the kinetic parameters of the cleavage reaction (Km and Vmax). Detailed description of the assay is shown below. From this assay, a variety of proteolytically active and structurally diverse linkers were identified and later used in making ADCs.

Cathepsin B cleavage activity using experimental linker-drugs as substrate was measured by monitoring the release of Norfloxacin using LC/MS. Varying concentrations of linker-drug (3-fold serial dilutions) were incubated in 20 uL reactions containing 20 nM Cathepsin B (EMD Millipore cat. #219364, human liver), 10 mM MES pH 6.0, 1 mM DTT, 0.03% CHAPS, and 25 nM Norfloxacin-d5 internal standard (Santa Cruz Biotechnology, cat. #sc-301482). Reactions were incubated for 1 hour at 37° C., followed by addition of 60 uL of 2% formic acid to quench the reactions. Samples were analyzed by injecting 2 uL of stopped reactions on a Waters Acquity UPLC BEH Phenyl column (2.1 mm×50 mm, Waters cat. #186002884). Samples were purified using a linear 2 minute gradient (0% to 80%) of acetonitrile, 0.1% formic acid on a Water Acquity UPLC. Norfloxacin and Norfloxacin-d5 internal standard were detected using an AB Sciex QTrap 5500 triple quadrupole mass spectrometer operating in positive MRM mode (Norfloxacin 320→233 m/z, Norfloxacin-d5 325→233 m/z). The quantified norfloxacin (normalized with internal standard) was plotted against linker-drug concentration, and the resulting plot was curve fitted with a Michaelis-Menten fit using GraphPad Prism software for the kinetic constants Km and Vmax.

In Vitro Cell Proliferation Assay

Efficacy of ADC was measured by a cell proliferation assay employing the following protocol (CELLTITER GLO™ Luminescent Cell Viability Assay, Promega Corp. Technical Bulletin TB288; Mendoza et al (2002) Cancer Res. 62:5485-5488):

1. An aliquot of 100 µl of cell culture containing about $10^4$ cells (SKBR-3, BT474, MCF7 or MDA-MB-468) in medium was deposited in each well of a 96-well, opaque-walled plate.
2. Control wells were prepared containing medium and without cells.
3. ADC was added to the experimental wells and incubated for 3-5 days.
4. The plates were equilibrated to room temperature for approximately 30 minutes.
5. A volume of CELLTITER GLO™ Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.

Data are plotted as the mean of luminescence for each set of replicates, with standard deviation error bars. The protocol is a modification of the CELLTITER GLO™ Luminescent Cell Media: SK-BR-3 grow in 50/50/10% FBS/glutamine/250 µg/mL G-418 OVCAR-3 grow in RPMI/20% FBS/glutamine In Vivo Assay 1. The efficacy of the anti-CD33 antibody-drug conjugates (ADCs) was investigated in a mouse xenograft model of HL-60 or EOL-1 (human acute myeloid leukemia). The HL-60 cell line was obtained from ATCC (American Type Culture Collection; Manassas, Va.) and EOL-1 cell line was originated from DSMZ (German Collection of Microorganisms and Cell Cultures; Braunschweig, Germany).

Female C.B-17 SCID mice (Charles River Laboratories; Hollister, Calif.) were each inoculated subcutaneously in the flank area with five million cells of HL-60 or EOL-1. When the xenograft tumors reached an average tumor volume of 100-300 mm3 (referred to as Day 0), animals were randomized into groups of 7-10 mice each and received a single intravenous injection of the ADCs. Approximately 4 hours prior to administration of ADCs, animals were dosed intraperitoneally with excess amount (30 mg/kg) of anti-gD control antibody to block possible nonspecific antibody binding sites on the tumor cells. Tumors and body weights of mice were measured 1-2 times a week throughout the study. Mice were promptly euthanized when body weight loss was >20% of their starting weight. All animals were euthanized before tumors reached 3000 mm3 or showed signs of impending ulceration.

2. The efficacy of the anti-Napi2B antibody-drug conjugates (ADCs) was investigated in a mouse xenograft model of OVCAR3-X2.1 (human ovarian cancer). The OVCAR3 cell line was obtained from ATCC (American Type Culture Collection; Manassas, Va.) and a sub-line OVCAR3-X2.1 was generated at Genentech for optimal growth in mice.

Female C.B-17 SCID-beige mice (Charles River Laboratories; San Diego, Calif.) were each inoculated in the thoracic mammary fat pad area with ten million OVCAR3-X2.1 cells. When the xenograft tumors reached an average tumor volume of 100-300 mm3 (referred to as Day 0), animals were randomized into groups of 7-10 mice each and received a single intravenous injection of the ADCs. Tumors and body weights of mice were measured 1-2 times a week throughout the study. Mice were promptly euthanized when body weight loss was >20% of their starting weight. All animals were euthanized before tumors reached 3000 mm3 or showed signs of impending ulceration.

3. The efficacy of the anti-CD22 antibody-drug conjugates (ADCs) is investigated in a mouse xenograft model of BJAB-luc (human Burkitt's lymphoma) or WSU-DLCL2 (human diffuse large B-cell lymphoma). The BJAB cell line is obtained from DSMZ (German Collection of Microorganisms and Cell Cultures; Braunschweig, Germany), and a sub-line BJAB-luc is generated at Genentech to stably express the luciferase gene. The WSU-DLCL2 cell line is also originated from DSMZ.

Female C.B-17 SCID mice (Charles River Laboratories; Hollister, Calif.) are each inoculated subcutaneously in the flank area with 20 million cells of BJAB-luc or WSU-DLCL2. When the xenograft tumors reached an average tumor volume of 100-300 mm3 (referred to as Day 0), animals are randomized into groups of 7-10 mice each and received a single intravenous injection of the ADCs. Tumors and body weights of mice are measured 1-2 times a week throughout the study. Mice are promptly euthanized when body weight loss is >20% of their starting weight. All animals are euthanized before tumors reached 3000 mm3 or showed signs of impending ulceration.

4. The efficacy of the anti-Her2 antibody-drug conjugates (ADCs) is investigated in a mouse allograft model of MMTV-HER2 Founder #5 (murine mammary tumor). The MMTV-HER2 Founder #5 (Fo5) model (developed at Genentech) is a transgenic mouse model in which the human HER2 gene, under transcriptional regulation of the murine mammary tumor virus promoter (MMTV-HER2), is overexpressed in mammary epithelium. The overexpression causes spontaneous development of mammary tumors that overexpress the human HER2 receptor. The mammary tumor from one of the founder animals (founder #5, Fo5) has been propagated in FVB mice (Charles River Laboratories) by serial transplantation of tumor fragments.

For efficacy studies, the Fo5 transgenic mammary tumor is surgically transplanted into the thoracic mammary fat pad of female nu/nu mice (Charles River Laboratories; Hollister, Calif.) as tumor fragments of approximately 2 mm×2 mm in size. When the allograft tumors reached an average tumor volume of 100-300 mm3 (referred to as Day 0), animals are randomized into groups of 7-10 mice each and received a single intravenous injection of the ADCs. Tumors and body weights of mice are measured 1-2 times a week throughout the study. Mice are promptly euthanized when body weight loss is >20% of their starting weight. All animals are euthanized before tumors reached 3000 mm3 or showed signs of impending ulceration.

Biological Data

Linker-drug compound structures and Cathepsin B cleavage data

The Linker-drug compounds below can be generialized as the following formula

Cap-PM-Sp-T

Where Cap is a capping group which protects the amino group in the Cathepsin B assay (for example, CBZ and ethyl); PM is a peptidomimetic moiety; sp is a spacer, T is substitute for drug moiety.

The CAT B cleavage data in the table below shows the cleavage rates of non-peptide linkers of the present inventions are comparable to peptide linkers (40-56). Peptide linkers have been widely used in antibody drug conjugates to release the active drug moiety; therefore, it is expected that conjugates comprising the present non-peptide linkers could achieve similar results in vitro and in vivo.

| Example | Structure | Series | CATB Cleavage MS (Vmax/Km) | P3 | CATB Cleavage MS Vmax/Km)-background corrected | Stereo |
|---|---|---|---|---|---|---|
| 1 | 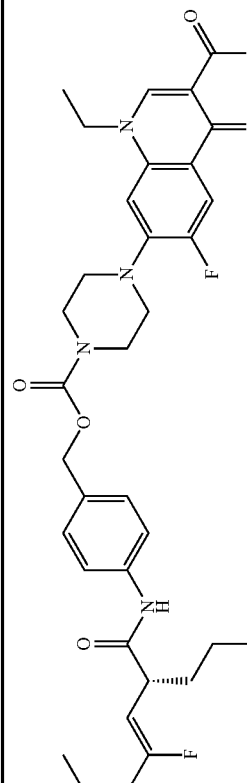 | F-olefin | 0.0050 | Cbz | 0.001095 | SKS |
| 2 | 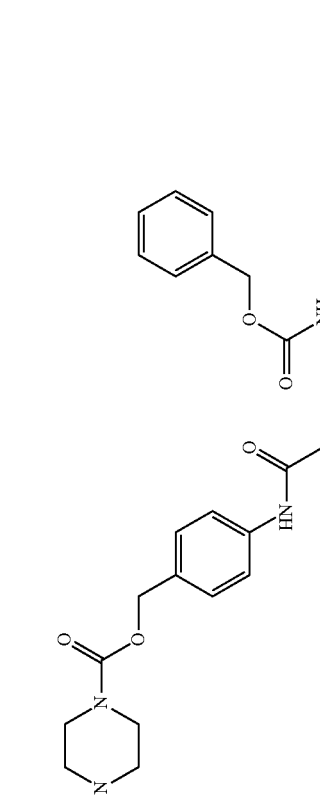 | F-olefin | 0.00132 | Cbz | 0.000189 | SKS |

| Example | Structure | Series | CATB Cleavage MS (Vmax/Km) | P3 | CATB Cleavage MS (Vmax/Km)-background corrected | Stereo |
|---|---|---|---|---|---|---|
| 3 | 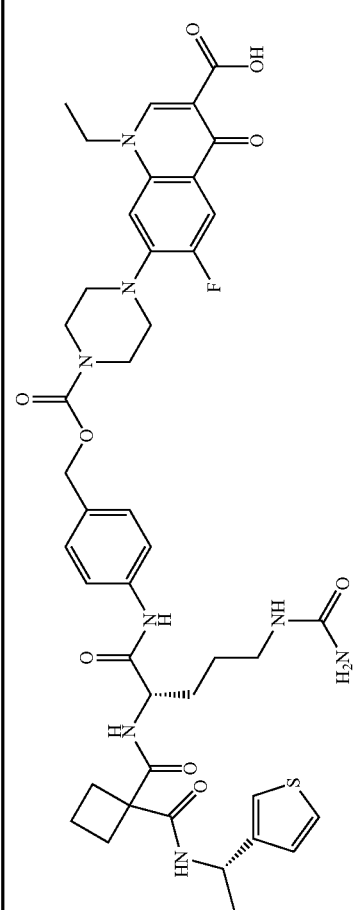 | cyclobutane-1,1-dicarbonyl | 0.119 | non-Cbz | 0.031021 | SUS |
| 4 | 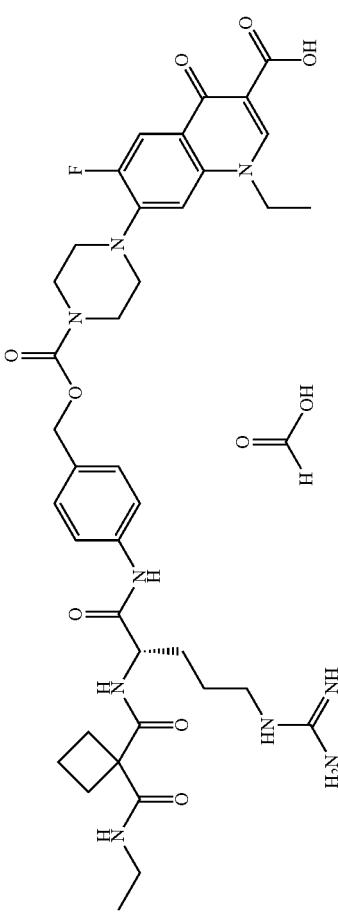 | cyclobutane-1,1-dicarbonyl | 0.105 | non-Cbz | 0.023418 | SKS |

| Example | Structure | Series | CATB Cleavage MS (Vmax/Km) | P3 | CATB Cleavage MS (Vmax/Km)-background corrected | Stereo |
|---|---|---|---|---|---|---|
| 5 | 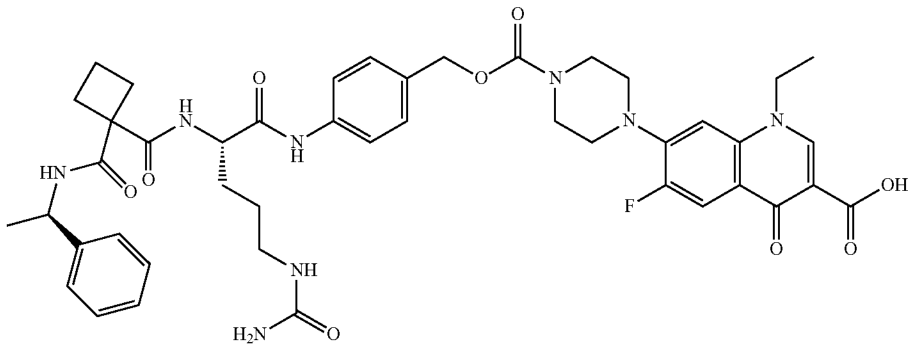 [SMILES: CCn1cc(C(=O)O)c(=O)c2cc(F)c(N3CCN(C(=O)OCc4ccc(NC(=O)[C@H](CCCNC(N)=O)NC(=O)C5(C(=O)N[C@H](C)c6ccccc6)CCC5)cc4)CC3)cc21] | cyclobutane-1,1-dicarbonyl | 0.072 | non-Cbz | 0.014058 | SKS |
| 6 | 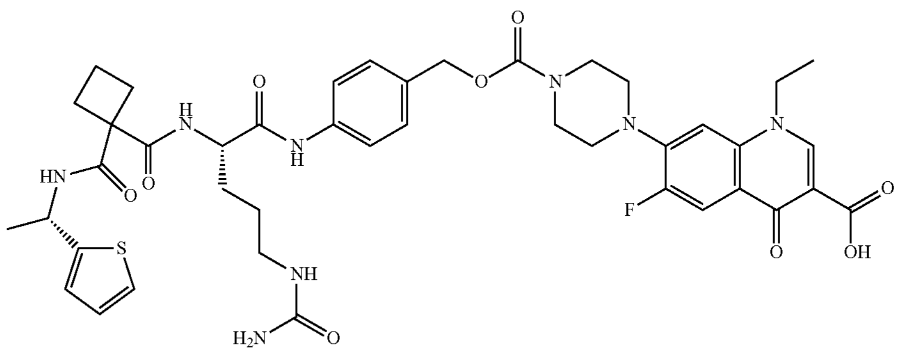 [SMILES: CCn1cc(C(=O)O)c(=O)c2cc(F)c(N3CCN(C(=O)OCc4ccc(NC(=O)[C@H](CCCNC(N)=O)NC(=O)C5(C(=O)N[C@@H](C)c6cccs6)CCC5)cc4)CC3)cc21] | cyclobutane-1,1-dicarbonyl | 0.065 | non-Cbz | 0.019174 | SUS |

-continued

| Example | Structure | Series | CATB Cleavage MS (Vmax/Km) | P3 | CATB Cleavage MS (Vmax/Km)-background corrected | Stereo |
|---|---|---|---|---|---|---|
| 7 | 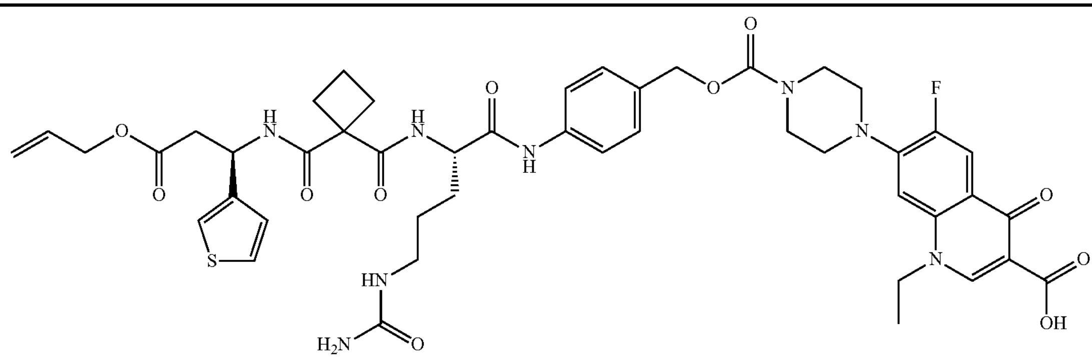 | cyclobutane-1,1-dicarbonyl | 0.0421 | non-Cbz | 0.028017 | SUS |
| 8 | 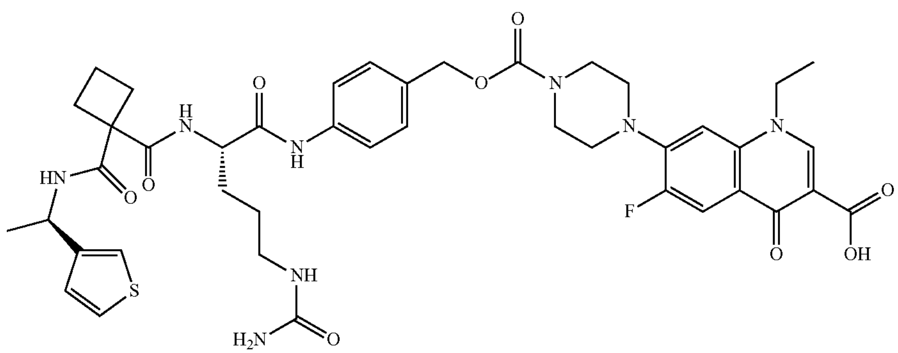 [SMILES: CCn1cc(C(=O)O)c(=O)c2cc(F)c(N3CCN(C(=O)OCc4ccc(NC(=O)[C@H](CCCNC(N)=O)NC(=O)C5(C(=O)N[C@H](C)c6ccsc6)CCC5)cc4)CC3)cc21] | cyclobutane-1,1-dicarbonyl | 0.023 | non-Cbz | 0.004154 | SUS |

-continued
| Example | Structure | Series | CATB Cleavage MS (Vmax/Km) | P3 | CATB Cleavage MS (Vmax/Km)-background corrected | Stereo |
|---|---|---|---|---|---|---|
| 9 | 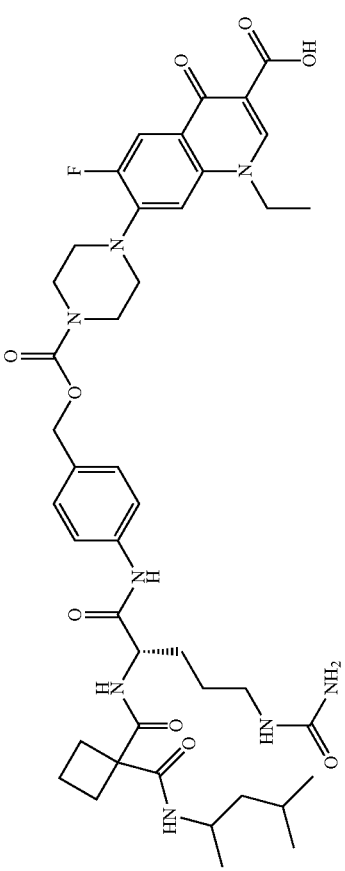 | cyclobutane-1,1-dicarbonyl | 0.023 | non-Cbz | 0.004148 | MD |
| 10 | 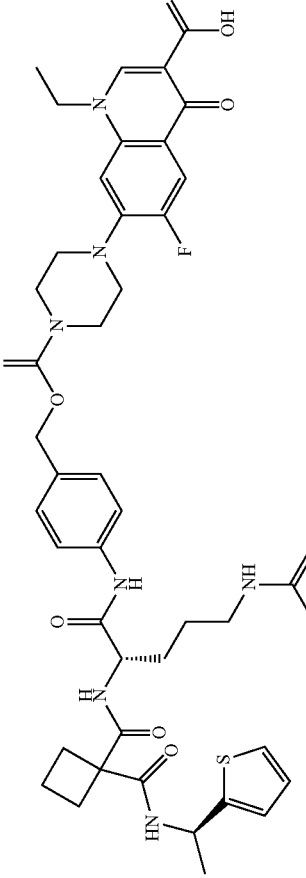 | cyclobutane-1,1-dicarbonyl | 0.017 | non-Cbz | 0.004573 | SUS |

| Example | Structure | Series | CATB Cleavage MS (Vmax/Km) | P3 | CATB Cleavage MS (Vmax/Km)-background corrected | Stereo |
|---|---|---|---|---|---|---|
| 11 | 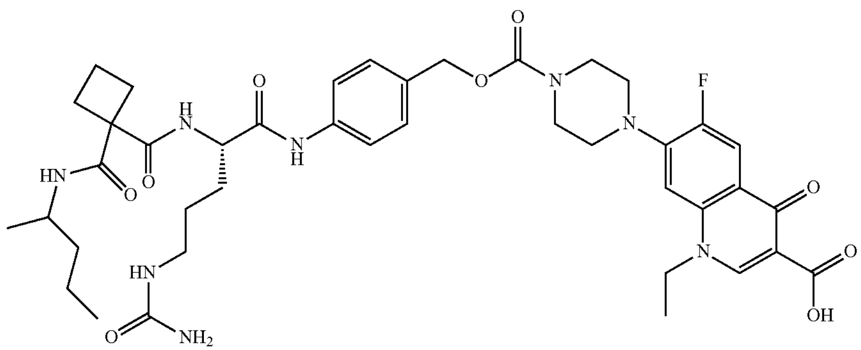 [SMILES: CCCC(C)NC(=O)C1(C(=O)N[C@@H](CCCNC(N)=O)C(=O)Nc2ccc(COC(=O)N3CCN(c4cc5c(cc4F)c(=O)c(C(=O)O)cn5CC)CC3)cc2)CCC1] | cyclobutane-1,1-dicarbonyl | 0.014 | non-Cbz | 0.002728 | MD |
| 12 | 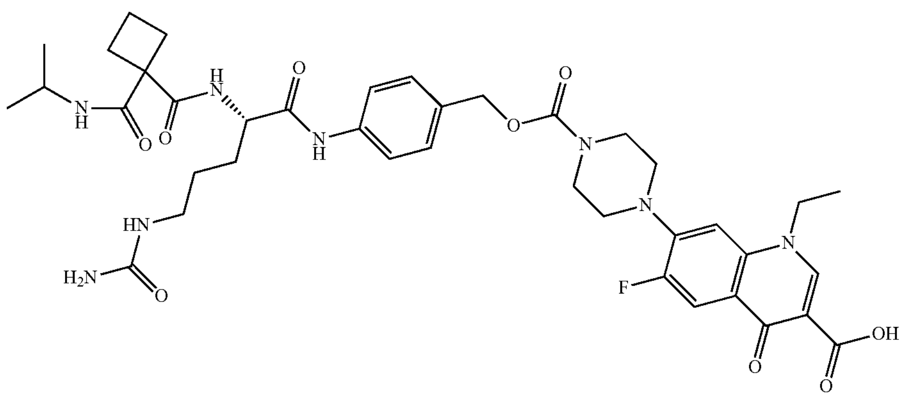 [SMILES: CCn1cc(C(=O)O)c(=O)c2cc(F)c(N3CCN(C(=O)OCc4ccc(NC(=O)[C@H](CCCNC(N)=O)NC(=O)C5(C(=O)NC(C)C)CCC5)cc4)CC3)cc21] | cyclobutane-1,1-dicarbonyl | 0.0139 | non-Cbz | 0.005125 | SKS |

| Example | Structure | Series | CATB Cleavage MS (Vmax/Km) | P3 | CATB Cleavage MS (Vmax/Km)-background corrected | Stereo |
|---|---|---|---|---|---|---|
| 13 | 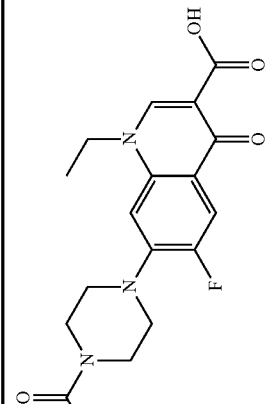 | cyclobutane-1,1-dicarbonyl | 0.0101 | non-Cbz | 0.003088 | SKS |
| 14 | 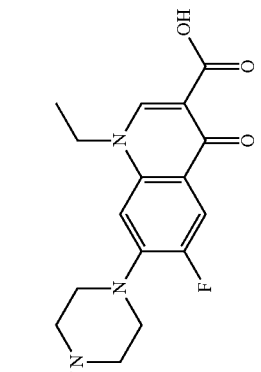 | cyclobutane-1,1-dicarbonyl | 0.0090 | non-Cbz | 0.003064 | SKS |

-continued

| Example | Structure | Series | CATB Cleavage MS (Vmax/Km) | P3 | CATB Cleavage MS (Vmax/Km)-background corrected | Stereo |
|---|---|---|---|---|---|---|
| 15 | 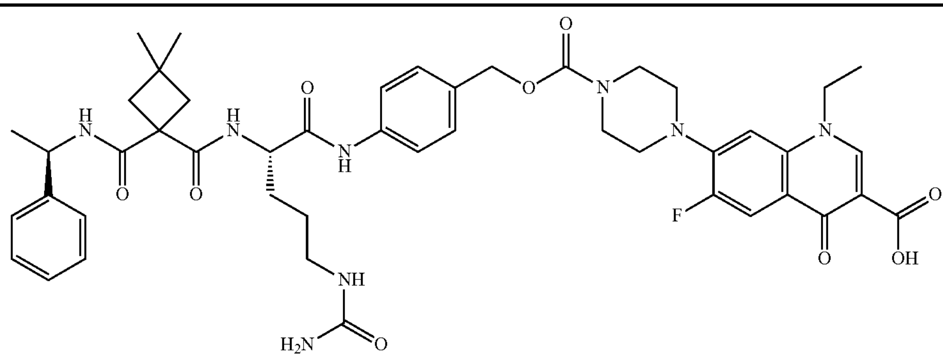 | cyclobutane-1,1-dicarbonyl | 0.00628 | non-Cbz | 0.002777 | SKS |
| 16 | 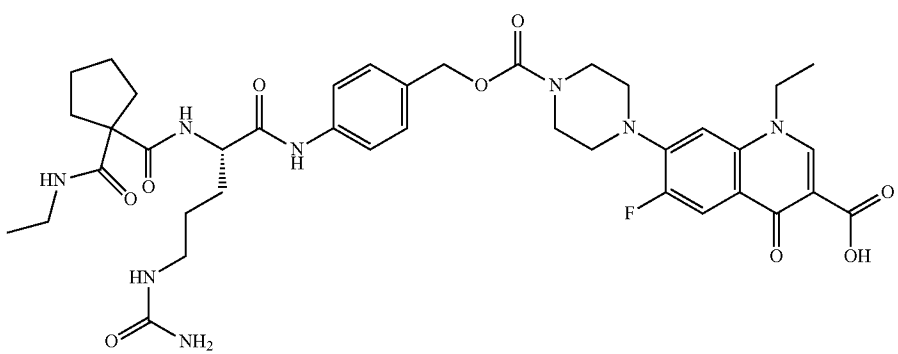 [SMILES: CCNC(=O)C1(C(=O)N[C@@H](CCCNC(N)=O)C(=O)Nc2ccc(COC(=O)N3CCN(c4cc5c(cc4F)c(=O)c(C(=O)O)cn5CC)CC3)cc2)CCCC1] | cyclobutane-1,1-dicarbonyl | 0.0060 | non-Cbz | 0.001749 | SKS |

-continued

| Example | Structure | Series | CATB Cleavage MS (Vmax/Km) | P3 | CATB Cleavage MS Vmax/Km)-background corrected | Stereo |
|---|---|---|---|---|---|---|
| 17 | 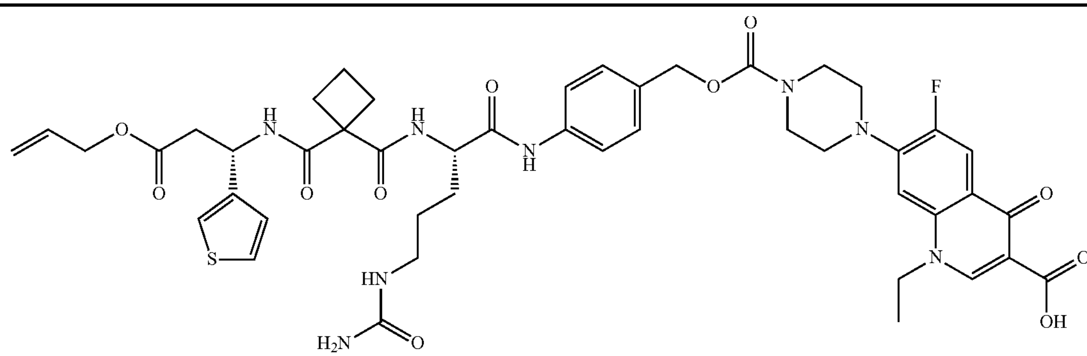 | cyclobutane-1,1-dicarbonyl | 0.00295 | non-Cbz | 0.002502 | SUS |
| 18 | 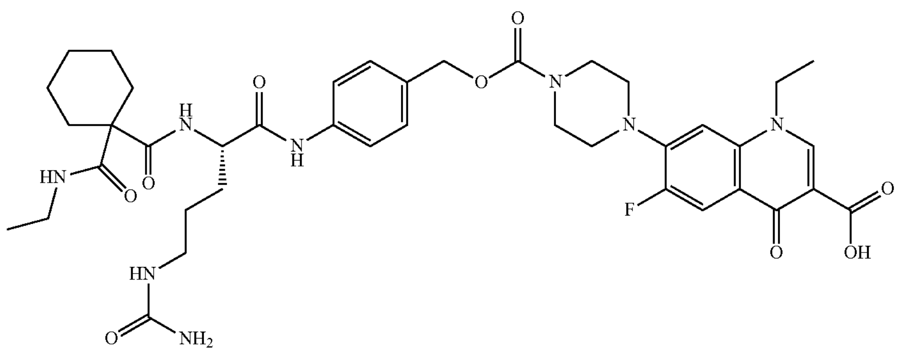 [SMILES: CCNC(=O)C1(C(=O)N[C@@H](CCCNC(N)=O)C(=O)Nc2ccc(COC(=O)N3CCN(c4cc5c(cc4F)c(=O)c(C(=O)O)cn5CC)CC3)cc2)CCCCC1] | cyclobutane-1,1-dicarbonyl | 0.000993 | non-Cbz | 0.000904 | SKS |

-continued
| Example | Structure | Series | CATB Cleavage MS (Vmax/Km) | P3 | CATB Cleavage MS Vmax/Km)-background corrected | Stereo |
|---|---|---|---|---|---|---|
| 19 | 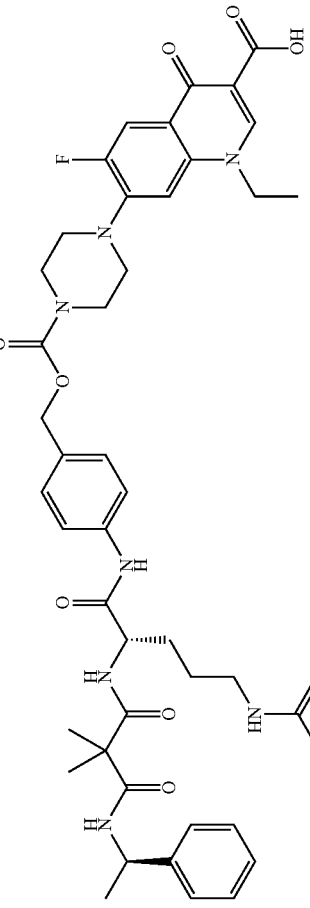 | cyclobutane-1,1-dicarbonyl | 0.000409 | non-Cbz | 0.000823 | SKS |
| 20 | 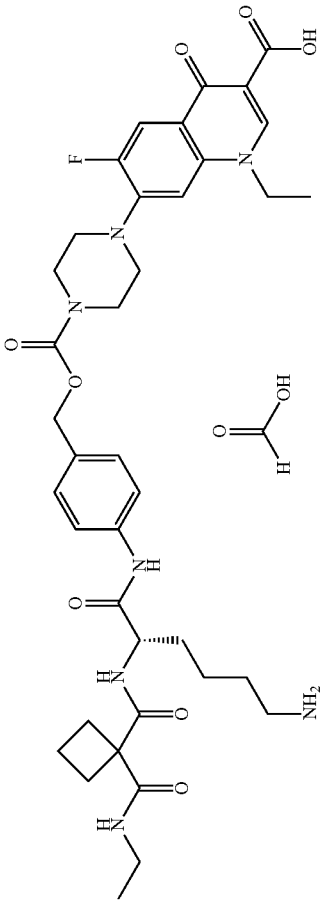 | cyclobutane-1,1-dicarbonyl | | non-Cbz | 0.004020 | SKS |

| Example | Structure | Series | CATB Cleavage MS (Vmax/Km) | P3 | CATB Cleavage MS (Vmax/Km)-background corrected | Stereo |
|---|---|---|---|---|---|---|
| 21 | 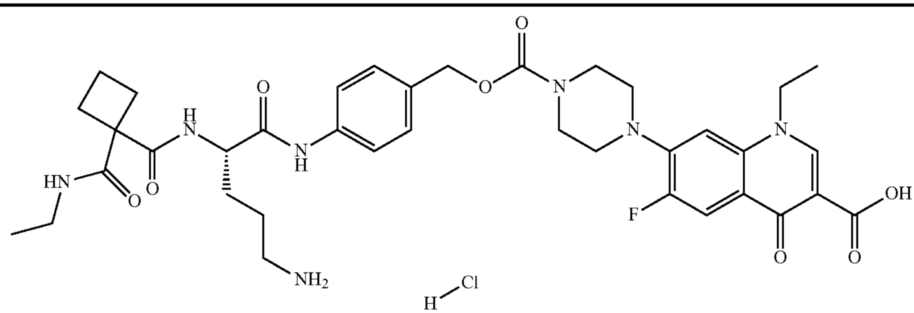 | cyclobutane-1,1-dicarbonyl | | non-Cbz | | SKS |
| 22 | 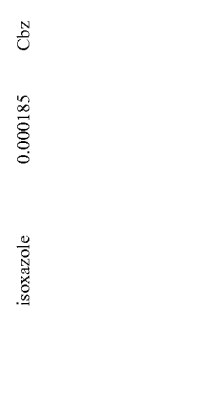 | isoxazole | 0.000185 | Cbz | 0.000426 | MD |

| Example | Structure | Series | CATB Cleavage MS (Vmax/Km) | P3 | CATB Cleavage MS (Vmax/Km)-background corrected | Stereo |
|---|---|---|---|---|---|---|
| 23 | 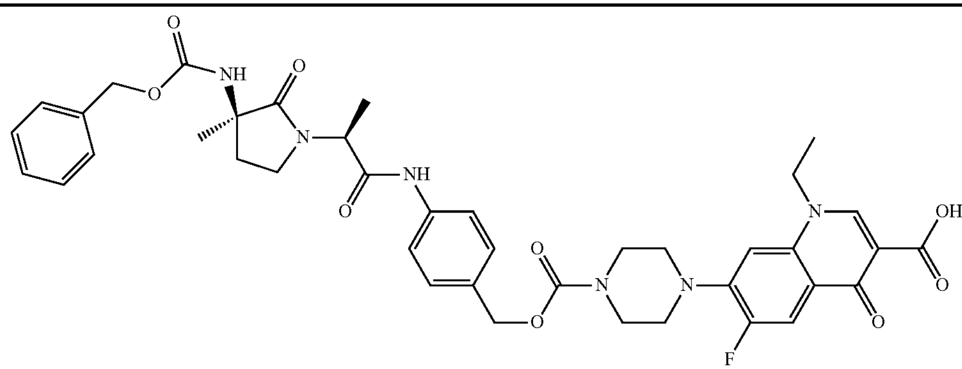 | others | | Cbz | 0.000094 | SKS |
| 24 | 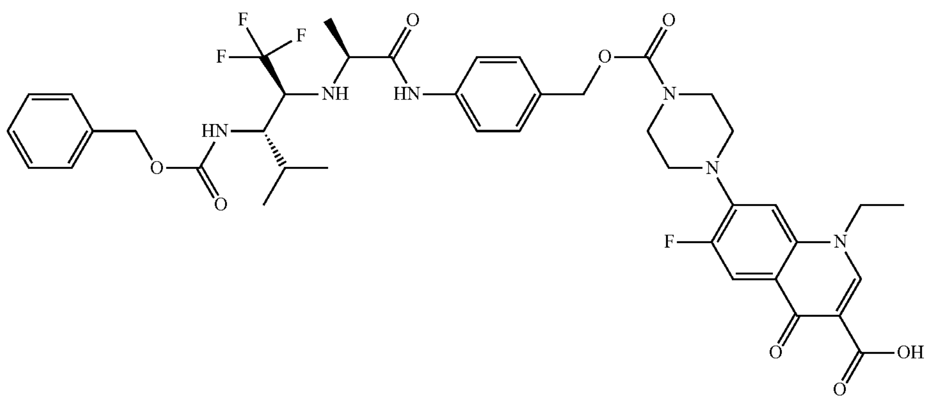 [SMILES: CCn1cc(C(=O)O)c(=O)c2cc(F)c(N3CCN(C(=O)OCc4ccc(NC(=O)[C@H](C)N[C@@H]([C@@H](NC(=O)OCc5ccccc5)C(C)C)C(F)(F)F)cc4)CC3)cc21] | others | | Cbz | | SUS |

-continued

| Example | Structure | Series | CATB Cleavage MS (Vmax/Km) | P3 | CATB Cleavage MS (Vmax/Km)-background corrected | Stereo |
|---|---|---|---|---|---|---|
| 25 | 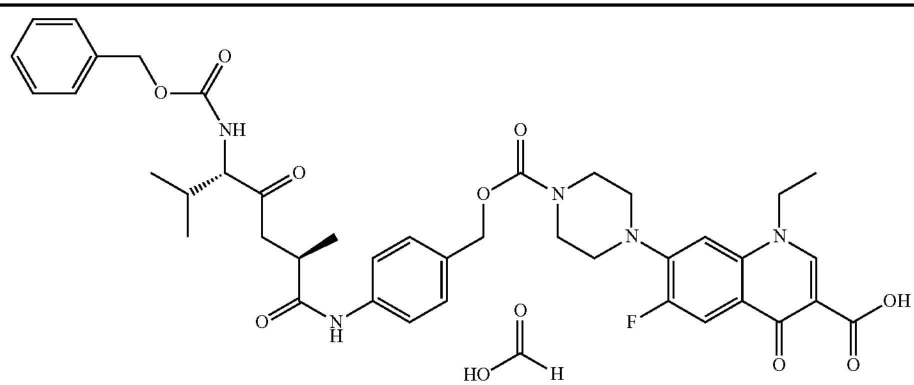 | others | | Cbz | | SUS |
| 26 | 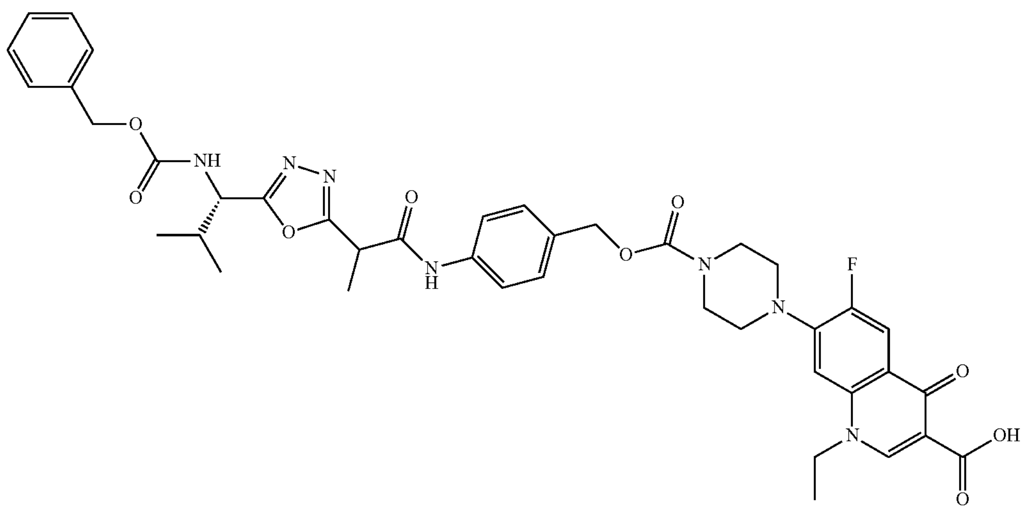 [SMILES: CCn1cc(C(=O)O)c(=O)c2cc(F)c(N3CCN(C(=O)OCc4ccc(NC(=O)C(C)c5nnc([C@@H](NC(=O)OCc6ccccc6)C(C)C)o5)cc4)CC3)cc21] | others | | Cbz | | MD |

| Example | Structure | Series | CATB Cleavage MS (Vmax/Km) | P3 | CATB Cleavage MS Vmax/Km)-background corrected | Stereo |
|---|---|---|---|---|---|---|
| 27 | 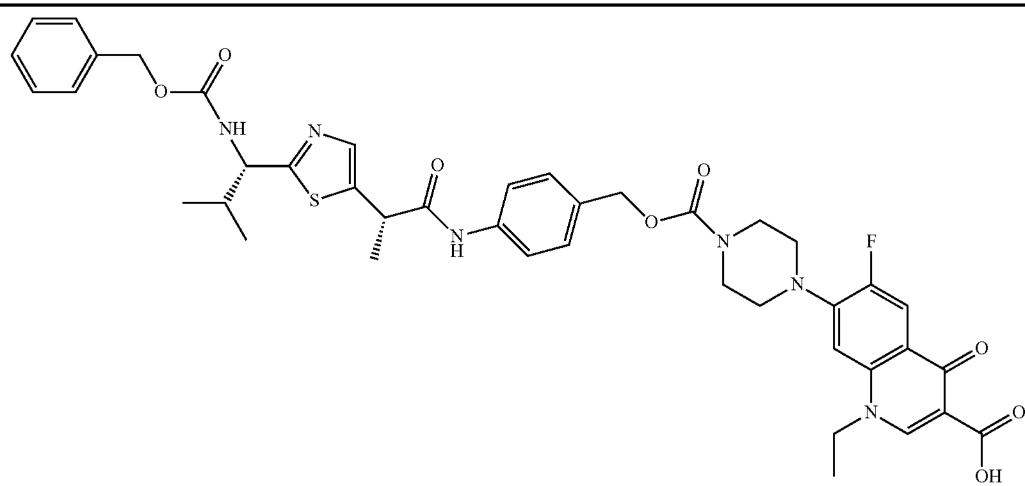 | others | | Cbz | | SUS |
| 28 | 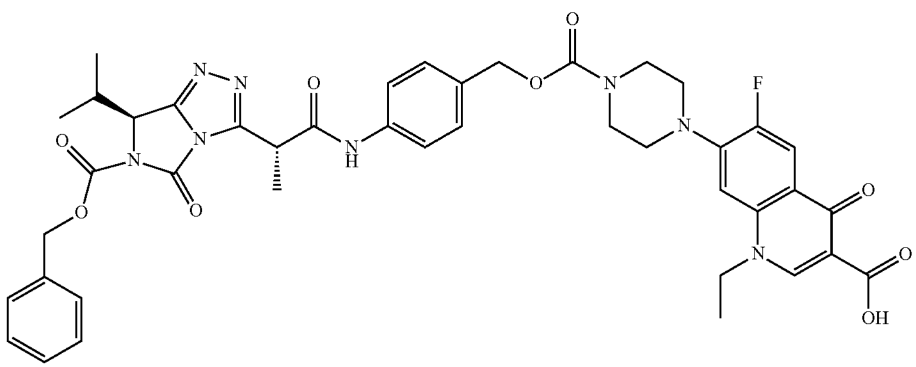 [SMILES: CCn1cc(C(=O)O)c(=O)c2cc(F)c(N3CCN(C(=O)OCc4ccc(NC(=O)[C@H](C)c5nnc6n5C(=O)N(C(=O)OCc5ccccc5)[C@H]6C(C)C)cc4)CC3)cc21] | others | | Cbz | | SUS |

| Example | Structure | Series | CATB Cleavage MS (Vmax/Km) | P3 | CATB Cleavage MS Vmax/Km)-background corrected | Stereo |
|---|---|---|---|---|---|---|
| 29 | 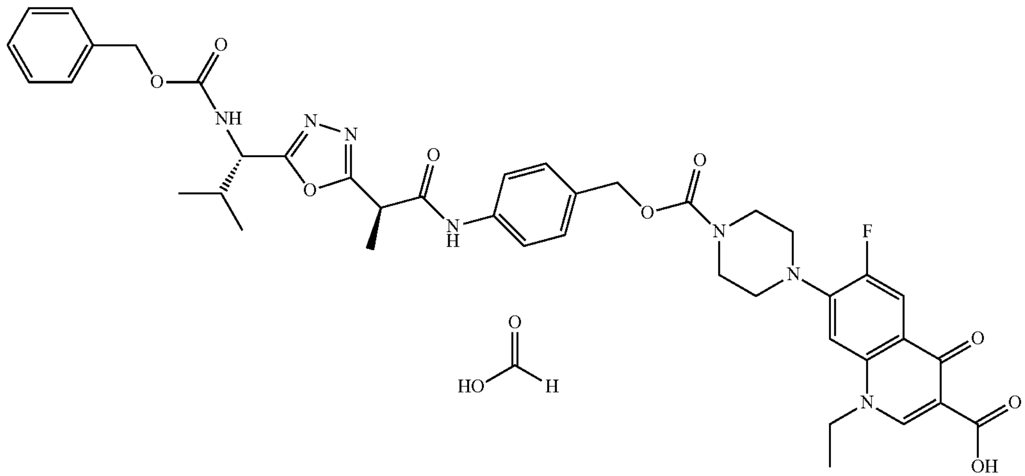 [SMILES: CCn1cc(C(=O)O)c(=O)c2cc(F)c(N3CCN(C(=O)OCc4ccc(NC(=O)[C@@H](C)c5nnc([C@@H](NC(=O)OCc6ccccc6)C(C)C)o5)cc4)CC3)cc21 ; O=CO] | others | | Cbz | 0.000047 | SUS |
| 30 | 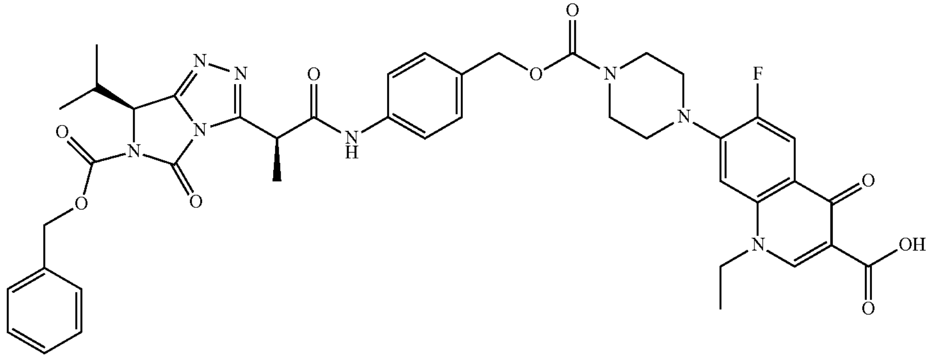 [SMILES: CCn1cc(C(=O)O)c(=O)c2cc(F)c(N3CCN(C(=O)OCc4ccc(NC(=O)[C@@H](C)c5nnc6n5C(=O)N(C(=O)OCc5ccccc5)[C@H]6C(C)C)cc4)CC3)cc21] | others | | Cbz | | SUS |

-continued

| Example | Structure | Series | CATB Cleavage MS (Vmax/Km) | P3 | CATB Cleavage MS (Vmax/Km)-background corrected | Stereo |
|---|---|---|---|---|---|---|
| 31 | 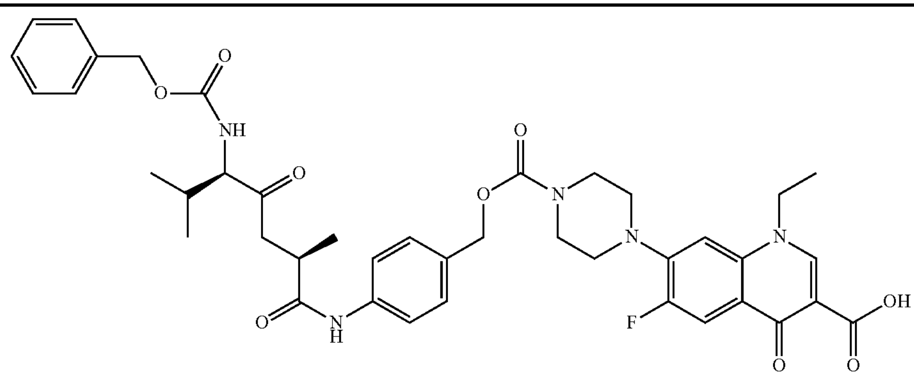 | others | | Cbz | | SUS |
| 32 | 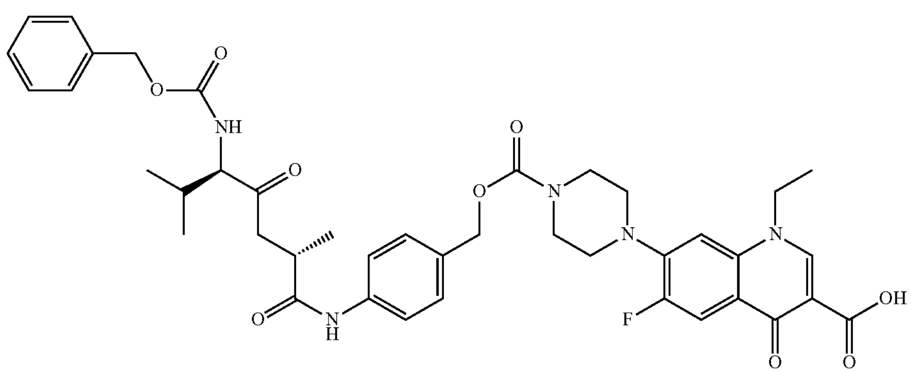 [SMILES: CCn1cc(C(=O)O)c(=O)c2cc(F)c(N3CCN(C(=O)OCc4ccc(NC(=O)[C@@H](C)CC(=O)[C@H](NC(=O)OCc5ccccc5)C(C)C)cc4)CC3)cc21] | others | | Cbz | | SUS |

-continued

| Example | Structure | Series | CATB Cleavage MS (Vmax/Km) | P3 | CATB Cleavage MS Vmax/Km)-background corrected | Stereo |
|---|---|---|---|---|---|---|
| 33 | 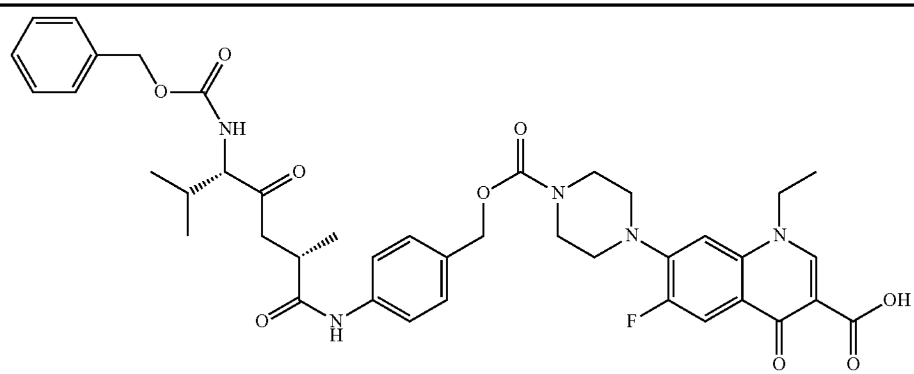 | others | | Cbz | 0.000013 | SUS |
| 34 | 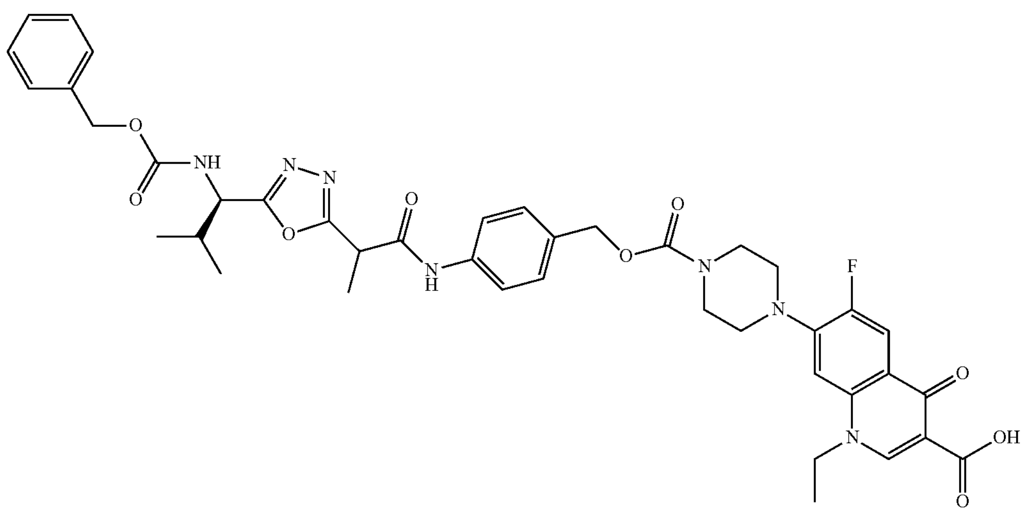 [SMILES: CCn1cc(C(=O)O)c(=O)c2cc(F)c(N3CCN(C(=O)OCc4ccc(NC(=O)C(C)c5nnc([C@H](NC(=O)OCc6ccccc6)C(C)C)o5)cc4)CC3)cc21] | others | | Cbz | | ME |

-continued

| Example | Structure | Series | CATB Cleavage MS (Vmax/Km) | P3 | CATB Cleavage MS (Vmax/Km)-background corrected | Stereo |
|---|---|---|---|---|---|---|
| 35 | 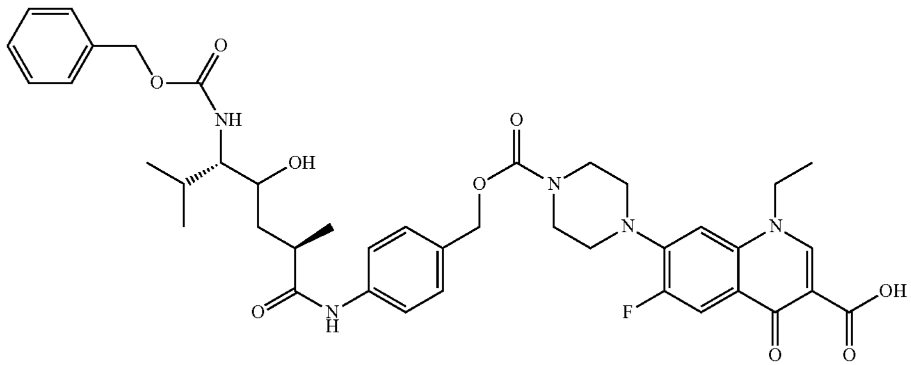 [SMILES: CCn1cc(C(=O)O)c(=O)c2cc(F)c(N3CCN(C(=O)OCc4ccc(NC(=O)[C@H](C)CC(O)[C@@H](NC(=O)OCc5ccccc5)C(C)C)cc4)CC3)cc21] | others | | Cbz | 0.009123 | MD |
| 36 | 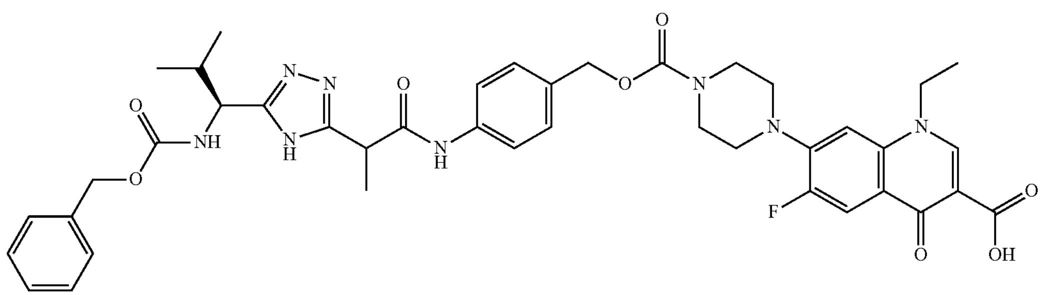 [SMILES: CCn1cc(C(=O)O)c(=O)c2cc(F)c(N3CCN(C(=O)OCc4ccc(NC(=O)C(C)c5nnc([C@@H](NC(=O)OCc6ccccc6)C(C)C)[nH]5)cc4)CC3)cc21] | others | | Cbz | 0.000014 | MD |

-continued

| Example | Structure | Series | CATB Cleavage MS (Vmax/Km) | P3 | CATB Cleavage MS (Vmax/Km)-background corrected | Stereo |
|---|---|---|---|---|---|---|
| 37 | 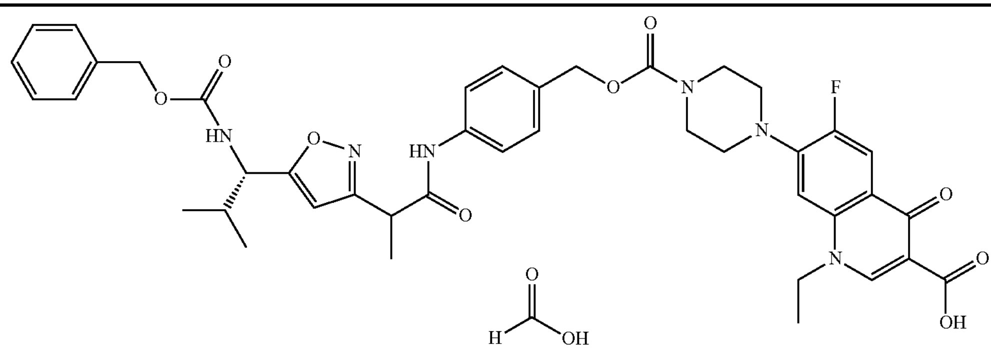 | others | | Cbz | 0.000054 | MD |
| 38 | 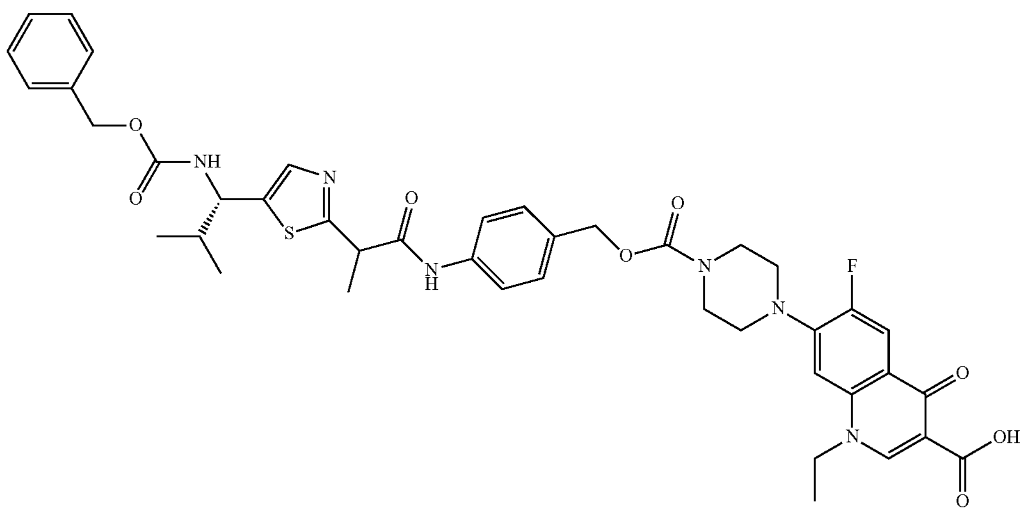 [SMILES: CCn1cc(C(=O)O)c(=O)c2cc(F)c(N3CCN(C(=O)OCc4ccc(NC(=O)C(C)c5ncc([C@@H](NC(=O)OCc6ccccc6)C(C)C)s5)cc4)CC3)cc21] | others | | Cbz | | MD |

| Example | Structure | Series | CATB Cleavage MS (Vmax/Km) | P3 | CATB Cleavage MS Vmax/Km)-background corrected | Stereo |
|---|---|---|---|---|---|---|
| 39 | 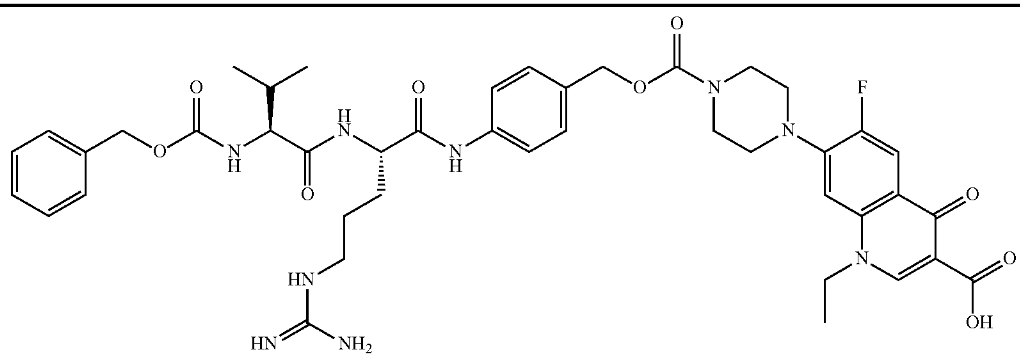 | peptide | 0.356 | Cbz | 0.375066 | SKS |
| 40 | 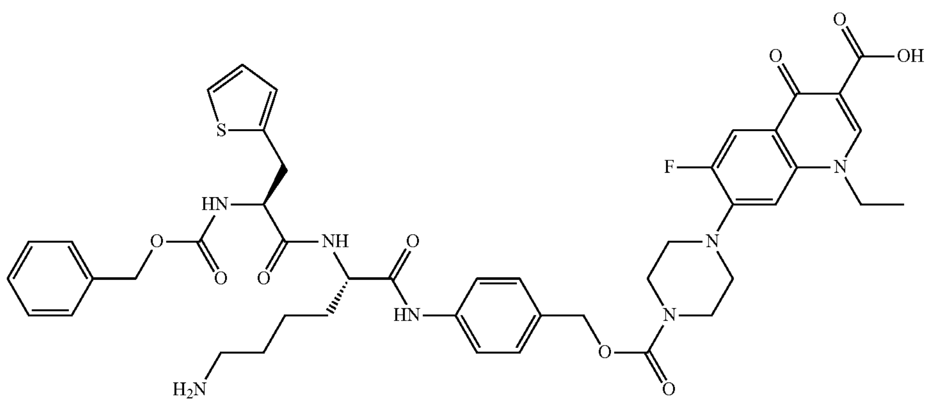 [SMILES: CCn1cc(C(=O)O)c(=O)c2cc(F)c(N3CCN(C(=O)OCc4ccc(NC(=O)[C@H](CCCCN)NC(=O)[C@H](Cc5cccs5)NC(=O)OCc5ccccc5)cc4)CC3)cc21] | peptide | 0.319 | Cbz | 0.257792 | SKS |

-continued
| Example | Structure | Series | CATB Cleavage MS (Vmax/Km) | P3 | CATB Cleavage MS Vmax/Km)-background corrected | Stereo |
|---|---|---|---|---|---|---|
| 41 | 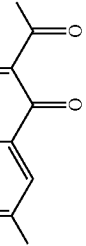 | peptide | 0.26 | non-Cbz | 0.101536 | SKS |

-continued

| Example | Structure | Series | CATB Cleavage MS (Vmax/Km) | P3 | CATB Cleavage MS Vmax/Km)-background corrected | Stereo |
|---|---|---|---|---|---|---|
| 42 | 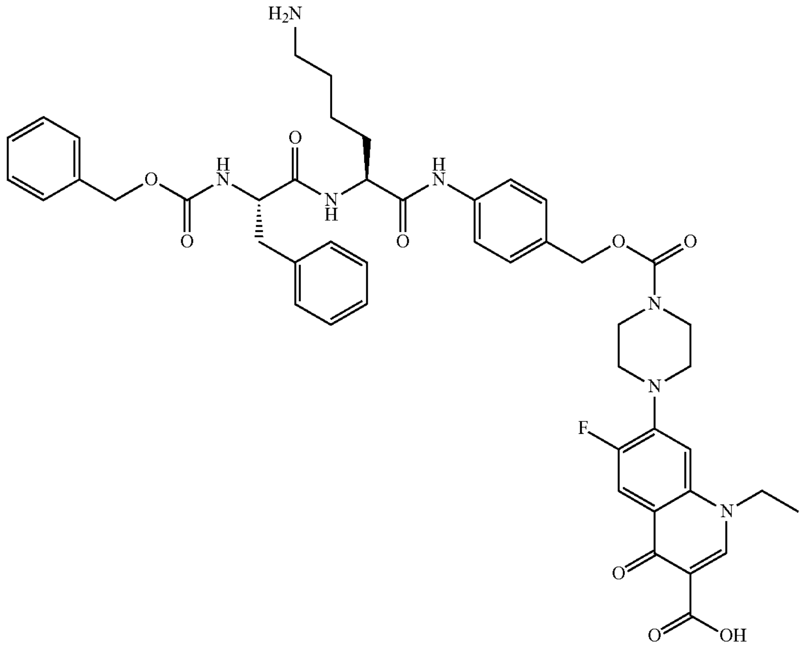 [SMILES: CCn1cc(C(=O)O)c(=O)c2cc(F)c(N3CCN(C(=O)OCc4ccc(NC(=O)[C@H](CCCCN)NC(=O)[C@H](Cc5ccccc5)NC(=O)OCc5ccccc5)cc4)CC3)cc21] | peptide | 0.245 | Cbz | | SKS |

| Example | Structure | Series | CATB Cleavage MS (Vmax/Km) | P3 | CATB Cleavage MS (Vmax/Km)-background corrected | Stereo |
|---|---|---|---|---|---|---|
| 43 | 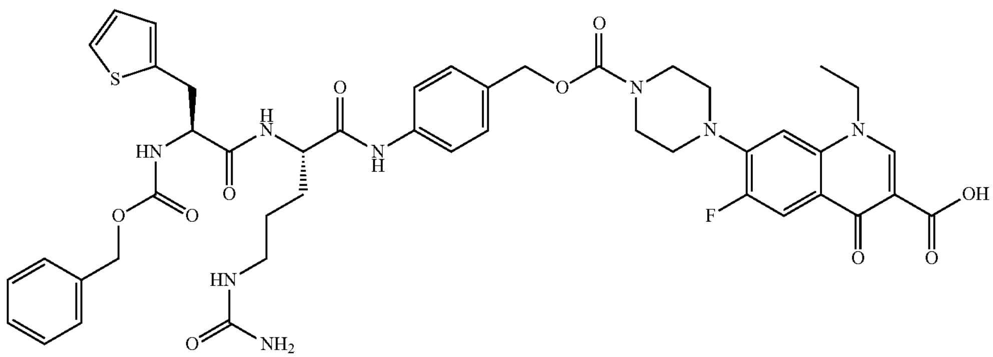 [SMILES: CCn1cc(C(=O)O)c(=O)c2cc(F)c(N3CCN(C(=O)OCc4ccc(NC(=O)[C@H](CCCNC(N)=O)NC(=O)[C@H](Cc5cccs5)NC(=O)OCc5ccccc5)cc4)CC3)cc21] | peptide | 0.224 | Cbz | 0.032208 | SKS |
| 44 | 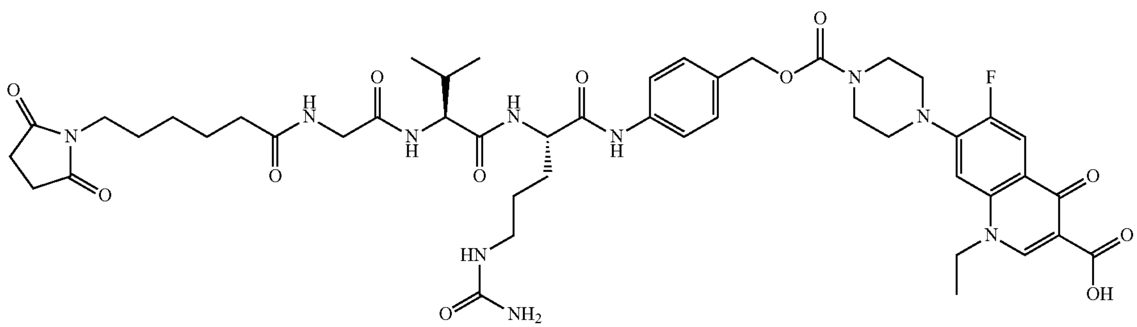 [SMILES: CCn1cc(C(=O)O)c(=O)c2cc(F)c(N3CCN(C(=O)OCc4ccc(NC(=O)[C@H](CCCNC(N)=O)NC(=O)[C@@H](NC(=O)CNC(=O)CCCCCN5C(=O)CCC5=O)C(C)C)cc4)CC3)cc21] | peptide | 0.205 | non-Cbz | 0.118705 | SKS |

-continued

| Example | Structure | Series | CATB Cleavage MS (Vmax/Km) | P3 | CATB Cleavage MS (Vmax/Km)-background corrected | Stereo |
|---|---|---|---|---|---|---|
| 45 | 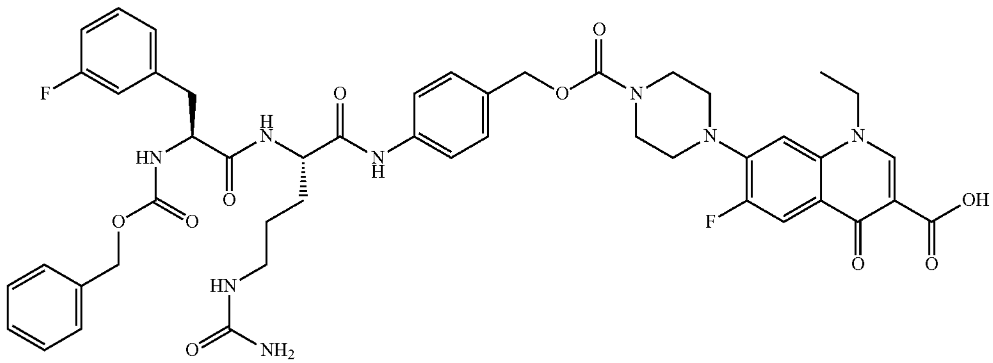 [SMILES: CCn1cc(C(=O)O)c(=O)c2cc(F)c(N3CCN(C(=O)OCc4ccc(NC(=O)[C@H](CCCNC(N)=O)NC(=O)[C@H](Cc5cccc(F)c5)NC(=O)OCc5ccccc5)cc4)CC3)cc21] | peptide | 0.204 | Cbz | 0.021417 | SKS |
| 46 | 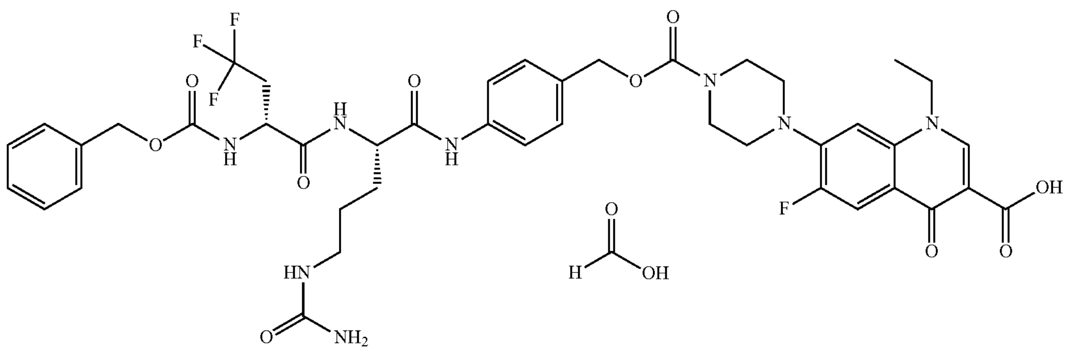 [SMILES: CCn1cc(C(=O)O)c(=O)c2cc(F)c(N3CCN(C(=O)OCc4ccc(NC(=O)[C@H](CCCNC(N)=O)NC(=O)[C@@H](CC(F)(F)F)NC(=O)OCc5ccccc5)cc4)CC3)cc21 ; O=CO] | peptide | 0.204 | Cbz | 0.041089 | SKS |

-continued

| Example | Structure | Series | CATB Cleavage MS (Vmax/Km) | P3 | CATB Cleavage MS (Vmax/Km)-background corrected | Stereo |
|---|---|---|---|---|---|---|
| 47 | (structure) | peptide | 0.168 | Cbz | 0.037286 | SKS |

-continued

| Example | Structure | Series | CATB Cleavage MS (Vmax/Km) | P3 | CATB Cleavage MS (Vmax/Km)-background corrected | Stereo |
|---|---|---|---|---|---|---|
| 48 | (structure) | peptide | 0.165 | Cbz | 0.068356 | SKS |

| Example | Structure | Series | CATB Cleavage MS (Vmax/Km) | P3 | CATB Cleavage MS (Vmax/Km)-background corrected | Stereo |
|---|---|---|---|---|---|---|
| 49 | 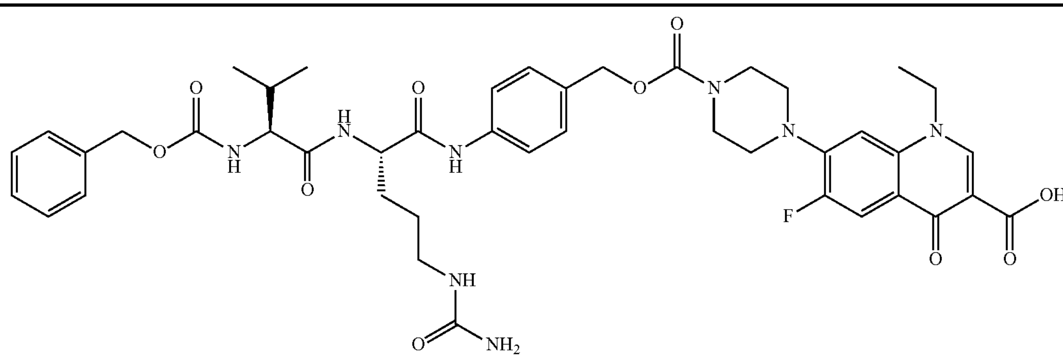 | peptide | 0.135 | Cbz | 0.041791 | SKS |
| 50 | 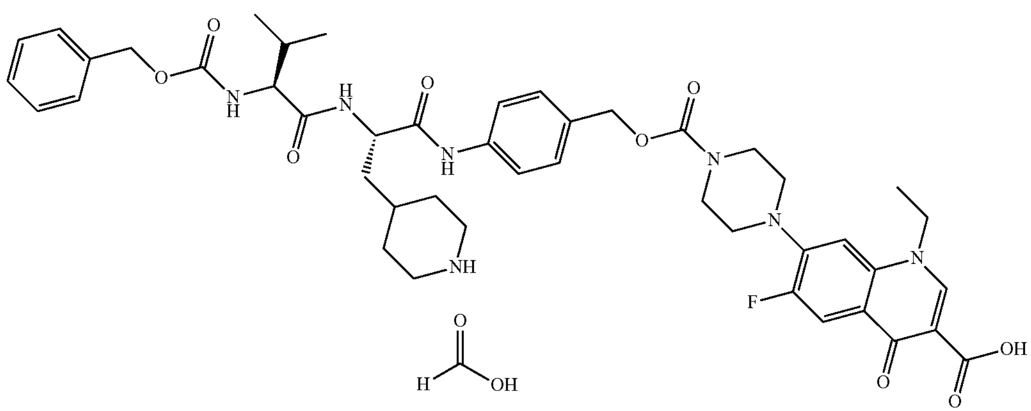 | peptide | 0.117 | Cbz | 0.025314 | SKS |

-continued

| Example | Structure | Series | CATB Cleavage MS (Vmax/Km) | P3 | CATB Cleavage MS Vmax/Km)-background corrected | Stereo |
|---|---|---|---|---|---|---|
| 51 | 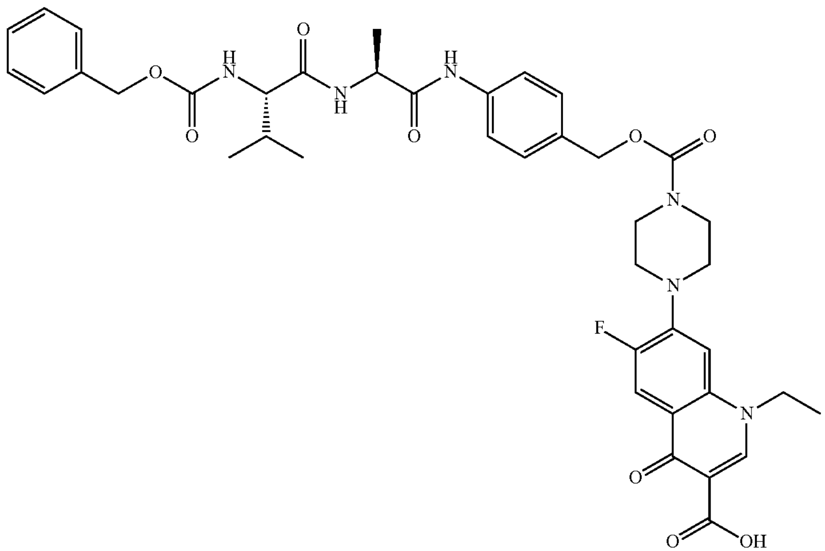 [SMILES: CCn1cc(C(=O)O)c(=O)c2cc(F)c(N3CCN(C(=O)OCc4ccc(NC(=O)[C@H](C)NC(=O)[C@@H](NC(=O)OCc5ccccc5)C(C)C)cc4)CC3)cc21] | peptide | 0.0786 | Cbz | 0.014192 | SKS |
| 52 | 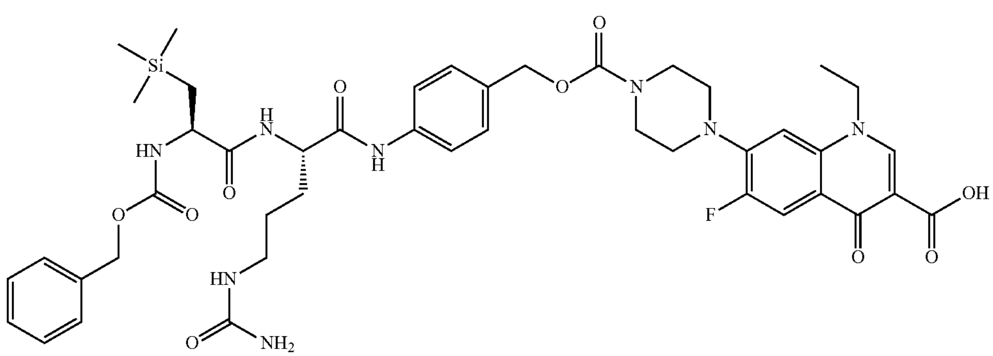 [SMILES: CCn1cc(C(=O)O)c(=O)c2cc(F)c(N3CCN(C(=O)OCc4ccc(NC(=O)[C@H](CCCNC(N)=O)NC(=O)[C@H](C[Si](C)(C)C)NC(=O)OCc5ccccc5)cc4)CC3)cc21] | peptide | 0.0261 | Cbz | 0.005928 | SUS |

-continued

| Example | Structure | Series | CATB Cleavage MS (Vmax/Km) | P3 | CATB Cleavage MS Vmax/Km)-background corrected | Stereo |
|---|---|---|---|---|---|---|
| 53 | 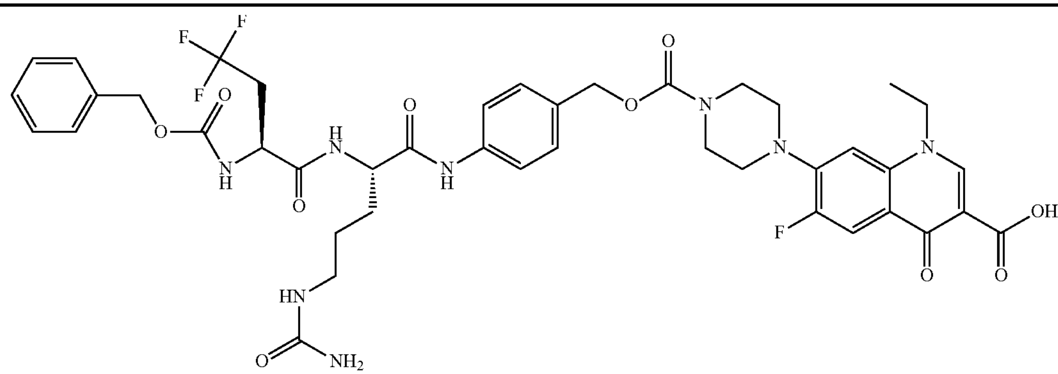 | peptide | 0.00262 | Cbz | 0.000848 | SKS |
| 54 | 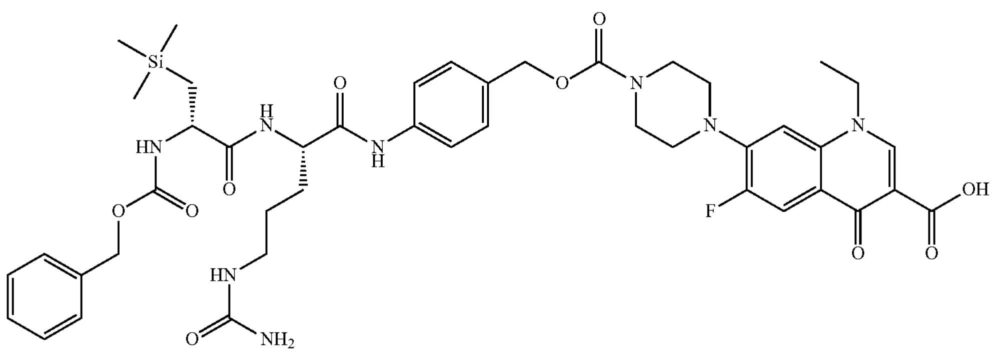 [SMILES: CCn1cc(C(=O)O)c(=O)c2cc(F)c(N3CCN(C(=O)OCc4ccc(NC(=O)[C@H](CCCNC(N)=O)NC(=O)[C@@H](C[Si](C)(C)C)NC(=O)OCc5ccccc5)cc4)CC3)cc21] | peptide | 0.00218 | Cbz | 0.000186 | SUS |

-continued

| Example | Structure | Series | CATB Cleavage MS (Vmax/Km) | P3 | CATB Cleavage MS Vmax/Km)- background corrected | Stereo |
|---|---|---|---|---|---|---|
| 55 | 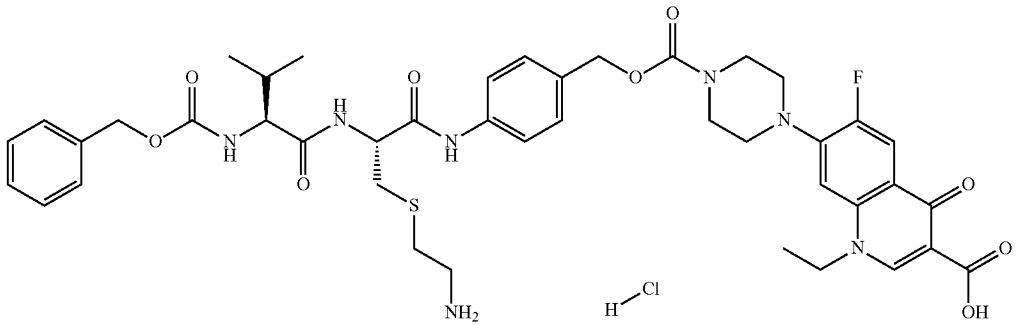 [SMILES: CCn1cc(C(=O)O)c(=O)c2cc(F)c(N3CCN(C(=O)OCc4ccc(NC(=O)[C@H](CSCCN)NC(=O)[C@@H](NC(=O)OCc5ccccc5)C(C)C)cc4)CC3)cc21 ; Cl] | peptide | | Cbz | 0.002961 | SKS |
| 56 | 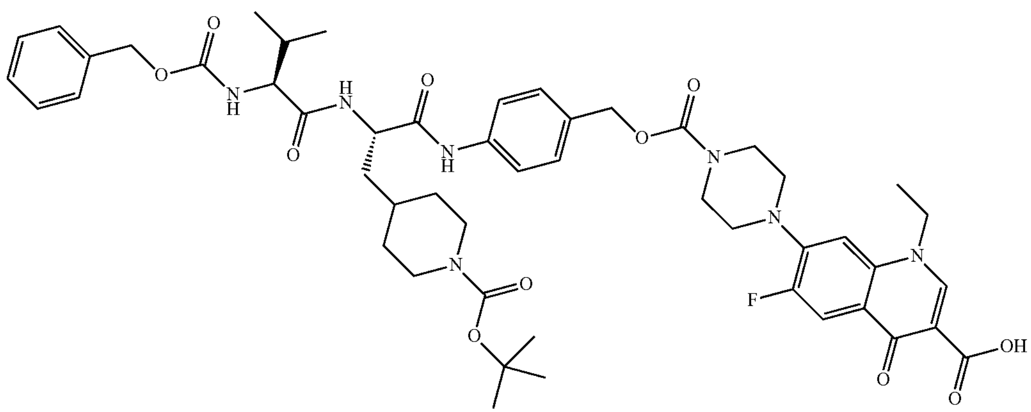 [SMILES: CCn1cc(C(=O)O)c(=O)c2cc(F)c(N3CCN(C(=O)OCc4ccc(NC(=O)[C@H](CC5CCN(C(=O)OC(C)(C)C)CC5)NC(=O)[C@@H](NC(=O)OCc5ccccc5)C(C)C)cc4)CC3)cc21] | peptide | | Cbz | | SKS |

-continued
| Example | Structure | Series | CATB Cleavage MS (Vmax/Km) | P3 | CATB Cleavage MS (Vmax/Km)-background corrected | Stereo |
|---|---|---|---|---|---|---|
| 57 | 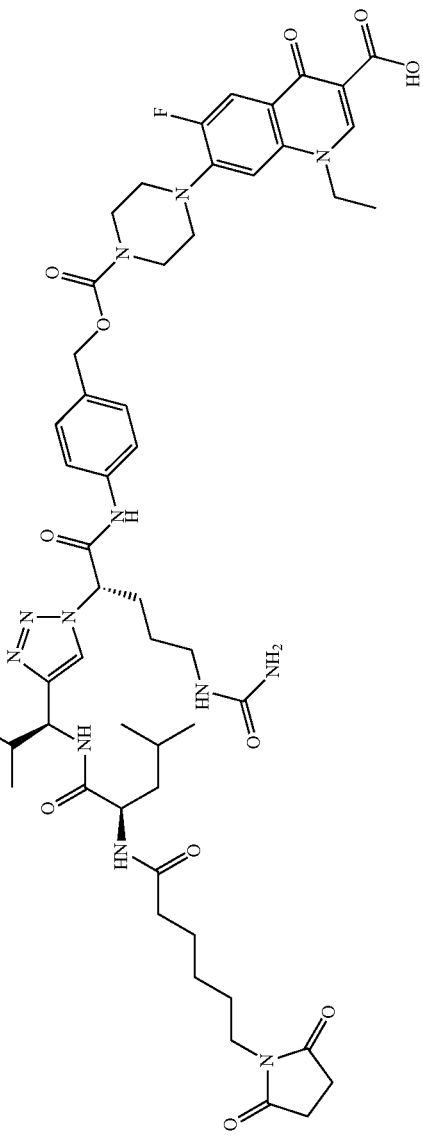 | triazole | 0.036 | non-Cbz | 0.007780 | SUS |

-continued
| Example | Structure | Series | CATB Cleavage MS (Vmax/Km) | P3 | CATB Cleavage MS Vmax/Km)-background corrected | Stereo |
|---|---|---|---|---|---|---|
| 58 | 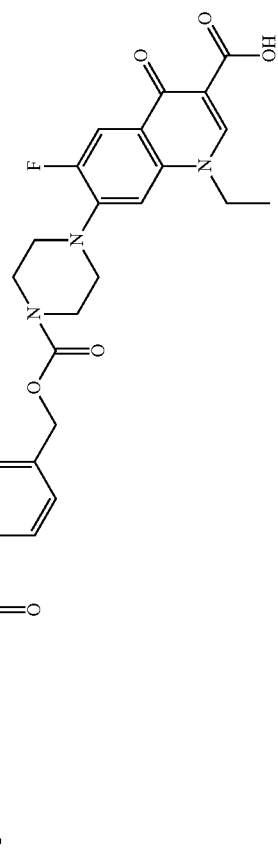 | triazole | 0.0176 | Cbz | 0.003519 | SKS |

| Example | Structure | Series | CATB Cleavage MS (Vmax/Km) | P3 | CATB Cleavage MS (Vmax/Km)-background corrected | Stereo |
|---|---|---|---|---|---|---|
| 59 | 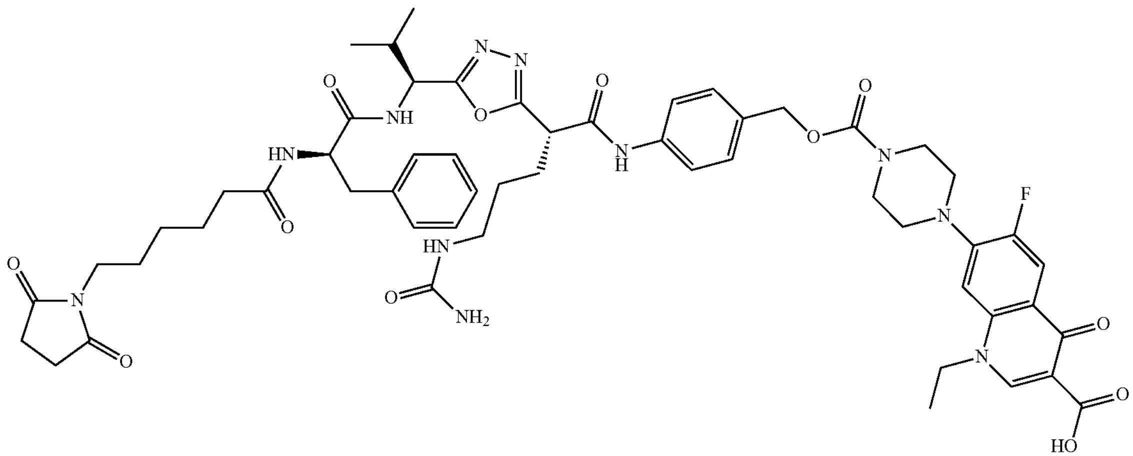 [SMILES: CCn1cc(C(=O)O)c(=O)c2cc(F)c(N3CCN(C(=O)OCc4ccc(NC(=O)[C@H](CCCNC(N)=O)c5nnc([C@@H](NC(=O)[C@@H](Cc6ccccc6)NC(=O)CCCCCN6C(=O)CCC6=O)C(C)C)o5)cc4)CC3)cc21] | triazole | 0.013 | non-Cbz | 0.003849 | SUS |
| 60 | 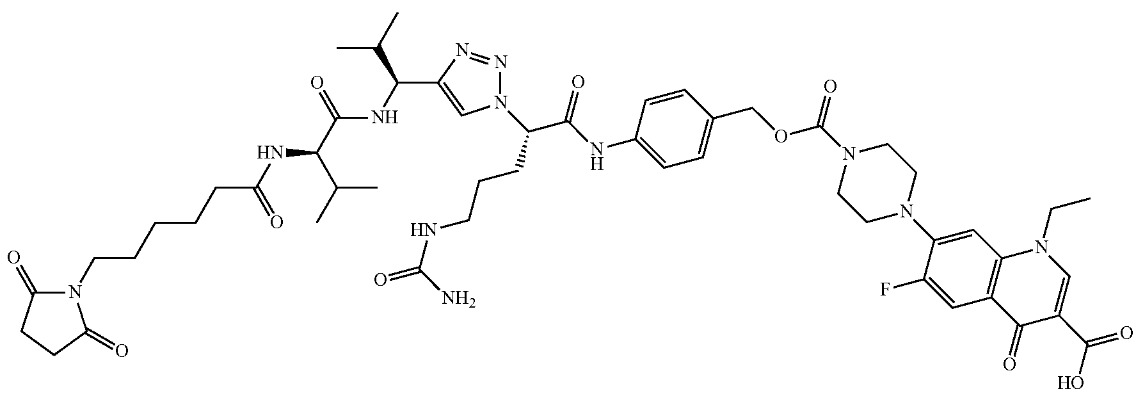 [SMILES: CCn1cc(C(=O)O)c(=O)c2cc(F)c(N3CCN(C(=O)OCc4ccc(NC(=O)[C@H](CCCNC(N)=O)n5cc([C@@H](NC(=O)[C@H](NC(=O)CCCCCN6C(=O)CCC6=O)C(C)C)C(C)C)nn5)cc4)CC3)cc21] | triazole | 0.010 | non-Cbz | 0.004285 | SUS |

-continued

| Example | Structure | Series | CATB Cleavage MS (Vmax/Km) | P3 | CATB Cleavage MS Vmax/Km)-background corrected | Stereo |
|---|---|---|---|---|---|---|
| 61 | 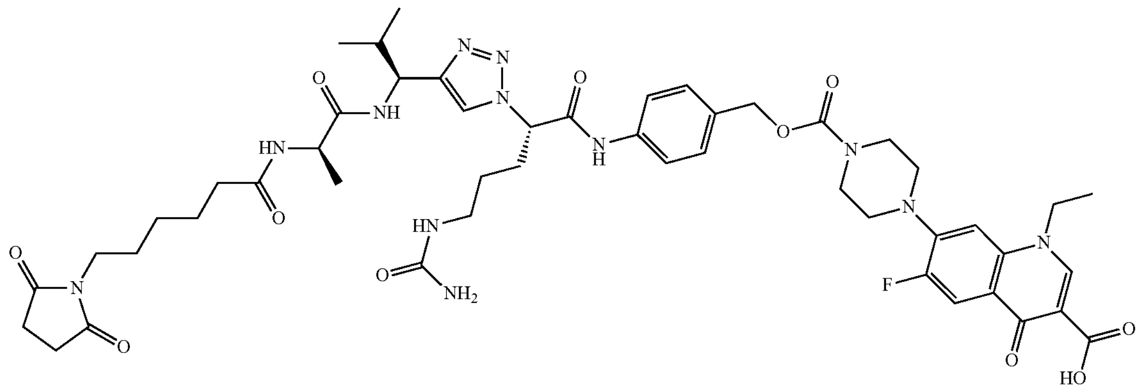 [SMILES: CCn1cc(C(=O)O)c(=O)c2cc(F)c(N3CCN(C(=O)OCc4ccc(NC(=O)[C@H](CCCNC(N)=O)n5cc([C@@H](NC(=O)[C@@H](C)NC(=O)CCCCCN6C(=O)CCC6=O)C(C)C)nn5)cc4)CC3)cc21] | triazole | 0.0050 | non-Cbz | 0.003133 | SUS |
| 62 | 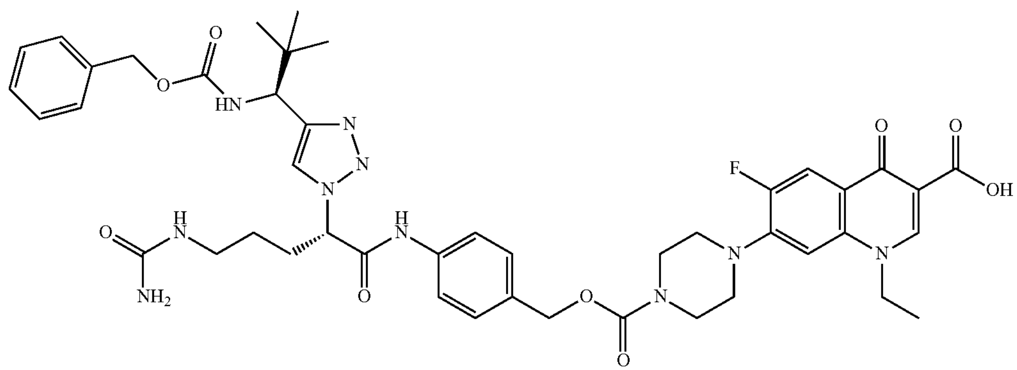 [SMILES: CCn1cc(C(=O)O)c(=O)c2cc(F)c(N3CCN(C(=O)OCc4ccc(NC(=O)[C@H](CCCNC(N)=O)N5C=C([C@@H](NC(=O)OCc6ccccc6)C(C)(C)C)NN5)cc4)CC3)cc21] | triazole | 0.00467 | Cbz | 0.000281 | SKS |

-continued

| Example | Structure | Series | CATB Cleavage MS (Vmax/Km) | P3 | CATB Cleavage MS (Vmax/Km)-background corrected | Stereo |
|---|---|---|---|---|---|---|
| 63 | 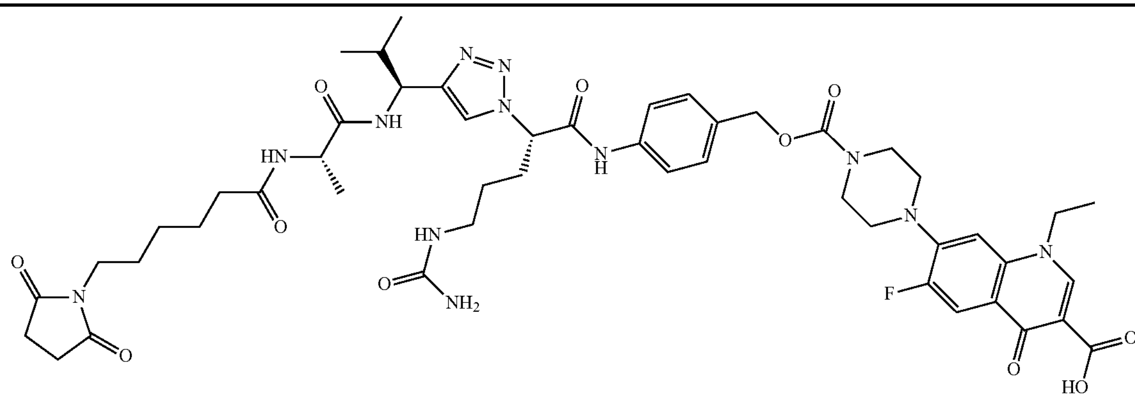 | triazole | 0.0030 | non-Cbz | 0.000638 | SUS |
| 64 | 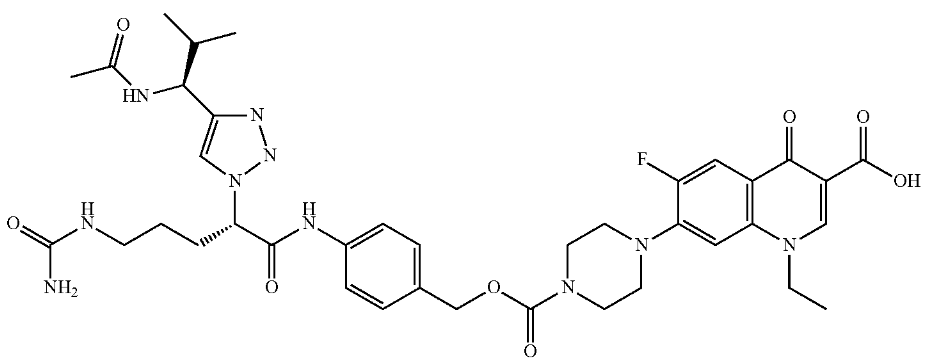 [SMILES: CCn1cc(C(=O)O)c(=O)c2cc(F)c(N3CCN(C(=O)OCc4ccc(NC(=O)[C@H](CCCNC(N)=O)N5C=C([C@@H](NC(C)=O)C(C)C)NN5)cc4)CC3)cc21] | triazole | 0.00273 | non-Cbz | | SKS |

| Example | Structure | Series | CATB Cleavage MS (Vmax/Km) | P3 | CATB Cleavage MS (Vmax/Km)-background corrected | Stereo |
|---|---|---|---|---|---|---|
| 65 | 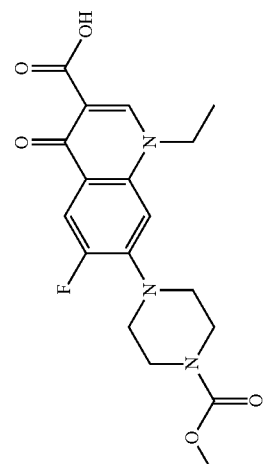 | triazole | 0.00272 | Cbz | 0.000199 | SKS |
| 66 | 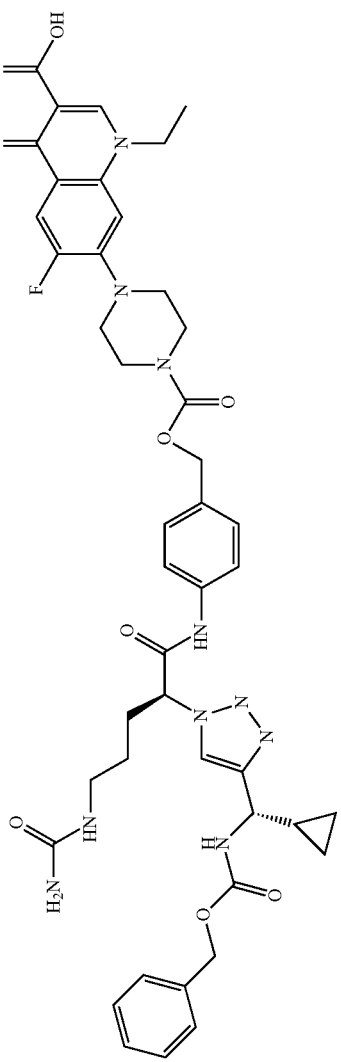 | triazole | 0.00218 | Cbz | 0.000169 | SKS |

-continued
| Example | Structure | Series | CATB Cleavage MS (Vmax/Km) | P3 | CATB Cleavage MS (Vmax/Km)-background corrected | Stereo |
|---|---|---|---|---|---|---|
| 67 | 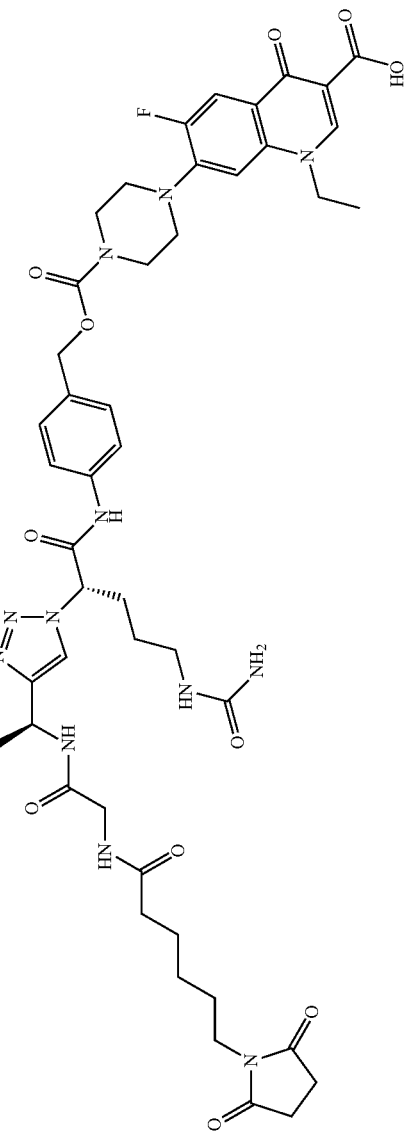 | triazole | 0.0020 | non-Cbz | 0.000245 | SKS |
| 68 | 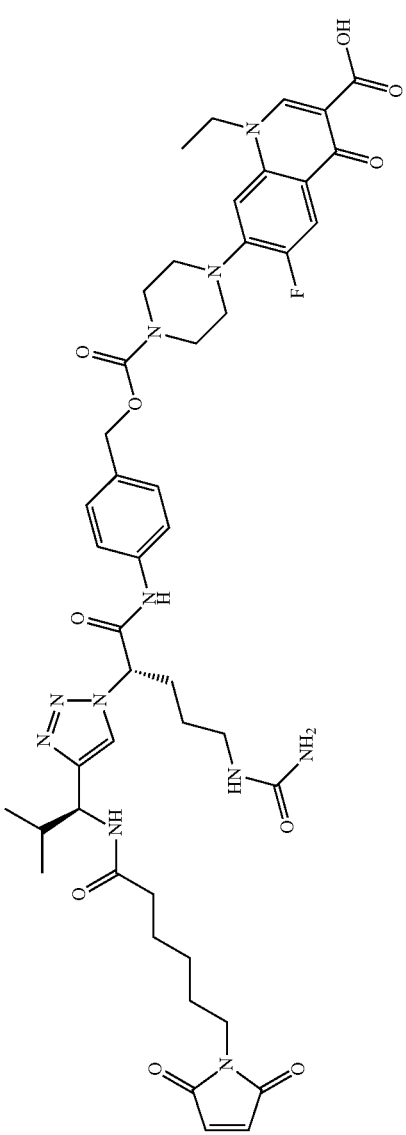 | triazole | 0.0012 | | 0.001601 | SKS |

| Example | Structure | Series | CATB Cleavage MS (Vmax/Km) | P3 | CATB Cleavage MS (Vmax/Km)-background corrected | Stereo |
|---|---|---|---|---|---|---|
| 69 | 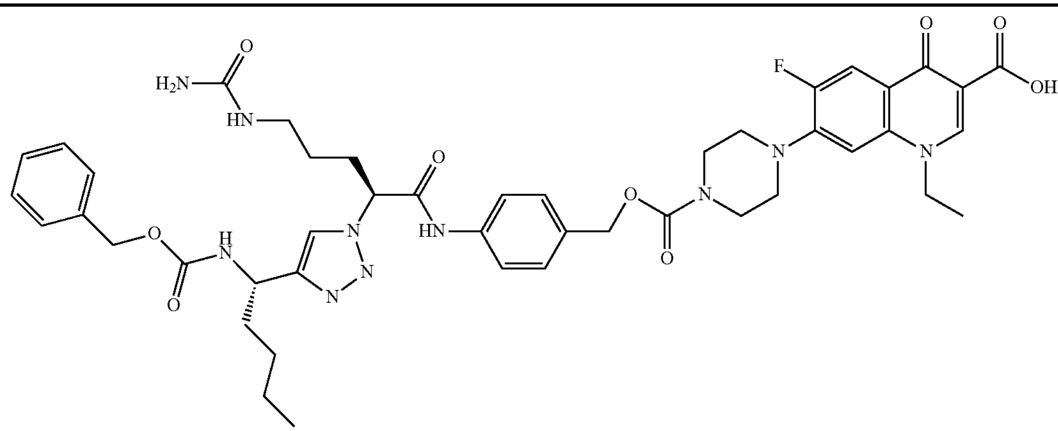 | triazole | 0.000852 | Cbz | | SKS |
| 70 | 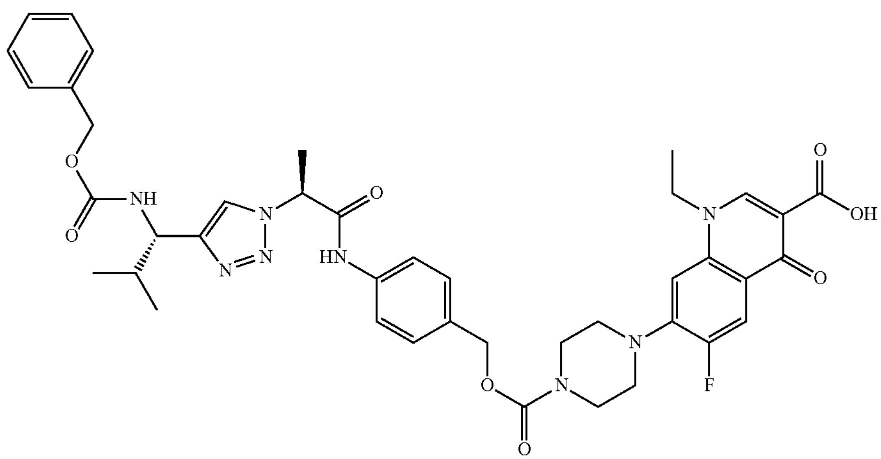 [SMILES: CCn1cc(C(=O)O)c(=O)c2cc(F)c(N3CCN(C(=O)OCc4ccc(NC(=O)[C@H](C)n5cc([C@@H](NC(=O)OCc6ccccc6)C(C)C)nn5)cc4)CC3)cc21] | triazole | 0.000603 | Cbz | | SKS |

-continued

| Example | Structure | Series | CATB Cleavage MS (Vmax/Km) | P3 | CATB Cleavage MS (Vmax/Km)-background corrected | Stereo |
|---|---|---|---|---|---|---|
| 71 | 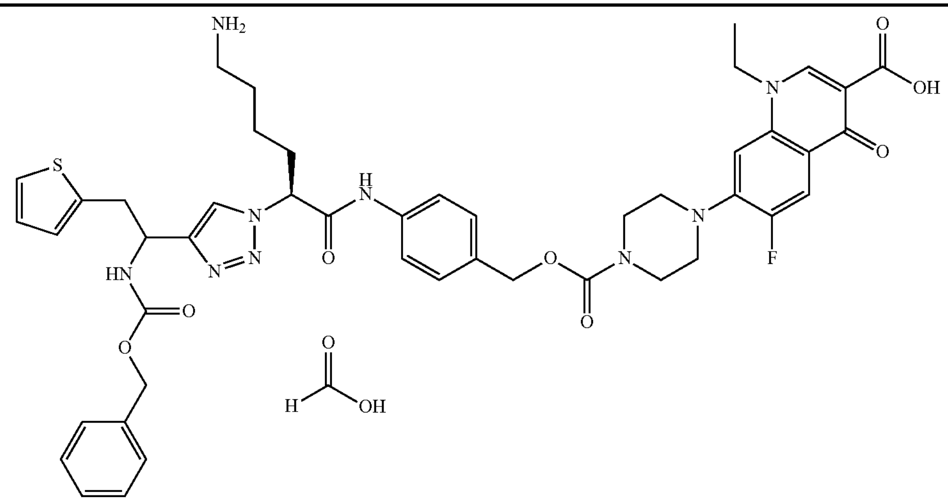 | triazole | 0.000571 | Cbz | 0.000156 | ME |
| 72 | 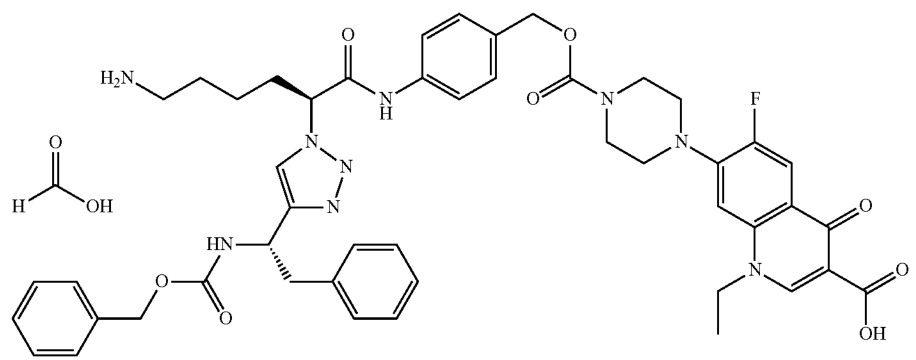 [SMILES: CCn1cc(C(=O)O)c(=O)c2cc(F)c(N3CCN(C(=O)OCc4ccc(NC(=O)[C@H](CCCCN)N5C=C([C@H](Cc6ccccc6)NC(=O)OCc6ccccc6)NN5)cc4)CC3)cc21 ; O=CO] | triazole | 0.000437 | Cbz | 0.000108 | SKS |

-continued
| Example | Structure | Series | CATB Cleavage MS (Vmax/Km) | P3 | CATB Cleavage MS (Vmax/Km)-background corrected | Stereo |
|---|---|---|---|---|---|---|
| 73 | 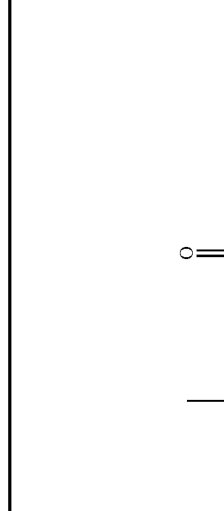 | triazole | 0.000241 | Cbz | 0.000059 | SKS |
| 74 | 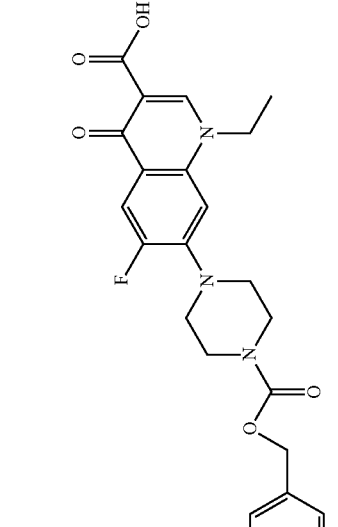 | triazole | 0.000195 | Cbz | | SKS |

-continued

| Example | Structure | Series | CATB Cleavage MS (Vmax/Km) | P3 | CATB Cleavage MS (Vmax/Km)-background corrected | Stereo |
|---|---|---|---|---|---|---|
| 75 | 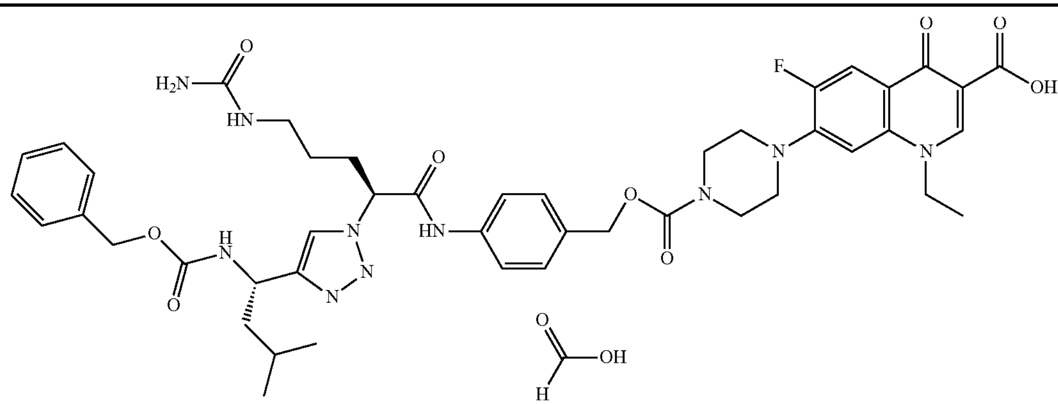 | triazole | 0.000152 | Cbz | | SKS |
| 76 | 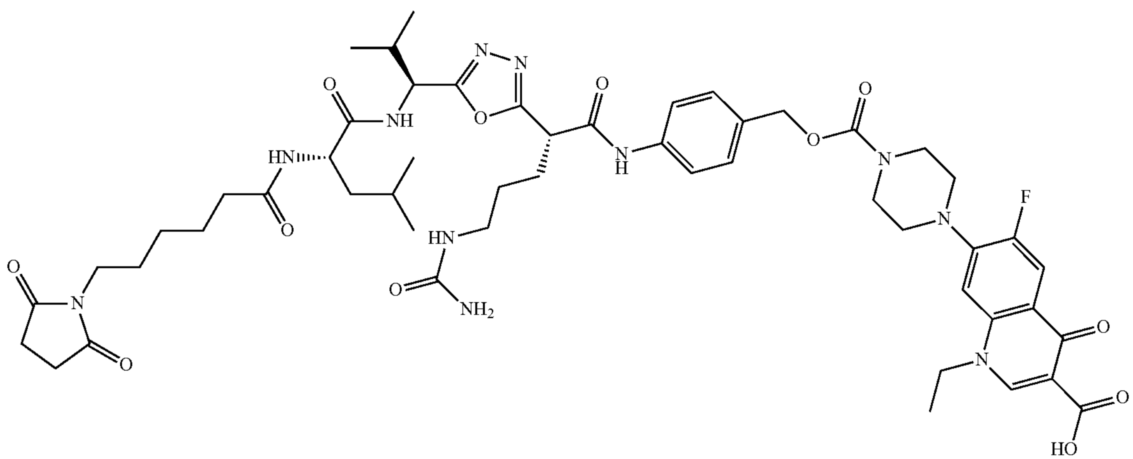 [SMILES: CCn1cc(C(=O)O)c(=O)c2cc(F)c(N3CCN(C(=O)OCc4ccc(NC(=O)[C@H](CCCNC(N)=O)c5nnc([C@@H](NC(=O)[C@H](CC(C)C)NC(=O)CCCCCN6C(=O)CCC6=O)C(C)C)o5)cc4)CC3)cc21] | triazole | 0.0 | non-Cbz | 0.000138 | SUS |

| Example | Structure | Series | CATB Cleavage MS (Vmax/Km) | P3 | CATB Cleavage MS Vmax/Km)-background corrected | Stereo |
|---|---|---|---|---|---|---|
| 77 | 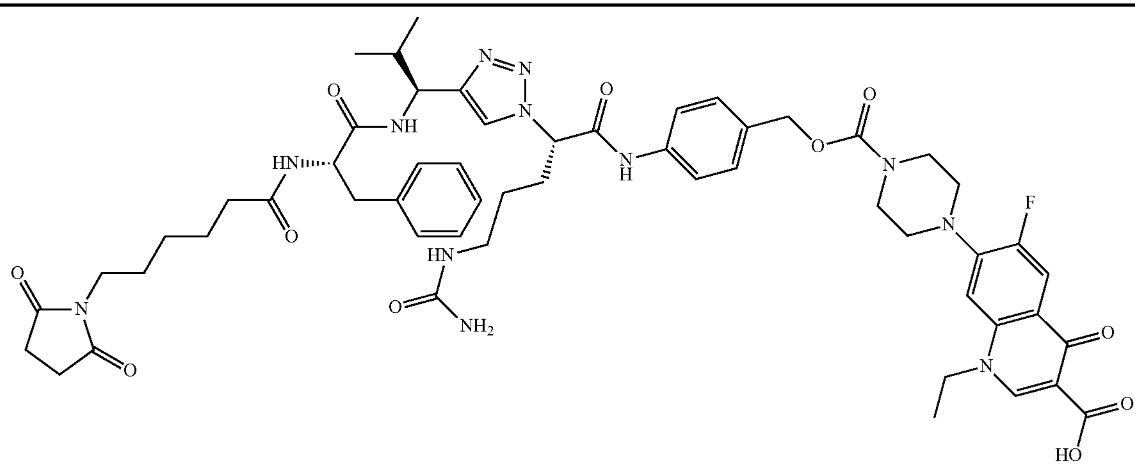 | triazole | 0.0 | non-Cbz | 0.000022 | SUS |
| 78 | 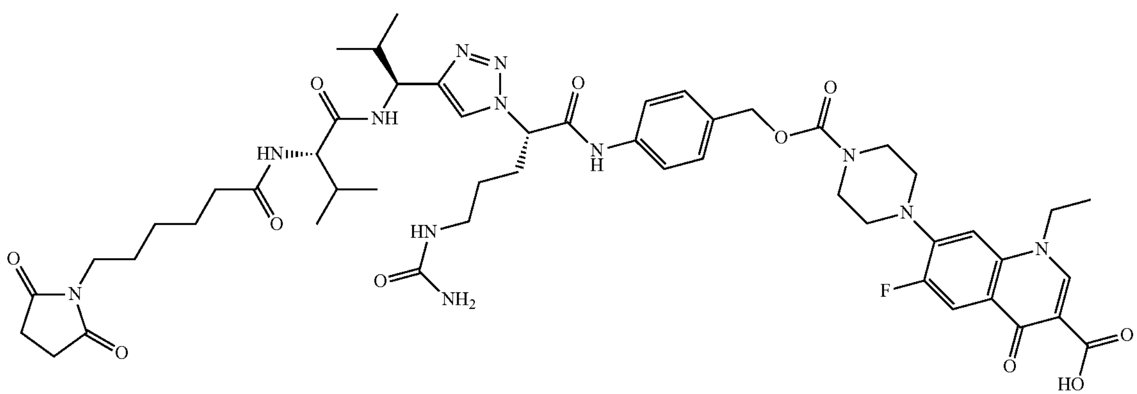 [SMILES: CCn1cc(C(=O)O)c(=O)c2cc(F)c(N3CCN(C(=O)OCc4ccc(NC(=O)[C@H](CCCNC(N)=O)n5cc([C@@H](NC(=O)[C@@H](NC(=O)CCCCCN6C(=O)CCC6=O)C(C)C)C(C)C)nn5)cc4)CC3)cc21] | triazole | 0.0 | non-Cbz | | SUS |

-continued

| Example | Structure | Series | CATB Cleavage MS (Vmax/Km) | P3 | CATB Cleavage MS Vmax/Km)-background corrected | Stereo |
|---|---|---|---|---|---|---|
| 79 | 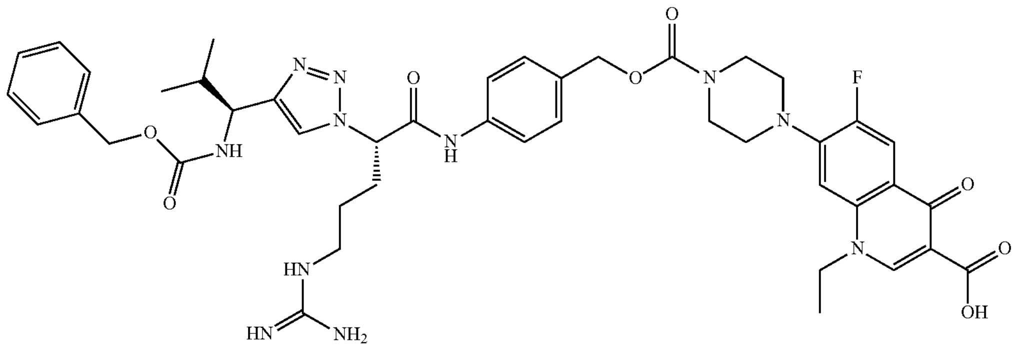 [SMILES: CCn1cc(C(=O)O)c(=O)c2cc(F)c(N3CCN(C(=O)OCc4ccc(NC(=O)[C@H](CCCNC(=N)N)n5cc([C@@H](NC(=O)OCc6ccccc6)C(C)C)nn5)cc4)CC3)cc21] | triazole | 0.0 | Cbz | 0.005698 | SKS |
| 80 | 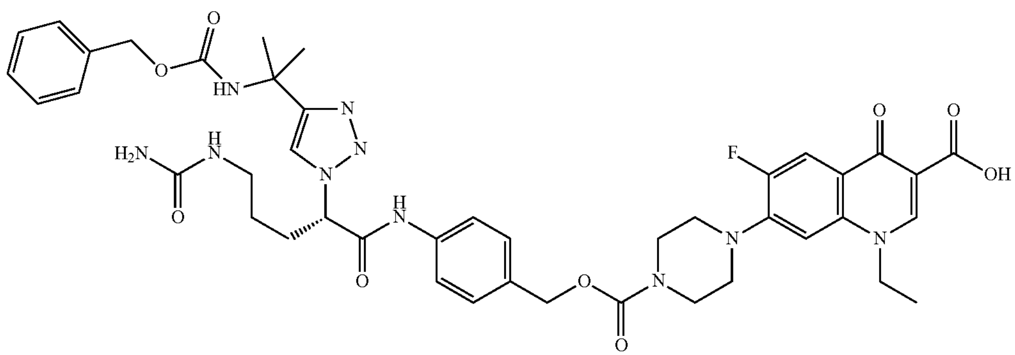 [SMILES: CCn1cc(C(=O)O)c(=O)c2cc(F)c(N3CCN(C(=O)OCc4ccc(NC(=O)[C@H](CCCNC(N)=O)N5C=C(C(C)(C)NC(=O)OCc6ccccc6)NN5)cc4)CC3)cc21] | triazole | | Cbz | | SKS |

| Example | Structure | Series | CATB Cleavage MS (Vmax/Km) | P3 | CATB Cleavage MS Vmax/Km)-background corrected | Stereo |
|---|---|---|---|---|---|---|
| 81 | 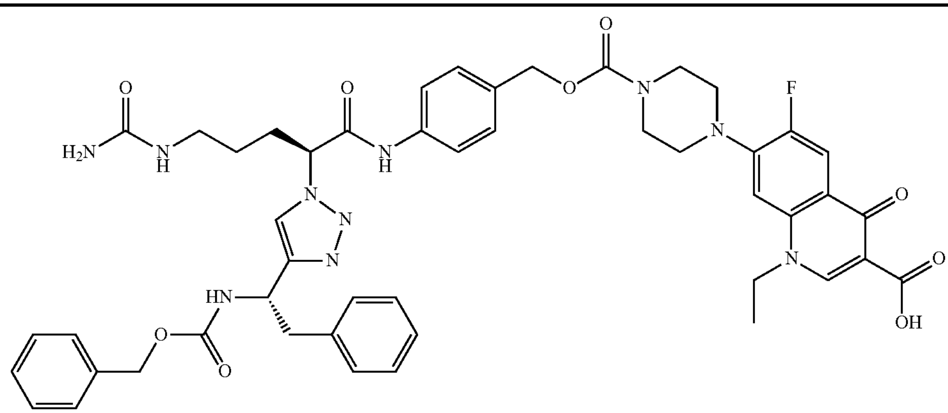 | triazole | | Cbz | 0.000019 | SKS |
| 82 | 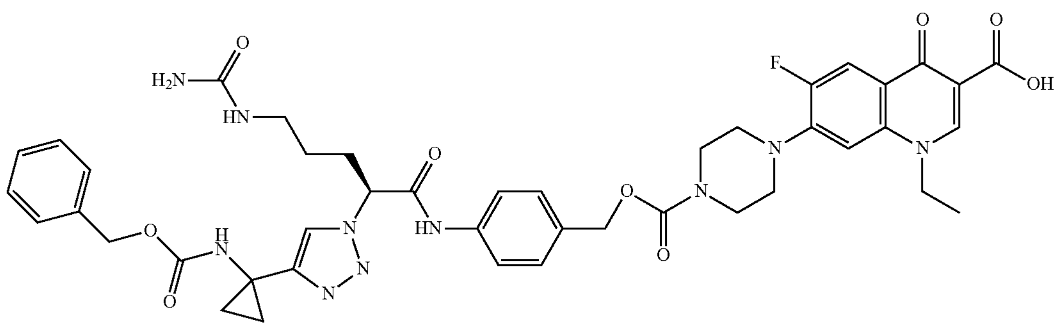 [SMILES: CCn1cc(C(=O)O)c(=O)c2cc(F)c(N3CCN(C(=O)OCc4ccc(NC(=O)[C@H](CCCNC(N)=O)N5C=C(C6(NC(=O)OCc7ccccc7)CC6)NN5)cc4)CC3)cc21] | triazole | | Cbz | | SKS |

-continued

| Example | Structure | Series | CATB Cleavage MS (Vmax/Km) | P3 | CATB Cleavage MS Vmax/Km)-background corrected | Stereo |
|---|---|---|---|---|---|---|
| 83 | 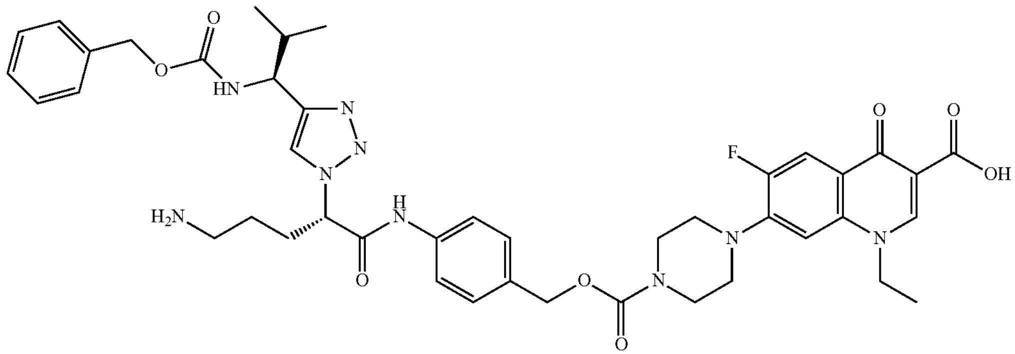 [SMILES: CCn1cc(C(=O)O)c(=O)c2cc(F)c(N3CCN(C(=O)OCc4ccc(NC(=O)[C@H](CCCN)N5C=C([C@@H](NC(=O)OCc6ccccc6)C(C)C)NN5)cc4)CC3)cc21] | triazole | | Cbz | | SKS |
| 84 | 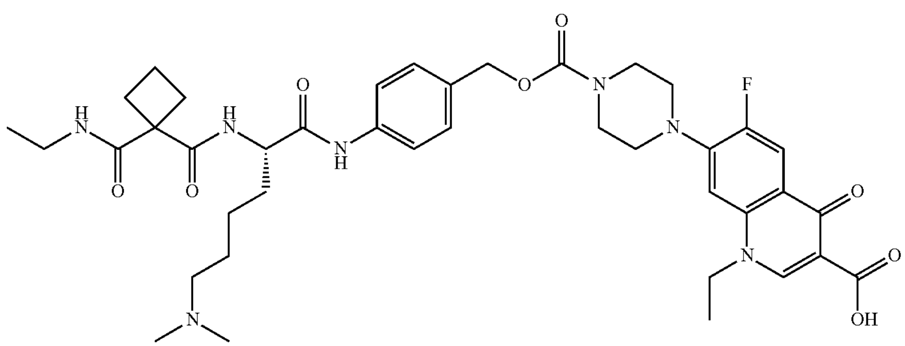 [SMILES: CCNC(=O)C1(C(=O)N[C@@H](CCCCN(C)C)C(=O)Nc2ccc(COC(=O)N3CCN(c4cc5c(cc4F)c(=O)c(C(=O)O)cn5CC)CC3)cc2)CCC1] | cyclobutane-1,1-dicarbonyl | | Non-Cbz | 0.009691 | SKS |

-continued
| Example | Structure | Series | CATB Cleavage MS (Vmax/Km) | P3 | CATB Cleavage MS (Vmax/Km)-background corrected | Stereo |
|---|---|---|---|---|---|---|
| 85 | 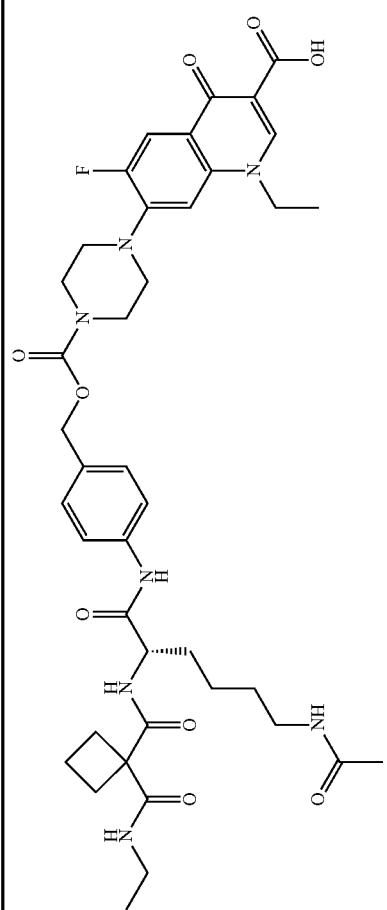 | cyclobutane-1,1-dicarbonyl | | Non-Cbz | 0.001715 | SKS |
| 86 | 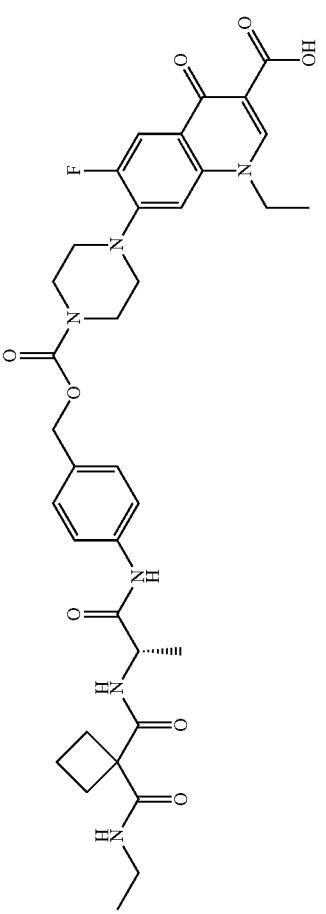 | cyclobutane-1,1-dicarbonyl | | Non-Cbz | 0.007420 | SKS |

ADC Linker-Drug Structures
| Linker-drug compound | Corresponding ADC | Structure | Name |
|---|---|---|---|
| CBI-PBD LD1 | | 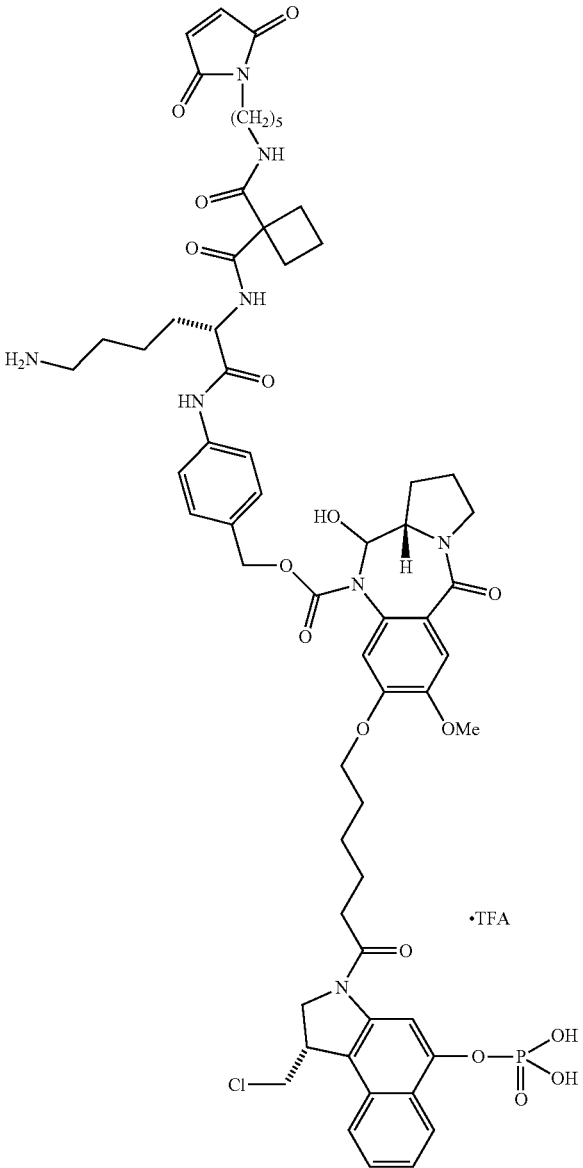 | (11 a S)-4-((S)-6-amino-2-(1-(5-(2,5-dioxo-2,5-dihydro-1H-pyrrol-1-yl)pentylcarbamoyl)cyclobutanecarboxamido)hexanamido)benzyl 8-(6-((S)-1-(chloromethyl)-5-(phosphonooxy)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate |

-continued

| Linker-drug compound | Corresponding ADC | Structure | Name |
|---|---|---|---|
| CBI-PBD LD2 | NaPi2b CBI-PBD ADC2-1 and CD33 CBI-PBD ADC2-2 | 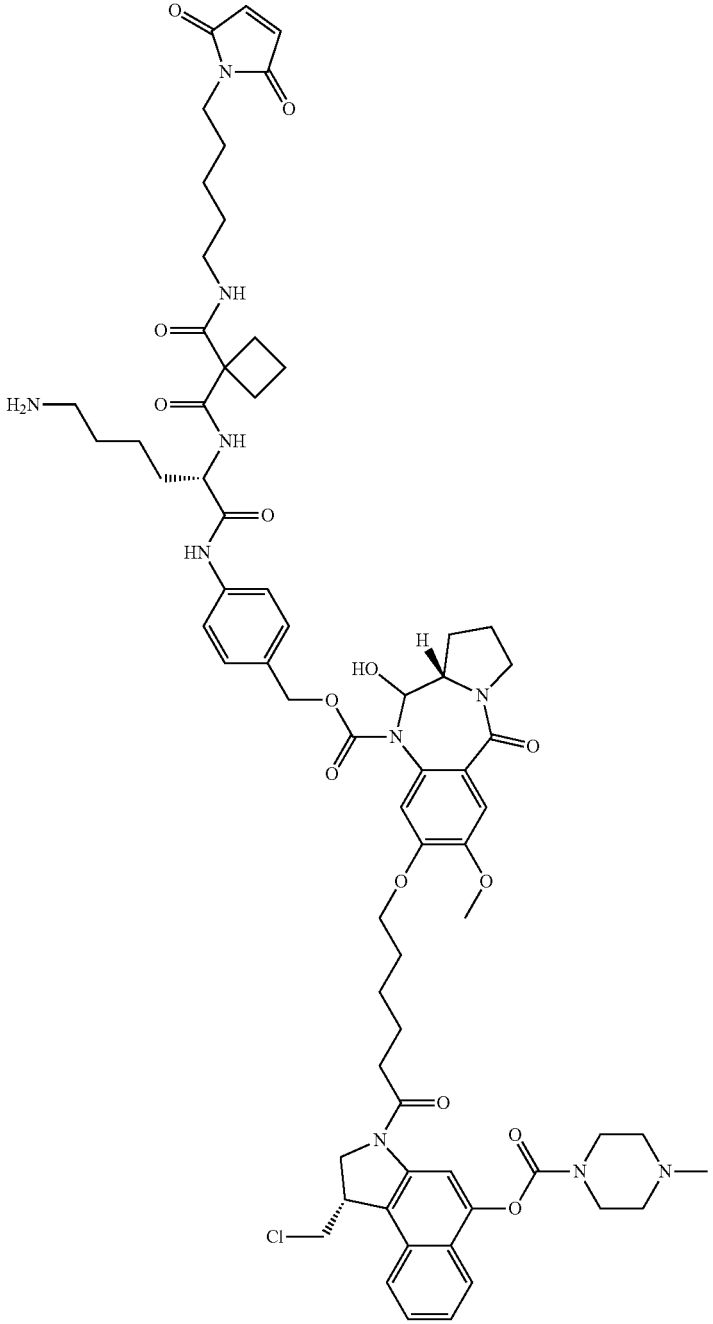 [SMILES: COc1cc2c(cc1OCCCCCC(=O)N1C[C@@H](CCl)c3c1cc(OC(=O)N1CCN(C)CC1)c1ccccc31)N(C(=O)OCc1ccc(NC(=O)[C@H](CCCCN)NC(=O)C3(C(=O)NCCCCCN4C(=O)C=CC4=O)CCC3)cc1)C(O)[C@@H]1CCCN1C2=O] | [4-[[(2S)-6-amino-2-[[1-[5-(2,5-dioxopyrrol-1-yl)pentylcarbamoyl]cyclobutanecarbonyl]amino]hexanoyl]amino]phenyl]methyl(6aS)-3-[6-[(1S)-1-(chloromethyl)-5-(4-methylpiperazine-1-carbonyl)oxy-1,2-dihydrobenzo[e]indol-3-yl]-6-oxo-hexoxy]-6-hydroxy-2-methoxy-11-oxo-6a,7,8,9-tetrahydro-6H-pyrrolo[2,1-c][1,4]benzodiazepine-5-carboxylate |

-continued

| Linker-drug compound | Corresponding ADC | Structure | Name |
|---|---|---|---|
| CBI-PBD LD3 | NaPi2b CBI-PBD ADC3-1 and CD33 CBI-PBD ADC3-2 | 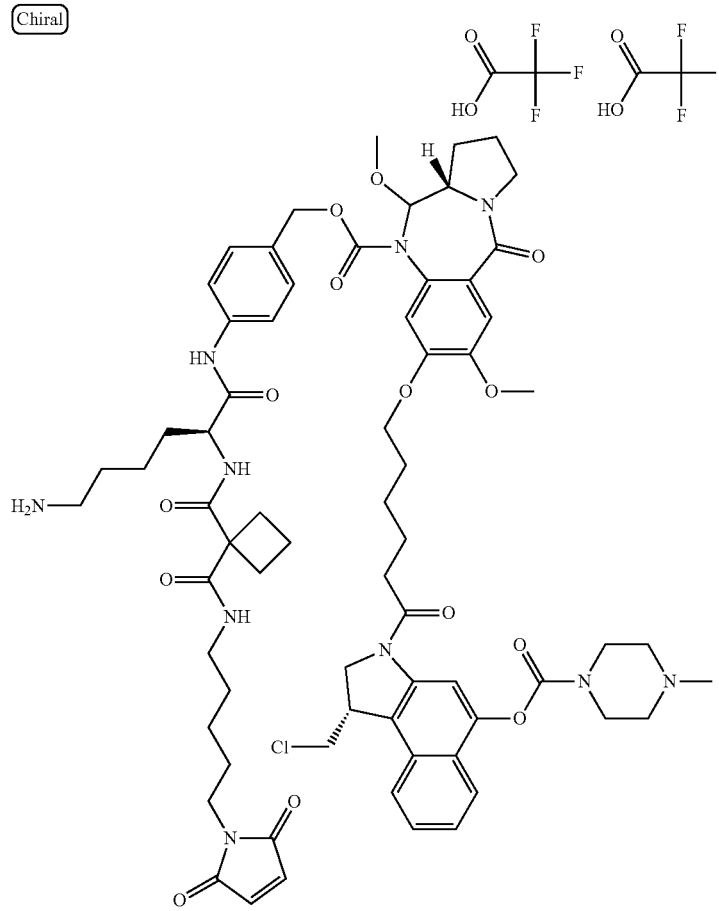 | [4-[[(2S)-6-amino-2-[[1-[5-(2,5-dioxopyrrol-1-yl)pentylcarbamoyl]cyclobutanecarbonyl]amino]hexanoyl]amino]phenyl]methyl (6aS)-3-[6-[(1S)-1-(chloromethyl)-5-(4-methylpiperazine-1-carbonyl)oxy-1,2-dihydrobenzo[e]indol-3-yl]-6-oxo-hexoxyl-2,6-dimethoxy-11-oxo-6a,7,8,9-tetrahydro-6H-pyrrolo[2,1-c][1,4]benzodiazepine-5-carboxylate;2,2,2-trifluoroacetic acid |
| CBI-CBI LD4 | | 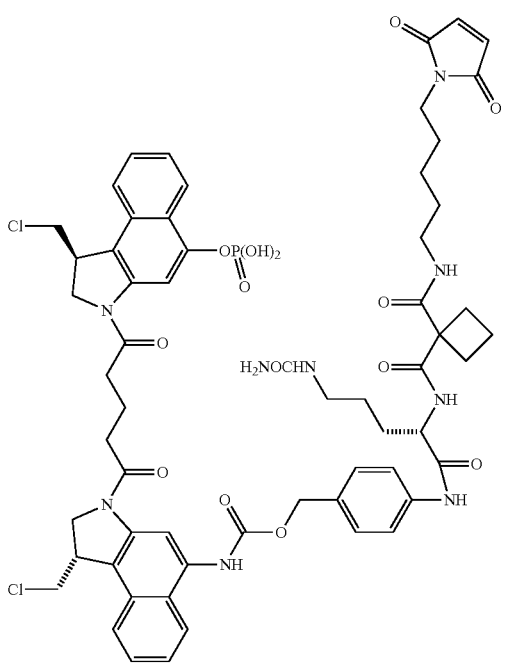 | 4-((S)-2-(1-(5-(2,5-dioxo-2,5-dihydro-1H-pyrrol-1-yl)pentylcarbamoyl)cyclobutanecarboxamido)-5-ureidopentanamido)benzyl (S)-1-(chloromethyl)-3-(5-((S)-1-(chloromethyl)-5-(phosphonooxy)-1H-benzo[e]indol-3(2H)-yl)-5-oxopentanoyl)-2,3-dihydro-1H-benzo[e]indol-5-ylcarbamate |

| Linker-drug compound | Corresponding ADC | Structure | Name |
|---|---|---|---|
| CBI-CBI LD5 | anti-Napi2b 10H1.11.4B LC K149C (CBI-CBI LD5) and anti-CD22 10F4v3 LC K149C (CBI-CBI LD5) | 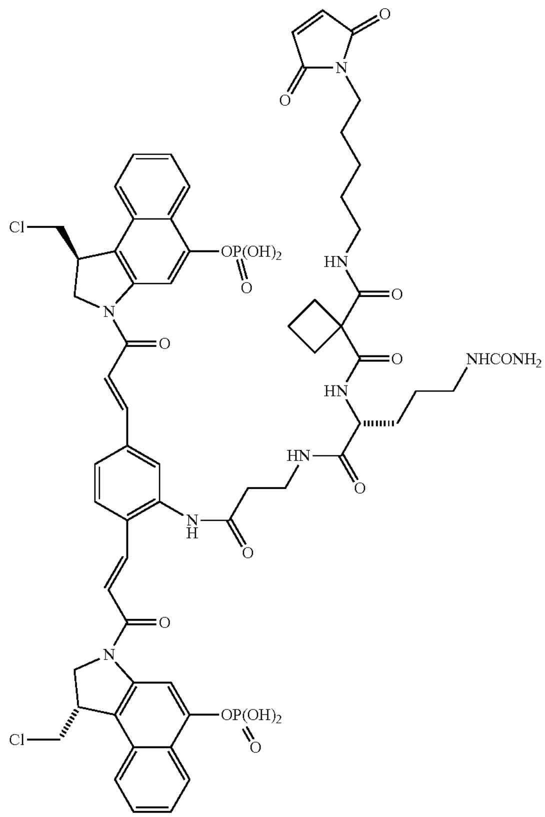 | 4-((S)-2-(1-(5-(2,5-dioxo-2,5-dihydro-1H-pyrrol-1-yl)pentylcarbamoyl)cyclobutanecarboxamido)-5-ureidopentanamido)benzyl 2,5-bis((E)-3-((S)-1-(chloromethyl)-5-(phosphonooxy)-1H-benzo[e]indol-3(2H)-yl)-3-oxoprop-1-enyl)phenylcarbamate |

| Linker-drug compound | Corresponding ADC | Structure | Name |
|---|---|---|---|
| CBI-CBI LD6 | anti-Napi2b 10H1.11.4B LC K149C (CBI-CBI LD6)/ anti-CD22 10F4v3 LC K149C (CBI-CBI LD6) | 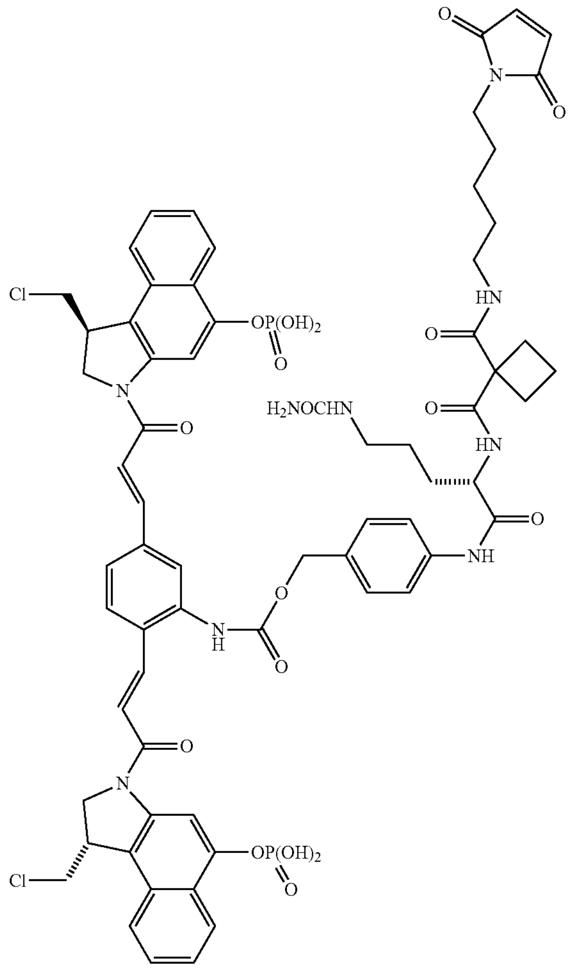 | 4-((S)-2-(1-(5-(2,5-dioxo-2,5-dihydro-1H-pyrrol-1-yl)pentylcarbamoyl)cyclobutanecarboxamido)-5-ureidopentanamido)benzyl 2,5-bis((E)-3-((S)-1-(chloromethyl)-5-(phosphonooxy)-1H-benzo[e]indol-3 (2H)-yl)-3-oxoprop-1-enyl)phenylcarbamate |

Sequences

NaPi2b humanized antibody:

In one embodiment, the NaPi2b antibody of ADCs of the present invention comprises three light chain hypervariable regions and three heavy chain hypervariable regions (SEQ ID NO: 1-6), the sequences of which are shown below.

In one embodiment, the NaPi2b antibody of ADCs of the present invention comprises the variable light chain sequence of SEQ ID NO: 7 and the variable heavy chain sequence of SEQ ID NO: 8 In one embodiment, the NaPi2b antibody of ADCs of the present invention comprises the light chain sequence of SEQ ID NO: 9 and the heavy chain sequence of SEQ ID NO: 10

| 10H1.11.4B HVR-L1 | RSSETLVHSSGNTYLE | Seq ID No: 1 |
|---|---|---|
| 10H1.11.4B HVR-L2 | RVSNRFS | Seq ID No: 2 |
| 10H1.11.4B HVR-L3 | FQGSFNPLT | Seq ID No: 3 |
| 10H1.11.4B HVR-H1 | GFSFSDFAMS | Seq ID No: 4 |
| 10H1.11.4B HVR-H2 | ATIGRVAFHTYYPDSMKG | Seq ID No: 5 |
| 10H1.11.4B HVR-H3 | ARHRGFDVGHFDF | Seq ID No: 6 |
| 10H1.11.4B $V_L$ | DIQMTQSPSSLSASVGDRVTITCRSSETLVHSSGNTYLEWYQQKPGKAPKLLIYRVSNRFSGVPSRFSGSGSGTDFTLTISSLQPEDFATYYCFQGSFNPLTFGQGTKVEIKR | Seq ID No: 7 |
| 10H1.11.4B $V_H$ | EVQLVESGGGLVQPGGSLRLSCAASGFSFSDFAMSWVRQAPGKGLEWVATIGRVAFHTYYPDSMKGRFTISRDNSKNTLYLQMNSLRAEDTAVYYCARHRGFDVGHFDFWGQGTLVTVSS | Seq ID No: 8 |
| 10H1.11.4B Light Chain | DIQMTQSPSSLSASVGDRVTITCRSSETLVHSSGNTYLEWYQQKPGKAPKLLIYRVSNRFSGVPSRFSGSGSGTDFTLTISSLQPEDFATYYCFQGSFNPLTFGQGTKVEIKRTVAAPSVFIFPPSDEQLKSGTASVVCLLNNFY | Seq ID No: 9 |

| | |
|---|---|
| | PREAKVQWKVDNALQSGNSQESVTEQDSK DSTYSLSSTLTLSKADYEKHKVYACEVTH QGLSSPVTKSFNRGEC |
| 10H1.11.4B Heavy Chain | EVQLVESGGGLVQPGGSLRLSCAASGFSF SDFAMSWVRQAPGKGLEWVATIGRVAFHT YYPDSMKGRFTISRDNSKNTLYLQMNSLR AEDTAVYYCARHRGFDVGHFDFWGQGTLV TVSSCSTKGPSVFPLAPSSKSTSGGTAAL GCLVKDYFPEPVTVSWNSGALTSGVHTFP AVLQSSGLYSLSSVVTVPSSSLGTQTYIC NVNHKPSNTKVDKKVEPKSCDKTHTCPPC PAPELLGGPSVFLFPPKPKDTLMISRTPE VTCVVVDVSHEDPEVKFNWYVDGVEVHNA KTKPREEQYNSTYRVVSVLTVLHQDWLNG KEYKCKVSNKALPAPIEKTISKAKGQPRE PQVYTLPPSREEMTKNQVSLTCLVKGFYP SDIAVEWESNGQPENNYKTTPPVLDSDGS FFLYSKLTVDKSRWQQGNVFSCSVMHEAL HNHYTQKSLSLSPGK | SEQ ID NO: 10 |

Anti-CD33 Humanized Antibody:

In one embodiment, the anti-CD33 antibody of ADCs of the present invention comprises three light chain hypervariable regions and three heavy chain hypervariable regions, the sequences (SEQ ID NO:11-16) of which are shown below In one embodiment, the anti-CD33 antibody of ADCs of the present invention comprises the variable light chain sequence of SEQ ID NO: 17 and the variable heavy chain sequence of SEQ ID NO: 18

| | | |
|---|---|---|
| 15G15.33-HVR L1 | RSSQSLLHSNGYNYLD | SEQ ID NO: 11 |
| 15G15.33-HVR L2 | LGVNSVS | SEQ ID NO: 12 |
| 15G15.33-HVR L3 | MQALQTPWT | SEQ ID NO: 13 |
| 15G15.33-HVR H1 | NHAIS | SEQ ID NO: 14 |
| 15G15.33-HVR H2 | GIIPIFGTANYAQKFQG | SEQ ID NO: 15 |
| 15G15.33-HVR H3 | EWADVFDI | SEQ ID NO: 16 |
| 15G15.33 $V_L$ | EIVLTQSPLSLPVTPGEPASISCRSSQSL LHSNGYNYLDWYLQKPGQSPQLLIYLGVN SVSGVPDRFSGSGSGTDFTLKISRVEAED VGVYYCMQALQTPWTFGQGTKVEIK | SEQ ID NO: 17 |
| 15G15.33 $V_H$ | QVQLVQSGAEVKKPGSSVKVSCKASGGIF SNHAISWVRQAPGQGLEWMGGIIPIFGTA NYAQKFQGRVTITADESTSTAFMELSSLR SEDTAVYYCAREWADVFDIWGQGTMVTVS S | SEQ ID NO: 18 |

In one embodiment, the anti-CD33 antibody of ADCs of the present invention comprises the light chain sequence of SEQ ID NO: 19 and the heavy chain sequence of SEQ ID NO: 20

In one embodiment, the anti-CD33 antibody of ADCs of the present invention comprises three light chain hypervariable regions and three heavy chain hypervariable regions, the sequences (Seq ID NO: 19-24) of which are shown below.

In one embodiment, the anti-CD33 antibody of ADCs of the present invention comprises the variable light chain sequence of SEQ ID NO: 25 and the variable heavy chain sequence of SEQ ID NO: 26

In one embodiment, the anti-CD33 antibody of ADCs of the present invention comprises the variable light chain sequence of SEQ ID NO: 27 and the variable heavy chain sequence of SEQ ID NO: 28

In one embodiment, the anti-CD33 antibody of ADCs of the present invention comprises the variable light chain sequence of SEQ ID NO: 29 and the variable heavy chain sequence of SEQ ID NO: 30

In one embodiment, the anti-CD33 antibody of ADCs of the present invention comprises the variable light chain sequence of SEQ ID NO: 31 and the variable heavy chain sequence of SEQ ID NO: 32

| | | |
|---|---|---|
| 9C3-HVR L1 | RASQGIRNDLG | Seq ID NO: 19 |
| 9C3-HVR L2 | AASSLQS | Seq ID NO: 20 |
| 9C3-HVR L3 | LQHNSYPWT | Seq ID NO: 21 |
| 9C3-HVR H1 | GNYMS | Seq ID NO: 22 |
| 9C3-HVR H2 | LIYSGDSTYYADSVKG | Seq ID NO: 23 |
| 9C3-HVR H3 | DGYYVSDMVV | Seq ID NO: 24 |
| 9C3 $V_L$ | DIQMTQSPSSLSASVGDRVTITCRASQG IRNDLGWYQQKPGKAPKRLIYAASSLQS GVPSRFSGSGSGTEFTLTISSLQPEDFA TYYCLQHNSYPWTFGQGTKLEIK | Seq ID NO: 25 |
| 9C3 $V_H$ | EVQLVESGGALIQPGGSLRLSCVASGFT ISGNYMSWVRQAPGKGLEWVSLIYSGDS TYYADSVKGRFNISRDISKNTVYLQMNS LRVEDTAVYYCVRDGYYVSDMVVWGKGT TVTVSS | Seq ID NO: 26 |
| 9C3.2 $V_L$ | DIQMTQSPSSLSASVGDRVTITCRASQG IRNDLGWYQQKPGKAPKRLIYAASSLQS GVPSRFSGSGSGTEFTLTISSLQPEDFA TYYCLQHNSYPWTFGQGTKLEIK | Seq ID NO: 27 |
| 9C3.2 $V_H$ | EVQLVESGGALIQPGGSLRLSCVASGFT ISGNYMSWVRQAPGKGLEWVSLIYSGDS TYYADSVKGRFTISRDISKNTVYLQMNS LRVEDTAVYYCVRDGYYVSDMVVWGKGT TVTVSS | Seq ID NO: 28 |
| 9C3.3 $V_L$ | DIQMTQSPSSLSASVGDRVTITCRASQG IRNDLGWYQQKPGKAPKRLIYAASSLQS GVPSRFSGSGSGTEFTLTISSLQPEDFA TYYCLQHNSYPWTFGQGTKLEIK | Seq ID NO: 29 |
| 9C3.3 $V_H$ | EVQLVESGGALIQPGGSLRLSCVASGFT ISGNYMSWVRQAPGKGLEWVSLIYSGDS TYYADSVKGRFSISRDISKNTVYLQMNS LRVEDTAVYYCVRDGYYVSDMVVWGKGT TVTVSS | Seq ID NO: 30 |
| 9C3.4 $V_L$ | DIQMTQSPSSLSASVGDRVTITCRASQG IRNDLGWYQQKPGKAPKRLIYAASSLQS GVPSRFSGSGSGTEFTLTISSLQPEDFA TYYCLQHNSYPWTFGQGTKLEIK | Seq ID NO: 31 |

| | | |
|---|---|---|
| 9C3.4 V_H | EVQLVESGGALIQPGGSLRLSCVASGFT ISGNYMSWVRQAPGKGLEWVSLIYSGDS TYYADSVKGRFAISRDISKNTVYLQMNS LRVEDTAVYYCVRDGYYVSDMVVWGKGT TVTVSS | Seq ID NO: 32 |

Anti-CD22 Humanized Antibody:

In one embodiment, the anti-CD22 antibody of ADCs of the present invention comprises three light chain hypervariable regions and three heavy chain hypervariable regions (SEQ ID NO: 41-46), the sequences of which are shown below.

In one embodiment, the anti-CD22 antibody of ADCs of the present invention comprises the variable light chain sequence of SEQ ID NO: 47 and the variable heavy chain sequence of SEQ ID NO: 48

In one embodiment, the anti-CD22 antibody of ADCs of the present invention comprises the light chain sequence of SEQ ID NO: 49 and the heavy chain sequence of SEQ ID NO: 50

| | | |
|---|---|---|
| h10F4.V3.K149C HVR-L1 | RSSQSIVHSVGNTFLE | Seq ID No: 41 |
| h10F4.V3.K149C HVR-L2 | KVSNRFS | Seq ID No: 42 |
| h10F4.V3.K149C HVR-L3 | FQGSQFPYT | Seq ID No: 43 |
| h10F4.V3.K149C HVR-H1 | GYEFSRSWMN | Seq ID No: 44 |
| h10F4.V3.K149C HVR-H2 | RIYPGDGDTNYSGKFKG | Seq ID No: 45 |
| h10F4.V3.K149C HVR-H3 | DGSSWDWYFDV | Seq ID No: 46 |
| h10F4.V3.K149C V_L | DIQMTQSPSSLSASVGDRVTITCRSSQ SIVHSVGNTFLEWYQQKPGKAPKLLIY KVSNRFSGVPSRFSGSGSGTDFTLTIS SLQPEDFATYYCFQGSQFPYTFGQGTK VEIKR | SEQ ID NO: 47 |
| h10F4.V3.K149C V_H | EVQLVESGGGLVQPGGSLRLSCAASGY EFSRSWMNWVRQAPGKGLEWVGRIYPG DGDTNYSGKFKGRFTISADTSKNTAYL QMNSLRAEDTAVYYCARDGSSWDWYFD VWGQGTLVTVSS | SEQ ID NO: 48 |
| h10F4.V3.K149C Light Chain | DIQMTQSPSSLSASVGDRVTITCRSSQ SIVHSVGNTFLEWYQQKPGKAPKLLIY KVSNRFSGVPSRFSGSGSGTDFTLTIS SLQPEDFATYYCFQGSQFPYTFGQGTK VEIKRTVAAPSVFIFPPSDEQLKSGTA SVVCLLNNFYPREAKVQWCVDNALQSG NSQESVTEQDSKDSTYSLSSTLTLSKA DYEKHKVYACEVTHQGLSSPVTKSFNR GEC | SEQ ID NO: 49 |
| h10F4.V3.K149C Heavy Chain | EVQLVESGGGLVQPGGSLRLSCAASGY EFSRSWMNWVRQAPGKGLEWVGRIYPG DGDTNYSGKFKGRFTISADTSKNTAYL QMNSLRAEDTAVYYCARDGSSWDWYFD VWGQGTLVTVSSASTKGPSVFPLAPSS KSTSGGTAALGCLVKDYFPEPVTVSWN SGALTSGVHTFPAVLQSSGLYSLSSVV TVPSSSLGTQTYICNVNHKPSNTKVDK KVEPKSCDKTHTCPPCPAPELLGGPSV FLFPPKPKDTLMISRTPEVTCVVVDVS HEDPEVKFNWYVDGVEVHNAKTKPREE QYNSTYRVVSVLTVLHQDWLNGKEYKC KVSNKALPAPIEKTISKAKGQPREPQV YTLPPSREEMTKNQVSLTCLVKGFYPS DIAVEWESNGQPENNYKTTPPVLDSDG SFFLYSKLTVDKSRWQQGNVFSCSVMH EALHNHYTQKSLSLSPGK | SEQ ID NO: 50 |

ADC In Vitro Data

The following ADCs were tested in in vitro assays described above and were found to be active. The activities of said ADCs are illustrated in the table below. The NaPi2b ADCs were used as a non-targeting control.

| Code | Antibody ID | EOL-1 IC$_{50}$ (ng/mL) |
|---|---|---|
| NaPi2b CBI-PBD ADC2-1 | 10H1.11.4B | 2187 |
| CD33 CBI-PBD ADC2-2 | 15G15.33 | 370 |
| NaPi2b CBI-PBD ADC3-1 | 10H1.11.4B | 590 |
| CD33 CBI-PBD ADC3-2 | 15G15.33 | 18.1 |

| | | IGROV-1 IC50 | | OVCAR-3 × 2.1 IC50 | | NCI-H441 IC50 | |
|---|---|---|---|---|---|---|---|
| Molecule Name | DAR | nM | ng/mL | nM | ng/mL | nM | ng/mL |
| anti-Napi2b 10H1.11.4B LC K149C (CBI-CBI LD5) | 2.0 | 0.398 | 59.7 | 0.147 | 22.1 | 2.9 | 435 |
| anti-CD22 10F4v3 LC K149C (CBI-CBI LD5) | 2.0 | 7.6 | 1140 | 17.4 | 2610 | 4.0 | 600 |

| | | BJAB IC50 | | WSU-DLCL2 IC50 | | Jurkat IC50 | |
|---|---|---|---|---|---|---|---|
| Molecule Name | DAR | nM | ng/mL | nM | ng/mL | nM | ng/mL |
| anti-CD22 10F4v3 LC K149C (CBI-CBI LD5) | 2.0 | 0.0243 | 3.6 | 0.0130 | 1.95 | 50.2 | 7530 |
| anti-Napi2b 10H1.11.4B LC K149C (CBI-CBI LD5) | 2.0 | 62.2 | 9330 | 48.1 | 7215 | 47.8 | 7170 |

| Molecule Name | DAR | IGROV-1 IC50 | | OVCAR-3 x 2.1 IC50 | | NCI-H441 IC50 | |
|---|---|---|---|---|---|---|---|
| | | nM | ng/mL | nM | ng/mL | nM | ng/mL |
| anti-Napi2b 10H1.11.4B LC K149C (CBI-CBI LD6) | 2.0 | 0.189 | 28.4 | 3.7 | 555 | 11.0 | 1650 |
| anti-CD22 10F4v3 LC K149C (CBI-CBI LD6) | 2.0 | 2.9 | 435 | >133.3 | >20000 | 81.2 | 12180 |

| Molecule Name | DAR | BJAB IC50 | | WSU-DLCL2 IC50 | | Jurkat IC50 | |
|---|---|---|---|---|---|---|---|
| | | nM | ng/mL | nM | ng/mL | nM | ng/mL |
| anti-CD22 10F4v3 LC K149C (CBI-CBI LD6) | 2.0 | 0.0441 | 6.6 | 0.0306 | 4.6 | >133.3 | >20000 |
| anti-Napi2b 10H1.11.4B LC K149C (CBI-CBI LD6) | 2.0 | >133.3 | >20000 | >133.3 | >20000 | >133.3 | >20000 |

ADC In Vivo Data

FIG. 1 shows efficacy comparison of CD33 ADCs in SCID mice with HL-60 human acute myeloid leukemia tumors. CD33 CBI-PBD ADC3-2 showed dose-dependent inhibition of tumor growth compared with vehicle group. The non-targeting control NaPi2b CBI-PBD ADC3-1 had minimal effect on the tumor growth.

FIG. 2 shows efficacy comparison of NaPi2b ADCs in SCID-beige mice with OVCAR3X2.1 human ovarian tumors. NaPi2b CBI-PBD ADC2-1 and ADC3-1 demonstrated modest inhibition of tumor growth compared with vehicle group. The anti-tumor activity of NaPi2b CBI-PBD ADC2-1 and ADC3-1 was comparable, resulting in tumor growth delay at antibody dose of 3 mg/kg (=drug dose of 73 ug/m2).

The invention claimed is:
1. An antibody-drug conjugate represented by Formula (I)

Ab-(L-D)$_p$,

Ab is an antibody, wherein the antibody binds to one or more of polypeptides selected from the group consisting of:
CLL1;
BMPR1B;
E16;
STEAP1;
0772P;
MPF;
NaPi2b;
Sema 5b;
PSCA hlg;
ETBR;
MSG783;
STEAP2;
TrpM4;
CRIPTO;
CD21;
CD79b;
FcRH2;
HER2;
NCA;
MDP;
IL20Rα;
Brevican;
EphB2R;
ASLG659;
PSCA;
GEDA;
BAFF-R;
CD22;
CD79a;
CXCR5;
HLA-DOB;
P2X5;
CD72;
LY64;
FcRH1;
IRTA2;
TENB2;
PMEL17;
TMEFF 1;
GDNF-Ra1;
TMEM46;
Ly6G6D;
LGR5;
RET;
LY6K;
GPR19;
GPR54;
ASPHD1;
Tyrosinase;
TMEM118;
GPR172A;
MUC16 and
CD33;
L is a peptidomimetic linker represented by the following formula -Str-(PM)-Spwherein
Str is a stretcher unit covalently attached to Ab; having the formulas:

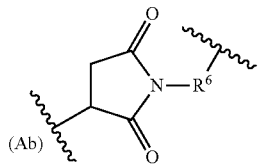

wherein R$^6$ is selected from the group consisting of C$_1$-C$_{10}$alkylene, C$_1$-C$_{10}$alkenyl, C$_3$-C$_8$cycloalkyl, (C$_1$-C$_8$alkylene)O—, and C$_1$-C$_{10}$alkyleneC(O)N(R$^a$)—C$_2$-C$_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, C$_3$-C$_8$cycloalkyl, C$_4$-C$_7$heterocycloalkyl, heteroarylalkyl, aryl arylalkyl, heteroarylalkyl and heteroaryl each R$^a$ is independently H or C$_1$-C$_6$alkyl; or

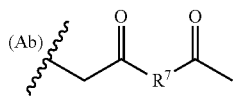

wherein R$^7$ is selected from C$_1$-C$_{10}$alkylene, C$_1$-C$_{10}$alkenyl, (C$_1$-C$_{10}$alkylene)O—, N(R$^c$)—(C$_2$-C$_6$alkylene)-N(R$^c$) or N(R$^c$)—(C$_2$-C$_6$alkylene); where each R$^c$ is independently H or C$_1$-C$_6$ alkyl;
Sp is a bond or spacer unit covalently attached to a drug moiety selected from —C$_1$-C$_6$ alkylene-C(O)NH— or —Ar—R$^b$—, wherein Ar is aryl or heteroaryl, and R$^b$ is (C$_1$-C$_{10}$alkylene)O—;
PM is a non-peptide chemical moiety-having the formula:

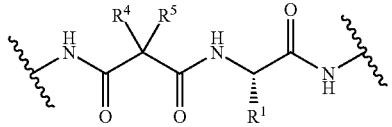

R$^1$ is C$_1$-C$_{10}$ alkyl, C$_1$-C$_{10}$ alkenyl, (C$_1$-C$_{10}$ alkyl)NHC(NH)NH$_2$ or (C$_1$-C$_{10}$ alkyl)NHC(O)NH$_2$;
R$^4$ and R$^5$ are each independently C$_1$-C$_{10}$ alkyl, C$_1$-C$_{10}$ alkenyl, arylalkyl, heteroarylalkyl, (C$_1$-C$_{10}$ alkyl)OCH$_2$—, or R$^4$ and R$^5$ together may form a C$_3$-C$_7$ cycloalkyl ring;
p is an integer from 1 to 8; and
D is a dimer drug moiety having the formula:

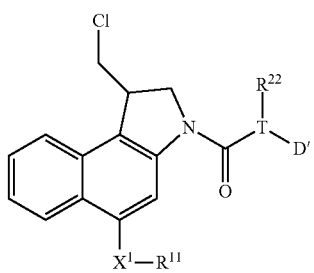

wherein
$R^{11}$ is selected from H, $P(O)_3H_2$, $C(O)NR^{aa}R^{bb}$, or a bond to L;
$R^{22}$ is selected from H, $P(O)_3H_2$, $C(O)NR^{aa}R^{bb}$, or a bond to L;
$R^{aa}$ and $R^{bb}$ are independently selected from H and $C_1$-$C_6$alkyl optionally substituted with one or more F, or $R^{aa}$ and $R^{bb}$ form a five or six membered heterocycloalkyl group;
T is a tether group selected from $C_3$-$C_{12}$alkylene, Y', $(C_1$-$C_6$alkylene$)$-$Y^1$—$(C_1$-$C_6$ alkylene$)$, $(C_1$-$C_6$alkylene$)$-$Y^1$—$(C_1$-$C_6$alkylene$)$-$Y^1$—$(C_1$-$C_6$alkylene$)$, $(C_2$-$C_6$alkenylene$)$-$Y^1$—$(C_2$-$C_6$alkenylene$)$, or $(C_2$-$C_6$alkynylene$)$-$Y^1$—$(C_2$-$C_6$alkynylene$)$;
where $Y^1$ is independently selected from O, S, $NR^{11}$, aryl, or heteroaryl;
where alkylene, alkenylene, aryl, and heteroaryl are independently and optionally substituted with F, OH, $O(C_1$-$C_6$alkyl$)$, $NH_2$, $NHCH_3$, $N(CH_3)_2$, $NHC(O)(C_1$-$C_6$alkylene$)$; $OP(O)_3H_2$, or $C_1$-$C_6$alkyl, where alkyl is optionally substituted with one or more F, m is 0 or 1;
or alkylene, alkenylene, aryl, and heteroaryl are independently and optionally substituted with a bond to L, wherein the bond to L may connect through one of the optional substituents;
D' is a drug moiety selected from:

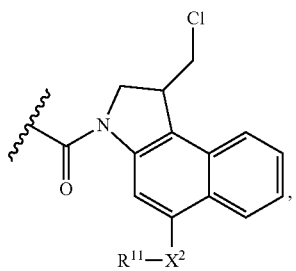

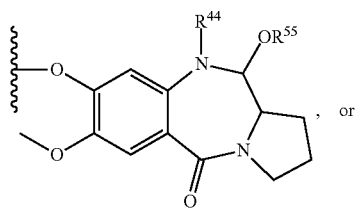

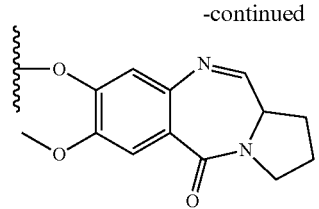

where the wavy line indicates the site of attachment to T;
$X^1$ and $X^2$ are independently selected from O or $NR^{33}$, where $R^{33}$ is selected from H, C(O), or $C_1$-$C_6$alkyl, optionally substituted with one or more F, or $X^1$ and $X^2$ are each independently absent;
$R^{44}$ is H, $CO_2R$, C(O), or a bond to L, where R is $C_1$-$C_6$alkyl or benzyl; and
$R^{55}$ is H or $C_1$-$C_6$alkyl.

2. The antibody-drug conjugate of claim 1 represented by the following formula:

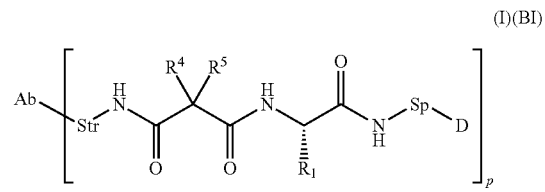

(I)(BI)

wherein
p is 1, 2, 3 or 4.

3. The antibody-drug conjugate compound of claim 2, wherein
Str is a chemical moiety represented by the following formula:

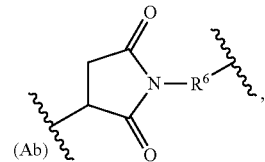

and $R^6$ is $C_1$-$C_6$ alkylene.

4. The antibody-drug conjugate compound of claim 1, which is represented by the following formula:

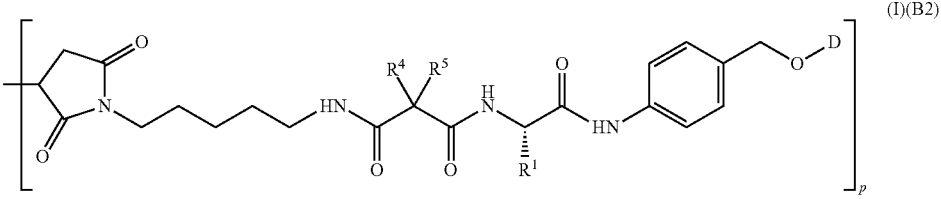

(I)(B2)

wherein
p is 1, 2, 3 or 4;
$R^1$ is $C_1$-$C_6$ alkyl-$NH_2$, ($C_1$-$C_6$ alkyl)NHC(NH)$NH_2$ or ($C_1$-$C_6$ alkyl)NHC(O)$NH_2$; and
$R^4$ and $R^5$ form a $C_3$-$C_7$ cycloalkyl ring.

5. The antibody-drug conjugate of claim 1, which is represented by the following formula:

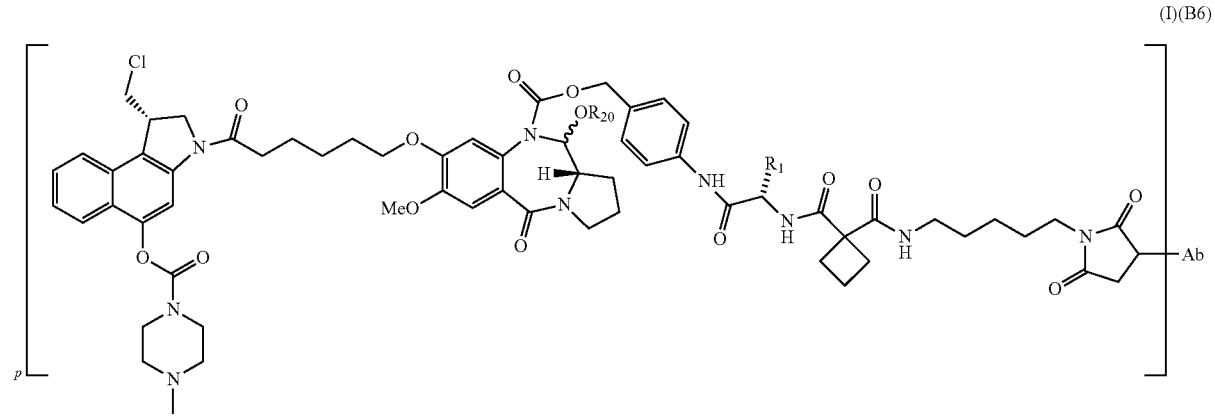

(I)(B6)

wherein,
Ab is an antibody that binds to a target selected from Her2, CLL1, CD33, CD22 or NaPi2b;
p is 1-4;
$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$; and
$R^{20}$ is H or Me.

6. The antibody-drug conjugate of claim 1, which is represented by the following formula:

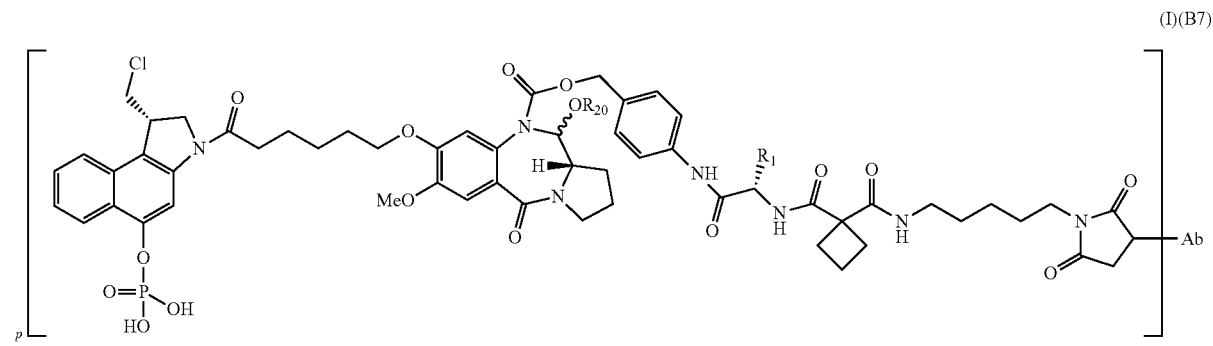

(I)(B7)

wherein,
Ab is an antibody that binds to a target selected from Her2, CLL1, CD33, CD22 or NaPi2b;
p is 1-4;
$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$; and
$R^{20}$ is H or Me.

7. The antibody-drug conjugate of claim 1, which is represented by the following formula:

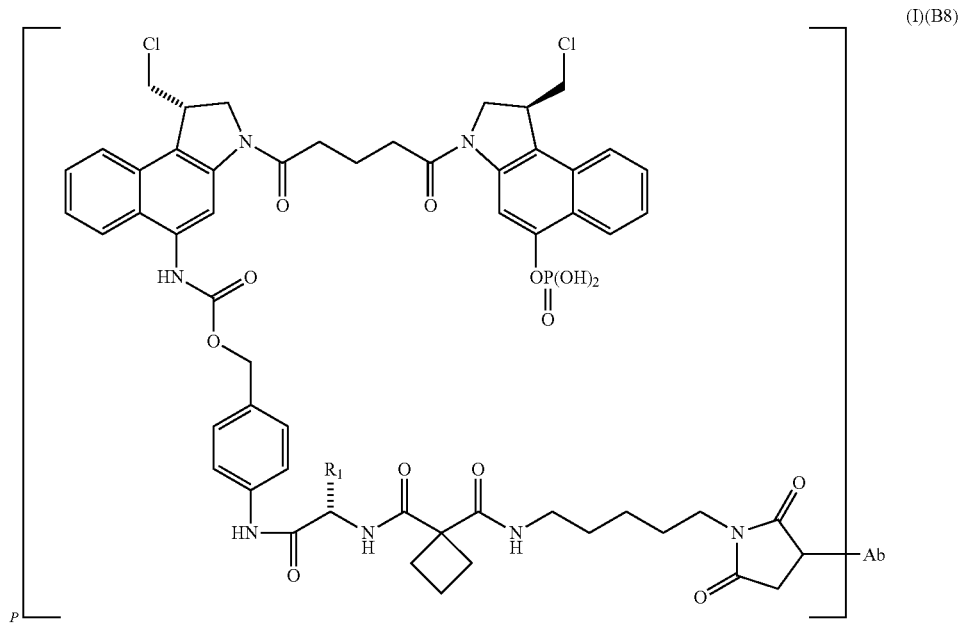
wherein,
Ab is an antibody that binds to a target selected from Her2, CLL1, CD33, CD22 or NaPi2b;
P is 1-4; and
$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$.
8. The antibody-drug conjugate of claim 1, which is represented by the following formula:
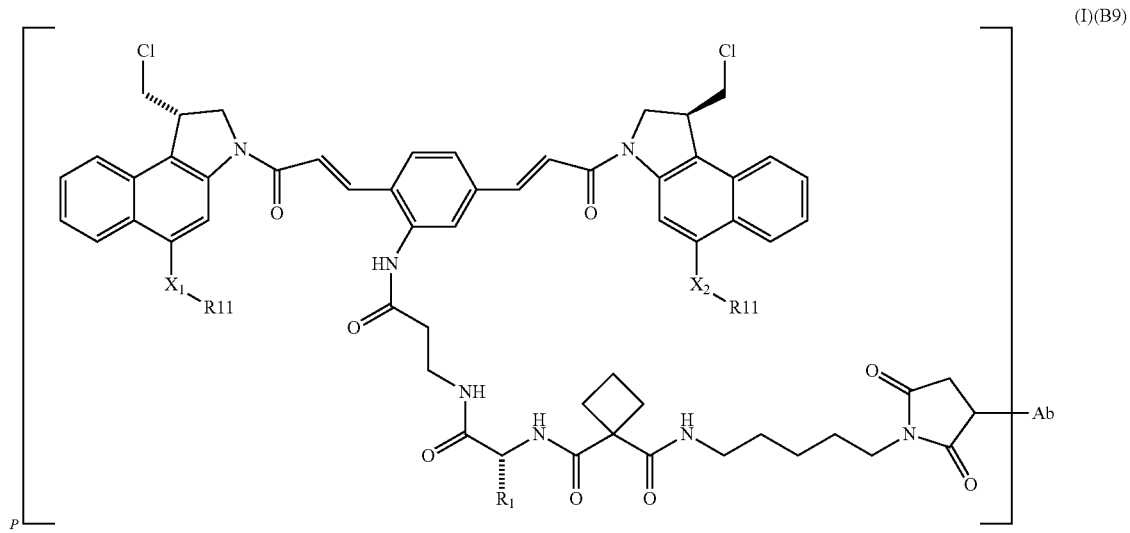

wherein,

Ab is an antibody that binds to a target selected from Her2, CLL1, CD33, CD22 or NaPi2b;

P is 1-4;

$R^1$ is $C_1$-$C_6$alkyl-$NH_2$, ($C_1$-$C_6$ alkyl)NHC(NH)$NH_2$ or ($C_1$-$C_6$alkyl)NHC(O)$NH_2$;

$X^1$ and $X^2$ are each independently absent or O; and each $R^{11}$ is independently C(O)N-piperazine($CH_3$) or $P(O)_3H_2$.

9. A non-peptide compound of Formula (I)(B)(LD1):

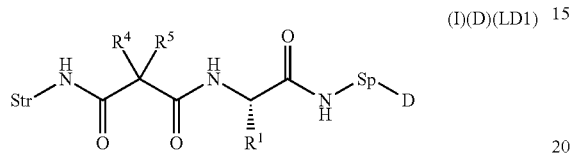

(I)(D)(LD1)

wherein

Str is a stretcher unit which can be covalently attached to an antibody, having the formula:

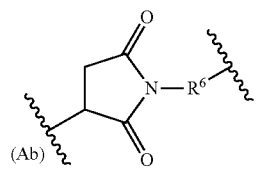

wherein $R^6$ is selected from the group consisting of $C_1$-$C_{10}$alkylene, $C_3$-$C_8$cycloalkyl, O—($C_1$-$C_8$alkylene), and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$cycloalkyl, $C_4$-$C_7$heterocycloalkyl aryl, arylalkyl, heteroarylalkyl and heteroaryl; each $R^a$ is independently H or $C_1$-$C_6$alkyl; or

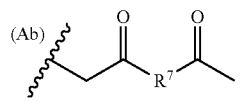

wherein $R^7$ is selected from $C_1$-$C_{10}$alkylene, $C_1$-$C_{10}$alkenyl, ($C_1$-$C_{10}$alkylene)O—, N($R^c$)—($C_2$-$C_6$ alkylene)-N($R^c$) or N($R^c$)—($C_2$-$C_6$alkylene); where each $R^c$ is independently H or $C_1$-$C_6$ alkyl;

Sp is a bond or a spacer unit covalently attached to a drug moiety selected from —$C_1$-$C_6$alkylene-C(O)NH— or —Ar—$R^b$—, wherein Ar is aryl or heteroaryl, $R^b$ is ($C_1$-$C_{10}$alkylene)O—;

$R^1$ is $C_1$-$C_{10}$alkyl, ($C_1$-$C_{10}$alkyl)NHC(NH)$NH_2$ or ($C_1$-$C_{10}$alkyl)NHC(O)$NH_2$;

$R^4$ and $R^5$ are each independently $C_1$-$C_{10}$alkyl, arylalkyl, heteroarylalkyl, or ($C_1$-$C_{10}$alkyl)OCH$_2$—, or $R^4$ and $R^5$ may form a $C_3$-$C_7$cycloalkyl ring; and D is a drug moiety having the formula:

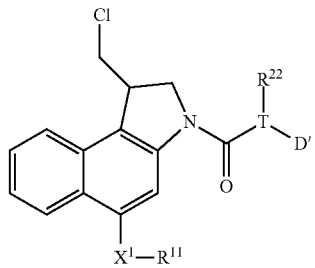

wherein $R^{11}$ is selected from H, $P(O)_3H_2$, C(O)NR$^{aa}$R$^{bb}$, or a bond to L;

$R^{22}$ is selected from H, $P(O)_3H_2$, C(O)NR$^{aa}$R$^{bb}$, or a bond to L;

$R^{aa}$ and $R^{bb}$ are independently selected from H and $C_1$-$C_6$alkyl optionally substituted with one or more F, or $R^{aa}$ and $R^{bb}$ form a five or six membered heterocycloalkyl group;

T is a tether group selected from $C_3$-$C_{12}$alkylene, Y', ($C_1$-$C_6$alkylene)-$Y^1$—($C_1$-$C_6$ alkylene), ($C_1$-$C_6$alkylene)-$Y^1$—($C_1$-$C_6$alkylene)-$Y^1$—($C_1$-$C_6$alkylene), ($C_2$-$C_6$alkenylene)-$Y^1$—($C_2$-$C_6$alkenylene), or ($C_2$-$C_6$alkynylene)-$Y^1$—($C_2$-$C_6$alkynylene);

where $Y^1$ is independently selected from O, S, NR$^{11}$, aryl, or heteroaryl;

where alkylene, alkenylene, aryl, and heteroaryl are independently and optionally substituted with F, OH, O($C_1$-$C_6$alkyl), $NH_2$, $NHCH_3$, $N(CH_3)_2$, NHC(O)($C_1$-$C_6$alkylene)$_m$, OP(O)$_3H_2$, or $C_1$-$C_6$alkyl, where alkyl is optionally substituted with one or more F, m is 0 or 1;

or alkylene, alkenylene, aryl, and heteroaryl are independently and optionally substituted with a bond to L, wherein the bond to L may connect through one of the optional substituents;

D' is a drug moiety selected from:

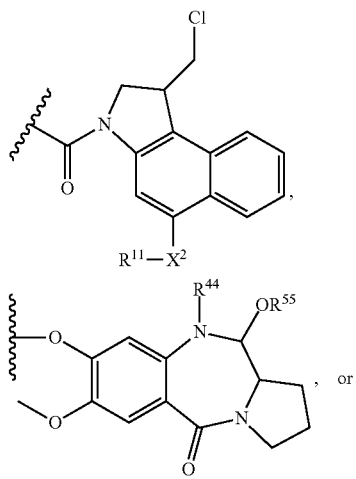

-continued

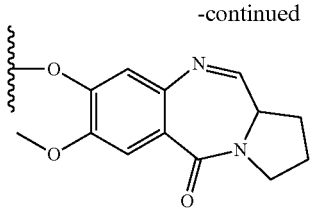

where the wavy line indicates the site of attachment to T;
$X^1$ and $X^2$ are independently selected from O or $NR^{33}$, where $R^{33}$ is selected from H, C(O), or $C_1$-$C_6$alkyl, optionally substituted with one or more F, or $X^1$ and $X^2$ are each independently absent;
$R^{44}$ is H, $CO_2R$, C(O), or a bond to L, where R is $C_1$-$C_6$alkyl or benzyl; and
$R^{55}$ is H or $C_1$-$C_6$alkyl.

10. The compound of claim 9 represented by the following formula

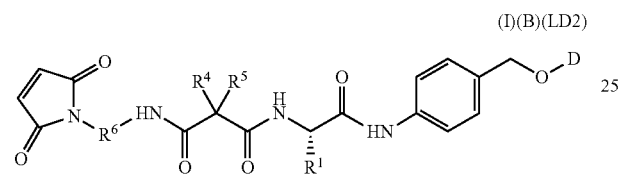

(I)(B)(LD2)

wherein $R^6$ is $C_1$-$C_{10}$alkylene; and $R^4$ and $R^5$ together form a $C_3$-$C_7$cycloalkyl ring.

11. The compound of claim 9 represented by the following formula

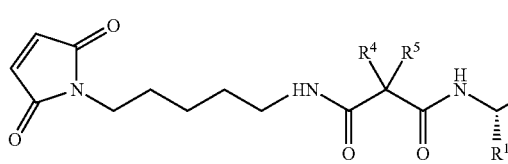

(I)(B)(LD3)

12. The compound of claim 9, wherein $R^6$ is $C_1$-$C_{10}$alkylene, Sp is —Ar—$R^b$—, wherein Ar is aryl $R^b$ is ($C_1$-$C_6$alkylene)O—.

13. The compound of claim 1, wherein Str has the formula:

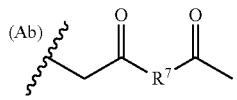

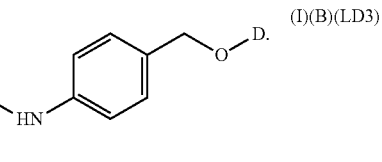

wherein $R^7$ is selected from $C_1$-$C_{10}$alkylene, $C_1$-$C_{10}$alkylene-O, $N(R^c)$—($C_2$-$C_6$ alkylene)-$N(R^c)$ or $N(R^c)$—($C_2$-$C_6$alkylene); where each $R^c$ is independently H or $C_1$-$C_6$ alkyl; and
Sp is —$C_1$-$C_6$alkylene-C(O)NH— or —Ar—$R^b$—, wherein Ar is aryl or heteroaryl, $R^b$ is alkylene)O—.

14. The antibody-drug conjugate according to claim 1, wherein p is 2.

15. A pharmaceutical composition comprising a compound of claim 1 and a pharmaceutically acceptable excipient.

16. The antibody-drug conjugate of claim 1, wherein the antibody binds to CD33; or
the antibody comprises an HVR-L1 comprising the amino acid sequence of SEQ ID NO:11, an HVR-L2 comprising the amino acid sequence of SEQ ID NO:12, an HVR-L3 comprising the amino acid sequence of SEQ ID NO:13, an HVR-H1 comprising the amino acid sequence of SEQ ID NO: 14, an HVR-H2 comprising the amino acid sequence of SEQ ID NO:15, and an HVR-H3 comprising the amino acid sequence of SEQ ID NO: 16; or
the antibody comprises a VL domain comprising the amino acid sequence of SEQ ID NO:17 and a VH domain comprising the amino acid sequence of SEQ ID NO:18; or
the antibody binds to NaPi2b; or
the antibody comprises an HVR-L1 comprising the amino acid sequence of SEQ ID NO:1, an HVR-L2 comprising the amino acid sequence of SEQ ID NO:2, an HVR-L3 comprising the amino acid sequence of SEQ ID NO:3, an HVR-H1 comprising the amino acid sequence of SEQ ID NO: 4, an HVR-H2 comprising the amino acid sequence of SEQ ID NO:5, and an HVR-H3 comprising the amino acid sequence of SEQ ID NO: 6; or
the antibody comprises a VL domain comprising the amino acid sequence of SEQ ID NO:7 and a VH domain comprising the amino acid sequence of SEQ ID NO:8; or
the antibody comprises an amino acid sequence of SEQ ID NO:9 and an amino acid sequence of SEQ ID NO: 10; or
the antibody binds to CD-22; or
the antibody comprises an HVR-L1 comprising the amino acid sequence of SEQ ID NO:41, an HVR-L2 comprising the amino acid sequence of SEQ ID NO:42, an HVR-L3 comprising the amino acid sequence of SEQ ID NO:43, an HVR-H1 comprising the amino acid sequence of SEQ ID NO: 44, an HVR-H2 comprising the amino acid sequence of SEQ ID NO:45, and an HVR-H3 comprising the amino acid sequence of SEQ ID NO: 46; or
the antibody comprises a VL domain comprising the amino acid sequence of SEQ ID NO:47 and a VH domain comprising the amino acid sequence of SEQ ID NO:48; or
the antibody comprises an amino acid sequence of SEQ ID NO:49 and an amino acid sequence of SEQ ID NO: 50.

17. An antibody-drug conjugate having the formula
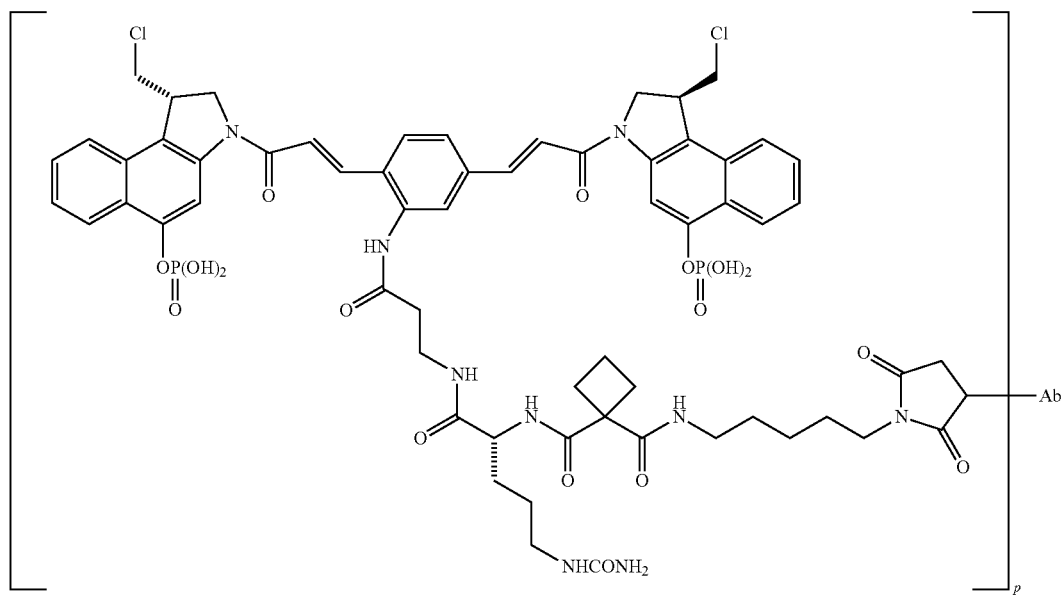
wherein p is 1-4; and Ab is an antibody that binds to CD22.
18. An antibody-drug conjugate having the formula
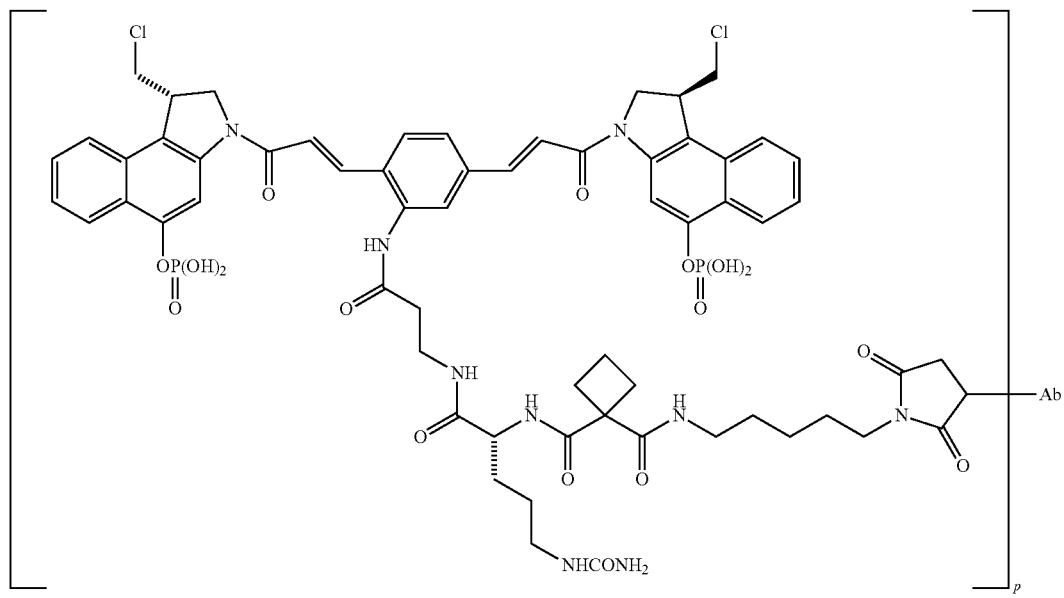
wherein p is 2; and Ab is an antibody that binds to CD22.

19. An antibody-drug conjugate having the formula
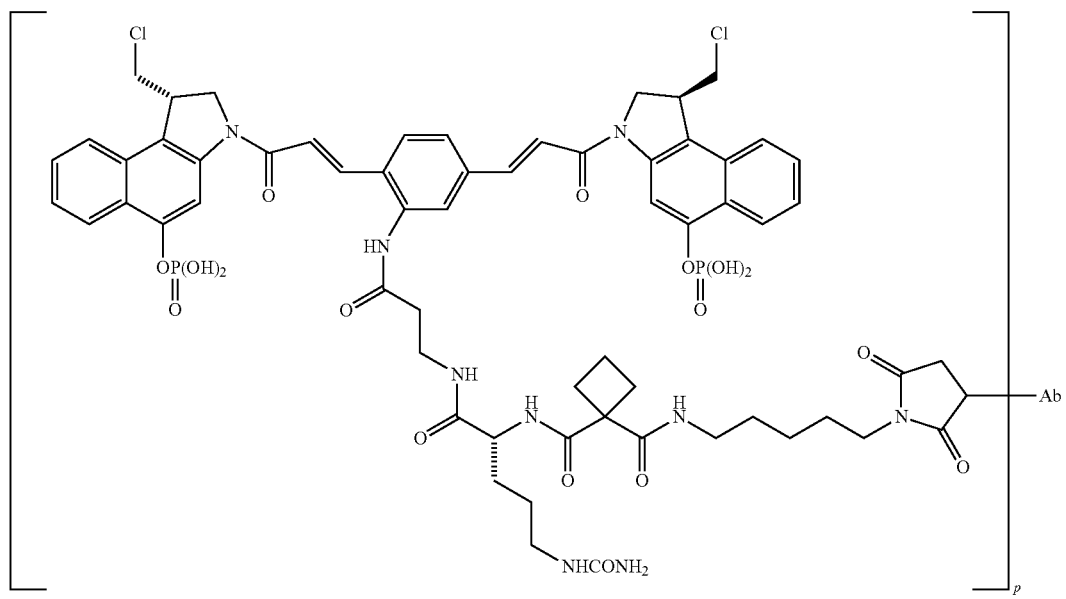
wherein p is 1-4; and Ab is a cysteine engineered antibody that binds to CD22.
20. An antibody-drug conjugate having the formula
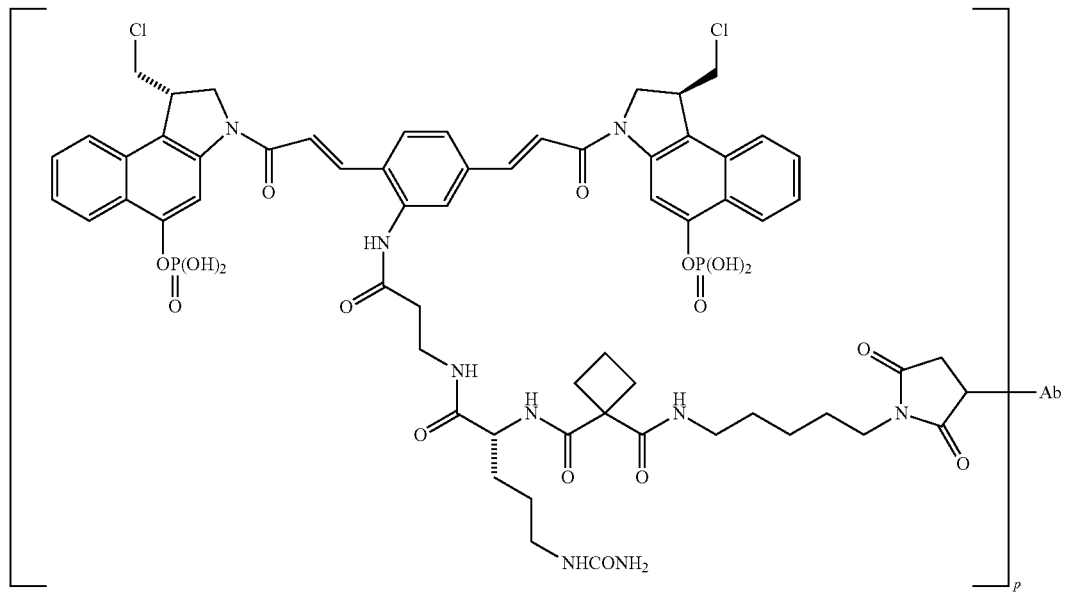
wherein p is 2; and Ab is a cysteine engineered antibody that binds to CD22.

21. An antibody-drug conjugate having the formula

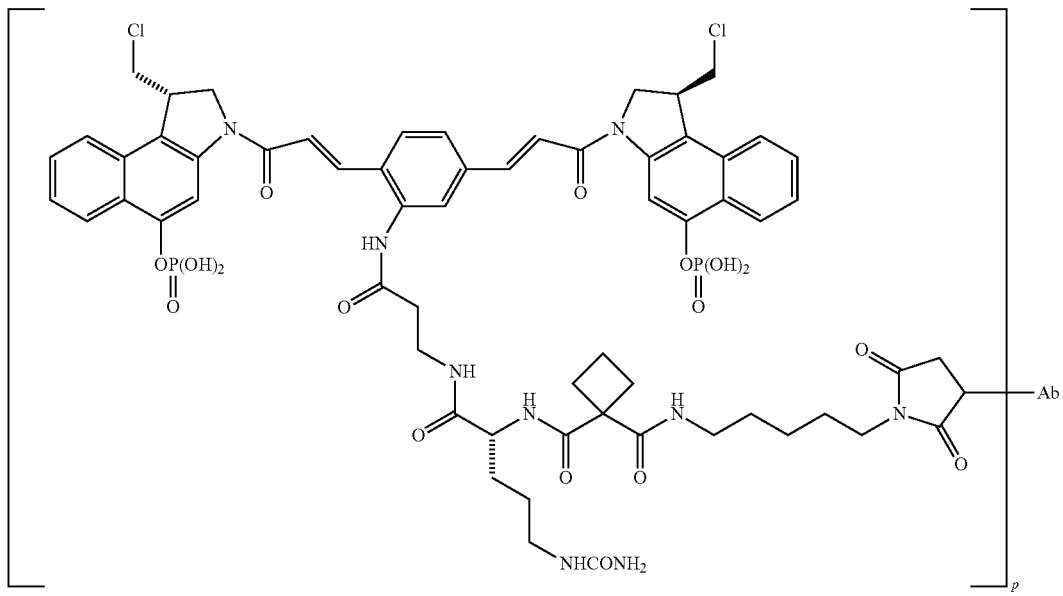

wherein p is 1-4; and Ab is a LC K149C cysteine engineered antibody that binds to CD22.

22. An antibody-drug conjugate having the formula

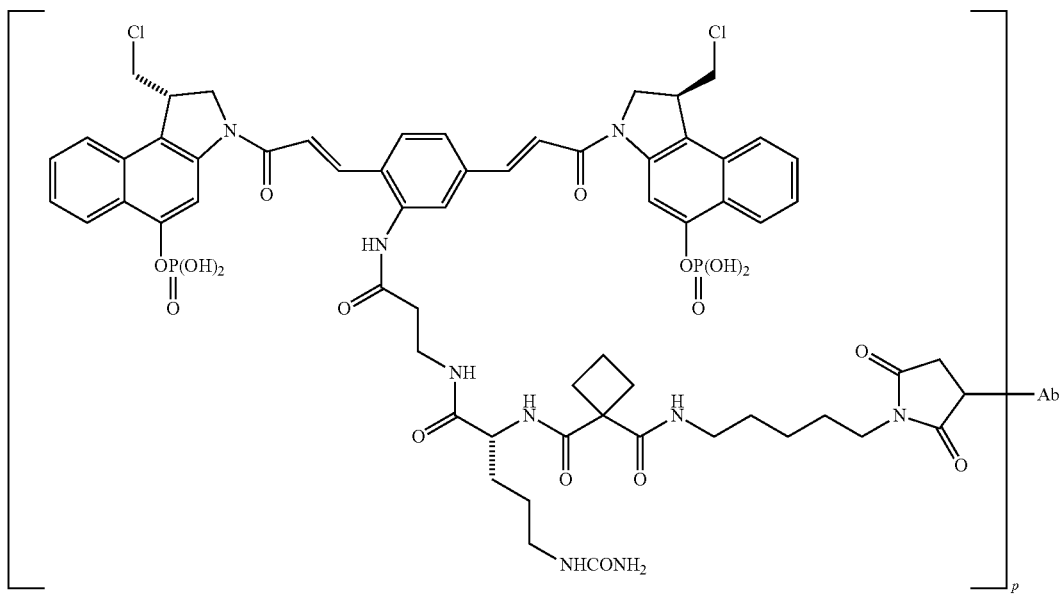

wherein p is 2; and Ab is a LC K149C cysteine engineered antibody that binds to CD22.

23. A pharmaceutical composition comprising an antibody-drug conjugate in accordance with any one of claims 17 to 22 and a pharmaceutically acceptable excipient.

24. The antibody-drug conjugate of claim 22 wherein the antibody comprises an HVR-L1 comprising the amino acid sequence of SEQ ID NO:41, an HVR-L2 comprising the amino acid sequence of SEQ ID NO:42, an HVR-L3 comprising the amino acid sequence of SEQ ID NO:43, an HVR-H1 comprising the amino acid sequence of SEQ ID NO: 44, an HVR-H2 comprising the amino acid sequence of SEQ ID NO:45, and an HVR-H3 comprising the amino acid sequence of SEQ ID NO: 46.

25. The antibody-drug conjugate of claim 22 wherein the antibody comprises a VL domain comprising the amino acid sequence of SEQ ID NO:47 and a VH domain comprising the amino acid sequence of SEQ ID NO:48.

26. The antibody-drug conjugate of claim 22 wherein the antibody comprises an amino acid sequence of SEQ ID NO:49 and an amino acid sequence of SEQ ID NO: 50.

* * * * *

UNITED STATES PATENT AND TRADEMARK OFFICE
CERTIFICATE OF CORRECTION

PATENT NO. : 10,124,069 B2
APPLICATION NO. : 15/182429
DATED : November 13, 2018
INVENTOR(S) : Ho Huat Lee et al.

It is certified that error appears in the above-identified patent and that said Letters Patent is hereby corrected as shown below:

In the Claims

Column 585, Lines 19-20, Claim 1, please delete "NHC(O)$C_1$-$C_6$alkylene);" and insert
-- NHC(O)$C_1$-$C_6$alkylene)$_m$; --;

Column 593, Line 65, Claim 13, please delete "$R^b$ is alkylene)O-." and insert
-- $R^b$ is ($C_1$-$C_{10}$alkylene)O-. -- therefor.

Signed and Sealed this
First Day of January, 2019

Andrei Iancu
*Director of the United States Patent and Trademark Office*

```
                        SEQUENCE LISTING

<160> NUMBER OF SEQ ID NOS: 50

<210> SEQ ID NO 1
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Arg Ser Ser Glu Thr Leu Val His Ser Ser Gly Asn Thr Tyr Leu Glu
1               5                   10                  15

<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Arg Val Ser Asn Arg Phe Ser
1               5

<210> SEQ ID NO 3
<211> LENGTH: 9
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 3

Phe Gln Gly Ser Phe Asn Pro Leu Thr
1               5

<210> SEQ ID NO 4
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Phe Ser Phe Ser Asp Phe Ala Met Ser
1               5                   10

<210> SEQ ID NO 5
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ala Thr Ile Gly Arg Val Ala Phe His Thr Tyr Tyr Pro Asp Ser Met
1               5                   10                  15

Lys Gly

<210> SEQ ID NO 6
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ala Arg His Arg Gly Phe Asp Val Gly His Phe Asp Phe
1               5                   10

<210> SEQ ID NO 7
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Thr Leu Val His Ser
            20                  25                  30

Ser Gly Asn Thr Tyr Leu Glu Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60
```

-continued

```
Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Phe Gln Gly
                 85                  90                  95

Ser Phe Asn Pro Leu Thr Phe Gly Gln Gly Thr Lys Val Glu Ile Lys
            100                 105                 110

Arg
```

<210> SEQ ID NO 8
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Phe Ser Asp Phe
             20                  25                  30

Ala Met Ser Trp Val Arg Gln Ala Pro Gly Lys Gly Leu Glu Trp Val
         35                  40                  45

Ala Thr Ile Gly Arg Val Ala Phe His Thr Tyr Tyr Pro Asp Ser Met
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Arg Gly Phe Asp Val Gly His Phe Asp Phe Trp Gly Gln
            100                 105                 110

Gly Thr Leu Val Thr Val Ser Ser
        115                 120
```

<210> SEQ ID NO 9
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

```
Asp Ile Gln Met Thr Gln Ser Pro Ser Ser Leu Ser Ala Ser Val Gly
 1               5                  10                  15

Asp Arg Val Thr Ile Thr Cys Arg Ser Ser Glu Thr Leu Val His Ser
             20                  25                  30

Ser Gly Asn Thr Tyr Leu Glu Trp Tyr Gln Gln Lys Pro Gly Lys Ala
         35                  40                  45

Pro Lys Leu Leu Ile Tyr Arg Val Ser Asn Arg Phe Ser Gly Val Pro
     50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Phe Gln Gly
                 85                  90                  95

Ser Phe Asn Pro Leu Thr Phe Gly Gln Gly Thr Lys Val Glu Ile Lys
            100                 105                 110
```

```
Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 10
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Ala Met Ser Trp Val Arg Gln Ala Pro Gly Lys Gly Leu Glu Trp Val
        35                  40                  45

Ala Thr Ile Gly Arg Val Ala Phe His Thr Tyr Tyr Pro Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Phe Asp Val Gly His Phe Asp Phe Trp Gly Gln
            100                 105                 110

Gly Thr Leu Val Thr Val Ser Ser Cys Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

-continued

```
Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 11
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Arg Ser Ser Gln Ser Leu Leu His Ser Asn Gly Tyr Asn Tyr Leu Asp
1               5                   10                  15

<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Leu Gly Val Asn Ser Val Ser
1               5

<210> SEQ ID NO 13
<211> LENGTH: 9
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 13

Met Gln Ala Leu Gln Thr Pro Trp Thr
1               5

<210> SEQ ID NO 14
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Asn His Ala Ile Ser
1               5

<210> SEQ ID NO 15
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Ile Ile Pro Ile Phe Gly Thr Ala Asn Tyr Ala Gln Lys Phe Gln
1               5                   10                  15

Gly

<210> SEQ ID NO 16
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Glu Trp Ala Asp Val Phe Asp Ile
1               5

<210> SEQ ID NO 17
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Val Asn Ser Val Ser Gly Val Pro
        50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 18
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Ile Phe Ser Asn His
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Phe
65                  70                  75                  80

Met Glu Leu Ser Ser Leu Arg Ser Glu Asp Thr Ala Val Tyr Tyr Cys
                85                  90                  95

Ala Arg Glu Trp Ala Asp Val Phe Asp Ile Trp Gly Gln Gly Thr Met
            100                 105                 110

Val Thr Val Ser Ser
        115

<210> SEQ ID NO 19
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Arg Ala Ser Gln Gly Ile Arg Asn Asp Leu Gly
1               5                   10

<210> SEQ ID NO 20
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ala Ala Ser Ser Leu Gln Ser
1               5

<210> SEQ ID NO 21
<211> LENGTH: 9
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Leu Gln His Asn Ser Tyr Pro Trp Thr
1               5

<210> SEQ ID NO 22
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Asn Tyr Met Ser
1               5

<210> SEQ ID NO 23
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Leu Ile Tyr Ser Gly Asp Ser Thr Tyr Tyr Ala Asp Ser Val Lys Gly
1               5                   10                  15

<210> SEQ ID NO 24
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Asp Gly Tyr Tyr Val Ser Asp Met Val Val
1               5                   10

<210> SEQ ID NO 25
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Leu Glu Ile Lys
            100                 105

<210> SEQ ID NO 26
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Glu Val Gln Leu Val Glu Ser Gly Gly Ala Leu Ile Gln Pro Gly Gly
  1               5                  10                  15

Ser Leu Arg Leu Ser Cys Val Ala Ser Gly Phe Thr Ile Ser Gly Asn
             20                  25                  30

Tyr Met Ser Trp Val Arg Gln Ala Pro Gly Lys Gly Leu Glu Trp Val
         35                  40                  45

Ser Leu Ile Tyr Ser Gly Asp Ser Thr Tyr Tyr Ala Asp Ser Val Lys
 50                  55                  60

Gly Arg Phe Asn Ile Ser Arg Asp Ile Ser Lys Asn Thr Val Tyr Leu
 65                  70                  75                  80

Gln Met Asn Ser Leu Arg Val Glu Asp Thr Ala Val Tyr Tyr Cys Val
                 85                  90                  95

Arg Asp Gly Tyr Tyr Val Ser Asp Met Val Val Trp Gly Lys Gly Thr
            100                 105                 110

Thr Val Thr Val Ser Ser
        115

<210> SEQ ID NO 27
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Leu Glu Ile Lys
            100                 105
```

<210> SEQ ID NO 28
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Thr Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115

<210> SEQ ID NO 29
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 30
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Ser Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115

<210> SEQ ID NO 31
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 32
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 32

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

-continued

```
Ser Leu Ile Tyr Ser Gly Asp Ser Thr Tyr Tyr Ala Asp Ser Val Lys
 50                 55                  60

Gly Arg Phe Ala Ile Ser Arg Asp Ile Ser Lys Asn Thr Val Tyr Leu
 65                  70                  75                  80

Gln Met Asn Ser Leu Arg Val Glu Asp Thr Ala Val Tyr Tyr Cys Val
                 85                  90                  95

Arg Asp Gly Tyr Tyr Val Ser Asp Met Val Val Trp Gly Lys Gly Thr
            100                 105                 110

Thr Val Thr Val Ser Ser
        115
```

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41
<211> LENGTH: 16
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 41

Arg Ser Ser Gln Ser Ile Val His Ser Val Gly Asn Thr Phe Leu Glu
1               5                   10                  15

<210> SEQ ID NO 42
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Lys Val Ser Asn Arg Phe Ser
1               5

<210> SEQ ID NO 43
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Phe Gln Gly Ser Gln Phe Pro Tyr Thr
1               5

<210> SEQ ID NO 44
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Tyr Glu Phe Ser Arg Ser Trp Met Asn
1               5                   10

<210> SEQ ID NO 45
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Arg Ile Tyr Pro Gly Asp Gly Asp Thr Asn Tyr Ser Gly Lys Phe Lys
1               5                   10                  15

Gly

<210> SEQ ID NO 46
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 46

Asp Gly Ser Ser Trp Asp Trp Tyr Phe Asp Val
1               5                   10

<210> SEQ ID NO 47
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
                20                  25                  30

Val Gly Asn Thr Phe Leu Glu Trp Tyr Gln Gln Lys Pro Gly Lys Ala
            35                  40                  45

Pro Lys Leu Leu Ile Tyr Lys Val Ser Asn Arg Phe Ser Gly Val Pro
        50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Gln Phe Pro Tyr Thr Phe Gly Gln Gly Thr Lys Val Glu Ile Lys
            100                 105                 110

Arg

<210> SEQ ID NO 48
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Glu Phe Ser Arg Ser
                20                  25                  30

Trp Met Asn Trp Val Arg Gln Ala Pro Gly Lys Gly Leu Glu Trp Val
            35                  40                  45

Gly Arg Ile Tyr Pro Gly Asp Gly Asp Thr Asn Tyr Ser Gly Lys Phe
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Asp Trp Tyr Phe Asp Val Trp Gly Gln
            100                 105                 110

Gly Thr Leu Val Thr Val Ser Ser
        115                 120

<210> SEQ ID NO 49
```

```
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49
```

Asp Ile Gln Met Thr Gln Ser Pro Ser Leu Ser Ala Ser Val Gly
1               5                   10                  15

Asp Arg Val Thr Ile Thr Cys Arg Ser Ser Gln Ser Ile Val His Ser
            20                  25                  30

Val Gly Asn Thr Phe Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Gln Phe Pro Tyr Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Cys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

```
<210> SEQ ID NO 50
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Glu Phe Ser Arg Ser
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Ser Gly Lys Phe
    50                  55                  60

Lys Gly Arg Phe Thr Ile Ser Ala Asp Thr Ser Lys Asn Thr Ala Tyr
65                  70                  75                  80

-continued

```
Leu Gln Met Asn Ser Leu Arg Ala Glu Asp Thr Ala Val Tyr Tyr Cys
                 85                  90                  95
Ala Arg Asp Gly Ser Ser Trp Asp Trp Tyr Phe Asp Val Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
450
```